US012790334B2

(12) United States Patent
Connolly et al.

(10) Patent No.: US 12,790,334 B2
(45) Date of Patent: Nov. 10, 2026

(54) SUBSTITUTED PIPERIDINYL-METHYLPURINE PYRIDINES AND RELATED COMPOUNDS AND THEIR USE IN TREATING DISEASES AND CONDITIONS

(71) Applicant: K36 Therapeutics, Inc., Cambridge, MA (US)

(72) Inventors: Terrence Joseph Connolly, Concord, MA (US); Chad Arthur Lewis, Boylston, MA (US)

(73) Assignee: K36 Therapeutics, Inc., Cambridge, MA (US)

( * ) Notice: Subject to any disclaimer, the term of this patent is extended or adjusted under 35 U.S.C. 154(b) by 301 days.

(21) Appl. No.: 18/750,167

(22) Filed: Jun. 21, 2024

(65) Prior Publication Data

US 2025/0011329 A1 Jan. 9, 2025

Related U.S. Application Data

(60) Provisional application No. 63/522,275, filed on Jun. 21, 2023.

(51) Int. Cl.

| | |
|---|---|
| ***C07D 473/34*** | (2006.01) |
| ***A61K 31/52*** | (2006.01) |
| ***A61K 31/675*** | (2006.01) |
| ***C07F 9/6561*** | (2006.01) |

(52) U.S. Cl.

CPC ............ *C07D 473/34* (2013.01); *A61K 31/52* (2013.01); *A61K 31/675* (2013.01); *C07F 9/65616* (2013.01)

(58) Field of Classification Search

None

See application file for complete search history.

(56) References Cited

U.S. PATENT DOCUMENTS

| | | | |
|---|---|---|---|
| 11,420,970 | B1 | 8/2022 | Deng et al. |
| 12,312,353 | B2 | 5/2025 | Deng et al. |
| 2006/0052403 | A1 | 3/2006 | Isobe et al. |
| 2014/0128389 | A1 | 5/2014 | Halcomb et al. |
| 2024/0002385 | A1 | 1/2024 | Connolly et al. |
| 2024/0352017 | A1 | 10/2024 | Connolly et al. |
| 2024/0415864 | A1 | 12/2024 | Connolly et al. |
| 2024/0417401 | A1 | 12/2024 | Connolly et al. |
| 2025/0011329 | A1 | 1/2025 | Connolly et al. |
| 2025/0163067 | A1 | 5/2025 | Lewis et al. |
| 2025/0206740 | A1 | 6/2025 | Connolly et al. |
| 2025/0276971 | A1 | 9/2025 | Deng et al. |

FOREIGN PATENT DOCUMENTS

| | | | | |
|---|---|---|---|---|
| CN | 1512992 | A | 7/2004 | |
| CN | 1684966 | A | 10/2005 | |
| CN | 1688580 | A | 10/2005 | |
| CN | 101679433 | A | 3/2010 | |
| CN | 102666541 | A | 9/2012 | |
| CN | 108853110 | A | 11/2018 | |
| CN | 109223794 | A | 1/2019 | |
| CN | 109734677 | A | 5/2019 | |
| CN | 117843641 | A | 4/2024 | |
| JP | 2004137157 | A | 5/2004 | |
| JP | 2013508373 | A | 3/2013 | |
| WO | WO-2000055161 | A1 | 9/2000 | |
| WO | WO-2002085905 | A1 | 10/2002 | |
| WO | WO-2003022219 | A2 | 3/2003 | |
| WO | WO-2004029054 | A1 | 4/2004 | |
| WO | WO-2004085418 | A2 | 10/2004 | |
| WO | WO-2005123697 | A1 | 12/2005 | |
| WO | WO-2006090261 | A1 | 8/2006 | |
| WO | WO-2008114817 | A1 | 9/2008 | |
| WO | WO-2008116129 | A2 | 9/2008 | |
| WO | WO-2011049825 | A1 | 4/2011 | |
| WO | WO-2011103028 | A2 | 8/2011 | |
| WO | WO-2013139882 | A1 | 9/2013 | |
| WO | WO-2015112809 | A2 | 7/2015 | |
| WO | WO-2015143424 | A2 | 9/2015 | |
| WO | WO-2019113469 | A1 | 6/2019 | |
| WO | WO-2019196918 | A1 | 10/2019 | |
| WO | WO 2021026803 | A1 * | 2/2021 | ........... C07D 473/34 |
| WO | WO-2021028854 | A1 | 2/2021 | |
| WO | WO-2021053617 | A1 | 3/2021 | |
| WO | WO-2021239077 | A1 | 12/2021 | |
| WO | WO-2023225141 | A1 | 11/2023 | |
| WO | WO-2023225144 | A1 | 11/2023 | |
| WO | WO-2023225150 | A1 | 11/2023 | |
| WO | WO-2023225154 | A1 | 11/2023 | |
| WO | WO-2023230026 | A1 | 11/2023 | |
| WO | WO-2023230038 | A1 | 11/2023 | |
| WO | WO-2024073282 | A2 | 4/2024 | |

OTHER PUBLICATIONS

International Search Report and Written Opinion for International Application No. PCT/CN2019/100542 (13 pages).
International Search Report and Written Opinion for International Application No. PCT/IB2020/057602 (8 pages).
Tisi, D. et al., "Structure of the Epigenetic Oncogene MMSET and Inhibition by N-Alkyl Sinefungin Derivatives," *ACS Chem. Bio.*, 2016, vol. 11, No. 11, p. 3093-3105.
Brusova, Chemistry, Moscow State University, (4 pages). Retrieved from the internet on Feb. 10, 2023 from: http://www.chem.msu.su/rus/teaching/brusova/4.html.
Berge, S. M. et al. "Pharmaceutical Salts," *J. Pharmaceutical Sciences*, 1977, vol. 66, No. 1, p. 1-19.
Zhang, L. et al. "Recent advances in nuclear receptor-binding SET domain 2 (NSD2) inhibitors: An update and perspectives," *Eur. J. Med. Chem.*, 2023, 250, 115232.
Caira, M. R. "Crystalline Polymorphism of Organic Compounds." In: *Design of Organic Solids. Topics in Current Chemistry*, ed. E. Weber, Springer, Berlin, 1998, vol. 198, p. 163-208.
International Search Report and Written Opinion for International Application No. PCT/US2023/022643 (8 pages).

(Continued)

*Primary Examiner* — Kortney L. Klinkel
*Assistant Examiner* — Cierra M Rochelle
(74) *Attorney, Agent, or Firm* — Morgan, Lewis & Bockius LLP

(57) ABSTRACT

The invention provides substituted piperidinyl-methylpurine pyridines and related compounds, pharmaceutical compositions, their use for inhibiting NSD2, and their use in the treatment of a disease or condition, such as cancer.

25 Claims, No Drawings

(56) References Cited

OTHER PUBLICATIONS

International Search Report and Written Opinion for International Application No. PCT/US2023/022646 (7 pages).
International Search Report and Written Opinion for International Application No. PCT/US2023/022656 (9 pages).
International Search Report and Written Opinion for International Application No. PCT/US2023/022665 (8 pages).
International Search Report and Written Opinion for International Application No. PCT/US2023/023178 (11 pages).
International Search Report and Written Opinion for International Application No. PCT/US2023/023202 (12 pages).
U.S. Appl. No. 18/867,113, Piperidinyl-Methylpurine Benzenes and Related Compounds and Their Use in Treating Diseases and Conditions, Nov. 19, 2024.
U.S. Appl. No. 18/867,118, Piperidinyl-Methylpurine Pyrimidines and Related Compounds and Their Use in Treating Diseases and Conditions, Nov. 19, 2024.
U.S. Appl. No. 18/735,459, Heterobicyclic-Methylpurine Pyridines and Related Compounds and Their Use in Treating Diseases and Conditions, Jun. 6, 2024.
U.S. Appl. No. 18/954,858, Nucleobase-Substituted Piperidinyl-Pyridines and Related Compounds and Their Use in Treating Diseases and Conditions, Nov. 21, 2024.
U.S. Appl. No. 18/735,568, Carbohydrate-Functionalized Piperidinyl-Methylpurine Pyridines and Related Compounds and Their Use in Treating Diseases and Conditions, Jun. 6, 2024.

* cited by examiner

SUBSTITUTED PIPERIDINYL-METHYLPURINE PYRIDINES AND RELATED COMPOUNDS AND THEIR USE IN TREATING DISEASES AND CONDITIONS

CROSS-REFERENCE TO RELATED APPLICATIONS

This application claims the benefit of and priority to U.S. Provisional Patent Application Ser. No. 63/522,275, filed Jun. 21, 2023; the contents of which are hereby incorporated by reference in their entirety.

FIELD OF THE INVENTION

The invention provides substituted piperidinyl-methylpurine pyridines and related compounds, pharmaceutical compositions, their use for inhibiting NSD2, and their use in the treatment of a disease or condition, such as cancer.

BACKGROUND

Cancer continues to be a significant health problem despite the substantial research efforts and scientific advances reported in the literature for treating this disease. Solid tumors, including prostate cancer, breast cancer, and lung cancer remain highly prevalent among the world population. Current treatment options for these cancers are not effective for all patients and/or can have substantial adverse side effects. New therapies are needed to address this unmet need in cancer therapy.

The nuclear receptor-binding SET domain protein 2 (NSD2), also known as multiple myeloma SET domain (MMSET) or Wolf-Hirschhorn syndrome candidate 1 (WHSC1), is an epigenetic modifier having a role in oncogenesis. Several human cancers are associated with NSD2 overexpression and/or activating point mutations. (Coussens et al., *J. Biol. Chem.* 293 (2018) 13750-13654.) For example, high expression of NSD2 has been reported in human cancers including bladder, brain, gastrointestinal, lung, liver, ovary, skin, uterus, breast, prostrate and glioblastoma. Additionally, pediatric cancer genomes appear to be particularly likely to contain NSD2 mutations. Finally, upregulation of NSD2 has been linked with aggressive tumor behavior and poor clinical outcomes. Certain compounds that inhibit NSD2 are described in international patent application publication WO 2021/028854. Additional compounds that inhibit NSD2 would be beneficial to patients suffering from an NSD2-related disease or condition.

The present invention addresses the foregoing needs and provides other related advantages.

SUMMARY

The invention provides substituted piperidinyl-methylpurine pyridines and related compounds, pharmaceutical compositions, their use for inhibiting NSD2, and their use in the treatment of a disease or condition, such as cancer. In particular, one aspect of the invention provides a collection of substituted piperidinyl-methylpurine pyridines and related compounds, such as a compound represented by Formula I:

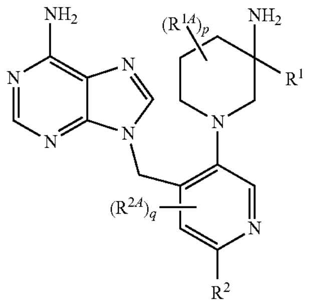

(I)

or a pharmaceutically acceptable salt thereof, where the variables are as defined in the detailed description. Further description of additional collections of substituted piperidinyl-methylpurine pyridines and related compounds are described in the detailed description. The compounds may be part of a pharmaceutical composition comprising a pharmaceutically acceptable carrier.

Another aspect of the invention provides a collection of substituted piperidinyl-methylpurine pyridines and related compounds, such as a compound represented by Formula II:

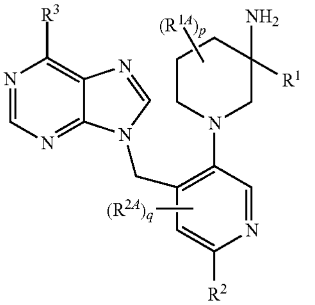

(II)

or a pharmaceutically acceptable salt thereof, where the variables are as defined in the detailed description. Further description of additional collections of substituted piperidinyl-methylpurine pyridines and related compounds are described in the detailed description. The compounds may be part of a pharmaceutical composition comprising a pharmaceutically acceptable carrier.

Another aspect of the invention provides a method of treating a disease or condition mediated by NSD2 in a subject. The method comprises administering a therapeutically effective amount of a compound described herein, such as a compound of Formula I, I-A, II, or II-A, to a subject in need thereof to treat the disease or condition, as further described in the detailed description.

Another aspect of the invention provides a method of inhibiting the activity of nuclear SET domain-containing protein 2 (NSD2). The method comprises contacting a NSD2 with an effective amount of a compound described herein, such as a compound of Formula I, I-A, II, or II-A, to inhibit the activity of said NSD2, as further described in the detailed description.

DETAILED DESCRIPTION

The invention provides substituted piperidinyl-methylpurine pyridines and related compounds, pharmaceutical compositions, their use for inhibiting NSD2, and their use in the treatment of a disease or condition, such as cancer. The practice of the present invention employs, unless otherwise indicated, conventional techniques of organic chemistry, pharmacology, molecular biology (including recombinant techniques), cell biology, biochemistry, and immunology. Such techniques are explained in the literature, such as in "Comprehensive Organic Synthesis" (B. M. Trost & I. Fleming, eds., 1991-1992); "Handbook of experimental immunology" (D. M. Weir & C. C. Blackwell, eds.); "Current protocols in molecular biology" (F. M. Ausubel et al., eds., 1987, and periodic updates); and "Current protocols in immunology" (J. E. Coligan et al., eds., 1991), each of which is herein incorporated by reference in its entirety.

Various aspects of the invention are set forth below in sections; however, aspects of the invention described in one particular section are not to be limited to any particular section. Further, when a variable is not accompanied by a definition, the previous definition of the variable controls.

Definitions

Compounds of the present invention include those described generally herein, and are further illustrated by the classes, subclasses, and species disclosed herein. As used herein, the following definitions shall apply unless otherwise indicated. These definitions apply regardless of whether a term is used by itself or in combination with other terms, unless otherwise indicated. Hence, the definition of "alkyl" applies to "alkyl" as well as the "alkyl" portions of "—O-alkyl" etc. For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "cycloaliphatic"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bicyclic ring" or "bicyclic ring system" refers to any bicyclic ring system, i.e., carbocyclic or heterocyclic, saturated or having one or more units of unsaturation, having one or more atoms in common between the two rings of the ring system. Thus, the term includes any permissible ring fusion, such as ortho-fused or spirocyclic. As used herein, the term "heterobicyclic" is a subset of "bicyclic" that requires that one or more heteroatoms are present in one or both rings of the bicycle. Such heteroatoms may be present at ring junctions and are optionally substituted, and may be selected from nitrogen (including N-oxides), oxygen, sulfur (including oxidized forms such as sulfones and sulfonates), phosphorus (including oxidized forms such as phosphates), boron, etc. In some embodiments, a bicyclic group has 7-12 ring members and 0-4 heteroatoms independently selected from nitrogen, oxygen, or sulfur. As used herein, the term "bridged bicyclic" refers to any bicyclic ring system, i.e., carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bicyclic rings include:

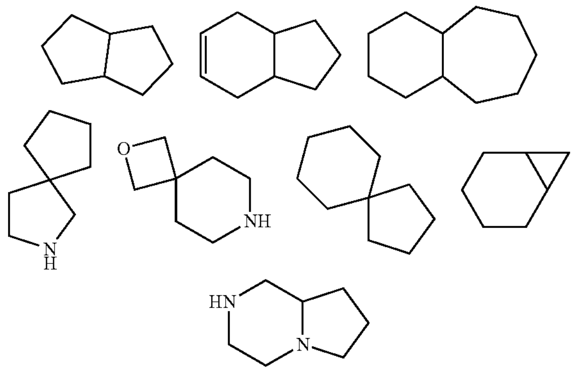

Exemplary bridged bicyclics include:

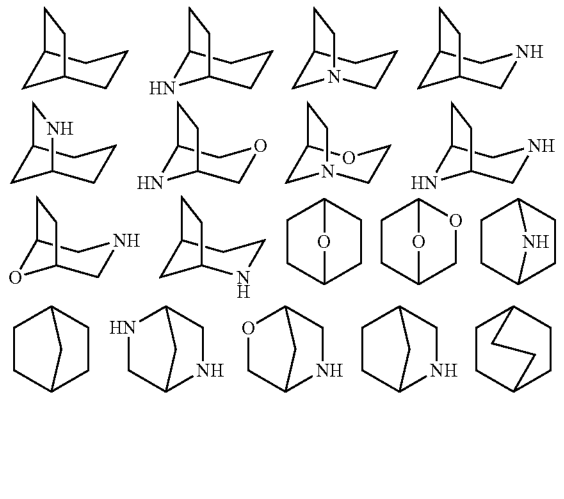

-continued

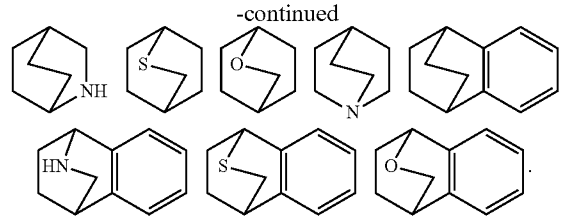

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^-$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "$-(C_0$ alkylene)-" refers to a bond. Accordingly, the term "$-(C_{0-3}$ alkylene)-" encompasses a bond (i.e., $C_0$) and a $-(C_{1-3}$ alkylene)- group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" or "halo" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like. The term "phenylene" refers to a multivalent phenyl group having the appropriate number of open valences to account for groups attached to it. For example, "phenylene" is a bivalent phenyl group when it has two groups attached to it (e.g., 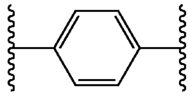);

"phenylene" is a trivalent phenyl group when it has three groups attached to it (e.g., 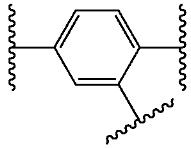).

The term "arylene" refers to a bivalent aryl group.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where unless otherwise specified, the radical or point of attachment is on the heteroaromatic ring or on one of the rings to which the heteroaromatic ring is fused. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

The term "heteroarylene" refers to a multivalent heteroaryl group having the appropriate number of open valences to account for groups attached to it. For example, "heteroarylene" is a bivalent heteroaryl group when it has two groups attached to it; "heteroarylene" is a trivalent heteroaryl group when it has three groups attached to it. The term "pyridinylene" refers to a multivalent pyridine radical having the appropriate number of open valences to account for groups attached to it. For example, "pyridinylene" is a bivalent pyridine radical when it has two groups attached to it (e.g., 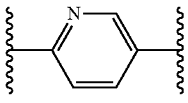);

"pyridinylene" is a trivalent pyridine radical when it has three groups attached to it (e.g., 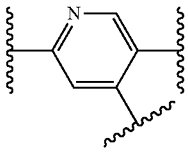).

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^{+}NR$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, 2-oxa-6-azaspiro[3.3]heptane, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted. The term "oxo-heterocyclyl" refers to a heterocyclyl substituted by an oxo group. The term "heterocyclylene" refers to a multivalent heterocyclyl group having the appropriate number of open valences to account for groups attached to it. For example, "heterocyclylene" is a bivalent heterocyclyl group when it has two groups attached to it; "heterocyclylene" is a trivalent heterocyclyl group when it has three groups attached to it.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Each optional substituent on a substitutable carbon is a monovalent substituent independently selected from halogen; $-(CH_2)_{0-4}R^{\circ}$; $-(CH_2)_{0-4}R^{\circ}$; $-O(CH_2)_{0-4}R^{\circ}$, $-O-(CH_2)_{0-4}C(O)OR^{\circ}$; $-(CH_2)_{0-4}CH(OR^{\circ})_2$; $-(CH_2)_{0-4}SR^{\circ}$; $-(CH_2)_{0-4}Ph$, which may be substituted with $R^{\circ}$; $-(CH_2)_{0-4}O(CH_2)_{0-1}Ph$ which may be substituted with $R^{\circ}$; $-CH{=}CHPh$, which may be substituted with $R^{\circ}$; $-(CH_2)_{0-4}O(CH_2)_{0-1}$-pyridyl which may be substituted with $R^{\circ}$; $-NO_2$; $-CN$; $-N_3$; $-(CH_2)_{0-4}N(R^{\circ})_2$; $-(CH_2)_{0-4}N(R^{\circ})C(O)R^{\circ}$; $-N(R^{\circ})C(S)R^{\circ}$; $-(CH_2)_{0-4}N(R^{\circ})C(O)NR^{\circ}_2$; $-N(R^{\circ})C(S)NR^{\circ}_2$; $-(CH_2)_{0-4}N(R^{\circ})C(O)OR^{\circ}$; $-N(R^{\circ})N(R^{\circ})C(O)R^{\circ}$; $-N(R^{\circ})N(R^{\circ})C(O)NR^{\circ}_2$; $-N(R^{\circ})N(R^{\circ})C(O)OR^{\circ}$; $-(CH_2)_{0-4}C(O)R^{\circ}$; $-C(S)R^{\circ}$; $-(CH_2)_{0-4}C(O)OR^{\circ}$; $-(CH_2)_{0-4}C(O)SR^{\circ}$; $-(CH_2)_{0-4}C(O)OSiR^{\circ}_3$; $-(CH_2)_{0-4}C(O)R^{\circ}$; $-OC(O)(CH_2)_{0-4}SR^{\circ}$, $SC(S)SR^{\circ}$; $-(CH_2)_{0-4}SC(O)R^{\circ}$; $-(CH_2)_{0-4}C(O)NR^{\circ}_2$; $-C(S)NR^{\circ}_2$; $-C(S)SR^{\circ}$; $-SC(S)SR^{\circ}$, $-(CH_2)_{0-4}OC(O)NR^{\circ}_2$; $-C(O)N(OR^{\circ})R^{\circ}$; $-C(O)C(O)R^{\circ}$; $-C(O)CH_2C(O)R^{\circ}$; $-C(NOR^{\circ})R^{\circ}$; $-(CH_2)_{0-4}SSR^{\circ}$; $-(CH_2)_{0-4}S(O)_2R^{\circ}$; $-(CH_2)_{0-4}S(O)_2OR^{\circ}$; $-(CH_2)_{0-4}OS(O)_2R^{\circ}$; $-S(O)_2NR^{\circ}_2$; $-S(O)(NR^{\circ})R^{\circ}$; $-S(O)_2N{=}C(NR^{\circ}_2)_2$; $-(CH_2)_{0-4}S(O)R^{\circ}$; $-N(R^{\circ})S(O)_2NR^{\circ}_2$; $-N(R^{\circ})S(O)_2R^{\circ}$; $-N(OR^{\circ})R^{\circ}$; $-C(NH)NR^{\circ}_2$; $-P(O)_2R^{\circ}$; $-P(O)R^{\circ}_2$; $-OP(O)R^{\circ}_2$; $-OP(O)(OR^{\circ})_2$; $SiR^{\circ}_3$; $-(C_{1-4}$ straight or branched alkylene)$O-N(R^{\circ})_2$; or $-(C_{1-4}$ straight or branched alkylene)$C(O)O-N(R^{\circ})_2$.

Each $R^{\circ}$ is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^{\circ}$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted by a divalent substituent on a saturated carbon atom of $R^{\circ}$ selected from $=O$ and $=S$; or each $R^{\circ}$ is optionally substituted with a monovalent substituent independently selected from halogen, $-(CH_2)_{0-2}R^{\bullet}$, -(halo$R^{\bullet}$), $-(CH_2)_{0-2}OH$, $-(CH_2)_{0-2}OR^{\bullet}$, $-(CH_2)_{0-2}CH(OR^{\bullet})_2$; $-O$(halo$R^{\bullet}$), $-CN$, $-N_3$, $-(CH_2)_{0-2}C(O)R^{\bullet}$, $-(CH_2)_{0-2}C(O)OH$, $-(CH_2)_{0-2}C(O)OR^{\bullet}$, $-(CH_2)_{0-2}SR^{\bullet}$, $-(CH_2)_{0-2}SH$, $-(CH_2)_{0-2}NH_2$, $-(CH_2)_{0-2}NHR^{\bullet}$, $-(CH_2)_{0-2}NR^{\bullet}_2$, $-NO_2$, $-SiR^{\bullet}_3$, $-OSiR^{\bullet}_3$, $-C(O)SR^{\bullet}$, $-(C_{1-4}$ straight or branched alkylene)$C(O)OR^{\bullet}$, or $-SSR^{\bullet}$.

Each $R^{\bullet}$ is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur, and wherein each $R^●$ is unsubstituted or where preceded by halo is substituted only with one or more halogens; or wherein an optional substituent on a saturated carbon is a divalent substituent independently selected from =O, =S, $=NNR^*_2$, =NNHC(O)R*, =NNHC(O)OR*, $=NNHS(O)_2R^*$, =NR*, =NOR*, $—O(C(R^*_2))_{2-3}O—$, or $—S(C(R^*_2))_{2-3}S—$, or a divalent substituent bound to vicinal substitutable carbons of an "optionally substituted" group is $—O(CR^*_2)_{2-3}O—$, wherein each independent occurrence of R* is selected from hydrogen, $C_{1-6}$ aliphatic or an unsubstituted 5-6-membered saturated, partially unsaturated, or aryl ring having 0-4 heteroatoms independently selected from nitrogen, oxygen, or sulfur.

When R* is $C_{1-6}$ aliphatic, R* is optionally substituted with halogen, —R*, -(halo$R^●$), —OH, —$OR^●$, —O(halo$R^●$), —CN, —C(O)OH, —C(O)$OR^●$, —$NH_2$, —$NHR^●$, —$NR^●_2$, or —$NO_2$, wherein each $R^●$ is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, and wherein each $R^●$ is unsubstituted or where preceded by halo is substituted only with one or more halogens.

An optional substituent on a substitutable nitrogen is independently —$R^†$, —$NR^†_2$, —C(O)$R^†$, —C(O)$OR^†$, —C(O)C(O)$R^†$, —C(O)$CH_2$C(O)$R^†$, —$S(O)_2R^†$, —$S(O)_2NR^†_2$, —C(S)$NR^†_2$, —C(NH)$NR^†_2$, or —$N(R^†)S(O)_2R^†$; wherein each RT is independently hydrogen, $C_{1-6}$ aliphatic, unsubstituted —OPh, or an unsubstituted 5-6-membered saturated, partially unsaturated, or aryl ring having 0-4 heteroatoms independently selected from nitrogen, oxygen, or sulfur, or, two independent occurrences of $R^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur; wherein when RT is $C_{1-6}$ aliphatic, RT is optionally substituted with halogen, —$R^●$, -(halo$R^●$), —OH, —$OR^●$, —O(halo$R^●$), —CN, —C(O)OH, —C(O)$OR^●$, —$NH_2$, —$NHR^●$, —$NR^●_2$, or —$NO_2$, wherein each $R^●$ is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, and wherein each $R^●$ is unsubstituted or where preceded by halo is substituted only with one or more halogens.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Further, acids which are generally considered suitable for the formation of pharmaceutically useful salts from basic pharmaceutical compounds are discussed, for example, by P. Stahl et al., Camille G. (eds.) *Handbook of Pharmaceutical Salts. Properties, Selection and Use*. (2002) Zurich: Wiley-VCH; S. Berge et al., *Journal of Pharmaceutical Sciences* (1977) 66(1) 1-19; P. Gould, *International J. of Pharmaceutics* (1986) 33 201-217; Anderson et al., The *Practice of Medicinal Chemistry* (1996), Academic Press, New York; and in *The Orange Book* (Food & Drug Administration, Washington, D.C. on their website). These disclosures are incorporated herein by reference.

Salts derived from appropriate bases include alkali metal, alkaline earth metal, ammonium and $N^-(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. The invention includes compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

Diastereomeric mixtures can be separated into their individual diastereomers on the basis of their physical chemical differences by methods known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Alternatively, a particular enantiomer of a compound of the present invention may be prepared by asymmetric synthesis. Still further, where the molecule contains a basic functional group (such as amino) or an acidic functional group (such as carboxylic acid)

diastereomeric salts are formed with an appropriate optically-active acid or base, followed by resolution of the diastereomers thus formed by fractional crystallization or chromatographic means known in the art, and subsequent recovery of the pure enantiomers.

Individual stereoisomers of the compounds of the invention may, for example, be substantially free of other isomers, or may be admixed, for example, as racemates or with all other, or other selected, stereoisomers. Chiral center(s) in a compound of the present invention can have the S or R configuration as defined by the IUPAC 1974 Recommendations. Further, to the extent a compound described herein may exist as an atropisomer (e.g., substituted biaryls), all forms of such atropisomer are considered part of this invention.

Chemical names, common names, and chemical structures may be used interchangeably to describe the same structure. If a chemical compound is referred to using both a chemical structure and a chemical name, and an ambiguity exists between the structure and the name, the structure predominates. It should also be noted that any carbon as well as heteroatom with unsatisfied valences in the text, schemes, examples and tables herein is assumed to have the sufficient number of hydrogen atom(s) to satisfy the valences.

Unless specified otherwise, the term "about" refers to within ±10% of the stated value. The invention encompasses embodiments where the value is within ±9%, ±8%, ±7%, ±6%, ±5%, ±4%, ±3%, ±2%, or ±1% of the stated value.

The terms "a" and "an" as used herein mean "one or more" and include the plural unless the context is inappropriate.

The term "alkyl" refers to a saturated straight or branched hydrocarbon, such as a straight or branched group of 1-12, 1-10, or 1-6 carbon atoms, referred to herein as $C_1$-$C_{12}$ alkyl, $C_1$-$C_{10}$ alkyl, and $C_1$-$C_6$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "$C_3$-$C_6$ cycloalkyl," derived from a cycloalkane. Exemplary cycloalkyl groups include cyclohexyl, cyclopentyl, cyclobutyl, and cyclopropyl. The term "cycloalkylene" refers to a bivalent cycloalkyl group.

The term "haloalkyl" refers to an alkyl group that is substituted with at least one halogen. Exemplary haloalkyl groups include $—CH_2F$, $—CHF_2$, $—CF_3$, $—CH_2CF_3$, $—CF_2CF_3$, and the like. The term "haloalkylene" refers to a bivalent haloalkyl group.

The terms "alkenyl" and "alkynyl" are art-recognized and refer to unsaturated aliphatic groups analogous in length and possible substitution to the alkyls described above, but that contain at least one double or triple bond respectively.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. The term "haloalkoxyl" refers to an alkoxyl group that is substituted with at least one halogen. Exemplary haloalkoxyl groups include $—OCH_2F$, $—OCHF_2$, $—OCF_3$, $—OCH_2CF_3$, $—OCF_2CF_3$, and the like. The term "hydroxyalkoxyl" refers to an alkoxyl group that is substituted with at least one hydroxyl. Exemplary hydroxyalkoxyl groups include $—OCH_2CH_2OH$, $—OCH_2C(H)(OH)CH_2CH_2OH$, and the like. The term "alkoxylene" refers to a bivalent alkoxyl group.

The term "oxo" is art-recognized and refers to a "=O" substituent. For example, a cyclopentane substituted with an oxo group is cyclopentanone.

The symbol "$\sim$" indicates a point of attachment.

When any substituent or variable occurs more than one time in any constituent or the compound of the invention, its definition on each occurrence is independent of its definition at every other occurrence, unless otherwise indicated.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

As used herein, the terms "subject" and "patient" are used interchangeably and refer to organisms to be treated by the methods of the present invention. Such organisms preferably include, but are not limited to, mammals (e.g., murines, simians, equines, bovines, porcines, canines, felines, and the like), and, most preferably, includes humans.

As used herein, the term "compound" refers to a quantity of molecules that is sufficient to be weighed, tested for its structural identity, and to have a demonstrable use (e.g., a quantity that can be shown to be active in an assay, an in vitro test, or in vivo test, or a quantity that can be administered to a patient and provide a therapeutic benefit).

The term "$IC_{50}$" is art-recognized and refers to the concentration of a compound that is required to achieve 50% inhibition of the target.

As used herein, the term "effective amount" refers to the amount of a compound sufficient to effect beneficial or desired results (e.g., a therapeutic, ameliorative, inhibitory, or preventative result). An effective amount can be administered in one or more administrations, applications, or dosages and is not intended to be limited to a particular formulation or administration route.

As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, PA [1975].

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

As a general matter, compositions specifying a percentage are by weight unless otherwise specified.

I. Substituted Piperidinyl-Methylpurine Pyridines and Related Compounds

The invention provides substituted piperidinyl-methylpurine pyridines and related compounds. The compounds may be used in the pharmaceutical compositions and therapeutic methods described herein. Exemplary compounds are described in the following sections, along with exemplary procedures for making the compounds.

One aspect of the invention provides a compound represented by Formula I:

(I)

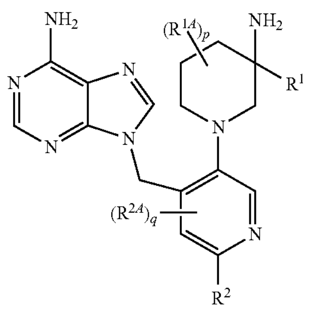

or a pharmaceutically acceptable salt thereof, wherein:

$R^1$ is selected from the group consisting of:

a. $C_{1-6}$ alkyl substituted with (i) 0, 1, 2, or 3 halo, and (ii) 0 or 1 occurrence of hydroxyl, $C_{1-6}$ alkoxyl, $C_{1-6}$ haloalkoxyl, —O—($C_{3-5}$ cycloalkyl), oxo, —C(O)OR$^3$, or —C(O)N($R^4$)$_2$;

b. —C(O)OR$^3$, —C(O)N($R^4$)$_2$, or —C(O)—($C_{0-4}$ alkylene)-($C_{3-7}$ cycloalkyl);

c. —($C_{0-2}$ alkylene)-(5-6 membered monocyclic heteroaryl having 1, 2, or 3 heteroatoms independently selected from nitrogen, oxygen, and sulfur), wherein said heteroaryl is substituted with m occurrences of $R^5$; and d. hydrogen;

$R^{1A}$ and $R^{2A}$ each represents independently for each occurrence halo, $C_{1-6}$ alkyl, $C_{1-6}$ haloalkyl, $C_{1-6}$ alkoxyl, or hydroxyl;

$R^2$ is phenyl; a 5-6 membered monocyclic heteroaryl having 1, 2, or 3 heteroatoms independently selected from nitrogen, oxygen, and sulfur; an 8-10 membered bicyclic heteroaryl having 1, 2, or 3 heteroatoms independently selected from nitrogen, oxygen, and sulfur; or $C_{3-7}$ cycloalkyl; each of which is substituted with (i) one —OR$^7$, and (ii) n occurrences of $R^6$;

$R^3$ represents independently for each occurrence $C_{1-6}$ alkyl or hydrogen;

$R^4$ represents independently for each occurrence $C_{1-6}$ alkyl or hydrogen, or two occurrences of $R^4$ attached to the same nitrogen atom are taken together with said nitrogen atom to form a 4-7 membered saturated ring having one nitrogen atom;

$R^5$ and $R^6$ each represents independently for each occurrence halo, $C_{1-4}$ alkyl, $C_{1-4}$ haloalkyl, $C_{1-4}$ hydroxyalkyl, $C_{3-7}$ cycloalkyl, $C_{1-4}$ alkoxyl, $C_{1-4}$ haloalkoxyl, hydroxyl, or cyano;

$R^7$ is —P(O)(OR$^8$)$_2$, —CH$_2$—P(O)(OR$^8$)$_2$, —C(O)R$^8$, —C(O)OR$^8$, —C(R$^3$)$_2$—OR$^8$, —C(R$^3$)$_2$—OC(O)R$^8$, —C(R$^3$)$_2$—OC(O)OR$^8$, —C(R$^3$)$_2$—OC(O)N(R$^4$)(R$^{11}$), —C(O)—C(H)(R$^9$)—N(R$^4$)$_2$, —C(O)—C(H)(R$^9$)—N(H)C(O)R$^3$, —C(O)N(R$^4$)—C(H)(R$^9$)—C(O)OH, or —C(O)N(R$^4$)—C(H)(R$^9$)—C(O)O($C_{1-20}$ aliphatic chain);

$R^8$ represents independently for each occurrence hydrogen, a $C_{1-20}$ aliphatic chain, $C_{3-7}$ cycloalkyl, phenyl, —CH$_2$-phenyl, or a 5-6 membered monocyclic heteroaryl having 1, 2, or 3 heteroatoms independently selected from nitrogen, oxygen, and sulfur; wherein said phenyl and heteroaryl is each substituted with r occurrences of $R^{10}$;

$R^9$ is hydrogen, $C_{1-6}$ alkyl, or —CH$_2$-phenyl;

$R^{10}$ represents independently for each occurrence halo, $C_{1-4}$ alkyl, $C_{1-4}$ haloalkyl, or $C_{1-4}$ alkoxyl;

$R^{11}$ is $C_{1-6}$ alkyl, phenyl, —CH$_2$-phenyl, or hydrogen; or $R^{11}$ and $R^4$ are taken together with the nitrogen atom to which they are attached to form a 4-7 membered saturated ring having one nitrogen atom and optionally one additional heteroatom selected from nitrogen, oxygen, and sulfur;

m and n are each independently 0, 1, 2, or 3; and p, q, and r are each independently 0, 1, or 2.

The definitions of variables in Formula I above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

In certain embodiments, the compound is a compound of Formula I.

As defined generally above, $R^1$ is selected from the group consisting of:

a. $C_{1-6}$ alkyl substituted with (i) 0, 1, 2, or 3 halo, and (ii) 0 or 1 occurrence of hydroxyl, $C_{1-6}$ alkoxyl, $C_{1-6}$ haloalkoxyl, —O—($C_{3-5}$ cycloalkyl), oxo, —C(O)OR$^3$, or —C(O)N($R^4$)$_2$;

b. —C(O)OR$^3$, —C(O)N($R^4$)$_2$, or —C(O)—($C_{0-4}$ alkylene)-($C_{3-7}$ cycloalkyl);

c. —($C_{0-2}$ alkylene)-(5-6 membered monocyclic heteroaryl having 1, 2, or 3 heteroatoms independently selected from nitrogen, oxygen, and sulfur), wherein said heteroaryl is substituted with m occurrences of $R^5$; and d. hydrogen.

In certain embodiments, $R^1$ is $C_{1-6}$ alkyl substituted with (i) 0, 1, 2, or 3 halo, and (ii) 0 or 1 occurrence of hydroxyl, $C_{1-6}$ alkoxyl, $C_{1-6}$ haloalkoxyl, —O—($C_{3-5}$ cycloalkyl), oxo, —C(O)OR$^3$, or —C(O)N($R^4$)$_2$. In certain embodiments, $R^1$ is $C_{1-6}$ alkyl substituted with (i) 1, 2, or 3 halo, and (ii) 0 or 1 occurrence of hydroxyl. In certain embodiments, $R^1$ is $C_{1-6}$ alkyl substituted with (i) 0, 1, 2, or 3 halo, and (ii) 1 occurrence of hydroxyl. In certain embodiments, $R^1$ is

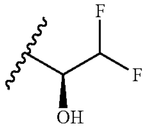

or

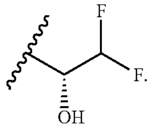

In certain embodiments, $R^1$ is —$CH_2CHF_2$.

In certain embodiments, $R^1$ is —C(O)$OR^3$, —C(O)$N(R^4)_2$, or —C(O)—($C_{0-4}$ alkylene)-($C_{3-7}$ cycloalkyl). In certain embodiments, $R^1$ is —C(O)$OR^3$. In certain embodiments, $R^1$ is —C(O)$N(R^4)_2$. In certain embodiments, $R^1$ is —C(O)—($C_{0-4}$ alkylene)-($C_{3-7}$ cycloalkyl). In certain embodiments, $R^1$ is —C(O)—($C_{1-4}$ alkylene)-($C_{3-7}$ cycloalkyl). In certain embodiments, $R^1$ is —C(O)—($C_{3-7}$ cycloalkyl).

In certain embodiments, $R^1$ is —($C_{0-2}$ alkylene)-(5-6 membered monocyclic heteroaryl having 1, 2, or 3 heteroatoms independently selected from nitrogen, oxygen, and sulfur), wherein said heteroaryl is substituted with m occurrences of $R^5$. In certain embodiments, $R^1$ is a 5-6 membered monocyclic heteroaryl having 1, 2, or 3 heteroatoms independently selected from nitrogen, oxygen, and sulfur, wherein said heteroaryl is substituted with m occurrences of $R^5$. In certain embodiments, $R^1$ is a 5-membered monocyclic heteroaryl having 1, 2, or 3 heteroatoms independently selected from nitrogen, oxygen, and sulfur, wherein said heteroaryl is substituted with m occurrences of $R^5$. In certain embodiments, $R^1$ is a 6-membered monocyclic heteroaryl having 1 or 2 nitrogen atoms, wherein said heteroaryl is substituted with m occurrences of $R^5$. In certain embodiments, $R^1$ is pyridinyl substituted with m occurrences of $R^5$. In certain embodiments, $R^1$ is pyridin-2-yl substituted with m occurrences of $R^5$. In certain embodiments, $R^1$ is

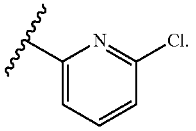 [SMILES: *c1cccc(Cl)n1]

In certain embodiments, $R^1$ is —($C_{1-2}$ alkylene)-(5-6 membered monocyclic heteroaryl having 1, 2, or 3 heteroatoms independently selected from nitrogen, oxygen, and sulfur), wherein said heteroaryl is substituted with m occurrences of $R^5$. In certain embodiments, $R^1$ is —($C_{1-2}$ alkylene)-(5-membered monocyclic heteroaryl having 1, 2, or 3 heteroatoms independently selected from nitrogen, oxygen, and sulfur), wherein said heteroaryl is substituted with m occurrences of $R^5$. In certain embodiments, $R^1$ is —($C_{1-2}$ alkylene)-(6-membered monocyclic heteroaryl having 1 or 2 nitrogen atoms), wherein said heteroaryl is substituted with m occurrences of $R^5$.

In certain embodiments, $R^1$ is hydrogen. In certain embodiments, $R^1$ is selected from the groups depicted in the compounds in Tables 1, 2, and 3, below.

As defined generally above, $R^{1A}$ represents independently for each occurrence halo, $C_{1-6}$ alkyl, $C_{1-6}$ haloalkyl, $C_{1-6}$ alkoxyl, or hydroxyl. In certain embodiments, $R^{1A}$ represents independently for each occurrence halo, $C_{1-6}$ alkyl, or $C_{1-6}$ haloalkyl. In certain embodiments, $R^{1A}$ represents independently for each occurrence $C_{1-6}$ alkyl or $C_{1-6}$ haloalkyl. In certain embodiments, $R^{1A}$ represents independently for each occurrence $C_{1-6}$ alkoxyl or hydroxyl.

In certain embodiments, $R^{1A}$ represents independently for each occurrence halo. In certain embodiments, $R^{1A}$ represents independently for each occurrence fluoro or chloro. In certain embodiments, $R^{1A}$ represents independently for each occurrence $C_{1-6}$ alkyl. In certain embodiments, $R^{1A}$ is methyl. In certain embodiments, $R^{1A}$ represents independently for each occurrence $C_{1-6}$ haloalkyl. In certain embodiments, $R^{1A}$ is trifluoromethyl. In certain embodiments, $R^{1A}$ represents independently for each occurrence $C_{1-6}$ alkoxyl. In certain embodiments, $R^{1A}$ is methoxy. In certain embodiments, $R^{1A}$ is hydroxyl. In certain embodiments, $R^{1A}$ is selected from the groups depicted in the compounds in Tables 1, 2, and 3, below.

As defined generally above, $R^2$ is phenyl; a 5-6 membered monocyclic heteroaryl having 1, 2, or 3 heteroatoms independently selected from nitrogen, oxygen, and sulfur; an 8-10 membered bicyclic heteroaryl having 1, 2, or 3 heteroatoms independently selected from nitrogen, oxygen, and sulfur; or $C_{3-7}$ cycloalkyl; each of which is substituted with (i) one —$OR^7$, and (ii) n occurrences of $R^6$.

In certain embodiments, $R^2$ is phenyl substituted with (i) one —$OR^7$, and (ii) n occurrences of $R^6$. In certain embodiments, $R^2$ is

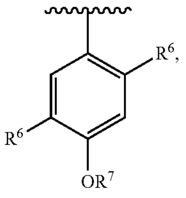

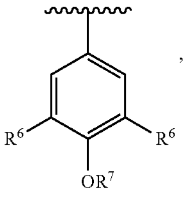

, or

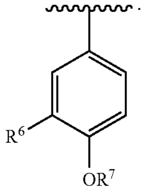

In certain embodiments, $R^2$ is

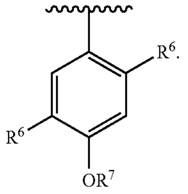

In certain embodiments, $R^2$ is

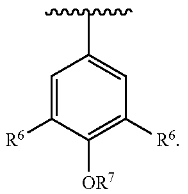

In certain embodiments, $R^2$ is

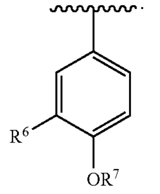

In certain embodiments, $R^2$ is

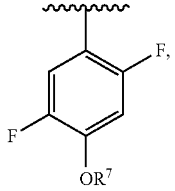

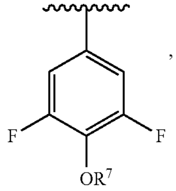

, or

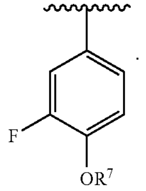

.

In certain embodiments, $R^2$ is

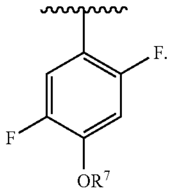

In certain embodiments, $R^2$ is

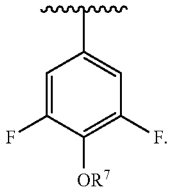

In certain embodiments, $R^2$ is

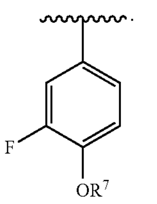

In certain embodiments, $R^2$ is a 5-6 membered monocyclic heteroaryl having 1, 2, or 3 heteroatoms independently selected from nitrogen, oxygen, and sulfur; wherein said heteroaryl is substituted with (i) one —$OR^7$, and (ii) n occurrences of $R^6$. In certain embodiments, $R^2$ is a 5-membered monocyclic heteroaryl having 1, 2, or 3 heteroatoms independently selected from nitrogen, oxygen, and sulfur; wherein said heteroaryl is substituted with (i) one —$OR^7$, and (ii) n occurrences of $R^6$. In certain embodiments, $R^2$ is a 6-membered monocyclic heteroaryl having 1 or 2 nitrogen atoms; wherein said heteroaryl is substituted with (i) one —$OR^7$, and (ii) n occurrences of $R^6$. In certain embodiments, $R^2$ is pyridinyl substituted with (i) one —$OR^7$, and (ii) n occurrences of $R^6$. In certain embodiments, $R^2$ is pyridin-2-yl substituted with (i) one —$OR^7$, and (ii) n occurrences of $R^6$. In certain embodiments, $R^2$ is

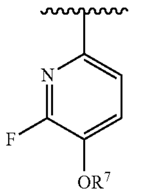

or

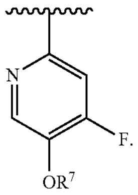

In certain embodiments, $R^2$ is an 8-10 membered bicyclic heteroaryl having 1, 2, or 3 heteroatoms independently selected from nitrogen, oxygen, and sulfur; wherein said heteroaryl is substituted with (i) one —$OR^7$, and (ii) n occurrences of $R^6$. In certain embodiments, $R^2$ is a 9-membered bicyclic heteroaryl having 1, 2, or 3 heteroatoms independently selected from nitrogen, oxygen, and sulfur; wherein said heteroaryl is substituted with (i) one —$OR^7$, and (ii) n occurrences of $R^6$. In certain embodiments, $R^2$ is an 8-10 membered bicyclic heteroaryl having 1 or 2 nitrogen atoms; wherein said heteroaryl is substituted with (i) one —$OR^7$, and (ii) n occurrences of $R^6$. In certain embodiments, $R^2$ is a 9-membered bicyclic heteroaryl having 1 or 2 nitrogen atoms; wherein said heteroaryl is substituted with (i) one —$OR^7$, and (ii) n occurrences of $R^6$. In certain embodiments, $R^2$ is indazolyl substituted with (i) one —$OR^7$, and (ii) n occurrences of $R^6$. In certain embodiments, $R^2$ is indazol-5-yl substituted with (i) one —$OR^7$, and (ii) n occurrences of $R^6$.

In certain embodiments, $R^2$ is $C_{3-7}$ cycloalkyl substituted with (i) one —$OR^7$, and (ii) n occurrences of $R^6$. In certain embodiments, $R^2$ is $C_{3-5}$ cycloalkyl substituted with (i) one —$OR^7$, and (ii) n occurrences of $R^6$. In certain embodiments, $R^2$ is cyclopropyl substituted with (i) one —$OR^7$, and (ii) n occurrences of $R^6$.

In certain embodiments, $R^2$ is selected from the groups depicted in the compounds in Tables 1, 2, and 3, below.

As defined generally above, $R^{2A}$ represents independently for each occurrence halo, $C_{1-6}$ alkyl, $C_{1-6}$ haloalkyl, $C_{1-6}$ alkoxyl, or hydroxyl. In certain embodiments, $R^{2A}$ represents independently for each occurrence halo, $C_{1-6}$ alkyl, or $C_{1-6}$ haloalkyl. In certain embodiments, $R^{2A}$ represents independently for each occurrence $C_{1-6}$ alkyl or $C_{1-6}$ haloalkyl. In certain embodiments, $R^{2A}$ represents independently for each occurrence $C_{1-6}$ alkoxyl or hydroxyl.

In certain embodiments, $R^{2A}$ represents independently for each occurrence halo. In certain embodiments, $R^{2A}$ represents independently for each occurrence fluoro or chloro. In certain embodiments, $R^{2A}$ represents independently for each occurrence $C_{1-6}$ alkyl. In certain embodiments, $R^{2A}$ is methyl. In certain embodiments, $R^{2A}$ represents independently for each occurrence $C_{1-6}$ haloalkyl. In certain embodiments, $R^{2A}$ is trifluoromethyl. In certain embodiments, $R^{2A}$ represents independently for each occurrence $C_{1-6}$ alkoxyl. In certain embodiments, $R^{2A}$ is methoxy. In certain embodiments, $R^{2A}$ is hydroxyl. In certain embodiments, $R^{2A}$ is selected from the groups depicted in the compounds in Tables 1, 2, and 3, below.

As defined generally above, $R^3$ represents independently for each occurrence $C_{1-6}$ alkyl or hydrogen. In certain embodiments, $R^3$ represents independently for each occurrence $C_{1-6}$ alkyl. In certain embodiments, $R^3$ represents independently for each occurrence $C_{1-4}$ alkyl. In certain embodiments, $R^3$ is methyl. In certain embodiments, $R^3$ is hydrogen. In certain embodiments, $R^3$ is selected from the groups depicted in the compounds in Tables 1, 2, and 3, below.

As defined generally above, $R^4$ represents independently for each occurrence $C_{1-6}$ alkyl or hydrogen, or two occurrences of $R^4$ attached to the same nitrogen atom are taken together with said nitrogen atom to form a 4-7 membered saturated ring having one nitrogen atom.

In certain embodiments, $R^4$ represents independently for each occurrence $C_{1-6}$ alkyl or hydrogen. In certain embodiments, $R^4$ represents independently for each occurrence $C_{1-4}$ alkyl or hydrogen. In certain embodiments, $R^4$ represents independently for each occurrence methyl or hydrogen. In certain embodiments, $R^4$ represents independently for each occurrence $C_{1-6}$ alkyl. In certain embodiments, $R^4$ represents independently for each occurrence $C_{1-4}$ alkyl. In certain embodiments, $R^4$ is methyl. In certain embodiments, $R^4$ is hydrogen.

In certain embodiments, two occurrences of $R^4$ attached to the same nitrogen atom are taken together with said nitrogen atom to form a 4-7 membered saturated ring having one nitrogen atom. In certain embodiments, two occurrences of $R^4$ attached to the same nitrogen atom are taken together with said nitrogen atom to form a 5-6 membered saturated ring having one nitrogen atom.

In certain embodiments, $R^4$ is selected from the groups depicted in the compounds in Tables 1, 2, and 3, below.

As defined generally above, $R^5$ represents independently for each occurrence halo, $C_{1-4}$ alkyl, $C_{1-4}$ haloalkyl, $C_{1-4}$ hydroxyalkyl, $C_{3-7}$ cycloalkyl, $C_{1-4}$ alkoxyl, $C_{1-4}$ haloalkoxyl, hydroxyl, or cyano.

In certain embodiments, $R^5$ represents independently for each occurrence halo, $C_{1-4}$ alkyl, $C_{1-4}$ haloalkyl, or $C_{1-4}$ alkoxyl. In certain embodiments, $R^5$ represents independently for each occurrence fluoro, chloro, methyl, trifluoromethyl, or methoxy. In certain embodiments, $R^5$ represents independently for each occurrence halo, $C_{1-4}$ alkyl, $C_{1-4}$ haloalkyl, $C_{1-4}$ hydroxyalkyl, or $C_{3-7}$ cycloalkyl. In certain embodiments, $R^5$ represents independently for each occurrence Cia alkyl, $C_{1-4}$ haloalkyl, $C_{1-4}$ hydroxyalkyl, or $C_{3-7}$ cycloalkyl. In certain embodiments, $R^5$ represents independently for each occurrence halo, $C_{1-4}$ alkoxyl, $C_{1-4}$ haloalkoxyl, hydroxyl, or cyano. In certain embodiments, $R^5$ represents independently for each occurrence $C_{1-4}$ alkoxyl, $C_{1-4}$ haloalkoxyl, or hydroxyl.

In certain embodiments, $R^5$ represents independently for each occurrence halo. In certain embodiments, $R^5$ represents independently for each occurrence fluoro or chloro. In certain embodiments, $R^5$ represents independently for each occurrence $C_{1-4}$ alkyl. In certain embodiments, $R^5$ is methyl. In certain embodiments, $R^5$ represents independently for each occurrence $C_{1-4}$ haloalkyl. In certain embodiments, $R^5$ is trifluoromethyl. In certain embodiments, $R^5$ represents independently for each occurrence $C_{1-4}$ hydroxyalkyl. In certain embodiments, $R^5$ represents independently for each occurrence $C_{3-7}$ cycloalkyl. In certain embodiments, $R^5$ represents independently for each occurrence $C_{1-4}$ alkoxyl. In certain embodiments, $R^5$ is methoxy. In certain embodiments, $R^5$ represents independently for each occurrence $C_{1-4}$ haloalkoxyl. In certain embodiments, $R^5$ is hydroxyl. In certain embodiments, $R^5$ is cyano.

In certain embodiments, $R^5$ is selected from the groups depicted in the compounds in Tables 1, 2, and 3, below.

As defined generally above, $R^6$ represents independently for each occurrence halo, $C_{1-4}$ alkyl, $C_{1-4}$ haloalkyl, $C_{1-4}$ hydroxyalkyl, $C_{3-7}$ cycloalkyl, $C_{1-4}$ alkoxyl, $C_{1-4}$ haloalkoxyl, hydroxyl, or cyano.

In certain embodiments, $R^6$ represents independently for each occurrence halo, $C_{1-4}$ alkyl, $C_{1-4}$ haloalkyl, or $C_{1-4}$ alkoxyl. In certain embodiments, $R^6$ represents independently for each occurrence fluoro, chloro, methyl, trifluoromethyl, or methoxy. In certain embodiments, $R^6$ represents independently for each occurrence halo, $C_{1-4}$ alkyl, $C_{1-4}$ haloalkyl, $C_{1-4}$ hydroxyalkyl, or $C_{3-7}$ cycloalkyl. In certain embodiments, $R^6$ represents independently for each occurrence $C_{1-4}$ alkyl, $C_{1-4}$ haloalkyl, $C_{1-4}$ hydroxyalkyl, or $C_{3-7}$ cycloalkyl. In certain embodiments, $R^6$ represents independently for each occurrence halo, $C_{1-4}$ alkoxyl, $C_{1-4}$ haloalkoxyl, hydroxyl, or cyano. In certain embodiments, $R^6$ represents independently for each occurrence $C_{1-4}$ alkoxyl, $C_{1-4}$ haloalkoxyl, or hydroxyl.

In certain embodiments, $R^6$ represents independently for each occurrence halo. In certain embodiments, $R^6$ represents independently for each occurrence fluoro or chloro. In certain embodiments, $R^6$ represents independently for each occurrence $C_{1-4}$ alkyl. In certain embodiments, $R^6$ is methyl. In certain embodiments, $R^6$ represents independently for each occurrence $C_{1-4}$ haloalkyl. In certain embodiments, $R^6$ is trifluoromethyl. In certain embodiments, $R^6$ represents independently for each occurrence $C_{1-4}$ hydroxyalkyl. In certain embodiments, $R^6$ represents independently for each occurrence $C_{3-7}$ cycloalkyl. In certain embodiments, $R^6$ represents independently for each occurrence $C_{1-4}$ alkoxyl. In certain embodiments, $R^6$ is methoxy. In certain embodiments, $R^6$ represents independently for each occurrence $C_{1-4}$ haloalkoxyl. In certain embodiments, $R^6$ is hydroxyl. In certain embodiments, $R^6$ is cyano.

In certain embodiments, $R^6$ is selected from the groups depicted in the compounds in Tables 1, 2, and 3, below.

As defined generally above, $R^7$ is $—P(O)(OR^8)_2$, $—CH_2—P(O)(OR^8)_2$, $—C(O)R^8$, $—C(O)OR^8$, $—C(R^3)_2—OR^8$, $—C(R^3)_2—OC(O)R^8$, $—C(R^3)_2—OC(O)OR^8$, $—C(R^3)_2—OC(O)N(R^4)(R^11)$, $—C(O)—C(H)(R^9)—N(R^4)_2$, $—C(O)—C(H)(R^9)—N(H)C(O)R^3$, $—C(O)N(R^4)—C(H)(R^9)—C(O)OH$, or $—C(O)N(R^4)—C(H)(R^9)—C(O)O(C_{1-20}$ aliphatic chain).

In certain embodiments, $R^7$ is $—P(O)(OR^8)_2$ or $—CH_2—P(O)(OR^8)_2$. In certain embodiments, $R^7$ is $—C(O)R^8$, $—C(O)OR^8$, or $—C(R^3)_2—OC(O)OR^8$. In certain embodiments, $R^7$ is $—C(O)R^8$ or $—C(O)OR^8$. In certain embodiments, $R^7$ is $—C(R^3)_2—OC(O)R^8$, $—C(R^3)_2—OC(O)OR^8$, or $—C(R^3)_2—OC(O)N(R^4)(R^{11})$. In certain embodiments, $R^7$ is $—C(R^3)_2—OR^8$, $—C(R^3)_2—OC(O)R^8$, $—C(R^3)_2—OC(O)OR^8$, or $—C(R^3)_2—OC(O)N(R^4)(R^{11})$. In certain embodiments, $R^7$ is $—C(R^3)_2—OC(O)R^8$ or $—C(R^3)_2—OC(O)OR^8$. In certain embodiments, $R^7$ is $—C(R^3)_2—OC(O)OR^8$ or $—C(R^3)_2—OC(O)N(R^4)(R^{11})$. In certain embodiments, $R^7$ is $—C(O)—C(H)(R^9)—N(R^4)_2$ or $—C(O)—C(H)(R^9)—N(H)C(O)R^3$. In certain embodiments, $R^7$ is $—C(O)N(R^4)—C(H)(R^9)—C(O)OH$ or $—C(O)N(R^4)—C(H)(R^9)—C(O)O(C_{1-20}$ aliphatic chain).

In certain embodiments, $R^7$ is $—P(O)(OR^8)_2$. In certain embodiments, $R^7$ is $—CH_2—P(O)(OR^8)_2$. In certain embodiments, $R^7$ is $—C(O)R^8$. In certain embodiments, $R^7$ is $—C(O)OR^8$. In certain embodiment, $R^7$ is $—C(R^3)_2—OR^8$. In certain embodiment, $R^7$ is $—CH_2—OR^8$. In certain embodiment, $R^7$ is $—C(H)(CH_3)—OR^8$. In certain embodiments, $R^7$ is $—C(R^3)_2—OC(O)R^8$. In certain embodiments, $R^7$ is $—CH_2—OC(O)R^8$. In certain embodiments, $R^7$ is $—C(H)(CH_3)—OC(O)R^8$. In certain embodiments, $R^7$ is —$C(R^3)_2$—OC(O)$OR^8$. In certain embodiments, $R^7$ is —$CH_2$—OC(O)$OR^8$. In certain embodiments, $R^7$ is —C(H)($CH_3$)—OC(O)$OR^8$. In certain embodiments, $R^7$ is —$C(R^3)_2$—OC(O)N($R^4$)($R^{11}$). In certain embodiments, $R^7$ is —$CH_2$—OC(O)N($R^4$)($R^{11}$). In certain embodiments, $R^7$ is —C(H)($CH_3$)—OC(O)N($R^4$)($R^{11}$). In certain embodiments, $R^7$ is —C(O)—C(H)($R^9$)—N$(R^4)_2$. In certain embodiments, $R^7$ is —C(O)—C(H)($R^9$)—$NH_2$. In certain embodiments, $R^7$ is —C(O)—C(H)($R^9$)—N(H)C(O)$R^3$. In certain embodiments, $R^7$ is —C(O)—C(H)($R^9$)—N(H)C(O)$CH_3$. In certain embodiments, $R^7$ is —C(O)N($R^4$)—C(H)($R^9$)—C(O)OH. In certain embodiments, $R^7$ is —C(O)N(H)—C(H)($R^9$)—C(O)OH. In certain embodiments, $R^7$ is —C(O)N($R^4$)—C(H)($R^9$)—C(O)O($C_{1-20}$ aliphatic chain). In certain embodiments, $R^7$ is —C(O)N(H)—C(H)($R^9$)—C(O)O($C_{1-20}$ aliphatic chain). In certain embodiments, $R^7$ is —C(O)N(H)—C(H)($R^9$)—C(O)O($C_{1-6}$ aliphatic chain). In certain embodiments, $R^7$ is —C(O)N(H)—C(H)($R^9$)—C(O)O($C_{7-20}$ aliphatic chain). In certain embodiments, $R^7$ is —C(O)N(H)—C(H)($R^9$)—C(O)O($C_{1-20}$ alkyl). In certain embodiments, $R^7$ is —C(O)N(H)—C(H)($R^9$)—C(O)O($C_{1-6}$ alkyl). In certain embodiments, $R^7$ is —C(O)N(H)—C(H)($R^9$)—C(O)O($C_{7-20}$ alkyl). In certain embodiments, $R^7$ is selected from the groups depicted in the compounds in Tables 1, 2, and 3, below.

As defined generally above, $R^8$ represents independently for each occurrence hydrogen, a $C_{1-20}$ aliphatic chain, $C_{3-7}$ cycloalkyl, phenyl, —$CH_2$-phenyl, or a 5-6 membered monocyclic heteroaryl having 1, 2, or 3 heteroatoms independently selected from nitrogen, oxygen, and sulfur; wherein said phenyl and heteroaryl is each substituted with r occurrences of $R^{10}$.

In some embodiments, $R^8$ represents independently for each occurrence hydrogen, a $C_{1-20}$ aliphatic chain, or $C_{3-7}$ cycloalkyl. In some embodiments, $R^8$ represents independently for each occurrence hydrogen or a $C_{1-20}$ aliphatic chain. In some embodiments, $R^8$ represents independently for each occurrence hydrogen or $C_{1-20}$ alkyl. In some embodiments, $R^8$ represents independently for each occurrence hydrogen or $C_{1-6}$ alkyl. In some embodiments, $R^8$ represents independently for each occurrence hydrogen or $C_{7-20}$ alkyl.

In some embodiments, $R^8$ represents independently for each occurrence phenyl, —$CH_2$— phenyl, or a 5-6 membered monocyclic heteroaryl having 1, 2, or 3 heteroatoms independently selected from nitrogen, oxygen, and sulfur; wherein said phenyl and heteroaryl is each substituted with r occurrences of $R^{10}$. In some embodiments, $R^8$ represents independently for each occurrence phenyl or —$CH_2$-phenyl; wherein each phenyl is substituted with r occurrences of $R^{10}$.

In some embodiments, $R^8$ represents independently for each occurrence a $C_{1-20}$ aliphatic chain, $C_{3-7}$ cycloalkyl, phenyl, or —$CH_2$-phenyl; wherein each phenyl is substituted with r occurrences of $R^{10}$. In some embodiments, $R^8$ represents independently for each occurrence a $C_{1-20}$ aliphatic chain, $C_{3-7}$ cycloalkyl, phenyl, or —$CH_2$-phenyl. In some embodiments, $R^8$ represents independently for each occurrence $C_{1-20}$ alkyl, $C_{3-7}$ cycloalkyl, phenyl, or —$CH_2$-phenyl. In some embodiments, $R^8$ independently for each occurrence $C_{3-7}$ cycloalkyl or phenyl.

In some embodiments, $R^8$ is hydrogen. In some embodiments, $R^8$ represents independently for each occurrence a $C_{1-20}$ aliphatic chain. In some embodiments, $R^8$ represents independently for each occurrence a $C_{1-10}$ aliphatic chain. In some embodiments, $R^8$ represents independently for each occurrence a $C_{1-6}$ aliphatic chain. In some embodiments, $R^8$ represents independently for each occurrence a $C_{7-20}$ aliphatic chain. In some embodiments, $R^8$ represents independently for each occurrence $C_{1-20}$ alkyl. In some embodiments, $R^8$ represents independently for each occurrence $C_{1-10}$ alkyl. In some embodiments, $R^8$ represents independently for each occurrence $C_{1-6}$ alkyl. In some embodiments, $R^8$ represents independently for each occurrence $C_{7-20}$ alkyl.

In some embodiments, $R^8$ represents independently for each occurrence phenyl substituted with r occurrences of $R^{10}$. In some embodiments, $R^8$ is phenyl. In some embodiments, $R^8$ represents independently for each occurrence —$CH_2$-phenyl substituted with r occurrences of $R^{10}$. In some embodiments, $R^8$ is —$CH_2$-phenyl.

In some embodiments, $R^8$ represents independently for each occurrence a 5-6 membered monocyclic heteroaryl having 1, 2, or 3 heteroatoms independently selected from nitrogen, oxygen, and sulfur; wherein said heteroaryl is substituted with r occurrences of $R^{10}$. In some embodiments, $R^8$ represents independently for each occurrence a 5-6 membered monocyclic heteroaryl having 1, 2, or 3 heteroatoms independently selected from nitrogen, oxygen, and sulfur.

In some embodiments, $R^8$ represents independently for each occurrence a 5-membered monocyclic heteroaryl having 1, 2, or 3 heteroatoms independently selected from nitrogen, oxygen, and sulfur. In some embodiments, $R^8$ represents independently for each occurrence a 5-membered monocyclic heteroaryl having 1, 2, or 3 nitrogen atoms. In some embodiments, $R^8$ represents independently for each occurrence a 5-membered monocyclic heteroaryl having 2 heteroatoms independently selected from nitrogen and oxygen. In some embodiments, $R^8$ represents independently for each occurrence a 5-membered monocyclic heteroaryl having 2 heteroatoms independently selected from nitrogen and sulfur. In some embodiments, $R^8$ represents independently for each occurrence a 5-membered monocyclic heteroaryl having one oxygen or sulfur atom. In some embodiments, $R^8$ represents independently for each occurrence a 5-membered monocyclic heteroaryl having 1, 2, or 3 heteroatoms independently selected from nitrogen and sulfur.

In some embodiments, $R^8$ represents independently for each occurrence a 6-membered monocyclic heteroaryl having 1, 2, or 3 heteroatoms independently selected from nitrogen, oxygen, and sulfur. In some embodiments, $R^8$ represents independently for each occurrence a 6-membered monocyclic heteroaryl having 1, 2, or 3 nitrogen atoms. In some embodiments, $R^8$ represents independently for each occurrence a 6-membered monocyclic heteroaryl having 1 or 2 nitrogen atoms.

In certain embodiments, $R^8$ is selected from the groups depicted in the compounds in Tables 1, 2, and 3, below.

As defined generally above, $R^9$ is hydrogen, $C_{1-6}$ alkyl, or —$CH_2$-phenyl. In some embodiments, $R^9$ is hydrogen. In some embodiments, $R^9$ is $C_{1-6}$ alkyl. In some embodiments, $R^9$ is methyl or ethyl. In some embodiments, $R^9$ is methyl. In some embodiments, $R^9$ is ethyl. In some embodiments, $R^9$ is —$CH_2$-phenyl. In certain embodiments, $R^9$ is selected from the groups depicted in the compounds in Tables 1, 2, and 3, below.

As defined generally above, $R^{10}$ represents independently for each occurrence halo, $C_{1-4}$ alkyl, $C_{1-4}$ haloalkyl, or $C_{1-4}$ alkoxyl. In certain embodiments, $R^{10}$ represents independently for each occurrence fluoro, chloro, methyl, trifluoromethyl, or methoxy. In certain embodiments, $R^{10}$ represents independently for each occurrence $C_{1-4}$ alkyl or $C_{1-4}$ haloalkyl. In certain embodiments, $R^{10}$ represents independently for each occurrence halo or $C_{1-4}$ alkoxyl.

In certain embodiments, $R^{10}$ represents independently for each occurrence halo. In certain embodiments, $R^{10}$ represents independently for each occurrence fluoro or chloro. In certain embodiments, $R^{10}$ represents independently for each occurrence $C_{1-4}$ alkyl. In certain embodiments, $R^{10}$ is methyl. In certain embodiments, $R^{10}$ represents independently for each occurrence $C_{1-4}$ haloalkyl. In certain embodiments, $R^{10}$ is trifluoromethyl. In certain embodiments, $R^{10}$ is $C_{1-4}$ alkoxyl. In certain embodiments, $R^{10}$ is methoxy.

In certain embodiments, $R^{10}$ represents independently for each occurrence methyl or ethyl. In certain embodiments, $R^{10}$ represents independently for each occurrence n-propyl or isopropyl. In certain embodiments, $R^{10}$ represents independently for each occurrence methyl or halomethyl. In certain embodiments, $R^{10}$ represents independently for each occurrence methoxy or ethoxy. In certain embodiments, $R^{10}$ is fluoromethyl or fluoroethyl. In certain embodiments, $R^{10}$ is 2-fluoroethyl. In certain embodiments, $R^{10}$ is selected from the groups depicted in the compounds in Tables 1, 2, and 3, below.

As defined generally above, $R^{11}$ is $C_{1-6}$ alkyl, phenyl, —$CH_2$-phenyl, or hydrogen; or $R^{11}$ and $R^4$ are taken together with the nitrogen atom to which they are attached to form a 4-7 membered saturated ring having one nitrogen atom and optionally one additional heteroatom selected from nitrogen, oxygen, and sulfur.

In certain embodiments, $R^{11}$ is $C_{1-6}$ alkyl, phenyl, —$CH_2$-phenyl, or hydrogen. In certain embodiments, $R^{11}$ is hydrogen. In certain embodiments, $R^{11}$ is $C_{1-6}$ alkyl. In certain embodiments, $R^{11}$ is methyl. In certain embodiments, $R^{11}$ is ethyl. In certain embodiments, $R^{11}$ is phenyl. In certain embodiments, $R^{11}$ is —$CH_2$-phenyl.

In certain embodiments, $R^{11}$ and $R^4$ are taken together with the nitrogen atom to which they are attached to form a 4-7 membered saturated ring having one nitrogen atom and optionally one additional heteroatom selected from nitrogen, oxygen, and sulfur. In certain embodiments, $R^{11}$ and $R^4$ are taken together with the nitrogen atom to which they are attached to form a 5-membered saturated ring having one nitrogen atom and optionally one additional heteroatom selected from nitrogen, oxygen, and sulfur. In certain embodiments, $R^{11}$ and $R^4$ are taken together with the nitrogen atom to which they are attached to form a 6-membered saturated ring having one nitrogen atom and optionally one additional heteroatom selected from nitrogen, oxygen, and sulfur. In certain embodiments, $R^{11}$ and $R^4$ are taken together with the nitrogen atom to which they are attached to form a 7-membered saturated ring having one nitrogen atom and optionally one additional heteroatom selected from nitrogen, oxygen, and sulfur.

In certain embodiments, $R^{11}$ and $R^4$ are taken together with the nitrogen atom to which they are attached to form a 5- or 6-membered saturated ring having one nitrogen atom. In certain embodiments, $R^{11}$ and $R^4$ are taken together with the nitrogen atom to which they are attached to form a 5- or 6-membered saturated ring having one nitrogen atom and optionally one additional nitrogen heteroatom. In certain embodiments, $R^{11}$ and $R^4$ are taken together with the nitrogen atom to which they are attached to form a 5- or 6-membered saturated ring having one nitrogen atom and optionally one additional oxygen heteroatom. In certain embodiments, $R^{11}$ and $R^4$ are taken together with the nitrogen atom to which they are attached to form a 5- or 6-membered saturated ring having one nitrogen atom and optionally one additional sulfur heteroatom. In certain embodiments, $R^{11}$ and $R^4$ are taken together with the nitrogen atom to which they are attached to form a morpholine or piperazine ring.

In certain embodiments, $R^{11}$ is selected from the groups depicted in the compounds in Tables 1, 2, and 3, below.

As defined generally above, m is 0, 1, 2, or 3. In certain embodiments, m is 0. In certain embodiments, m is 1. In certain embodiments, m is 2. In certain embodiments, m is 3. In certain embodiments, m is 0 or 1. In certain embodiments, m is 1 or 2. In certain embodiments, m is 2 or 3. In certain embodiments, m is 0, 1, or 2. In certain embodiments, m is 1, 2, or 3. In certain embodiments, m is selected from the values represented in the compounds in Tables 1, 2, and 3, below.

As defined generally above, n is 0, 1, 2, or 3. In certain embodiments, n is 0. In certain embodiments, n is 1. In certain embodiments, n is 2. In certain embodiments, n is 3. In certain embodiments, n is 0 or 1. In certain embodiments, n is 1 or 2. In certain embodiments, n is 2 or 3. In certain embodiments, n is 0, 1, or 2. In certain embodiments, n is 1, 2, or 3. In certain embodiments, n is selected from the values represented in the compounds in Tables 1, 2, and 3, below.

As defined generally above, p is 0, 1, or 2. In certain embodiments, p is 0. In certain embodiments, p is 1. In certain embodiments, p is 2. In certain embodiments, p is 0 or 1. In certain embodiments, p is 1 or 2. In certain embodiments, p is selected from the values represented in the compounds in Tables 1, 2, and 3, below.

In certain embodiments, p and q are 0.

As defined generally above, q is 0, 1, or 2. In certain embodiments, q is 0. In certain embodiments, q is 1. In certain embodiments, q is 2. In certain embodiments, q is 0 or 1. In certain embodiments, q is 1 or 2. In certain embodiments, q is selected from the values represented in the compounds in Tables 1, 2 and 3, below.

As defined generally above, r is 0, 1, or 2. In certain embodiments, r is 0. In certain embodiments, r is 1. In certain embodiments, r is 2. In certain embodiments, r is 0 or 1. In certain embodiments, r is 1 or 2. In certain embodiments, r is selected from the values represented in the compounds in Tables 1, 2, and 3, below.

The description above describes multiple embodiments relating to compounds of Formula I. The Patent Application specifically contemplates all combinations of the embodiments.

Another aspect of the invention provides a compound represented by Formula I-A:

(I-A)

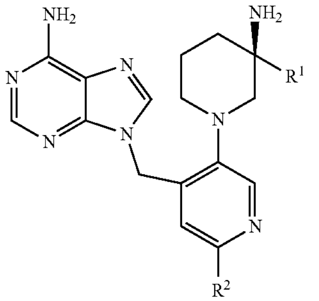

or a pharmaceutically acceptable salt thereof, wherein:

$R^1$ is selected from the group consisting of:

a. $C_{1-6}$ alkyl substituted with (i) 0, 1, 2, or 3 halo, and (ii) 0 or 1 occurrence of hydroxyl, $C_{1-6}$ alkoxyl, $C_{1-6}$ haloalkoxyl, —O—($C_{3-5}$ cycloalkyl), oxo, —C(O)$OR^3$, or —C(O)N$(R^4)_2$;

b. $—C(O)OR^3$, $—C(O)N(R^4)_2$, or $—C(O)—(C_{0-4}$ alkylene) $—(C_{3-7}$ cycloalkyl);

c. $—(C_{0-2}$ alkylene)-(5-6 membered monocyclic heteroaryl having 1, 2, or 3 heteroatoms independently selected from nitrogen, oxygen, and sulfur), wherein said heteroaryl is substituted with m occurrences of $R^5$; and d. hydrogen;

$R^2$ is phenyl; a 5-6 membered monocyclic heteroaryl having 1, 2, or 3 heteroatoms independently selected from nitrogen, oxygen, and sulfur; an 8-10 membered bicyclic heteroaryl having 1, 2, or 3 heteroatoms independently selected from nitrogen, oxygen, and sulfur; or $C_{3-7}$ cycloalkyl; each of which is substituted with (i) one $—OR^7$, and (ii) n occurrences of $R^6$;

$R^3$ represents independently for each occurrence $C_{1-6}$ alkyl or hydrogen;

$R^4$ represents independently for each occurrence $C_{1-6}$ alkyl or hydrogen, or two occurrences of $R^4$ attached to the same nitrogen atom are taken together with said nitrogen atom to form a 4-7 membered saturated ring having one nitrogen atom;

$R^5$ and $R^6$ each represents independently for each occurrence halo, $C_{1-4}$ alkyl, $C_{1-4}$ haloalkyl, $C_{1-4}$ hydroxyalkyl, $C_{3-7}$ cycloalkyl, $C_{1-4}$ alkoxyl, $C_{1-4}$ haloalkoxyl, hydroxyl, or cyano;

$R^7$ is $—P(O)(OR^8)_2$, $—CH_2—P(O)(OR^8)_2$, $—C(O)R^8$, $—C(O)OR^8$, $—C(R^3)_2—OR^8$, $—C(R^3)_2—OC(O)R^8$, $—C(R^3)_2—OC(O)OR^8$, $—C(R^3)_2—OC(O)N(R^4)(R^{11})$, $—C(O)—C(H)(R^9)—N(R^4)_2$, $—C(O)—C(H)(R^9)—N(H)C(O)R^3$, $—C(O)N(R^4)—C(H)(R^9)—C(O)OH$, or $—C(O)N(R^4)—C(H)(R^9)—C(O)O(C_{1-20}$ aliphatic chain);

$R^8$ represents independently for each occurrence hydrogen, a $C_{1-20}$ aliphatic chain, $C_{3-7}$ cycloalkyl, phenyl, $—CH_2$-phenyl, or a 5-6 membered monocyclic heteroaryl having 1, 2, or 3 heteroatoms independently selected from nitrogen, oxygen, and sulfur; wherein said phenyl and heteroaryl is each substituted with r occurrences of $R^{10}$;

$R^9$ is hydrogen, $C_{1-6}$ alkyl, or $—CH_2$-phenyl;

$R^{10}$ represents independently for each occurrence halo, $C_{1-4}$ alkyl, $C_{1-4}$ haloalkyl, or $C_{1-4}$ alkoxyl;

$R^{11}$ is $C_{1-6}$ alkyl, phenyl, $—CH_2$-phenyl, or hydrogen; or $R^{11}$ and $R^4$ are taken together with the nitrogen atom to which they are attached to form a 4-7 membered saturated ring having one nitrogen atom and optionally one additional heteroatom selected from nitrogen, oxygen, and sulfur;

m and n are each independently 0, 1, 2, or 3; and r is 0, 1, or 2.

The definitions of variables in Formula I-A above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

In certain embodiments, the compound is a compound of Formula I-A.

As defined generally above, $R^1$ is selected from the group consisting of:

a. $C_{1-6}$ alkyl substituted with (i) 0, 1, 2, or 3 halo, and (ii) 0 or 1 occurrence of hydroxyl, $C_{1-6}$ alkoxyl, $C_{1-6}$ haloalkoxyl, $—O—(C_{3-5}$ cycloalkyl), oxo, $—C(O)OR^3$, or $—C(O)N(R^4)_2$;

b. $—C(O)OR^3$, $—C(O)N(R^4)_2$, or $—C(O)—(C_{0-4}$ alkylene)-$(C_{3-7}$ cycloalkyl);

c. $—(C_{0-2}$ alkylene)-(5-6 membered monocyclic heteroaryl having 1, 2, or 3 heteroatoms independently selected from nitrogen, oxygen, and sulfur), wherein said heteroaryl is substituted with m occurrences of $R^5$; and d. hydrogen.

In certain embodiments, $R^1$ is $C_{1-6}$ alkyl substituted with (i) 0, 1, 2, or 3 halo, and (ii) 0 or 1 occurrence of hydroxyl, $C_{1-6}$ alkoxyl, $C_{1-6}$ haloalkoxyl, $—O—(C_{3-5}$ cycloalkyl), oxo, $—C(O)OR^3$, or $—C(O)N(R^4)_2$. In certain embodiments, $R^1$ is $C_{1-6}$ alkyl substituted with (i) 1, 2, or 3 halo, and (ii) 0 or 1 occurrence of hydroxyl. In certain embodiments, $R^1$ is $C_{1-6}$ alkyl substituted with (i) 0, 1, 2, or 3 halo, and (ii) 1 occurrence of hydroxyl. In certain embodiments, $R^1$ is

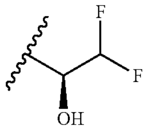 or 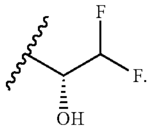

In certain embodiments, $R^1$ is $—CH_2CHF_2$.

In certain embodiments, $R^1$ is $—C(O)OR^3$, $—C(O)N(R^4)_2$, or $—C(O)—(C_{0-4}$ alkylene)-$(C_{3-7}$ cycloalkyl). In certain embodiments, $R^1$ is $—C(O)OR^3$. In certain embodiments, $R^1$ is $—C(O)N(R^4)_2$. In certain embodiments, $R^1$ is $—C(O)—(C_{0-4}$ alkylene)-$(C_{3-7}$ cycloalkyl). In certain embodiments, $R^1$ is $—C(O)—(C_{1-4}$ alkylene)-$(C_{3-7}$ cycloalkyl). In certain embodiments, $R^1$ is $—C(O)—(C_{3-7}$ cycloalkyl).

In certain embodiments, $R^1$ is $—(C_{0-2}$ alkylene)-(5-6 membered monocyclic heteroaryl having 1, 2, or 3 heteroatoms independently selected from nitrogen, oxygen, and sulfur), wherein said heteroaryl is substituted with m occurrences of $R^5$. In certain embodiments, $R^1$ is a 5-6 membered monocyclic heteroaryl having 1, 2, or 3 heteroatoms independently selected from nitrogen, oxygen, and sulfur, wherein said heteroaryl is substituted with m occurrences of $R^5$. In certain embodiments, $R^1$ is a 5-membered monocyclic heteroaryl having 1, 2, or 3 heteroatoms independently selected from nitrogen, oxygen, and sulfur, wherein said heteroaryl is substituted with m occurrences of $R^5$. In certain embodiments, $R^1$ is a 6-membered monocyclic heteroaryl having 1 or 2 nitrogen atoms, wherein said heteroaryl is substituted with m occurrences of $R^5$. In certain embodiments, $R^1$ is pyridinyl substituted with m occurrences of $R^5$. In certain embodiments, $R^1$ is pyridin-2-yl substituted with m occurrences of $R^5$. In certain embodiments, $R^1$ is

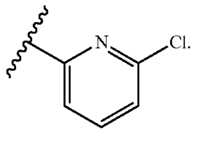 [SMILES: *c1cccc(Cl)n1]

In certain embodiments, $R^1$ is $—(C_{1-2}$ alkylene)-(5-6 membered monocyclic heteroaryl having 1, 2, or 3 heteroatoms independently selected from nitrogen, oxygen, and sulfur), wherein said heteroaryl is substituted with m occurrences of $R^5$. In certain embodiments, $R^1$ is —($C_{1-2}$ alkylene)-(5-membered monocyclic heteroaryl having 1, 2, or 3 heteroatoms independently selected from nitrogen, oxygen, and sulfur), wherein said heteroaryl is substituted with m occurrences of $R^5$. In certain embodiments, $R^1$ is —($C_{1-2}$ alkylene)-(6-membered monocyclic heteroaryl having 1 or 2 nitrogen atoms), wherein said heteroaryl is substituted with m occurrences of $R^5$.

In certain embodiments, $R^1$ is hydrogen.

As defined generally above, $R^2$ is phenyl; a 5-6 membered monocyclic heteroaryl having 1, 2, or 3 heteroatoms independently selected from nitrogen, oxygen, and sulfur; an 8-10 membered bicyclic heteroaryl having 1, 2, or 3 heteroatoms independently selected from nitrogen, oxygen, and sulfur; or $C_{3-7}$ cycloalkyl; each of which is substituted with (i) one —$OR^7$, and (ii) n occurrences of $R^6$.

In certain embodiments, $R^2$ is phenyl substituted with (i) one —$OR^7$, and (ii) n occurrences of $R^6$. In certain embodiments, $R^2$ is

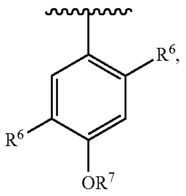

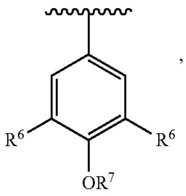

, or

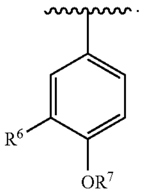

In certain embodiments, $R^2$ is

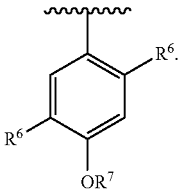

In certain embodiments, $R^2$ is

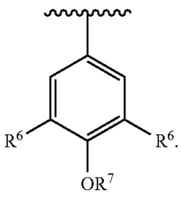

In certain embodiments, $R^2$ is

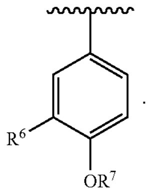

In certain embodiments, $R^2$ is

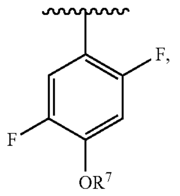

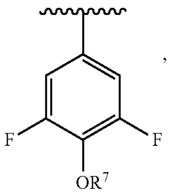

, or

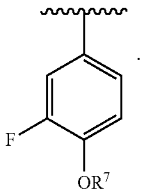

In certain embodiments, $R^2$ is

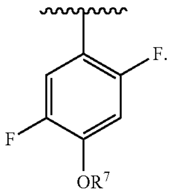

In certain embodiments, $R^2$ is

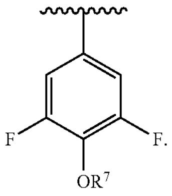

In certain embodiments, $R^2$ is

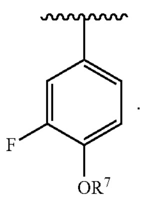

In certain embodiments, $R^2$ is a 5-6 membered monocyclic heteroaryl having 1, 2, or 3 heteroatoms independently selected from nitrogen, oxygen, and sulfur; wherein said heteroaryl is substituted with (i) one —$OR^7$, and (ii) n occurrences of $R^6$. In certain embodiments, $R^2$ is a 5-membered monocyclic heteroaryl having 1, 2, or 3 heteroatoms independently selected from nitrogen, oxygen, and sulfur; wherein said heteroaryl is substituted with (i) one —$OR^7$, and (ii) n occurrences of $R^6$. In certain embodiments, $R^2$ is a 6-membered monocyclic heteroaryl having 1 or 2 nitrogen atoms; wherein said heteroaryl is substituted with (i) one —$OR^7$, and (ii) n occurrences of $R^6$. In certain embodiments, $R^2$ is pyridinyl substituted with (i) one —$OR^7$, and (ii) n occurrences of $R^6$. In certain embodiments, $R^2$ is pyridin-2-yl substituted with (i) one —$OR^7$, and (ii) n occurrences of $R^6$. In certain embodiments, $R^2$ is

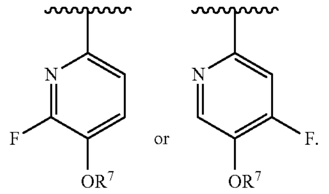

In certain embodiments, $R^2$ is an 8-10 membered bicyclic heteroaryl having 1, 2, or 3 heteroatoms independently selected from nitrogen, oxygen, and sulfur; wherein said heteroaryl is substituted with (i) one —$OR^7$, and (ii) n occurrences of $R^6$. In certain embodiments, $R^2$ is a 9-membered bicyclic heteroaryl having 1, 2, or 3 heteroatoms independently selected from nitrogen, oxygen, and sulfur; wherein said heteroaryl is substituted with (i) one —$OR^7$, and (ii) n occurrences of $R^6$. In certain embodiments, $R^2$ is an 8-10 membered bicyclic heteroaryl having 1 or 2 nitrogen atoms; wherein said heteroaryl is substituted with (i) one —$OR^7$, and (ii) n occurrences of R. In certain embodiments, $R^2$ is a 9-membered bicyclic heteroaryl having 1 or 2 nitrogen atoms; wherein said heteroaryl is substituted with (i) one —$OR^7$, and (ii) n occurrences of $R^6$. In certain embodiments, $R^2$ is indazolyl substituted with (i) one —$OR^7$, and (ii) n occurrences of $R^6$. In certain embodiments, $R^2$ is indazol-5-yl substituted with (i) one —$OR^7$, and (ii) n occurrences of $R^6$.

In certain embodiments, $R^2$ is $C_{3-7}$ cycloalkyl substituted with (i) one —$OR^7$, and (ii) n occurrences of $R^6$. In certain embodiments, $R^2$ is $C_{3-5}$ cycloalkyl substituted with (i) one —$OR^7$, and (ii) n occurrences of $R^6$. In certain embodiments, $R^2$ is cyclopropyl substituted with (i) one —$OR^7$, and (ii) n occurrences of $R^6$.

As defined generally above, $R^3$ represents independently for each occurrence $C_{1-6}$ alkyl or hydrogen. In certain embodiments, $R^3$ represents independently for each occurrence $C_{1-6}$ alkyl. In certain embodiments, $R^3$ represents independently for each occurrence $C_{1-4}$ alkyl. In certain embodiments, $R^3$ is methyl. In certain embodiments, $R^3$ is hydrogen.

As defined generally above, $R^4$ represents independently for each occurrence $C_{1-6}$ alkyl or hydrogen, or two occurrences of $R^4$ attached to the same nitrogen atom are taken together with said nitrogen atom to form a 4-7 membered saturated ring having one nitrogen atom.

In certain embodiments, $R^4$ represents independently for each occurrence $C_{1-6}$ alkyl or hydrogen. In certain embodiments, $R^4$ represents independently for each occurrence $C_{1-4}$ alkyl or hydrogen. In certain embodiments, $R^4$ represents independently for each occurrence methyl or hydrogen. In certain embodiments, $R^4$ represents independently for each occurrence $C_{1-6}$ alkyl. In certain embodiments, $R^4$ represents independently for each occurrence $C_{1-4}$ alkyl. In certain embodiments, $R^4$ is methyl. In certain embodiments, $R^4$ is hydrogen.

In certain embodiments, two occurrences of $R^4$ attached to the same nitrogen atom are taken together with said nitrogen atom to form a 4-7 membered saturated ring having one nitrogen atom. In certain embodiments, two occurrences of $R^4$ attached to the same nitrogen atom are taken together with said nitrogen atom to form a 5-6 membered saturated ring having one nitrogen atom.

As defined generally above, $R^5$ represents independently for each occurrence halo, $C_{1-4}$ alkyl, $C_{1-4}$ haloalkyl, $C_{1-4}$ hydroxyalkyl, $C_{3-7}$ cycloalkyl, $C_{1-4}$ alkoxyl, $C_{1-4}$ haloalkoxyl, hydroxyl, or cyano.

In certain embodiments, $R^5$ represents independently for each occurrence halo, $C_{1-4}$ alkyl, $C_{1-4}$ haloalkyl, or $C_{1-4}$ alkoxyl. In certain embodiments, $R^5$ represents independently for each occurrence fluoro, chloro, methyl, trifluoromethyl, or methoxy. In certain embodiments, $R^5$ represents independently for each occurrence halo, $C_{1-4}$ alkyl, $C_{1-4}$ haloalkyl, $C_{1-4}$ hydroxyalkyl, or $C_{3-7}$ cycloalkyl. In certain embodiments, $R^5$ represents independently for each occurrence $C_{1-4}$ alkyl, $C_{1-4}$ haloalkyl, $C_{1-4}$ hydroxyalkyl, or $C_{3-7}$ cycloalkyl. In certain embodiments, $R^5$ represents independently for each occurrence halo, $C_{1-4}$ alkoxyl, $C_{1-4}$ haloalkoxyl, hydroxyl, or cyano. In certain embodiments, $R^5$ represents independently for each occurrence $C_{1-4}$ alkoxyl, $C_{1-4}$ haloalkoxyl, or hydroxyl.

In certain embodiments, $R^5$ represents independently for each occurrence halo. In certain embodiments, $R^5$ represents independently for each occurrence fluoro or chloro. In certain embodiments, $R^5$ represents independently for each occurrence $C_{1-4}$ alkyl. In certain embodiments, $R^5$ is methyl. In certain embodiments, $R^5$ represents independently for each occurrence $C_{1-4}$ haloalkyl. In certain embodiments, $R^5$ is trifluoromethyl. In certain embodiments, $R^5$ represents independently for each occurrence $C_{1-4}$ hydroxyalkyl. In certain embodiments, $R^5$ represents independently for each occurrence $C_{3-7}$ cycloalkyl. In certain embodiments, $R^5$ represents independently for each occurrence $C_{1-4}$ alkoxyl. In certain embodiments, $R^5$ is methoxy. In certain embodiments, $R^5$ represents independently for each occurrence $C_{1-4}$ haloalkoxyl. In certain embodiments, $R^5$ is hydroxyl. In certain embodiments, $R^5$ is cyano.

As defined generally above, $R^6$ represents independently for each occurrence halo, $C_{1-4}$ alkyl, $C_{1-4}$ haloalkyl, $C_{1-4}$ hydroxyalkyl, $C_{3-7}$ cycloalkyl, $C_{1-4}$ alkoxyl, $C_{1-4}$ haloalkoxyl, hydroxyl, or cyano.

In certain embodiments, $R^6$ represents independently for each occurrence halo, $C_{1-4}$ alkyl, $C_{1-4}$ haloalkyl, or $C_{1-4}$ alkoxyl. In certain embodiments, $R^6$ represents independently for each occurrence fluoro, chloro, methyl, trifluoromethyl, or methoxy. In certain embodiments, $R^6$ represents independently for each occurrence halo, $C_{1-4}$ alkyl, $C_{1-4}$ haloalkyl, $C_{1-4}$ hydroxyalkyl, or $C_{3-7}$ cycloalkyl. In certain embodiments, $R^6$ represents independently for each occurrence $C_{1-4}$ alkyl, $C_{1-4}$ haloalkyl, $C_{1-4}$ hydroxyalkyl, or $C_{3-7}$ cycloalkyl. In certain embodiments, $R^6$ represents independently for each occurrence halo, $C_{1-4}$ alkoxyl, $C_{1-4}$ haloalkoxyl, hydroxyl, or cyano. In certain embodiments, $R^6$ represents independently for each occurrence $C_{1-4}$ alkoxyl, $C_{1-4}$ haloalkoxyl, or hydroxyl.

In certain embodiments, $R^6$ represents independently for each occurrence halo. In certain embodiments, $R^6$ represents independently for each occurrence fluoro or chloro. In certain embodiments, $R^6$ represents independently for each occurrence $C_{1-4}$ alkyl. In certain embodiments, $R^6$ is methyl. In certain embodiments, $R^6$ represents independently for each occurrence $C_{1-4}$ haloalkyl. In certain embodiments, $R^6$ is trifluoromethyl. In certain embodiments, $R^6$ represents independently for each occurrence $C_{1-4}$ hydroxyalkyl. In certain embodiments, $R^6$ represents independently for each occurrence $C_{3-7}$ cycloalkyl. In certain embodiments, $R^6$ represents independently for each occurrence $C_{1-4}$ alkoxyl.

In certain embodiments, $R^6$ is methoxy. In certain embodiments, $R^6$ represents independently for each occurrence $C_{1-4}$ haloalkoxyl. In certain embodiments, $R^6$ is hydroxyl. In certain embodiments, $R^6$ is cyano.

As defined generally above, $R^7$ is —P(O)($OR^8$)$_2$, —$CH_2$—P(O)($OR^8$)$_2$, —C(O)$R^8$, —C(O)$OR^8$, —C($R^3$)$_2$—$OR^8$, —C($R^3$)$_2$—OC(O)$R^8$, —C($R^3$)$_2$—OC(O)$OR^8$, —C($R^3$)$_2$—OC(O)N($R^4$)($R^{11}$), —C(O)—C(H)($R^9$)—N($R^4$)$_2$, —C(O)—C(H)($R^9$)—N(H)C(O)$R^3$, —C(O)N($R^4$)—C(H)($R^9$)—C(O)OH, or —C(O)N($R^4$)—C(H)($R^9$)—C(O)O($C_{1-20}$ aliphatic chain).

In certain embodiments, $R^7$ is —P(O)($OR^8$)$_2$ or —$CH_2$—P(O)($OR^8$)$_2$. In certain embodiments, $R^7$ is —C(O)$R^8$, —C(O)$OR^8$, or —C($R^3$)$_2$—OC(O)$OR^8$. In certain embodiments, $R^7$ is —C(O)$R^8$ or —C(O)$OR^8$. In certain embodiments, $R^7$ is —C($R^3$)$_2$—OC(O)$R^8$, —C($R^3$)$_2$—OC(O)$OR^8$, or —C($R^3$)$_2$—OC(O)N($R^4$)($R^{11}$). In certain embodiments, $R^7$ is —C($R^3$)$_2$—$OR^8$, —C($R^3$)$_2$—OC(O)$R^8$, —C($R^3$)$_2$—OC(O)$OR^8$, or —C($R^3$)$_2$—OC(O)N($R^4$)($R^{11}$). In certain embodiments, $R^7$ is —C($R^3$)$_2$—OC(O)$R^8$ or —C($R^3$)$_2$—OC(O)$OR^8$. In certain embodiments, $R^7$ is —C($R^3$)$_2$—OC(O)$OR^8$ or —C($R^3$)$_2$—OC(O)N($R^4$)($R^{11}$). In certain embodiments, $R^7$ is —C(O)—C(H)($R^9$)—N($R^4$)$_2$ or —C(O)—C(H)($R^9$)—N(H)C(O)$R^3$. In certain embodiments, $R^7$ is —C(O)N($R^4$)—C(H)($R^9$)—C(O)OH or —C(O)N($R^4$)—C(H)($R^9$)—C(O)O($C_{1-20}$ aliphatic chain).

In certain embodiments, $R^8$ is —P(O)($OR^8$)$_2$. In certain embodiments, $R^7$ is —$CH_2$—P(O)($OR^8$)$_2$. In certain embodiments, $R^7$ is —C(O)$R^8$. In certain embodiments, $R^7$ is —C(O)$OR^8$. In certain embodiment, $R^7$ is —C($R^3$)$_2$—$OR^8$. In certain embodiment, $R^7$ is —$CH_2$—$OR^8$. In certain embodiment, $R^7$ is —C(H)($CH_3$)—$OR^8$. In certain embodiments, $R^7$ is —C($R^3$)$_2$—OC(O)$R^8$. In certain embodiments, $R^7$ is —$CH_2$—OC(O)$R^8$. In certain embodiments, $R^7$ is —C(H)($CH_3$)—OC(O)$R^8$. In certain embodiments, $R^7$ is —C($R^3$)$_2$—OC(O)$OR^8$. In certain embodiments, $R^7$ is —$CH_2$—OC(O)$OR^8$. In certain embodiments, $R^7$ is —C(H)($CH_3$)—OC(O)$OR^8$. In certain embodiments, $R^7$ is —C($R^3$)$_2$—OC(O)N($R^4$)($R^{11}$). In certain embodiments, $R^7$ is —$CH_2$—OC(O)N($R^4$)($R^{11}$). In certain embodiments, $R^7$ is —C(H)($CH_3$)—OC(O)N($R^4$)($R^{11}$). In certain embodiments, $R^7$ is —C(O)—C(H)($R^9$)—N($R^4$)$_2$. In certain embodiments, $R^7$ is —C(O)—C(H)($R^9$)—$NH_2$. In certain embodiments, $R^7$ is —C(O)—C(H)($R^9$)—N(H)C(O)$R^3$. In certain embodiments, $R^7$ is —C(O)—C(H)($R^9$)—N(H)C(O)$CH_3$. In certain embodiments, $R^7$ is —C(O)N($R^4$)—C(H)($R^9$)—C(O)OH. In certain embodiments, $R^7$ is —C(O)N(H)—C(H)($R^9$)—C(O)OH. In certain embodiments, $R^7$ is —C(O)N($R^4$)—C(H)($R^9$)—C(O)O($C_{1-20}$ aliphatic chain). In certain embodiments, $R^7$ is —C(O)N(H)—C(H)($R^9$)—C(O)O($C_{1-20}$ aliphatic chain). In certain embodiments, $R^7$ is —C(O)N(H)—C(H)($R^9$)—C(O)O($C_{1-6}$ aliphatic chain). In certain embodiments, $R^7$ is —C(O)N(H)—C(H)($R^9$)—C(O)O($C_{7-20}$ aliphatic chain). In certain embodiments, $R^7$ is —C(O)N(H)—C(H)($R^9$)—C(O)O($C_{1-20}$ alkyl). In certain embodiments, $R^7$ is —C(O)N(H)—C(H)($R^9$)—C(O)O($C_{1-6}$ alkyl). In certain embodiments, $R^7$ is —C(O)N(H)—C(H)($R^9$)—C(O)O($C_{7-20}$ alkyl).

As defined generally above, $R^8$ represents independently for each occurrence hydrogen, a $C_{1-20}$ aliphatic chain, $C_{3-7}$ cycloalkyl, phenyl, —$CH_2$-phenyl, or a 5-6 membered monocyclic heteroaryl having 1, 2, or 3 heteroatoms independently selected from nitrogen, oxygen, and sulfur; wherein said phenyl and heteroaryl is each substituted with r occurrences of $R^{10}$.

In some embodiments, $R^8$ represents independently for each occurrence hydrogen, a $C_{1-20}$ aliphatic chain, or $C_{3-7}$ cycloalkyl. In some embodiments, $R^8$ represents independently for each occurrence hydrogen or a $C_{1-20}$ aliphatic chain. In some embodiments, $R^8$ represents independently for each occurrence hydrogen or $C_{1-20}$ alkyl. In some embodiments, $R^8$ represents independently for each occurrence hydrogen or $C_{1-6}$ alkyl. In some embodiments, $R^8$ represents independently for each occurrence hydrogen or $C_{7-20}$ alkyl.

In some embodiments, $R^8$ represents independently for each occurrence phenyl, —$CH_2$— phenyl, or a 5-6 membered monocyclic heteroaryl having 1, 2, or 3 heteroatoms independently selected from nitrogen, oxygen, and sulfur; wherein said phenyl and heteroaryl is each substituted with r occurrences of $R^1$. In some embodiments, $R^8$ represents independently for each occurrence phenyl or —$CH_2$-phenyl; wherein each phenyl is substituted with r occurrences of $R^{10}$.

In some embodiments, $R^8$ represents independently for each occurrence a $C_{1-20}$ aliphatic chain, $C_{3-7}$ cycloalkyl, phenyl, or —$CH_2$-phenyl; wherein each phenyl is substituted with r occurrences of $R^{10}$. In some embodiments, $R^8$ represents independently for each occurrence a $C_{1-20}$ aliphatic chain, $C_{3-7}$ cycloalkyl, phenyl, or —$CH_2$-phenyl. In some embodiments, $R^8$ represents independently for each occurrence $C_{1-20}$ alkyl, $C_{3-7}$ cycloalkyl, phenyl, or —$CH_2$-phenyl. In some embodiments, $R^8$ independently for each occurrence $C_{3-7}$ cycloalkyl or phenyl.

In some embodiments, $R^8$ is hydrogen. In some embodiments, $R^8$ represents independently for each occurrence a $C_{1-20}$ aliphatic chain. In some embodiments, $R^8$ represents independently for each occurrence a $C_{1-10}$ aliphatic chain. In some embodiments, $R^8$ represents independently for each occurrence a $C_{1-6}$ aliphatic chain. In some embodiments, $R^8$ represents independently for each occurrence a $C_{7-20}$ aliphatic chain. In some embodiments, $R^8$ represents independently for each occurrence $C_{1-20}$ alkyl. In some embodiments, $R^8$ represents independently for each occurrence $C_{1-10}$ alkyl. In some embodiments, $R^8$ represents independently for each occurrence $C_{1-6}$ alkyl. In some embodiments, $R^8$ represents independently for each occurrence $C_{7-20}$ alkyl.

In some embodiments, $R^8$ represents independently for each occurrence phenyl substituted with r occurrences of $R^{10}$. In some embodiments, $R^8$ is phenyl. In some embodiments, $R^8$ represents independently for each occurrence —$CH_2$-phenyl substituted with r occurrences of $R^{10}$. In some embodiments, $R^8$ is —$CH_2$-phenyl.

In some embodiments, $R^8$ represents independently for each occurrence a 5-6 membered monocyclic heteroaryl having 1, 2, or 3 heteroatoms independently selected from nitrogen, oxygen, and sulfur; wherein said heteroaryl is substituted with r occurrences of $R^{10}$. In some embodiments, $R^8$ represents independently for each occurrence a 5-6 membered monocyclic heteroaryl having 1, 2, or 3 heteroatoms independently selected from nitrogen, oxygen, and sulfur.

In some embodiments, $R^8$ represents independently for each occurrence a 5-membered monocyclic heteroaryl having 1, 2, or 3 heteroatoms independently selected from nitrogen, oxygen, and sulfur. In some embodiments, $R^8$ represents independently for each occurrence a 5-membered monocyclic heteroaryl having 1, 2, or 3 nitrogen atoms. In some embodiments, $R^8$ represents independently for each occurrence a 5-membered monocyclic heteroaryl having 2 heteroatoms independently selected from nitrogen and oxygen. In some embodiments, $R^8$ represents independently for each occurrence a 5-membered monocyclic heteroaryl having 2 heteroatoms independently selected from nitrogen and sulfur. In some embodiments, $R^8$ represents independently for each occurrence a 5-membered monocyclic heteroaryl having one oxygen or sulfur atom. In some embodiments, $R^8$ represents independently for each occurrence a 5-membered monocyclic heteroaryl having 1, 2, or 3 heteroatoms independently selected from nitrogen and sulfur.

In some embodiments, $R^8$ represents independently for each occurrence a 6-membered monocyclic heteroaryl having 1, 2, or 3 heteroatoms independently selected from nitrogen, oxygen, and sulfur. In some embodiments, $R^8$ represents independently for each occurrence a 6-membered monocyclic heteroaryl having 1, 2, or 3 nitrogen atoms. In some embodiments, $R^8$ represents independently for each occurrence a 6-membered monocyclic heteroaryl having 1 or 2 nitrogen atoms.

As defined generally above, $R^9$ is hydrogen, $C_{1-6}$ alkyl, or —$CH_2$-phenyl. In some embodiments, $R^9$ is hydrogen. In some embodiments, $R^9$ is $C_{1-6}$ alkyl. In some embodiments, $R^9$ is methyl or ethyl. In some embodiments, $R^9$ is methyl. In some embodiments, $R^9$ is ethyl. In some embodiments, $R^9$ is —$CH_2$-phenyl.

As defined generally above, $R^{10}$ represents independently for each occurrence halo, $C_{1-4}$ alkyl, $C_{1-4}$ haloalkyl, or $C_{1-4}$ alkoxyl. In certain embodiments, $R^{10}$ represents independently for each occurrence fluoro, chloro, methyl, trifluoromethyl, or methoxy. In certain embodiments, $R^{10}$ represents independently for each occurrence $C_{1-4}$ alkyl or $C_{1-4}$ haloalkyl. In certain embodiments, $R^{10}$ represents independently for each occurrence halo or $C_{1-4}$ alkoxyl.

In certain embodiments, $R^{10}$ represents independently for each occurrence halo. In certain embodiments, $R^{10}$ represents independently for each occurrence fluoro or chloro. In certain embodiments, $R^{10}$ represents independently for each occurrence $C_{1-4}$ alkyl. In certain embodiments, $R^{10}$ is methyl. In certain embodiments, $R^{10}$ represents independently for each occurrence $C_{1-4}$ haloalkyl. In certain embodiments, $R^{10}$ is trifluoromethyl. In certain embodiments, $R^{10}$ is $C_{1-4}$ alkoxyl. In certain embodiments, $R^{10}$ is methoxy.

In certain embodiments, $R^{10}$ represents independently for each occurrence methyl or ethyl. In certain embodiments, $R^{10}$ represents independently for each occurrence n-propyl or isopropyl. In certain embodiments, $R^{10}$ represents independently for each occurrence methyl or halomethyl. In certain embodiments, $R^{10}$ represents independently for each occurrence methoxy or ethoxy. In certain embodiments, $R^{10}$ is fluoromethyl or fluoroethyl. In certain embodiments, $R^{10}$ is 2-fluoroethyl.

As defined generally above, $R^{11}$ is $C_{1-6}$ alkyl, phenyl, —$CH_2$-phenyl, or hydrogen; or $R^{11}$ and $R^4$ are taken together with the nitrogen atom to which they are attached to form a 4-7 membered saturated ring having one nitrogen atom and optionally one additional heteroatom selected from nitrogen, oxygen, and sulfur.

In certain embodiments, $R^{11}$ is $C_{1-6}$ alkyl, phenyl, —$CH_2$-phenyl, or hydrogen. In certain embodiments, $R^{11}$ is hydrogen. In certain embodiments, $R^{11}$ is $C_{1-6}$ alkyl. In certain embodiments, $R^{11}$ is methyl. In certain embodiments, $R^{11}$ is ethyl. In certain embodiments, $R^{11}$ is phenyl. In certain embodiments, $R^{11}$ is —$CH_2$-phenyl.

In certain embodiments, $R^{11}$ and $R^4$ are taken together with the nitrogen atom to which they are attached to form a 4-7 membered saturated ring having one nitrogen atom and optionally one additional heteroatom selected from nitrogen, oxygen, and sulfur. In certain embodiments, $R^{11}$ and $R^4$ are taken together with the nitrogen atom to which they are attached to form a 5-membered saturated ring having one nitrogen atom and optionally one additional heteroatom selected from nitrogen, oxygen, and sulfur. In certain embodiments, $R^{11}$ and $R^4$ are taken together with the nitrogen atom to which they are attached to form a 6-membered saturated ring having one nitrogen atom and optionally one additional heteroatom selected from nitrogen, oxygen, and sulfur. In certain embodiments, $R^{11}$ and $R^4$ are taken together with the nitrogen atom to which they are attached to form a 7-membered saturated ring having one nitrogen atom and optionally one additional heteroatom selected from nitrogen, oxygen, and sulfur.

In certain embodiments, $R^{11}$ and $R^4$ are taken together with the nitrogen atom to which they are attached to form a 5- or 6-membered saturated ring having one nitrogen atom. In certain embodiments, $R^{11}$ and $R^4$ are taken together with the nitrogen atom to which they are attached to form a 5- or 6-membered saturated ring having one nitrogen atom and optionally one additional nitrogen heteroatom. In certain embodiments, $R^{11}$ and $R^4$ are taken together with the nitrogen atom to which they are attached to form a 5- or 6-membered saturated ring having one nitrogen atom and optionally one additional oxygen heteroatom. In certain embodiments, $R^{11}$ and $R^4$ are taken together with the nitrogen atom to which they are attached to form a 5- or 6-membered saturated ring having one nitrogen atom and optionally one additional sulfur heteroatom. In certain embodiments, $R^{11}$ and $R^4$ are taken together with the nitrogen atom to which they are attached to form a morpholine or piperazine ring.

As defined generally above, m is 0, 1, 2, or 3. In certain embodiments, m is 0. In certain embodiments, m is 1. In certain embodiments, m is 2. In certain embodiments, m is 3. In certain embodiments, m is 0 or 1. In certain embodiments, m is 1 or 2. In certain embodiments, m is 2 or 3. In certain embodiments, m is 0, 1, or 2. In certain embodiments, m is 1, 2, or 3.

As defined generally above, n is 0, 1, 2, or 3. In certain embodiments, n is 0. In certain embodiments, n is 1. In certain embodiments, n is 2. In certain embodiments, n is 3. In certain embodiments, n is 0 or 1. In certain embodiments, n is 1 or 2. In certain embodiments, n is 2 or 3. In certain embodiments, n is 0, 1, or 2. In certain embodiments, n is 1, 2, or 3.

As defined generally above, r is 0, 1, or 2. In certain embodiments, r is 0. In certain embodiments, r is 1. In certain embodiments, r is 2. In certain embodiments, r is 0 or 1. In certain embodiments, r is 1 or 2.

The description above describes multiple embodiments relating to compounds of Formula I-A. The patent application specifically contemplates all combinations of the embodiments.

Another aspect of the invention provides a compound represented by Formula II:

(II)

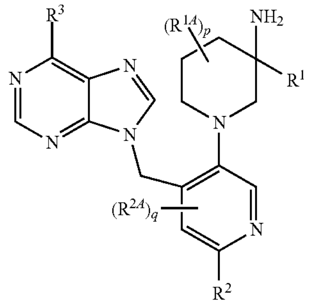

or a pharmaceutically acceptable salt thereof, wherein:

$R^1$ is selected from the group consisting of:

a. $C_{1-6}$ alkyl substituted with (i) 0, 1, 2, or 3 halo, and (ii) 0 or 1 occurrence of hydroxyl, $C_{1-6}$ alkoxyl, $C_{1-6}$ haloalkoxyl, —O—($C_{3-5}$ cycloalkyl), oxo, —C(O)OR$^4$, or —C(O)N($R^4$)$_2$;

b. —C(O)OR$^4$, —C(O)N($R^4$)$_2$, or —C(O)—($C_{0-4}$ alkylene)-($C_{3-7}$ cycloalkyl);

c. —($C_{0-2}$ alkylene)-(5-6 membered monocyclic heteroaryl having 1, 2, or 3 heteroatoms independently selected from nitrogen, oxygen, and sulfur), wherein said heteroaryl is substituted with m occurrences of $R^5$; and d. hydrogen;

$R^{1A}$ and $R^{2A}$ each represents independently for each occurrence halo, $C_{1-6}$ alkyl, $C_{1-6}$ haloalkyl, $C_{1-6}$ alkoxyl, or hydroxyl;

$R^2$ is phenyl; a 5-6 membered monocyclic heteroaryl having 1, 2, or 3 heteroatoms independently selected from nitrogen, oxygen, and sulfur; an 8-10 membered bicyclic heteroaryl having 1, 2, or 3 heteroatoms independently selected from nitrogen, oxygen, and sulfur; or $C_{3-7}$ cycloalkyl; each of which is substituted with n occurrences of $R^6$;

$R^3$ is —N(H)$R^7$ or —N═N—$R^{12}$.

$R^4$ represents independently for each occurrence $C_{1-6}$ alkyl or hydrogen, or two occurrences of $R^4$ attached to the same nitrogen atom are taken together with said nitrogen atom to form a 4-7 membered saturated ring having one nitrogen atom;

$R^5$ and $R^6$ each represents independently for each occurrence halo, $C_{1-4}$ alkyl, $C_{1-4}$ haloalkyl, $C_{1-4}$ hydroxyalkyl, $C_{3-7}$ cycloalkyl, $C_{1-4}$ alkoxyl, $C_{1-4}$ haloalkoxyl, hydroxyl, or cyano;

$R^7$ is —P(O)(OR$^8$)$_2$, —CH$_2$—P(O)(OR$^8$)$_2$, —C(O)R$^8$, —C(O)OR$^8$, —C($R^4$)$_2$—OR$^8$, —C($R^4$)$_2$—OC(O)R$^8$, —C($R^4$)$_2$—OC(O)OR$^8$, —C($R^4$)$_2$—OC(O)N($R^4$)($R^{11}$), —C(O)—C(H)($R^9$)—N($R^4$)$_2$, —C(O)—C(H)($R^9$)—N(H)C(O)R$^4$, —C(O)N($R^4$)—C(H)($R^9$)—C(O)OH, or —C(O)N($R^4$)—C(H)($R^9$)—C(O)O($C_{1-20}$ aliphatic chain);

$R^8$ represents independently for each occurrence hydrogen, a $C_{1-20}$ aliphatic chain, $C_{3-7}$ cycloalkyl, phenyl, —CH$_2$-phenyl, or a 5-6 membered monocyclic heteroaryl having 1, 2, or 3 heteroatoms independently selected from nitrogen, oxygen, and sulfur; wherein said phenyl and heteroaryl is each substituted with r occurrences of $R^{10}$;

$R^9$ is hydrogen, $C_{1-6}$ alkyl, or —CH$_2$-phenyl;

$R^{10}$ represents independently for each occurrence halo, $C_{1-4}$ alkyl, $C_{1-4}$ haloalkyl, or $C_{1-4}$ alkoxyl;

$R^{11}$ is $C_{1-6}$ alkyl, phenyl, —CH$_2$-phenyl, or hydrogen; or $R^{11}$ and $R^4$ are taken together with the nitrogen atom to which they are attached to form a 4-7 membered saturated ring having one nitrogen atom and optionally one additional heteroatom selected from nitrogen, oxygen, and sulfur;

$R^{12}$ is (i) —C(H)($R^9$)—C(O)OR$^4$, or (ii) phenyl substituted with 0, 1, or 2 substituents independently selected from hydroxyl and —($C_{0-2}$ alkylene)-C(O)OR$^4$;

m and n are each independently 0, 1, 2, or 3; and p, q, and r are each independently 0, 1, or 2.

The definitions of variables in Formula II above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

In certain embodiments, the compound is a compound of Formula II.

As defined generally above, $R^1$ is selected from the group consisting of:

a. $C_{1-6}$ alkyl substituted with (i) 0, 1, 2, or 3 halo, and (ii) 0 or 1 occurrence of hydroxyl, $C_{1-6}$ alkoxyl, $C_{1-6}$ haloalkoxyl, —O—($C_{3-5}$ cycloalkyl), oxo, —C(O)OR$^4$, or —C(O)N($R^4$)$_2$;

b. —C(O)OR$^4$, —C(O)N($R^4$)$_2$, or —C(O)—($C_{0-4}$ alkylene)-($C_{3-7}$ cycloalkyl);

c. —($C_{0-2}$ alkylene)-(5-6 membered monocyclic heteroaryl having 1, 2, or 3 heteroatoms independently selected from nitrogen, oxygen, and sulfur), wherein said heteroaryl is substituted with m occurrences of $R^5$; and d. hydrogen.

In certain embodiments, $R^1$ is $C_{1-6}$ alkyl substituted with (i) 0, 1, 2, or 3 halo, and (ii) 0 or 1 occurrence of hydroxyl, $C_{1-6}$ alkoxyl, $C_{1-6}$ haloalkoxyl, —O—($C_{3-5}$ cycloalkyl), oxo, —C(O)OR$^4$, or —C(O)N($R^4$)$_2$. In certain embodiments, $R^1$ is $C_{1-6}$ alkyl substituted with (i) 1, 2, or 3 halo, and (ii) 0 or 1 occurrence of hydroxyl. In certain embodiments, $R^1$ is $C_{1-6}$ alkyl substituted with (i) 0, 1, 2, or 3 halo, and (ii) 1 occurrence of hydroxyl. In certain embodiments, $R^1$ is

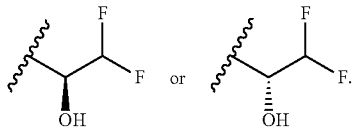 [SMILES: *[C@H](O)C(F)F ; *[C@@H](O)C(F)F]

In certain embodiments, $R^1$ is —CH$_2$CHF$_2$.

In certain embodiments, $R^1$ is —C(O)OR$^4$, —C(O)N($R^4$)$_2$, or —C(O)—($C_{0-4}$ alkylene)-($C_{3-7}$ cycloalkyl). In certain embodiments, $R^1$ is —C(O)OR$^4$. In certain embodiments, $R^1$ is —C(O)N($R^4$)$_2$. In certain embodiments, $R^1$ is —C(O)—($C_{0-4}$ alkylene)-($C_{3-7}$ cycloalkyl). In certain embodiments, $R^1$ is —C(O)—($C_{1-4}$ alkylene)-($C_{3-7}$ cycloalkyl). In certain embodiments, $R^1$ is —C(O)—($C_{3-7}$ cycloalkyl).

In certain embodiments, $R^1$ is —($C_{0-2}$ alkylene)-(5-6 membered monocyclic heteroaryl having 1, 2, or 3 heteroatoms independently selected from nitrogen, oxygen, and sulfur), wherein said heteroaryl is substituted with m occurrences of $R^5$. In certain embodiments, $R^1$ is a 5-6 membered monocyclic heteroaryl having 1, 2, or 3 heteroatoms independently selected from nitrogen, oxygen, and sulfur, wherein said heteroaryl is substituted with m occurrences of $R^5$. In certain embodiments, $R^1$ is a 5-membered monocyclic heteroaryl having 1, 2, or 3 heteroatoms independently selected from nitrogen, oxygen, and sulfur, wherein said heteroaryl is substituted with m occurrences of $R^5$. In certain embodiments, $R^1$ is a 6-membered monocyclic heteroaryl having 1 or 2 nitrogen atoms, wherein said heteroaryl is substituted with m occurrences of $R^5$. In certain embodiments, $R^1$ is pyridinyl substituted with m occurrences of $R^5$. In certain embodiments, $R^1$ is pyridin-2-yl substituted with m occurrences of $R^5$. In certain embodiments, $R^1$ is

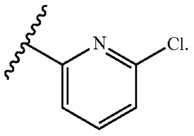 [SMILES: *c1cccc(Cl)n1]

In certain embodiments, $R^1$ is —($C_{1-2}$ alkylene)-(5-6 membered monocyclic heteroaryl having 1, 2, or 3 heteroatoms independently selected from nitrogen, oxygen, and sulfur), wherein said heteroaryl is substituted with m occurrences of $R^5$. In certain embodiments, $R^1$ is —($C_{1-2}$ alkylene)-(5-membered monocyclic heteroaryl having 1, 2, or 3 heteroatoms independently selected from nitrogen, oxygen, and sulfur), wherein said heteroaryl is substituted with m occurrences of $R^5$. In certain embodiments, $R^1$ is —($C_{1-2}$ alkylene)-(6-membered monocyclic heteroaryl having 1 or 2 nitrogen atoms), wherein said heteroaryl is substituted with m occurrences of $R^5$.

In certain embodiments, $R^1$ is hydrogen. In certain embodiments, $R^1$ is selected from the groups depicted in the compounds in Tables 4, 5, and 6, below.

As defined generally above, $R^{1A}$ represents independently for each occurrence halo, $C_{1-6}$ alkyl, $C_{1-6}$ haloalkyl, $C_{1-6}$ alkoxyl, or hydroxyl. In certain embodiments, $R^{1A}$ represents independently for each occurrence halo, $C_{1-6}$ alkyl, or $C_{1-6}$ haloalkyl. In certain embodiments, $R^{1A}$ represents independently for each occurrence $C_{1-6}$ alkyl or $C_{1-6}$ haloalkyl. In certain embodiments, $R^{1A}$ represents independently for each occurrence $C_{1-6}$ alkoxyl or hydroxyl.

In certain embodiments, $R^{1A}$ represents independently for each occurrence halo. In certain embodiments, $R^{1A}$ represents independently for each occurrence fluoro or chloro. In certain embodiments, $R^{1A}$ represents independently for each occurrence $C_{1-6}$ alkyl. In certain embodiments, $R^{1A}$ is methyl. In certain embodiments, $R^{1A}$ represents independently for each occurrence $C_{1-6}$ haloalkyl. In certain embodiments, $R^{1A}$ is trifluoromethyl. In certain embodiments, $R^{1A}$ represents independently for each occurrence $C_{1-6}$ alkoxyl. In certain embodiments, $R^{1A}$ is methoxy. In certain embodiments, $R^{1A}$ is hydroxyl. In certain embodiments, $R^{1A}$ is selected from the groups depicted in the compounds in Tables 4, 5, and 6, below.

As defined generally above, $R^2$ is phenyl; a 5-6 membered monocyclic heteroaryl having 1, 2, or 3 heteroatoms independently selected from nitrogen, oxygen, and sulfur; an 8-10 membered bicyclic heteroaryl having 1, 2, or 3 heteroatoms independently selected from nitrogen, oxygen, and sulfur; or $C_{3-7}$ cycloalkyl; each of which is substituted with n occurrences of $R^6$.

In certain embodiments, $R^2$ is phenyl substituted with n occurrences of $R^6$. In certain embodiments, $R^2$ is

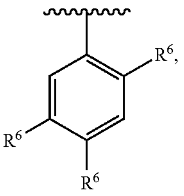

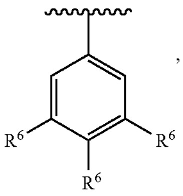

, or

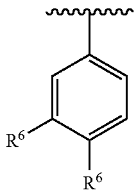

.

In certain embodiments, $R^2$ is

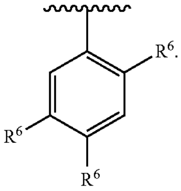

In certain embodiments, $R^2$ is

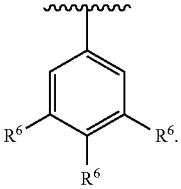

In certain embodiments, $R^2$ is

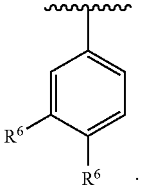

.

In certain embodiments, $R^2$ is

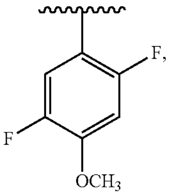

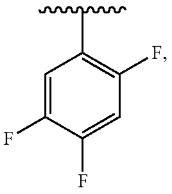

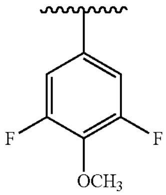

, or

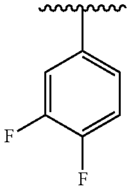

.

In certain embodiments, $R^2$ is

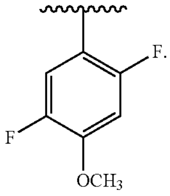

In certain embodiments, $R^2$ is

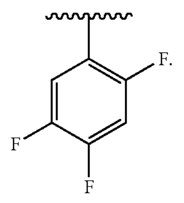

In certain embodiments, $R^2$ is

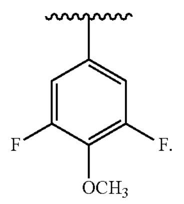

In certain embodiments, $R^2$ is

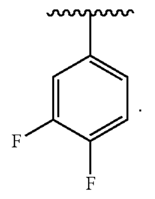

In certain embodiments, $R^2$ is a 5-6 membered monocyclic heteroaryl having 1, 2, or 3 heteroatoms independently selected from nitrogen, oxygen, and sulfur; wherein said heteroaryl is substituted with n occurrences of $R^6$. In certain embodiments, $R^2$ is a 5-membered monocyclic heteroaryl having 1, 2, or 3 heteroatoms independently selected from nitrogen, oxygen, and sulfur; wherein said heteroaryl is substituted with n occurrences of $R^6$. In certain embodiments, $R^2$ is a 6-membered monocyclic heteroaryl having 1 or 2 nitrogen atoms; wherein said heteroaryl is substituted with n occurrences of $R^6$. In certain embodiments, $R^2$ is pyridinyl substituted with n occurrences of $R^6$. In certain embodiments, $R^2$ is pyridin-2-yl substituted with n occurrences of $R^6$. In certain embodiments, $R^2$ is

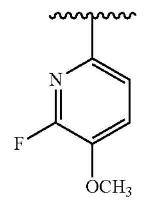

or

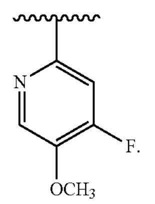

In certain embodiments, $R^2$ is an 8-10 membered bicyclic heteroaryl having 1, 2, or 3 heteroatoms independently selected from nitrogen, oxygen, and sulfur; wherein said heteroaryl is substituted with n occurrences of $R^6$. In certain embodiments, $R^2$ is a 9-membered bicyclic heteroaryl having 1, 2, or 3 heteroatoms independently selected from nitrogen, oxygen, and sulfur; wherein said heteroaryl is substituted with n occurrences of $R^6$. In certain embodiments, $R^2$ is an 8-10 membered bicyclic heteroaryl having 1 or 2 nitrogen atoms; wherein said heteroaryl is substituted with n occurrences of $R^6$. In certain embodiments, $R^2$ is a 9-membered bicyclic heteroaryl having 1 or 2 nitrogen atoms; wherein said heteroaryl is substituted with n occurrences of $R^6$. In certain embodiments, $R^2$ is indazolyl substituted with n occurrences of $R^6$. In certain embodiments, $R^2$ is indazol-5-yl substituted with n occurrences of $R^6$. In certain embodiments, $R^2$ is

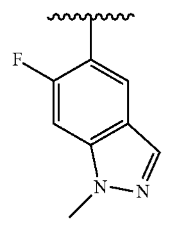

or

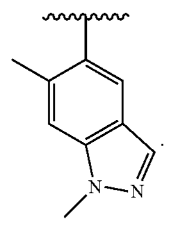

In certain embodiments, $R^2$ is $C_{3-7}$ cycloalkyl substituted with n occurrences of $R^6$. In certain embodiments, $R^2$ is $C_{3-5}$ cycloalkyl substituted with n occurrences of $R^6$. In certain embodiments, $R^2$ is cyclopropyl substituted with n occurrences of $R^6$. In certain embodiments, $R^2$ is $C_{3-7}$ cycloalkyl. In certain embodiments, $R^2$ is $C_{3-5}$ cycloalkyl. In certain embodiments, $R^2$ is cyclopropyl.

In certain embodiments, $R^2$ is selected from the groups depicted in the compounds in Tables 4, 5, and 6, below.

As defined generally above, $R^{2A}$ represents independently for each occurrence halo, $C_{1-6}$ alkyl, $C_{1-6}$ haloalkyl, $C_{1-6}$ alkoxyl, or hydroxyl. In certain embodiments, $R^{2A}$ represents independently for each occurrence halo, $C_{1-6}$ alkyl, or $C_{1-6}$ haloalkyl. In certain embodiments, $R^{2A}$ represents independently for each occurrence $C_{1-6}$ alkyl or $C_{1-6}$ haloalkyl. In certain embodiments, $R^{2A}$ represents independently for each occurrence $C_{1-6}$ alkoxyl or hydroxyl.

In certain embodiments, $R^{2A}$ represents independently for each occurrence halo. In certain embodiments, $R^{2A}$ represents independently for each occurrence fluoro or chloro. In certain embodiments, $R^{2A}$ represents independently for each occurrence $C_{1-6}$ alkyl. In certain embodiments, $R^{2A}$ is methyl. In certain embodiments, $R^{2A}$ represents independently for each occurrence $C_{1-6}$ haloalkyl. In certain embodiments, $R^{2A}$ is trifluoromethyl. In certain embodiments, $R^{2A}$ represents independently for each occurrence $C_{1-6}$ alkoxyl. In certain embodiments, $R^{2A}$ is methoxy. In certain embodiments, $R^{2A}$ is hydroxyl. In certain embodiments, $R^{2A}$ is selected from the groups depicted in the compounds in Tables 4, 5, and 6, below.

As defined generally above, $R^3$ is —N(H)$R^7$ or —N═N—$R^{12}$. In certain embodiments, $R^3$ is —N(H)$R^7$. In certain embodiments, $R^3$ is —N═N—$R^{12}$. In certain embodiments, $R^3$ is selected from the groups depicted in the compounds in Tables 4, 5, and 6, below.

As defined generally above, $R^4$ represents independently for each occurrence $C_{1-6}$ alkyl or hydrogen; or two occurrences of $R^4$ attached to the same nitrogen atom are taken together with said nitrogen atom to form a 4-7 membered saturated ring having one nitrogen atom; or $R^9$ and $R^4$ are taken together with the nitrogen atom to which they are attached to form a 4-7 membered saturated ring having one nitrogen atom and optionally one additional heteroatom selected from nitrogen, oxygen, and sulfur.

In certain embodiments, $R^4$ represents independently for each occurrence $C_{1-6}$ alkyl or hydrogen. In certain embodiments, $R^4$ represents independently for each occurrence $C_{1-4}$ alkyl or hydrogen. In certain embodiments, $R^4$ represents independently for each occurrence methyl or hydrogen. In certain embodiments, $R^4$ represents independently for each occurrence $C_{1-6}$ alkyl. In certain embodiments, $R^4$ represents independently for each occurrence $C_{1-4}$ alkyl. In certain embodiments, $R^4$ is methyl. In certain embodiments, $R^4$ is hydrogen.

In certain embodiments, two occurrences of $R^4$ attached to the same nitrogen atom are taken together with said nitrogen atom to form a 4-7 membered saturated ring having one nitrogen atom. In certain embodiments, two occurrences of $R^4$ attached to the same nitrogen atom are taken together with said nitrogen atom to form a 5-6 membered saturated ring having one nitrogen atom.

In certain embodiments, $R^4$ is selected from the groups depicted in the compounds in Tables 4, 5, and 6, below.

As defined generally above, $R^5$ represents independently for each occurrence halo, $C_{1-4}$ alkyl, $C_{1-4}$ haloalkyl, $C_{1-4}$ hydroxyalkyl, $C_{3-7}$ cycloalkyl, $C_{1-4}$ alkoxyl, $C_{1-4}$ haloalkoxyl, hydroxyl, or cyano.

In certain embodiments, $R^5$ represents independently for each occurrence halo, $C_{1-4}$ alkyl, $C_{1-4}$ haloalkyl, or $C_{1-4}$ alkoxyl. In certain embodiments, $R^5$ represents independently for each occurrence fluoro, chloro, methyl, trifluoromethyl, or methoxy. In certain embodiments, $R^5$ represents independently for each occurrence halo, $C_{1-4}$ alkyl, $C_{1-4}$ haloalkyl, $C_{1-4}$ hydroxyalkyl, or $C_{3-7}$ cycloalkyl. In certain embodiments, $R^5$ represents independently for each occurrence $C_{1-4}$ alkyl, $C_{1-4}$ haloalkyl, $C_{1-4}$ hydroxyalkyl, or $C_{3-7}$ cycloalkyl. In certain embodiments, $R^5$ represents independently for each occurrence halo, $C_{1-4}$ alkoxyl, $C_{1-4}$ haloalkoxyl, hydroxyl, or cyano. In certain embodiments, $R^5$ represents independently for each occurrence $C_{1-4}$ alkoxyl, $C_{1-4}$ haloalkoxyl, or hydroxyl.

In certain embodiments, $R^5$ represents independently for each occurrence halo. In certain embodiments, $R^5$ represents independently for each occurrence fluoro or chloro. In certain embodiments, $R^5$ represents independently for each occurrence $C_{1-4}$ alkyl. In certain embodiments, $R^5$ is methyl. In certain embodiments, $R^5$ represents independently for each occurrence $C_{1-4}$ haloalkyl. In certain embodiments, $R^5$ is trifluoromethyl. In certain embodiments, $R^5$ represents independently for each occurrence $C_{1-4}$ hydroxyalkyl. In certain embodiments, $R^5$ represents independently for each occurrence $C_{3-7}$ cycloalkyl. In certain embodiments, $R^5$ represents independently for each occurrence $C_{1-4}$ alkoxyl. In certain embodiments, $R^5$ is methoxy. In certain embodiments, $R^5$ represents independently for each occurrence $C_{1-4}$ haloalkoxyl. In certain embodiments, $R^5$ is hydroxyl. In certain embodiments, $R^5$ is cyano.

In certain embodiments, $R^5$ is selected from the groups depicted in the compounds in Tables 4, 5 and 6, below.

As defined generally above, $R^6$ represents independently for each occurrence halo, $C_{1-4}$ alkyl, $C_{1-4}$ haloalkyl, $C_{1-4}$ hydroxyalkyl, $C_{3-7}$ cycloalkyl, $C_{1-4}$ alkoxyl, $C_{1-4}$ haloalkoxyl, hydroxyl, or cyano.

In certain embodiments, $R^6$ represents independently for each occurrence halo, $C_{1-4}$ alkyl, $C_{1-4}$ haloalkyl, or $C_{1-4}$ alkoxyl. In certain embodiments, $R^6$ represents independently for each occurrence fluoro, chloro, methyl, trifluoromethyl, or methoxy. In certain embodiments, $R^6$ represents independently for each occurrence halo, $C_{1-4}$ alkyl, $C_{1-4}$ haloalkyl, $C_{1-4}$ hydroxyalkyl, or $C_{3-7}$ cycloalkyl. In certain embodiments, $R^6$ represents independently for each occurrence $C_{1-4}$ alkyl, $C_{1-4}$ haloalkyl, $C_{1-4}$ hydroxyalkyl, or $C_{3-7}$ cycloalkyl. In certain embodiments, $R^6$ represents independently for each occurrence halo, $C_{1-4}$ alkoxyl, $C_{1-4}$ haloalkoxyl, hydroxyl, or cyano. In certain embodiments, $R^6$ represents independently for each occurrence $C_{1-4}$ alkoxyl, $C_{1-4}$ haloalkoxyl, or hydroxyl.

In certain embodiments, $R^6$ represents independently for each occurrence halo. In certain embodiments, $R^6$ represents independently for each occurrence fluoro or chloro. In certain embodiments, $R^6$ represents independently for each occurrence $C_{1-4}$ alkyl. In certain embodiments, $R^6$ is methyl. In certain embodiments, $R^6$ represents independently for each occurrence $C_{1-4}$ haloalkyl. In certain embodiments, $R^6$ is trifluoromethyl. In certain embodiments, $R^6$ represents independently for each occurrence $C_{1-4}$ hydroxyalkyl. In certain embodiments, $R^6$ represents independently for each occurrence $C_{3-7}$ cycloalkyl. In certain embodiments, $R^6$ represents independently for each occurrence $C_{1-4}$ alkoxyl. In certain embodiments, $R^6$ is methoxy. In certain embodiments, $R^6$ represents independently for each occurrence $C_{1-4}$ haloalkoxyl. In certain embodiments, $R^6$ is hydroxyl. In certain embodiments, $R^6$ is cyano.

In certain embodiments, $R^6$ is selected from the groups depicted in the compounds in Tables 4, 5, and 6, below.

As defined generally above, $R^7$ is $—P(O)(OR^8)_2$, $—CH_2—P(O)(OR^8)_2$, $—C(O)R^8$, $—C(O)OR^8$, $—C(R^4)_2—OR^8$, $—C(R^4)_2—OC(O)R^8$, $—C(R^4)_2—OC(O)OR^8$, $—C(R^4)_2—OC(O)N(R^4)(R^{11})$, $—C(O)—C(H)(R^9)—N(R^4)_2$, $—C(O)—C(H)(R^9)—N(H)C(O)R^4$, $—C(O)N(R^4)—C(H)(R^9)—C(O)OH$, or $—C(O)N(R^4)—C(H)(R^9)—C(O)O(C_{1-20}$ aliphatic chain).

In certain embodiments, $R^7$ is $—P(O)(OR^8)_2$ or $—CH_2—P(O)(OR^8)_2$. In certain embodiments, $R^7$ is $—C(O)R^8$, $—C(O)OR^8$, or $—C(R^4)_2—OC(O)OR^8$. In certain embodiments, $R^7$ is $—C(O)R^8$ or $—C(O)OR^8$. In certain embodiments, $R^7$ is $—C(R^4)_2—OC(O)R^8$, $—C(R^4)_2—OC(O)OR^8$, or $—C(R^4)_2—OC(O)N(R^4)(R^{11})$. In certain embodiments, $R^7$ is $—C(R^4)_2—OR^8$, $—C(R^4)_2—OC(O)R^8$, $—C(R^4)_2—OC(O)OR^8$, or $—C(R^4)_2—OC(O)N(R^4)(R^{11})$. In certain embodiments, $R^7$ is $—C(R^4)_2—OC(O)R^8$ or $—C(R^4)_2—OC(O)OR^8$. In certain embodiments, $R^7$ is $—C(R^4)_2—OC(O)OR^8$ or $—C(R^4)_2—OC(O)N(R^4)(R^{11})$. In certain embodiments, $R^7$ is $—C(O)—C(H)(R^9)—N(R^4)_2$ or $—C(O)—C(H)(R^9)—N(H)C(O)R^4$. In certain embodiments, $R^7$ is $—C(O)N(R^4)—C(H)(R^9)—C(O)OH$ or $—C(O)N(R^4)—C(H)(R^9)—C(O)O(C_{1-20}$ aliphatic chain).

In certain embodiments, $R^7$ is $—P(O)(OR^8)_2$. In certain embodiments, $R^7$ is $—CH_2—P(O)(OR^8)_2$. In certain embodiments, $R^7$ is $—C(O)R^8$. In certain embodiments, $R^7$ is $—C(O)OR^8$. In certain embodiment, $R^7$ is $—C(R^4)_2—OR^8$. In certain embodiment, $R^7$ is $—CH_2—OR^8$. In certain embodiment, $R^7$ is $—C(H)(CH_3)—OR^8$. In certain embodiments, $R^7$ is $—C(R^4)_2—OC(O)R^8$. In certain embodiments, $R^7$ is $—CH_2—OC(O)R^8$. In certain embodiments, $R^7$ is $—C(H)(CH_3)—OC(O)R^8$. In certain embodiments, $R^7$ is $—C(R^4)_2—OC(O)OR^8$. In certain embodiments, $R^7$ is $—CH_2—OC(O)OR^8$. In certain embodiments, $R^7$ is $—C(H)(CH_3)—OC(O)OR^8$. In certain embodiments, $R^7$ is $—C(R^4)_2—OC(O)N(R^4)(R^{11})$. In certain embodiments, $R^7$ is $—CH_2—OC(O)N(R^4)(R^{11})$. In certain embodiments, $R^7$ is $—C(H)(CH_3)—OC(O)N(R^4)(R^{11})$. In certain embodiments, $R^7$ is $—C(O)—C(H)(R^9)—N(R^4)_2$. In certain embodiments, $R^7$ is $—C(O)—C(H)(R^9)—NH_2$. In certain embodiments, $R^7$ is $—C(O)—C(H)(R^9)—N(H)C(O)R^4$. In certain embodiments, $R^7$ is $—C(O)—C(H)(R^9)—N(H)C(O)CH_3$. In certain embodiments, $R^7$ is $—C(O)N(R^4)—C(H)(R^9)—C(O)OH$. In certain embodiments, $R^7$ is $—C(O)N(H)—C(H)(R^9)—C(O)OH$. In certain embodiments, $R^7$ is $—C(O)N(R^4)—C(H)(R^9)—C(O)O(C_{1-20}$ aliphatic chain). In certain embodiments, $R^7$ is $—C(O)N(H)—C(H)(R^9)—C(O)O(C_{1-20}$ aliphatic chain). In certain embodiments, $R^7$ is —C(O)N(H)—C(H)($R^9$)—C(O)O($C_{1-6}$ aliphatic chain). In certain embodiments, $R^7$ is —C(O)N(H)—C(H)($R^9$)—C(O)O($C_{7-20}$ aliphatic chain). In certain embodiments, $R^7$ is —C(O)N(H)—C(H)($R^9$)—C(O)O($C_{1-20}$ alkyl). In certain embodiments, $R^7$ is —C(O)N(H)—C(H)($R^9$)—C(O)O($C_{1-6}$ alkyl). In certain embodiments, $R^7$ is —C(O)N(H)—C(H)($R^9$)—C(O)O($C_{7-20}$ alkyl). In certain embodiments, $R^7$ is selected from the groups depicted in the compounds in Tables 4, 5, and 6, below.

As defined generally above, $R^8$ represents independently for each occurrence hydrogen, a $C_{1-20}$ aliphatic chain, $C_{3-7}$ cycloalkyl, phenyl, —$CH_2$-phenyl, or a 5-6 membered monocyclic heteroaryl having 1, 2, or 3 heteroatoms independently selected from nitrogen, oxygen, and sulfur; wherein said phenyl and heteroaryl is each substituted with r occurrences of $R^{10}$.

In some embodiments, $R^8$ represents independently for each occurrence hydrogen, a $C_{1-20}$ aliphatic chain, or $C_{3-7}$ cycloalkyl. In some embodiments, $R^8$ represents independently for each occurrence hydrogen or a $C_{1-20}$ aliphatic chain. In some embodiments, $R^8$ represents independently for each occurrence hydrogen or $C_{1-20}$ alkyl. In some embodiments, $R^8$ represents independently for each occurrence hydrogen or $C_{1-6}$ alkyl. In some embodiments, $R^8$ represents independently for each occurrence hydrogen or $C_{7-20}$ alkyl.

In some embodiments, $R^8$ represents independently for each occurrence phenyl, —$CH_2$— phenyl, or a 5-6 membered monocyclic heteroaryl having 1, 2, or 3 heteroatoms independently selected from nitrogen, oxygen, and sulfur; wherein said phenyl and heteroaryl is each substituted with r occurrences of $R^{10}$. In some embodiments, $R^8$ represents independently for each occurrence phenyl or —$CH_2$-phenyl; wherein each phenyl is substituted with r occurrences of $R^{10}$.

In some embodiments, $R^8$ represents independently for each occurrence a $C_{1-20}$ aliphatic chain, $C_{3-7}$ cycloalkyl, phenyl, or —$CH_2$-phenyl; wherein each phenyl is substituted with r occurrences of $R^{10}$. In some embodiments, $R^8$ represents independently for each occurrence a $C_{1-20}$ aliphatic chain, $C_{3-7}$ cycloalkyl, phenyl, or —$CH_2$-phenyl. In some embodiments, $R^8$ represents independently for each occurrence $C_{1-20}$ alkyl, $C_{3-7}$ cycloalkyl, phenyl, or —$CH_2$-phenyl. In some embodiments, $R^8$ independently for each occurrence $C_{3-7}$ cycloalkyl or phenyl.

In some embodiments, $R^8$ is hydrogen. In some embodiments, $R^8$ represents independently for each occurrence a $C_{1-20}$ aliphatic chain. In some embodiments, $R^8$ represents independently for each occurrence a $C_{1-10}$ aliphatic chain. In some embodiments, $R^8$ represents independently for each occurrence a $C_{1-6}$ aliphatic chain. In some embodiments, $R^8$ represents independently for each occurrence a $C_{7-20}$ aliphatic chain. In some embodiments, $R^8$ represents independently for each occurrence $C_{1-20}$ alkyl. In some embodiments, $R^8$ represents independently for each occurrence $C_{1-10}$ alkyl. In some embodiments, $R^8$ represents independently for each occurrence $C_{1-6}$ alkyl. In some embodiments, $R^8$ represents independently for each occurrence $C_{7-20}$ alkyl.

In some embodiments, $R^8$ represents independently for each occurrence phenyl substituted with r occurrences of $R^{10}$. In some embodiments, $R^8$ is phenyl. In some embodiments, $R^8$ represents independently for each occurrence —$CH_2$-phenyl substituted with r occurrences of $R^{10}$. In some embodiments, $R^8$ is —$CH_2$-phenyl.

In some embodiments, $R^8$ represents independently for each occurrence a 5-6 membered monocyclic heteroaryl having 1, 2, or 3 heteroatoms independently selected from nitrogen, oxygen, and sulfur; wherein said heteroaryl is substituted with r occurrences of $R^{10}$. In some embodiments, $R^8$ represents independently for each occurrence a 5-6 membered monocyclic heteroaryl having 1, 2, or 3 heteroatoms independently selected from nitrogen, oxygen, and sulfur.

In some embodiments, $R^8$ represents independently for each occurrence a 5-membered monocyclic heteroaryl having 1, 2, or 3 heteroatoms independently selected from nitrogen, oxygen, and sulfur. In some embodiments, $R^8$ represents independently for each occurrence a 5-membered monocyclic heteroaryl having 1, 2, or 3 nitrogen atoms. In some embodiments, $R^8$ represents independently for each occurrence a 5-membered monocyclic heteroaryl having 2 heteroatoms independently selected from nitrogen and oxygen. In some embodiments, $R^8$ represents independently for each occurrence a 5-membered monocyclic heteroaryl having 2 heteroatoms independently selected from nitrogen and sulfur. In some embodiments, $R^8$ represents independently for each occurrence a 5-membered monocyclic heteroaryl having one oxygen or sulfur atom. In some embodiments, $R^8$ represents independently for each occurrence a 5-membered monocyclic heteroaryl having 1, 2, or 3 heteroatoms independently selected from nitrogen and sulfur.

In some embodiments, $R^8$ represents independently for each occurrence a 6-membered monocyclic heteroaryl having 1, 2, or 3 heteroatoms independently selected from nitrogen, oxygen, and sulfur. In some embodiments, $R^8$ represents independently for each occurrence a 6-membered monocyclic heteroaryl having 1, 2, or 3 nitrogen atoms. In some embodiments, $R^8$ represents independently for each occurrence a 6-membered monocyclic heteroaryl having 1 or 2 nitrogen atoms.

In certain embodiments, $R^8$ is selected from the groups depicted in the compounds in Tables 4, 5, and 6, below.

As defined generally above, $R^9$ is hydrogen, $C_{1-6}$ alkyl, or —$CH_2$-phenyl. In some embodiments, $R^9$ is hydrogen. In some embodiments, $R^9$ is $C_{1-6}$ alkyl. In some embodiments, $R^9$ is methyl or ethyl. In some embodiments, $R^9$ is methyl. In some embodiments, $R^9$ is ethyl. In some embodiments, $R^9$ is —$CH_2$-phenyl. In certain embodiments, $R^9$ is selected from the groups depicted in the compounds in Tables 4, 5, and 6, below.

As defined generally above, $R^{10}$ represents independently for each occurrence halo, $C_{1-4}$ alkyl, $C_{1-4}$ haloalkyl, or $C_{1-4}$ alkoxyl. In certain embodiments, $R^{10}$ represents independently for each occurrence fluoro, chloro, methyl, trifluoromethyl, or methoxy. In certain embodiments, $R^{10}$ represents independently for each occurrence $C_{1-4}$ alkyl or $C_{1-4}$ haloalkyl. In certain embodiments, $R^{10}$ represents independently for each occurrence halo or $C_{1-4}$ alkoxyl.

In certain embodiments, $R^{10}$ represents independently for each occurrence halo. In certain embodiments, $R^{10}$ represents independently for each occurrence fluoro or chloro. In certain embodiments, $R^{10}$ represents independently for each occurrence $C_{1-4}$ alkyl. In certain embodiments, $R^{10}$ is methyl. In certain embodiments, $R^{10}$ represents independently for each occurrence $C_{1-4}$ haloalkyl. In certain embodiments, $R^{10}$ is trifluoromethyl. In certain embodiments, $R^{10}$ is $C_{1-4}$ alkoxyl. In certain embodiments, $R^{10}$ is methoxy.

In certain embodiments, $R^{10}$ represents independently for each occurrence methyl or ethyl. In certain embodiments, $R^{10}$ represents independently for each occurrence n-propyl or isopropyl. In certain embodiments, $R^{10}$ represents independently for each occurrence methyl or halomethyl. In certain embodiments, $R^{10}$ represents independently for each occurrence methoxy or ethoxy. In certain embodiments, $R^{10}$ is fluoromethyl or fluoroethyl. In certain embodiments, $R^{10}$ is 2-fluoroethyl.

In certain embodiments, $R^{10}$ is selected from the groups depicted in the compounds in Tables 4, 5, and 6, below.

As defined generally above, $R^{11}$ is $C_{1-6}$ alkyl, phenyl, —$CH_2$-phenyl, or hydrogen; or $R^{11}$ and $R^4$ are taken together with the nitrogen atom to which they are attached to form a 4-7 membered saturated ring having one nitrogen atom and optionally one additional heteroatom selected from nitrogen, oxygen, and sulfur.

In certain embodiments, $R^{11}$ is $C_{1-6}$ alkyl, phenyl, —$CH_2$-phenyl, or hydrogen. In certain embodiments, $R^{11}$ is hydrogen. In certain embodiments, $R^{11}$ is $C_{1-6}$ alkyl. In certain embodiments, $R^{11}$ is methyl. In certain embodiments, $R^{11}$ is ethyl. In certain embodiments, $R^{11}$ is phenyl. In certain embodiments, $R^{11}$ is —$CH_2$-phenyl.

In certain embodiments, $R^{11}$ and $R^4$ are taken together with the nitrogen atom to which they are attached to form a 4-7 membered saturated ring having one nitrogen atom and optionally one additional heteroatom selected from nitrogen, oxygen, and sulfur. In certain embodiments, $R^{11}$ and $R^4$ are taken together with the nitrogen atom to which they are attached to form a 5-membered saturated ring having one nitrogen atom and optionally one additional heteroatom selected from nitrogen, oxygen, and sulfur. In certain embodiments, $R^{11}$ and $R^4$ are taken together with the nitrogen atom to which they are attached to form a 6-membered saturated ring having one nitrogen atom and optionally one additional heteroatom selected from nitrogen, oxygen, and sulfur. In certain embodiments, $R^{11}$ and $R^4$ are taken together with the nitrogen atom to which they are attached to form a 7-membered saturated ring having one nitrogen atom and optionally one additional heteroatom selected from nitrogen, oxygen, and sulfur.

In certain embodiments, $R^{11}$ and $R^4$ are taken together with the nitrogen atom to which they are attached to form a 5- or 6-membered saturated ring having one nitrogen atom. In certain embodiments, $R^{11}$ and $R^4$ are taken together with the nitrogen atom to which they are attached to form a 5- or 6-membered saturated ring having one nitrogen atom and optionally one additional nitrogen heteroatom. In certain embodiments, $R^{11}$ and $R^4$ are taken together with the nitrogen atom to which they are attached to form a 5- or 6-membered saturated ring having one nitrogen atom and optionally one additional oxygen heteroatom. In certain embodiments, $R^{11}$ and $R^4$ are taken together with the nitrogen atom to which they are attached to form a 5- or 6-membered saturated ring having one nitrogen atom and optionally one additional sulfur heteroatom. In certain embodiments, $R^{11}$ and $R^4$ are taken together with the nitrogen atom to which they are attached to form a morpholine or piperazine ring.

In certain embodiments, $R^{11}$ is selected from the groups depicted in the compounds in Tables 4, 5, and 6, below.

As defined generally above, $R^{12}$ is (i) —C(H)($R^9$)—C(O)$OR^4$, or (ii) phenyl substituted with 0, 1, or 2 substituents independently selected from hydroxyl and —($C_{0-2}$ alkylene)-C(O)$OR^4$. In certain embodiments, $R^{12}$ is —C(H)($R^9$)—C(O)$OR^4$. In certain embodiments, $R^{12}$ is phenyl substituted with 0, 1, or 2 substituents independently selected from hydroxyl and —($C_{0-2}$ alkylene)-C(O)$OR^4$. In certain embodiments, $R^{12}$ is phenyl substituted with 0 or 1 substituents independently selected from hydroxyl and —($C_{0-2}$ alkylene)-C(O)$OR^4$. In certain embodiments, $R^{12}$ is phenyl substituted with 1 or 2 substituents independently selected from hydroxyl and —($C_{0-2}$ alkylene)-C(O)$OR^4$. In certain embodiments, $R^{12}$ is phenyl substituted with one hydroxyl and one —($C_{0-2}$ alkylene)-C(O)$OR^4$. In certain embodiments, $R^{12}$ is phenyl substituted with one hydroxyl and one —C(O)$OR^4$. In certain embodiments, $R^{12}$ is

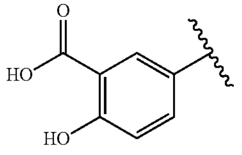

or

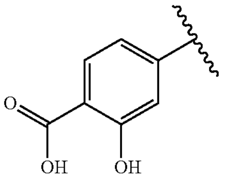

In certain embodiments, $R^{12}$ is selected from the groups depicted in the compounds in Tables 4, 5, and 6, below.

As defined generally above, m is 0, 1, 2, or 3. In certain embodiments, m is 0. In certain embodiments, m is 1. In certain embodiments, m is 2. In certain embodiments, m is 3. In certain embodiments, m is 0 or 1. In certain embodiments, m is 1 or 2. In certain embodiments, m is 2 or 3. In certain embodiments, m is 0, 1, or 2. In certain embodiments, m is 1, 2, or 3. In certain embodiments, m is selected from the values represented in the compounds in Tables 4, 5, and 6, below.

As defined generally above, n is 0, 1, 2, or 3. In certain embodiments, n is 0. In certain embodiments, n is 1. In certain embodiments, n is 2. In certain embodiments, n is 3. In certain embodiments, n is 0 or 1. In certain embodiments, n is 1 or 2. In certain embodiments, n is 2 or 3. In certain embodiments, n is 0, 1, or 2. In certain embodiments, n is 1, 2, or 3. In certain embodiments, n is selected from the values represented in the compounds in Tables 4, 5, and 6, below.

As defined generally above, p is 0, 1, or 2. In certain embodiments, p is 0. In certain embodiments, p is 1. In certain embodiments, p is 2. In certain embodiments, p is 0 or 1. In certain embodiments, p is 1 or 2. In certain embodiments, p is selected from the values represented in the compounds in Tables 4, 5, and 6, below.

In certain embodiments, p and q are 0.

As defined generally above, q is 0, 1, or 2. In certain embodiments, q is 0. In certain embodiments, q is 1. In certain embodiments, q is 2. In certain embodiments, q is 0 or 1. In certain embodiments, q is 1 or 2. In certain embodiments, q is selected from the values represented in the compounds in Tables 4, 5, and 6, below.

As defined generally above, r is 0, 1, or 2. In certain embodiments, r is 0. In certain embodiments, r is 1. In certain embodiments, r is 2. In certain embodiments, r is 0 or 1. In certain embodiments, r is 1 or 2. In certain embodiments, r is selected from the values represented in the compounds in Tables 4, 5, and 6, below.

The description above describes multiple embodiments relating to compounds of Formula II. The patent application specifically contemplates all combinations of the embodiments.

Another aspect of the invention provides a compound represented by Formula II-A:

(II-A)

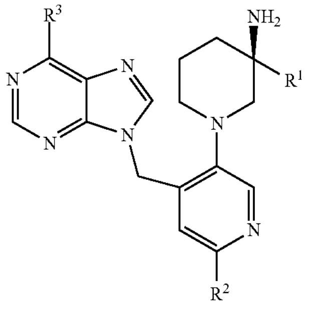

or a pharmaceutically acceptable salt thereof, wherein:

$R^1$ is selected from the group consisting of:

a. $C_{1-6}$ alkyl substituted with (i) 0, 1, 2, or 3 halo, and (ii) 0 or 1 occurrence of hydroxyl, $C_{1-6}$ alkoxyl, $C_{1-6}$ haloalkoxyl, —O—($C_{3-5}$ cycloalkyl), oxo, —C(O)$OR^4$, or —C(O)N($R^4$)$_2$;

b. —C(O)$OR^4$, —C(O)N($R^4$)$_2$, or —C(O)—($C_{0-4}$ alkylene)-($C_{3-7}$ cycloalkyl);

c. —($C_{0-2}$ alkylene)-(5-6 membered monocyclic heteroaryl having 1, 2, or 3 heteroatoms independently selected from nitrogen, oxygen, and sulfur), wherein said heteroaryl is substituted with m occurrences of $R^5$; and d. hydrogen;

$R^2$ is phenyl; a 5-6 membered monocyclic heteroaryl having 1, 2, or 3 heteroatoms independently selected from nitrogen, oxygen, and sulfur; an 8-10 membered bicyclic heteroaryl having 1, 2, or 3 heteroatoms independently selected from nitrogen, oxygen, and sulfur; or $C_{3-7}$ cycloalkyl; each of which is substituted with n occurrences of $R^6$;

$R^3$ is —N(H)$R^7$ or —N═N—$R^{12}$.

$R^4$ represents independently for each occurrence $C_{1-6}$ alkyl or hydrogen, or two occurrences of $R^4$ attached to the same nitrogen atom are taken together with said nitrogen atom to form a 4-7 membered saturated ring having one nitrogen atom;

$R^5$ and $R^6$ each represents independently for each occurrence halo, $C_{1-4}$ alkyl, $C_{1-4}$ haloalkyl, $C_{1-4}$ hydroxyalkyl, $C_{3-7}$ cycloalkyl, $C_{1-4}$ alkoxyl, $C_{1-4}$ haloalkoxyl, hydroxyl, or cyano;

$R^7$ is —P(O)($OR^8$)$_2$, —$CH_2$—P(O)($OR^8$)$_2$, —C(O)$R^8$, —C(O)$OR^8$, —C($R^4$)$_2$—$OR^8$, —C($R^4$)$_2$—OC(O)$R^8$, —C($R^4$)$_2$—OC(O)$OR^8$, —C($R^4$)$_2$—OC(O)N($R^4$)($R^{11}$), —C(O)—C(H)($R^9$)—N($R^4$)$_2$, —C(O)—C(H)($R^9$)—N(H)C(O)$R^4$, —C(O)N($R^4$)—C(H)($R^9$)—C(O)OH, or —C(O)N($R^4$)—C(H)($R^9$)—C(O)O($C_{1-20}$ aliphatic chain);

$R^8$ represents independently for each occurrence hydrogen, a $C_{1-20}$ aliphatic chain, $C_{3-7}$ cycloalkyl, phenyl, —$CH_2$-phenyl, or a 5-6 membered monocyclic heteroaryl having 1, 2, or 3 heteroatoms independently selected from nitrogen, oxygen, and sulfur; wherein said phenyl and heteroaryl is each substituted with r occurrences of $R^{10}$;

$R^9$ is hydrogen, $C_{1-6}$ alkyl, or —$CH_2$-phenyl;

$R^{10}$ represents independently for each occurrence halo, $C_{1-4}$ alkyl, $C_{1-4}$ haloalkyl, or $C_{1-4}$ alkoxyl;

$R^{11}$ is $C_{1-6}$ alkyl, phenyl, —$CH_2$-phenyl, or hydrogen; or $R^{11}$ and $R^4$ are taken together with the nitrogen atom to which they are attached to form a 4-7 membered saturated ring having one nitrogen atom and optionally one additional heteroatom selected from nitrogen, oxygen, and sulfur;

$R^{12}$ is (i) —C(H)($R^9$)—C(O)$OR^4$, or (ii) phenyl substituted with 0, 1, or 2 substituents independently selected from hydroxyl and —($C_{0-2}$ alkylene)-C(O)$OR^4$;

m and n are each independently 0, 1, 2, or 3; and r is 0, 1, or 2.

The definitions of variables in Formula II-A above encompass multiple chemical groups. The application contemplates embodiments where, for example, i) the definition of a variable is a single chemical group selected from those chemical groups set forth above, ii) the definition of a variable is a collection of two or more of the chemical groups selected from those set forth above, and iii) the compound is defined by a combination of variables in which the variables are defined by (i) or (ii).

In certain embodiments, the compound is a compound of Formula II-A.

As defined generally above, $R^1$ is selected from the group consisting of:

a. $C_{1-6}$ alkyl substituted with (i) 0, 1, 2, or 3 halo, and (ii) 0 or 1 occurrence of hydroxyl, $C_{1-6}$ alkoxyl, $C_{1-6}$ haloalkoxyl, —O—($C_{3-5}$ cycloalkyl), oxo, —C(O)$OR^4$, or —C(O)N($R^4$)$_2$;

b. —C(O)$OR^4$, —C(O)N($R^4$)$_2$, or —C(O)—($C_{0-4}$ alkylene)-($C_{3-7}$ cycloalkyl);

c. —($C_{0-2}$ alkylene)-(5-6 membered monocyclic heteroaryl having 1, 2, or 3 heteroatoms independently selected from nitrogen, oxygen, and sulfur), wherein said heteroaryl is substituted with m occurrences of $R^5$; and d. hydrogen.

In certain embodiments, $R^1$ is $C_{1-6}$ alkyl substituted with (i) 0, 1, 2, or 3 halo, and (ii) 0 or 1 occurrence of hydroxyl, $C_{1-6}$ alkoxyl, $C_{1-6}$ haloalkoxyl, —O—($C_{3-5}$ cycloalkyl), oxo, —C(O)$OR^4$, or —C(O)N($R^4$)$_2$. In certain embodiments, $R^1$ is $C_{1-6}$ alkyl substituted with (i) 1, 2, or 3 halo, and (ii) 0 or 1 occurrence of hydroxyl. In certain embodiments, $R^1$ is $C_{1-6}$ alkyl substituted with (i) 0, 1, 2, or 3 halo, and (ii) 1 occurrence of hydroxyl. In certain embodiments, $R^1$ is

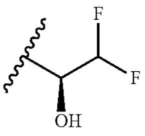 or 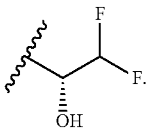

In certain embodiments, $R^1$ is —$CH_2CHF_2$.

In certain embodiments, $R^1$ is —C(O)$OR^4$, —C(O)N($R^4$)$_2$, or —C(O)—($C_{0-4}$ alkylene)-($C_{3-7}$ cycloalkyl). In certain embodiments, $R^1$ is —C(O)$OR^4$. In certain embodiments, $R^1$ is —C(O)N($R^4$)$_2$. In certain embodiments, $R^1$ is —C(O)—($C_{0-4}$ alkylene)-($C_{3-7}$ cycloalkyl). In certain embodiments, $R^1$ is —C(O)—($C_{1-4}$ alkylene)-($C_{3-7}$ cycloalkyl). In certain embodiments, $R^1$ is —C(O)—($C_{3-7}$ cycloalkyl).

In certain embodiments, $R^1$ is —($C_{0-2}$ alkylene)-(5-6 membered monocyclic heteroaryl having 1, 2, or 3 heteroatoms independently selected from nitrogen, oxygen, and sulfur), wherein said heteroaryl is substituted with m occurrences of $R^5$. In certain embodiments, $R^1$ is a 5-6 membered monocyclic heteroaryl having 1, 2, or 3 heteroatoms independently selected from nitrogen, oxygen, and sulfur, wherein said heteroaryl is substituted with m occurrences of $R^5$. In certain embodiments, $R^1$ is a 5-membered monocyclic heteroaryl having 1, 2, or 3 heteroatoms independently selected from nitrogen, oxygen, and sulfur, wherein said heteroaryl is substituted with m occurrences of $R^5$. In certain embodiments, $R^1$ is a 6-membered monocyclic heteroaryl having 1 or 2 nitrogen atoms, wherein said heteroaryl is substituted with m occurrences of $R^5$. In certain embodiments, $R^1$ is pyridinyl substituted with m occurrences of $R^5$. In certain embodiments, $R^1$ is pyridin-2-yl substituted with m occurrences of $R^5$. In certain embodiments, $R^1$ is

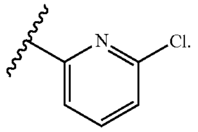 [SMILES: *c1cccc(Cl)n1]

In certain embodiments, $R^1$ is —($C_{1-2}$ alkylene)-(5-6 membered monocyclic heteroaryl having 1, 2, or 3 heteroatoms independently selected from nitrogen, oxygen, and sulfur), wherein said heteroaryl is substituted with m occurrences of $R^5$. In certain embodiments, $R^1$ is —($C_{1-2}$ alkylene)-(5-membered monocyclic heteroaryl having 1, 2, or 3 heteroatoms independently selected from nitrogen, oxygen, and sulfur), wherein said heteroaryl is substituted with m occurrences of $R^5$. In certain embodiments, $R^1$ is —($C_{1-2}$ alkylene)-(6-membered monocyclic heteroaryl having 1 or 2 nitrogen atoms), wherein said heteroaryl is substituted with m occurrences of $R^5$.

As defined generally above, $R^2$ is phenyl; a 5-6 membered monocyclic heteroaryl having 1, 2, or 3 heteroatoms independently selected from nitrogen, oxygen, and sulfur; an 8-10 membered bicyclic heteroaryl having 1, 2, or 3 heteroatoms independently selected from nitrogen, oxygen, and sulfur; or $C_{3-7}$ cycloalkyl; each of which is substituted with n occurrences of $R^6$.

In certain embodiments, $R^2$ is phenyl substituted with n occurrences of $R^6$. In certain embodiments, $R^2$ is

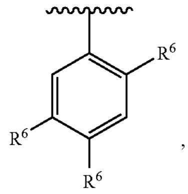
,
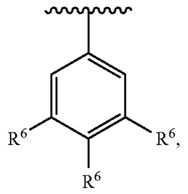
or
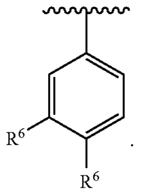

In certain embodiments, $R^2$ is

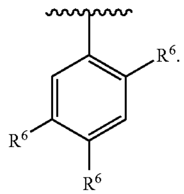

In certain embodiments, $R^2$ is

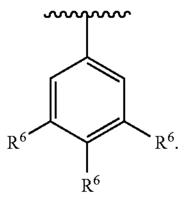

In certain embodiments, $R^2$ is

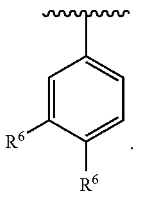

In certain embodiments, $R^2$ is

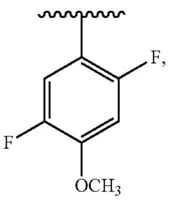
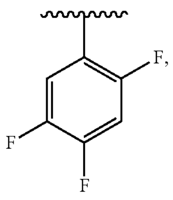
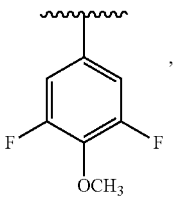
, or
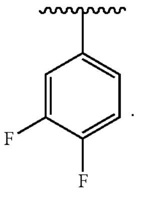

In certain embodiments, $R^2$ is

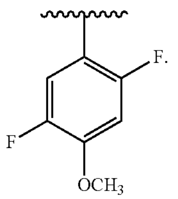 [SMILES: *c1cc(F)c(OC)cc1F]

In certain embodiments, $R^2$ is

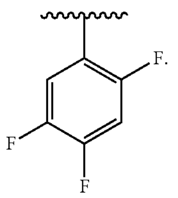 [SMILES: *c1cc(F)c(F)cc1F]

In certain embodiments, $R^2$ is

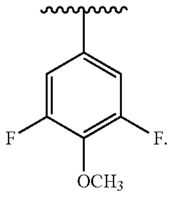

In certain embodiments, $R^2$ is

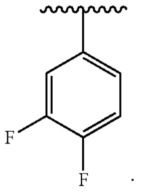 [SMILES: *c1ccc(F)c(F)c1]

In certain embodiments, $R^2$ is a 5-6 membered monocyclic heteroaryl having 1, 2, or 3 heteroatoms independently selected from nitrogen, oxygen, and sulfur; wherein said heteroaryl is substituted with n occurrences of $R^6$. In certain embodiments, $R^2$ is a 5-membered monocyclic heteroaryl having 1, 2, or 3 heteroatoms independently selected from nitrogen, oxygen, and sulfur; wherein said heteroaryl is substituted with n occurrences of $R^6$. In certain embodiments, $R^2$ is a 6-membered monocyclic heteroaryl having 1 or 2 nitrogen atoms; wherein said heteroaryl is substituted with n occurrences of $R^6$. In certain embodiments, $R^2$ is pyridinyl substituted with n occurrences of $R^6$. In certain embodiments, $R^2$ is pyridin-2-yl substituted with n occurrences of $R^6$. In certain embodiments, $R^2$ is

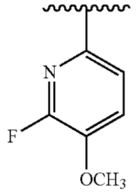

or

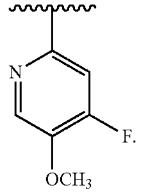

In certain embodiments, $R^2$ is an 8-10 membered bicyclic heteroaryl having 1, 2, or 3 heteroatoms independently selected from nitrogen, oxygen, and sulfur; wherein said heteroaryl is substituted with n occurrences of $R^6$. In certain embodiments, $R^2$ is a 9-membered bicyclic heteroaryl having 1, 2, or 3 heteroatoms independently selected from nitrogen, oxygen, and sulfur; wherein said heteroaryl is substituted with n occurrences of $R^6$. In certain embodiments, $R^2$ is an 8-10 membered bicyclic heteroaryl having 1 or 2 nitrogen atoms; wherein said heteroaryl is substituted with n occurrences of $R^6$. In certain embodiments, $R^2$ is a 9-membered bicyclic heteroaryl having 1 or 2 nitrogen atoms; wherein said heteroaryl is substituted with n occurrences of $R^6$. In certain embodiments, $R^2$ is indazolyl substituted with n occurrences of $R^6$. In certain embodiments, $R^2$ is indazol-5-yl substituted with n occurrences of $R^6$. In certain embodiments, $R^2$ is

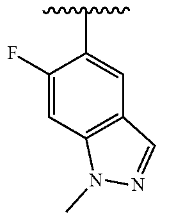

or

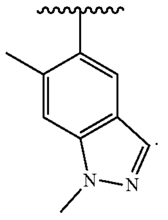

In certain embodiments, $R^2$ is $C_{3-7}$ cycloalkyl substituted with n occurrences of $R^6$. In certain embodiments, $R^2$ is $C_{3-5}$ cycloalkyl substituted with n occurrences of $R^6$. In certain embodiments, $R^2$ is cyclopropyl substituted with n occurrences of $R^6$. In certain embodiments, $R^2$ is $C_{3-7}$ cycloalkyl. In certain embodiments, $R^2$ is $C_{3-5}$ cycloalkyl. In certain embodiments, $R^2$ is cyclopropyl.

As defined generally above, $R^3$ is —N(H)$R^7$ or —N═N—$R^{12}$. In certain embodiments, $R^3$ is —N(H)$R^7$. In certain embodiments, $R^3$ is —N═N—$R^{12}$.

As defined generally above, $R^4$ represents independently for each occurrence $C_{1-6}$ alkyl or hydrogen; or two occurrences of $R^4$ attached to the same nitrogen atom are taken together with said nitrogen atom to form a 4-7 membered saturated ring having one nitrogen atom; or $R^9$ and $R^4$ are taken together with the nitrogen atom to which they are attached to form a 4-7 membered saturated ring having one nitrogen atom and optionally one additional heteroatom selected from nitrogen, oxygen, and sulfur.

In certain embodiments, $R^4$ represents independently for each occurrence $C_{1-6}$ alkyl or hydrogen. In certain embodiments, $R^4$ represents independently for each occurrence $C_{1-4}$ alkyl or hydrogen. In certain embodiments, $R^4$ represents independently for each occurrence methyl or hydrogen. In certain embodiments, $R^4$ represents independently for each occurrence $C_{1-6}$ alkyl. In certain embodiments, $R^4$ represents independently for each occurrence $C_{1-4}$ alkyl. In certain embodiments, $R^4$ is methyl. In certain embodiments, $R^4$ is hydrogen.

In certain embodiments, two occurrences of $R^4$ attached to the same nitrogen atom are taken together with said nitrogen atom to form a 4-7 membered saturated ring having one nitrogen atom. In certain embodiments, two occurrences of $R^4$ attached to the same nitrogen atom are taken together with said nitrogen atom to form a 5-6 membered saturated ring having one nitrogen atom.

As defined generally above, $R^5$ represents independently for each occurrence halo, $C_{1-4}$ alkyl, $C_{1-4}$ haloalkyl, $C_{1-4}$ hydroxyalkyl, $C_{3-7}$ cycloalkyl, $C_{1-4}$ alkoxyl, $C_{1-4}$ haloalkoxyl, hydroxyl, or cyano.

In certain embodiments, $R^5$ represents independently for each occurrence halo, $C_{1-4}$ alkyl, $C_{1-4}$ haloalkyl, or $C_{1-4}$ alkoxyl. In certain embodiments, $R^5$ represents independently for each occurrence fluoro, chloro, methyl, trifluoromethyl, or methoxy. In certain embodiments, $R^5$ represents independently for each occurrence halo, $C_{1-4}$ alkyl, $C_{1-4}$ haloalkyl, $C_{1-4}$ hydroxyalkyl, or $C_{3-7}$ cycloalkyl. In certain embodiments, $R^5$ represents independently for each occurrence $C_{1-4}$ alkyl, $C_{1-4}$ haloalkyl, $C_{1-4}$ hydroxyalkyl, or $C_{3-7}$ cycloalkyl. In certain embodiments, $R^5$ represents independently for each occurrence halo, $C_{1-4}$ alkoxyl, $C_{1-4}$ haloalkoxyl, hydroxyl, or cyano. In certain embodiments, $R^5$ represents independently for each occurrence $C_{1-4}$ alkoxyl, $C_{1-4}$ haloalkoxyl, or hydroxyl.

In certain embodiments, $R^5$ represents independently for each occurrence halo. In certain embodiments, $R^5$ represents independently for each occurrence fluoro or chloro. In certain embodiments, $R^5$ represents independently for each occurrence $C_{1-4}$ alkyl. In certain embodiments, $R^5$ is methyl. In certain embodiments, $R^5$ represents independently for each occurrence $C_{1-4}$ haloalkyl. In certain embodiments, $R^5$ is trifluoromethyl. In certain embodiments, $R^5$ represents independently for each occurrence $C_{1-4}$ hydroxyalkyl. In certain embodiments, $R^5$ represents independently for each occurrence $C_{3-7}$ cycloalkyl. In certain embodiments, $R^5$ represents independently for each occurrence $C_{1-4}$ alkoxyl. In certain embodiments, $R^5$ is methoxy. In certain embodiments, $R^5$ represents independently for each occurrence $C_{1-4}$ haloalkoxyl. In certain embodiments, $R^5$ is hydroxyl. In certain embodiments, $R^5$ is cyano.

As defined generally above, $R^6$ represents independently for each occurrence halo, $C_{1-4}$ alkyl, $C_{1-4}$ haloalkyl, $C_{1-4}$ hydroxyalkyl, $C_{3-7}$ cycloalkyl, $C_{1-4}$ alkoxyl, $C_{1-4}$ haloalkoxyl, hydroxyl, or cyano.

In certain embodiments, $R^6$ represents independently for each occurrence halo, $C_{1-4}$ alkyl, $C_{1-4}$ haloalkyl, or $C_{1-4}$ alkoxyl. In certain embodiments, $R^6$ represents independently for each occurrence fluoro, chloro, methyl, trifluoromethyl, or methoxy. In certain embodiments, $R^6$ represents independently for each occurrence halo, $C_{1-4}$ alkyl, $C_{1-4}$ haloalkyl, $C_{1-4}$ hydroxyalkyl, or $C_{3-7}$ cycloalkyl. In certain embodiments, $R^6$ represents independently for each occurrence $C_{1-4}$ alkyl, $C_{1-4}$ haloalkyl, $C_{1-4}$ hydroxyalkyl, or $C_{3-7}$ cycloalkyl. In certain embodiments, $R^6$ represents independently for each occurrence halo, $C_{1-4}$ alkoxyl, $C_{1-4}$ haloalkoxyl, hydroxyl, or cyano. In certain embodiments, $R^6$ represents independently for each occurrence $C_{1-4}$ alkoxyl, $C_{1-4}$ haloalkoxyl, or hydroxyl.

In certain embodiments, $R^6$ represents independently for each occurrence halo. In certain embodiments, $R^6$ represents independently for each occurrence fluoro or chloro. In certain embodiments, $R^6$ represents independently for each occurrence $C_{1-4}$ alkyl. In certain embodiments, $R^6$ is methyl. In certain embodiments, $R^6$ represents independently for each occurrence $C_{1-4}$ haloalkyl. In certain embodiments, $R^6$ is trifluoromethyl. In certain embodiments, $R^6$ represents independently for each occurrence $C_{1-4}$ hydroxyalkyl. In certain embodiments, $R^6$ represents independently for each occurrence $C_{3-7}$ cycloalkyl. In certain embodiments, $R^6$ represents independently for each occurrence $C_{1-4}$ alkoxyl. In certain embodiments, $R^6$ is methoxy. In certain embodiments, $R^6$ represents independently for each occurrence $C_{1-4}$ haloalkoxyl. In certain embodiments, $R^6$ is hydroxyl. In certain embodiments, $R^6$ is cyano.

As defined generally above, $R^7$ is $—P(O)(OR^8)_2$, $—CH_2—P(O)(OR^8)_2$, $—C(O)R^8$, $—C(O)OR^8$, $—C(R^4)_2—OR^8$, $—C(R^4)_2—OC(O)R^8$, $—C(R^4)_2—OC(O)OR^8$, $—C(R^4)_2—OC(O)N(R^4)(R^{11})$, $—C(O)—C(H)(R^9)—N(R^4)_2$, $—C(O)—C(H)(R^9)—N(H)C(O)R^4$, $—C(O)N(R^4)—C(H)(R^9)—C(O)OH$, or $—C(O)N(R^4)—C(H)(R^9)—C(O)O(C_{1-20}$ aliphatic chain).

In certain embodiments, $R^7$ is $—P(O)(OR^8)_2$ or $—CH_2—P(O)(OR^8)_2$. In certain embodiments, $R^7$ is $—C(O)R^8$, $—C(O)OR^8$, or $—C(R^4)_2—OC(O)OR^8$. In certain embodiments, $R^7$ is $—C(O)R^8$ or $—C(O)OR^8$. In certain embodiments, $R^7$ is $—C(R^4)_2—OC(O)R^8$, $—C(R^4)_2—OC(O)OR^8$, or $—C(R^4)_2—OC(O)N(R^4)(R^{11})$. In certain embodiments, $R^7$ is $—C(R^4)_2—OR^8$, $—C(R^4)_2—OC(O)R^8$, $—C(R^4)_2—OC(O)OR^8$, or $—C(R^4)_2—OC(O)N(R^4)(R^{11})$. In certain embodiments, $R^7$ is $—C(R^4)_2—OC(O)R^8$ or $—C(R^4)_2—OC(O)OR^8$. In certain embodiments, $R^7$ is $—C(R^4)_2—OC(O)OR^8$ or $—C(R^4)_2—OC(O)N(R^4)(R^{11})$. In certain embodiments, $R^7$ is $—C(O)—C(H)(R^9)—N(R^4)_2$ or $—C(O)—C(H)(R^9)—N(H)C(O)R^4$. In certain embodiments, $R^7$ is $—C(O)N(R^4)—C(H)(R^9)—C(O)OH$ or $—C(O)N(R^4)—C(H)(R^9)—C(O)O(C_{1-20}$ aliphatic chain).

In certain embodiments, $R^7$ is $—P(O)(OR^8)_2$. In certain embodiments, $R^7$ is $—CH_2—P(O)(OR^8)_2$. In certain embodiments, $R^7$ is $—C(O)R^8$. In certain embodiments, $R^7$ is $—C(O)OR^8$. In certain embodiment, $R^7$ is $—C(R^4)_2—OR^8$. In certain embodiment, $R^7$ is $—CH_2—OR^8$. In certain embodiment, $R^7$ is $—C(H)(CH_3)—OR^8$. In certain embodiments, $R^7$ is $—C(R^4)_2—OC(O)R^8$. In certain embodiments, $R^7$ is $—CH_2—OC(O)R^8$. In certain embodiments, $R^7$ is $—C(H)(CH_3)—OC(O)R^8$. In certain embodiments, $R^7$ is $—C(R^4)_2—OC(O)OR^8$. In certain embodiments, $R^7$ is $—CH_2—OC(O)OR^8$. In certain embodiments, $R^7$ is $—C(H)(CH_3)—OC(O)OR^8$. In certain embodiments, $R^7$ is $—C(R^4)_2—OC(O)N(R^4)(R^{11})$. In certain embodiments, $R^7$ is $—CH_2—OC(O)N(R^4)(R^{11})$. In certain embodiments, $R^7$ is $—C(H)(CH_3)—OC(O)N(R^4)(R^{11})$. In certain embodiments, $R^7$ is $—C(O)—C(H)(R^9)—N(R^4)_2$. In certain embodiments, $R^7$ is $—C(O)—C(H)(R^9)—NH_2$. In certain embodiments, $R^7$ is $—C(O)—C(H)(R^9)—N(H)C(O)R^4$. In certain embodiments, $R^7$ is $—C(O)—C(H)(R^9)—N(H)C(O)CH_3$. In certain embodiments, $R^7$ is $—C(O)N(R^4)—C(H)(R^9)—C(O)OH$. In certain embodiments, $R^7$ is $—C(O)N(H)—C(H)(R^9)—C(O)OH$. In certain embodiments, $R^7$ is $—C(O)N(R^4)—C(H)(R^9)—C(O)O(C_{1-20}$ aliphatic chain). In certain embodiments, $R^7$ is $—C(O)N(H)—C(H)(R^9)—C(O)O(C_{1-20}$ aliphatic chain). In certain embodiments, $R^7$ is $—C(O)N(H)—C(H)(R^9)—C(O)O(C_{1-6}$ aliphatic chain). In certain embodiments, $R^7$ is $—C(O)N(H)—C(H)(R^9)—C(O)O(C_{7-20}$ aliphatic chain). In certain embodiments, $R^7$ is $—C(O)N(H)—C(H)(R^9)—C(O)O(C_{1-20}$ alkyl). In certain embodiments, $R^7$ is $—C(O)N(H)—C(H)(R^9)—C(O)O(C_{1-6}$ alkyl). In certain embodiments, $R^7$ is $—C(O)N(H)—C(H)(R^9)—C(O)O(C_{7-20}$ alkyl).

As defined generally above, $R^8$ represents independently for each occurrence hydrogen, a $C_{1-20}$ aliphatic chain, $C_{3-7}$ cycloalkyl, phenyl, $—CH_2$-phenyl, or a 5-6 membered monocyclic heteroaryl having 1, 2, or 3 heteroatoms independently selected from nitrogen, oxygen, and sulfur; wherein said phenyl and heteroaryl is each substituted with r occurrences of $R^{10}$.

In some embodiments, $R^8$ represents independently for each occurrence hydrogen, a $C_{1-20}$ aliphatic chain, or $C_{3-7}$ cycloalkyl. In some embodiments, $R^8$ represents independently for each occurrence hydrogen or a $C_{1-20}$ aliphatic chain. In some embodiments, $R^8$ represents independently for each occurrence hydrogen or $C_{1-20}$ alkyl. In some embodiments, $R^8$ represents independently for each occurrence hydrogen or $C_{1-6}$ alkyl. In some embodiments, $R^8$ represents independently for each occurrence hydrogen or $C_{7-20}$ alkyl.

In some embodiments, $R^8$ represents independently for each occurrence phenyl, $—CH_2—$ phenyl, or a 5-6 membered monocyclic heteroaryl having 1, 2, or 3 heteroatoms independently selected from nitrogen, oxygen, and sulfur; wherein said phenyl and heteroaryl is each substituted with r occurrences of $R^{10}$. In some embodiments, $R^8$ represents independently for each occurrence phenyl or $—CH_2$-phenyl; wherein each phenyl is substituted with r occurrences of $R^{10}$.

In some embodiments, $R^8$ represents independently for each occurrence a $C_{1-20}$ aliphatic chain, $C_{3-7}$ cycloalkyl, phenyl, or $—CH_2$-phenyl; wherein each phenyl is substituted with r occurrences of $R^{10}$. In some embodiments, $R^8$ represents independently for each occurrence a $C_{1-20}$ aliphatic chain, $C_{3-7}$ cycloalkyl, phenyl, or $—CH_2$-phenyl. In some embodiments, $R^8$ represents independently for each occurrence $C_{1-20}$ alkyl, $C_{3-7}$ cycloalkyl, phenyl, or —$CH_2$-phenyl. In some embodiments, $R^8$ independently for each occurrence $C_{3-7}$ cycloalkyl or phenyl.

In some embodiments, $R^8$ is hydrogen. In some embodiments, $R^8$ represents independently for each occurrence a $C_{1-20}$ aliphatic chain. In some embodiments, $R^8$ represents independently for each occurrence a $C_{1-10}$ aliphatic chain. In some embodiments, $R^8$ represents independently for each occurrence a $C_{1-6}$ aliphatic chain. In some embodiments, $R^8$ represents independently for each occurrence a $C_{7-20}$ aliphatic chain. In some embodiments, $R^8$ represents independently for each occurrence $C_{1-20}$ alkyl. In some embodiments, $R^8$ represents independently for each occurrence $C_{1-10}$ alkyl. In some embodiments, $R^8$ represents independently for each occurrence $C_{1-6}$ alkyl. In some embodiments, $R^8$ represents independently for each occurrence $C_{7-20}$ alkyl.

In some embodiments, $R^8$ represents independently for each occurrence phenyl substituted with r occurrences of $R^{10}$. In some embodiments, $R^8$ is phenyl. In some embodiments, $R^8$ represents independently for each occurrence —$CH_2$-phenyl substituted with r occurrences of $R^{10}$. In some embodiments, $R^8$ is —$CH_2$-phenyl.

In some embodiments, $R^8$ represents independently for each occurrence a 5-6 membered monocyclic heteroaryl having 1, 2, or 3 heteroatoms independently selected from nitrogen, oxygen, and sulfur; wherein said heteroaryl is substituted with r occurrences of $R^{10}$. In some embodiments, $R^8$ represents independently for each occurrence a 5-6 membered monocyclic heteroaryl having 1, 2, or 3 heteroatoms independently selected from nitrogen, oxygen, and sulfur.

In some embodiments, $R^8$ represents independently for each occurrence a 5-membered monocyclic heteroaryl having 1, 2, or 3 heteroatoms independently selected from nitrogen, oxygen, and sulfur. In some embodiments, $R^8$ represents independently for each occurrence a 5-membered monocyclic heteroaryl having 1, 2, or 3 nitrogen atoms. In some embodiments, $R^8$ represents independently for each occurrence a 5-membered monocyclic heteroaryl having 2 heteroatoms independently selected from nitrogen and oxygen. In some embodiments, $R^8$ represents independently for each occurrence a 5-membered monocyclic heteroaryl having 2 heteroatoms independently selected from nitrogen and sulfur. In some embodiments, $R^8$ represents independently for each occurrence a 5-membered monocyclic heteroaryl having one oxygen or sulfur atom. In some embodiments, $R^8$ represents independently for each occurrence a 5-membered monocyclic heteroaryl having 1, 2, or 3 heteroatoms independently selected from nitrogen and sulfur.

In some embodiments, $R^8$ represents independently for each occurrence a 6-membered monocyclic heteroaryl having 1, 2, or 3 heteroatoms independently selected from nitrogen, oxygen, and sulfur. In some embodiments, $R^8$ represents independently for each occurrence a 6-membered monocyclic heteroaryl having 1, 2, or 3 nitrogen atoms. In some embodiments, $R^8$ represents independently for each occurrence a 6-membered monocyclic heteroaryl having 1 or 2 nitrogen atoms.

As defined generally above, $R^9$ is hydrogen, $C_{1-6}$ alkyl, or —$CH_2$-phenyl. In some embodiments, $R^9$ is hydrogen. In some embodiments, $R^9$ is $C_{1-6}$ alkyl. In some embodiments, $R^9$ is methyl or ethyl. In some embodiments, $R^9$ is methyl. In some embodiments, $R^9$ is ethyl. In some embodiments, $R^9$ is —$CH_2$-phenyl.

As defined generally above, $R^{10}$ represents independently for each occurrence halo, $C_{1-4}$ alkyl, $C_{1-4}$ haloalkyl, or $C_{1-4}$ alkoxyl. In certain embodiments, $R^{10}$ represents independently for each occurrence fluoro, chloro, methyl, trifluoromethyl, or methoxy. In certain embodiments, $R^{10}$ represents independently for each occurrence $C_{1-4}$ alkyl or $C_{1-4}$ haloalkyl. In certain embodiments, $R^{10}$ represents independently for each occurrence halo or $C_{1-4}$ alkoxyl.

In certain embodiments, $R^{10}$ represents independently for each occurrence halo. In certain embodiments, $R^{10}$ represents independently for each occurrence fluoro or chloro. In certain embodiments, $R^{10}$ represents independently for each occurrence $C_{1-4}$ alkyl. In certain embodiments, $R^{10}$ is methyl. In certain embodiments, $R^{10}$ represents independently for each occurrence $C_{1-4}$ haloalkyl. In certain embodiments, $R^{10}$ is trifluoromethyl. In certain embodiments, $R^{10}$ is $C_{1-4}$ alkoxyl. In certain embodiments, $R^{10}$ is methoxy.

In certain embodiments, $R^{10}$ represents independently for each occurrence methyl or ethyl. In certain embodiments, $R^{10}$ represents independently for each occurrence n-propyl or isopropyl. In certain embodiments, $R^{10}$ represents independently for each occurrence methyl or halomethyl. In certain embodiments, $R^{10}$ represents independently for each occurrence methoxy or ethoxy. In certain embodiments, $R^{10}$ is fluoromethyl or fluoroethyl. In certain embodiments, $R^{10}$ is 2-fluoroethyl.

As defined generally above, $R^{11}$ is $C_{1-6}$ alkyl, phenyl, —$CH_2$-phenyl, or hydrogen; or $R^{11}$ and $R^4$ are taken together with the nitrogen atom to which they are attached to form a 4-7 membered saturated ring having one nitrogen atom and optionally one additional heteroatom selected from nitrogen, oxygen, and sulfur.

In certain embodiments, $R^{11}$ is $C_{1-6}$ alkyl, phenyl, —$CH_2$-phenyl, or hydrogen. In certain embodiments, $R^{11}$ is hydrogen. In certain embodiments, $R^{11}$ is $C_{1-6}$ alkyl. In certain embodiments, $R^{11}$ is methyl. In certain embodiments, $R^{11}$ is ethyl. In certain embodiments, $R^{11}$ is phenyl. In certain embodiments, $R^{11}$ is —$CH_2$-phenyl.

In certain embodiments, $R^{11}$ and $R^4$ are taken together with the nitrogen atom to which they are attached to form a 4-7 membered saturated ring having one nitrogen atom and optionally one additional heteroatom selected from nitrogen, oxygen, and sulfur. In certain embodiments, $R^{11}$ and $R^4$ are taken together with the nitrogen atom to which they are attached to form a 5-membered saturated ring having one nitrogen atom and optionally one additional heteroatom selected from nitrogen, oxygen, and sulfur. In certain embodiments, $R^{11}$ and $R^4$ are taken together with the nitrogen atom to which they are attached to form a 6-membered saturated ring having one nitrogen atom and optionally one additional heteroatom selected from nitrogen, oxygen, and sulfur. In certain embodiments, $R^{11}$ and $R^4$ are taken together with the nitrogen atom to which they are attached to form a 7-membered saturated ring having one nitrogen atom and optionally one additional heteroatom selected from nitrogen, oxygen, and sulfur.

In certain embodiments, $R^{11}$ and $R^4$ are taken together with the nitrogen atom to which they are attached to form a 5- or 6-membered saturated ring having one nitrogen atom. In certain embodiments, $R^{11}$ and $R^4$ are taken together with the nitrogen atom to which they are attached to form a 5- or 6-membered saturated ring having one nitrogen atom and optionally one additional nitrogen heteroatom. In certain embodiments, $R^{11}$ and $R^4$ are taken together with the nitrogen atom to which they are attached to form a 5- or 6-membered saturated ring having one nitrogen atom and optionally one additional oxygen heteroatom. In certain embodiments, $R^{11}$ and $R^4$ are taken together with the nitrogen atom to which they are attached to form a 5- or 6-membered saturated ring having one nitrogen atom and optionally one additional sulfur heteroatom. In certain embodiments, $R^{11}$ and $R^4$ are taken together with the nitrogen atom to which they are attached to form a morpholine or piperazine ring.

As defined generally above, $R^{12}$ is (i) —C(H)($R^9$)—C(O)$OR^4$, or (ii) phenyl substituted with 0, 1, or 2 substituents independently selected from hydroxyl and —($C_{0-2}$ alkylene)-C(O)$OR^4$. In certain embodiments, $R^{12}$ is —C(H)($R^9$)—C(O)$OR^4$. In certain embodiments, $R^{12}$ is phenyl substituted with 0, 1, or 2 substituents independently selected from hydroxyl and —($C_{0-2}$ alkylene)-C(O)$OR^4$. In certain embodiments, $R^{12}$ is phenyl substituted with 0 or 1 substituents independently selected from hydroxyl and —($C_{0-2}$ alkylene)-C(O)$OR^4$. In certain embodiments, $R^{12}$ is phenyl substituted with 1 or 2 substituents independently selected from hydroxyl and —($C_{0-2}$ alkylene)-C(O)$OR^4$. In certain embodiments, $R^{12}$ is phenyl substituted with one hydroxyl and one —($C_{0-2}$ alkylene)-C(O)$OR^4$. In certain embodiments, $R^{12}$ is phenyl substituted with one hydroxyl and one —C(O)$OR^4$. In certain embodiments, $R^{12}$ is

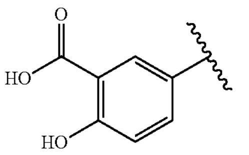

or

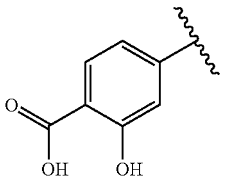

As defined generally above, m is 0, 1, 2, or 3. In certain embodiments, m is 0. In certain embodiments, m is 1. In certain embodiments, m is 2. In certain embodiments, m is 3. In certain embodiments, m is 0 or 1. In certain embodiments, m is 1 or 2. In certain embodiments, m is 2 or 3. In certain embodiments, m is 0, 1, or 2. In certain embodiments, m is 1, 2, or 3.

As defined generally above, n is 0, 1, 2, or 3. In certain embodiments, n is 0. In certain embodiments, n is 1. In certain embodiments, n is 2. In certain embodiments, n is 3. In certain embodiments, n is 0 or 1. In certain embodiments, n is 1 or 2. In certain embodiments, n is 2 or 3. In certain embodiments, n is 0, 1, or 2. In certain embodiments, n is 1, 2, or 3.

As defined generally above, r is 0, 1, or 2. In certain embodiments, r is 0. In certain embodiments, r is 1. In certain embodiments, r is 2. In certain embodiments, r is 0 or 1. In certain embodiments, r is 1 or 2.

The description above describes multiple embodiments relating to compounds of Formula II-A. The patent application specifically contemplates all combinations of the embodiments.

Another aspect of the invention provides a compound in Table 1, 2, 3, 4, 5, 6, or 7 below, or a pharmaceutically acceptable salt thereof. In certain embodiments, the compound is a compound in Table 1, 2, 3, 4, 5, or 7 below. In certain embodiments, the compound is a compound in Table 1, 2, 3, 4, 5, or 6 below, or a pharmaceutically acceptable salt thereof. In certain embodiments, the compound is a compound in Table 1, 2, 3, 4, 5, or 6 below. In certain embodiments, the compound is a compound in Table 1, 2, or 3 below, or a pharmaceutically acceptable salt thereof. In certain embodiments, the compound is a compound in Table 1, 2, or 3 below. In certain embodiments, the compound is a compound in Table 4, 5, 6, or 7 below, or a pharmaceutically acceptable salt thereof. In certain embodiments, the compound is a compound in Table 4, 5, 6, or 7 below. In certain embodiments, the compound is a compound in Table 4, 5, or 6 below, or a pharmaceutically acceptable salt thereof. In certain embodiments, the compound is a compound in Table 4, 5, or 6 below.

In certain embodiments, the compound is a compound in Table 1 below, or a pharmaceutically acceptable salt thereof. In certain embodiments, the compound is a compound in Table 1 below. In certain embodiments, the compound is a compound in Table 2 below, or a pharmaceutically acceptable salt thereof. In certain embodiments, the compound is a compound in Table 2 below. In certain embodiments, the compound is a compound in Table 3 below, or a pharmaceutically acceptable salt thereof. In certain embodiments, the compound is a compound in Table 3 below. In certain embodiments, the compound is a compound in Table 4 below, or a pharmaceutically acceptable salt thereof. In certain embodiments, the compound is a compound in Table 4 below. In certain embodiments, the compound is a compound in Table 5 below, or a pharmaceutically acceptable salt thereof. In certain embodiments, the compound is a compound in Table 5 below. In certain embodiments, the compound is a compound in Table 6 below, or a pharmaceutically acceptable salt thereof. In certain embodiments, the compound is a compound in Table 6 below. In certain embodiments, the compound is a compound in Table 7 below, or a pharmaceutically acceptable salt thereof. In certain embodiments, the compound is a compound in Table 7 below.

TABLE 1

| Compound No. | Chemical Structure |
| --- | --- |
| I-1 | 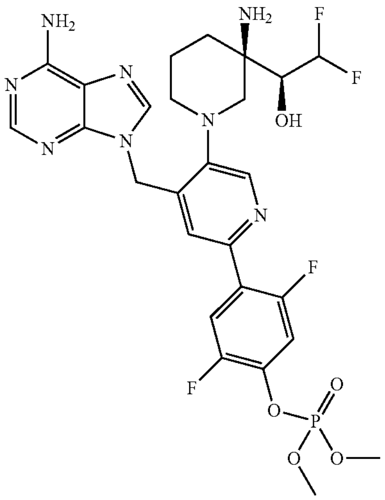 [SMILES: COP(=O)(OC)Oc1cc(F)c(-c2cc(Cn3cnc4c(N)ncnc43)c(N3CCC[C@](N)([C@H](O)C(F)F)C3)cn2)cc1F] |

TABLE 1-continued
| Compound No. | Chemical Structure |
| --- | --- |
| I-2 | 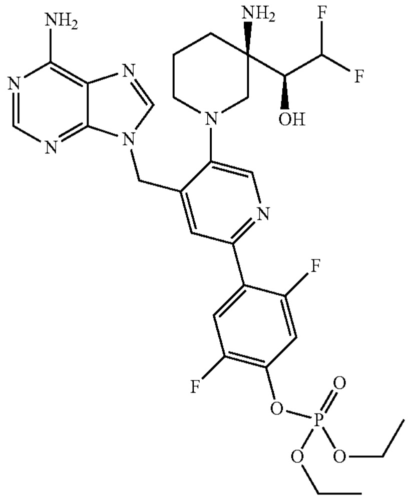 [SMILES: CCOP(=O)(OCC)Oc1cc(F)c(-c2cc(Cn3cnc4c(N)ncnc43)c(N3CCC[C@](N)([C@H](O)C(F)F)C3)cn2)cc1F] |
| I-3 | 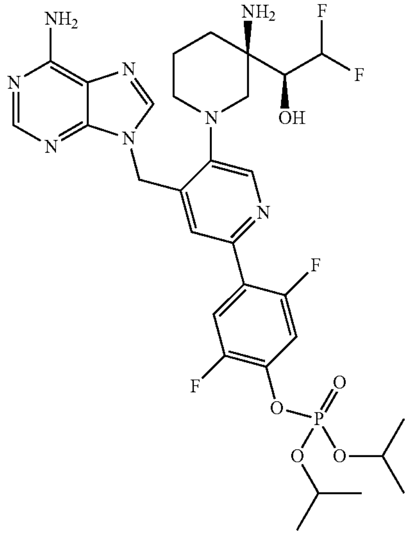 [SMILES: CC(C)OP(=O)(Oc1cc(F)c(-c2cc(Cn3cnc4c(N)ncnc43)c(N3CCC[C@](N)([C@H](O)C(F)F)C3)cn2)cc1F)OC(C)C] |
| I-4 | 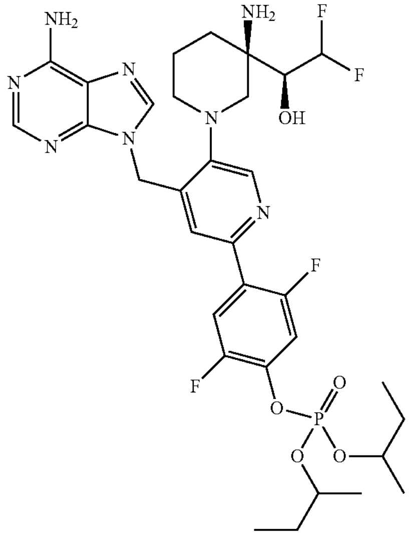 [SMILES: CCC(C)OP(=O)(Oc1cc(F)c(-c2cc(Cn3cnc4c(N)ncnc43)c(N3CCC[C@](N)([C@H](O)C(F)F)C3)cn2)cc1F)OC(C)CC] |

TABLE 1-continued
| Compound No. | Chemical Structure |
|---|---|
| I-5 | 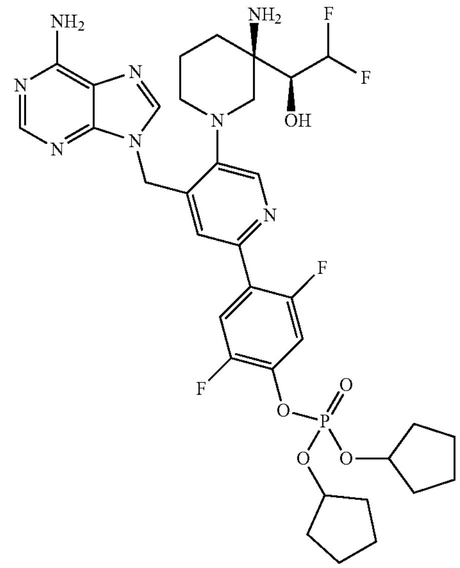 [SMILES: Nc1ncnc2c1ncn2Cc1cc(-c2cc(F)c(OP(=O)(OC3CCCC3)OC3CCCC3)cc2F)ncc1N1CCC[C@](N)([C@H](O)C(F)F)C1] |
| I-6 | 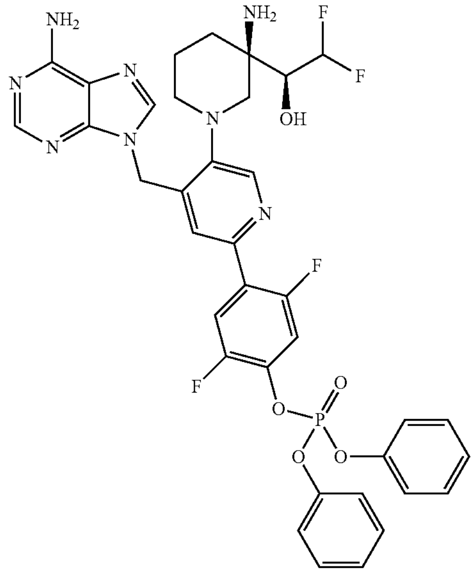 [SMILES: Nc1ncnc2c1ncn2Cc1cc(-c2cc(F)c(OP(=O)(Oc3ccccc3)Oc3ccccc3)cc2F)ncc1N1CCC[C@](N)([C@H](O)C(F)F)C1] |

TABLE 1-continued
| Compound No. | Chemical Structure |
| --- | --- |
| I-7 | 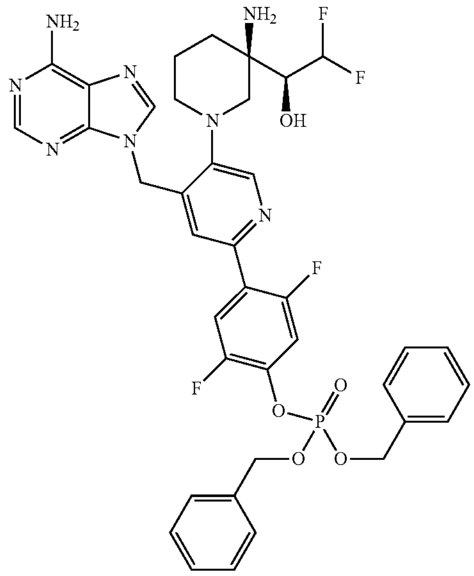 [SMILES: Nc1ncnc2c1ncn2Cc1cc(-c2cc(F)c(OP(=O)(OCc3ccccc3)OCc3ccccc3)cc2F)ncc1N1CCC[C@](N)([C@H](O)C(F)F)C1] |
| I-8 | 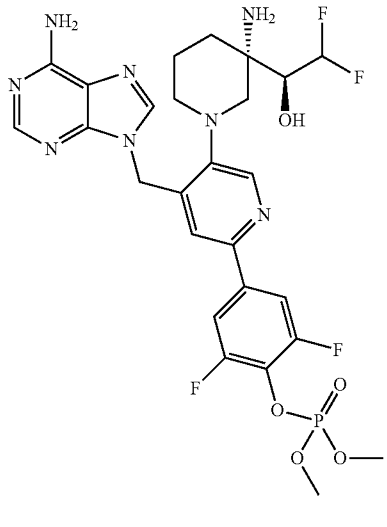 [SMILES: COP(=O)(OC)Oc1c(F)cc(-c2cc(Cn3cnc4c(N)ncnc43)c(N3CCC[C@@](N)([C@H](O)C(F)F)C3)cn2)cc1F] |

TABLE 1-continued
| Compound No. | Chemical Structure |
| --- | --- |
| I-9 | 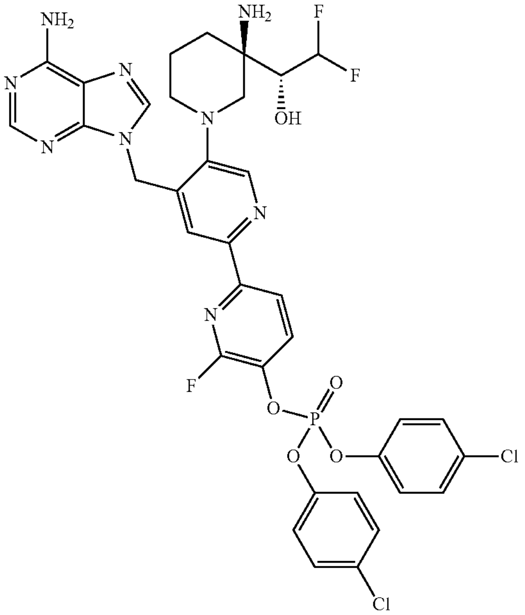 [SMILES: Nc1ncnc2c1ncn2Cc1cc(-c2ccc(OP(=O)(Oc3ccc(Cl)cc3)Oc3ccc(Cl)cc3)c(F)n2)ncc1N1CCC[C@](N)([C@@H](O)C(F)F)C1] |
| I-10 | 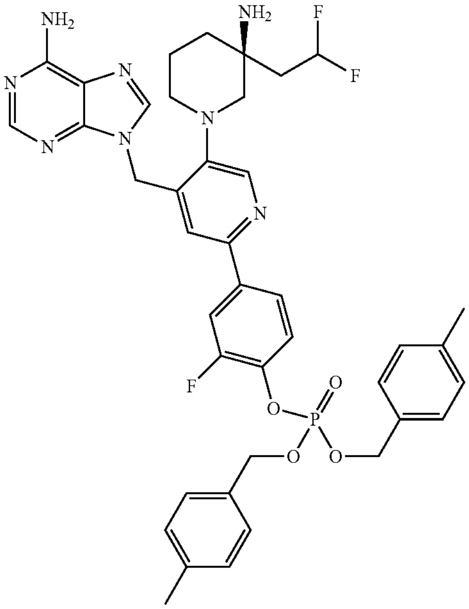 [SMILES: Cc1ccc(COP(=O)(OCc2ccc(C)cc2)Oc2ccc(-c3cc(Cn4cnc5c(N)ncnc54)c(N4CCC[C@](N)(CC(F)F)C4)cn3)cc2F)cc1] |

TABLE 1-continued
| Compound No. | Chemical Structure |
|---|---|
| I-11 | 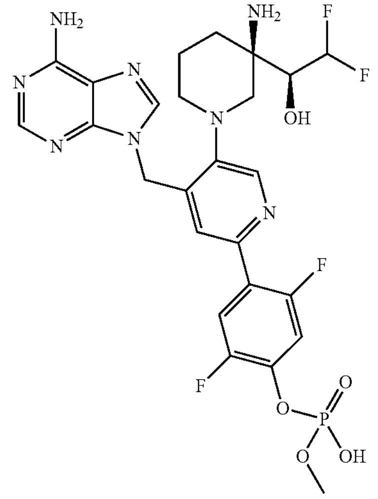 [SMILES: COP(=O)(O)Oc1cc(F)c(-c2cc(Cn3cnc4c(N)ncnc43)c(N3CCC[C@](N)([C@H](O)C(F)F)C3)cn2)cc1F] |
| I-12 | 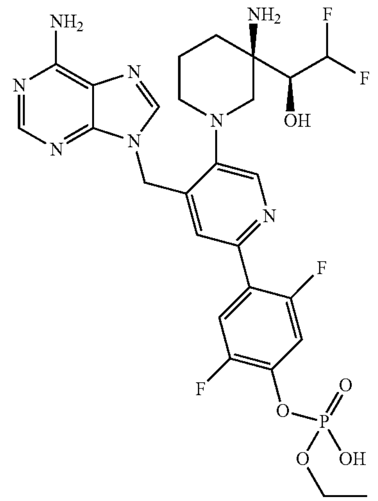 [SMILES: CCOP(=O)(O)Oc1cc(F)c(-c2cc(Cn3cnc4c(N)ncnc43)c(N3CCC[C@](N)([C@H](O)C(F)F)C3)cn2)cc1F] |
| I-13 | 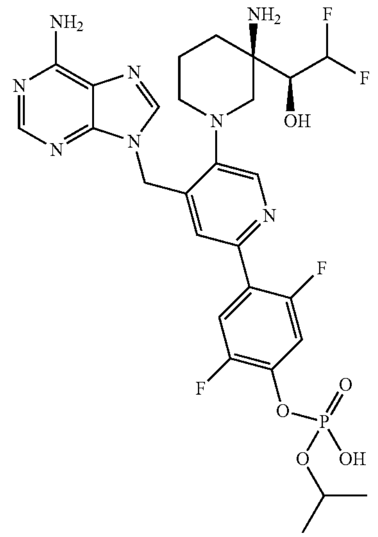 [SMILES: CC(C)OP(=O)(O)Oc1cc(F)c(-c2cc(Cn3cnc4c(N)ncnc43)c(N3CCC[C@](N)([C@H](O)C(F)F)C3)cn2)cc1F] |

TABLE 1-continued
| Compound No. | Chemical Structure |
| --- | --- |
| I-14 | 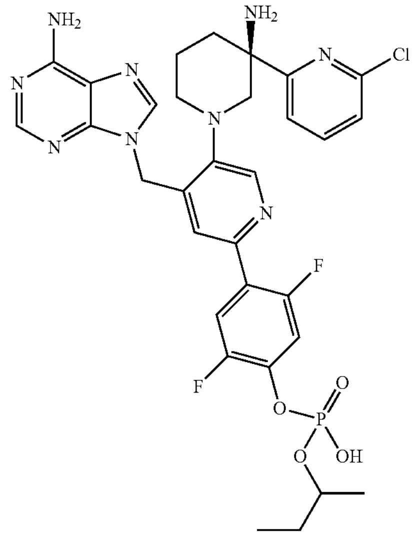 [SMILES: CCC(C)OP(=O)(O)Oc1cc(F)c(-c2cc(Cn3cnc4c(N)ncnc43)c(N3CCC[C@](N)(c4cccc(Cl)n4)C3)cn2)cc1F] |
| I-15 | 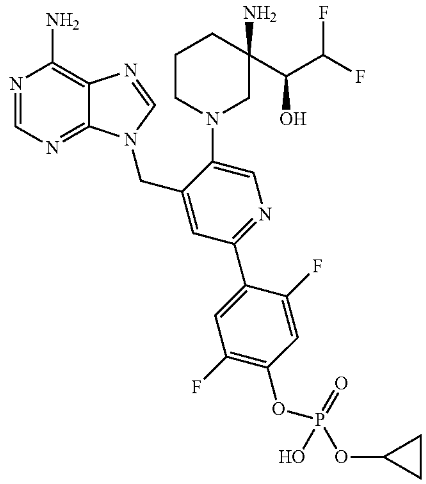 [SMILES: Nc1ncnc2c1ncn2Cc1cc(-c2cc(F)c(OP(=O)(O)OC3CC3)cc2F)ncc1N1CCC[C@](N)([C@H](O)C(F)F)C1] |
| I-16 | 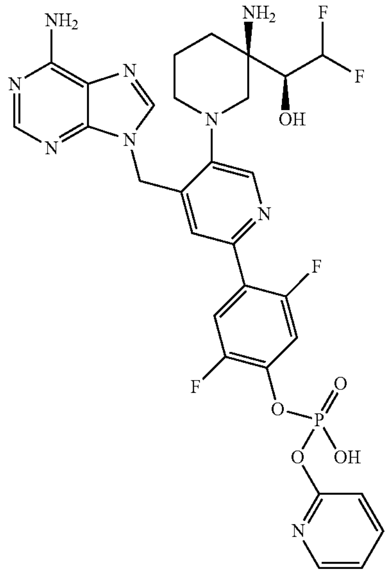 [SMILES: Nc1ncnc2c1ncn2Cc1cc(-c2cc(F)c(OP(=O)(O)Oc3ccccn3)cc2F)ncc1N1CCC[C@](N)([C@H](O)C(F)F)C1] |

TABLE 1-continued
| Compound No. | Chemical Structure |
|---|---|
| I-17 | 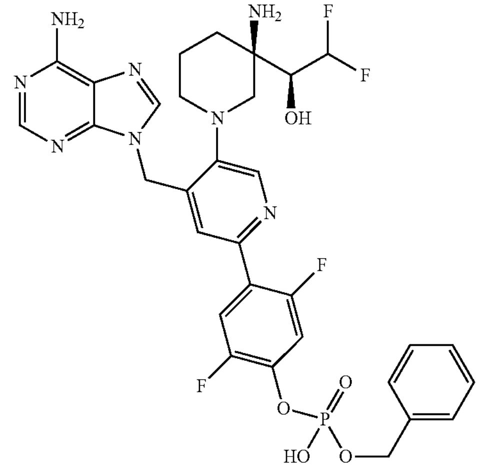 [SMILES: Nc1ncnc2c1ncn2Cc1cc(-c2cc(F)c(OP(=O)(O)OCc3ccccc3)cc2F)ncc1N1CCC[C@](N)([C@H](O)C(F)F)C1] |
| I-18 | 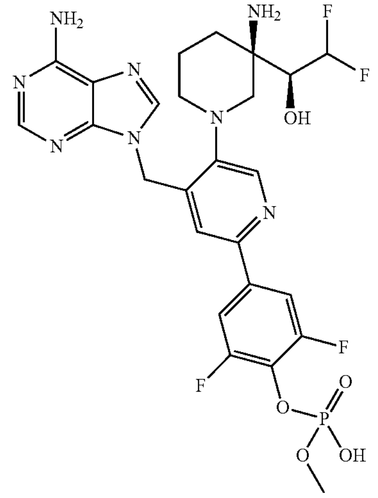 [SMILES: COP(=O)(O)Oc1c(F)cc(-c2cc(Cn3cnc4c(N)ncnc43)c(N3CCC[C@](N)([C@H](O)C(F)F)C3)cn2)cc1F] |
| I-19 | 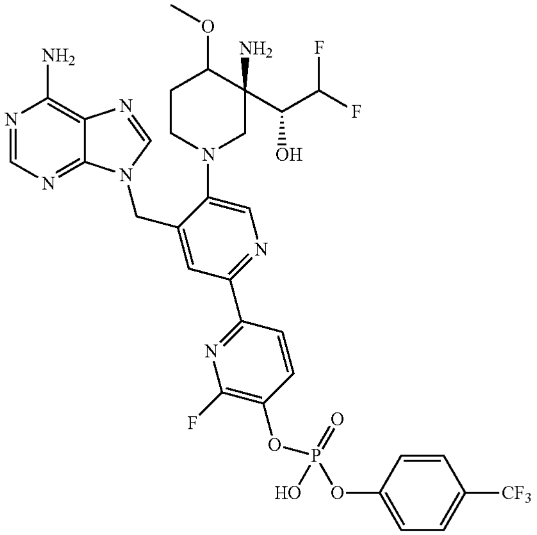 [SMILES: COC1CCN(c2cnc(-c3ccc(OP(=O)(O)Oc4ccc(C(F)(F)F)cc4)c(F)n3)cc2Cn2cnc3c(N)ncnc32)C[C@@]1(N)[C@@H](O)C(F)F] |

TABLE 1-continued
| Compound No. | Chemical Structure |
| --- | --- |
| I-20 | 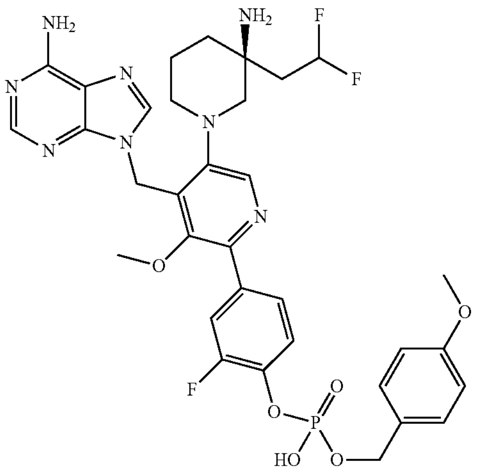 [SMILES: COc1ccc(COP(=O)(O)Oc2ccc(-c3ncc(N4CCC[C@](N)(CC(F)F)C4)c(Cn4cnc5c(N)ncnc54)c3OC)cc2F)cc1] |
| I-21 | 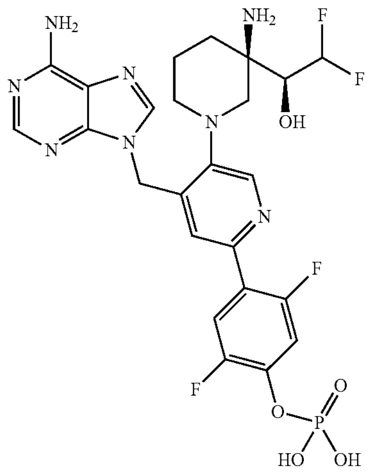 [SMILES: Nc1ncnc2c1ncn2Cc1cc(-c2cc(F)c(OP(=O)(O)O)cc2F)ncc1N1CCC[C@](N)([C@H](O)C(F)F)C1] |
| I-22 | 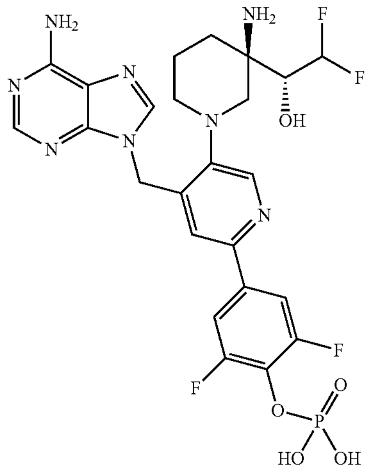 [SMILES: Nc1ncnc2c1ncn2Cc1cc(-c2cc(F)c(OP(=O)(O)O)c(F)c2)ncc1N1CCC[C@](N)([C@@H](O)C(F)F)C1] |

TABLE 1-continued
| Compound No. | Chemical Structure |
| --- | --- |
| I-23 | 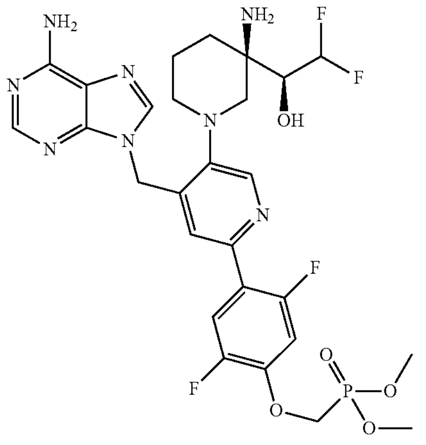 [SMILES: COP(=O)(COc1cc(F)c(-c2cc(Cn3cnc4c(N)ncnc43)c(N3CCC[C@](N)([C@H](O)C(F)F)C3)cn2)cc1F)OC] |
| I-24 | 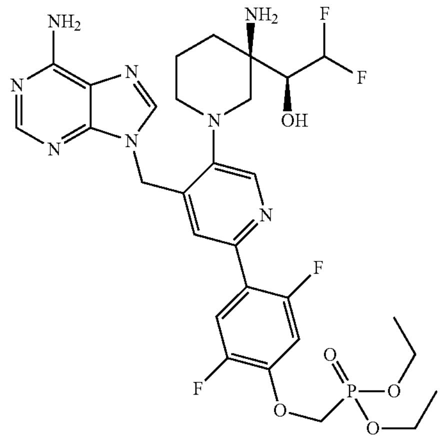 [SMILES: CCOP(=O)(COc1cc(F)c(-c2cc(Cn3cnc4c(N)ncnc43)c(N3CCC[C@](N)([C@H](O)C(F)F)C3)cn2)cc1F)OCC] |
| I-25 | 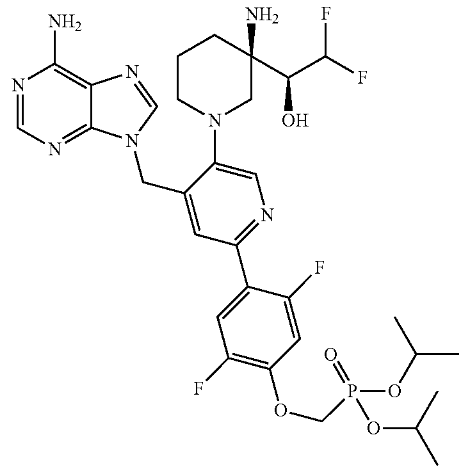 [SMILES: CC(C)OP(=O)(COc1cc(F)c(-c2cc(Cn3cnc4c(N)ncnc43)c(N3CCC[C@](N)([C@H](O)C(F)F)C3)cn2)cc1F)OC(C)C] |

TABLE 1-continued
| Compound No. | Chemical Structure |
|---|---|
| I-26 | 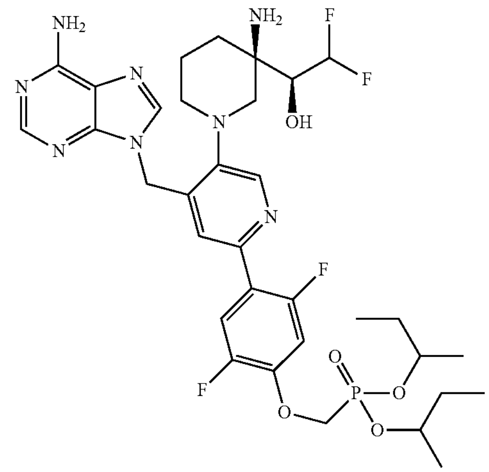 [SMILES: CCC(C)OP(=O)(COc1cc(F)c(-c2cc(Cn3cnc4c(N)ncnc43)c(N3CCC[C@](N)([C@H](O)C(F)F)C3)cn2)cc1F)OC(C)CC] |
| I-27 | 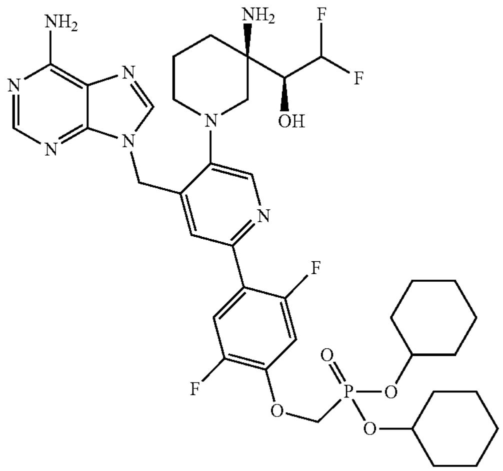 [SMILES: Nc1ncnc2c1ncn2Cc1cc(-c2cc(F)c(OCP(=O)(OC3CCCCC3)OC3CCCCC3)cc2F)ncc1N1CCC[C@](N)([C@H](O)C(F)F)C1] |
| I-28 | 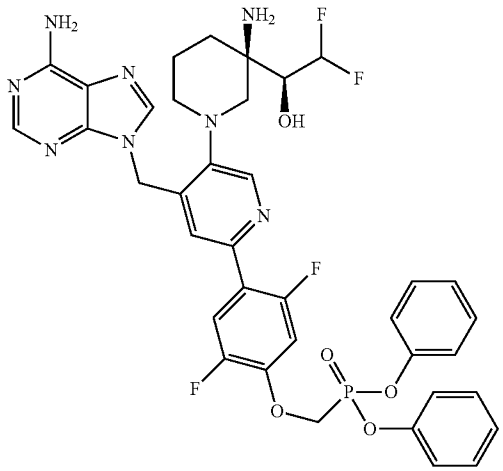 [SMILES: Nc1ncnc2c1ncn2Cc1cc(-c2cc(F)c(OCP(=O)(Oc3ccccc3)Oc3ccccc3)cc2F)ncc1N1CCC[C@](N)([C@H](O)C(F)F)C1] |

TABLE 1-continued
| Compound No. | Chemical Structure |
| --- | --- |
| I-29 | 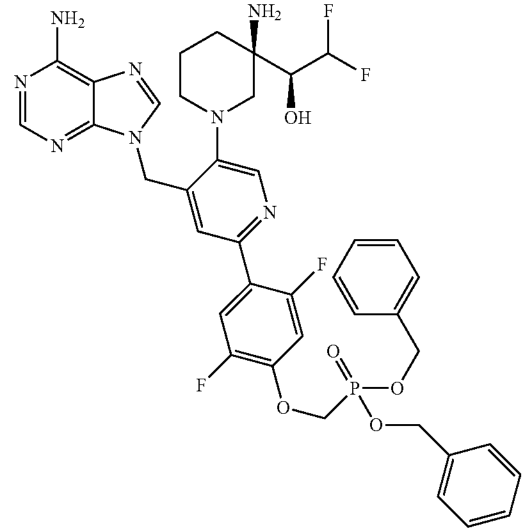 [SMILES: Nc1ncnc2c1ncn2Cc1cc(-c2cc(F)c(OCP(=O)(OCc3ccccc3)OCc3ccccc3)cc2F)ncc1N1CCC[C@](N)([C@H](O)C(F)F)C1] |
| I-30 | 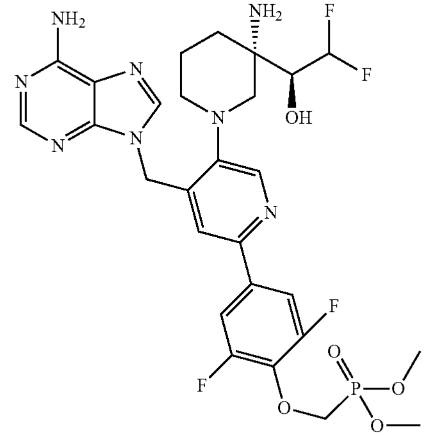 [SMILES: COP(=O)(COc1c(F)cc(-c2cc(Cn3cnc4c(N)ncnc43)c(N3CCC[C@@](N)([C@H](O)C(F)F)C3)cn2)cc1F)OC] |
| I-31 | 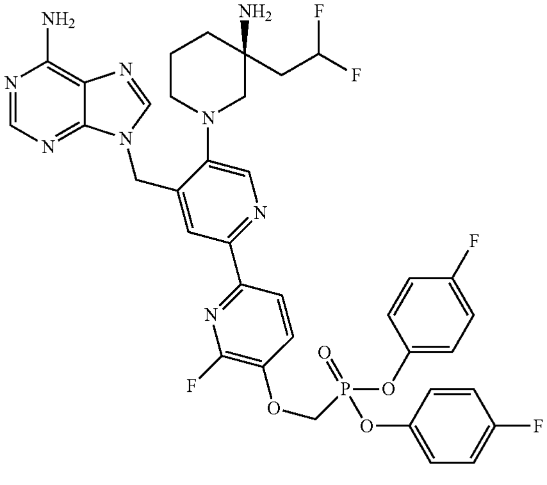 [SMILES: Nc1ncnc2c1ncn2Cc1cc(-c2ccc(OCP(=O)(Oc3ccc(F)cc3)Oc3ccc(F)cc3)c(F)n2)ncc1N1CCC[C@](N)(CC(F)F)C1] |

TABLE 1-continued
| Compound No. | Chemical Structure |
| --- | --- |
| I-32 | 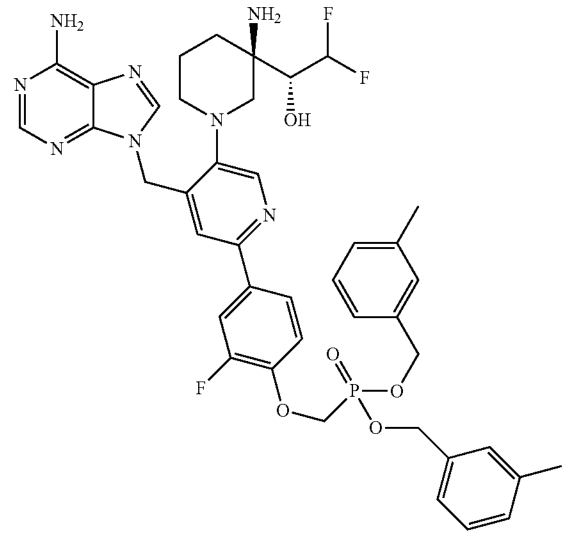 [SMILES: Cc1cccc(COP(=O)(COc2ccc(-c3cc(Cn4cnc5c(N)ncnc54)c(N4CCC[C@](N)([C@@H](O)C(F)F)C4)cn3)cc2F)OCc2cccc(C)c2)c1] |
| I-33 | 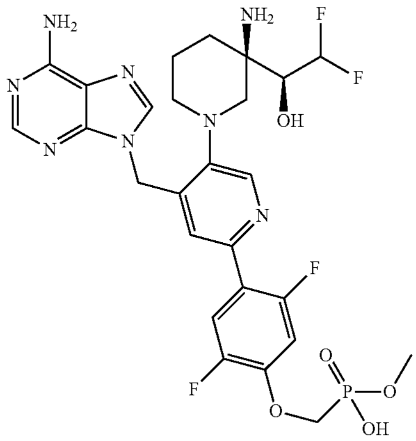 [SMILES: COP(=O)(O)COc1cc(F)c(-c2cc(Cn3cnc4c(N)ncnc43)c(N3CCC[C@](N)([C@H](O)C(F)F)C3)cn2)cc1F] |
| I-34 | 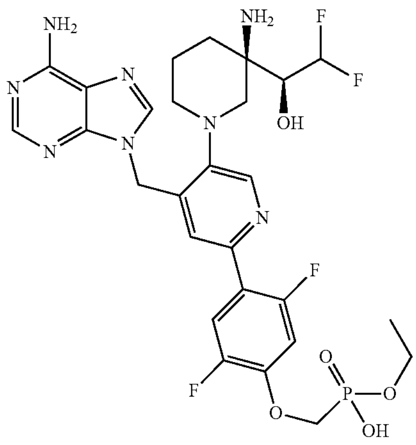 [SMILES: CCOP(=O)(O)COc1cc(F)c(-c2cc(Cn3cnc4c(N)ncnc43)c(N3CCC[C@](N)([C@H](O)C(F)F)C3)cn2)cc1F] |

TABLE 1-continued
| Compound No. | Chemical Structure |
| --- | --- |
| I-35 | 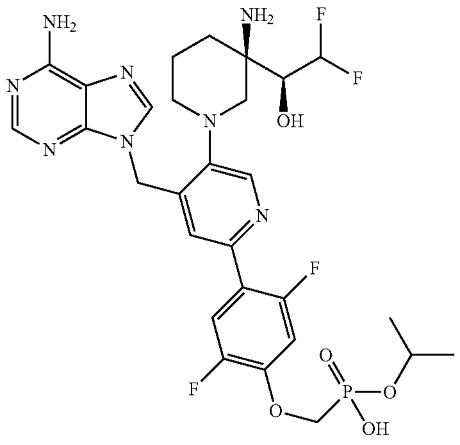 [SMILES: CC(C)OP(=O)(O)COc1cc(F)c(-c2cc(Cn3cnc4c(N)ncnc43)c(N3CCC[C@](N)([C@H](O)C(F)F)C3)cn2)cc1F] |
| I-36 | 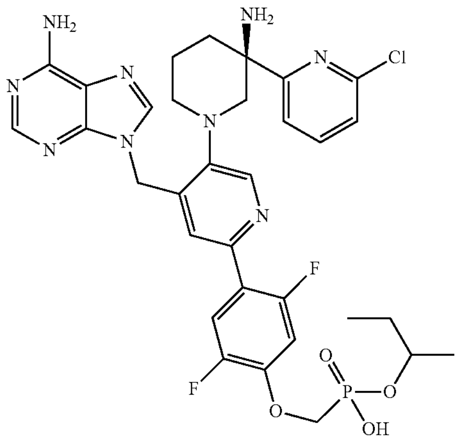 [SMILES: CCC(C)OP(=O)(O)COc1cc(F)c(-c2cc(Cn3cnc4c(N)ncnc43)c(N3CCC[C@](N)(c4cccc(Cl)n4)C3)cn2)cc1F] |
| I-37 | 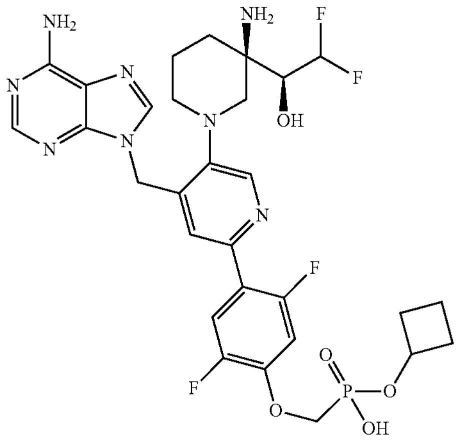 [SMILES: Nc1ncnc2c1ncn2Cc1cc(-c2cc(F)c(OCP(=O)(O)OC3CCC3)cc2F)ncc1N1CCC[C@](N)([C@H](O)C(F)F)C1] |

TABLE 1-continued
| Compound No. | Chemical Structure |
|---|---|
| I-38 | 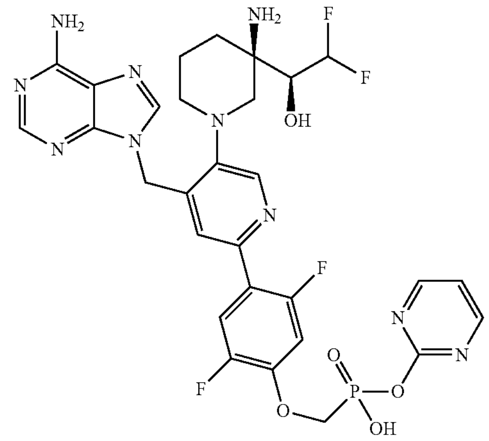 [SMILES: Nc1ncnc2c1ncn2Cc1cc(-c2cc(F)c(OCP(=O)(O)Oc3ncccn3)cc2F)ncc1N1CCC[C@](N)([C@H](O)C(F)F)C1] |
| I-39 | 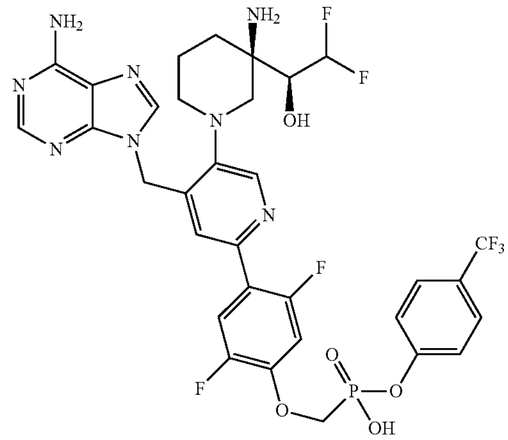 [SMILES: Nc1ncnc2c1ncn2Cc1cc(-c2cc(F)c(OCP(=O)(O)Oc3ccc(C(F)(F)F)cc3)cc2F)ncc1N1CCC[C@](N)([C@H](O)C(F)F)C1] |
| I-40 | 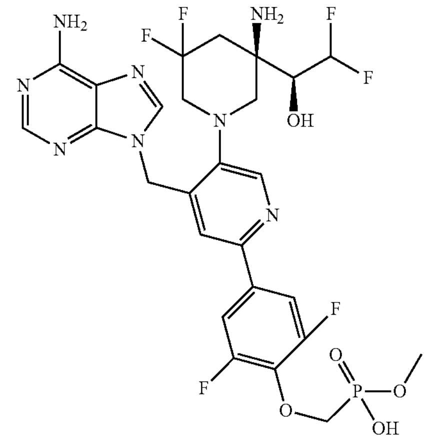 [SMILES: COP(=O)(O)COc1c(F)cc(-c2cc(Cn3cnc4c(N)ncnc43)c(N3CC(F)(F)C[C@](N)([C@H](O)C(F)F)C3)cn2)cc1F] |

TABLE 1-continued
| Compound No. | Chemical Structure |
| --- | --- |
| I-41 | 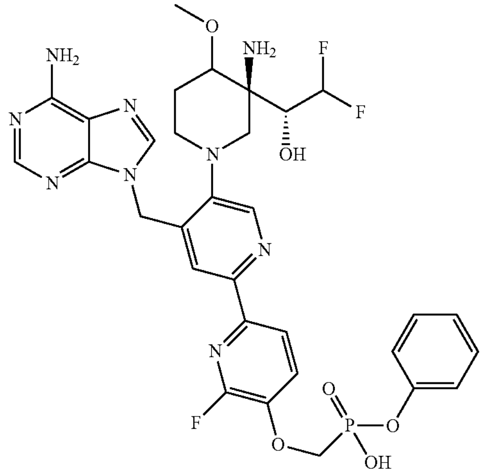 [SMILES: COC1CCN(c2cnc(-c3ccc(OCP(=O)(O)Oc4ccccc4)c(F)n3)cc2Cn2cnc3c(N)ncnc32)C[C@@]1(N)[C@@H](O)C(F)F] |
| I-42 | 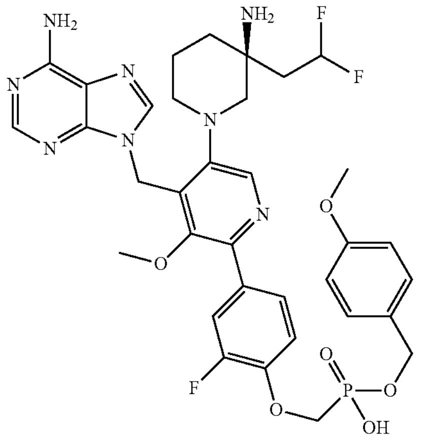 [SMILES: COc1ccc(COP(=O)(O)COc2ccc(-c3ncc(N4CCC[C@](N)(CC(F)F)C4)c(Cn4cnc5c(N)ncnc54)c3OC)cc2F)cc1] |
| I-43 | 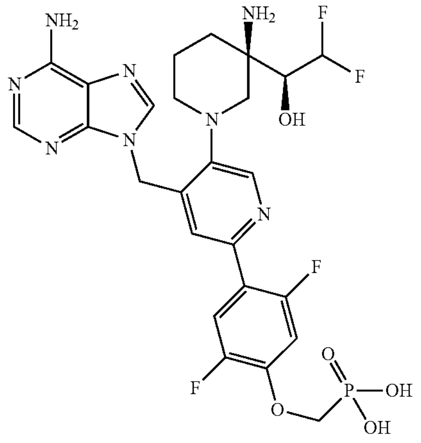 [SMILES: Nc1ncnc2c1ncn2Cc1cc(-c2cc(F)c(OCP(=O)(O)O)cc2F)ncc1N1CCC[C@](N)([C@H](O)C(F)F)C1] |

TABLE 1-continued
| Compound No. | Chemical Structure |
|---|---|
| I-44 | 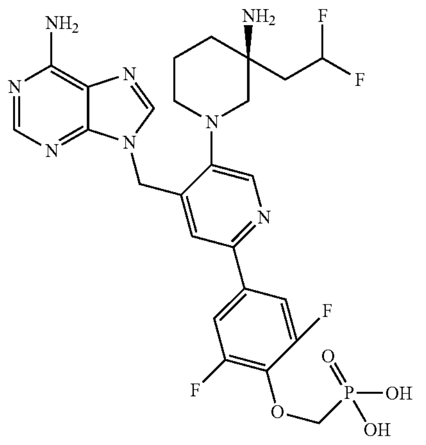 [SMILES: Nc1ncnc2c1ncn2Cc1cc(-c2cc(F)c(OCP(=O)(O)O)c(F)c2)ncc1N1CCC[C@](N)(CC(F)F)C1] |
| I-45 | 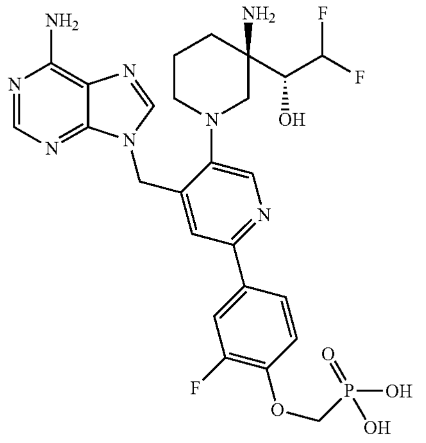 [SMILES: Nc1ncnc2c1ncn2Cc1cc(-c2ccc(OCP(=O)(O)O)c(F)c2)ncc1N1CCC[C@](N)([C@@H](O)C(F)F)C1] |
TABLE 2
| Compound No. | Chemical Structure |
|---|---|
| II-1 | 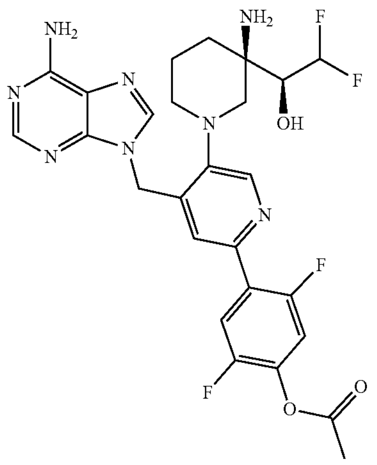 [SMILES: CC(=O)Oc1cc(F)c(-c2cc(Cn3cnc4c(N)ncnc43)c(N3CCC[C@](N)([C@H](O)C(F)F)C3)cn2)cc1F] |

TABLE 2-continued
| Compound No. | Chemical Structure |
| --- | --- |
| II-2 | 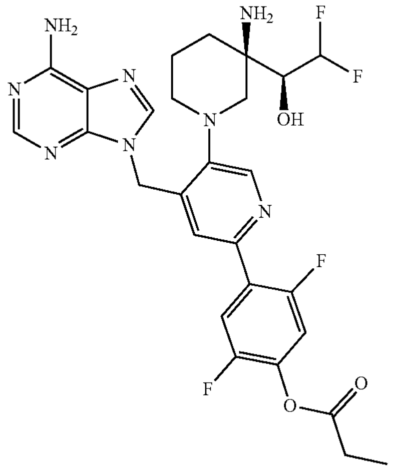 [SMILES: CCC(=O)Oc1cc(F)c(-c2cc(Cn3cnc4c(N)ncnc43)c(N3CCC[C@](N)([C@H](O)C(F)F)C3)cn2)cc1F] |
| II-3 | 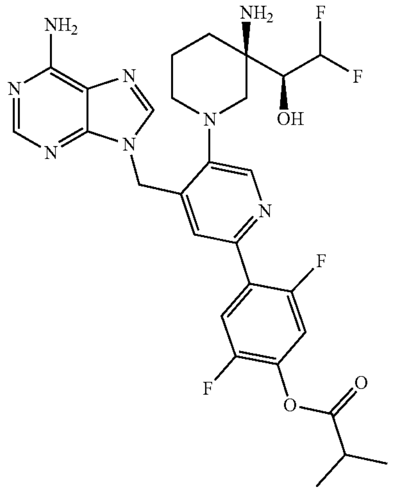 [SMILES: CC(C)C(=O)Oc1cc(F)c(-c2cc(Cn3cnc4c(N)ncnc43)c(N3CCC[C@](N)([C@H](O)C(F)F)C3)cn2)cc1F] |
| II-4 | 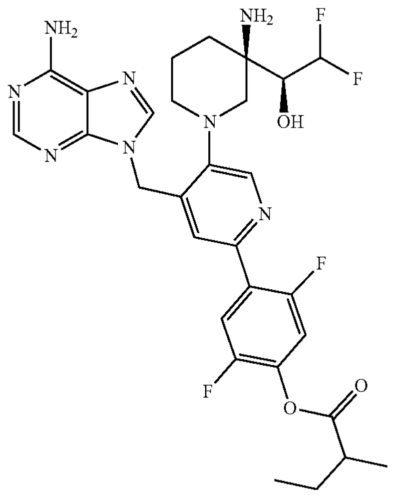 [SMILES: CCC(C)C(=O)Oc1cc(F)c(-c2cc(Cn3cnc4c(N)ncnc43)c(N3CCC[C@](N)([C@H](O)C(F)F)C3)cn2)cc1F] |

TABLE 2-continued
| Compound No. | Chemical Structure |
| --- | --- |
| II-5 | 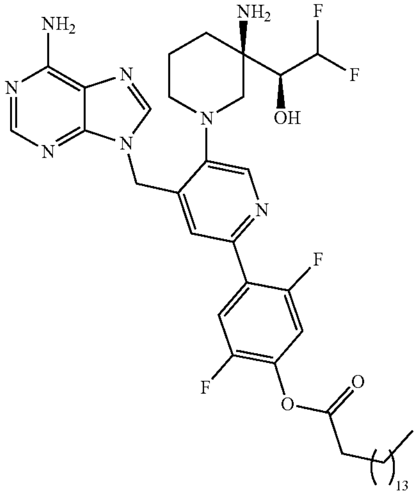 |
| II-6 | 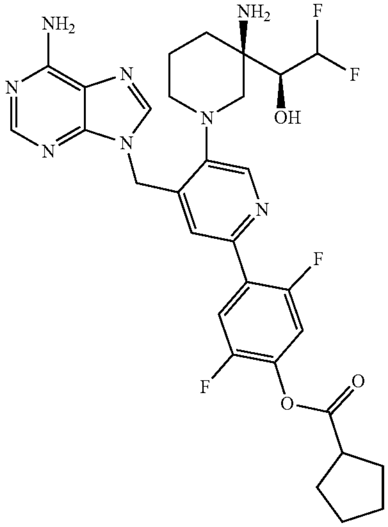 [SMILES: Nc1ncnc2c1ncn2Cc1cc(-c2cc(F)c(OC(=O)C3CCCC3)cc2F)ncc1N1CCC[C@](N)([C@H](O)C(F)F)C1] |
| II-7 | 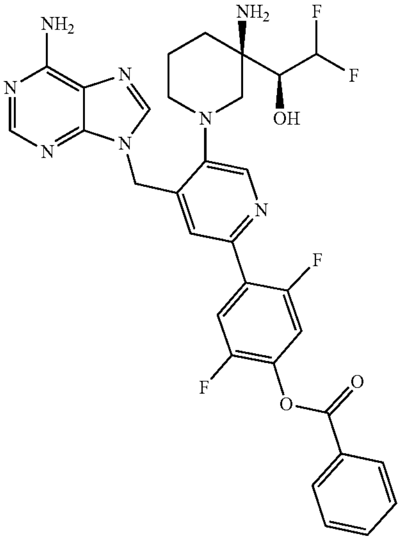 [SMILES: Nc1ncnc2c1ncn2Cc1cc(-c2cc(F)c(OC(=O)c3ccccc3)cc2F)ncc1N1CCC[C@](N)([C@H](O)C(F)F)C1] |

TABLE 2-continued
| Compound No. | Chemical Structure |
|---|---|
| II-8 | 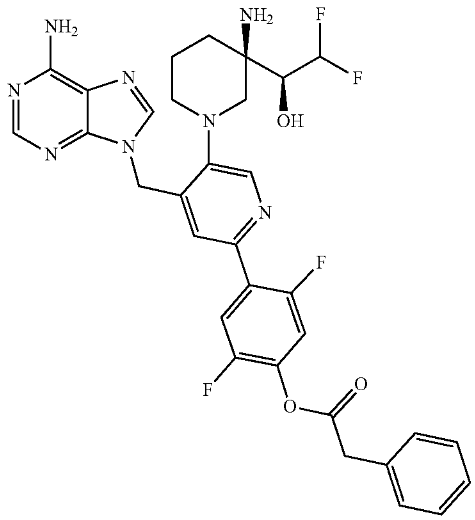 [SMILES: Nc1ncnc2c1ncn2Cc1cc(-c2cc(F)c(OC(=O)Cc3ccccc3)cc2F)ncc1N1CCC[C@](N)([C@H](O)C(F)F)C1] |
| II-9 | 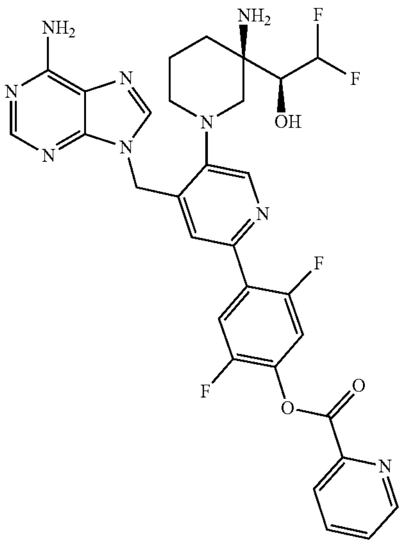 [SMILES: Nc1ncnc2c1ncn2Cc1cc(-c2cc(F)c(OC(=O)c3ccccn3)cc2F)ncc1N1CCC[C@](N)([C@H](O)C(F)F)C1] |
| II-10 | 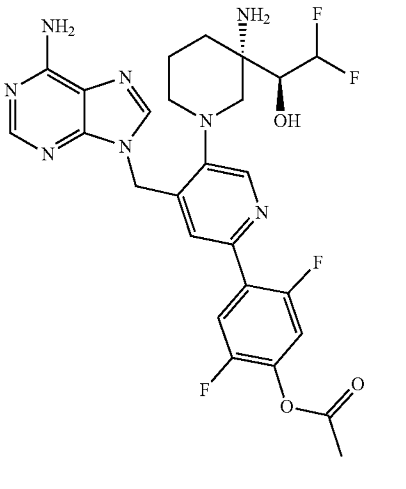 [SMILES: CC(=O)Oc1cc(F)c(-c2cc(Cn3cnc4c(N)ncnc43)c(N3CCC[C@@](N)([C@H](O)C(F)F)C3)cn2)cc1F] |

TABLE 2-continued
| Compound No. | Chemical Structure |
| --- | --- |
| II-11 | 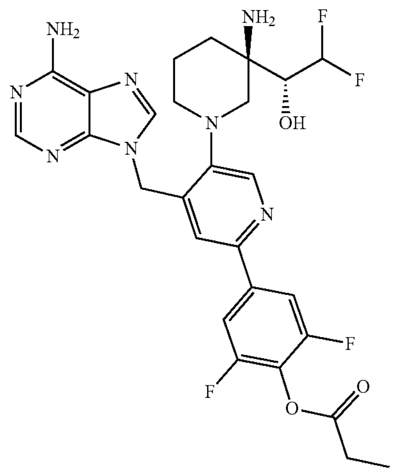 [SMILES: CCC(=O)Oc1c(F)cc(-c2cc(Cn3cnc4c(N)ncnc43)c(N3CCC[C@](N)([C@@H](O)C(F)F)C3)cn2)cc1F] |
| II-12 | 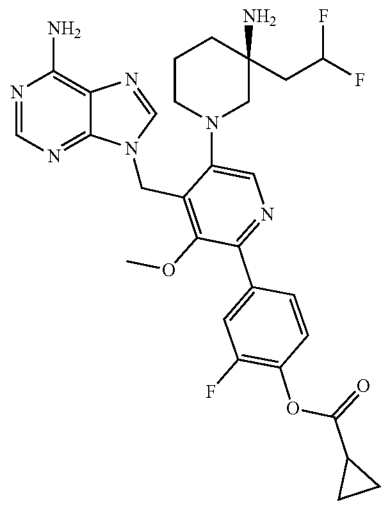 [SMILES: COc1c(-c2ccc(OC(=O)C3CC3)c(F)c2)ncc(N2CCC[C@](N)(CC(F)F)C2)c1Cn1cnc2c(N)ncnc21] |
| II-13 | 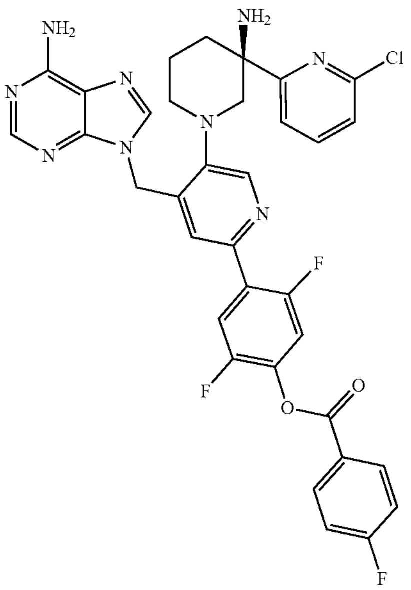 [SMILES: Nc1ncnc2c1ncn2Cc1cc(-c2cc(F)c(OC(=O)c3ccc(F)cc3)cc2F)ncc1N1CCC[C@](N)(c2cccc(Cl)n2)C1] |

TABLE 2-continued
| Compound No. | Chemical Structure |
|---|---|
| II-14 | 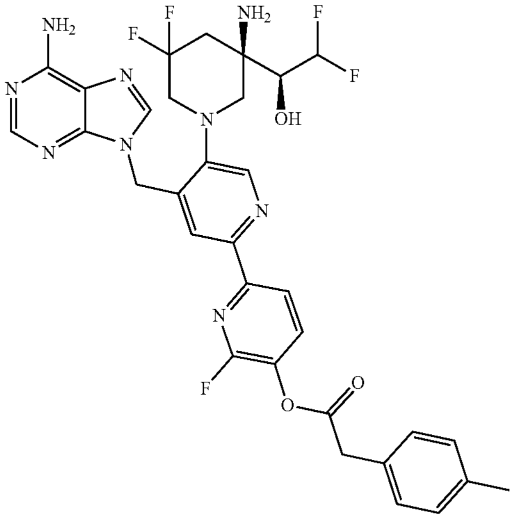 [SMILES: Cc1ccc(CC(=O)Oc2ccc(-c3cc(Cn4cnc5c(N)ncnc54)c(N4CC(F)(F)C[C@](N)([C@H](O)C(F)F)C4)cn3)nc2F)cc1] |
| II-15 | 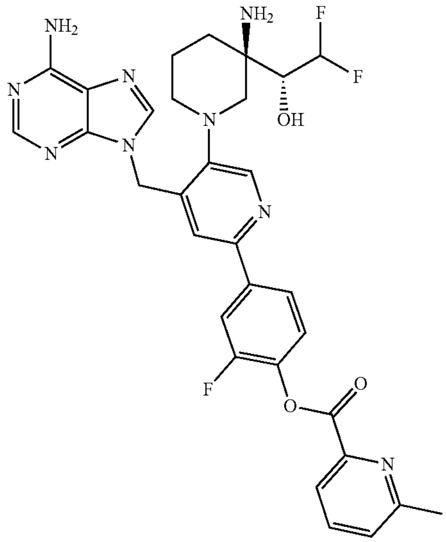 [SMILES: Cc1cccc(C(=O)Oc2ccc(-c3cc(Cn4cnc5c(N)ncnc54)c(N4CCC[C@](N)([C@@H](O)C(F)F)C4)cn3)cc2F)n1] |
| II-16 | 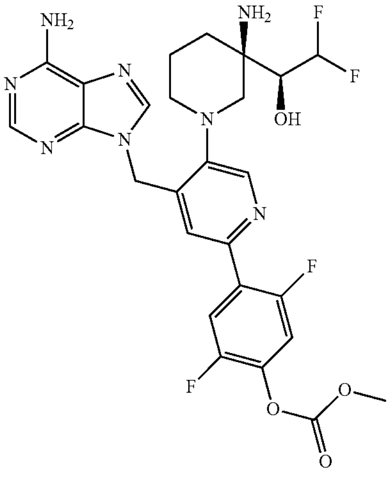 [SMILES: COC(=O)Oc1cc(F)c(-c2cc(Cn3cnc4c(N)ncnc43)c(N3CCC[C@](N)([C@H](O)C(F)F)C3)cn2)cc1F] |

TABLE 2-continued
| Compound No. | Chemical Structure |
| --- | --- |
| II-17 | 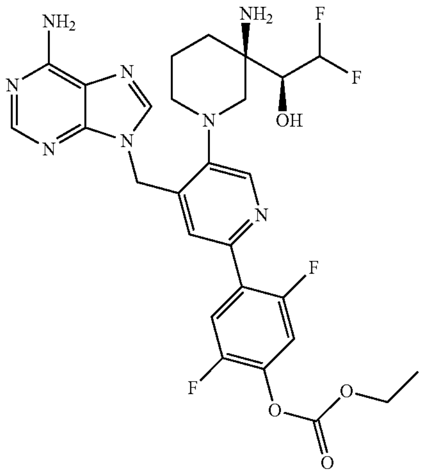 [SMILES: CCOC(=O)Oc1cc(F)c(-c2cc(Cn3cnc4c(N)ncnc43)c(N3CCC[C@](N)([C@H](O)C(F)F)C3)cn2)cc1F] |
| II-18 | 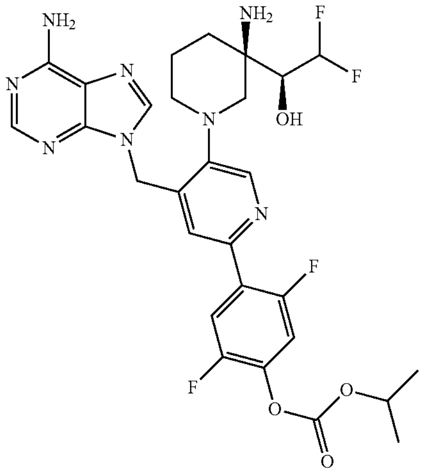 [SMILES: CC(C)OC(=O)Oc1cc(F)c(-c2cc(Cn3cnc4c(N)ncnc43)c(N3CCC[C@](N)([C@H](O)C(F)F)C3)cn2)cc1F] |
| II-19 | 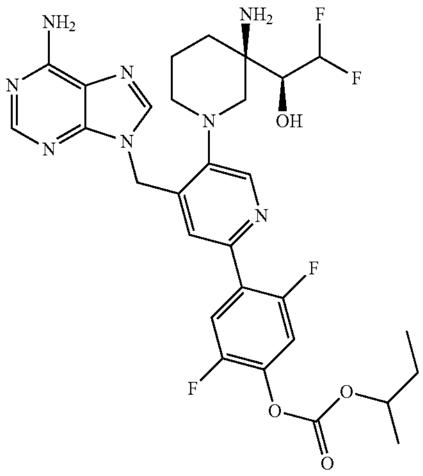 [SMILES: CCC(C)OC(=O)Oc1cc(F)c(-c2cc(Cn3cnc4c(N)ncnc43)c(N3CCC[C@](N)([C@H](O)C(F)F)C3)cn2)cc1F] |

TABLE 2-continued
| Compound No. | Chemical Structure |
|---|---|
| II-20 | 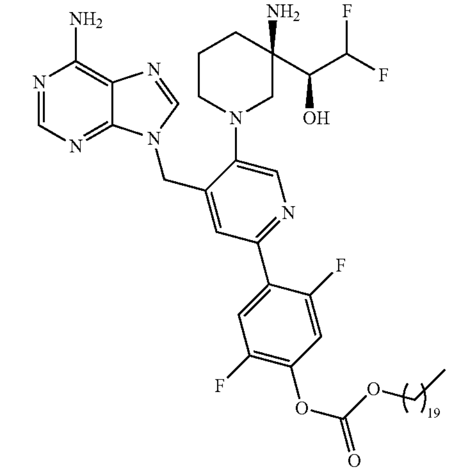 |
| II-21 | 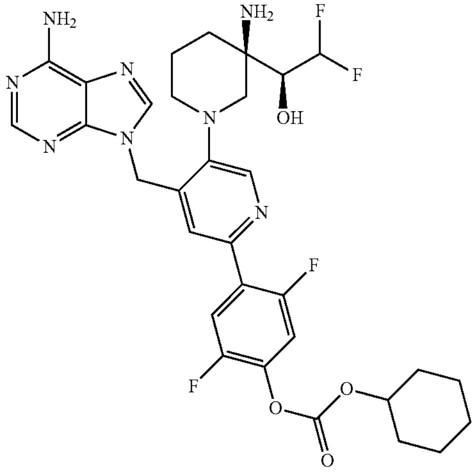 [SMILES: Nc1ncnc2c1ncn2Cc1cc(-c2cc(F)c(OC(=O)OC3CCCCC3)cc2F)ncc1N1CCC[C@](N)([C@H](O)C(F)F)C1] |
| II-22 | 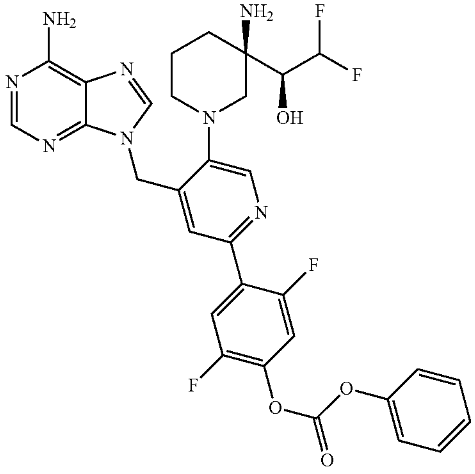 [SMILES: Nc1ncnc2c1ncn2Cc1cc(-c2cc(F)c(OC(=O)Oc3ccccc3)cc2F)ncc1N1CCC[C@](N)([C@H](O)C(F)F)C1] |

TABLE 2-continued
| Compound No. | Chemical Structure |
|---|---|
| II-23 | 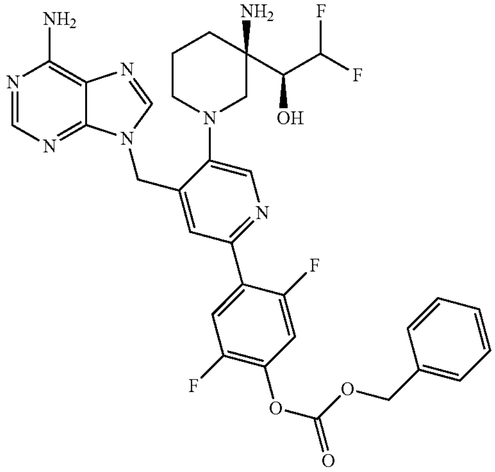 [SMILES: Nc1ncnc2c1ncn2Cc1cc(-c2cc(F)c(OC(=O)OCc3ccccc3)cc2F)ncc1N1CCC[C@](N)([C@H](O)C(F)F)C1] |
| II-24 | 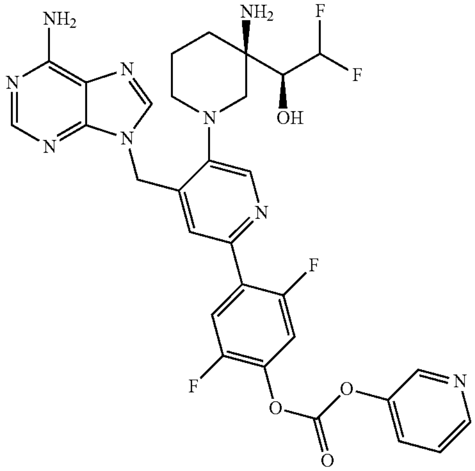 [SMILES: Nc1ncnc2c1ncn2Cc1cc(-c2cc(F)c(OC(=O)Oc3cccnc3)cc2F)ncc1N1CCC[C@](N)([C@H](O)C(F)F)C1] |
| II-25 | 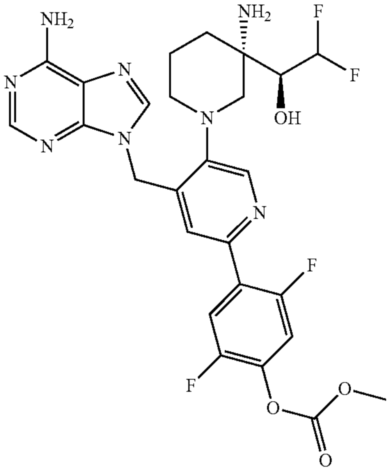 [SMILES: COC(=O)Oc1cc(F)c(-c2cc(Cn3cnc4c(N)ncnc43)c(N3CCC[C@@](N)([C@H](O)C(F)F)C3)cn2)cc1F] |

TABLE 2-continued
| Compound No. | Chemical Structure |
|---|---|
| II-26 | 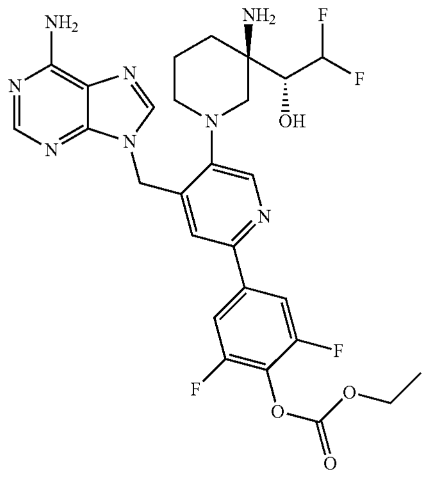 [SMILES: CCOC(=O)Oc1c(F)cc(-c2cc(Cn3cnc4c(N)ncnc43)c(N3CCC[C@](N)([C@@H](O)C(F)F)C3)cn2)cc1F] |
| II-27 | 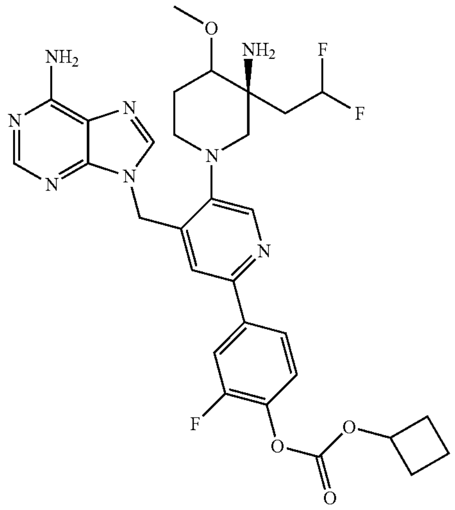 [SMILES: COC1CCN(c2cnc(-c3ccc(OC(=O)OC4CCC4)c(F)c3)cc2Cn2cnc3c(N)ncnc32)C[C@@]1(N)CC(F)F] |
| II-28 | 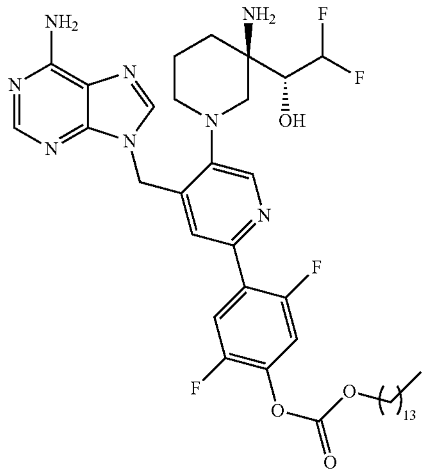 |

TABLE 2-continued
| Compound No. | Chemical Structure |
| --- | --- |
| II-29 | 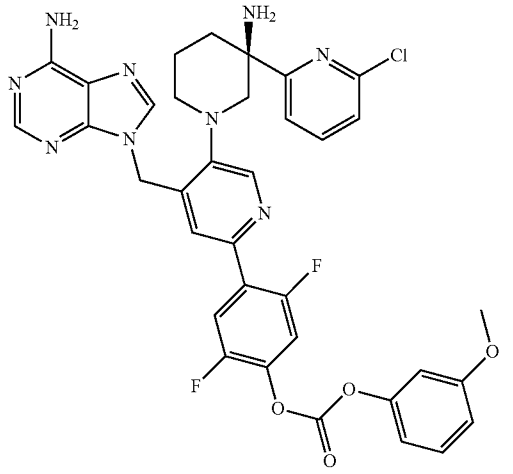 [SMILES: COc1cccc(OC(=O)Oc2cc(F)c(-c3cc(Cn4cnc5c(N)ncnc54)c(N4CCC[C@](N)(c5cccc(Cl)n5)C4)cn3)cc2F)c1] |
| II-30 | 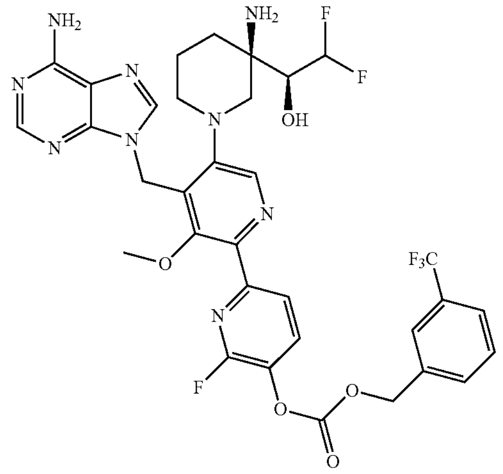 [SMILES: COc1c(-c2ccc(OC(=O)OCc3cccc(C(F)(F)F)c3)c(F)n2)ncc(N2CCC[C@](N)([C@H](O)C(F)F)C2)c1Cn1cnc2c(N)ncnc21] |
| II-31 | 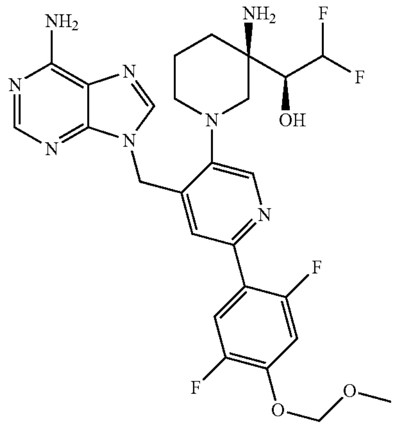 [SMILES: COCOc1cc(F)c(-c2cc(Cn3cnc4c(N)ncnc43)c(N3CCC[C@](N)([C@H](O)C(F)F)C3)cn2)cc1F] |

TABLE 2-continued
| Compound No. | Chemical Structure |
|---|---|
| II-32 | 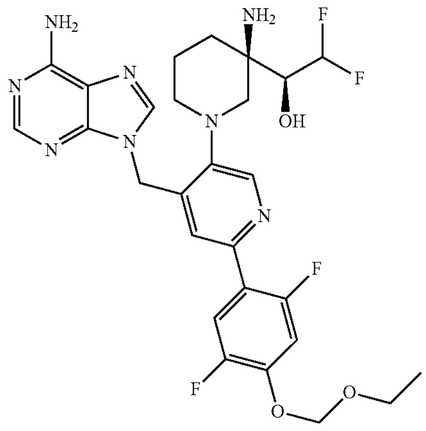 [SMILES: CCOCOc1cc(F)c(-c2cc(Cn3cnc4c(N)ncnc43)c(N3CCC[C@](N)([C@H](O)C(F)F)C3)cn2)cc1F] |
| II-33 | 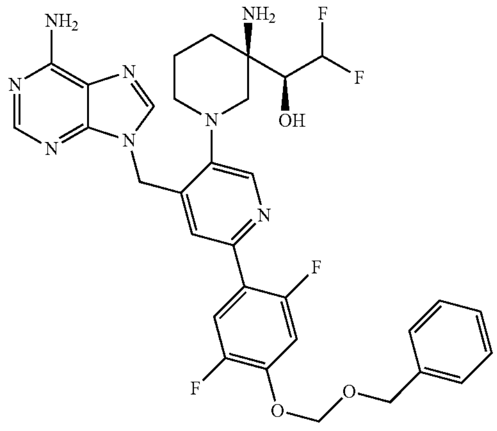 [SMILES: Nc1ncnc2c1ncn2Cc1cc(-c2cc(F)c(OCOCc3ccccc3)cc2F)ncc1N1CCC[C@](N)([C@H](O)C(F)F)C1] |
| II-34 | 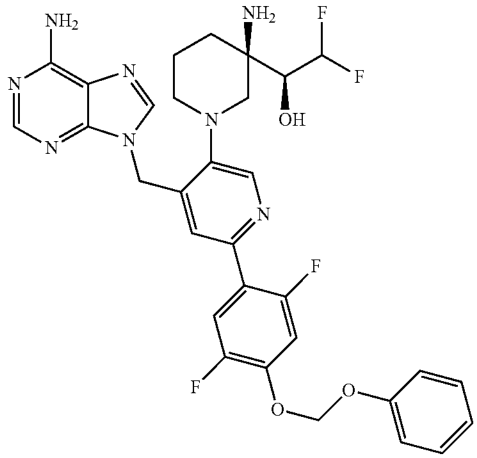 [SMILES: Nc1ncnc2c1ncn2Cc1cc(-c2cc(F)c(OCOc3ccccc3)cc2F)ncc1N1CCC[C@](N)([C@H](O)C(F)F)C1] |

TABLE 2-continued
| Compound No. | Chemical Structure |
|---|---|
| II-35 | 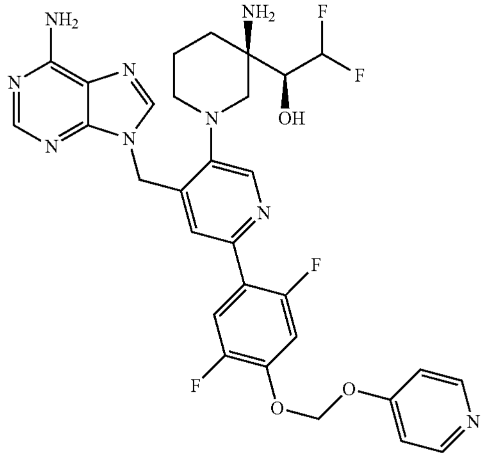 [SMILES: Nc1ncnc2c1ncn2Cc1cc(-c2cc(F)c(OCOc3ccncc3)cc2F)ncc1N1CCC[C@](N)([C@H](O)C(F)F)C1] |
| II-36 | 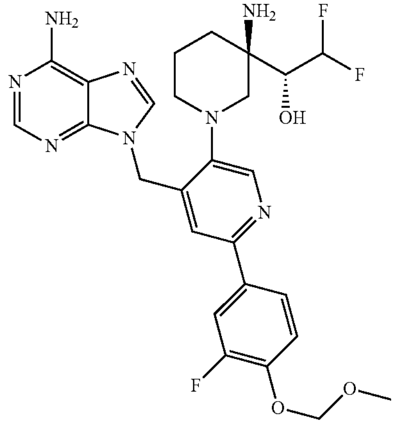 [SMILES: COCOc1ccc(-c2cc(Cn3cnc4c(N)ncnc43)c(N3CCC[C@](N)([C@@H](O)C(F)F)C3)cn2)cc1F] |
| II-37 | 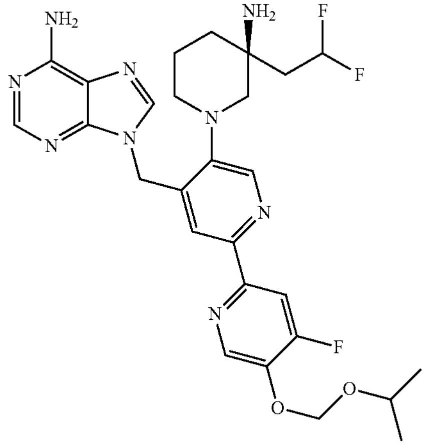 [SMILES: CC(C)OCOc1cnc(-c2cc(Cn3cnc4c(N)ncnc43)c(N3CCC[C@](N)(CC(F)F)C3)cn2)cc1F] |

TABLE 2-continued
| Compound No. | Chemical Structure |
|---|---|
| II-38 | 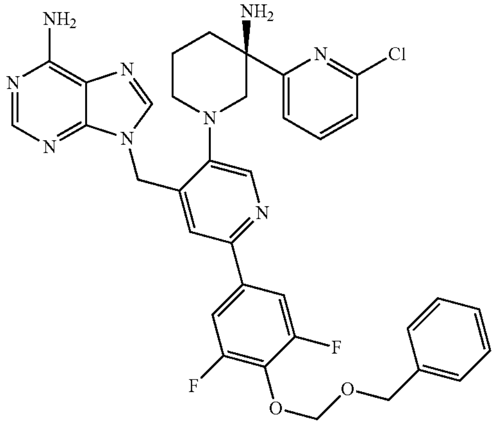 [SMILES: Nc1ncnc2c1ncn2Cc1cc(-c2cc(F)c(OCOCc3ccccc3)c(F)c2)ncc1N1CCC[C@](N)(c2cccc(Cl)n2)C1] |
| II-39 | 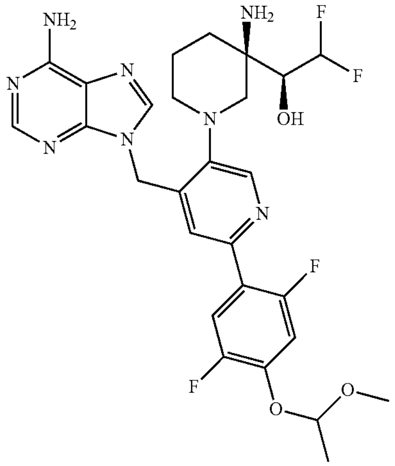 [SMILES: COC(C)Oc1cc(F)c(-c2cc(Cn3cnc4c(N)ncnc43)c(N3CCC[C@](N)([C@H](O)C(F)F)C3)cn2)cc1F] |
| II-40 | 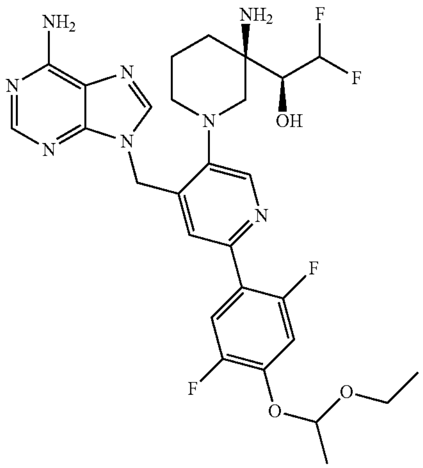 [SMILES: CCOC(C)Oc1cc(F)c(-c2cc(Cn3cnc4c(N)ncnc43)c(N3CCC[C@](N)([C@H](O)C(F)F)C3)cn2)cc1F] |

TABLE 2-continued
| Compound No. | Chemical Structure |
|---|---|
| II-41 | 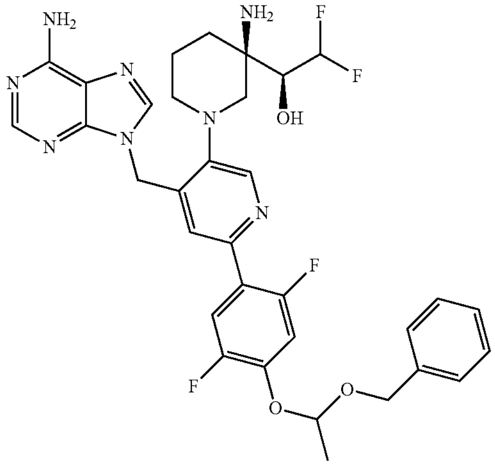 [SMILES: CC(OCc1ccccc1)Oc1cc(F)c(-c2cc(Cn3cnc4c(N)ncnc43)c(N3CCC[C@](N)([C@H](O)C(F)F)C3)cn2)cc1F] |
| II-42 | 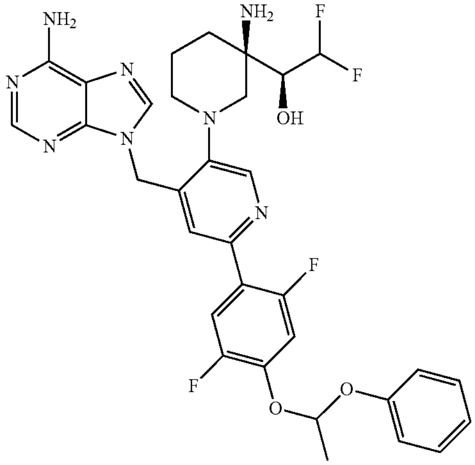 [SMILES: CC(Oc1ccccc1)Oc1cc(F)c(-c2cc(Cn3cnc4c(N)ncnc43)c(N3CCC[C@](N)([C@H](O)C(F)F)C3)cn2)cc1F] |
| II-43 | 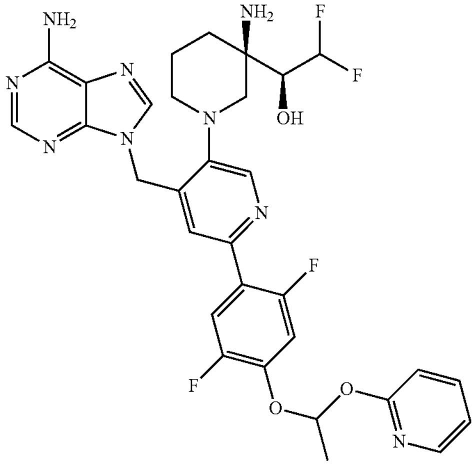 [SMILES: CC(Oc1ccccn1)Oc1cc(F)c(-c2cc(Cn3cnc4c(N)ncnc43)c(N3CCC[C@](N)([C@H](O)C(F)F)C3)cn2)cc1F] |

TABLE 2-continued
| Compound No. | Chemical Structure |
| --- | --- |
| II-44 | 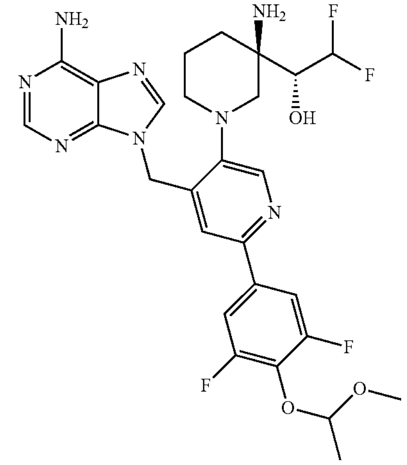 [SMILES: COC(C)Oc1c(F)cc(-c2cc(Cn3cnc4c(N)ncnc43)c(N3CCC[C@](N)([C@@H](O)C(F)F)C3)cn2)cc1F] |
| II-45 | 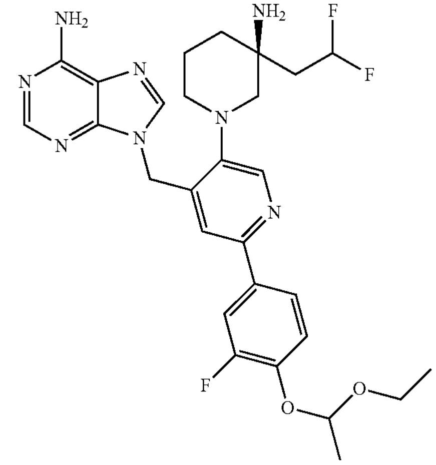 [SMILES: CCOC(C)Oc1ccc(-c2cc(Cn3cnc4c(N)ncnc43)c(N3CCC[C@](N)(CC(F)F)C3)cn2)cc1F] |
| II-46 | 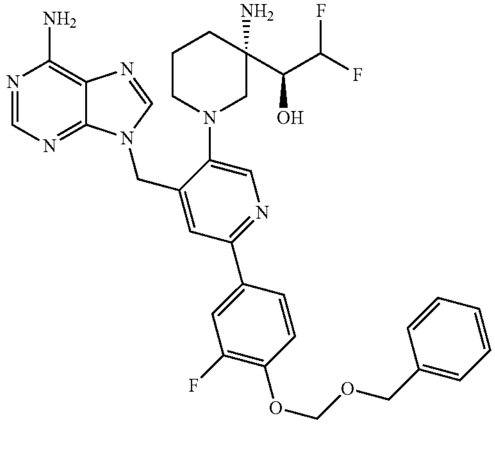 [SMILES: Nc1ncnc2c1ncn2Cc1cc(-c2ccc(OCOCc3ccccc3)c(F)c2)ncc1N1CCC[C@@](N)([C@H](O)C(F)F)C1] |

TABLE 2-continued
| Compound No. | Chemical Structure |
| --- | --- |
| II-47 | 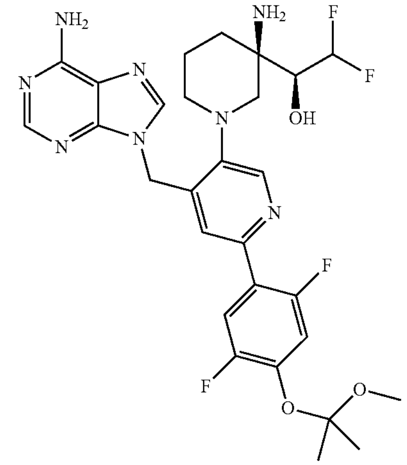 [SMILES: COC(C)(C)Oc1cc(F)c(-c2cc(Cn3cnc4c(N)ncnc43)c(N3CCC[C@](N)([C@H](O)C(F)F)C3)cn2)cc1F] |
| II-48 | 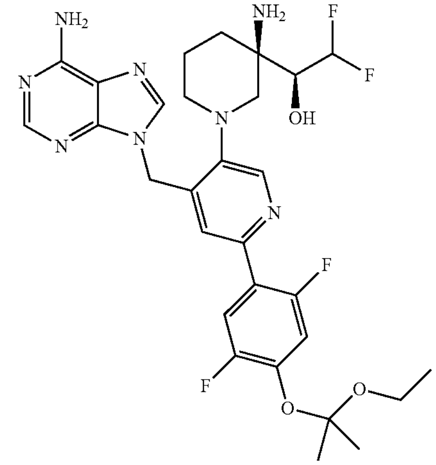 [SMILES: CCOC(C)(C)Oc1cc(F)c(-c2cc(Cn3cnc4c(N)ncnc43)c(N3CCC[C@](N)([C@H](O)C(F)F)C3)cn2)cc1F] |
| II-49 | 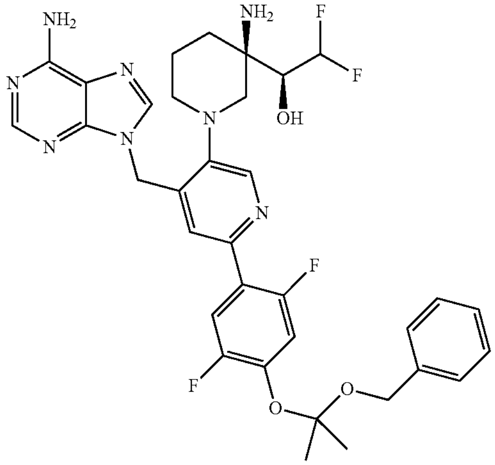 [SMILES: CC(C)(OCc1ccccc1)Oc1cc(F)c(-c2cc(Cn3cnc4c(N)ncnc43)c(N3CCC[C@](N)([C@H](O)C(F)F)C3)cn2)cc1F] |

TABLE 2-continued
| Compound No. | Chemical Structure |
| --- | --- |
| II-50 | 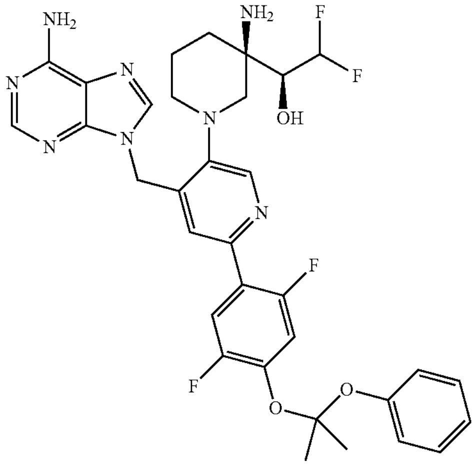 [SMILES: CC(C)(Oc1ccccc1)Oc1cc(F)c(-c2cc(Cn3cnc4c(N)ncnc43)c(N3CCC[C@](N)([C@H](O)C(F)F)C3)cn2)cc1F] |
| II-51 | 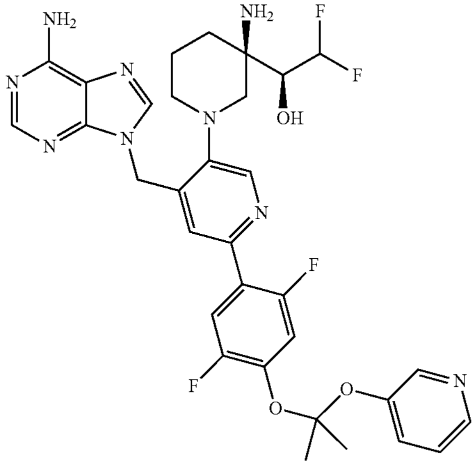 [SMILES: CC(C)(Oc1cccnc1)Oc1cc(F)c(-c2cc(Cn3cnc4c(N)ncnc43)c(N3CCC[C@](N)([C@H](O)C(F)F)C3)cn2)cc1F] |
| II-52 | 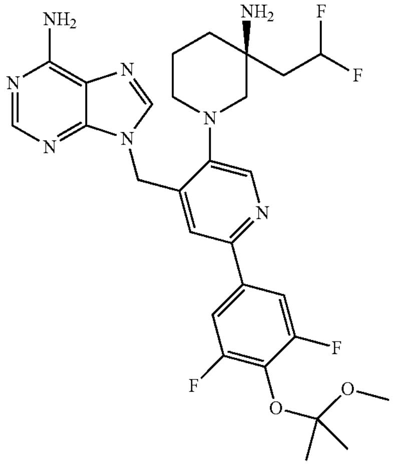 [SMILES: COC(C)(C)Oc1c(F)cc(-c2cc(Cn3cnc4c(N)ncnc43)c(N3CCC[C@](N)(CC(F)F)C3)cn2)cc1F] |

TABLE 2-continued
| Compound No. | Chemical Structure |
| --- | --- |
| II-53 | 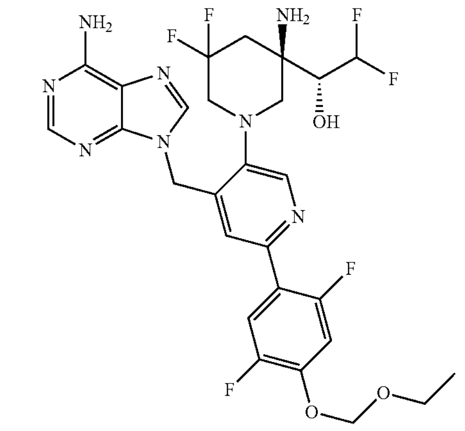 [SMILES: CCOCOc1cc(F)c(-c2cc(Cn3cnc4c(N)ncnc43)c(N3CC(F)(F)C[C@](N)([C@@H](O)C(F)F)C3)cn2)cc1F] |
| II-54 | 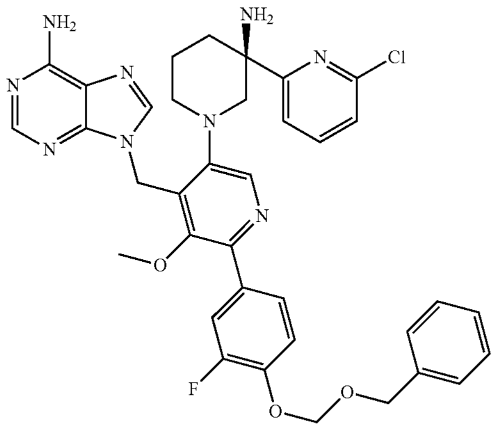 [SMILES: COc1c(-c2ccc(OCOCc3ccccc3)c(F)c2)ncc(N2CCC[C@](N)(c3cccc(Cl)n3)C2)c1Cn1cnc2c(N)ncnc21] |
| II-55 | 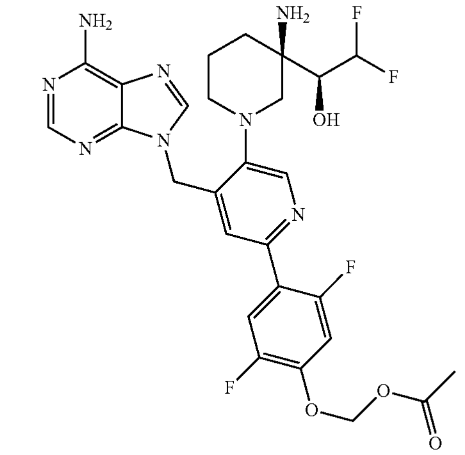 [SMILES: CC(=O)OCOc1cc(F)c(-c2cc(Cn3cnc4c(N)ncnc43)c(N3CCC[C@](N)([C@H](O)C(F)F)C3)cn2)cc1F] |

TABLE 2-continued
| Compound No. | Chemical Structure |
| --- | --- |
| II-56 | 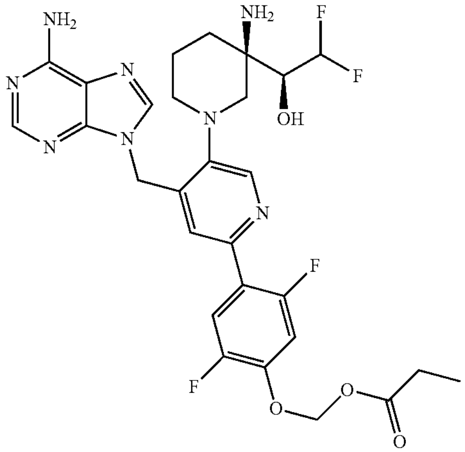 [SMILES: CCC(=O)OCOc1cc(F)c(-c2cc(Cn3cnc4c(N)ncnc43)c(N3CCC[C@](N)([C@H](O)C(F)F)C3)cn2)cc1F] |
| II-57 | 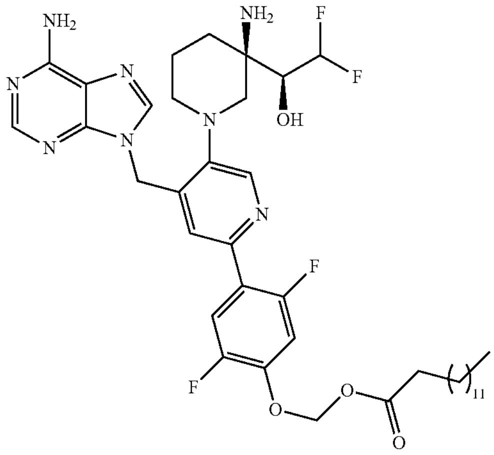 |
| II-58 | 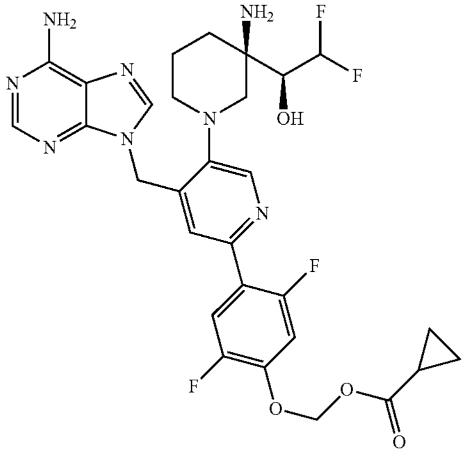 [SMILES: Nc1ncnc2c1ncn2Cc1cc(-c2cc(F)c(OCOC(=O)C3CC3)cc2F)ncc1N1CCC[C@](N)([C@H](O)C(F)F)C1] |

TABLE 2-continued
| Compound No. | Chemical Structure |
| --- | --- |
| II-59 | 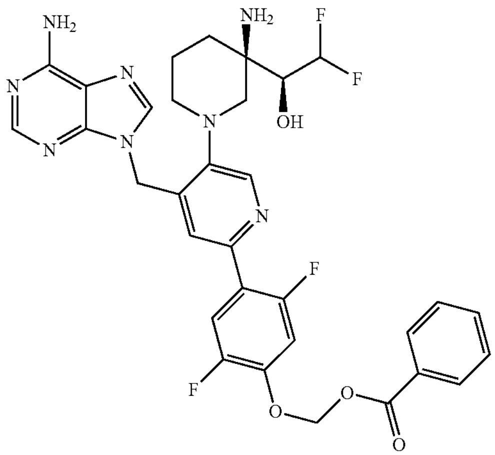 [SMILES: Nc1ncnc2c1ncn2Cc1cc(-c2cc(F)c(OCOC(=O)c3ccccc3)cc2F)ncc1N1CCC[C@](N)([C@H](O)C(F)F)C1] |
| II-60 | 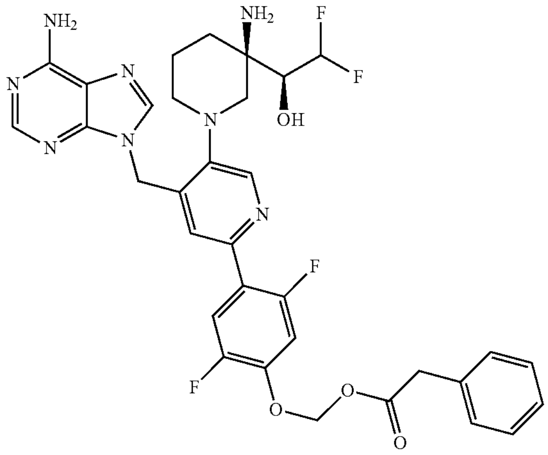 [SMILES: Nc1ncnc2c1ncn2Cc1cc(-c2cc(F)c(OCOC(=O)Cc3ccccc3)cc2F)ncc1N1CCC[C@](N)([C@H](O)C(F)F)C1] |
| II-61 | 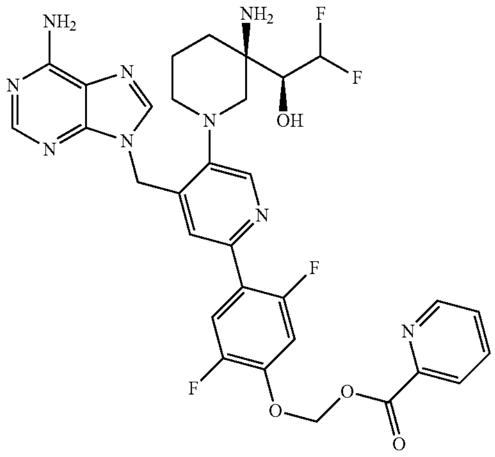 [SMILES: Nc1ncnc2c1ncn2Cc1cc(-c2cc(F)c(OCOC(=O)c3ccccn3)cc2F)ncc1N1CCC[C@](N)([C@H](O)C(F)F)C1] |

TABLE 2-continued
| Compound No. | Chemical Structure |
| --- | --- |
| II-62 | 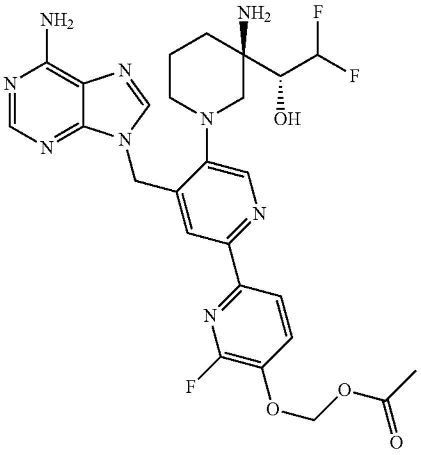 [SMILES: CC(=O)OCOc1ccc(-c2cc(Cn3cnc4c(N)ncnc43)c(N3CCC[C@](N)([C@@H](O)C(F)F)C3)cn2)nc1F] |
| II-63 | 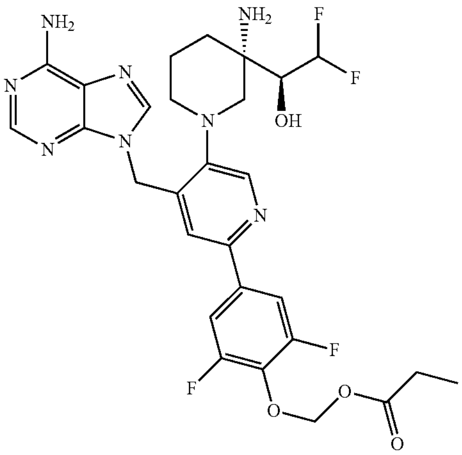 [SMILES: CCC(=O)OCOc1c(F)cc(-c2cc(Cn3cnc4c(N)ncnc43)c(N3CCC[C@@](N)([C@H](O)C(F)F)C3)cn2)cc1F] |
| II-64 | 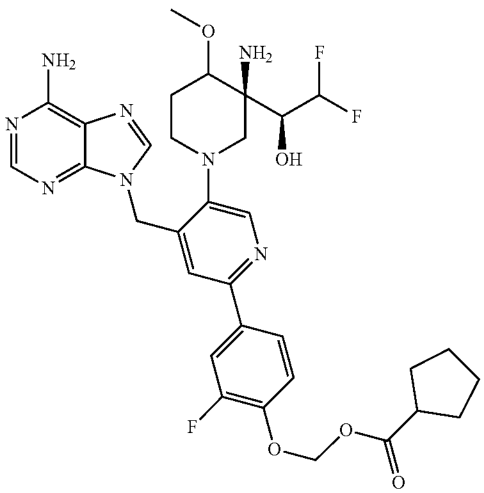 [SMILES: COC1CCN(c2cnc(-c3ccc(OCOC(=O)C4CCCC4)c(F)c3)cc2Cn2cnc3c(N)ncnc32)C[C@@]1(N)[C@H](O)C(F)F] |

TABLE 2-continued
| Compound No. | Chemical Structure |
| --- | --- |
| II-65 | 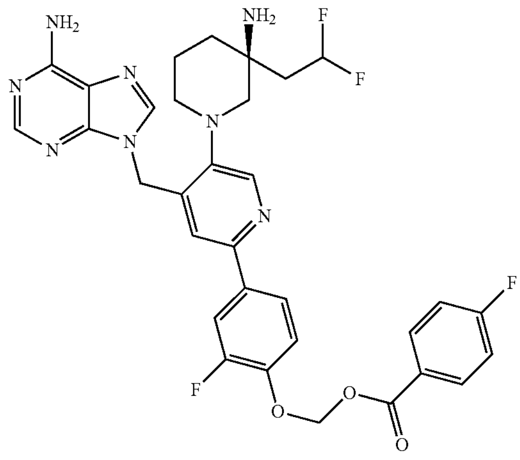 [SMILES: Nc1ncnc2c1ncn2Cc1cc(-c2ccc(OCOC(=O)c3ccc(F)cc3)c(F)c2)ncc1N1CCC[C@](N)(CC(F)F)C1] |
| II-66 | 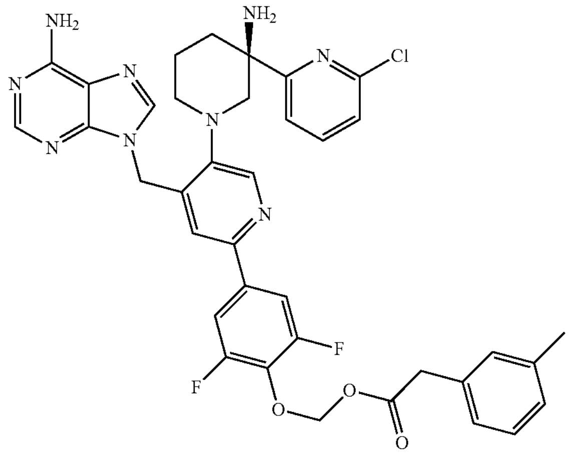 [SMILES: Cc1cccc(CC(=O)OCOc2c(F)cc(-c3cc(Cn4cnc5c(N)ncnc54)c(N4CCC[C@](N)(c5cccc(Cl)n5)C4)cn3)cc2F)c1] |
| II-67 | 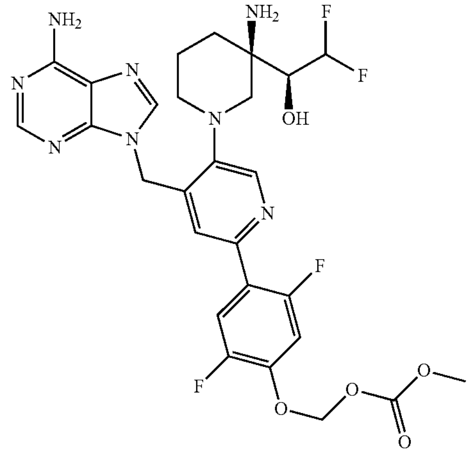 [SMILES: COC(=O)OCOc1cc(F)c(-c2cc(Cn3cnc4c(N)ncnc43)c(N3CCC[C@](N)([C@H](O)C(F)F)C3)cn2)cc1F] |

TABLE 2-continued
| Compound No. | Chemical Structure |
| --- | --- |
| II-68 | 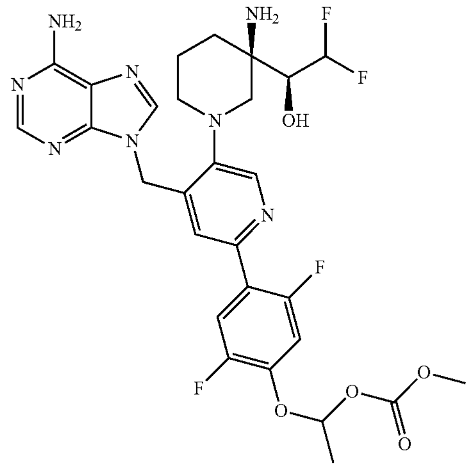 [SMILES: COC(=O)OC(C)Oc1cc(F)c(-c2cc(Cn3cnc4c(N)ncnc43)c(N3CCC[C@](N)([C@H](O)C(F)F)C3)cn2)cc1F] |
| II-69 | 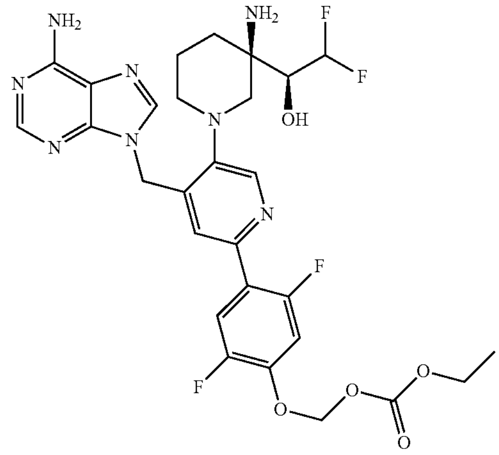 [SMILES: CCOC(=O)OCOc1cc(F)c(-c2cc(Cn3cnc4c(N)ncnc43)c(N3CCC[C@](N)([C@H](O)C(F)F)C3)cn2)cc1F] |
| II-70 | 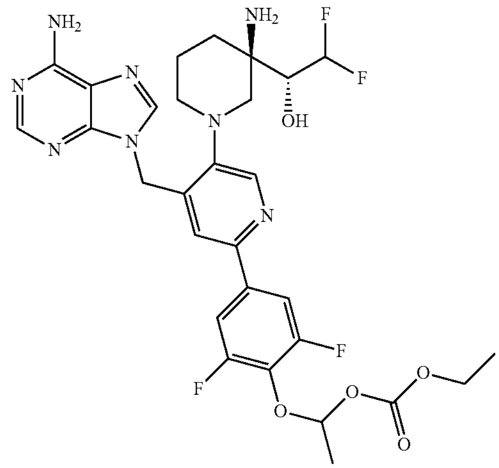 [SMILES: CCOC(=O)OC(C)Oc1c(F)cc(-c2cc(Cn3cnc4c(N)ncnc43)c(N3CCC[C@](N)([C@@H](O)C(F)F)C3)cn2)cc1F] |

TABLE 2-continued
| Compound No. | Chemical Structure |
| --- | --- |
| II-71 | 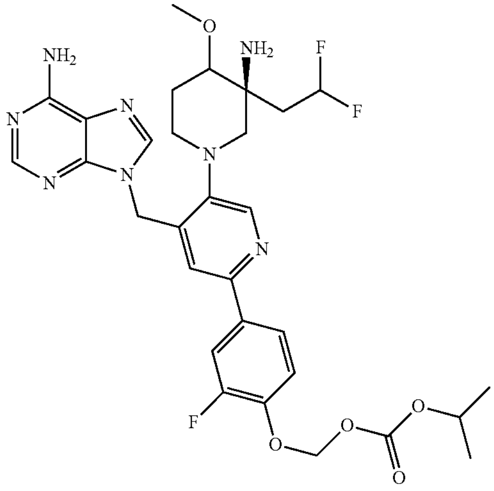 [SMILES: COC1CCN(c2cnc(-c3ccc(OCOC(=O)OC(C)C)c(F)c3)cc2Cn2cnc3c(N)ncnc32)C[C@@]1(N)CC(F)F] |
| II-72 | 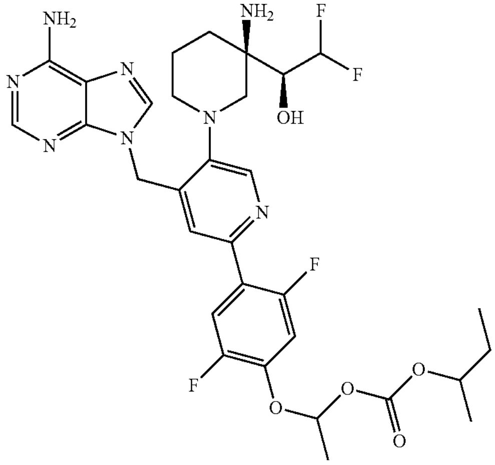 [SMILES: CCC(C)OC(=O)OC(C)Oc1cc(F)c(-c2cc(Cn3cnc4c(N)ncnc43)c(N3CCC[C@](N)([C@H](O)C(F)F)C3)cn2)cc1F] |
| II-73 | 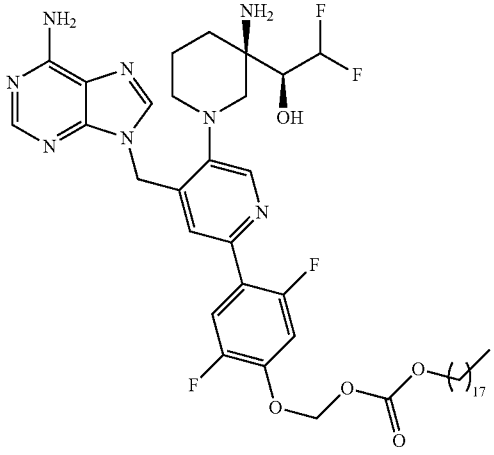 |

TABLE 2-continued
| Compound No. | Chemical Structure |
|---|---|
| II-74 | 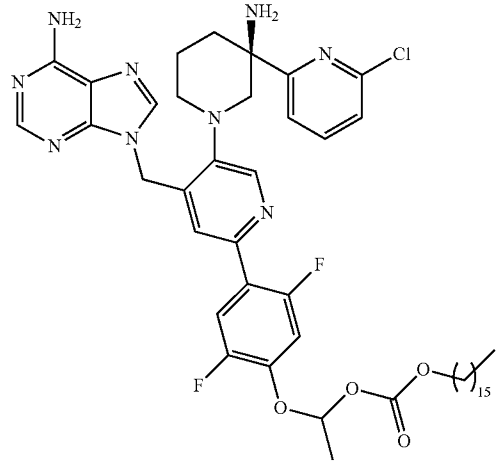 |
| II-75 | 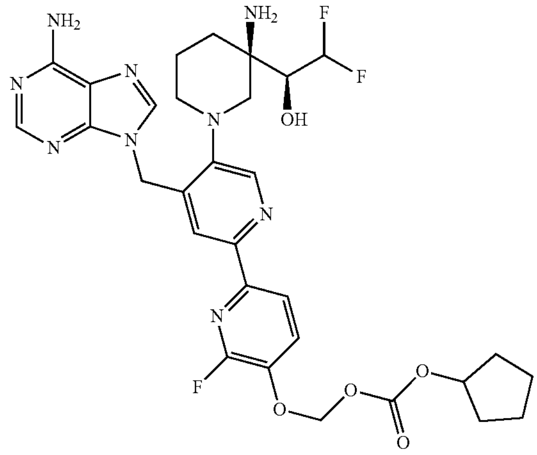 [SMILES: Nc1ncnc2c1ncn2Cc1cc(-c2ccc(OCOC(=O)OC3CCCC3)c(F)n2)ncc1N1CCC[C@](N)([C@H](O)C(F)F)C1] |
| II-76 | 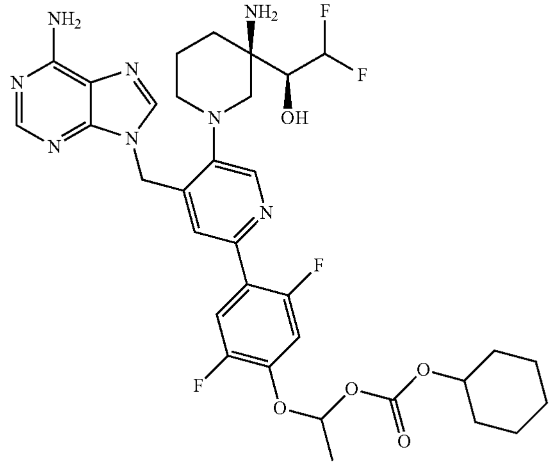 [SMILES: CC(OC(=O)OC1CCCCC1)Oc1cc(F)c(-c2cc(Cn3cnc4c(N)ncnc43)c(N3CCC[C@](N)([C@H](O)C(F)F)C3)cn2)cc1F] |

TABLE 2-continued
| Compound No. | Chemical Structure |
| --- | --- |
| II-77 | 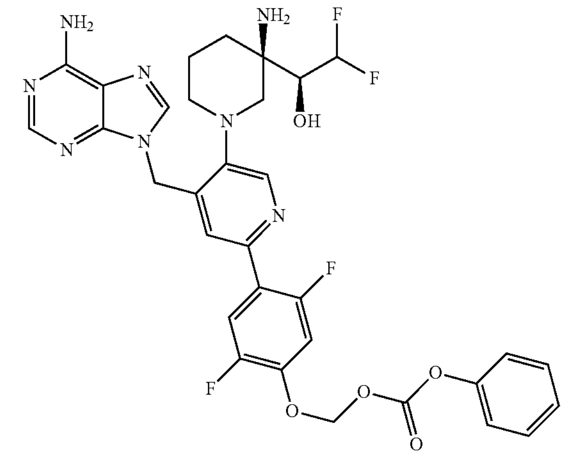 [SMILES: Nc1ncnc2c1ncn2Cc1cc(-c2cc(F)c(OCOC(=O)Oc3ccccc3)cc2F)ncc1N1CCC[C@](N)([C@H](O)C(F)F)C1] |
| II-78 | 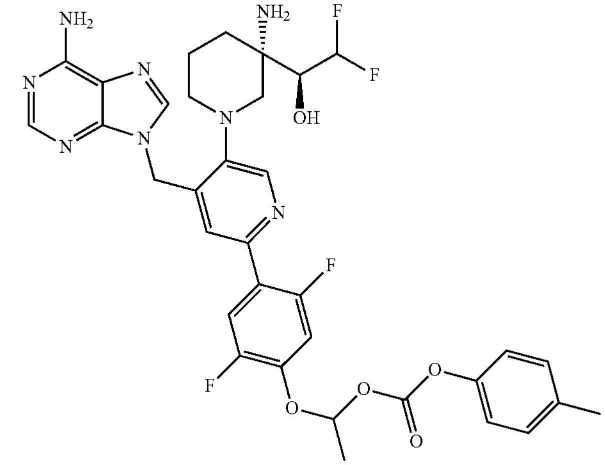 [SMILES: Cc1ccc(OC(=O)OC(C)Oc2cc(F)c(-c3cc(Cn4cnc5c(N)ncnc54)c(N4CCC[C@@](N)([C@H](O)C(F)F)C4)cn3)cc2F)cc1] |
| II-79 | 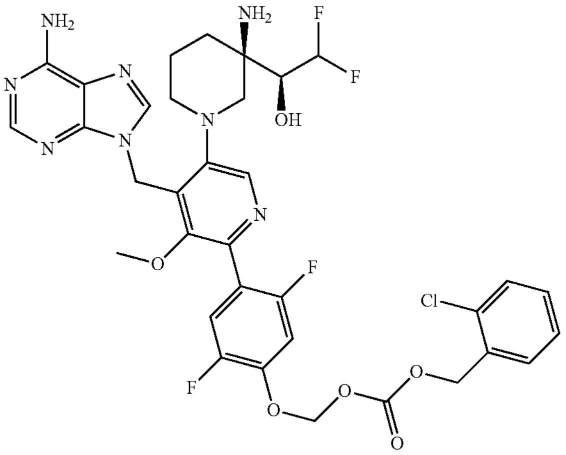 [SMILES: COc1c(-c2cc(F)c(OCOC(=O)OCc3ccccc3Cl)cc2F)ncc(N2CCC[C@](N)([C@H](O)C(F)F)C2)c1Cn1cnc2c(N)ncnc21] |

TABLE 2-continued
| Compound No. | Chemical Structure |
|---|---|
| II-80 | 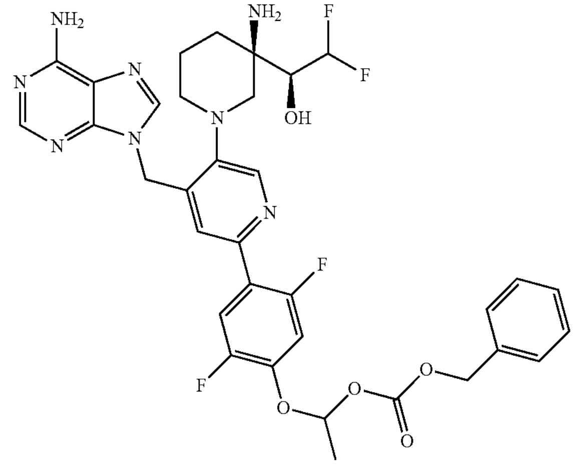 [SMILES: CC(OC(=O)OCc1ccccc1)Oc1cc(F)c(-c2cc(Cn3cnc4c(N)ncnc43)c(N3CCC[C@](N)([C@H](O)C(F)F)C3)cn2)cc1F] |
| II-81 | 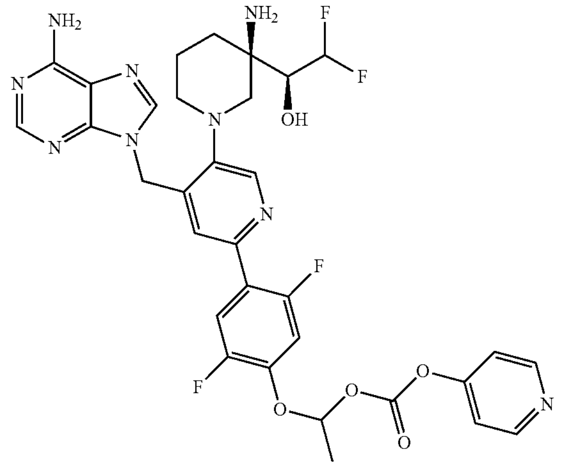 [SMILES: CC(OC(=O)Oc1ccncc1)Oc1cc(F)c(-c2cc(Cn3cnc4c(N)ncnc43)c(N3CCC[C@](N)([C@H](O)C(F)F)C3)cn2)cc1F] |
| II-82 | 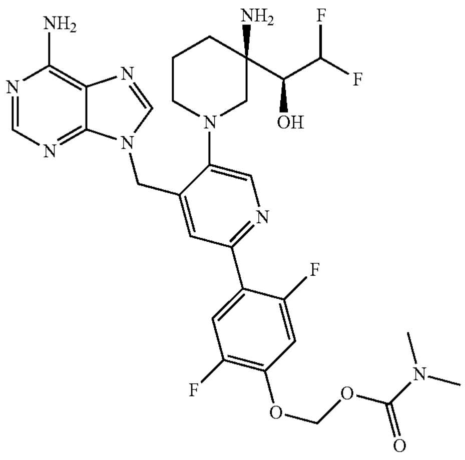 [SMILES: CN(C)C(=O)OCOc1cc(F)c(-c2cc(Cn3cnc4c(N)ncnc43)c(N3CCC[C@](N)([C@H](O)C(F)F)C3)cn2)cc1F] |

TABLE 2-continued
| Compound No. | Chemical Structure |
| --- | --- |
| II-83 | 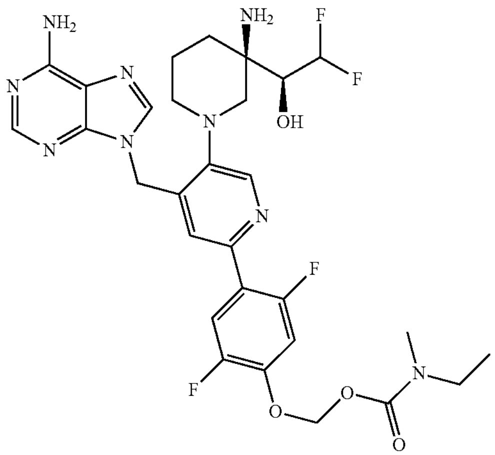 [SMILES: CCN(C)C(=O)OCOc1cc(F)c(-c2cc(Cn3cnc4c(N)ncnc43)c(N3CCC[C@](N)([C@H](O)C(F)F)C3)cn2)cc1F] |
| II-84 | 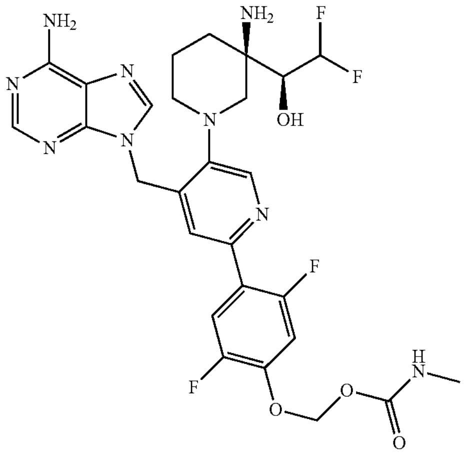 [SMILES: CNC(=O)OCOc1cc(F)c(-c2cc(Cn3cnc4c(N)ncnc43)c(N3CCC[C@](N)([C@H](O)C(F)F)C3)cn2)cc1F] |
| II-85 | 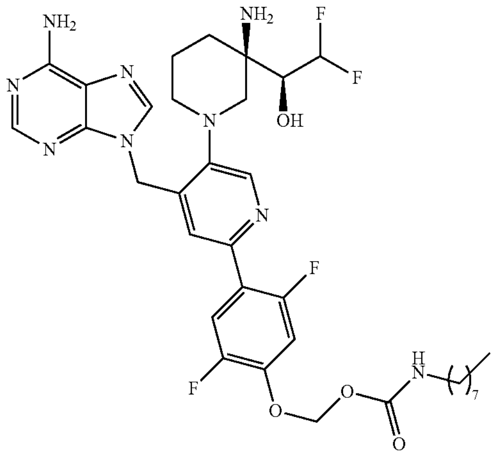 |

TABLE 2-continued
| Compound No. | Chemical Structure |
|---|---|
| II-86 | 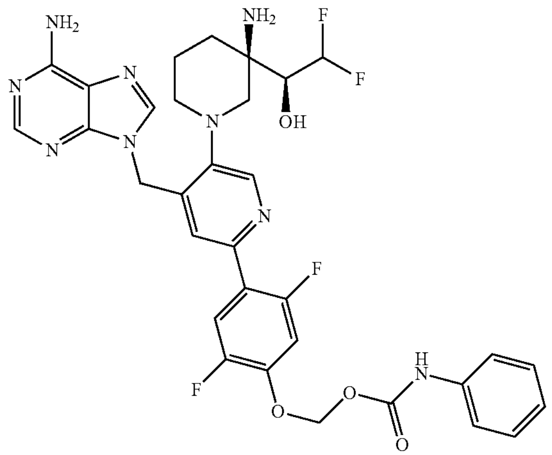 [SMILES: Nc1ncnc2c1ncn2Cc1cc(-c2cc(F)c(OCOC(=O)Nc3ccccc3)cc2F)ncc1N1CCC[C@](N)([C@H](O)C(F)F)C1] |
| II-87 | 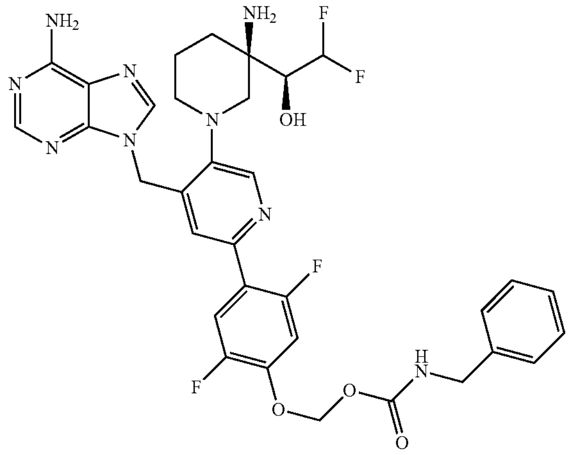 [SMILES: Nc1ncnc2c1ncn2Cc1cc(-c2cc(F)c(OCOC(=O)NCc3ccccc3)cc2F)ncc1N1CCC[C@](N)([C@H](O)C(F)F)C1] |
| II-88 | 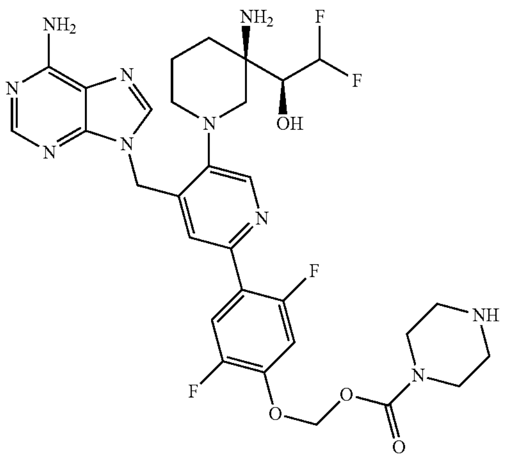 [SMILES: Nc1ncnc2c1ncn2Cc1cc(-c2cc(F)c(OCOC(=O)N3CCNCC3)cc2F)ncc1N1CCC[C@](N)([C@H](O)C(F)F)C1] |

TABLE 2-continued
| Compound No. | Chemical Structure |
|---|---|
| II-89 | 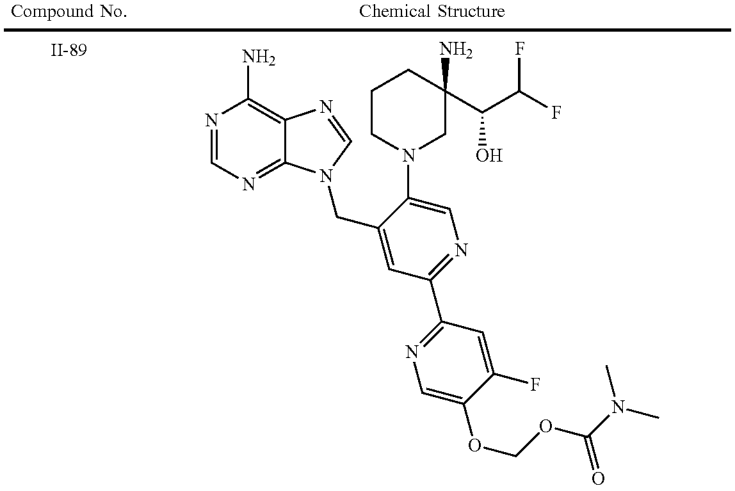 |
| II-90 | 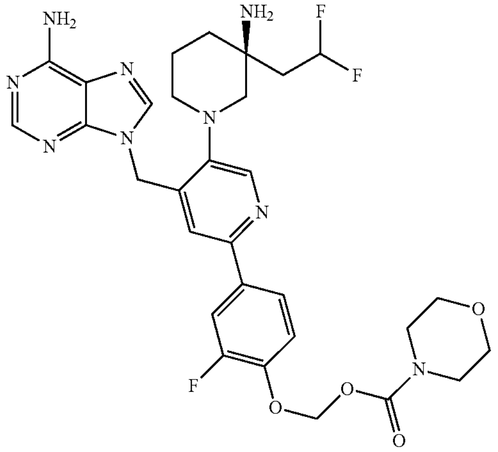 [SMILES: Nc1ncnc2c1ncn2Cc1cc(-c2ccc(OCOC(=O)N3CCOCC3)c(F)c2)ncc1N1CCC[C@](N)(CC(F)F)C1] |
TABLE 3
| Compound No. | Chemical Structure |
|---|---|
| III-1 | 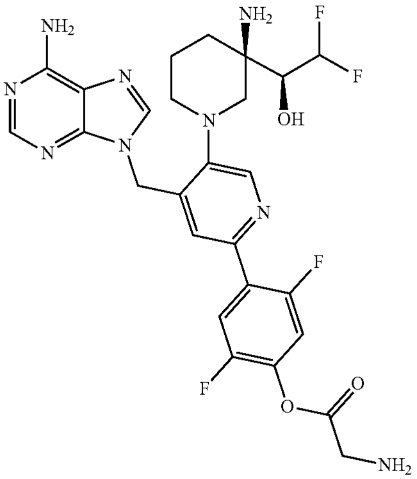 [SMILES: NCC(=O)Oc1cc(F)c(-c2cc(Cn3cnc4c(N)ncnc43)c(N3CCC[C@](N)([C@H](O)C(F)F)C3)cn2)cc1F] |
TABLE 3-continued
| Compound No. | Chemical Structure |
|---|---|
| III-2 | 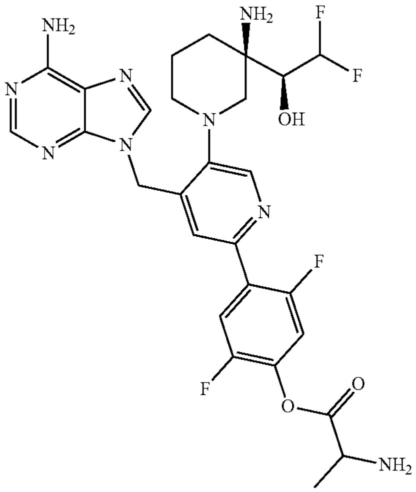 [SMILES: CC(N)C(=O)Oc1cc(F)c(-c2cc(Cn3cnc4c(N)ncnc43)c(N3CCC[C@](N)([C@H](O)C(F)F)C3)cn2)cc1F] |

TABLE 3-continued
| Compound No. | Chemical Structure |
|---|---|
| III-3 | 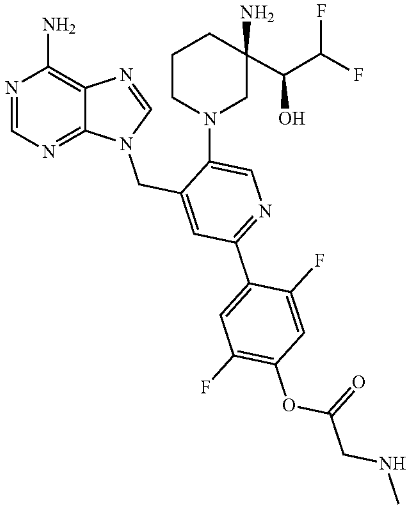 [SMILES: CNCC(=O)Oc1cc(F)c(-c2cc(Cn3cnc4c(N)ncnc43)c(N3CCC[C@](N)([C@H](O)C(F)F)C3)cn2)cc1F] |
| III-4 | 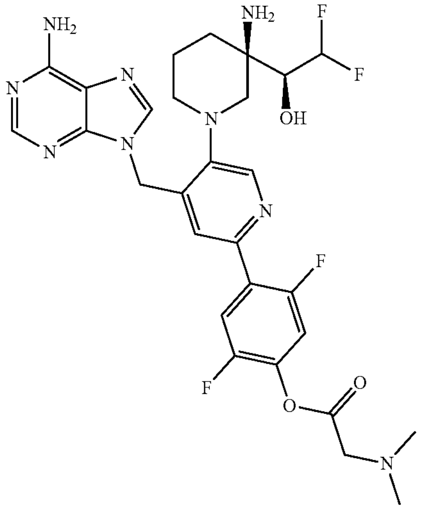 [SMILES: CN(C)CC(=O)Oc1cc(F)c(-c2cc(Cn3cnc4c(N)ncnc43)c(N3CCC[C@](N)([C@H](O)C(F)F)C3)cn2)cc1F] |
| III-5 | 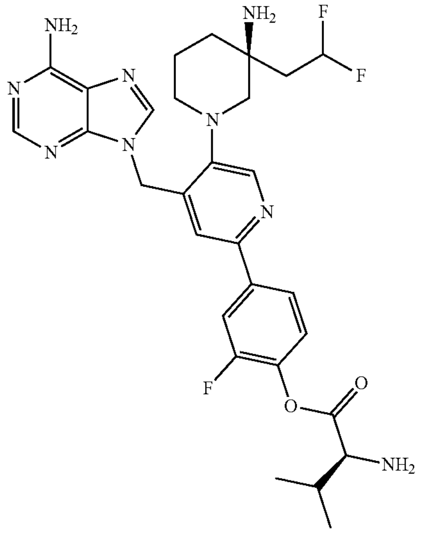 [SMILES: CC(C)[C@H](N)C(=O)Oc1ccc(-c2cc(Cn3cnc4c(N)ncnc43)c(N3CCC[C@](N)(CC(F)F)C3)cn2)cc1F] |
TABLE 3-continued
| Compound No. | Chemical Structure |
|---|---|
| III-6 | 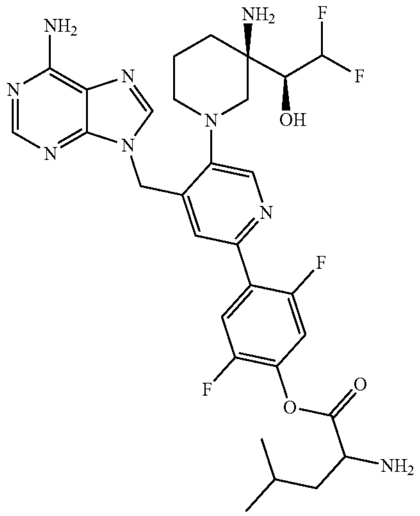 [SMILES: CC(C)CC(N)C(=O)Oc1cc(F)c(-c2cc(Cn3cnc4c(N)ncnc43)c(N3CCC[C@](N)([C@H](O)C(F)F)C3)cn2)cc1F] |
| III-7 | 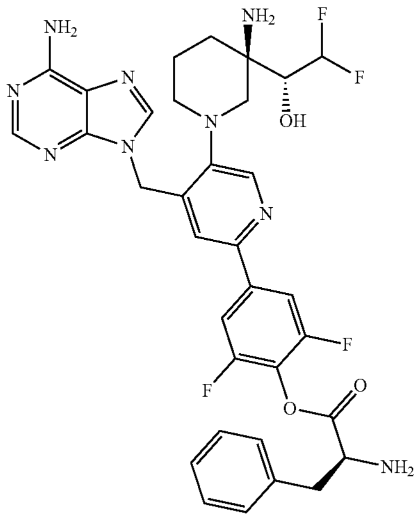 [SMILES: Nc1ncnc2c1ncn2Cc1cc(-c2cc(F)c(OC(=O)[C@@H](N)Cc3ccccc3)c(F)c2)ncc1N1CCC[C@](N)([C@@H](O)C(F)F)C1] |
| III-8 | 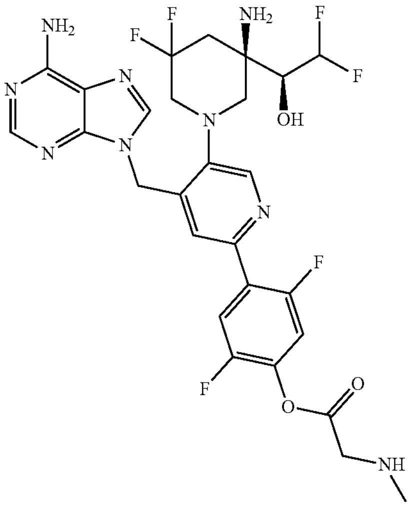 [SMILES: CNCC(=O)Oc1cc(F)c(-c2cc(Cn3cnc4c(N)ncnc43)c(N3CC(F)(F)C[C@](N)([C@H](O)C(F)F)C3)cn2)cc1F] |

TABLE 3-continued
| Compound No. | Chemical Structure |
|---|---|
| III-9 | 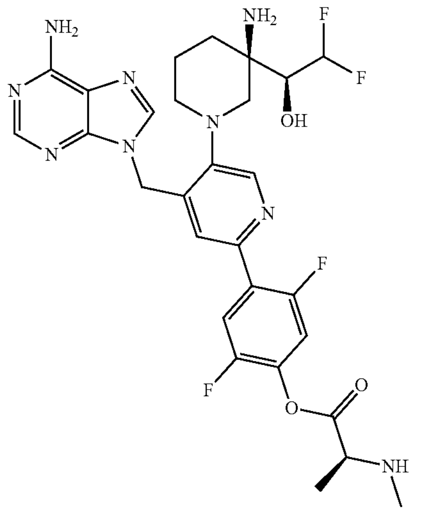 [SMILES: CN[C@@H](C)C(=O)Oc1cc(F)c(-c2cc(Cn3cnc4c(N)ncnc43)c(N3CCC[C@](N)([C@H](O)C(F)F)C3)cn2)cc1F] |
| III-10 | 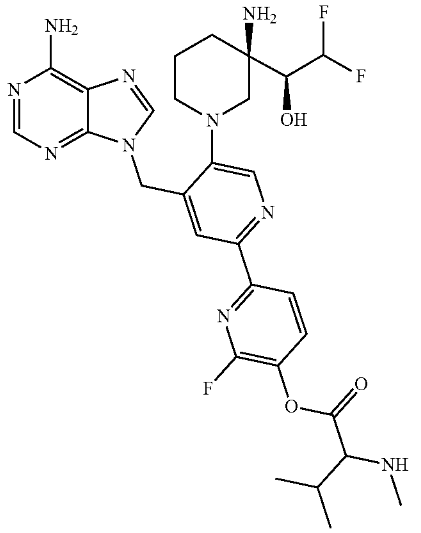 [SMILES: CNC(C(=O)Oc1ccc(-c2cc(Cn3cnc4c(N)ncnc43)c(N3CCC[C@](N)([C@H](O)C(F)F)C3)cn2)nc1F)C(C)C] |
| III-11 | 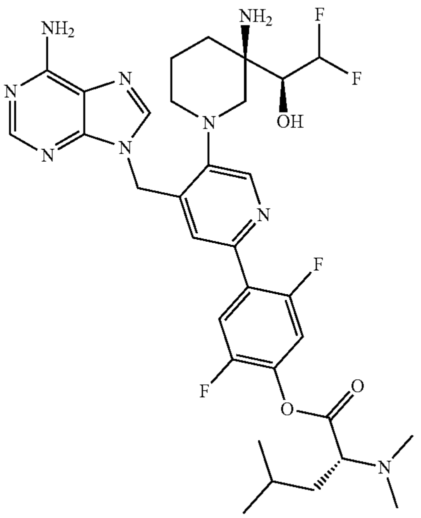 [SMILES: CC(C)C[C@H](C(=O)Oc1cc(F)c(-c2cc(Cn3cnc4c(N)ncnc43)c(N3CCC[C@](N)([C@H](O)C(F)F)C3)cn2)cc1F)N(C)C] |
TABLE 3-continued
| Compound No. | Chemical Structure |
|---|---|
| III-12 | 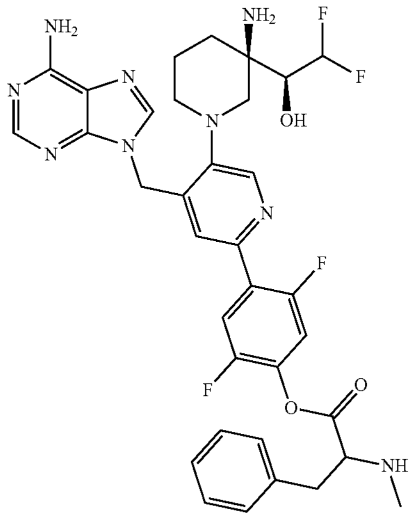 [SMILES: CNC(Cc1ccccc1)C(=O)Oc1cc(F)c(-c2cc(Cn3cnc4c(N)ncnc43)c(N3CCC[C@](N)([C@H](O)C(F)F)C3)cn2)cc1F] |
| III-13 | 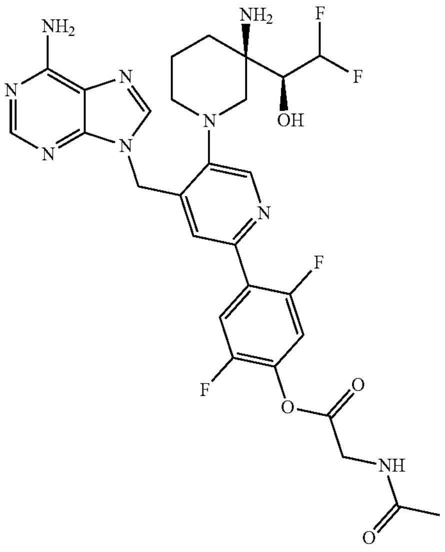 [SMILES: CC(=O)NCC(=O)Oc1cc(F)c(-c2cc(Cn3cnc4c(N)ncnc43)c(N3CCC[C@](N)([C@H](O)C(F)F)C3)cn2)cc1F] |

TABLE 3-continued
| Compound No. | Chemical Structure |
|---|---|
| III-14 | 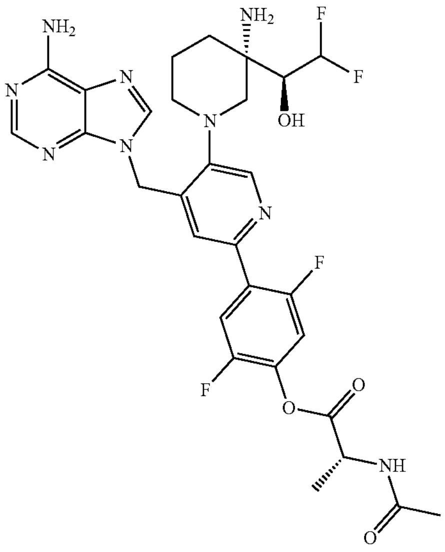 [SMILES: CC(=O)N[C@H](C)C(=O)Oc1cc(F)c(-c2cc(Cn3cnc4c(N)ncnc43)c(N3CCC[C@@](N)([C@H](O)C(F)F)C3)cn2)cc1F] |
| III-15 | 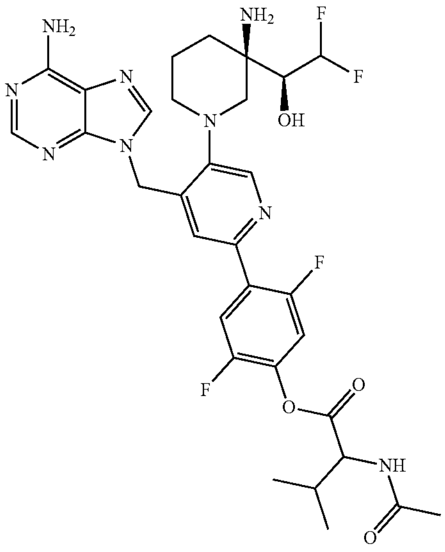 [SMILES: CC(=O)NC(C(=O)Oc1cc(F)c(-c2cc(Cn3cnc4c(N)ncnc43)c(N3CCC[C@](N)([C@H](O)C(F)F)C3)cn2)cc1F)C(C)C] |
TABLE 3-continued
| Compound No. | Chemical Structure |
|---|---|
| III-16 | 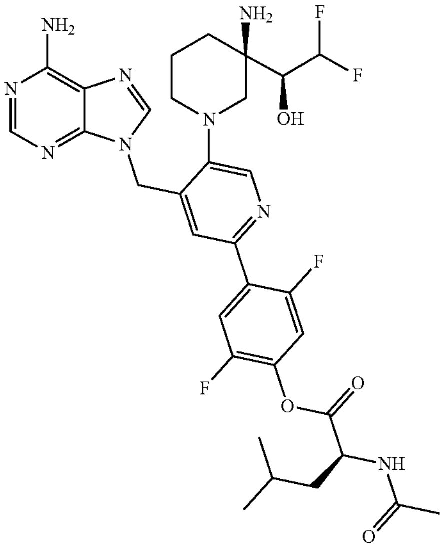 [SMILES: CC(=O)N[C@@H](CC(C)C)C(=O)Oc1cc(F)c(-c2cc(Cn3cnc4c(N)ncnc43)c(N3CCC[C@](N)([C@H](O)C(F)F)C3)cn2)cc1F] |
| III-17 | 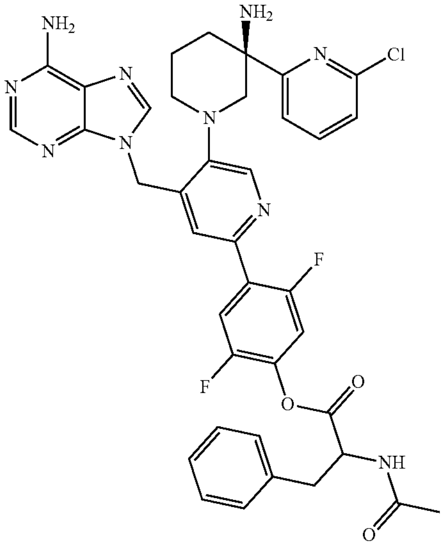 [SMILES: CC(=O)NC(Cc1ccccc1)C(=O)Oc1cc(F)c(-c2cc(Cn3cnc4c(N)ncnc43)c(N3CCC[C@](N)(c4cccc(Cl)n4)C3)cn2)cc1F] |

TABLE 3-continued
| Compound No. | Chemical Structure |
|---|---|
| III-18 | 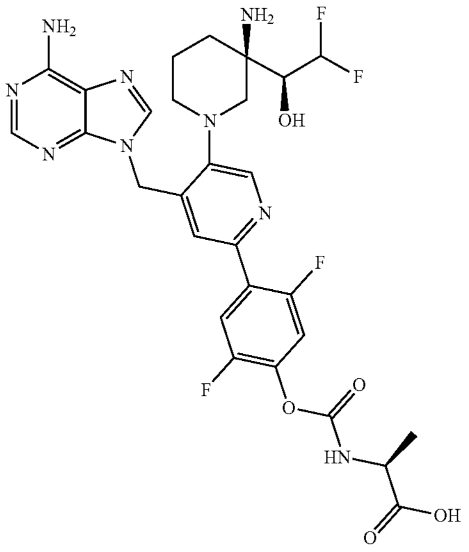 [SMILES: C[C@H](NC(=O)Oc1cc(F)c(-c2cc(Cn3cnc4c(N)ncnc43)c(N3CCC[C@](N)([C@H](O)C(F)F)C3)cn2)cc1F)C(=O)O] |
| III-19 | 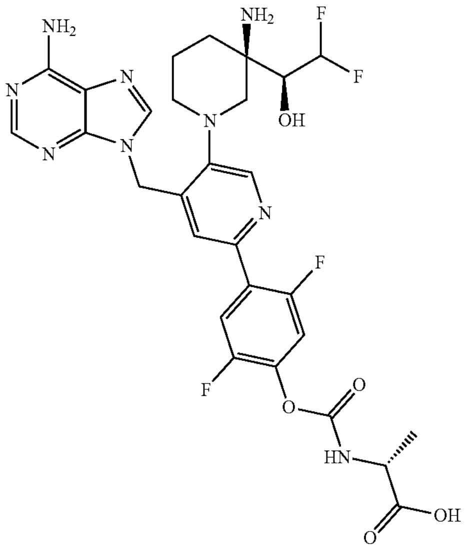 [SMILES: C[C@@H](NC(=O)Oc1cc(F)c(-c2cc(Cn3cnc4c(N)ncnc43)c(N3CCC[C@](N)([C@H](O)C(F)F)C3)cn2)cc1F)C(=O)O] |
| III-20 | 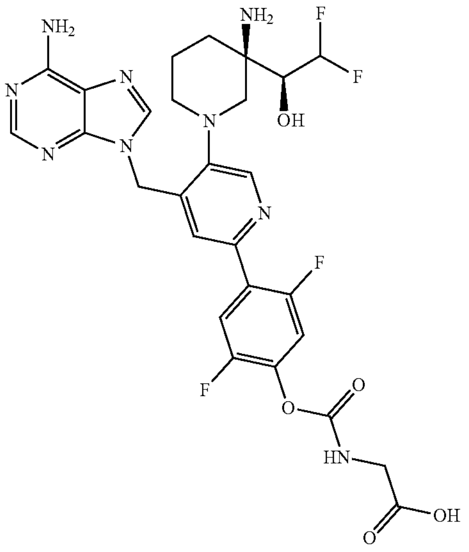 [SMILES: Nc1ncnc2c1ncn2Cc1cc(-c2cc(F)c(OC(=O)NCC(=O)O)cc2F)ncc1N1CCC[C@](N)([C@H](O)C(F)F)C1] |
| III-21 | 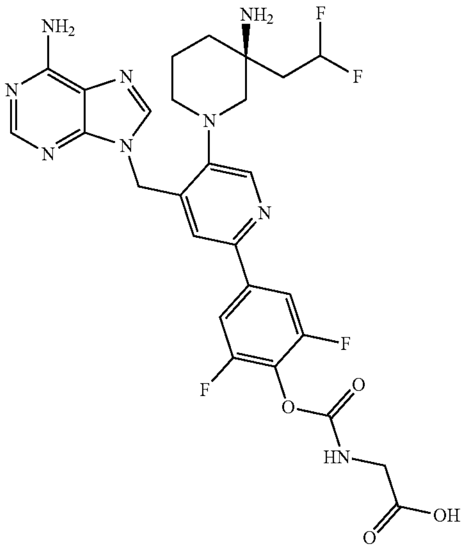 [SMILES: Nc1ncnc2c1ncn2Cc1cc(-c2cc(F)c(OC(=O)NCC(=O)O)c(F)c2)ncc1N1CCC[C@](N)(CC(F)F)C1] |

TABLE 3-continued
| Compound No. | Chemical Structure |
|---|---|
| III-22 | 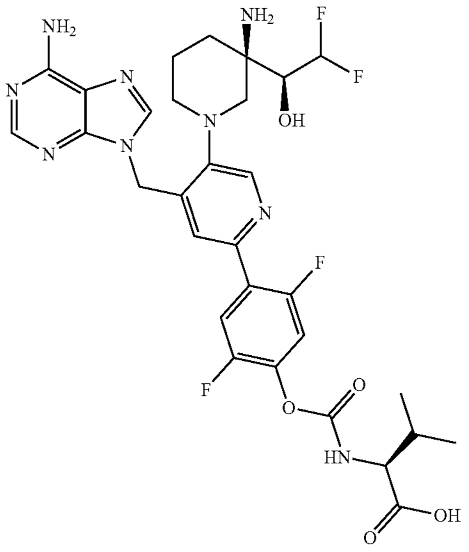 [SMILES: CC(C)[C@H](NC(=O)Oc1cc(F)c(-c2cc(Cn3cnc4c(N)ncnc43)c(N3CCC[C@](N)([C@H](O)C(F)F)C3)cn2)cc1F)C(=O)O] |
| III-23 | 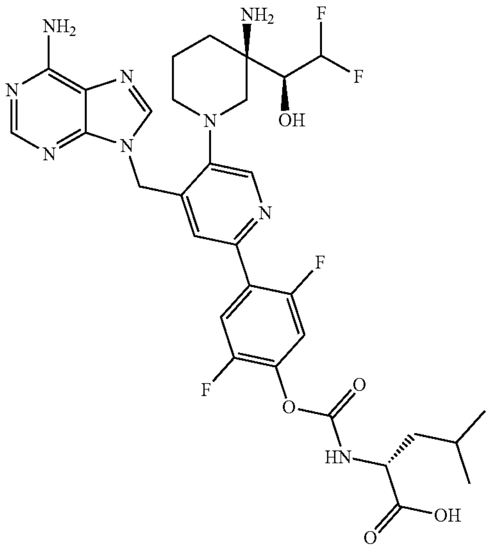 [SMILES: CC(C)C[C@@H](NC(=O)Oc1cc(F)c(-c2cc(Cn3cnc4c(N)ncnc43)c(N3CCC[C@](N)([C@H](O)C(F)F)C3)cn2)cc1F)C(=O)O] |
TABLE 3-continued
| Compound No. | Chemical Structure |
|---|---|
| III-24 | 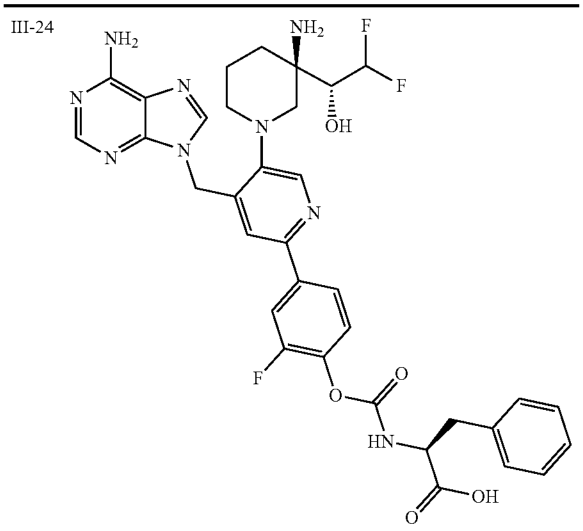 |
| III-25 | 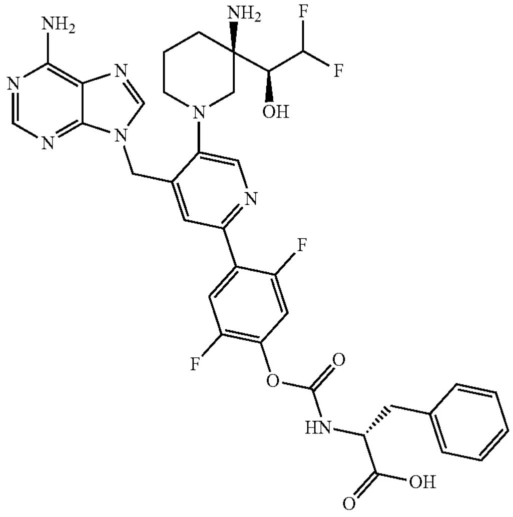 [SMILES: Nc1ncnc2c1ncn2Cc1cc(-c2cc(F)c(OC(=O)N[C@H](Cc3ccccc3)C(=O)O)cc2F)ncc1N1CCC[C@](N)([C@H](O)C(F)F)C1] |
| III-26 | 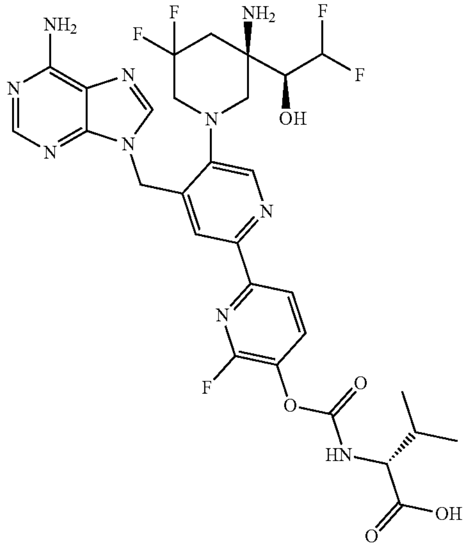 [SMILES: CC(C)[C@@H](NC(=O)Oc1ccc(-c2cc(Cn3cnc4c(N)ncnc43)c(N3CC(F)(F)C[C@](N)([C@H](O)C(F)F)C3)cn2)nc1F)C(=O)O] |

TABLE 3-continued
| Compound No. | Chemical Structure |
|---|---|
| III-27 | 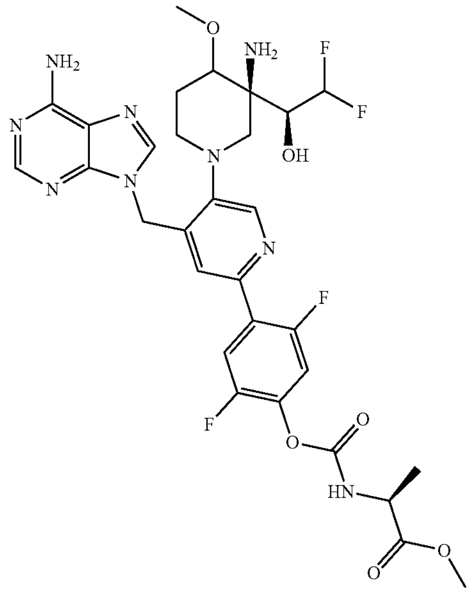 [SMILES: COC(=O)[C@H](C)NC(=O)Oc1cc(F)c(-c2cc(Cn3cnc4c(N)ncnc43)c(N3CCC(OC)[C@](N)([C@H](O)C(F)F)C3)cn2)cc1F] |
| III-28 | 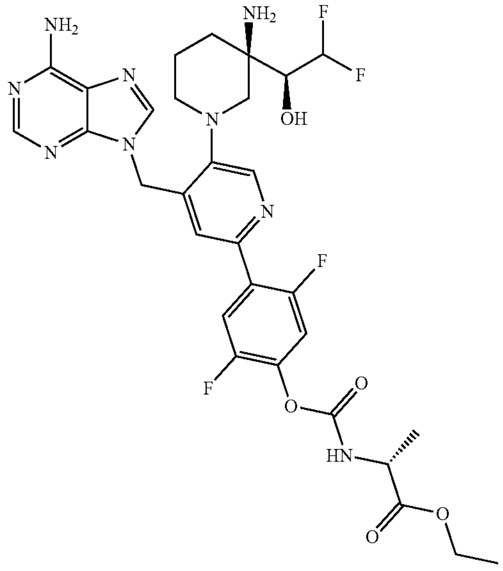 [SMILES: CCOC(=O)[C@@H](C)NC(=O)Oc1cc(F)c(-c2cc(Cn3cnc4c(N)ncnc43)c(N3CCC[C@](N)([C@H](O)C(F)F)C3)cn2)cc1F] |
TABLE 3-continued
| Compound No. | Chemical Structure |
|---|---|
| III-29 | 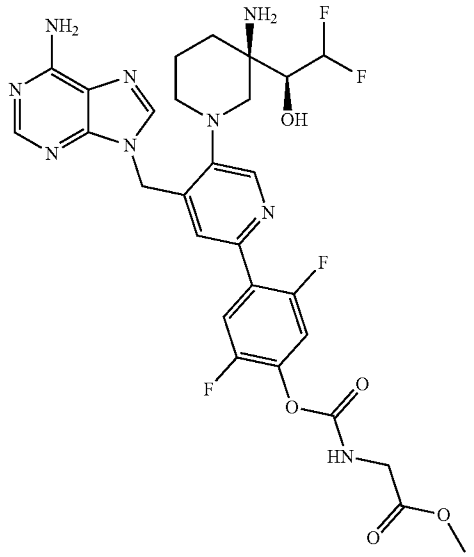 [SMILES: COC(=O)CNC(=O)Oc1cc(F)c(-c2cc(Cn3cnc4c(N)ncnc43)c(N3CCC[C@](N)([C@H](O)C(F)F)C3)cn2)cc1F] |
| III-30 | 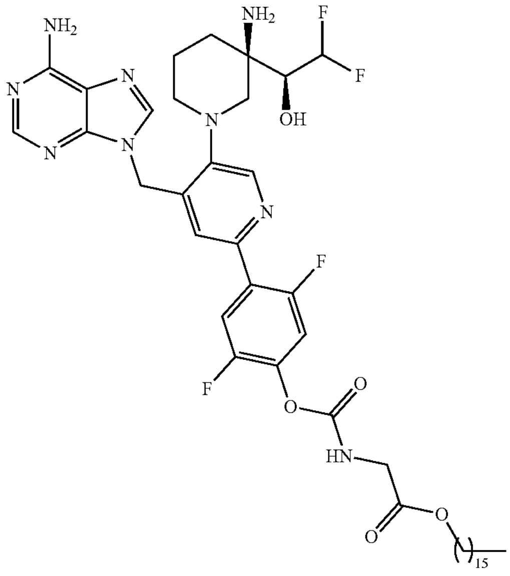 |

TABLE 3-continued
| Compound No. | Chemical Structure |
|---|---|
| III-31 | 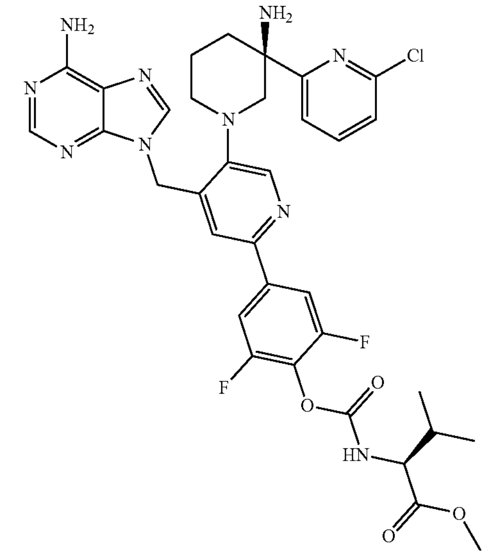 [SMILES: COC(=O)[C@@H](NC(=O)Oc1c(F)cc(-c2cc(Cn3cnc4c(N)ncnc43)c(N3CCC[C@](N)(c4cccc(Cl)n4)C3)cn2)cc1F)C(C)C] |
| III-32 | 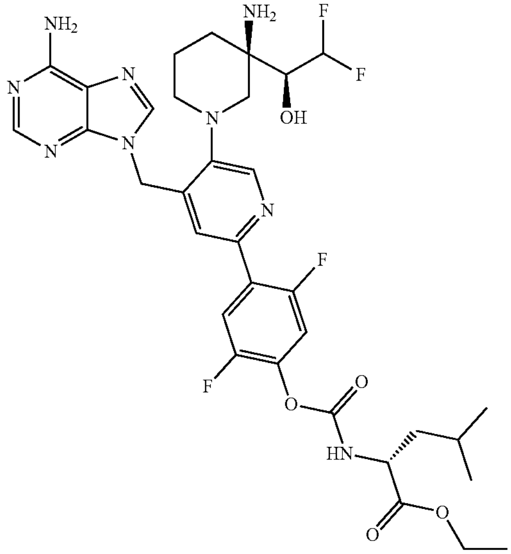 [SMILES: CCOC(=O)[C@@H](CC(C)C)NC(=O)Oc1cc(F)c(-c2cc(Cn3cnc4c(N)ncnc43)c(N3CCC[C@](N)([C@H](O)C(F)F)C3)cn2)cc1F] |
TABLE 3-continued
| Compound No. | Chemical Structure |
|---|---|
| III-33 | 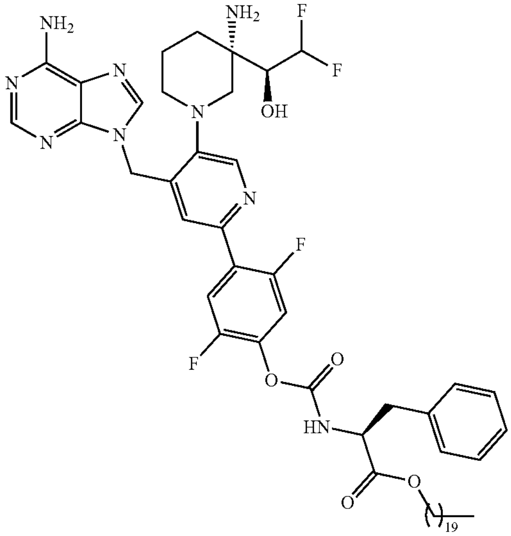 |
| III-34 | 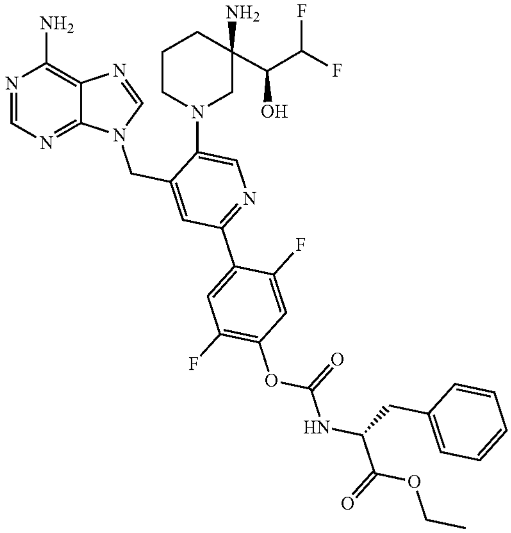 [SMILES: CCOC(=O)[C@@H](Cc1ccccc1)NC(=O)Oc1cc(F)c(-c2cc(Cn3cnc4c(N)ncnc43)c(N3CCC[C@](N)([C@H](O)C(F)F)C3)cn2)cc1F] |
| III-35 | 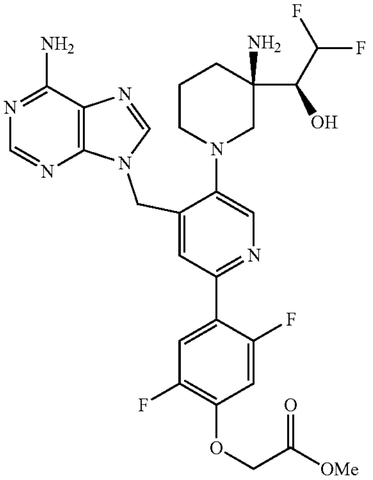 [SMILES: COC(=O)COc1cc(F)c(-c2cc(Cn3cnc4c(N)ncnc43)c(N3CCC[C@](N)([C@H](O)C(F)F)C3)cn2)cc1F] |

TABLE 4
| Compound No. | Chemical Structure |
|---|---|
| IV-1 | 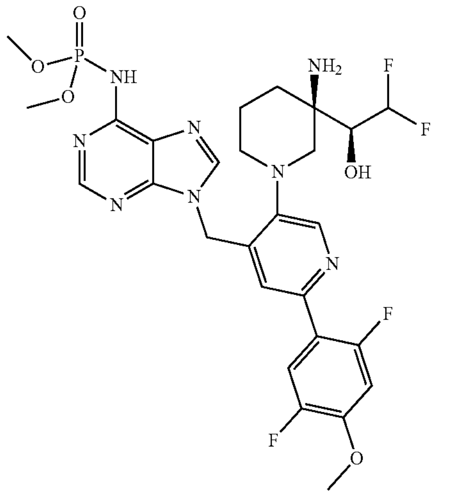 [SMILES: COc1cc(F)c(-c2cc(Cn3cnc4c(NP(=O)(OC)OC)ncnc43)c(N3CCC[C@](N)([C@H](O)C(F)F)C3)cn2)cc1F] |
| IV-2 | 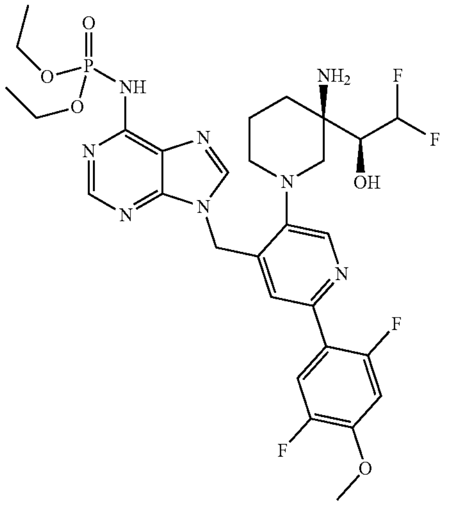 [SMILES: CCOP(=O)(Nc1ncnc2c1ncn2Cc1cc(-c2cc(F)c(OC)cc2F)ncc1N1CCC[C@](N)([C@H](O)C(F)F)C1)OCC] |
| IV-3 | 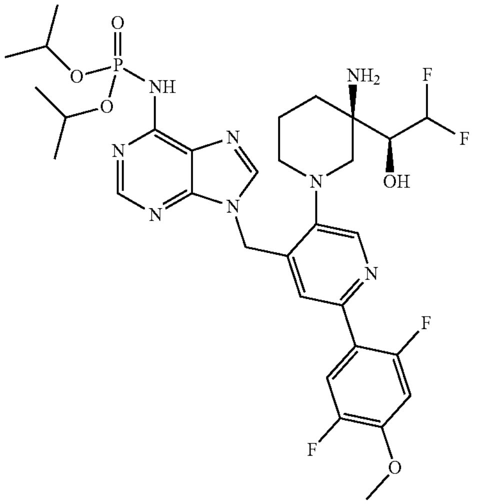 [SMILES: COc1cc(F)c(-c2cc(Cn3cnc4c(NP(=O)(OC(C)C)OC(C)C)ncnc43)c(N3CCC[C@](N)([C@H](O)C(F)F)C3)cn2)cc1F] |

TABLE 4-continued
| Compound No. | Chemical Structure |
| --- | --- |
| IV-4 | 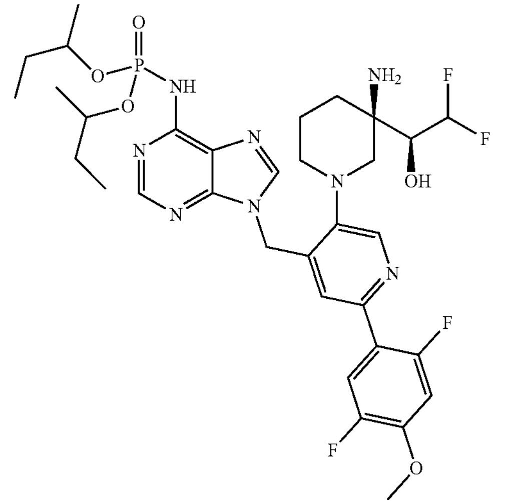 [SMILES: CCC(C)OP(=O)(Nc1ncnc2c1ncn2Cc1cc(-c2cc(F)c(OC)cc2F)ncc1N1CCC[C@](N)([C@H](O)C(F)F)C1)OC(C)CC] |
| IV-5 | 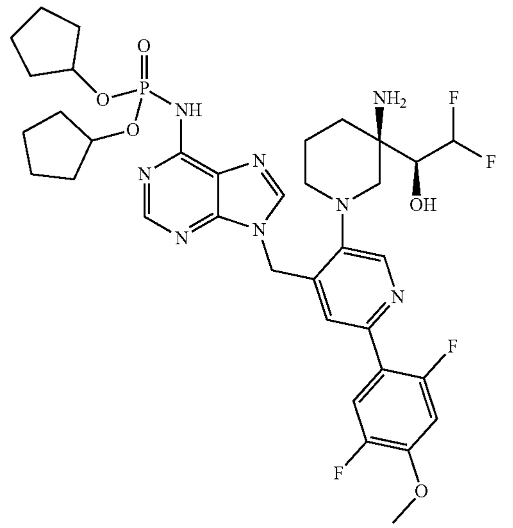 [SMILES: COc1cc(F)c(-c2cc(Cn3cnc4c(NP(=O)(OC5CCCC5)OC5CCCC5)ncnc43)c(N3CCC[C@](N)([C@H](O)C(F)F)C3)cn2)cc1F] |
| IV-6 | 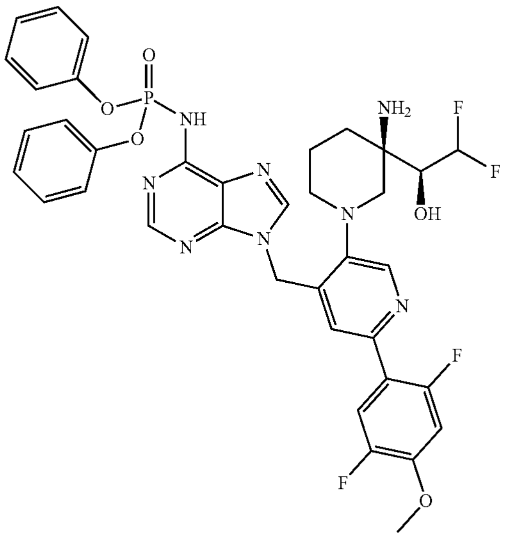 [SMILES: COc1cc(F)c(-c2cc(Cn3cnc4c(NP(=O)(Oc5ccccc5)Oc5ccccc5)ncnc43)c(N3CCC[C@](N)([C@H](O)C(F)F)C3)cn2)cc1F] |

TABLE 4-continued
| Compound No. | Chemical Structure |
| --- | --- |
| IV-7 | 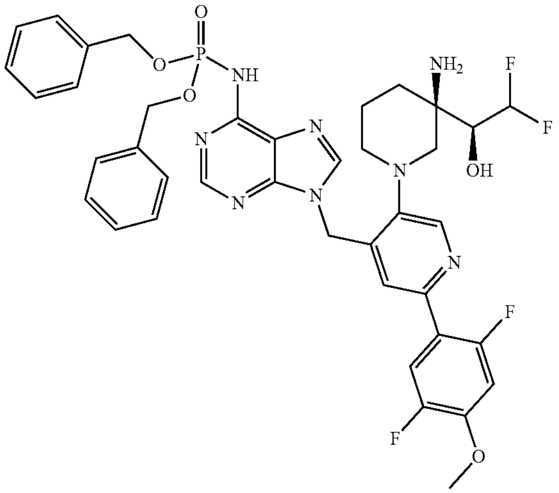 [SMILES: COc1cc(F)c(-c2cc(Cn3cnc4c(NP(=O)(OCc5ccccc5)OCc5ccccc5)ncnc43)c(N3CCC[C@](N)([C@H](O)C(F)F)C3)cn2)cc1F] |
| IV-8 | 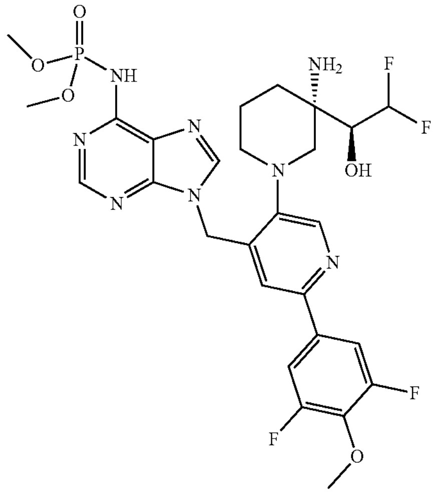 [SMILES: COc1c(F)cc(-c2cc(Cn3cnc4c(NP(=O)(OC)OC)ncnc43)c(N3CCC[C@@](N)([C@H](O)C(F)F)C3)cn2)cc1F] |
| IV-9 | 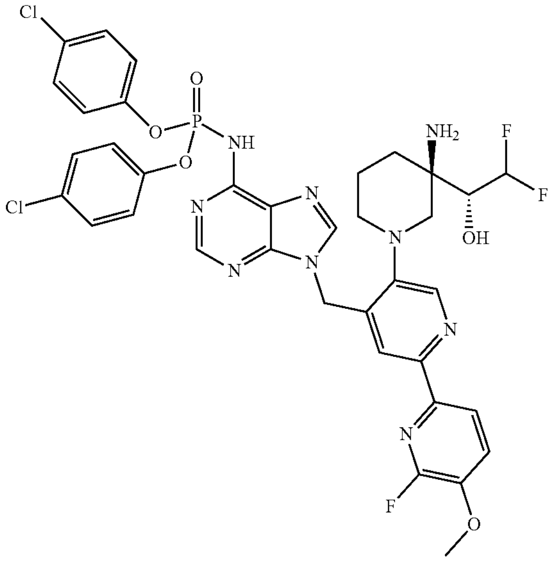 [SMILES: COc1ccc(-c2cc(Cn3cnc4c(NP(=O)(Oc5ccc(Cl)cc5)Oc5ccc(Cl)cc5)ncnc43)c(N3CCC[C@](N)([C@@H](O)C(F)F)C3)cn2)nc1F] |

TABLE 4-continued
| Compound No. | Chemical Structure |
| --- | --- |
| IV-10 | 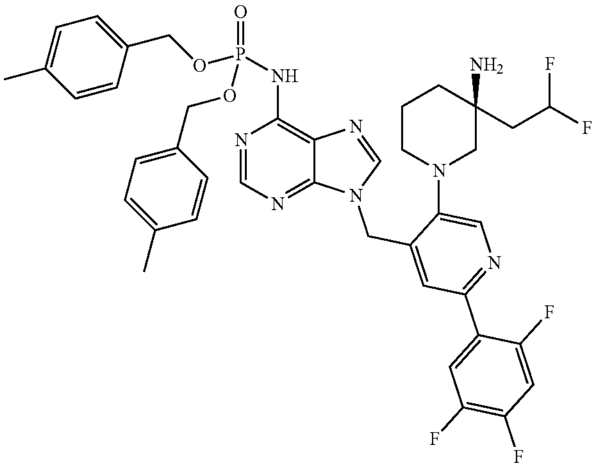 [SMILES: Cc1ccc(COP(=O)(Nc2ncnc3c2ncn3Cc2cc(-c3cc(F)c(F)cc3F)ncc2N2CCC[C@](N)(CC(F)F)C2)OCc2ccc(C)cc2)cc1] |
| IV-11 | 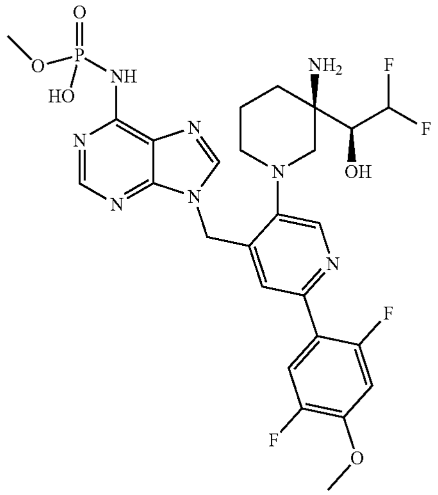 [SMILES: COc1cc(F)c(-c2cc(Cn3cnc4c(NP(=O)(O)OC)ncnc43)c(N3CCC[C@](N)([C@H](O)C(F)F)C3)cn2)cc1F] |
| IV-12 | 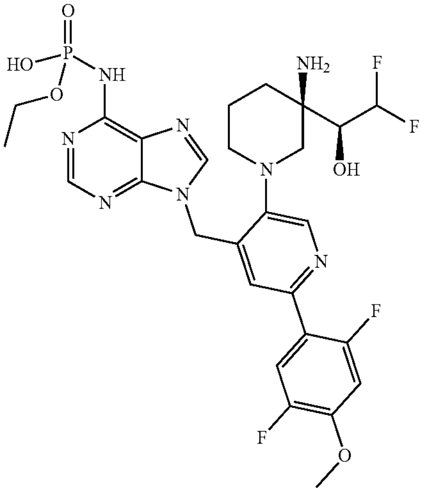 [SMILES: CCOP(=O)(O)Nc1ncnc2c1ncn2Cc1cc(-c2cc(F)c(OC)cc2F)ncc1N1CCC[C@](N)([C@H](O)C(F)F)C1] |

TABLE 4-continued
| Compound No. | Chemical Structure |
|---|---|
| IV-13 | 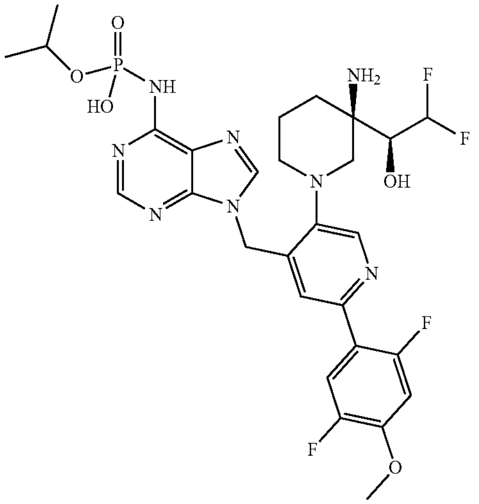 [SMILES: COc1cc(F)c(-c2cc(Cn3cnc4c(NP(=O)(O)OC(C)C)ncnc43)c(N3CCC[C@](N)([C@H](O)C(F)F)C3)cn2)cc1F] |
| IV-14 | 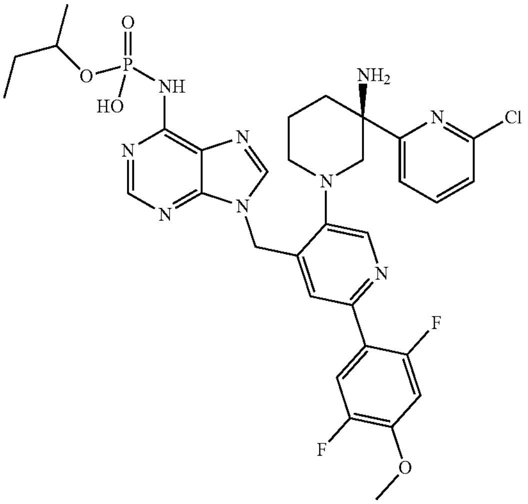 [SMILES: CCC(C)OP(=O)(O)Nc1ncnc2c1ncn2Cc1cc(-c2cc(F)c(OC)cc2F)ncc1N1CCC[C@](N)(c2cccc(Cl)n2)C1] |
| IV-15 | 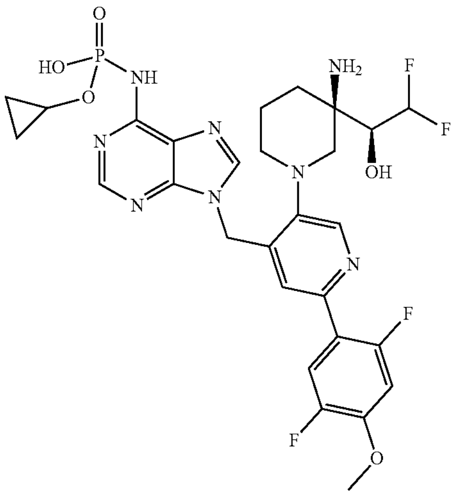 [SMILES: COc1cc(F)c(-c2cc(Cn3cnc4c(NP(=O)(O)OC5CC5)ncnc43)c(N3CCC[C@](N)([C@H](O)C(F)F)C3)cn2)cc1F] |

TABLE 4-continued
| Compound No. | Chemical Structure |
|---|---|
| IV-16 | 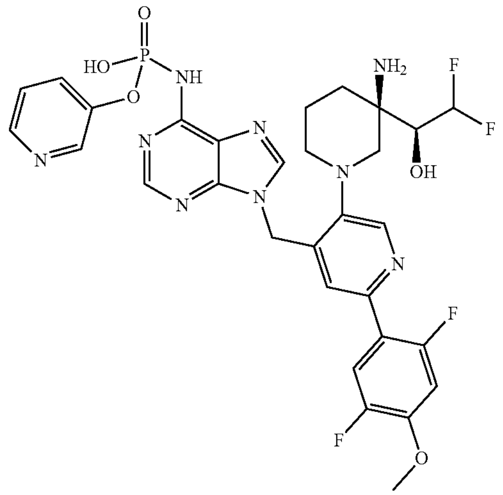 [SMILES: COc1cc(F)c(-c2cc(Cn3cnc4c(NP(=O)(O)Oc5cccnc5)ncnc43)c(N3CCC[C@](N)([C@H](O)C(F)F)C3)cn2)cc1F] |
| IV-17 | 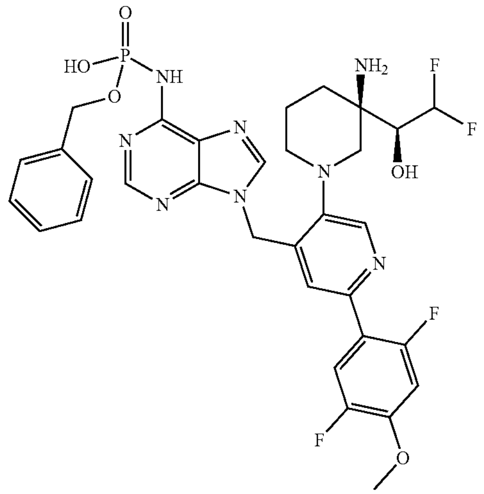 [SMILES: COc1cc(F)c(-c2cc(Cn3cnc4c(NP(=O)(O)OCc5ccccc5)ncnc43)c(N3CCC[C@](N)([C@H](O)C(F)F)C3)cn2)cc1F] |
| IV-18 | 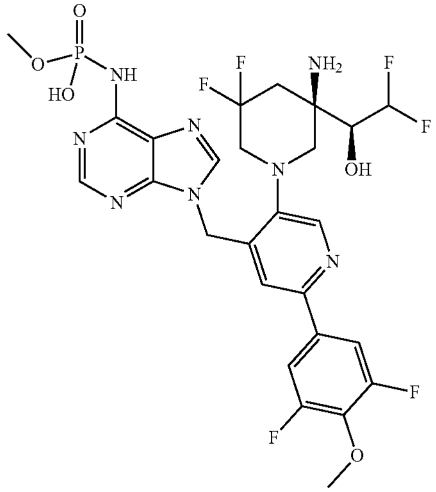 [SMILES: COc1c(F)cc(-c2cc(Cn3cnc4c(NP(=O)(O)OC)ncnc43)c(N3CC(F)(F)C[C@](N)([C@H](O)C(F)F)C3)cn2)cc1F] |

TABLE 4-continued
| Compound No. | Chemical Structure |
|---|---|
| IV-19 | 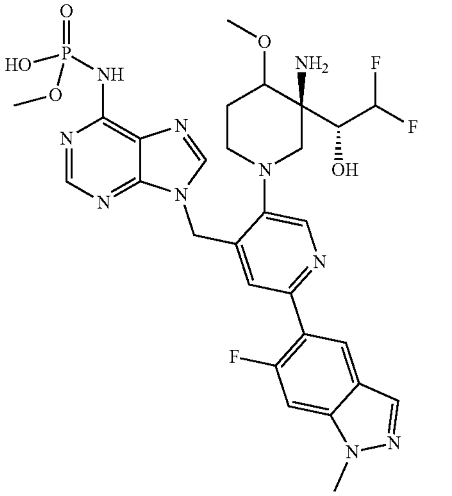 [SMILES: COC1CCN(c2cnc(-c3cc4cnn(C)c4cc3F)cc2Cn2cnc3c(NP(=O)(O)OC)ncnc32)C[C@@]1(N)[C@@H](O)C(F)F] |
| IV-20 | 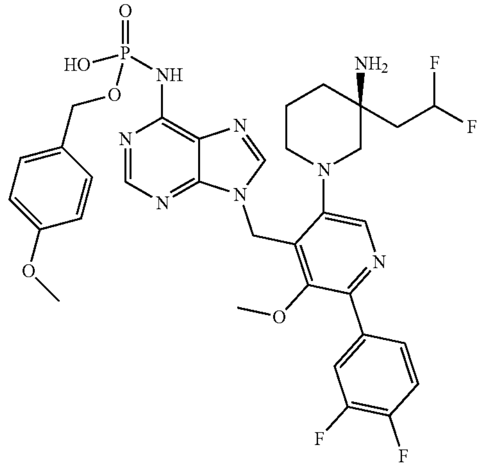 [SMILES: COc1ccc(COP(=O)(O)Nc2ncnc3c2ncn3Cc2c(N3CCC[C@](N)(CC(F)F)C3)cnc(-c3ccc(F)c(F)c3)c2OC)cc1] |
| IV-21 | 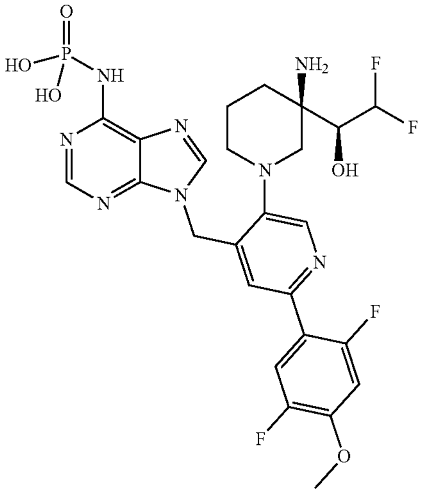 [SMILES: COc1cc(F)c(-c2cc(Cn3cnc4c(NP(=O)(O)O)ncnc43)c(N3CCC[C@](N)([C@H](O)C(F)F)C3)cn2)cc1F] |

TABLE 4-continued
| Compound No. | Chemical Structure |
|---|---|
| IV-22 | 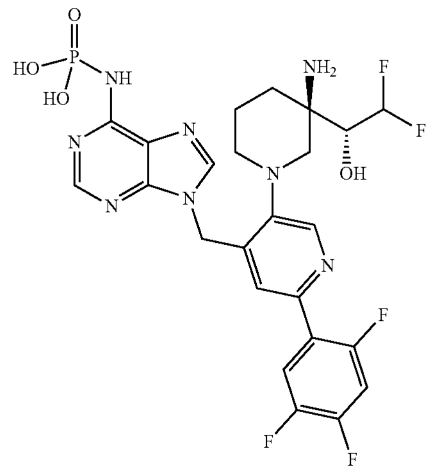 [SMILES: N[C@]1([C@@H](O)C(F)F)CCCN(c2cnc(-c3cc(F)c(F)cc3F)cc2Cn2cnc3c(NP(=O)(O)O)ncnc32)C1] |
| IV-23 | 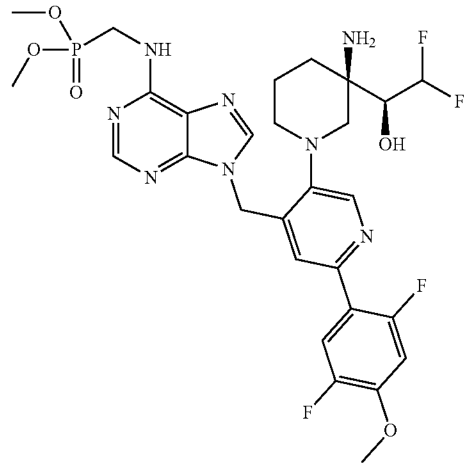 [SMILES: COc1cc(F)c(-c2cc(Cn3cnc4c(NCP(=O)(OC)OC)ncnc43)c(N3CCC[C@](N)([C@H](O)C(F)F)C3)cn2)cc1F] |
| IV-24 | 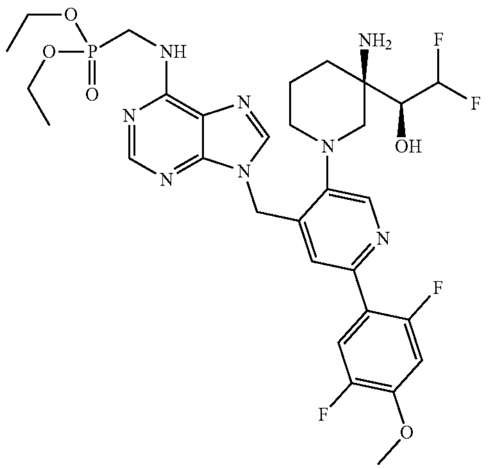 [SMILES: CCOP(=O)(CNc1ncnc2c1ncn2Cc1cc(-c2cc(F)c(OC)cc2F)ncc1N1CCC[C@](N)([C@H](O)C(F)F)C1)OCC] |

TABLE 4-continued
| Compound No. | Chemical Structure |
|---|---|
| IV-25 | 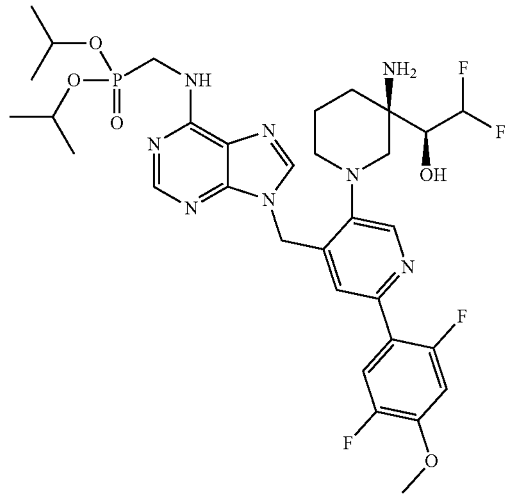 [SMILES: COc1cc(F)c(-c2cc(Cn3cnc4c(NCP(=O)(OC(C)C)OC(C)C)ncnc43)c(N3CCC[C@](N)([C@H](O)C(F)F)C3)cn2)cc1F] |
| IV-26 | 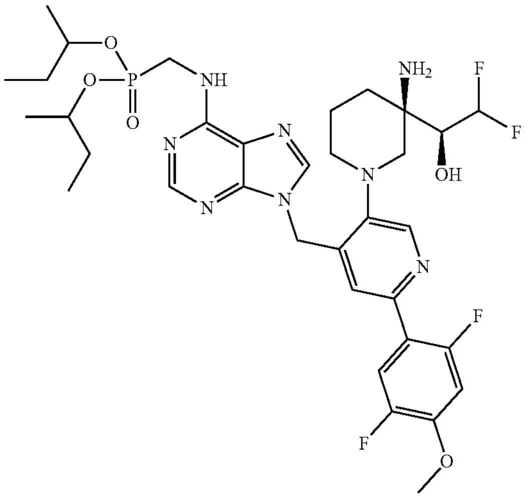 [SMILES: CCC(C)OP(=O)(CNc1ncnc2c1ncn2Cc1cc(-c2cc(F)c(OC)cc2F)ncc1N1CCC[C@](N)([C@H](O)C(F)F)C1)OC(C)CC] |
| IV-27 | 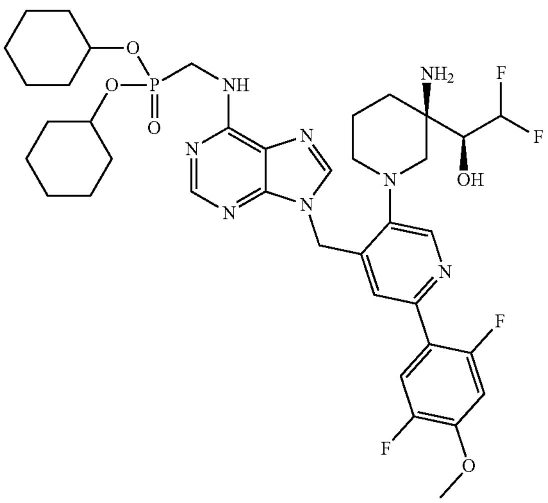 [SMILES: COc1cc(F)c(-c2cc(Cn3cnc4c(NCP(=O)(OC5CCCCC5)OC5CCCCC5)ncnc43)c(N3CCC[C@](N)([C@H](O)C(F)F)C3)cn2)cc1F] |

TABLE 4-continued
| Compound No. | Chemical Structure |
| --- | --- |
| IV-28 | 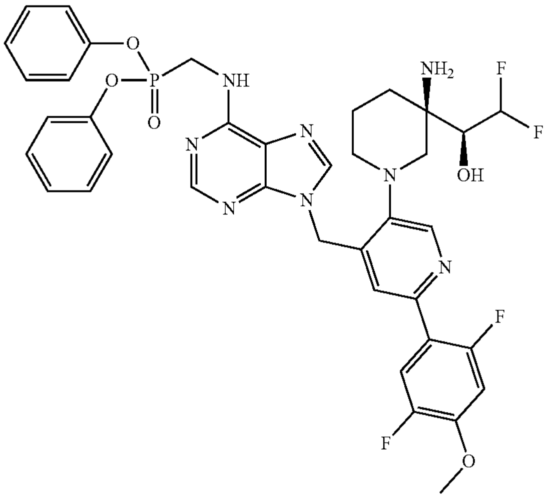 [SMILES: COc1cc(F)c(-c2cc(Cn3cnc4c(NCP(=O)(Oc5ccccc5)Oc5ccccc5)ncnc43)c(N3CCC[C@](N)([C@H](O)C(F)F)C3)cn2)cc1F] |
| IV-29 | 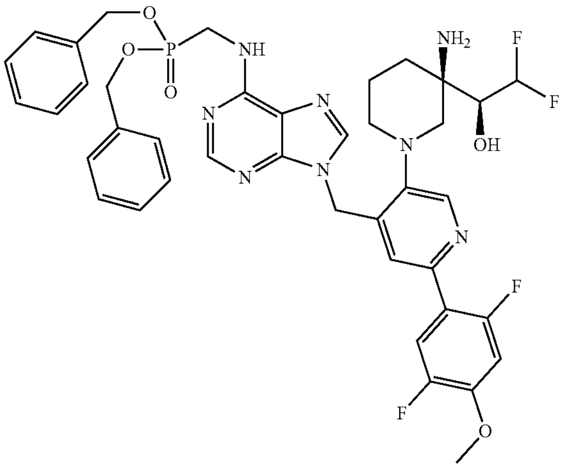 [SMILES: COc1cc(F)c(-c2cc(Cn3cnc4c(NCP(=O)(OCc5ccccc5)OCc5ccccc5)ncnc43)c(N3CCC[C@](N)([C@H](O)C(F)F)C3)cn2)cc1F] |
| IV-30 | 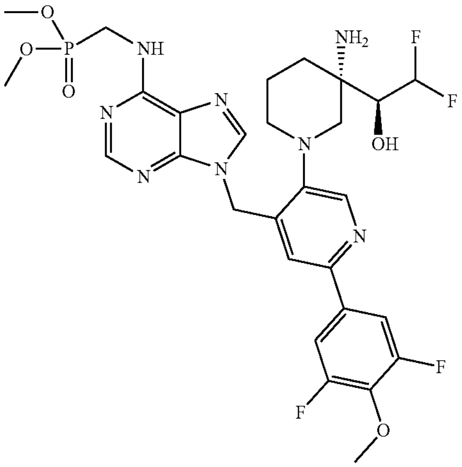 [SMILES: COc1c(F)cc(-c2cc(Cn3cnc4c(NCP(=O)(OC)OC)ncnc43)c(N3CCC[C@@](N)([C@H](O)C(F)F)C3)cn2)cc1F] |

TABLE 4-continued
| Compound No. | Chemical Structure |
| --- | --- |
| IV-31 | 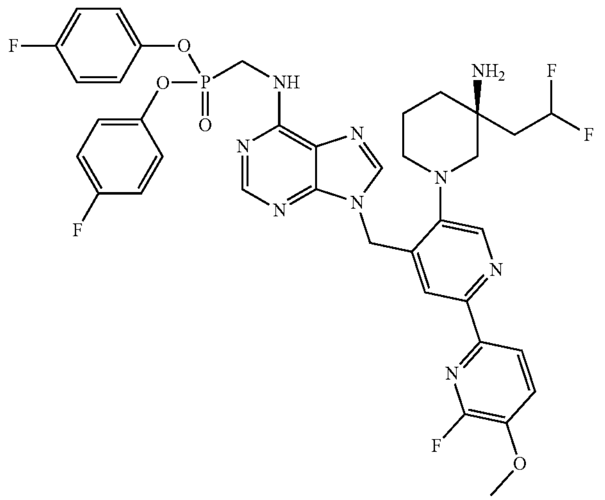 [SMILES: COc1ccc(-c2cc(Cn3cnc4c(NCP(=O)(Oc5ccc(F)cc5)Oc5ccc(F)cc5)ncnc43)c(N3CCC[C@](N)(CC(F)F)C3)cn2)nc1F] |
| IV-32 | 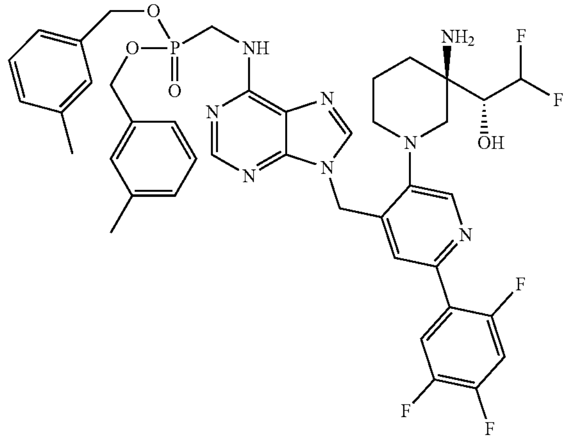 [SMILES: Cc1cccc(COP(=O)(CNc2ncnc3c2ncn3Cc2cc(-c3cc(F)c(F)cc3F)ncc2N2CCC[C@](N)([C@@H](O)C(F)F)C2)OCc2cccc(C)c2)c1] |
| IV-33 | 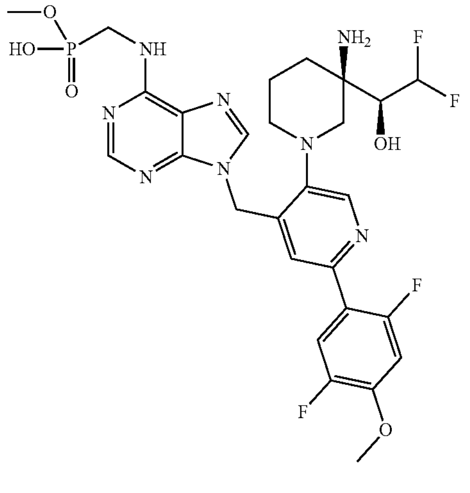 [SMILES: COc1cc(F)c(-c2cc(Cn3cnc4c(NCP(=O)(O)OC)ncnc43)c(N3CCC[C@](N)([C@H](O)C(F)F)C3)cn2)cc1F] |

TABLE 4-continued
| Compound No. | Chemical Structure |
| --- | --- |
| IV-34 | 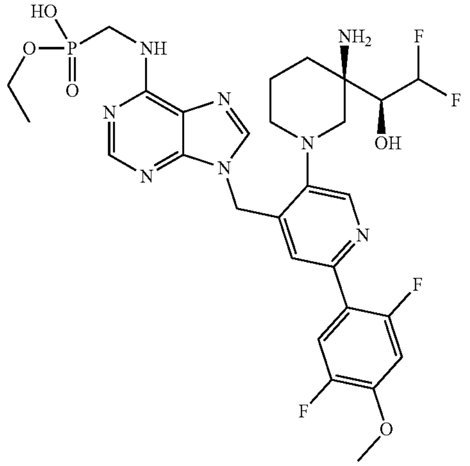 [SMILES: CCOP(=O)(O)CNc1ncnc2c1ncn2Cc1cc(-c2cc(F)c(OC)cc2F)ncc1N1CCC[C@](N)([C@H](O)C(F)F)C1] |
| IV-35 | 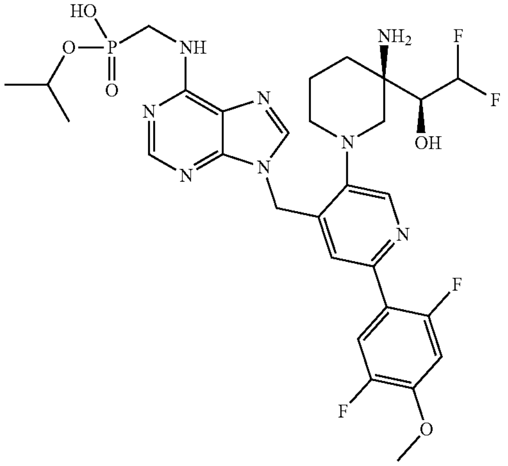 [SMILES: COc1cc(F)c(-c2cc(Cn3cnc4c(NCP(=O)(O)OC(C)C)ncnc43)c(N3CCC[C@](N)([C@H](O)C(F)F)C3)cn2)cc1F] |
| IV-36 | 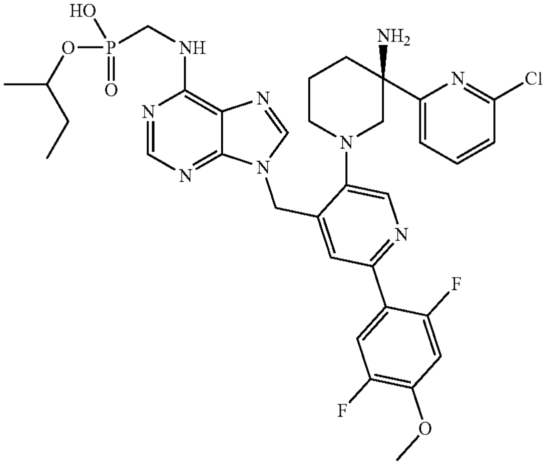 [SMILES: CCC(C)OP(=O)(O)CNc1ncnc2c1ncn2Cc1cc(-c2cc(F)c(OC)cc2F)ncc1N1CCC[C@](N)(c2cccc(Cl)n2)C1] |

TABLE 4-continued
| Compound No. | Chemical Structure |
|---|---|
| IV-37 | 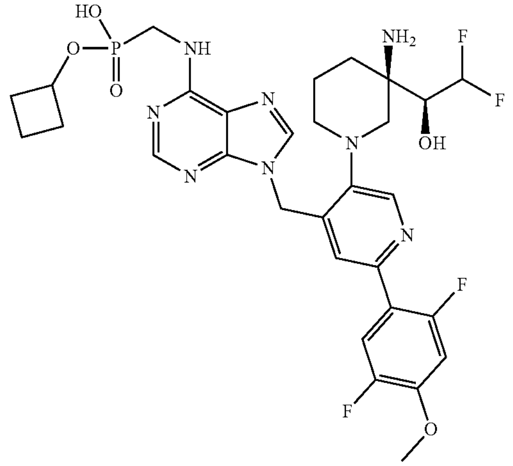 [SMILES: COc1cc(F)c(-c2cc(Cn3cnc4c(NCP(=O)(O)OC5CCC5)ncnc43)c(N3CCC[C@](N)([C@H](O)C(F)F)C3)cn2)cc1F] |
| IV-38 | 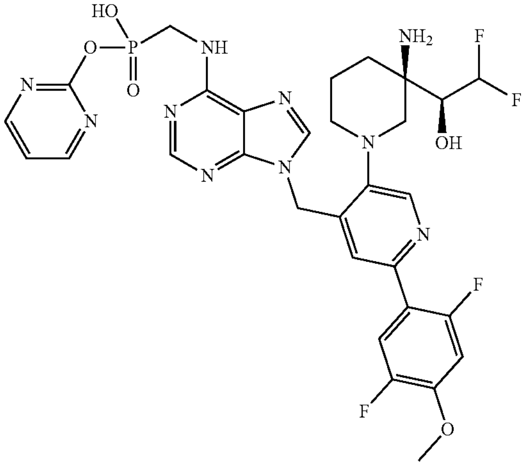 [SMILES: COc1cc(F)c(-c2cc(Cn3cnc4c(NCP(=O)(O)Oc5ncccn5)ncnc43)c(N3CCC[C@](N)([C@H](O)C(F)F)C3)cn2)cc1F] |
| IV-39 | 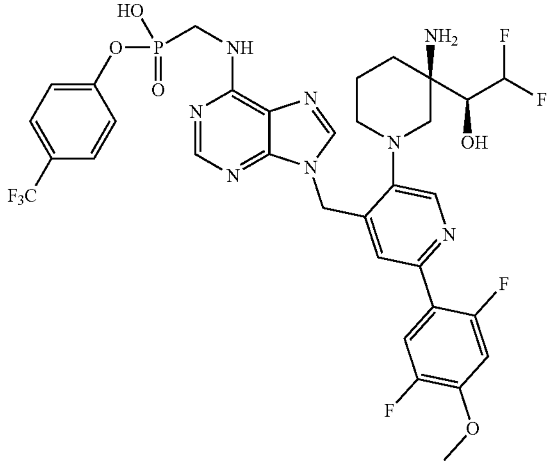 [SMILES: COc1cc(F)c(-c2cc(Cn3cnc4c(NCP(=O)(O)Oc5ccc(C(F)(F)F)cc5)ncnc43)c(N3CCC[C@](N)([C@H](O)C(F)F)C3)cn2)cc1F] |

TABLE 4-continued
| Compound No. | Chemical Structure |
|---|---|
| IV-40 | 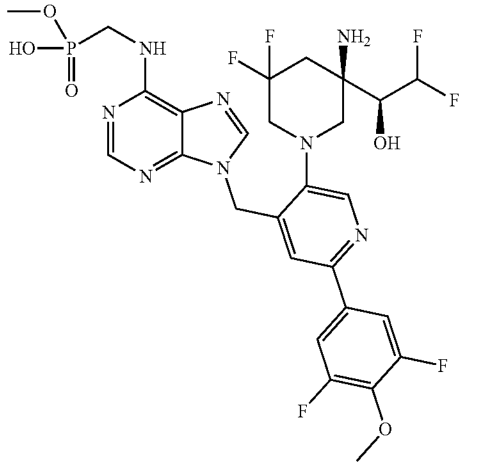 [SMILES: COc1c(F)cc(-c2cc(Cn3cnc4c(NCP(=O)(O)OC)ncnc43)c(N3CC(F)(F)C[C@](N)([C@H](O)C(F)F)C3)cn2)cc1F] |
| IV-41 | 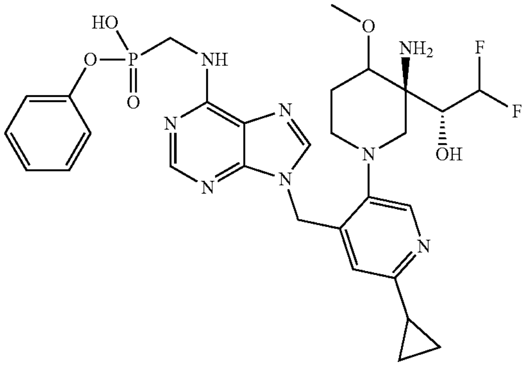 [SMILES: COC1CCN(c2cnc(C3CC3)cc2Cn2cnc3c(NCP(=O)(O)Oc4ccccc4)ncnc32)C[C@@]1(N)[C@@H](O)C(F)F] |
| IV-42 | 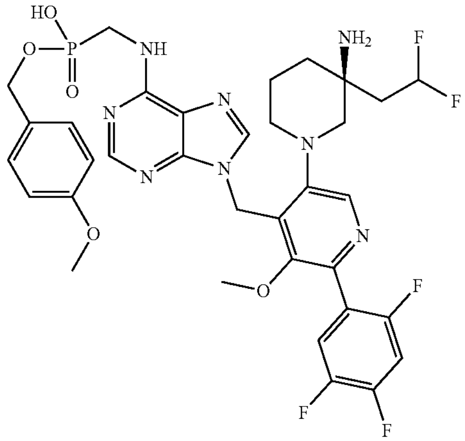 [SMILES: COc1ccc(COP(=O)(O)CNc2ncnc3c2ncn3Cc2c(N3CCC[C@](N)(CC(F)F)C3)cnc(-c3cc(F)c(F)cc3F)c2OC)cc1] |

TABLE 4-continued
| Compound No. | Chemical Structure |
| --- | --- |
| IV-43 | 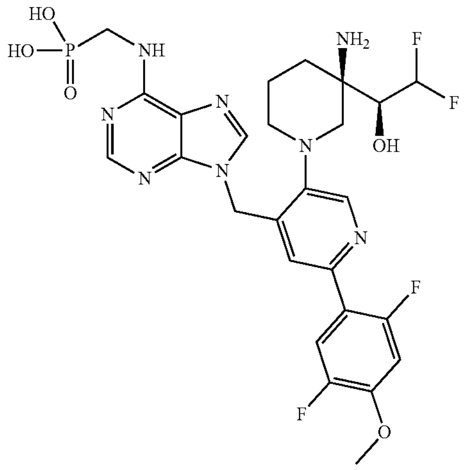 [SMILES: COc1cc(F)c(-c2cc(Cn3cnc4c(NCP(=O)(O)O)ncnc43)c(N3CCC[C@](N)([C@H](O)C(F)F)C3)cn2)cc1F] |
| IV-44 | 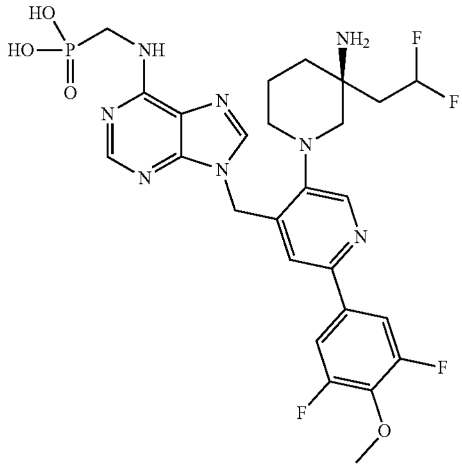 [SMILES: COc1c(F)cc(-c2cc(Cn3cnc4c(NCP(=O)(O)O)ncnc43)c(N3CCC[C@](N)(CC(F)F)C3)cn2)cc1F] |
| IV-45 | 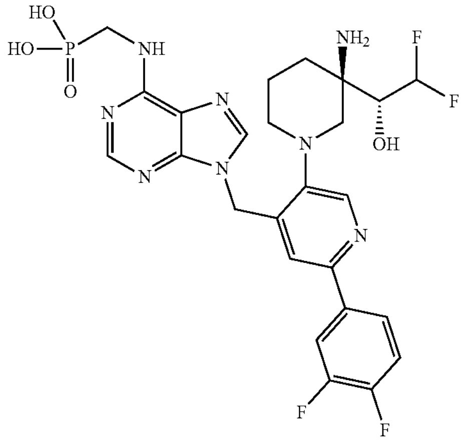 [SMILES: N[C@]1([C@@H](O)C(F)F)CCCN(c2cnc(-c3ccc(F)c(F)c3)cc2Cn2cnc3c(NCP(=O)(O)O)ncnc32)C1] |

TABLE 5
| Compound No. | Chemical Structure |
| --- | --- |
| V-1 | 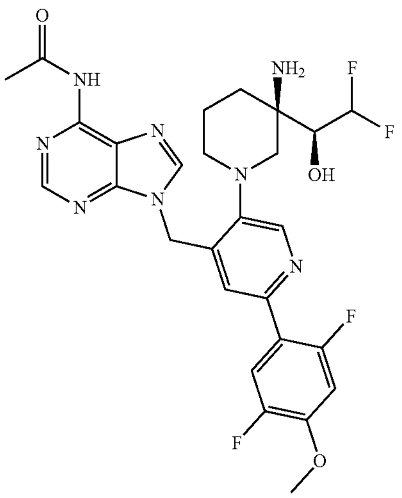 [SMILES: COc1cc(F)c(-c2cc(Cn3cnc4c(NC(C)=O)ncnc43)c(N3CCC[C@](N)([C@H](O)C(F)F)C3)cn2)cc1F] |
| V-2 | 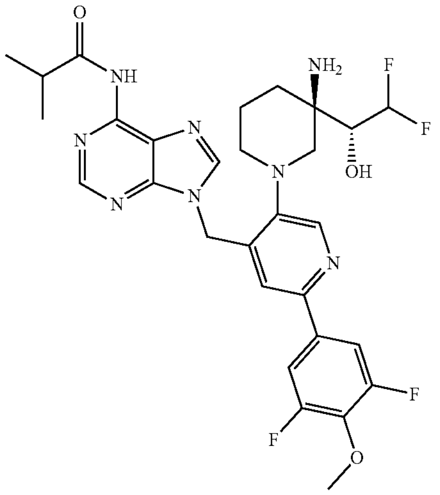 [SMILES: COc1c(F)cc(-c2cc(Cn3cnc4c(NC(=O)C(C)C)ncnc43)c(N3CCC[C@](N)([C@@H](O)C(F)F)C3)cn2)cc1F] |
| V-3 | 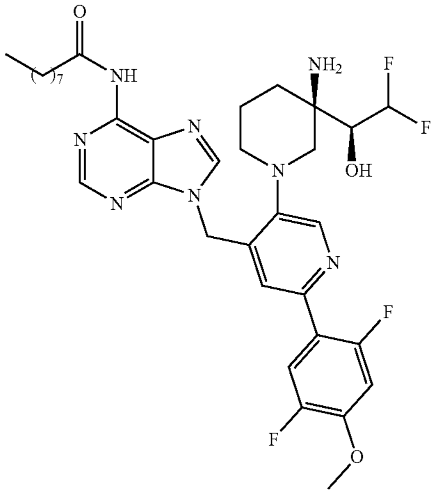 |

TABLE 5-continued
| Compound No. | Chemical Structure |
| --- | --- |
| V-4 | 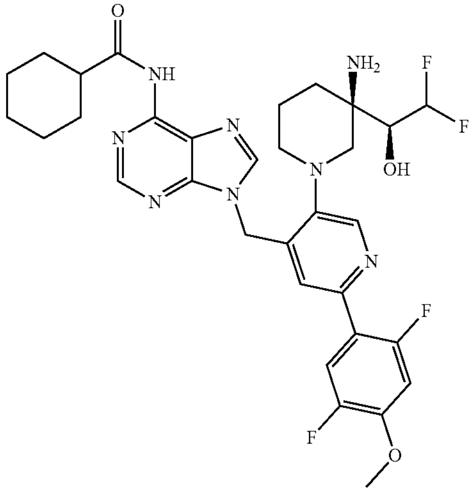 [SMILES: COc1cc(F)c(-c2cc(Cn3cnc4c(NC(=O)C5CCCCC5)ncnc43)c(N3CCC[C@](N)([C@H](O)C(F)F)C3)cn2)cc1F] |
| V-5 | 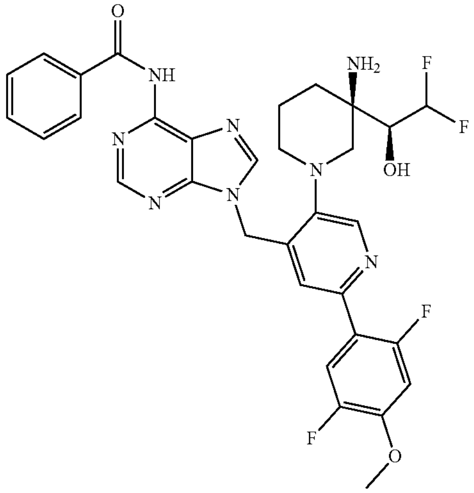 [SMILES: COc1cc(F)c(-c2cc(Cn3cnc4c(NC(=O)c5ccccc5)ncnc43)c(N3CCC[C@](N)([C@H](O)C(F)F)C3)cn2)cc1F] |
| V-6 | 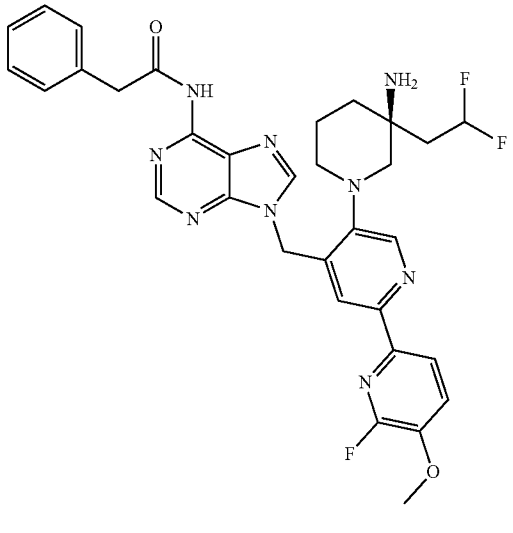 [SMILES: COc1ccc(-c2cc(Cn3cnc4c(NC(=O)Cc5ccccc5)ncnc43)c(N3CCC[C@](N)(CC(F)F)C3)cn2)nc1F] |

TABLE 5-continued
| Compound No. | Chemical Structure |
| --- | --- |
| V-7 | 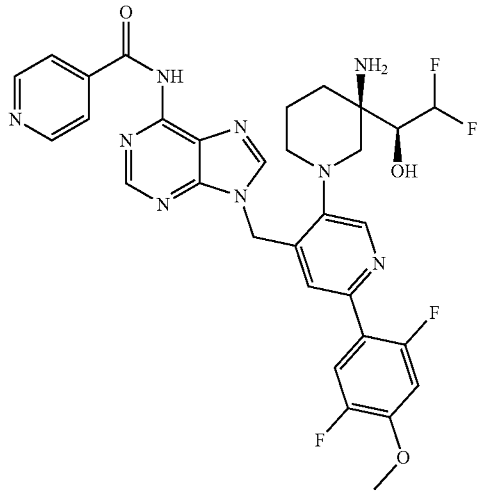 [SMILES: COc1cc(F)c(-c2cc(Cn3cnc4c(NC(=O)c5ccncc5)ncnc43)c(N3CCC[C@](N)([C@H](O)C(F)F)C3)cn2)cc1F] |
| V-8 | 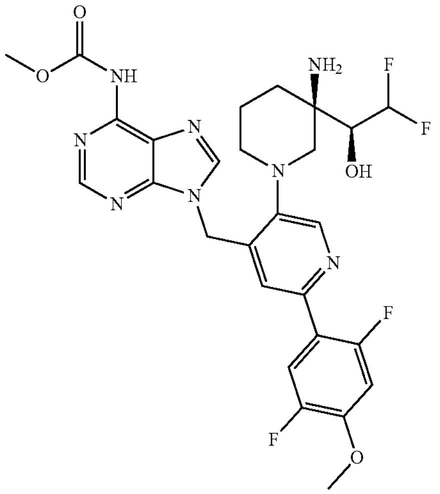 |
| V-9 | 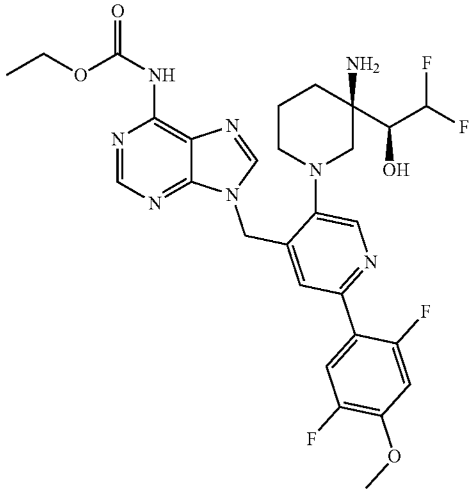 [SMILES: CCOC(=O)Nc1ncnc2c1ncn2Cc1cc(-c2cc(F)c(OC)cc2F)ncc1N1CCC[C@](N)([C@H](O)C(F)F)C1] |

TABLE 5-continued
| Compound No. | Chemical Structure |
| --- | --- |
| V-10 | 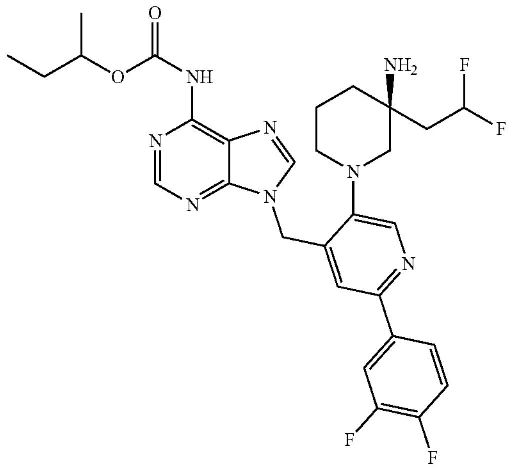 [SMILES: CCC(C)OC(=O)Nc1ncnc2c1ncn2Cc1cc(-c2ccc(F)c(F)c2)ncc1N1CCC[C@](N)(CC(F)F)C1] |
| V-11 | 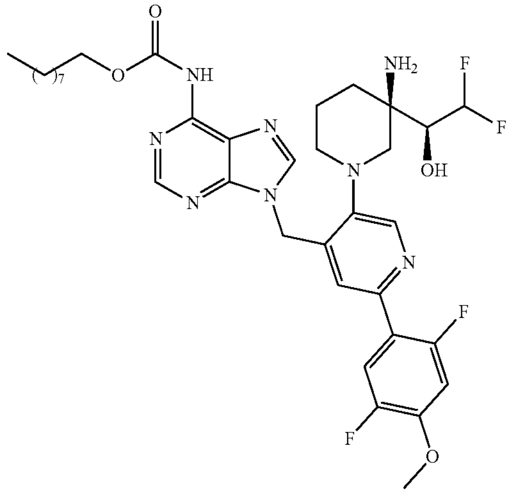 |
| V-12 | 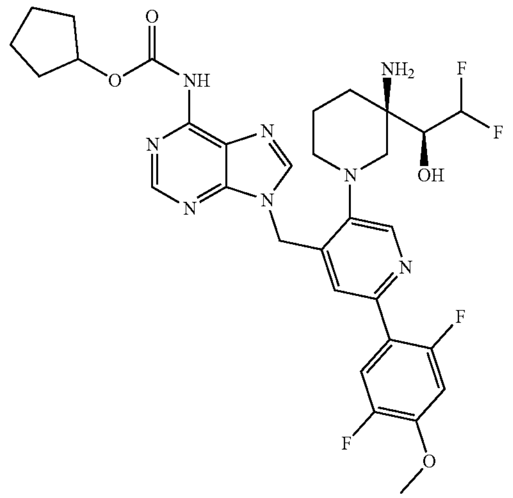 [SMILES: COc1cc(F)c(-c2cc(Cn3cnc4c(NC(=O)OC5CCCC5)ncnc43)c(N3CCC[C@](N)([C@H](O)C(F)F)C3)cn2)cc1F] |

TABLE 5-continued
| Compound No. | Chemical Structure |
| --- | --- |
| V-13 | 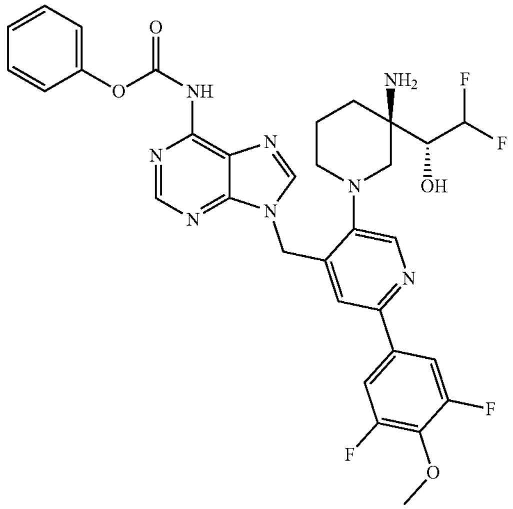 [SMILES: COc1c(F)cc(-c2cc(Cn3cnc4c(NC(=O)Oc5ccccc5)ncnc43)c(N3CCC[C@](N)([C@@H](O)C(F)F)C3)cn2)cc1F] |
| V-14 | 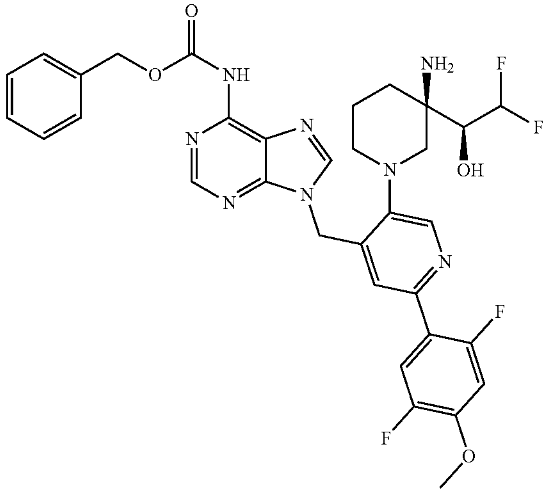 [SMILES: COc1cc(F)c(-c2cc(Cn3cnc4c(NC(=O)OCc5ccccc5)ncnc43)c(N3CCC[C@](N)([C@H](O)C(F)F)C3)cn2)cc1F] |
| V-15 | 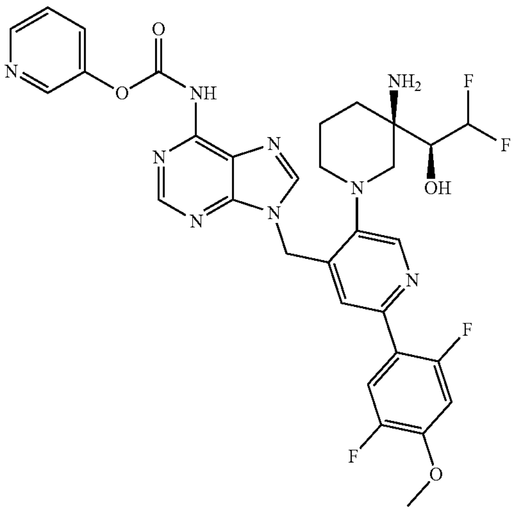 [SMILES: COc1cc(F)c(-c2cc(Cn3cnc4c(NC(=O)Oc5cccnc5)ncnc43)c(N3CCC[C@](N)([C@H](O)C(F)F)C3)cn2)cc1F] |

TABLE 5-continued
| Compound No. | Chemical Structure |
| --- | --- |
| V-16 | 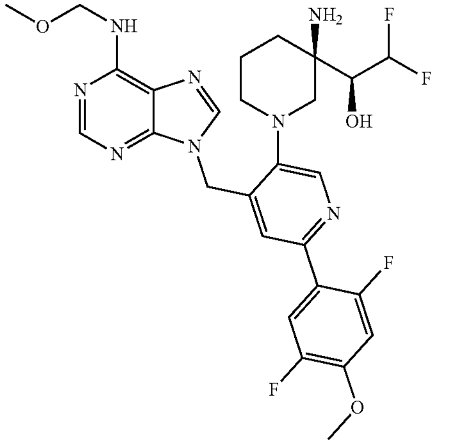 [SMILES: COCNc1ncnc2c1ncn2Cc1cc(-c2cc(F)c(OC)cc2F)ncc1N1CCC[C@](N)([C@H](O)C(F)F)C1] |
| V-17 | 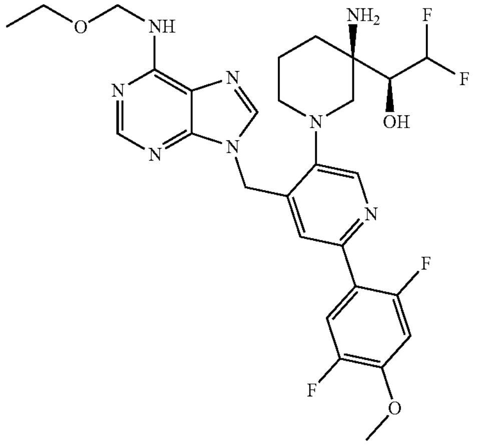 [SMILES: CCOCNc1ncnc2c1ncn2Cc1cc(-c2cc(F)c(OC)cc2F)ncc1N1CCC[C@](N)([C@H](O)C(F)F)C1] |
| V-18 | 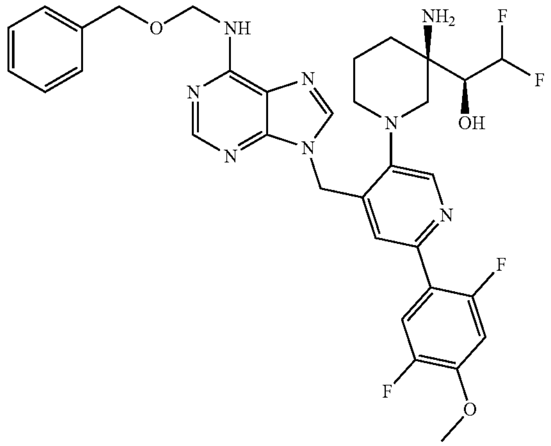 [SMILES: COc1cc(F)c(-c2cc(Cn3cnc4c(NCOCc5ccccc5)ncnc43)c(N3CCC[C@](N)([C@H](O)C(F)F)C3)cn2)cc1F] |

TABLE 5-continued
| Compound No. | Chemical Structure |
|---|---|
| V-19 | 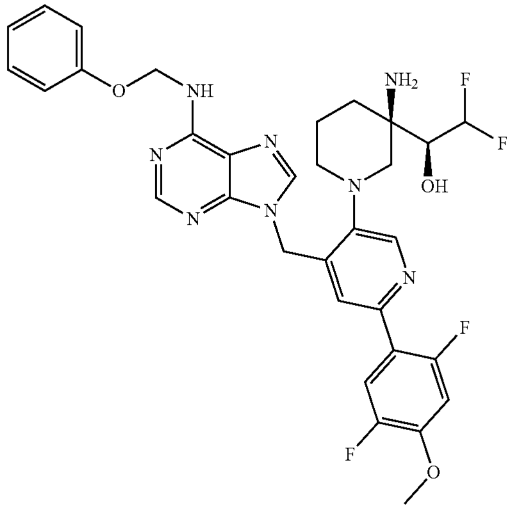 [SMILES: COc1cc(F)c(-c2cc(Cn3cnc4c(NCOc5ccccc5)ncnc43)c(N3CCC[C@](N)([C@H](O)C(F)F)C3)cn2)cc1F] |
| V-20 | 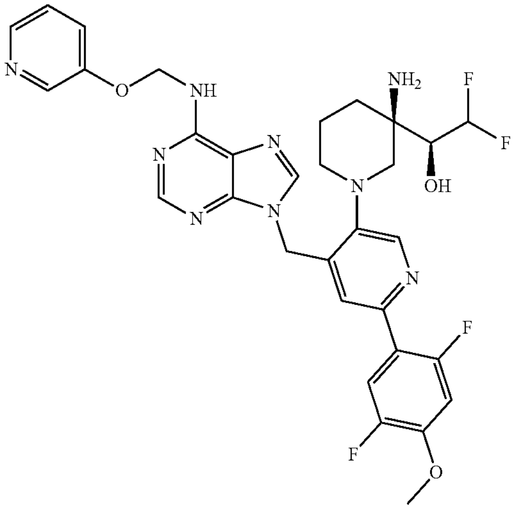 [SMILES: COc1cc(F)c(-c2cc(Cn3cnc4c(NCOc5cccnc5)ncnc43)c(N3CCC[C@](N)([C@H](O)C(F)F)C3)cn2)cc1F] |
| V-21 | 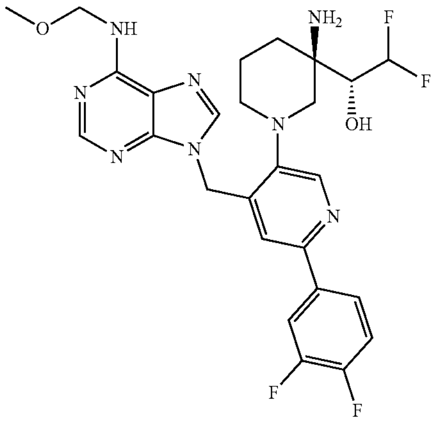 [SMILES: COCNc1ncnc2c1ncn2Cc1cc(-c2ccc(F)c(F)c2)ncc1N1CCC[C@](N)([C@@H](O)C(F)F)C1] |

TABLE 5-continued
| Compound No. | Chemical Structure |
| --- | --- |
| V-22 | 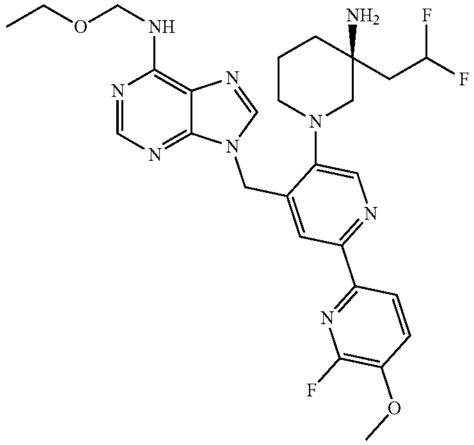 [SMILES: CCOCNc1ncnc2c1ncn2Cc1cc(-c2ccc(OC)c(F)n2)ncc1N1CCC[C@](N)(CC(F)F)C1] |
| V-23 | 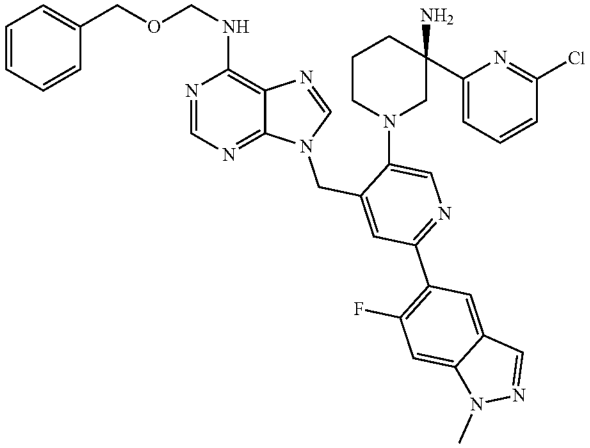 [SMILES: Cn1ncc2cc(-c3cc(Cn4cnc5c(NCOCc6ccccc6)ncnc54)c(N4CCC[C@](N)(c5cccc(Cl)n5)C4)cn3)c(F)cc21] |
| V-24 | 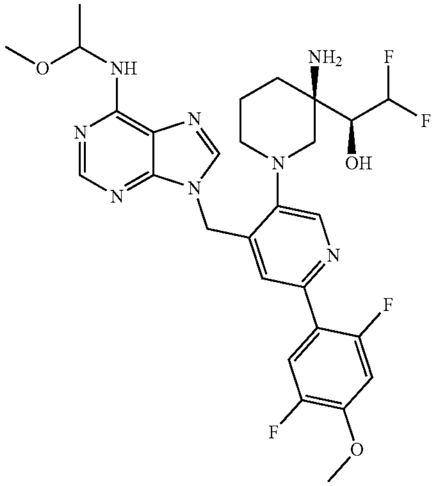 [SMILES: COc1cc(F)c(-c2cc(Cn3cnc4c(NC(C)OC)ncnc43)c(N3CCC[C@](N)([C@H](O)C(F)F)C3)cn2)cc1F] |

TABLE 5-continued
| Compound No. | Chemical Structure |
|---|---|
| V-25 | 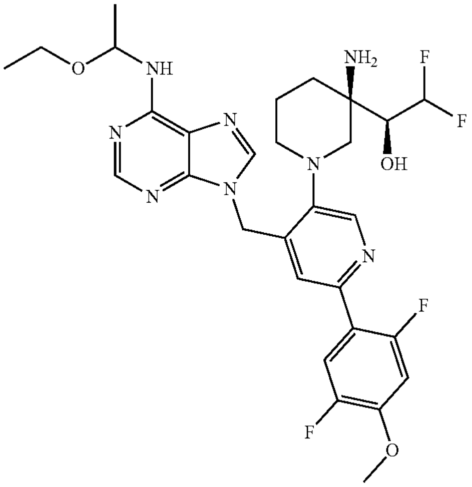 [SMILES: CCOC(C)Nc1ncnc2c1ncn2Cc1cc(-c2cc(F)c(OC)cc2F)ncc1N1CCC[C@](N)([C@H](O)C(F)F)C1] |
| V-26 | 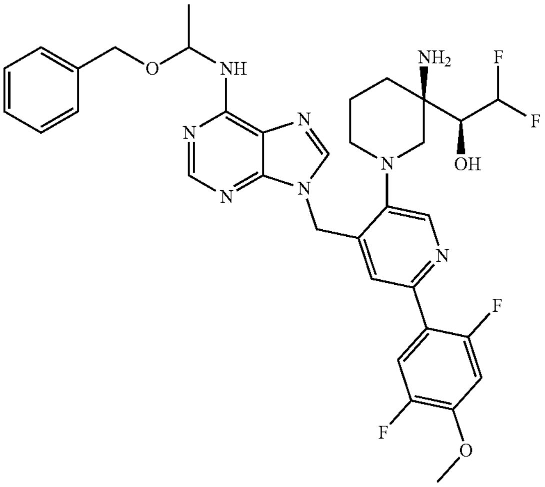 [SMILES: COc1cc(F)c(-c2cc(Cn3cnc4c(NC(C)OCc5ccccc5)ncnc43)c(N3CCC[C@](N)([C@H](O)C(F)F)C3)cn2)cc1F] |
| V-27 | 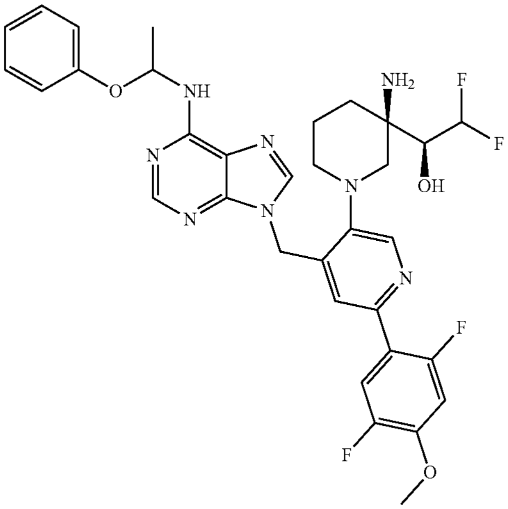 [SMILES: COc1cc(F)c(-c2cc(Cn3cnc4c(NC(C)Oc5ccccc5)ncnc43)c(N3CCC[C@](N)([C@H](O)C(F)F)C3)cn2)cc1F] |

TABLE 5-continued
| Compound No. | Chemical Structure |
| --- | --- |
| V-28 | 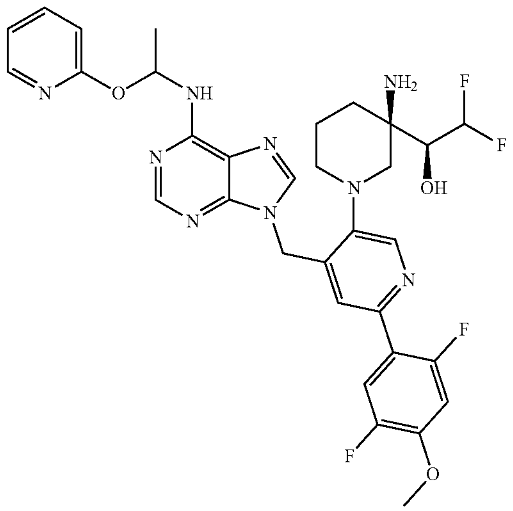 [SMILES: COc1cc(F)c(-c2cc(Cn3cnc4c(NC(C)Oc5ccccn5)ncnc43)c(N3CCC[C@](N)([C@H](O)C(F)F)C3)cn2)cc1F] |
| V-29 | 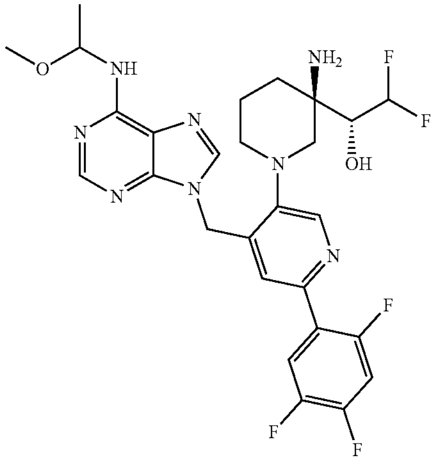 [SMILES: COC(C)Nc1ncnc2c1ncn2Cc1cc(-c2cc(F)c(F)cc2F)ncc1N1CCC[C@](N)([C@@H](O)C(F)F)C1] |
| V-30 | 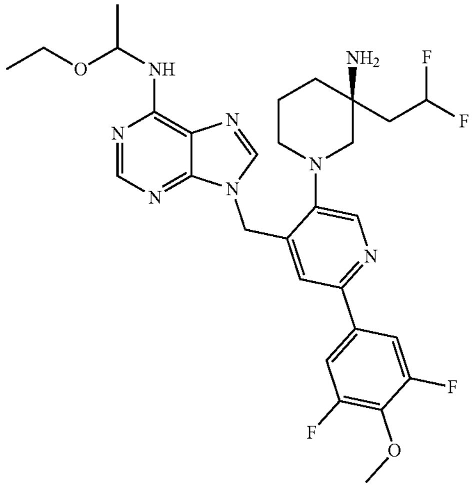 [SMILES: CCOC(C)Nc1ncnc2c1ncn2Cc1cc(-c2cc(F)c(OC)c(F)c2)ncc1N1CCC[C@](N)(CC(F)F)C1] |

TABLE 5-continued
| Compound No. | Chemical Structure |
| --- | --- |
| V-31 | 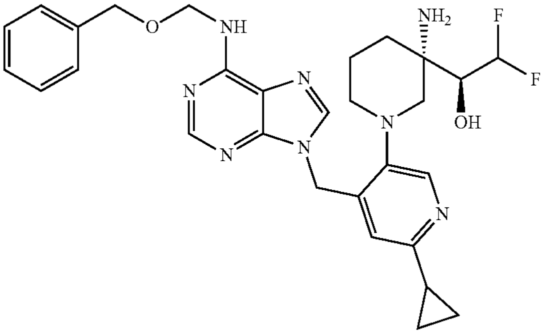 [SMILES: N[C@@]1([C@H](O)C(F)F)CCCN(c2cnc(C3CC3)cc2Cn2cnc3c(NCOCc4ccccc4)ncnc32)C1] |
| V-32 | 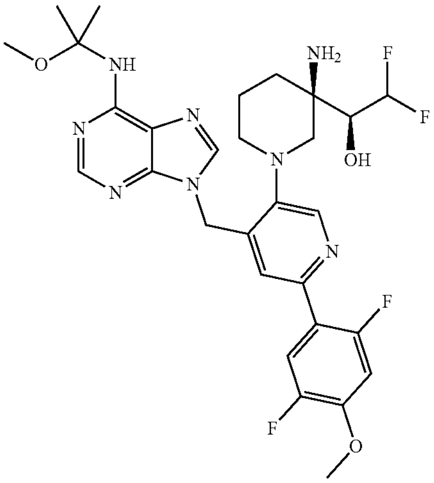 [SMILES: COc1cc(F)c(-c2cc(Cn3cnc4c(NC(C)(C)OC)ncnc43)c(N3CCC[C@](N)([C@H](O)C(F)F)C3)cn2)cc1F] |
| V-33 | 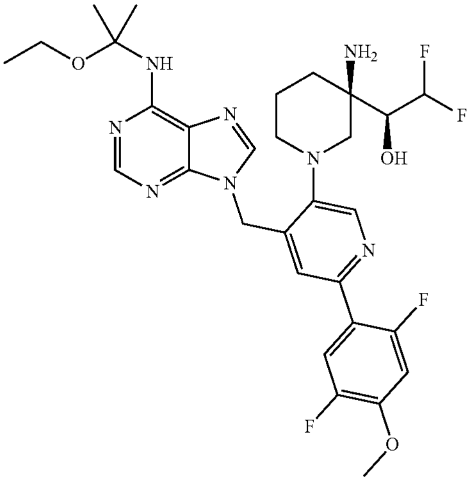 [SMILES: CCOC(C)(C)Nc1ncnc2c1ncn2Cc1cc(-c2cc(F)c(OC)cc2F)ncc1N1CCC[C@](N)([C@H](O)C(F)F)C1] |

TABLE 5-continued
| Compound No. | Chemical Structure |
|---|---|
| V-34 | 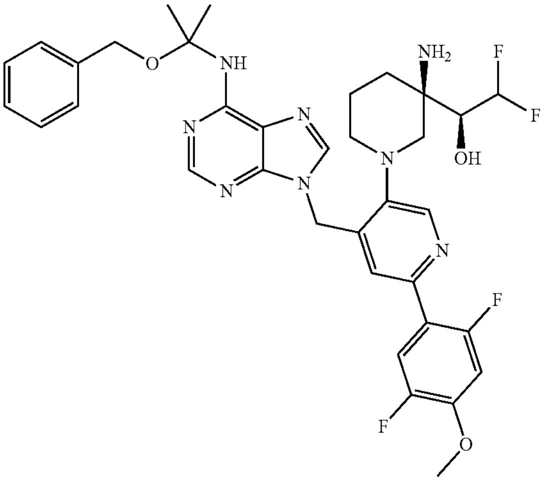 [SMILES: COc1cc(F)c(-c2cc(Cn3cnc4c(NC(C)(C)OCc5ccccc5)ncnc43)c(N3CCC[C@](N)([C@H](O)C(F)F)C3)cn2)cc1F] |
| V-35 | 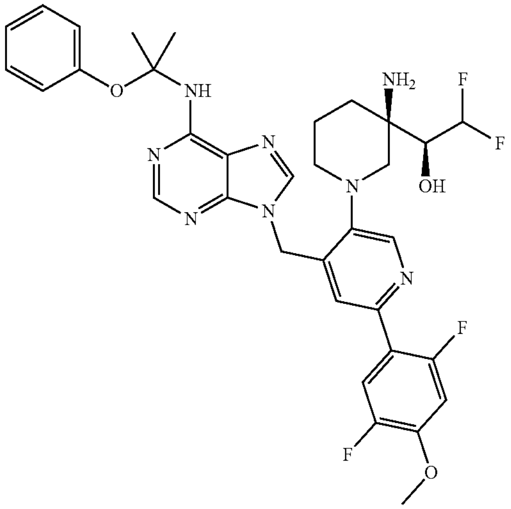 [SMILES: COc1cc(F)c(-c2cc(Cn3cnc4c(NC(C)(C)Oc5ccccc5)ncnc43)c(N3CCC[C@](N)([C@H](O)C(F)F)C3)cn2)cc1F] |
| V-36 | 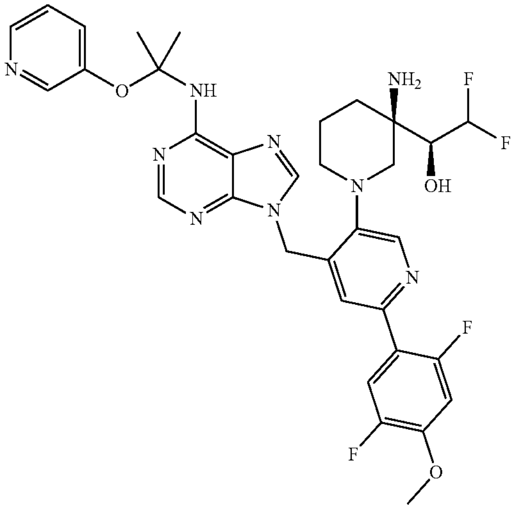 [SMILES: COc1cc(F)c(-c2cc(Cn3cnc4c(NC(C)(C)Oc5cccnc5)ncnc43)c(N3CCC[C@](N)([C@H](O)C(F)F)C3)cn2)cc1F] |

TABLE 5-continued
| Compound No. | Chemical Structure |
|---|---|
| V-37 | 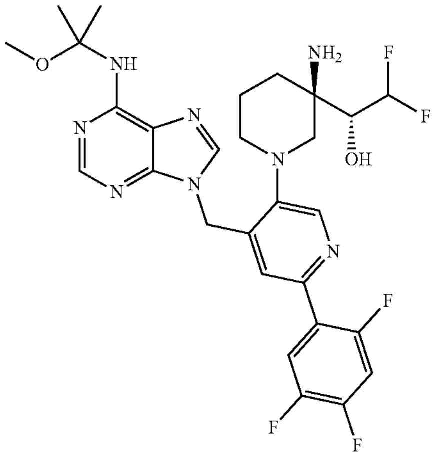 [SMILES: COC(C)(C)Nc1ncnc2c1ncn2Cc1cc(-c2cc(F)c(F)cc2F)ncc1N1CCC[C@](N)([C@@H](O)C(F)F)C1] |
| V-38 | 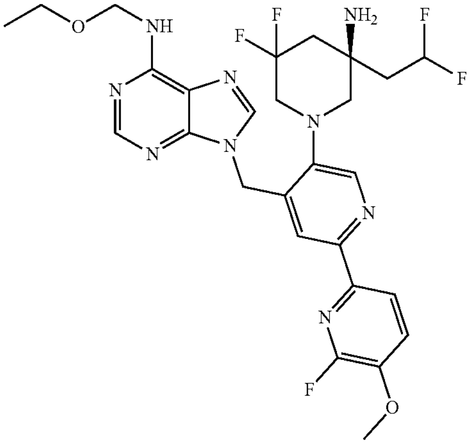 [SMILES: CCOCNc1ncnc2c1ncn2Cc1cc(-c2ccc(OC)c(F)n2)ncc1N1CC(F)(F)C[C@](N)(CC(F)F)C1] |
| V-39 | 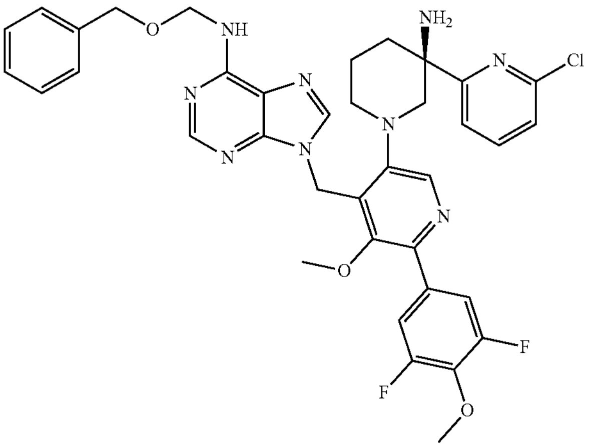 [SMILES: COc1c(F)cc(-c2ncc(N3CCC[C@](N)(c4cccc(Cl)n4)C3)c(Cn3cnc4c(NCOCc5ccccc5)ncnc43)c2OC)cc1F] |

TABLE 5-continued
| Compound No. | Chemical Structure |
| --- | --- |
| V-40 | 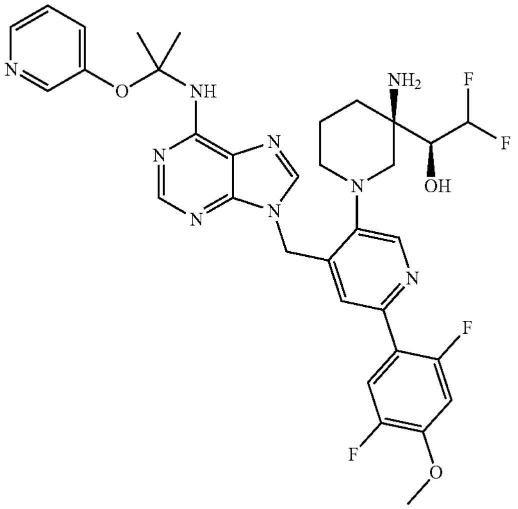 [SMILES: COc1cc(F)c(-c2cc(Cn3cnc4c(NC(C)(C)Oc5cccnc5)ncnc43)c(N3CCC[C@](N)([C@H](O)C(F)F)C3)cn2)cc1F] |
| V-41 | 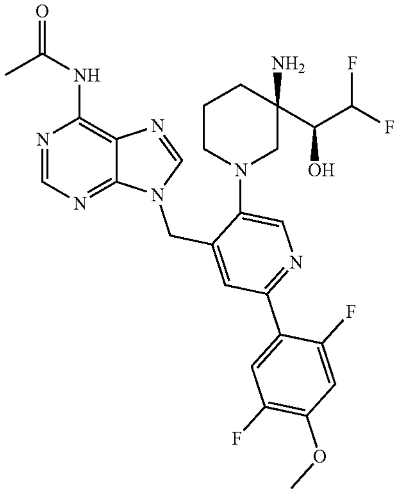 [SMILES: COc1cc(F)c(-c2cc(Cn3cnc4c(NC(C)=O)ncnc43)c(N3CCC[C@](N)([C@H](O)C(F)F)C3)cn2)cc1F] |
| V-42 | 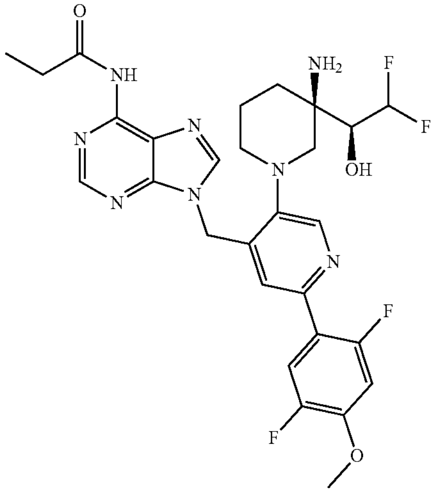 [SMILES: CCC(=O)Nc1ncnc2c1ncn2Cc1cc(-c2cc(F)c(OC)cc2F)ncc1N1CCC[C@](N)([C@H](O)C(F)F)C1] |

TABLE 5-continued
| Compound No. | Chemical Structure |
| --- | --- |
| V-43 | 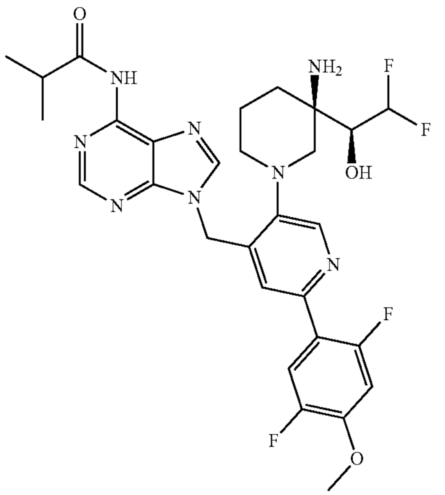 [SMILES: COc1cc(F)c(-c2cc(Cn3cnc4c(NC(=O)C(C)C)ncnc43)c(N3CCC[C@](N)([C@H](O)C(F)F)C3)cn2)cc1F] |
| V-44 | 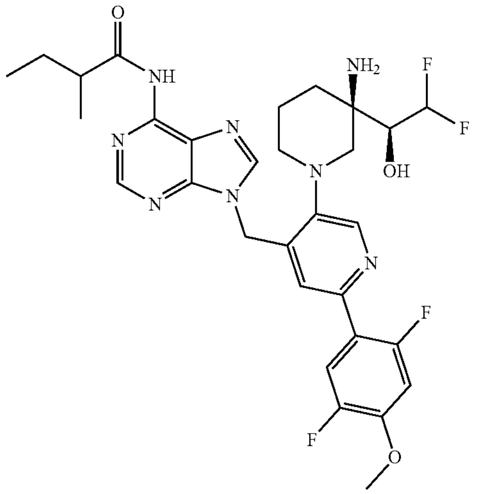 [SMILES: CCC(C)C(=O)Nc1ncnc2c1ncn2Cc1cc(-c2cc(F)c(OC)cc2F)ncc1N1CCC[C@](N)([C@H](O)C(F)F)C1] |
| V-45 | 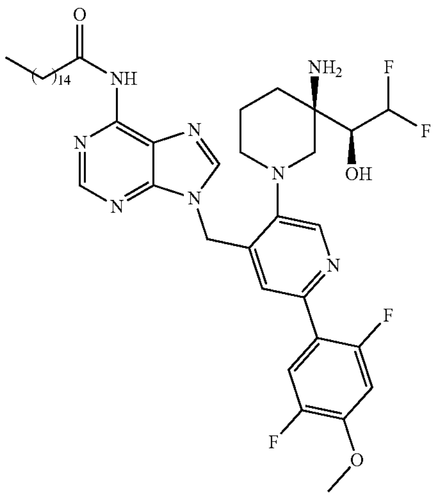 |

TABLE 5-continued
| Compound No. | Chemical Structure |
| --- | --- |
| V-46 | 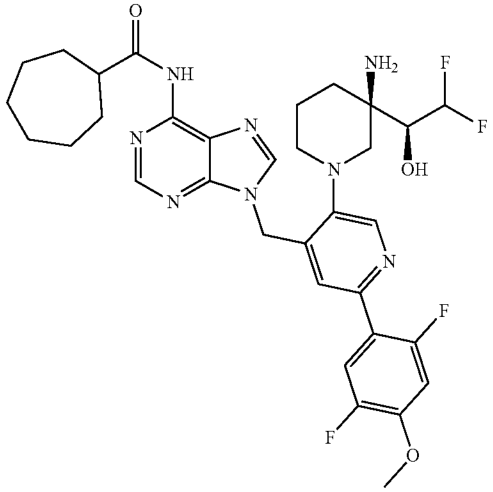 [SMILES: COc1cc(F)c(-c2cc(Cn3cnc4c(NC(=O)C5CCCCCC5)ncnc43)c(N3CCC[C@](N)([C@H](O)C(F)F)C3)cn2)cc1F] |
| V-47 | 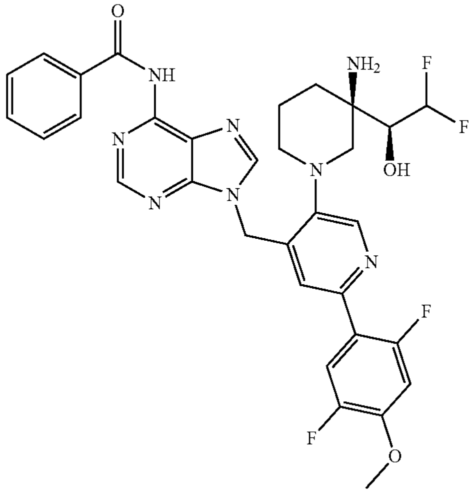 [SMILES: COc1cc(F)c(-c2cc(Cn3cnc4c(NC(=O)c5ccccc5)ncnc43)c(N3CCC[C@](N)([C@H](O)C(F)F)C3)cn2)cc1F] |
| V-48 | 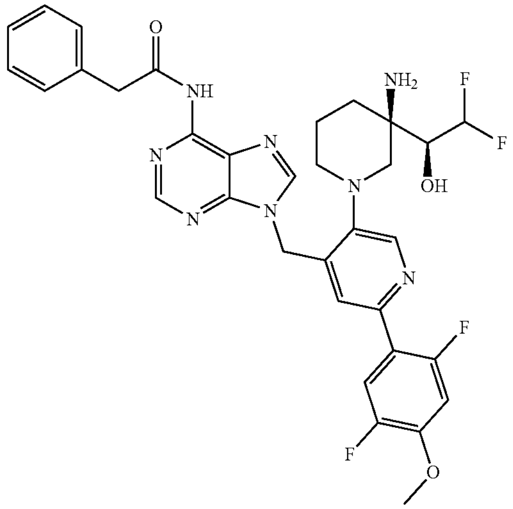 [SMILES: COc1cc(F)c(-c2cc(Cn3cnc4c(NC(=O)Cc5ccccc5)ncnc43)c(N3CCC[C@](N)([C@H](O)C(F)F)C3)cn2)cc1F] |

TABLE 5-continued
| Compound No. | Chemical Structure |
| --- | --- |
| V-49 | 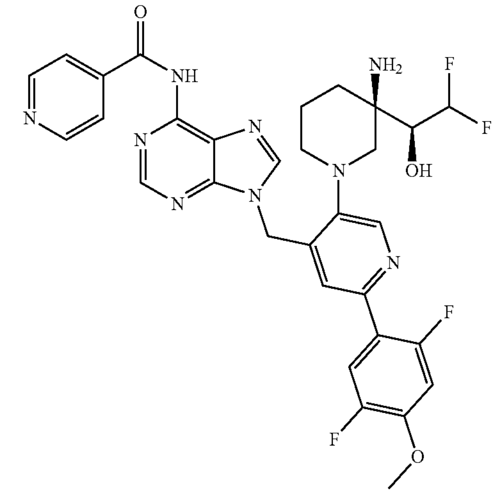 [SMILES: COc1cc(F)c(-c2cc(Cn3cnc4c(NC(=O)c5ccncc5)ncnc43)c(N3CCC[C@](N)([C@H](O)C(F)F)C3)cn2)cc1F] |
| V-50 | 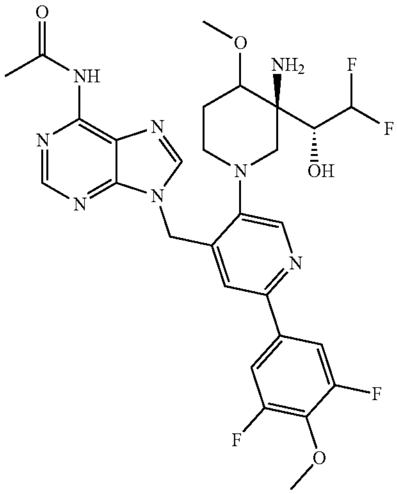 [SMILES: COc1c(F)cc(-c2cc(Cn3cnc4c(NC(C)=O)ncnc43)c(N3CCC(OC)[C@](N)([C@@H](O)C(F)F)C3)cn2)cc1F] |
| V-51 | 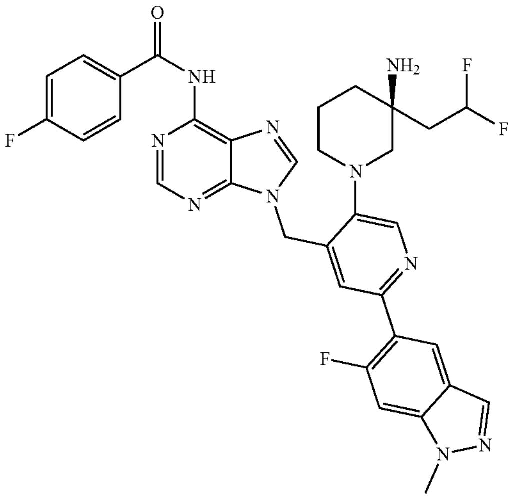 [SMILES: Cn1ncc2cc(-c3cc(Cn4cnc5c(NC(=O)c6ccc(F)cc6)ncnc54)c(N4CCC[C@](N)(CC(F)F)C4)cn3)c(F)cc21] |

TABLE 5-continued
| Compound No. | Chemical Structure |
|---|---|
| V-52 | 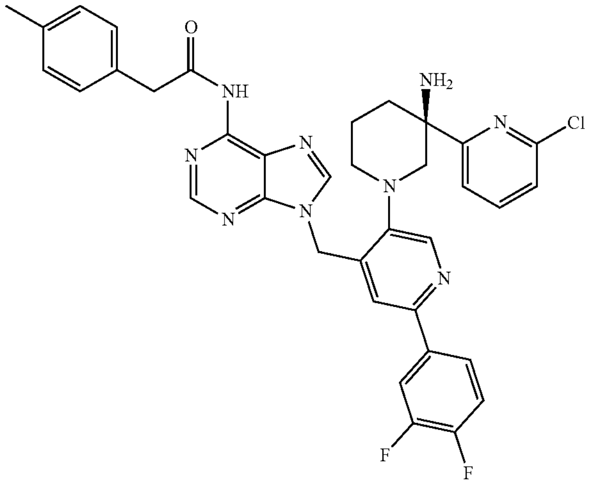 [SMILES: Cc1ccc(CC(=O)Nc2ncnc3c2ncn3Cc2cc(-c3ccc(F)c(F)c3)ncc2N2CCC[C@](N)(c3cccc(Cl)n3)C2)cc1] |
| V-53 | 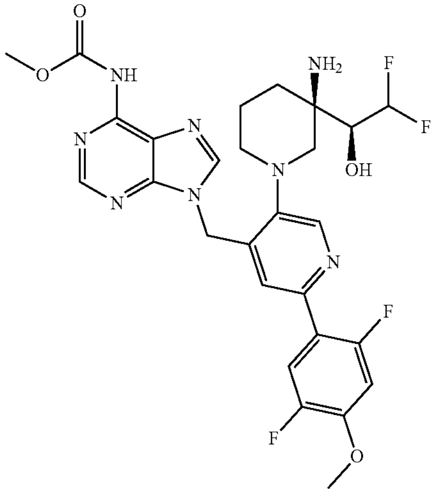 |
| V-54 | 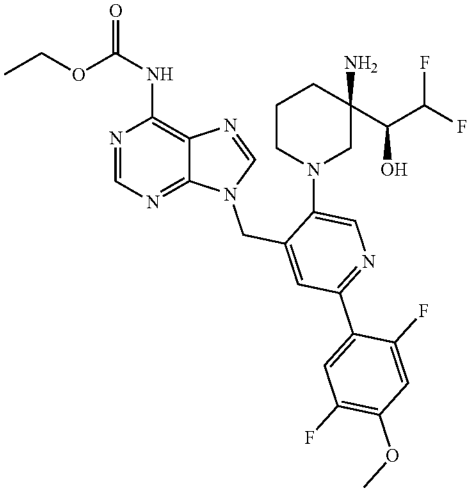 [SMILES: CCOC(=O)Nc1ncnc2c1ncn2Cc1cc(-c2cc(F)c(OC)cc2F)ncc1N1CCC[C@](N)([C@H](O)C(F)F)C1] |

TABLE 5-continued
| Compound No. | Chemical Structure |
| --- | --- |
| V-55 | 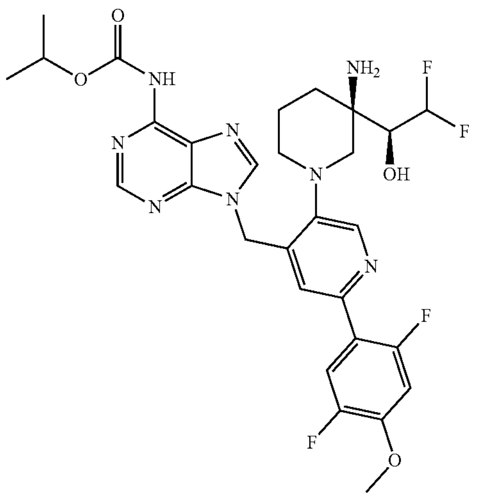 |
| V-56 | 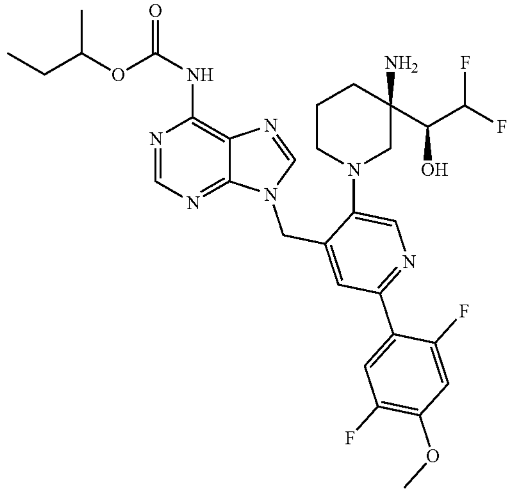 [SMILES: CCC(C)OC(=O)Nc1ncnc2c1ncn2Cc1cc(-c2cc(F)c(OC)cc2F)ncc1N1CCC[C@](N)([C@H](O)C(F)F)C1] |
| V-57 | 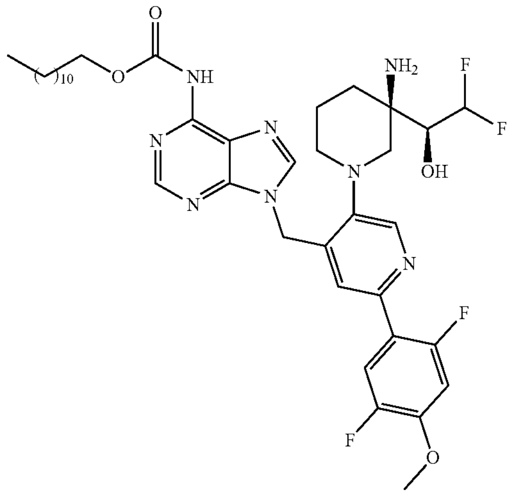 |

TABLE 5-continued
| Compound No. | Chemical Structure |
| --- | --- |
| V-58 | 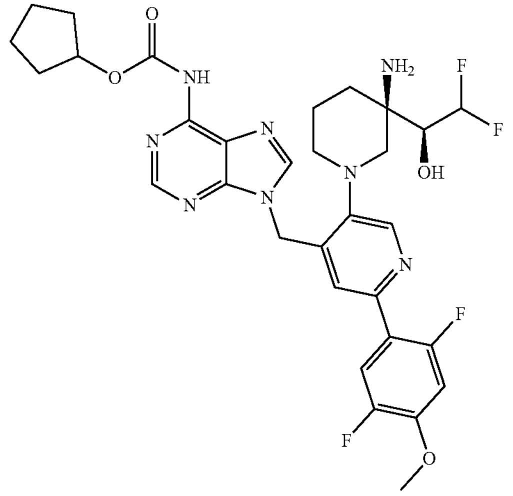 [SMILES: COc1cc(F)c(-c2cc(Cn3cnc4c(NC(=O)OC5CCCC5)ncnc43)c(N3CCC[C@](N)([C@H](O)C(F)F)C3)cn2)cc1F] |
| V-59 | 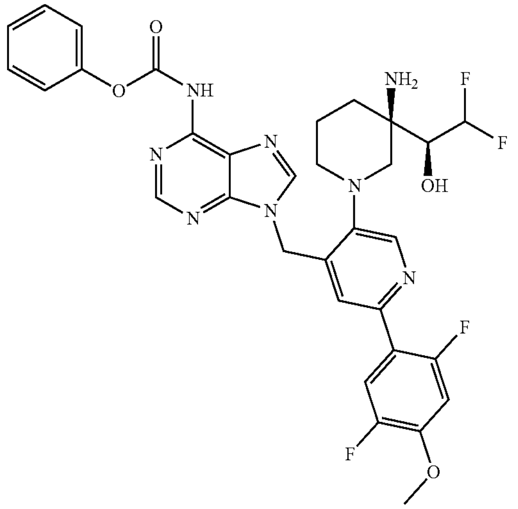 |
| V-60 | 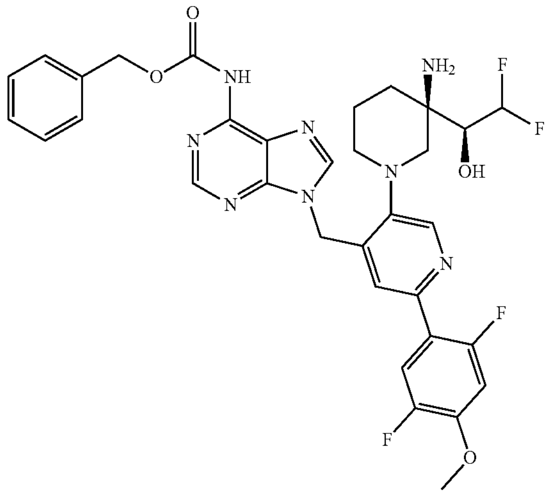 [SMILES: COc1cc(F)c(-c2cc(Cn3cnc4c(NC(=O)OCc5ccccc5)ncnc43)c(N3CCC[C@](N)([C@H](O)C(F)F)C3)cn2)cc1F] |

TABLE 5-continued
| Compound No. | Chemical Structure |
| --- | --- |
| V-61 | 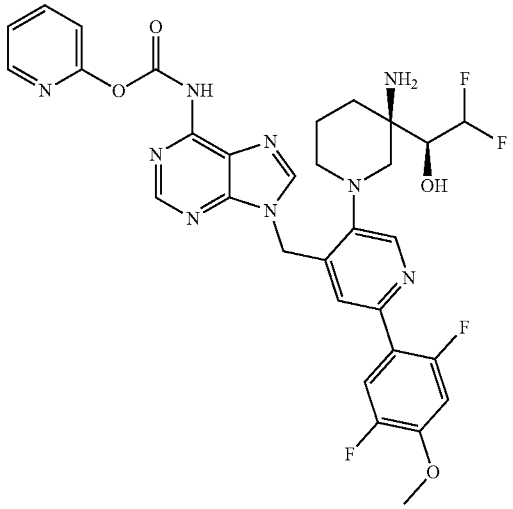 [SMILES: COc1cc(F)c(-c2cc(Cn3cnc4c(NC(=O)Oc5ccccn5)ncnc43)c(N3CCC[C@](N)([C@H](O)C(F)F)C3)cn2)cc1F] |
| V-62 | 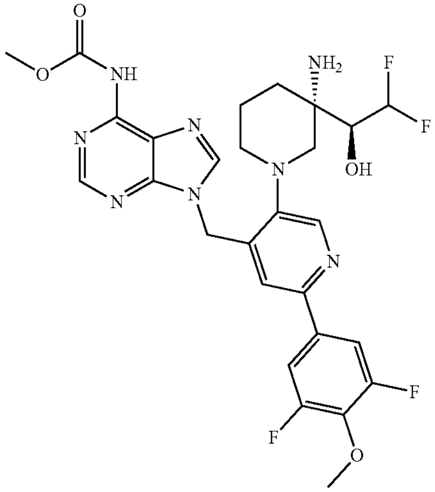 [SMILES: COC(=O)Nc1ncnc2c1ncn2Cc1cc(-c2cc(F)c(OC)c(F)c2)ncc1N1CCC[C@@](N)([C@H](O)C(F)F)C1] |
| V-63 | 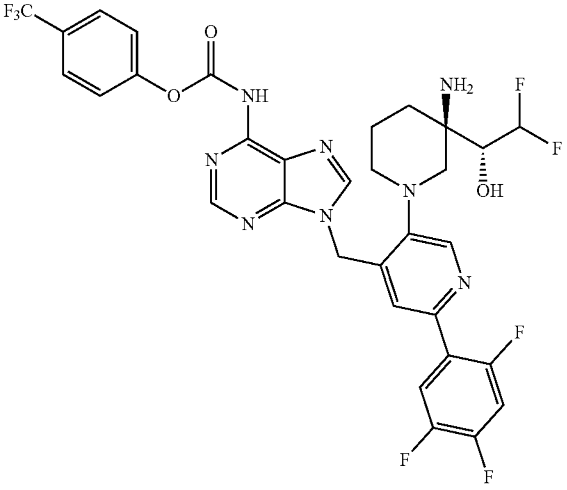 [SMILES: N[C@]1([C@@H](O)C(F)F)CCCN(c2cnc(-c3cc(F)c(F)cc3F)cc2Cn2cnc3c(NC(=O)Oc4ccc(C(F)(F)F)cc4)ncnc32)C1] |

TABLE 5-continued
| Compound No. | Chemical Structure |
| --- | --- |
| V-64 | 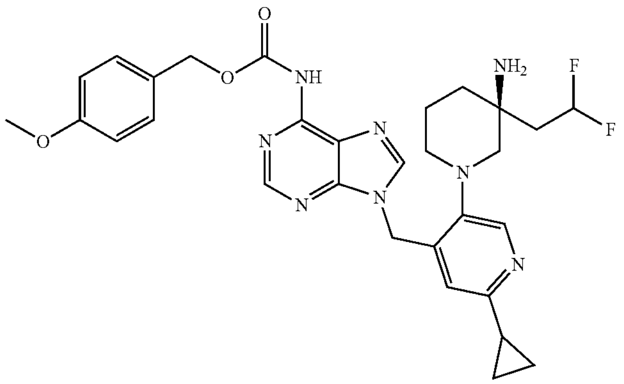 [SMILES: COc1ccc(COC(=O)Nc2ncnc3c2ncn3Cc2cc(C3CC3)ncc2N2CCC[C@](N)(CC(F)F)C2)cc1] |
| V-65 | 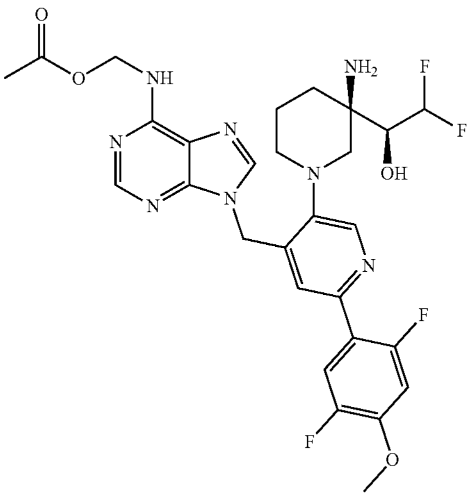 [SMILES: COc1cc(F)c(-c2cc(Cn3cnc4c(NCOC(C)=O)ncnc43)c(N3CCC[C@](N)([C@H](O)C(F)F)C3)cn2)cc1F] |
| V-66 | 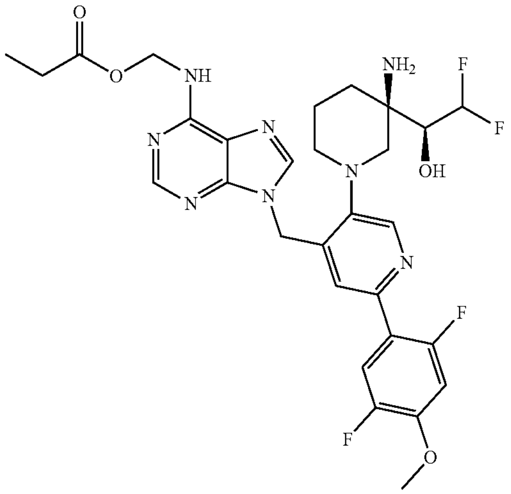 [SMILES: CCC(=O)OCNc1ncnc2c1ncn2Cc1cc(-c2cc(F)c(OC)cc2F)ncc1N1CCC[C@](N)([C@H](O)C(F)F)C1] |

TABLE 5-continued
| Compound No. | Chemical Structure |
| --- | --- |
| V-67 | 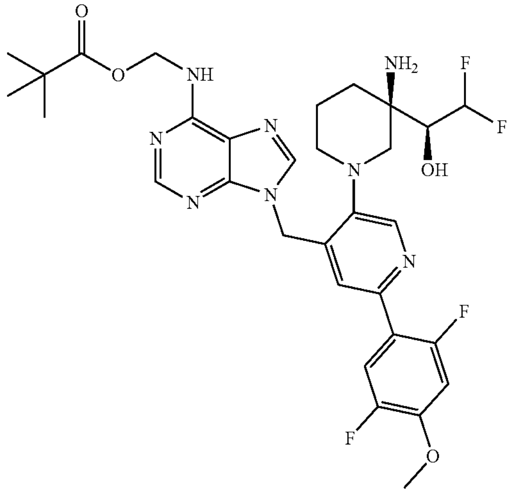 [SMILES: COc1cc(F)c(-c2cc(Cn3cnc4c(NCOC(=O)C(C)(C)C)ncnc43)c(N3CCC[C@](N)([C@H](O)C(F)F)C3)cn2)cc1F] |
| V-68 | 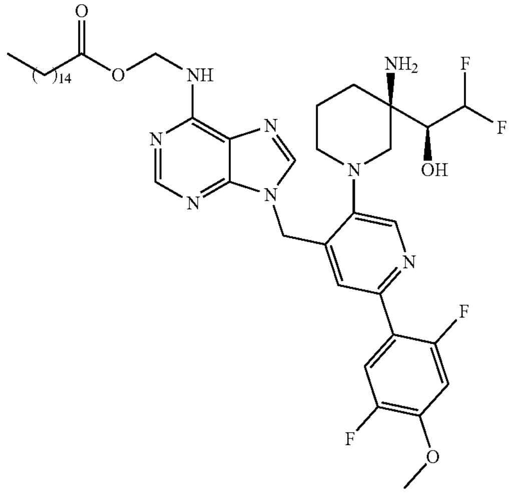 |
| V-69 | 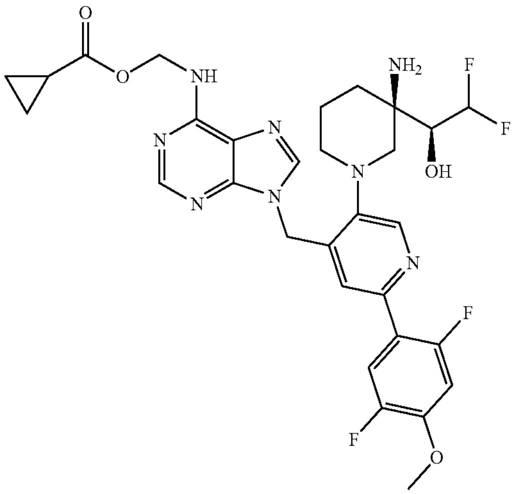 [SMILES: COc1cc(F)c(-c2cc(Cn3cnc4c(NCOC(=O)C5CC5)ncnc43)c(N3CCC[C@](N)([C@H](O)C(F)F)C3)cn2)cc1F] |

TABLE 5-continued
| Compound No. | Chemical Structure |
| --- | --- |
| V-70 | 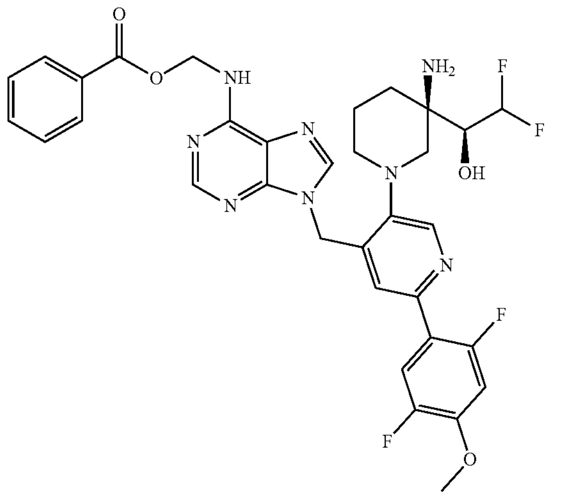 [SMILES: COc1cc(F)c(-c2cc(Cn3cnc4c(NCOC(=O)c5ccccc5)ncnc43)c(N3CCC[C@](N)([C@H](O)C(F)F)C3)cn2)cc1F] |
| V-71 | 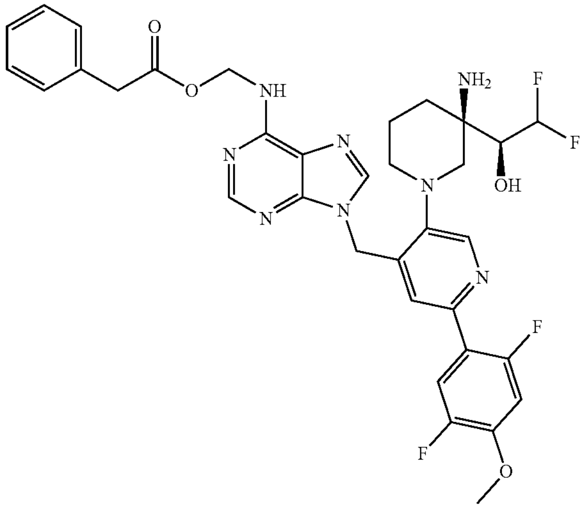 [SMILES: COc1cc(F)c(-c2cc(Cn3cnc4c(NCOC(=O)Cc5ccccc5)ncnc43)c(N3CCC[C@](N)([C@H](O)C(F)F)C3)cn2)cc1F] |
| V-72 | 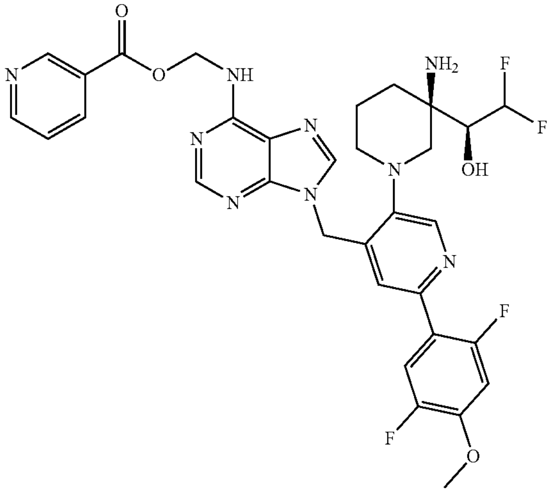 |

TABLE 5-continued
| Compound No. | Chemical Structure |
|---|---|
| V-73 | 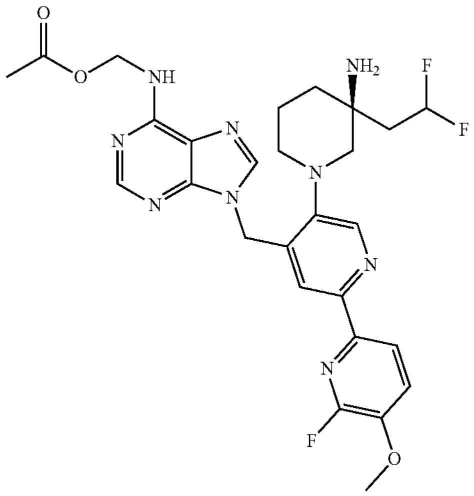 [SMILES: COc1ccc(-c2cc(Cn3cnc4c(NCOC(C)=O)ncnc43)c(N3CCC[C@](N)(CC(F)F)C3)cn2)nc1F] |
| V-74 | 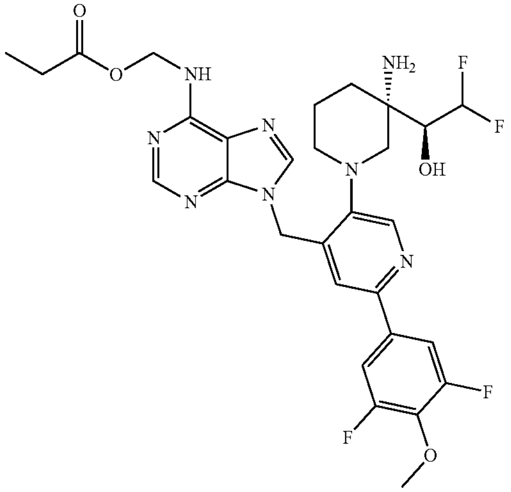 [SMILES: CCC(=O)OCNc1ncnc2c1ncn2Cc1cc(-c2cc(F)c(OC)c(F)c2)ncc1N1CCC[C@@](N)([C@H](O)C(F)F)C1] |
| V-75 | 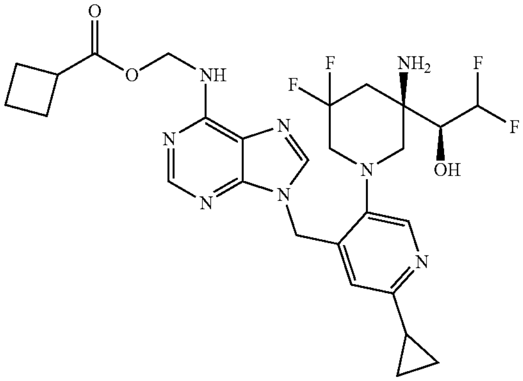 [SMILES: N[C@@]1([C@H](O)C(F)F)CN(c2cnc(C3CC3)cc2Cn2cnc3c(NCOC(=O)C4CCC4)ncnc32)CC(F)(F)C1] |

TABLE 5-continued
| Compound No. | Chemical Structure |
| --- | --- |
| V-76 | 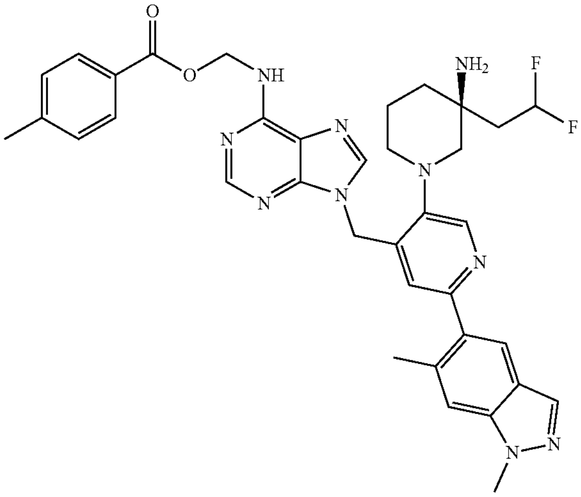 [SMILES: Cc1ccc(C(=O)OCNc2ncnc3c2ncn3Cc2cc(-c3cc4cnn(C)c4cc3C)ncc2N2CCC[C@](N)(CC(F)F)C2)cc1] |
| V-77 | 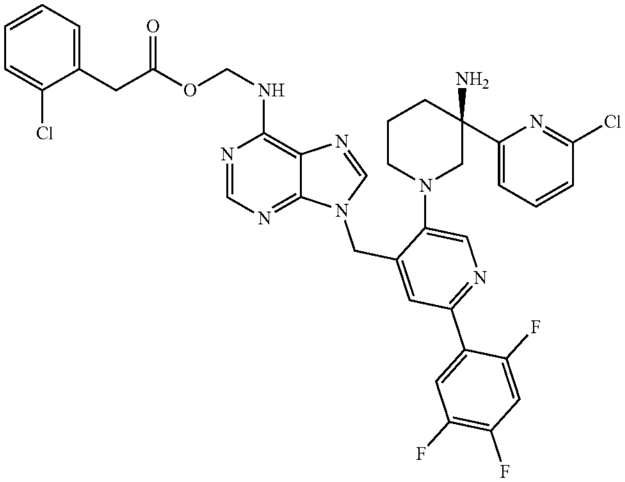 [SMILES: N[C@]1(c2cccc(Cl)n2)CCCN(c2cnc(-c3cc(F)c(F)cc3F)cc2Cn2cnc3c(NCOC(=O)Cc4ccccc4Cl)ncnc32)C1] |
| V-78 | 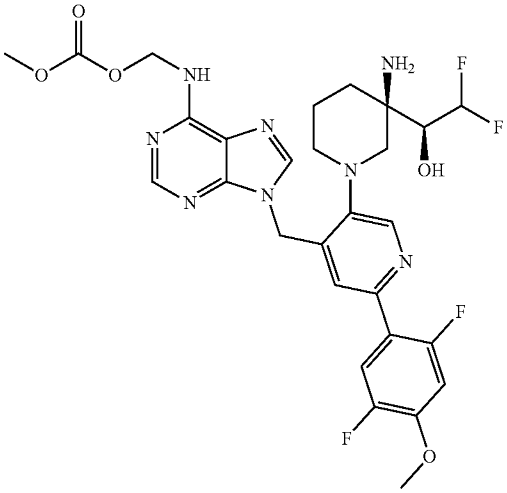 [SMILES: COC(=O)OCNc1ncnc2c1ncn2Cc1cc(-c2cc(F)c(OC)cc2F)ncc1N1CCC[C@](N)([C@H](O)C(F)F)C1] |

TABLE 5-continued
| Compound No. | Chemical Structure |
| --- | --- |
| V-79 | 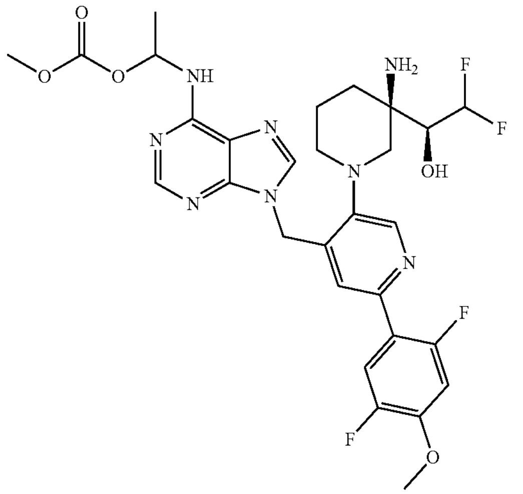 [SMILES: COC(=O)OC(C)Nc1ncnc2c1ncn2Cc1cc(-c2cc(F)c(OC)cc2F)ncc1N1CCC[C@](N)([C@H](O)C(F)F)C1] |
| V-80 | 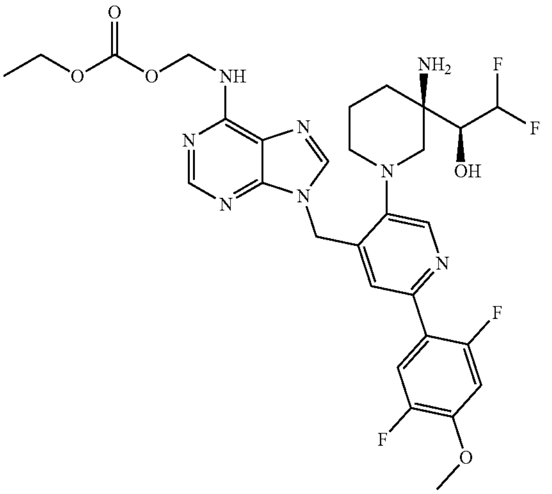 [SMILES: CCOC(=O)OCNc1ncnc2c1ncn2Cc1cc(-c2cc(F)c(OC)cc2F)ncc1N1CCC[C@](N)([C@H](O)C(F)F)C1] |
| V-81 | 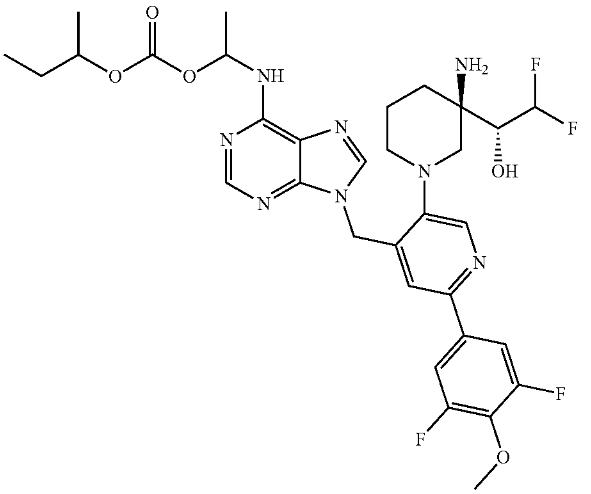 [SMILES: CCC(C)OC(=O)OC(C)Nc1ncnc2c1ncn2Cc1cc(-c2cc(F)c(OC)c(F)c2)ncc1N1CCC[C@](N)([C@@H](O)C(F)F)C1] |

TABLE 5-continued
| Compound No. | Chemical Structure |
|---|---|
| V-82 | 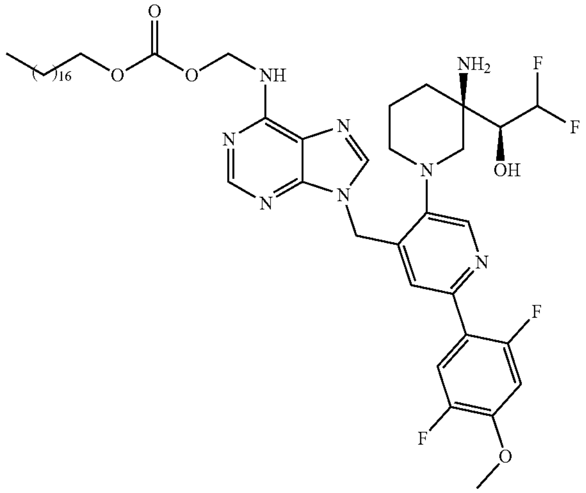 |
| V-83 | 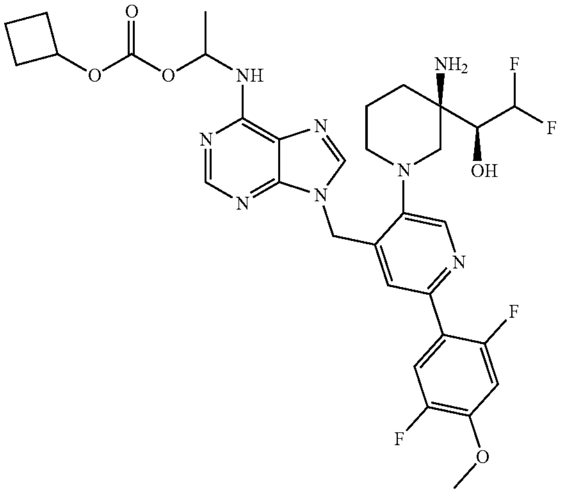 [SMILES: COc1cc(F)c(-c2cc(Cn3cnc4c(NC(C)OC(=O)OC5CCC5)ncnc43)c(N3CCC[C@](N)([C@H](O)C(F)F)C3)cn2)cc1F] |
| V-84 | 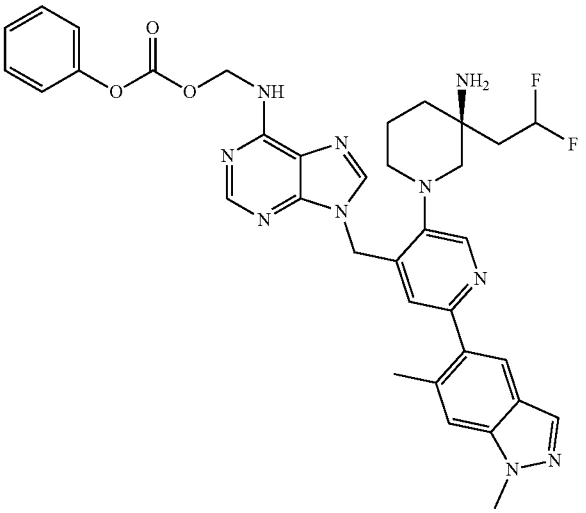 [SMILES: Cc1cc2c(cnn2C)cc1-c1cc(Cn2cnc3c(NCOC(=O)Oc4ccccc4)ncnc32)c(N2CCC[C@](N)(CC(F)F)C2)cn1] |

TABLE 5-continued
| Compound No. | Chemical Structure |
| --- | --- |
| V-85 | 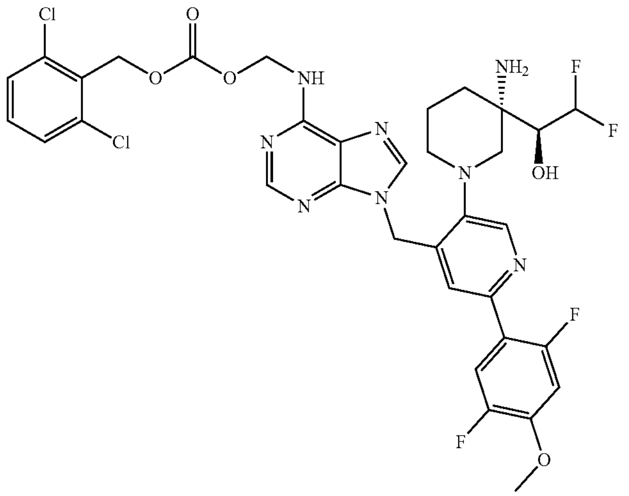 [SMILES: COc1cc(F)c(-c2cc(Cn3cnc4c(NCOC(=O)OCc5c(Cl)cccc5Cl)ncnc43)c(N3CCC[C@@](N)([C@H](O)C(F)F)C3)cn2)cc1F] |
| V-86 | 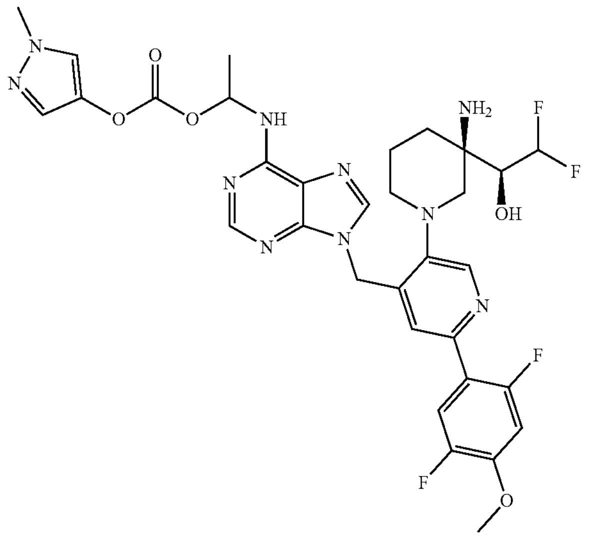 [SMILES: COc1cc(F)c(-c2cc(Cn3cnc4c(NC(C)OC(=O)Oc5cnn(C)c5)ncnc43)c(N3CCC[C@](N)([C@H](O)C(F)F)C3)cn2)cc1F] |
| V-87 | 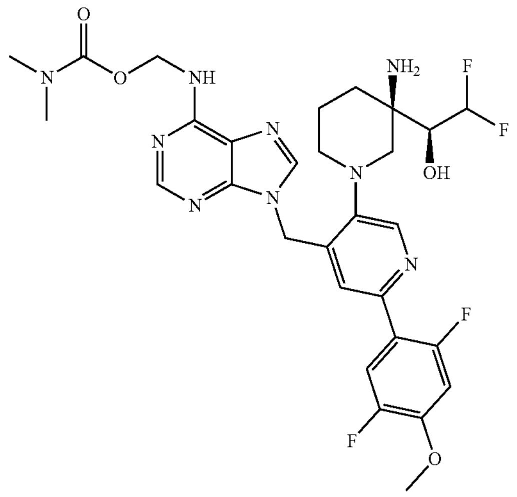 [SMILES: COc1cc(F)c(-c2cc(Cn3cnc4c(NCOC(=O)N(C)C)ncnc43)c(N3CCC[C@](N)([C@H](O)C(F)F)C3)cn2)cc1F] |

TABLE 5-continued
| Compound No. | Chemical Structure |
|---|---|
| V-88 | 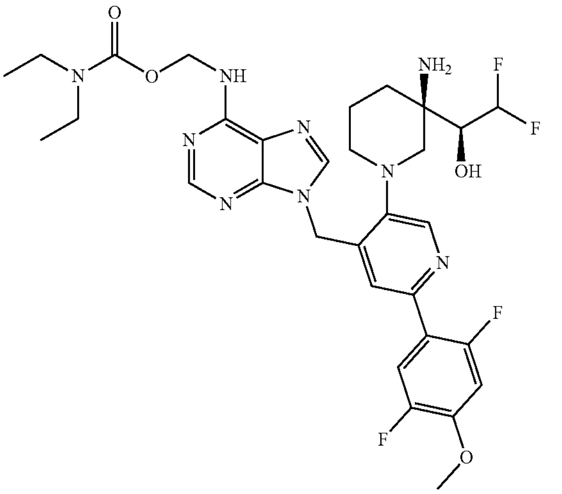 [SMILES: CCN(CC)C(=O)OCNc1ncnc2c1ncn2Cc1cc(-c2cc(F)c(OC)cc2F)ncc1N1CCC[C@](N)([C@H](O)C(F)F)C1] |
| V-89 | 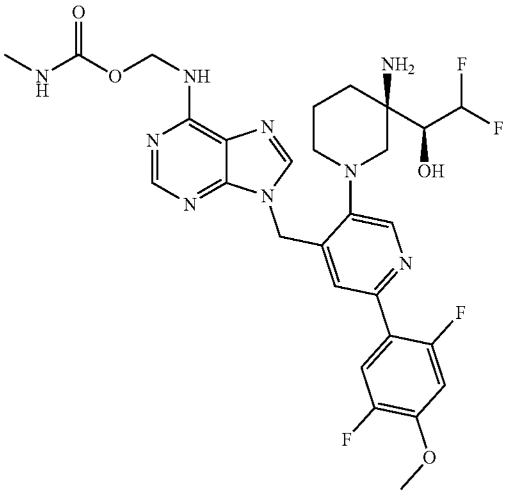 [SMILES: CNC(=O)OCNc1ncnc2c1ncn2Cc1cc(-c2cc(F)c(OC)cc2F)ncc1N1CCC[C@](N)([C@H](O)C(F)F)C1] |
| V-90 | 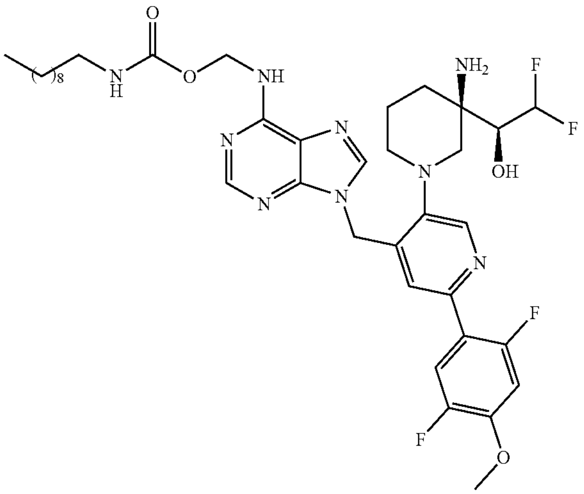 |

TABLE 5-continued
| Compound No. | Chemical Structure |
|---|---|
| V-91 | 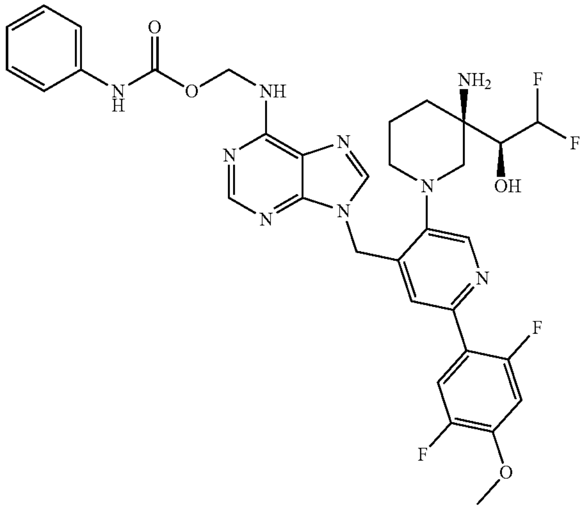 [SMILES: COc1cc(F)c(-c2cc(Cn3cnc4c(NCOC(=O)Nc5ccccc5)ncnc43)c(N3CCC[C@](N)([C@H](O)C(F)F)C3)cn2)cc1F] |
| V-92 | 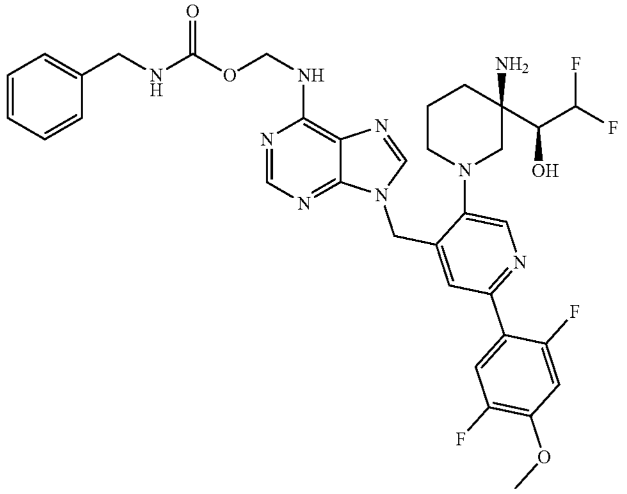 [SMILES: COc1cc(F)c(-c2cc(Cn3cnc4c(NCOC(=O)NCc5ccccc5)ncnc43)c(N3CCC[C@](N)([C@H](O)C(F)F)C3)cn2)cc1F] |
| V-93 | 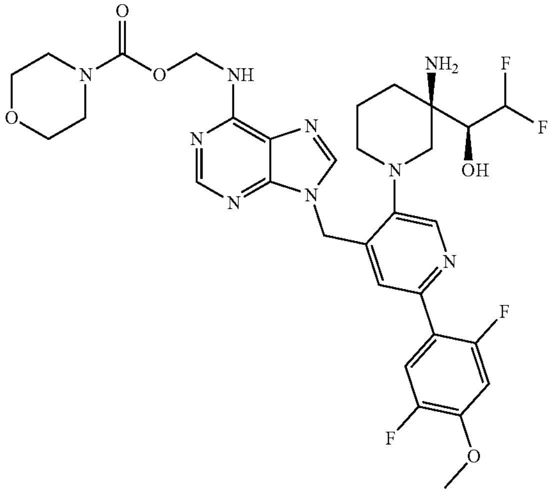 [SMILES: COc1cc(F)c(-c2cc(Cn3cnc4c(NCOC(=O)N5CCOCC5)ncnc43)c(N3CCC[C@](N)([C@H](O)C(F)F)C3)cn2)cc1F] |

TABLE 5-continued
| Compound No. | Chemical Structure |
|---|---|
| V-94 | 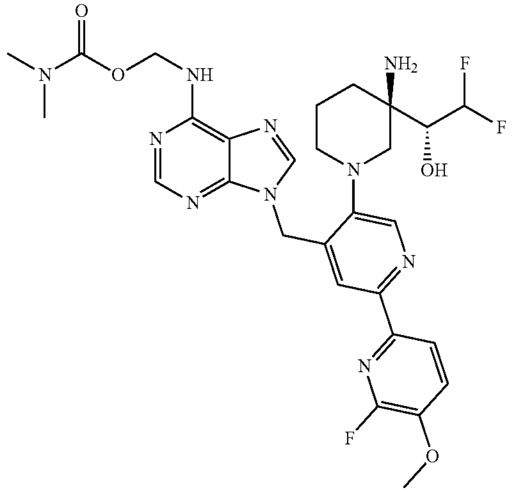 [SMILES: COc1ccc(-c2cc(Cn3cnc4c(NCOC(=O)N(C)C)ncnc43)c(N3CCC[C@](N)([C@@H](O)C(F)F)C3)cn2)nc1F] |
| V-95 | 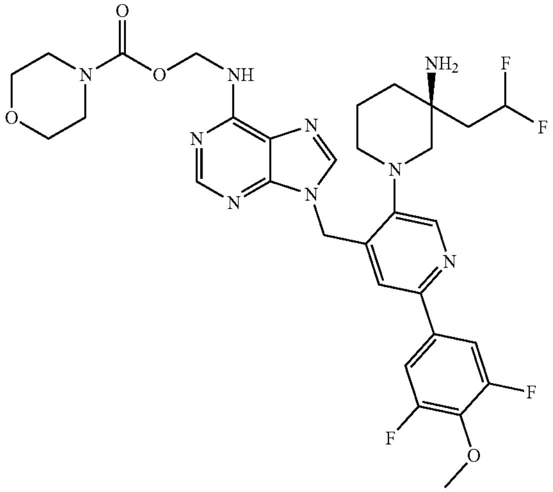 [SMILES: COc1c(F)cc(-c2cc(Cn3cnc4c(NCOC(=O)N5CCOCC5)ncnc43)c(N3CCC[C@](N)(CC(F)F)C3)cn2)cc1F] |
TABLE 6
| Compound No. | Chemical Structure |
|---|---|
| VI-1 | 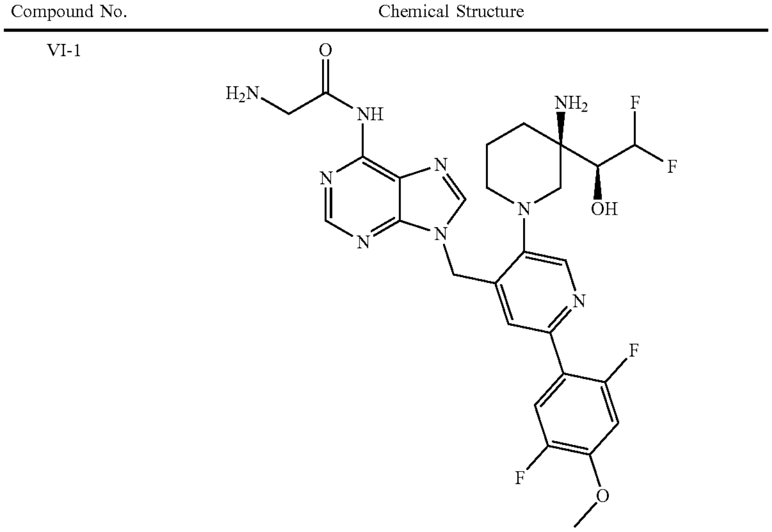 |

TABLE 6-continued
| Compound No. | Chemical Structure |
|---|---|
| VI-2 | 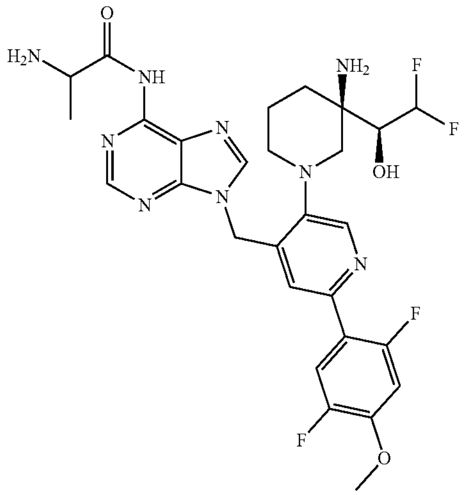 [SMILES: COc1cc(F)c(-c2cc(Cn3cnc4c(NC(=O)C(C)N)ncnc43)c(N3CCC[C@](N)([C@H](O)C(F)F)C3)cn2)cc1F] |
| VI-3 | 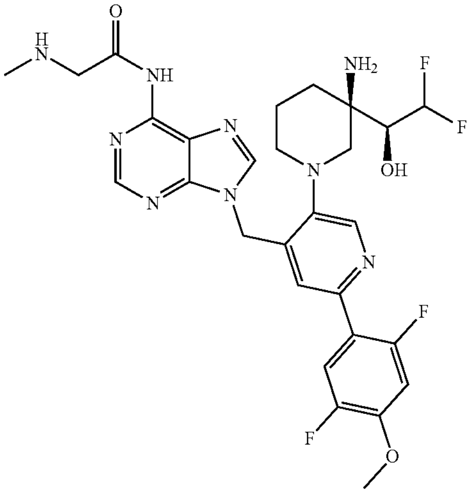 [SMILES: CNCC(=O)Nc1ncnc2c1ncn2Cc1cc(-c2cc(F)c(OC)cc2F)ncc1N1CCC[C@](N)([C@H](O)C(F)F)C1] |
| VI-4 | 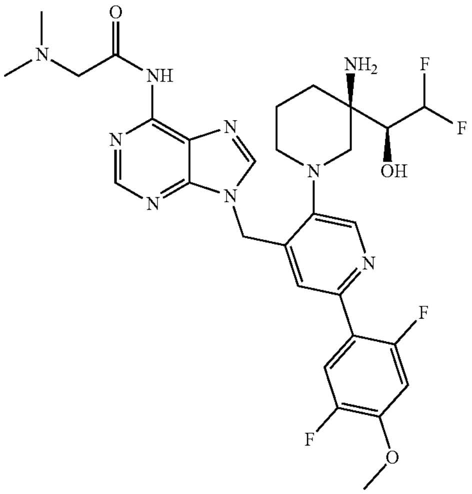 [SMILES: COc1cc(F)c(-c2cc(Cn3cnc4c(NC(=O)CN(C)C)ncnc43)c(N3CCC[C@](N)([C@H](O)C(F)F)C3)cn2)cc1F] |

TABLE 6-continued
| Compound No. | Chemical Structure |
| --- | --- |
| VI-5 | 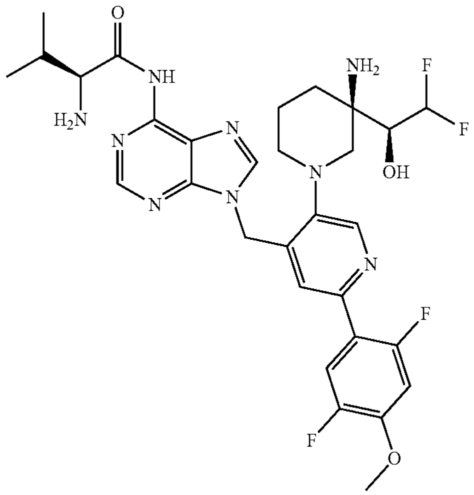 [SMILES: COc1cc(F)c(-c2cc(Cn3cnc4c(NC(=O)[C@@H](N)C(C)C)ncnc43)c(N3CCC[C@](N)([C@H](O)C(F)F)C3)cn2)cc1F] |
| VI-6 | 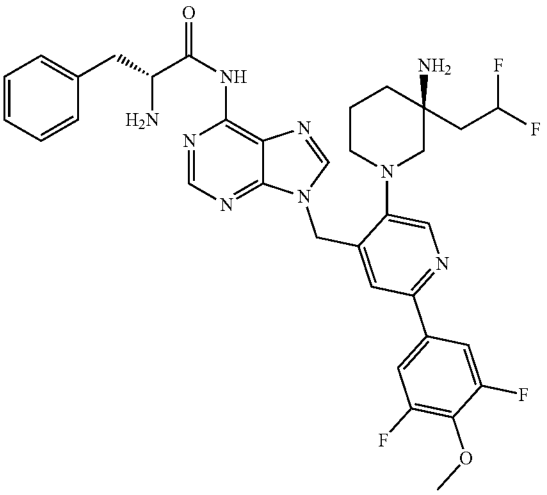 [SMILES: COc1c(F)cc(-c2cc(Cn3cnc4c(NC(=O)[C@H](N)Cc5ccccc5)ncnc43)c(N3CCC[C@](N)(CC(F)F)C3)cn2)cc1F] |
| VI-7 | 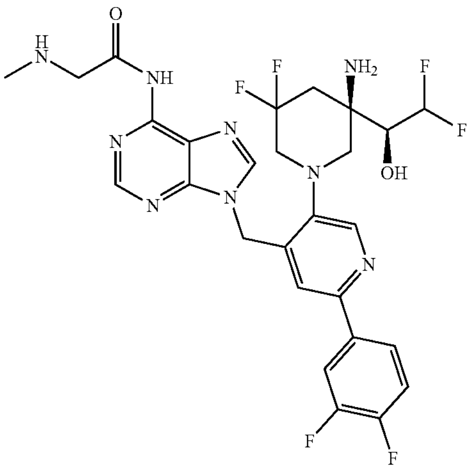 [SMILES: CNCC(=O)Nc1ncnc2c1ncn2Cc1cc(-c2ccc(F)c(F)c2)ncc1N1CC(F)(F)C[C@](N)([C@H](O)C(F)F)C1] |

TABLE 6-continued
| Compound No. | Chemical Structure |
|---|---|
| VI-8 | 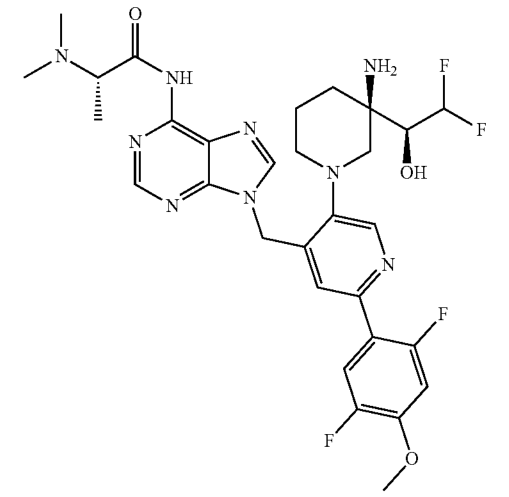 [SMILES: COc1cc(F)c(-c2cc(Cn3cnc4c(NC(=O)[C@H](C)N(C)C)ncnc43)c(N3CCC[C@](N)([C@H](O)C(F)F)C3)cn2)cc1F] |
| VI-9 | 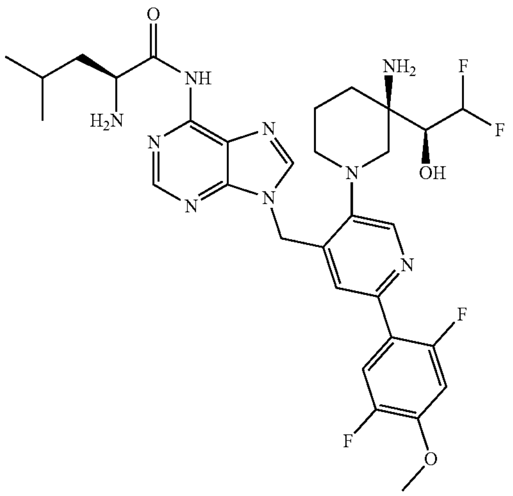 [SMILES: COc1cc(F)c(-c2cc(Cn3cnc4c(NC(=O)[C@@H](N)CC(C)C)ncnc43)c(N3CCC[C@](N)([C@H](O)C(F)F)C3)cn2)cc1F] |
| VI-10 | 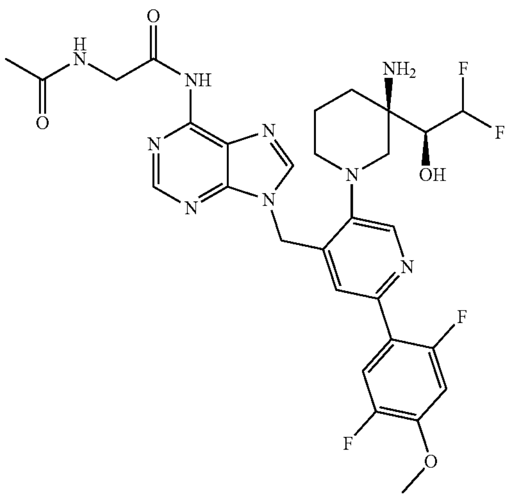 [SMILES: COc1cc(F)c(-c2cc(Cn3cnc4c(NC(=O)CNC(C)=O)ncnc43)c(N3CCC[C@](N)([C@H](O)C(F)F)C3)cn2)cc1F] |

TABLE 6-continued
| Compound No. | Chemical Structure |
| --- | --- |
| VI-11 | 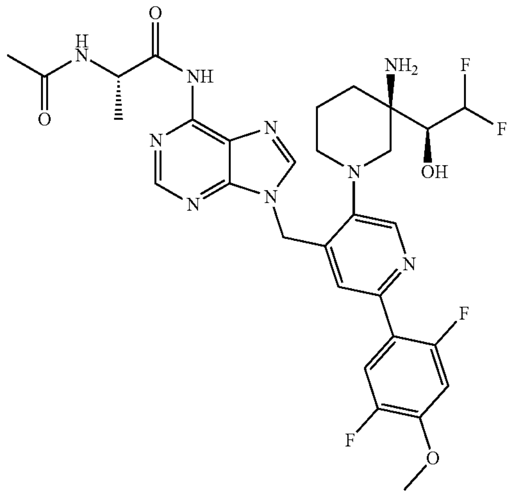 [SMILES: COc1cc(F)c(-c2cc(Cn3cnc4c(NC(=O)[C@H](C)NC(C)=O)ncnc43)c(N3CCC[C@](N)([C@H](O)C(F)F)C3)cn2)cc1F] |
| VI-12 | 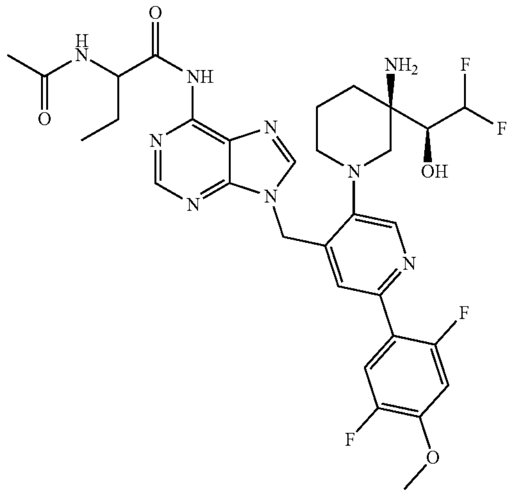 [SMILES: CCC(NC(C)=O)C(=O)Nc1ncnc2c1ncn2Cc1cc(-c2cc(F)c(OC)cc2F)ncc1N1CCC[C@](N)([C@H](O)C(F)F)C1] |
| VI-13 | 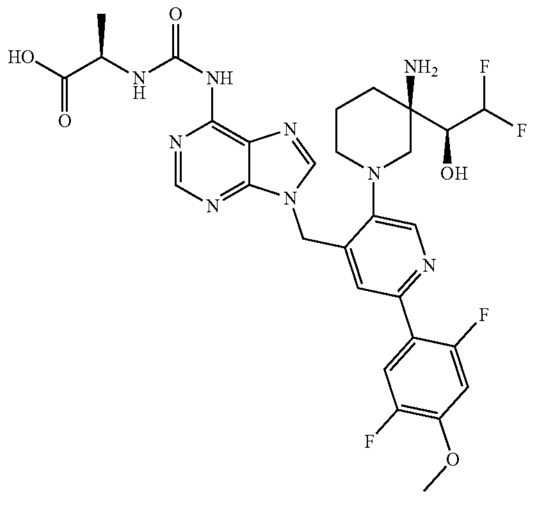 [SMILES: COc1cc(F)c(-c2cc(Cn3cnc4c(NC(=O)N[C@H](C)C(=O)O)ncnc43)c(N3CCC[C@](N)([C@H](O)C(F)F)C3)cn2)cc1F] |

TABLE 6-continued
| Compound No. | Chemical Structure |
|---|---|
| VI-14 | 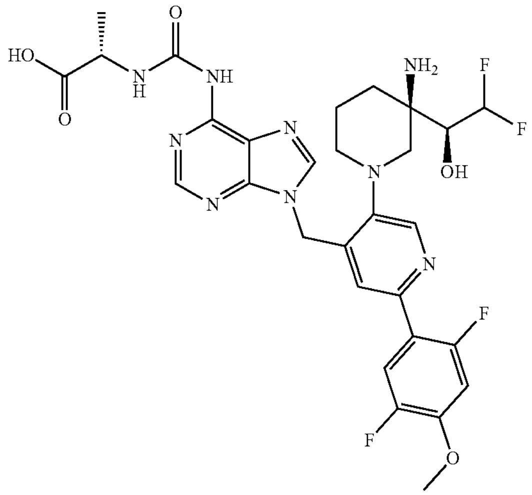 [SMILES: COc1cc(F)c(-c2cc(Cn3cnc4c(NC(=O)N[C@@H](C)C(=O)O)ncnc43)c(N3CCC[C@](N)([C@H](O)C(F)F)C3)cn2)cc1F] |
| VI-15 | 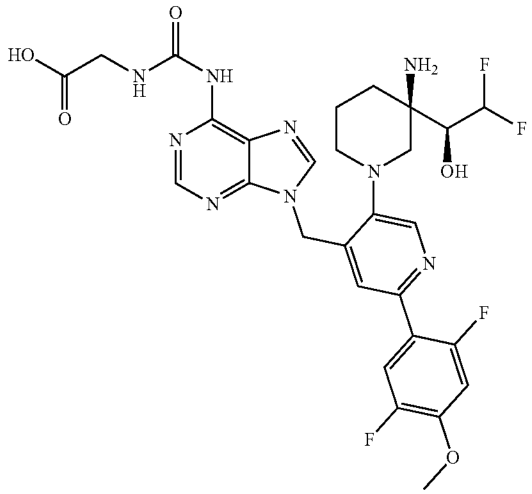 [SMILES: COc1cc(F)c(-c2cc(Cn3cnc4c(NC(=O)NCC(=O)O)ncnc43)c(N3CCC[C@](N)([C@H](O)C(F)F)C3)cn2)cc1F] |
| VI-16 | 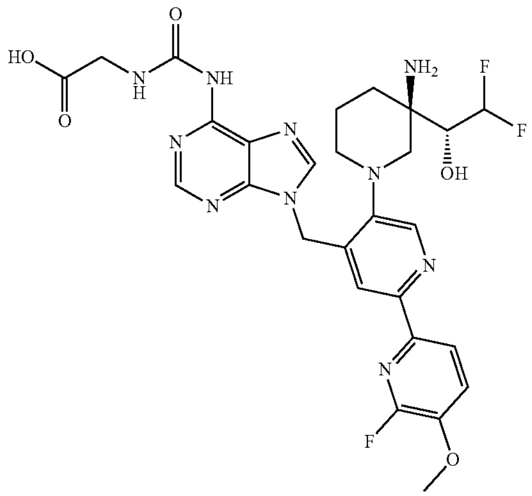 [SMILES: COc1ccc(-c2cc(Cn3cnc4c(NC(=O)NCC(=O)O)ncnc43)c(N3CCC[C@](N)([C@@H](O)C(F)F)C3)cn2)nc1F] |

TABLE 6-continued
| Compound No. | Chemical Structure |
| --- | --- |
| VI-17 | 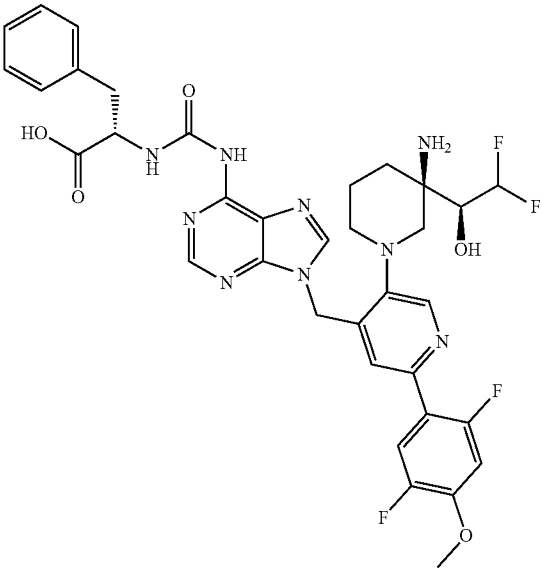 [SMILES: COc1cc(F)c(-c2cc(Cn3cnc4c(NC(=O)N[C@@H](Cc5ccccc5)C(=O)O)ncnc43)c(N3CCC[C@](N)([C@H](O)C(F)F)C3)cn2)cc1F] |
| VI-18 | 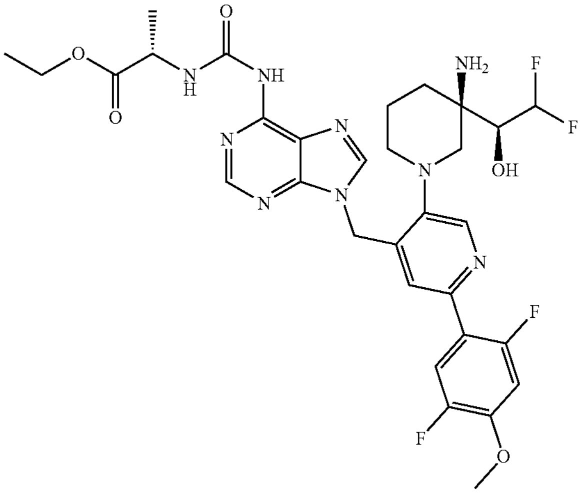 [SMILES: CCOC(=O)[C@H](C)NC(=O)Nc1ncnc2c1ncn2Cc1cc(-c2cc(F)c(OC)cc2F)ncc1N1CCC[C@](N)([C@H](O)C(F)F)C1] |
| VI-19 | 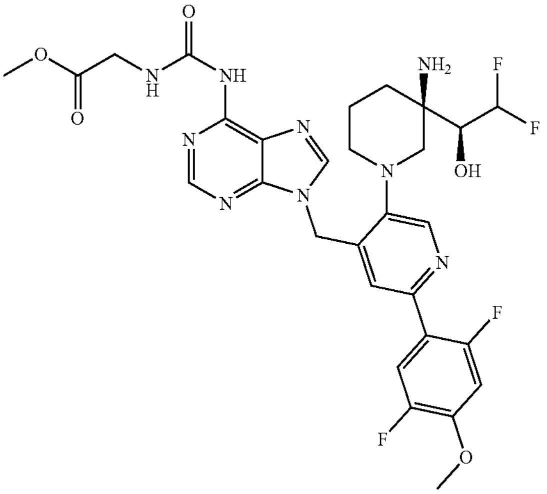 [SMILES: COC(=O)CNC(=O)Nc1ncnc2c1ncn2Cc1cc(-c2cc(F)c(OC)cc2F)ncc1N1CCC[C@](N)([C@H](O)C(F)F)C1] |

TABLE 6-continued
| Compound No. | Chemical Structure |
|---|---|
| VI-20 | 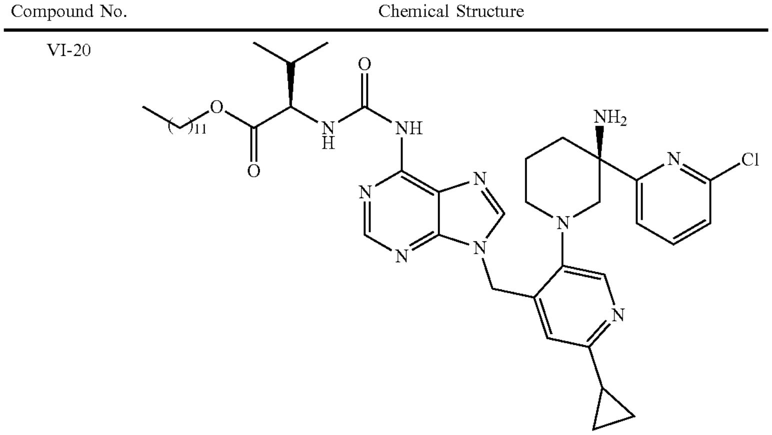 |
TABLE 7
| Compound No. | Chemical Structure |
|---|---|
| VII-1 | 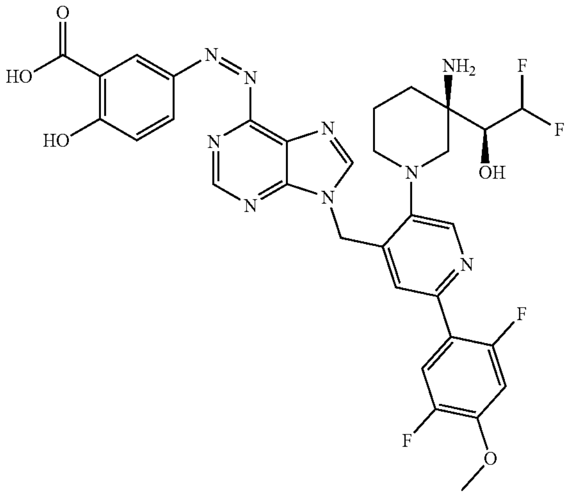 [SMILES: COc1cc(F)c(-c2cc(Cn3cnc4c(/N=N\c5ccc(O)c(C(=O)O)c5)ncnc43)c(N3CCC[C@](N)([C@H](O)C(F)F)C3)cn2)cc1F] |
| VII-2 | 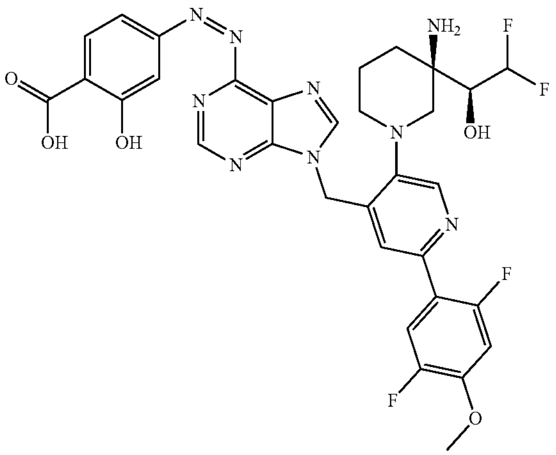 [SMILES: COc1cc(F)c(-c2cc(Cn3cnc4c(/N=N\c5ccc(C(=O)O)c(O)c5)ncnc43)c(N3CCC[C@](N)([C@H](O)C(F)F)C3)cn2)cc1F] |

TABLE 7-continued
| Compound No. | Chemical Structure |
| --- | --- |
| VII-3 | 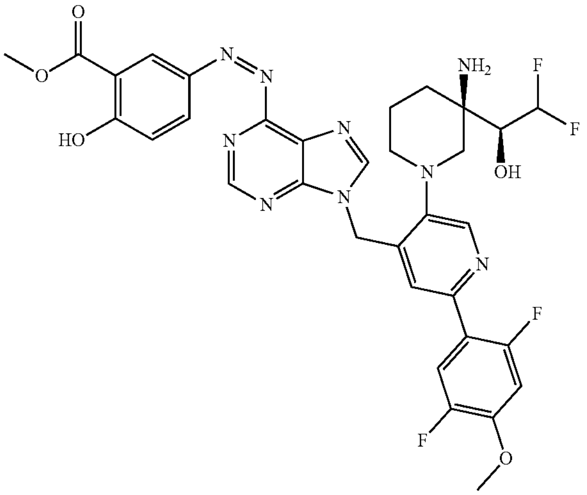 [SMILES: COC(=O)c1cc(/N=N\c2ncnc3c2ncn3Cc2cc(-c3cc(F)c(OC)cc3F)ncc2N2CCC[C@](N)([C@H](O)C(F)F)C2)ccc1O] |
| VII-4 | 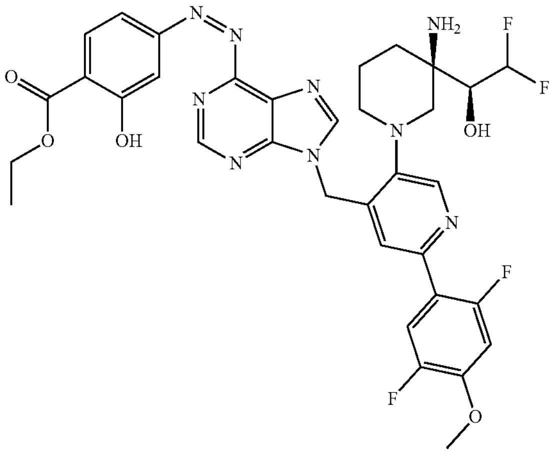 [SMILES: CCOC(=O)c1ccc(/N=N\c2ncnc3c2ncn3Cc2cc(-c3cc(F)c(OC)cc3F)ncc2N2CCC[C@](N)([C@H](O)C(F)F)C2)cc1O] |
| VII-5 | 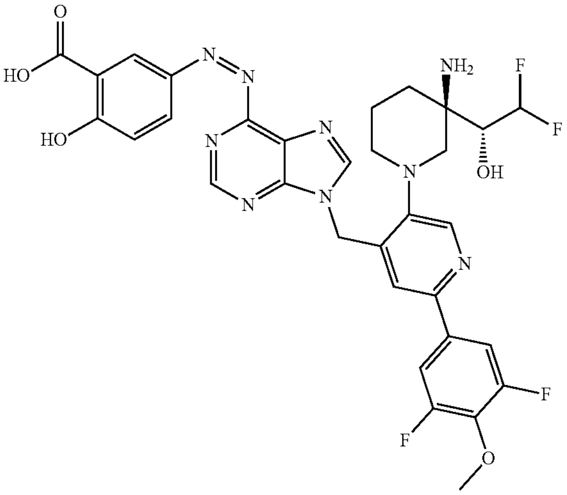 [SMILES: COc1c(F)cc(-c2cc(Cn3cnc4c(/N=N\c5ccc(O)c(C(=O)O)c5)ncnc43)c(N3CCC[C@](N)([C@@H](O)C(F)F)C3)cn2)cc1F] |

TABLE 7-continued
| Compound No. | Chemical Structure |
|---|---|
| VII-6 | 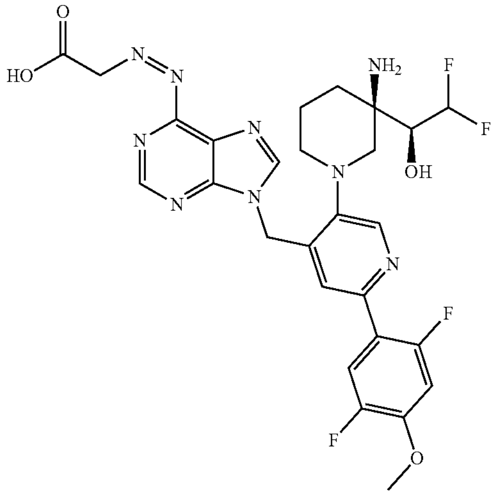 [SMILES: COc1cc(F)c(-c2cc(Cn3cnc4c(/N=N\CC(=O)O)ncnc43)c(N3CCC[C@](N)([C@H](O)C(F)F)C3)cn2)cc1F] |
| VII-7 | 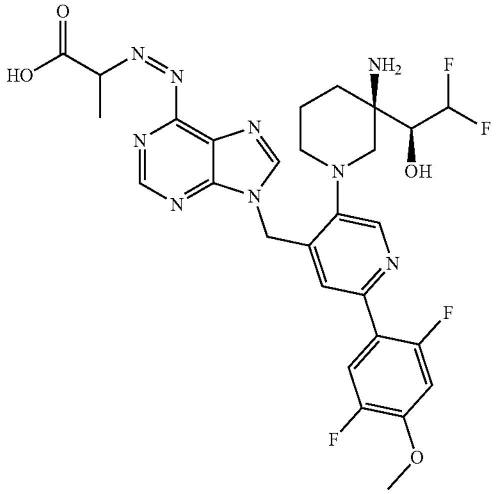 [SMILES: COc1cc(F)c(-c2cc(Cn3cnc4c(/N=N\C(C)C(=O)O)ncnc43)c(N3CCC[C@](N)([C@H](O)C(F)F)C3)cn2)cc1F] |
| VII-8 | 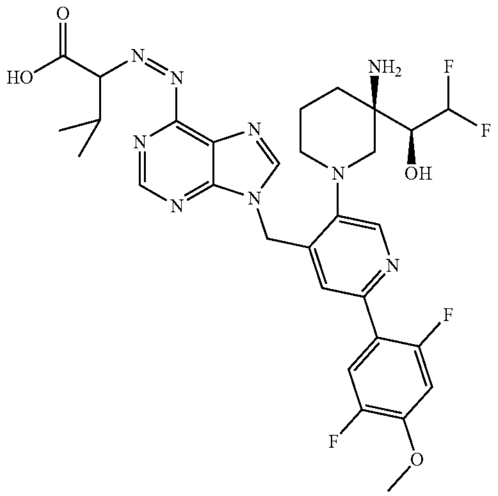 [SMILES: COc1cc(F)c(-c2cc(Cn3cnc4c(/N=N\C(C(=O)O)C(C)C)ncnc43)c(N3CCC[C@](N)([C@H](O)C(F)F)C3)cn2)cc1F] |

TABLE 7-continued
| Compound No. | Chemical Structure |
| --- | --- |
| VII-9 | 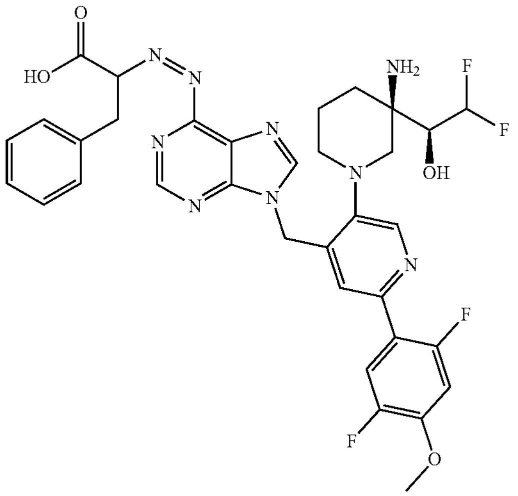 [SMILES: COc1cc(F)c(-c2cc(Cn3cnc4c(/N=N\C(Cc5ccccc5)C(=O)O)ncnc43)c(N3CCC[C@](N)([C@H](O)C(F)F)C3)cn2)cc1F] |
| VII-10 | 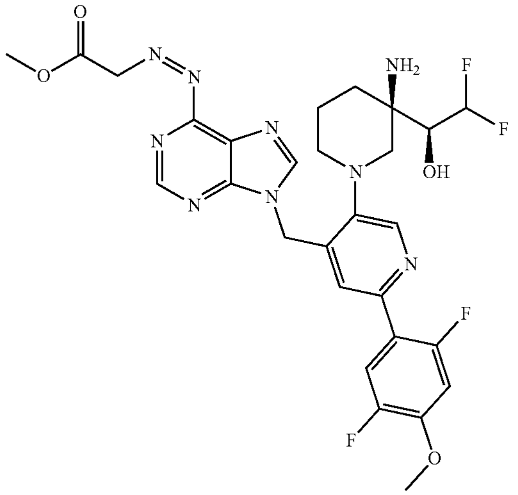 [SMILES: COC(=O)C/N=N\c1ncnc2c1ncn2Cc1cc(-c2cc(F)c(OC)cc2F)ncc1N1CCC[C@](N)([C@H](O)C(F)F)C1] |
| VII-11 | 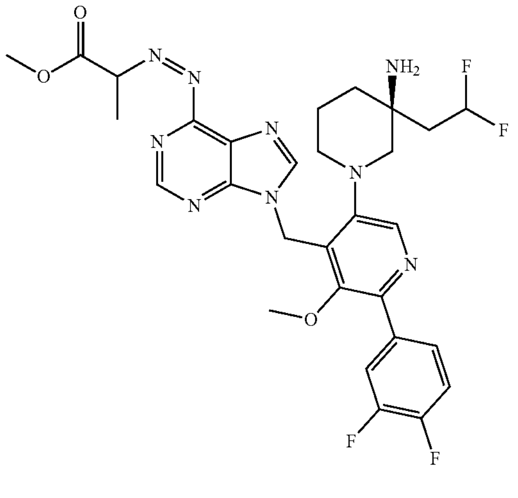 [SMILES: COC(=O)C(C)/N=N\c1ncnc2c1ncn2Cc1c(N2CCC[C@](N)(CC(F)F)C2)cnc(-c2ccc(F)c(F)c2)c1OC] |

TABLE 7-continued

| Compound No. | Chemical Structure |
| --- | --- |
| VII-12 | 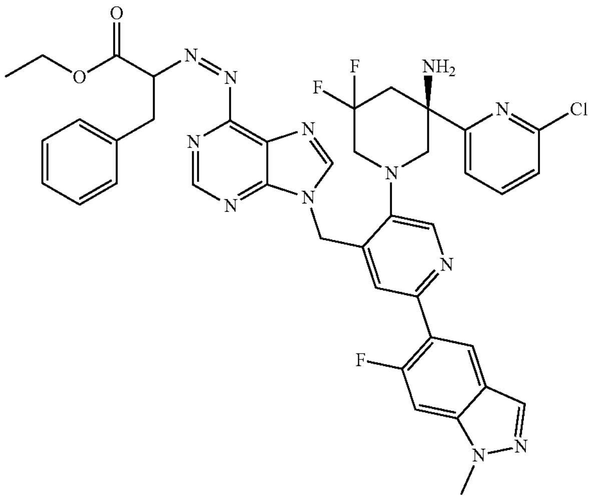 [SMILES: CCOC(=O)C(Cc1ccccc1)/N=N\c1ncnc2c1ncn2Cc1cc(-c2cc3cnn(C)c3cc2F)ncc1N1CC(F)(F)C[C@](N)(c2cccc(Cl)n2)C1] |

Methods for preparing compounds described herein are illustrated in the following synthetic Schemes. The Schemes are given for the purpose of illustrating the invention, and are not intended to limit the scope or spirit of the invention. Starting materials shown in the Schemes can be obtained from commercial sources or can be prepared based on procedures described in the literature. Additional strategies for preparing starting materials and piperidinyl-methylpurine pyridines and related compounds are described in, for example, WO 2021/028854, the entirety of which is hereby incorporated by reference.

In the Schemes, it is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated (for example, use of protecting groups or alternative reactions). Protecting group chemistry and strategy is well known in the art, for example, as described in detail in "Protecting Groups in Organic Synthesis", T. W. Greene and P. G. M. Wuts, 3rd edition, John Wiley & Sons, 1999, the entire contents of which are hereby incorporated by reference.

Scheme 1 provides a general method for preparing phenolphosphate piperidinyl-methylpurine pyridines and related compounds B, C, and D. The reaction of phenol or related compound A using disubstituted phosphoryl chloride (wherein R' and R" are each independently $R^8$ or a protecting group) affords trisubstituted phosphate B. Conversion of trisubstituted phosphate B to mono-phosphoric acid C or di-phosphoric acid D proceeds under appropriate hydrolysis and/or deprotection conditions.

SCHEME 1.

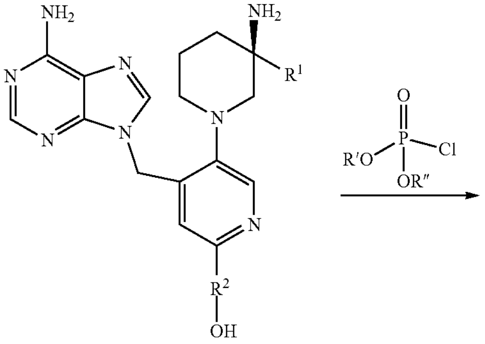

A

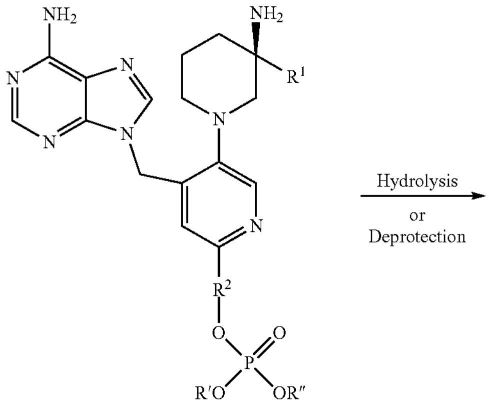

B

-continued

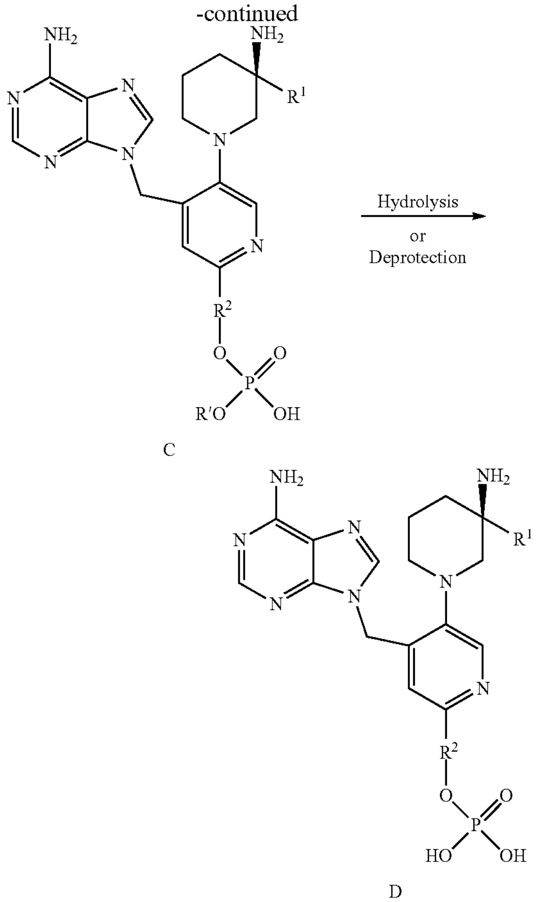

C

D

Scheme 2 provides a general method for preparing phenolmethylphosphate piperidinyl-methylpurine pyridines and related compounds B, C, and D. The reaction of phenol or related compound A using disubstituted P-(methyl)phosphonate (wherein LG is a leaving group, such as chloride or bromide, and R' and R" are each independently $R^8$ or a protecting group) affords disubstituted phosphonate B. Conversion of disubstituted phosphonate B to afford mono-phosphoric acid C or di-phosphoric acid D proceeds under appropriate hydrolysis and/or deprotection conditions.

SCHEME 2.

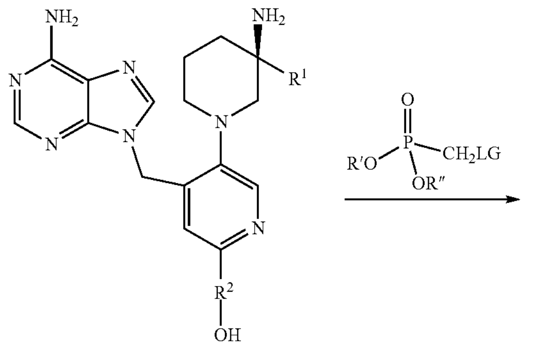

A

-continued

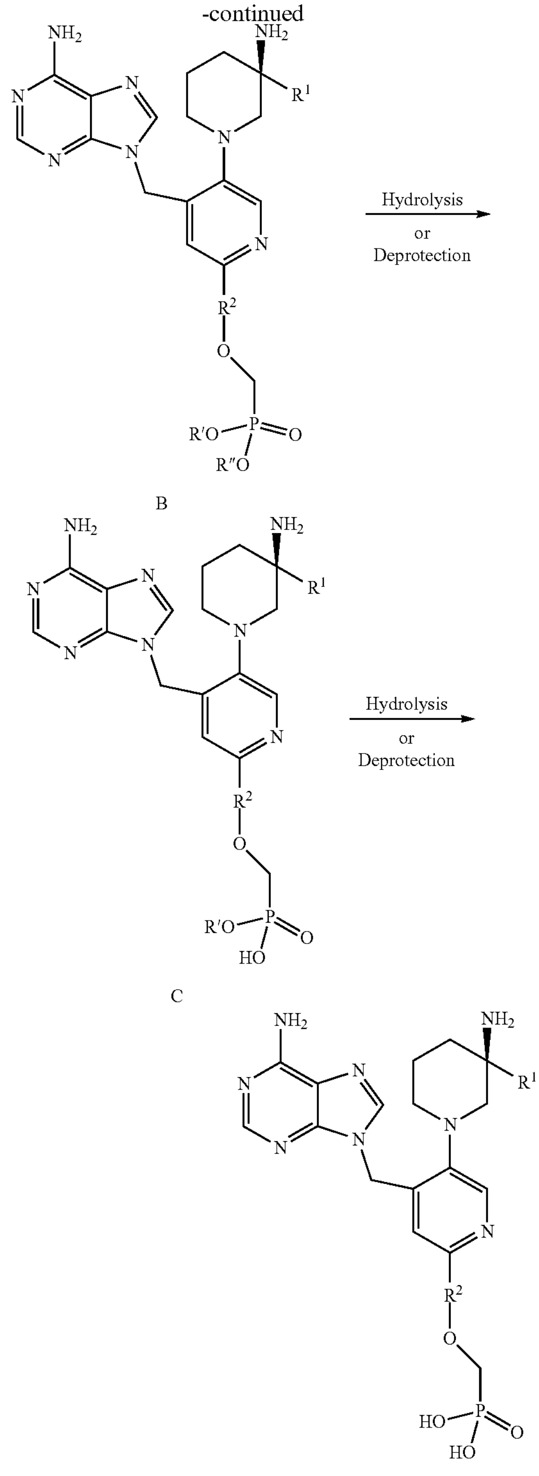

B

C

D

Scheme 3 provides a general method for the preparation of ester and carbonate piperidinyl-methylpurine pyridines and related compounds B, C, D, and E. Reacting phenol or related compound A with pre-activated carboxylic acids, for example, carboxylic acyl halides (wherein LG is chloride, bromide, or iodide), N-hydroxysuccinimide esters (wherein LG is N-hydroxysuccinimide), carboxylic acid anhydrides (wherein LG is —OC(O)R) affords ester B. Alternatively, reacting carboxylic acids with phenol or related compound A in the presence of carbodiimides or other carboxylic acid activating reagents similarly affords ester B As described generally above, suitable N-protection and deprotection of any free amino groups in either coupling partner may be necessary to avoid the formation of undesirable amidation reactions resulting from unwanted reactions of amines with activated carboxylic acids. Reacting phenol or related compounds A with chloroformates affords carbonate C. Phenol or related compounds A are converted to both L- and D-amino acid derivatives D using L- or D-amino acids with carbodiimide coupling reagents or other carboxylic acid activating groups, optionally with suitable N-protection on the amino-acid. Reacting phenol or related compounds A with haloalkyl carbonates (for example, alkyl halomethyl carbonates) affords compound E.

SCHEME 3.

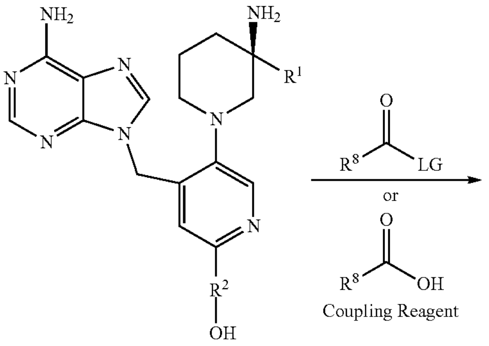

A

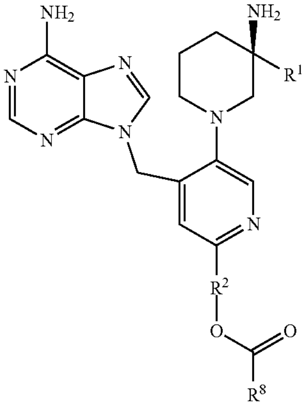

B

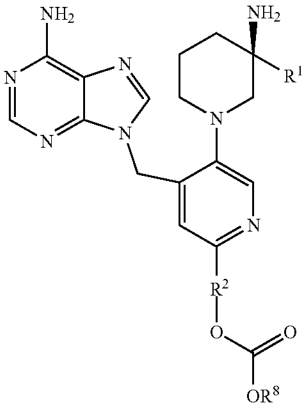

C

-continued

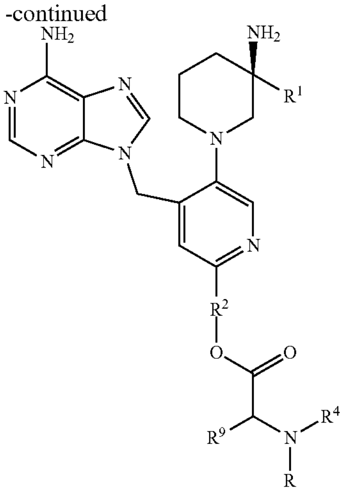

D

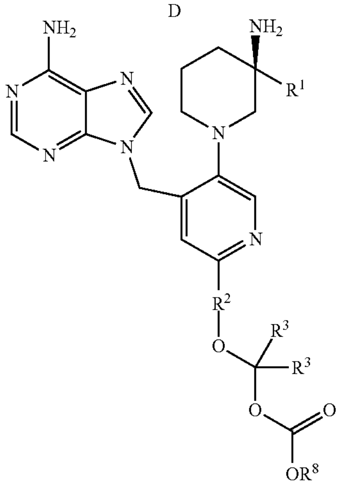

E $R = R^4$ or $C(O)R^3$

Scheme 4 provides a general method for the preparation of both L- and D-amino acid carbamate piperidinyl-methylpurine pyridines and related compounds, B and C respectively. As described generally above, suitable N-protection and deprotection of the primary amino group of phenol and related compounds A may be required to avoid unwanted amidation reactions or other unwanted byproducts. Condensation of phenol or related compound A with phosgene (wherein LG and LG' are Cl) or a synthetic equivalent (for example, b is —(4-nitrophenyl)carbonate or CDI) and an amino acid affords amino acid carbamates B or C. For example, activating tert-butyl ester protected amino acids with b is —(4-nitrophenyl)carbonate, resulting in the intermediate 4-nitrophenylcarbamate of the amino acid, can be condensed with phenol and related compounds A to provide amino acid carbamates B or C (for a related procedure, see, for example, DOI: 10.1038/srep15216).

SCHEME 4.

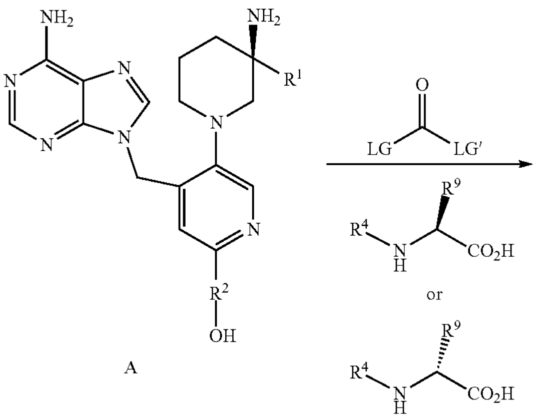

A

-continued

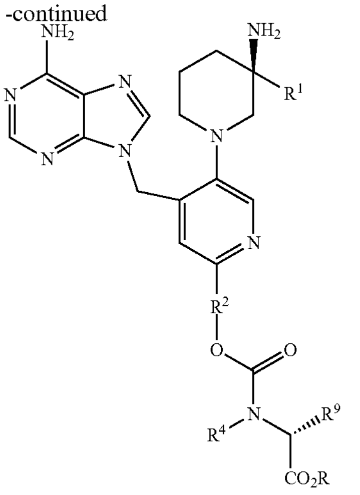

C

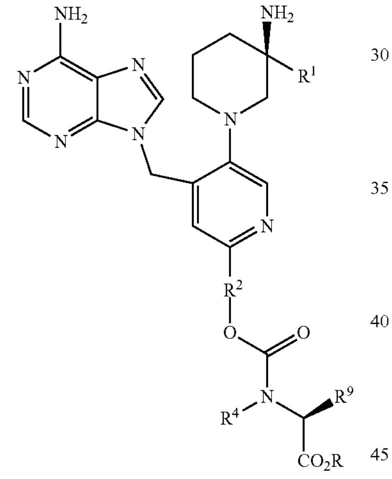

B

R = H or $C_{1-20}$ aliphatic chain

Scheme 5 provides a general method to prepare phosphatyl piperidinyl-methylpurine pyridines and related compounds B, C, and D. Reaction of adenine A with disubstituted phosporyl chloride (wherein R' and R" are each independently $R^8$ or a protecting group) affords phosphoramidate B. As described generally above, protecting group strategies may be employed as needed. Partial hydrolysis or deprotection of compound B affords compound C, which may be further hydrolyzed or deprotected to phosphoramidic acid D. Alternatively, reacting activated intermediate E (wherein LG is a leaving group, for example, Cl, Br, or a sulfonate, such as OMs or OTs) with phosphoramidate adenine F affords compound B.

SCHEME 5.

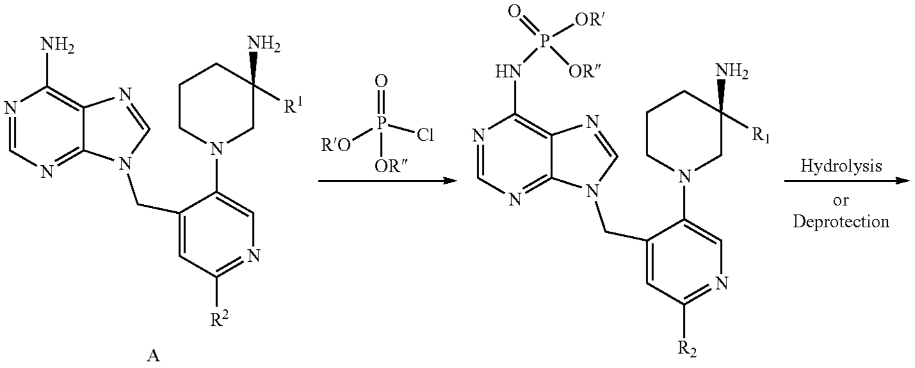

A

B

-continued

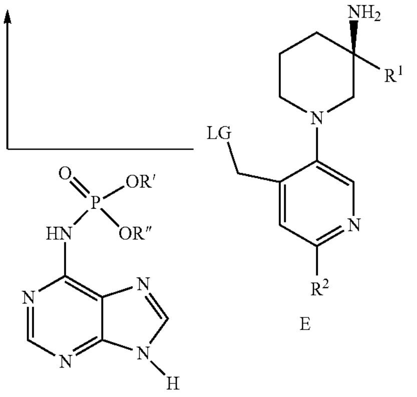

E

F

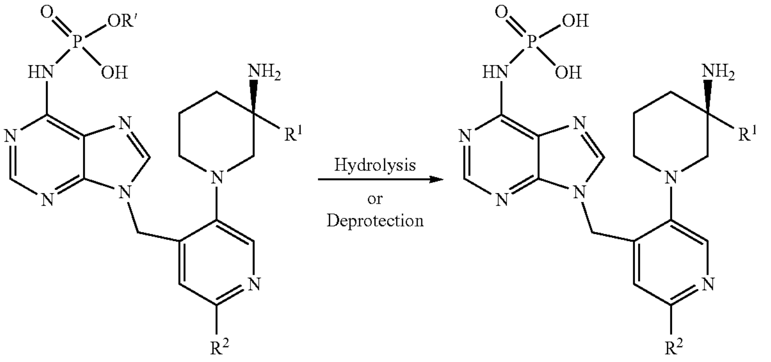

C

D

Scheme 6 provides a general method for preparing phenolmethylphosphatyl piperidinyl-methylpurine pyridines and related compounds B, C, and D. adding alkylphosphates using P-(chloro/bromomethyl)phosphonic acids (CAS Nos 2565-58-4/13298-02-7) respectively. Reacting adenine A with disubstituted P-(halomethyl)phosphonate (wherein LG is a leaving group, such as chloride or bromide, and R' and R" are each independently $R^8$ or a protecting group) affords disubstituted phosphonate B. Conversion of disubstituted phosphonate B to afford mono-phosphoric acid C or diphosphoric acid D proceeds under appropriate hydrolysis and/or deprotection conditions. Alternatively, the a functionalized adenine F may be condensed with activated intermediate E (wherein LG is a leaving group, for example, Cl, Br, or a sulfonate, such as OMs or OTs) to provide disubstituted phosphonate B.

SCHEME 6.

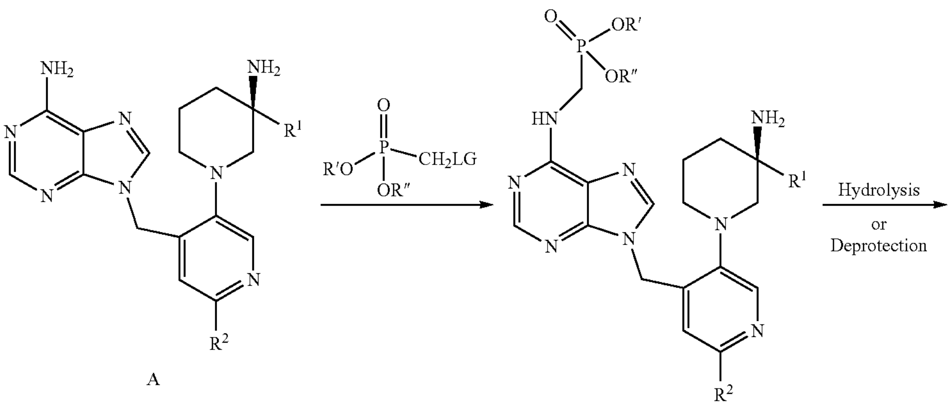

A

B

-continued

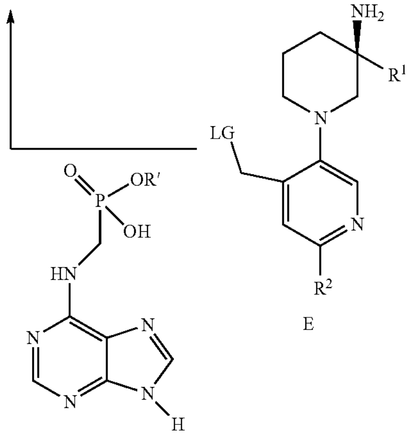

F

E

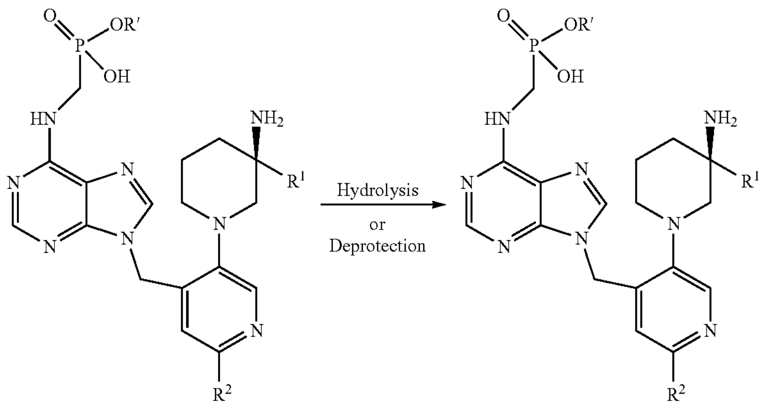

C

D

Scheme 7 provides a general method to synthesize aminal, carbamate, aminal ester, or aminal carbamate piperidinyl-methylpurine pyridines and related compounds B, using suitable protecting group strategies as needed, as described generally above. The conversion of adenine A to the aminal B (wherein R is —C($R^4$)$_2$—O$R^8$) is accomplished by reacting adenine A with activated-methyl alkyl ethers (wherein LG is a leaving group, such as chloride). Carbamates B (wherein R is —C(O)O$R^8$) are provided by reacting adenine A with appropriate chloroformates (wherein LG is chloride, or another suitable leaving group). Reacting adenine A with appropriate chloromethylesters (wherein R is —C($R^4$)$_2$—OC(O)$R^8$, and LG is chloride, or another suitable leaving group), for example, with chloromethyl pivalate, affords aminal ester B (wherein R is —C($R^4$)$_2$—OC(O)$R^8$). Reacting adenine A with appropriate chloromethylamides (wherein R is —C($R^4$)$_2$—OC(O)N($R^4$)($R^9$), and LG is chloride, or another suitable leaving group), for example, with N-(chloromethyl)-N-methylformamide, affords aminal carbamates B (wherein R is —C($R^4$)$_2$—OC(O)N($R^4$)($R^9$)). Alternatively, reacting a prefunctionalized adenine D with compound C (wherein LG is a leaving group, for example Cl, Br, or a sulfonate, such as OMs or OTs) affords compounds B.

SCHEME 7.

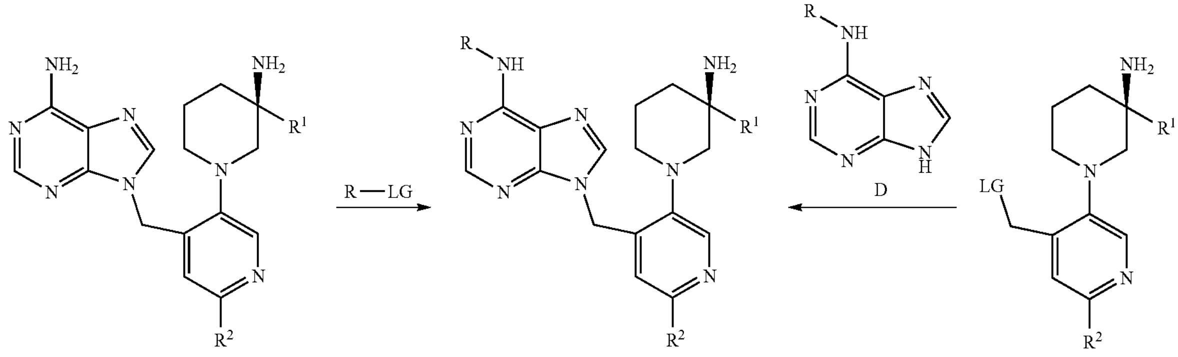

A B C

R = —C(O)OR[8], —C(R[4])[2]—OR[8], —C(R[4])[2]—OC(O)R[8], or —C(R[4])[2]—OC(O)N(R[4])(R[9])

The modular synthetic routes illustrated in Schemes 1-7 can also be readily modified by one of skill in the art to provide additional substituted piperidinyl-methylpurine pyridines and related compounds by conducting functional group transformations on the intermediate and final compounds. Such functional group transformations are well known in the art, as described in, for example, "Comprehensive Organic Synthesis" (B. M. Trost & I. Fleming, eds., 1991-1992).

II. Therapeutic Applications of Substituted Piperidinyl-Methylpurine Pyridines and Related Compounds The substituted piperidinyl-methylpurine pyridines and related compounds described herein, such as a compound of Formula I, I-A, II, or II-A, or other compounds in Section I, provide therapeutic benefits to subjects suffering from cancer and other diseases or conditions. Accordingly, one aspect of the invention provides a method for treating a disease or condition mediated by nuclear SET domain-containing protein 2 (NSD2). The method comprises administering a therapeutically effective amount of a compound described herein, such as a compound of Formula I, I-A, II, or II-A, to a subject in need thereof to treat the disease or condition. In certain embodiments, the compound is a compound of Formula I, I-A, II, or II-A defined by one of the embodiments described above.

Examples of diseases or conditions that are mediated by NSD2 include but is not limited to breast cancer, cervical cancer, skin cancer (particularly skin squamous cell carcinoma), ovarian cancer, gastric cancer, prostate cancer, pancreatic cancer, lung cancer, hepatocellular carcinoma, head and neck cancer, peripheral nerve sheath tumor, osteosarcoma, multiple myeloma, neuroblastoma, leukemia (particularly acute lymphoblastic leukemia), non-Hodgkin's lymphoma (particularly mantle cell lymphoma), and pulmonary arterial hypertension.

In certain embodiments, said disease or condition mediated by NSD2 is cancer.

In certain embodiments, said disease or condition mediated by NSD2 is selected from a solid tumor, leukemia, myeloma, lymphoma, and hypertension. In certain embodiments, said disease or condition mediated by NSD2 is a solid tumor. In certain embodiments, said disease or condition mediated by NSD2 is selected from leukemia, myeloma, and lymphoma. In certain embodiments, said disease or condition mediated by NSD2 is leukemia. In certain embodiments, said disease or condition mediated by NSD2 is myeloma. In certain embodiments, said disease or condition mediated by NSD2 is lymphoma. In certain embodiments, said disease or condition mediated by NSD2 is hypertension.

In certain embodiments, said disease or condition mediated by NSD2 is breast cancer, cervical cancer, skin cancer, ovarian cancer, gastric cancer, prostate cancer, pancreatic cancer, lung cancer, hepatocellular carcinoma, head and neck cancer, peripheral nerve sheath tumor, osteosarcoma, multiple myeloma, neuroblastoma, leukemia, non-Hodgkin's lymphoma, or pulmonary arterial hypertension. In certain embodiments, said disease or condition mediated by NSD2 is breast cancer. In certain embodiments, said disease or condition mediated by NSD2 is cervical cancer. In certain embodiments, said disease or condition mediated by NSD2 is ovarian cancer. In certain embodiments, said disease or condition mediated by NSD2 is gastric cancer. In certain embodiments, said disease or condition mediated by NSD2 is prostate cancer. In certain embodiments, said disease or condition mediated by NSD2 is pancreatic cancer. In certain embodiments, said disease or condition mediated by NSD2 is hepatocellular carcinoma. In certain embodiments, said disease or condition mediated by NSD2 is head and neck cancer. In certain embodiments, said disease or condition mediated by NSD2 is a peripheral nerve sheath tumor. In certain embodiments, said disease or condition mediated by NSD2 is osteosarcoma. In certain embodiments, said disease or condition mediated by NSD2 is multiple myeloma. In certain embodiments, said disease or condition mediated by NSD2 is neuroblastoma. In certain embodiments, said disease or condition mediated by NSD2 is pulmonary arterial hypertension.

In certain embodiments, said disease or condition mediated by NSD2 is acute lymphoblastic leukaemia, skin squamous cell carcinoma, or mantle cell lymphoma. In certain embodiments, said disease or condition mediated by NSD2 is acute lymphoblastic leukaemia. In certain embodiments, said disease or condition mediated by NSD2 is skin squamous cell carcinoma. In certain embodiments, said disease or condition mediated by NSD2 is mantle cell lymphoma.

In certain embodiments, said disease or condition mediated by NSD2 is lung cancer. In certain embodiments, said disease or condition mediated by NSD2 is small cell or non-small cell lung cancer. In certain embodiments, said disease or condition mediated by NSD2 is small cell lung cancer. In certain embodiments, said disease or condition mediated by NSD2 is non-small cell lung cancer.

In certain embodiments, said disease or condition mediated by NSD2 is leukemia. In certain embodiments, said disease or condition mediated by NSD2 is acute lymphoblastic leukemia (ALL), acute myeloid leukemia (AML), chronic myeloid leukemia (CML), or chronic myelomonocytic leukemia (CMML). In certain embodiments, said disease or condition mediated by NSD2 is AML. In certain embodiments, said disease or condition mediated by NSD2 is CML. In certain embodiments, said disease or condition mediated by NSD2 is CMML.

In certain embodiments, said disease or condition mediated by NSD2 is skin cancer. In certain embodiments, said disease or condition mediated by NSD2 is melanoma, basal cell carcinoma, or squamous cell carcinoma. In certain embodiments, said disease or condition mediated by NSD2 is melanoma. In certain embodiments, said disease or condition mediated by NSD2 is basal cell carcinoma.

In certain embodiments, said disease or condition mediated by NSD2 is lymphoma. In certain embodiments, said disease or condition mediated by NSD2 is Hodgkin's lymphoma or non-Hodgkin's lymphoma. In certain embodiments, said disease or condition mediated by NSD2 is Hodgkin's lymphoma. In certain embodiments, said disease or condition mediated by NSD2 is non-Hodgkin's lymphoma. In certain embodiments, said disease or condition mediated by NSD2 is mantle cell lymphoma or diffuse large B cell lymphoma. In certain embodiments, said disease or condition mediated by NSD2 is diffuse large B cell lymphoma.

In certain embodiments, said disease or condition mediated by NSD2 is myeloma.

In certain embodiments, said disease or condition mediated by NSD2 is thyroid cancer. In certain embodiments, said disease or condition mediated by NSD2 is colon cancer.

In certain embodiments, the cancer overexpresses NSD2. In certain embodiments, the cancer has a mutation in NSD2. In certain embodiments, the cancer has an activating mutation in NSD2. In certain embodiments, the cancer has the t(4; 14)(p16.3; q32.3) translocation in NSD2. In certain embodiments, the cancer has an E1099K mutation in NSD2. In certain embodiments, the cancer has an Ti 150A mutation in NSD2.

In certain embodiments, the subject is a human. In certain embodiments, the subject is an adult human. In certain embodiments, the subject is a pediatric human. In certain embodiments, the subject is a geriatric human.

Another aspect of the invention provides for the use of a compound described herein (such as a compound of Formula I, I-A, II, or II-A, or other compounds in Section I) in the manufacture of a medicament. In certain embodiments, the medicament is for treating a disease or condition described herein, such as cancer.

Another aspect of the invention provides for the use of a compound described herein (such as a compound of Formula I, I-A, II, or II-A, or other compounds in Section I) for treating a disease or condition, such as a disease or condition described herein (for example, cancer).

Further, compounds described herein, such as a compound of Formula I, I-A, II, or II-A, or other compounds in Section I, inhibit the activity of nuclear SET domain-containing protein 2 (NSD2). Accordingly, another aspect of the invention provides a method of inhibiting the activity of nuclear SET domain-containing protein 2 (NSD2). The method comprises contacting a NSD2 with an effective amount of a prodrug of a piperidinyl-methylpurine pyridine or related compound described herein, such as a compound of Formula I, I-A, II, or II-A, or other compounds in Section I, to inhibit the activity of said NSD2. In certain embodiments, the compound is a compound of Formula I, I-A, II, or II-A defined by one of the embodiments described above.

Compounds may be tested for ability to bind to and/or inhibit NSD2 activity according to any of various assays known in the art, including, for example, LC-MS/MS enzymatic assays monitoring SAH production, cellular FRET assays, cellular ELISA assays, methyltransferase enzymatic luminescence assays monitoring SAH production, and radiometric assays using tritium-labeled SAM. Such assays are described in, for example, WO 2021/028854 and Coussens, N. P. et al. *J Biol. Chem.* (2018) Vol. 293, No. 35, pp. 13750-13755; the entirety of each of which is hereby incorporated by reference.

III. Combination Therapy

Another aspect of the invention provides for combination therapy. Substituted piperidinyl-methylpurine pyridine or related compounds described herein (e.g., a compound of Formula I, I-A, II, or II-A, or other compounds in Section I) or their pharmaceutically acceptable salts may be used in combination with additional therapeutic agents to treat diseases or conditions, such as a cancer.

Accordingly, in some embodiments, the present invention provides a method of treating a disclosed disease or condition comprising administering to a patient in need thereof an effective amount of a compound disclosed herein and co-administering simultaneously or sequentially an effective amount of one or more additional therapeutic agents, such as those described herein. In some embodiments, the method includes co-administering one additional therapeutic agent. In some embodiments, the method includes co-administering two additional therapeutic agents.

One or more other therapeutic agents may be administered separately from a compound or composition of the invention, as part of a multiple dosage regimen. Alternatively, one or more other therapeutic agents may be part of a single dosage form, mixed together with a compound of this invention in a single composition. If administered as a multiple dosage regime, one or more other therapeutic agent and a compound or composition of the invention may be administered simultaneously, sequentially or within a period of time from one another.

In certain embodiments, the additional therapeutic agent is an anti-cancer agent, anti-allergic agent, anti-nausea agent (or anti-emetic), pain reliever, cytoprotective agent, or a combination thereof. In certain embodiments, the additional therapeutic agent is an anti-cancer agent, an analgesic, an anti-inflammatory agent, or a combination thereof.

In certain embodiments, the additional therapeutic agent is an anti-cancer agent or chemo-therapeutic agent. Examples of anti-cancer agents considered for use in combination therapies of the invention include but are not limited erlotinib, bortezomib, fulvestrant, sunitib, imatinib mesylate, letrozole, finasunate, platins such as oxaliplatin, carboplatin, and cisplatin, finasunate, fluorouracil, rapamycin, leucovorin, lapatinib, lonafamib, sorafenib, gefitinib, camptothecin, topotecan, bryostatin, adezelesin, anthracyclin, carzelesin, bizelesin, dolastatin, auristatins, duocarmycin, eleutherobin, taxols such as paclitaxel or docetaxel, cyclophosphamide, doxorubicin, vincristine, prednisone or prednisolone, other alkylating agents such as mechlorethamine, chlorambucil, and ifosfamide, antimetabolites such as azathioprine or mercaptopurine, other microtubule inhibitors (vinca alkaloids like vincristine, vinblastine, vinorelbine, and vindesine, as well as taxanes), podophyllotoxins (etoposide, teniposide, etoposide phosphate, and epipodophyllotoxins), topoisomerase inhibitors, other cytotoxins such as actinomycin, daunorubicin, valrubicin, idarubicin, edrecolomab, epirubicin, bleomycin, plicamycin, mitomycin, as well as other anticancer antibodies (cetuximab, bevacizumab, ibritumomab, abagovomab, adecatumumab, afutuzumab, alacizumab, alemtuzumab, anatumomab, apolizumab, bavituximab, belimumab, bivatuzumab mertansine, blinatumomab, brentuximab vedotin, cantuzumab mertansine, catumazomab, cetuximab, citatuzumab bogatox, cixutumumab, clivatuzumab tetraxetan, conatumumab, dacetuzumab, daclizumab, detumomab, ecromeximab, edrecolomab, elotuzumab, epratuzumab, ertumaxomab, etaracizumab, farletuzumab, figitumumab, fresolimumab, galiximab, gembatumumab vedotin, gemtuzumab, ibritumomab tiuxetan, inotuzumab ozogamicin, intetumumab, ipilimumab, iratumumab, labetuzumab, lexatumumab, lintuzumab, lucatumumab, lumilisimab, mapatumumab, matuzumab, milatuzumab, mitumomab, nacolomab tafenatox, naptumomab estafenatox, necitumumab, nimotuzumab, ofatumumab, olaratumab, oportuzumab monatox, oregovomab, panitumumab, pemtumomab, pertuzumab, pintumomab, pritumumab, ramucirumab, rilotumumab, robatumumab, rituximab, sibrotuzumab, tacatuzumab tetraxetan, taplitumomab paptox, tenatumomab, ticilimumab, tigatuzumab, tositumomab or $^{131}$-tositumomab, trastuzumab, tremelimumab, tuocotuzumab celmoleukin, veltuzumab, visilizumab, volocixumab, votumumab, zalutumumab, zanolimumab, IGN-101, MDX-010, ABX-EGR, EMD72000, ior-t1, MDX-220, MRA, H-11 scFv, huJ591, TriGem, TriAb, $R^3$, MT-201, G-250, ACA-125, Onyvax-105, CD:-960, Cea-Vac, BrevaRex AR54, IMC-$1C_{11}$, GlioMab-H, ING-1, anti-LCG MAbs, MT-103, KSB-303, Therex, KW2871, anti-HMI.24, Anti-PTHrP, 2C4 antibody, SGN-30, TRAIL-RI MAb, Prostate Cancer antibody, H22xKi-r, ABX-Mai, Imuteran, Monopharm-C), and antibody-drug conjugates comprising any of the above agents (especially auristatins MMAE and MMAF, maytansinoids like DM-1, calicheamycins, or various cytotoxins).

In certain embodiments, the additional therapeutic agent is selected from anastrozole (ARIMIDEX®), bicalutamide (CASODEX®), bleomycin sulfate (BLENOXANE®), busulfan (MYLERAN®), busulfan injection (BUSULFEX®), capecitabine (XELODA®), N4-pentoxycarbonyl-5-deoxy-5-fluorocytidine, carboplatin (PARAPLATIN®), carmustine (BiCNU®), chlorambucil (LEUKERAN®), cisplatin (PLATINOL®), cladribine (LEUSTATIN®), cyclophosphamide (CYTOXAN® or NEOSAR®), cytarabine, cytosine arabinoside (CYTOSAR-U®), cytarabine liposome injection (DEPOCYT®), dacarbazine (DTIC-Dome®), dactinomycin (actinomycin D, COSMEGAN®), daunorubicin hydrochloride (CERUBIDINE®), daunorubicin citrate liposome injection (DAUNOXOME®), dexamethasone, docetaxel (TAXOTERE®), doxorubicin hydrochloride (ADRIAMYCIN®, RUBEX®), etoposide (VEPESID®), fludarabine phosphate (FLUDARA®), 5-fluorouracil (ADRUCIL®, EFUDEX®), flutamide (EULEXIN®), tezacitibine, gemcitabine (difluorodeoxycitidine), hydroxyurea (HYDREA®), idarubicin (IDAMYCIN®), ifosfamide (IFEX®), irinotecan (CAMPTOSAR®), L-asparaginase (ELSPAR®), leucovorin calcium, melphalan (ALKERAN®), 6-mercaptopurine (PURINETHOL®), methotrexate (FOLEX®), mitoxantrone (NOVANTRONE®), gemtuzumab ozogamicin (MYLOTARG™), paclitaxel (TAXOL®), nab-paclitaxel (ABRAXANE®), phoenix (Yttrium90/MX-DTPA), pentostatin, polifeprosan 20 with carmustine implant (GLIADEL®), tamoxifen citrate (NOLVADEX®), teniposide (VUMON®), 6-thioguanine, thiotepa, tirapazamine (TIRAZONE®), topotecan hydrochloride for injection (HYCAMPTIN®), vinblastine (VELBAN®), vincristine (ONCOVIN®), and vinorelbine (NAVELBINE®).

In certain embodiments, the additional therapeutic agent is capable of inhibiting BRAF, MEK, CDK4/6, SHP-2, HDAC, EGFR, MET, mTOR, PI3K or AKT, or a combination thereof. In a particular embodiment, the compounds of the present invention are combined with another therapeutic agent selected from vemurafinib, debrafinib, LGX818, trametinib, MEK162, LEE011, PD-0332991, panobinostat, verinostat, romidepsin, cetuximab, gefitinib, erlotinib, lapatinib, panitumumab, vandetanib, INC280, everolimus, simolimus, BMK120, BYL719 or CLR457, or a combination thereof.

In certain embodiments, the additional therapeutic agent is selected based on the disease or condition that is being treated. For example, in the treatment of melanoma, the additional therapeutic agent is selected from aldesleukin (e.g., PROLEUKIN®), dabrafenib (e.g., TAFINLAR®), dacarbazine, recombinant interferon alfa-2b (e.g., INTRON® A), ipilimumab, trametinib (e.g., MEKINIST®), peginterferon alfa-2b (e.g., PEGINTRON®, SYLATRON™), vemurafenib (e.g., ZELBORAF®)), and ipilimumab (e.g., YERVOY®).

For the treatment of ovarian cancer, the additional therapeutic agent is selected from doxorubicin hydrochloride (Adriamycin®), carboplatin (PARAPLATIN®), cyclophosphamide (CYTOXAN®, NEOSAR®), cisplatin (PLATINOL®, PLATINOL-AQ®), doxorubicin hydrochloride liposome (DOXIL®, DOX-SL®, EVACET®, LIPODOX®), gemcitabine hydrochloride (GEMZAR®), topotecan hydrochloride (HYCAMTIN®), and paclitaxel (TAXOL®).

For the treatment of thyroid cancer, the additional therapeutic agent is selected from doxorubicin hydrochloride (Adriamycin®), cabozantinib-S-malate (COMETRIQ®), and vandetanib (CAPRELSA®).

For the treatment of colon cancer, the additional therapeutic agent is selected from fluorouracil (e.g., ADRUCIL@, EFUDEX®, FLUOROPLEX®), bevacizumab (AVASTIN®), irinotecan hydrochloride (CAMPTOSTAR®), capecitabine (XELODA®), cetuximab (ERBITUX®), oxaliplatin (ELOXATIN®), leucovorin calcium (WELLCOVORIN®), regorafenib (STIVARGA®), panitumumab (VECTIBIX®), and ziv-aflibercept (ZALTRAP®).

For the treatment of lung cancer, the additional therapeutic agent is selected from methotrexate, methotrexate LPF (e.g., FOLEX®, FOLEX PFS®, Abitrexate®, MEXATE®, MEXATE-AQ®), paclitaxel (TAXOL®), paclitaxel albumin-stabilized nanoparticle formulation (ABRAXANE®), afatinib dimaleate (GILOTRIF®), pemetrexed disodium (ALIMTA®), bevacizumab (AVASTIN®), carboplatin (PARAPLATIN®), cisplatin (PLATINOL®, PLATINOL-AQ®), crizotinib (XALKORI®), erlotinib hydrochloride (TARCEVA®), gefitinib (TRESSA®), and gemcitabine hydrochloride (GEMZAR®).

For the treatment of pancreatic cancer, the other therapeutic agent may be selected from fluorouracil (ADRUCIL®), EFUDEX®, FLUOROPLEX®), erlotinib hydrochloride (TARCEVA®), gemcitabine hydrochloride (GEMZAR®), and mitomycin or mitomycin C (MITOZYTREX™, MUTAMYCIN®).

For the treatment of cervical cancer, the additional therapeutic agent is selected from bleomycin (BLENOXANE®), cisplatin (PLATINOL®, PLATINOL-AQ®) and topotecan hydrochloride (HYCAMTIN®).

For the treatment of head and neck cancer, the additional therapeutic agent is selected from methotrexate, methotrexate LPF (e.g., FOLEX®, FOLEX PFS®, Abitrexate®, MEXATE®, MEXATE-AQ®), fluorouracil (ADRUCIL@, EFUDEX®, FLUOROPLEX®), bleomycin (BLENOXANE®), cetuximab (ERBITUX®), cisplatin (PLATINOL®, PLATINOL-AQ®) and docetaxel (TAXOTERE®).

For the treatment of leukemia, including chronic myelomonocytic leukemia (CMML), the additional therapeutic agent is selected from bosutinib (BOSULIF®), cyclophosphamide (CYTOXAN®, NEOSAR®), cytarabine (CYTOSAR-U®, TARABINE PFS®), dasatinib (SPRYCEL®), imatinib mesylate (GLEEVEC®), ponatinib (ICLUSIG®), nilotinib (TASIGNA®) and omacetaxine mepesuccinate (SYNRIBO®).

In some instances, patients may experience allergic reactions to the compounds of the present invention and/or other anti-cancer agent(s) during or after administration. Therefore, anti-allergic agents may be administered to minimize the risk of an allergic reaction. Suitable anti-allergic agents include corticosteroids, such as dexamethasone (e.g., DECADRON®), beclomethasone (e.g., BECLOVENT®), hydrocortisone (also known as cortisone, hydrocortisone sodium succinate, hydrocortisone sodium phosphate; e.g., ALA-CORT®, hydrocortisone phosphate, Solu-CORTEF®, HYDROCORT Acetate® and LANACORT®), prednisolone (e.g., DELTA-Cortel®, ORAPRED®, PEDIAPRED® and PRELONE®), prednisone (e.g., DELTASONE®, LIQUID RED®, METICORTEN® and ORASONE®), methylprednisolone (also known as 6-methylprednisolone, methylprednisolone acetate, methylprednisolone sodium succinate; e.g., DURALONE®, MEDRALONE®, MEDROL®, M-PREDNISOL® and SOLU-MEDROL®); antihistamines, such as diphenhydramine (e.g., BENADRYL®), hydroxyzine, and cyproheptadine; and bronchodilators, such as the beta-adrenergic receptor agonists, albuterol (e.g., PROVENTIL®), and terbutaline (BRETHINE®).

In other instances, patients may experience nausea during and after administration of the compound of the present invention and/or other anti-cancer agent(s). Therefore, antiemetics may be administered in preventing nausea (upper stomach) and vomiting. Suitable anti-emetics include aprepitant (EMEND®), ondansetron (ZOFRAN®), granisetron HCl (KYTRIL®), lorazepam (ATIVAN®. dexamethasone (DECADRON®), prochlorperazine (COMPAZINE®), casopitant (REZONIC® and Zunrisa®), and combinations thereof.

In yet other instances, medication to alleviate the pain experienced during the treatment period is prescribed to make the patient more comfortable. Common over-the-counter analgesics, such TYLENOL®, are often used. Opioid analgesic drugs such as hydrocodone/paracetamol or hydrocodone/acetaminophen (e.g., VICODIN®), morphine (e.g., ASTRAMORPH® or AVINZA®), oxycodone (e.g., OXYCONTIN® or PERCOCET®), oxymorphone hydrochloride (OPANA®), and fentanyl (e.g., DURAGESIC®) are also useful for moderate or severe pain.

Furthermore, cytoprotective agents (such as neuroprotectants, free-radical scavengers, cardioprotectors, anthracycline extravasation neutralizers, nutrients and the like) may be used as an adjunct therapy to protect normal cells from treatment toxicity and to limit organ toxicities. Suitable cytoprotective agents include amifostine (ETHYOL®), glutamine, dimesna (TAVOCEPT®), mesna (MESNEX®), dexrazoxane (ZINECARD® or TOTECT®), xaliproden (XAPRILA®), and leucovorin (also known as calcium leucovorin, citrovorum factor and folinic acid).

In yet another aspect, a compound of the present invention may be used in combination with known therapeutic processes, for example, with the administration of hormones or in radiation therapy. In certain instances, a compound of the present invention may be used as a radiosensitizer, especially for the treatment of tumors which exhibit poor sensitivity to radiotherapy.

The doses and dosage regimen of the active ingredients used in the combination therapy may be determined by an attending clinician. In certain embodiments, the compound described herein (e.g., a compound of Formula I, I-A, II, or II-A, or other compounds in Section I) and the additional therapeutic agent(s) are administered in doses commonly employed when such agents are used as monotherapy for treating the disease or condition. In other embodiments, the compound described herein (e.g., a compound of Formula I, I-A, II, or II-A, or other compounds in Section I) and the additional therapeutic agent(s) are administered in doses lower than the doses commonly employed when such agents are used as monotherapy for treating the disease or condition. In certain embodiments, the compound described herein (e.g., a compound of Formula I, I-A, II, or II-A, or other compounds in Section I) and the additional therapeutic agent(s) are present in the same composition, which is suitable for oral administration.

In certain embodiments, the compound described herein (e.g., a compound of Formula I, I-A, II, or II-A, or other compounds in Section I) and the additional therapeutic agent(s) may act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

Another aspect of this invention is a kit comprising a therapeutically effective amount of a compound described herein (e.g., a compound of Formula I, I-A, II, or II-A, or other compounds in Section I), a pharmaceutically acceptable carrier, vehicle or diluent, and optionally at least one additional therapeutic agent listed above. In certain embodiments, the kit further comprises instructions, such as instructions for treating a disease described herein.

IV. Pharmaceutical Compositions and Dosing Considerations

As indicated above, the invention provides pharmaceutical compositions, which comprise a therapeutically-effective amount of one or more of the compounds described above, formulated together with one or more pharmaceutically acceptable carriers (additives) and/or diluents. The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally. In certain embodiments, the invention provides a pharmaceutical composition comprising a compound described herein (e.g., a compound of Formula I, I-A, II, or II-A) and a pharmaceutically acceptable carrier.

The phrase "therapeutically effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

If desired, the effective daily dose of the active compound may be administered as two, three, four, five, six or more sub-doses administered separately at appropriate intervals throughout the day, optionally, in unit dosage forms. Preferred dosing is one administration per day.

The invention further provides a unit dosage form (such as a tablet or capsule) comprising a prodrug of a piperidinylmethylpurine pyridine or related compound described herein in a therapeutically effective amount for the treatment of a disease or condition described herein.

EXAMPLES

The invention now being generally described, will be more readily understood by reference to the following examples, which are included merely for purposes of illustrating certain aspects and embodiments of the present invention, and are not intended to limit the invention. Abbreviations used include: equiv or eq: molar equivalents; DCM: dichloromethane; DMF: dimethylformamide; DMAc: dimethylacetamide; DMSO: dimethylsulfoxide; DIPEA: diisopropylethylamine; IPA: isopropyl alcohol; TFA: trifluoroacetic acid; and $PdCl_2$(dppf): bis(diphenylphosphino) ferrocene]dichloropalladium(II).

Example 1—Synthesis of 4-(5-((R)-3-amino-3-((S)-2,2-difluoro-1-hydroxyethyl)piperidin-1-yl)-4-((6-amino-9H-purin-9-yl)methyl)pyridin-2-yl)-2,5-difluorophenol (Compound J)

The title compound was prepared according to the following procedures.

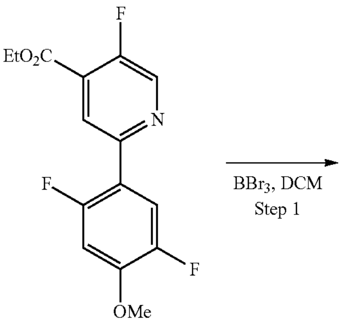

A

-continued
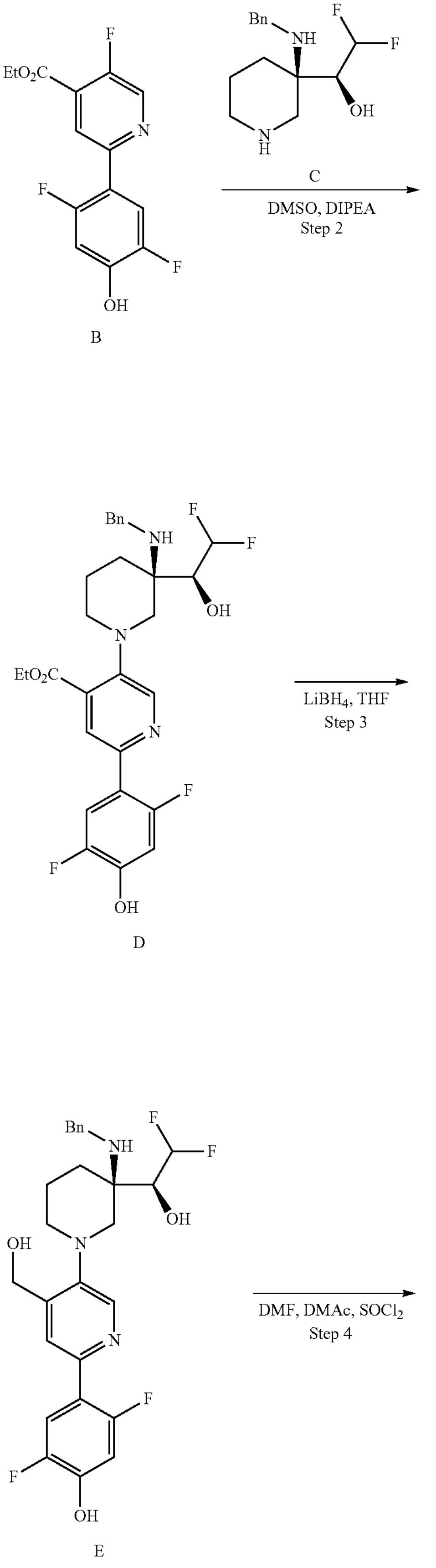
-continued
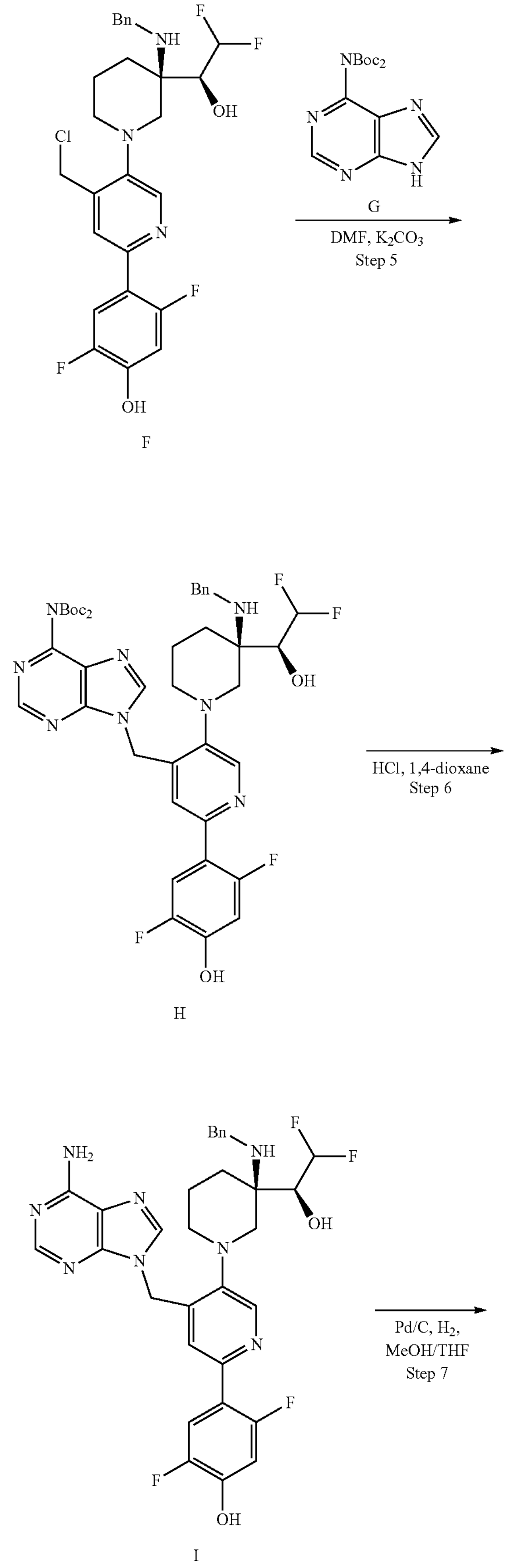

-continued

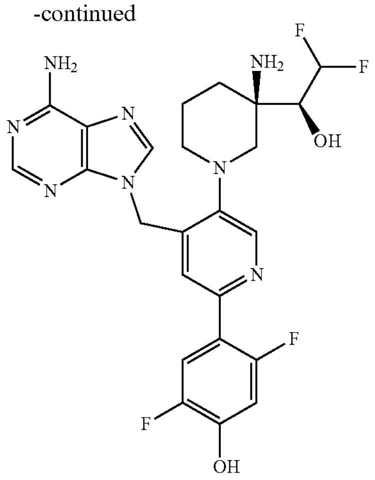

J

Step 1: Synthesis of B

Compound A (10.0 g, 1.0 equiv.) in 10 volumes of DCM was exposed to a solution of $BBr_3$ (1M solution in DCM, 6.0 equiv) at 0° C. Then, the reaction mixture was warmed to room temperature and stirred for 16 hours to generate compound B.

Step 2: Synthesis of D

Compound B (4.0 g, 1.0 equiv.) and compound C (1.1 equiv.) were combined in 10 volumes of DMSO with DIPEA (6.0 equiv), and the resulting mixture was heated to 120° C. for 16 hours to generate compound D.

Step 3: Synthesis of E

Compound D (5.0 g, 1.0 equiv) was reduced using $LiBH_4$ (10.0 equiv.) in 10 volumes of THF at 0° C. Then, the reaction was warmed to room temperature and stirred for 20 hours to generate compound E.

Step 4: Synthesis of F

Compound E (3 g, 1.0 equiv) was reacted with $SOCl_2$ (5.0 equiv) in 5 volumes of DMAc and 0.1 volumes of DMF at 0° C. Then, the mixture was allowed to warm to room temperature and stirred for 3 hours to generate compound F.

Step 5: Synthesis of H

Crude compound F (3.2 g, 1.0 equiv) was charged with 10 volumes of DMF and compound G (1.0 equiv). $K_2CO_3$ (3.0 equiv) was added to the reaction mixture at 0° C., and then the mixture warmed to room temperature and stirred for 12 hours to generate compound H.

Step 6: Synthesis of I

Compound H (1.0 g, 1.0 equiv) was exposed to 10 volumes of 4M HCl in 10 volumes of 1,4-dioxane at 0° C., and then the reaction mixture was allowed to warm to room temperature for 16 hours to generate compound I.

Step 7: Synthesis of J

Compound I (0.8 g, 1.0 equiv) was charged with 10 volumes of methanol/THF (1/1, v/v), then Pd/C (10%, 0.2 equiv), under hydrogen gas for 16 hours to generate compound J. $^1$H NMR (DMSO-$d_6$, 400 MHz): 8.47 (s, 1H), 8.28 (br s, 1H), 8.25 (s, 1H), 8.11 (s, 1H), 7.62 (dd, J=12.4, 7.6 Hz, 1H), 7.28 (s, 2H), 6.95 (s, 1H), 6.74 (dd, J=12.4, 7.2 Hz, 1H), 6.18 (td, J=56.0, 3.2 Hz, 1H), 5.49 (s, 2H), 3.79 (br s, 1H), 3.12-3.00 (m, 2H), 2.92-2.78 (2H), 1.88-1.65 (m, 3H), 1.47-1.53 (m, 1H). MS (ESI+): $[M+H]^+$=533.05.

Example 2—Synthesis of methyl 2-(4-(5-((R)-3-amino-3-((S)-2,2-difluoro-1-hydroxyethyl)piperidin-1-yl)-4-((6-amino-9H-purin-9-yl)methyl)pyridin-2-yl)-2,5-difluorophenoxy)acetate (III-35)

The title compound was prepared according to the following procedures.

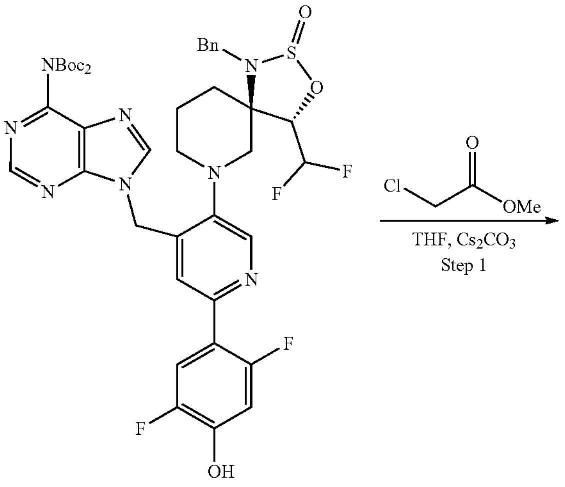

A

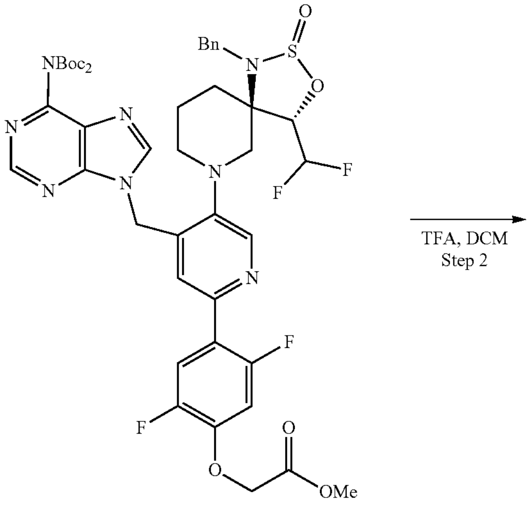

B

-continued

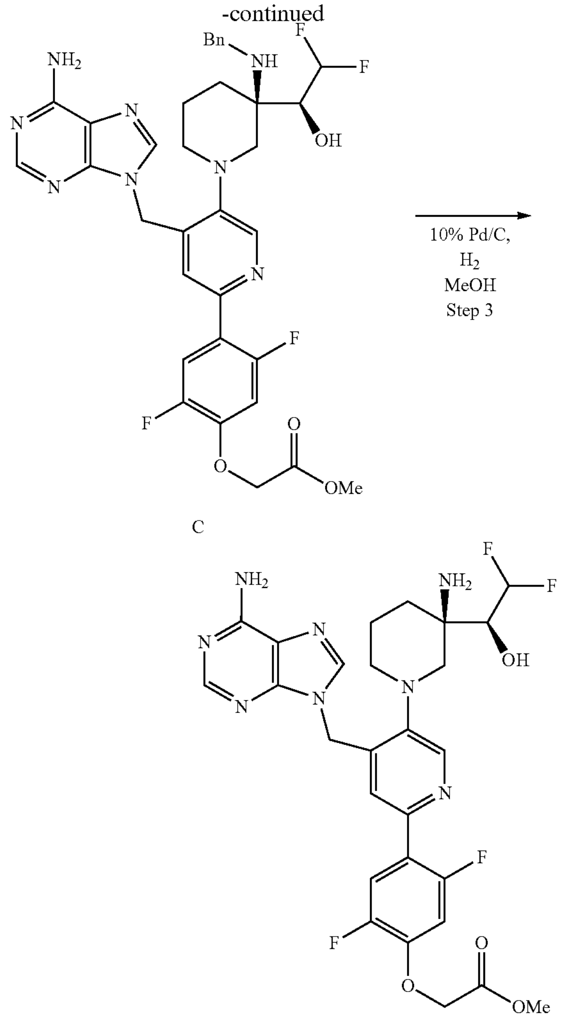

C

III-35

Step 1: Synthesis of B

Compound A (2.0 g, 1.0 equiv) was charged with 10 volumes of THF, methyl 2-chloroacetate (1.5 equiv), and $Cs_2CO_3$ (1.5 equiv) at 0° C., and then the reaction mixture was allowed to warm to room temperature over 12 hours to generate compound B.

Step 2: Synthesis of C

Compound B (1.1 g, 1.0 equiv) was charged with 10 volumes of DCM and 2 volumes of TFA at 0° C., and then the reaction mixture was allowed to warm to room temperature over 6 hours to generate compound C.

Step 3: Synthesis of III-35

Compound C (1.0 g, 1.0 equiv) was charged with 10 volumes of methanol, Pd/C (10%, 0.2 equiv), and hydrogen gas at room temperature for 20 hours to generate compound III-35. $^1$H NMR (DMSO-$d_6$, 400 MHz): 8.51 (s, 1H), 8.32 (br s, 1H), 8.27 (s, 1H), 8.13 (s, 1H), 7.71 (dd, J=12.4, 7.6 Hz, 1H), 7.12 (dd, J=12.8, 6.8 Hz, 1H), 6.95 (s, 1H), 6.20 (td, J=55.6, 3.6 Hz, 1H), 5.57 (s, 2H), 4.93 (s, 2H), 3.88-3.84 (m, 1H), 3.70 (s, 3H), 3.16 (d, J=11.6 Hz, 1H), 3.04-3.01 (m, 1H), 2.94-2.85 (2H), 1.91-1.75 (m, 3H), 1.57-1.53 (m, 1H). MS (ESI+): $[M+H]^+$=605.15.

Example 3—Synthesis of 4-(5-((R)-3-amino-3-((S)-2,2-difluoro-1-hydroxyethyl)piperidin-1-yl)-4-((6-amino-9H-purin-9-yl)methyl)pyridin-2-yl)-2,5-difluorophenyl dihydrogen phosphate (I-21)

The title compound was prepared according to the following procedures.

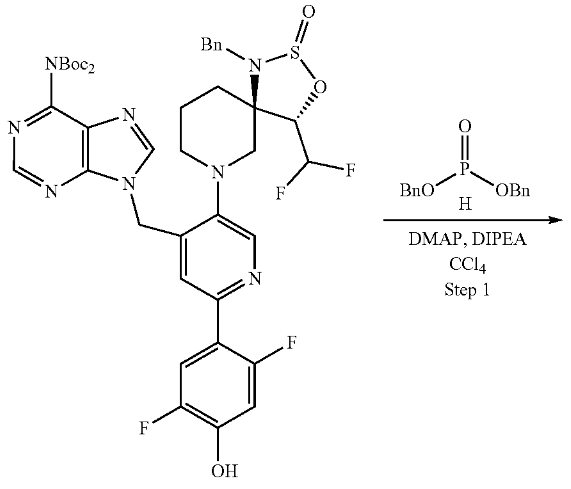

A

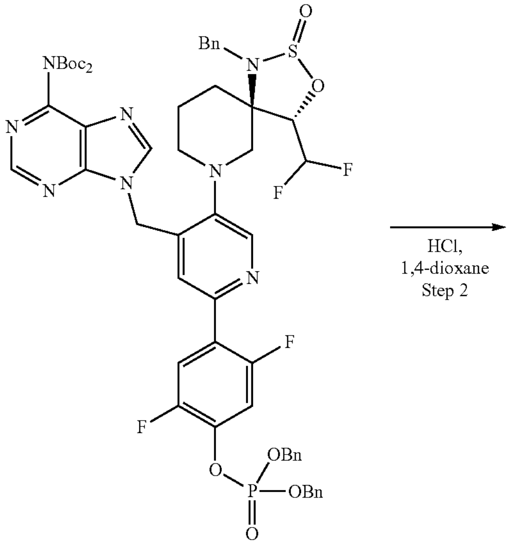

B

-continued

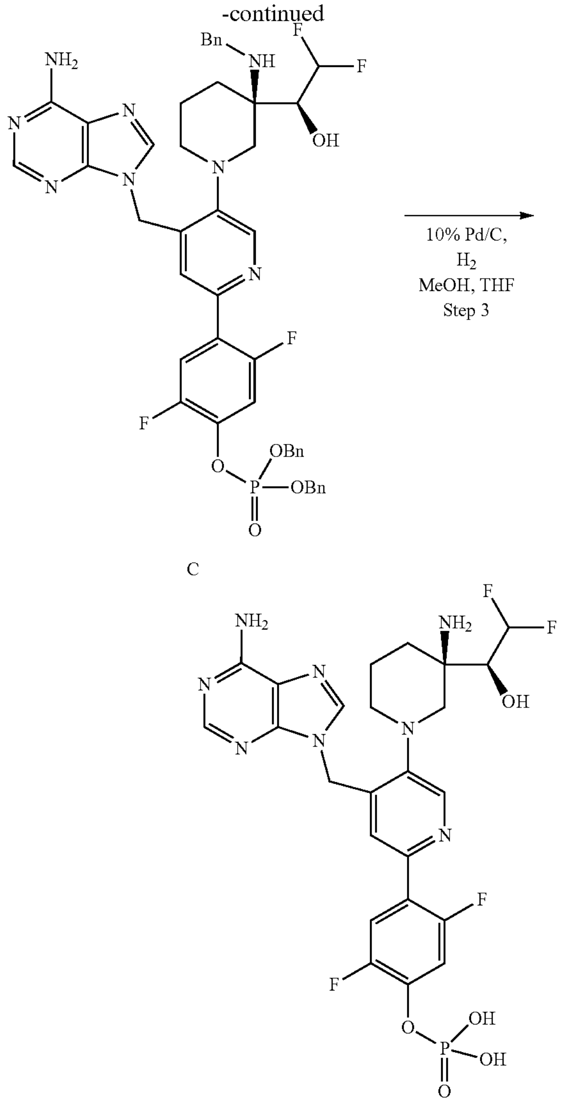

C

I-21

Step 1: Synthesis of B

Compound A (2.0 g, 1.0 equiv) was charged with 10 volumes of MeCN, dibenzyl phosphite (2.1 equiv), DMAP (0.1 equiv), DIPEA (2.1 equiv), and $CCl_4$ (5.0 equiv) at 0° C., and then the reaction mixture was allowed to warm to room temperature over 12 hours to generate compound B.

Step 2: Synthesis of C

Compound B (2.6 g, 1.0 equiv) was exposed to HCl (6N, 20 mL) in 1,4-dioxane (20 mL) at 0° C., and then the reaction mixture was allowed to warm to room temperature over 6 hours to generate compound C.

Step 3: Synthesis of I-21

Compound C (1.2 g, 1.0 equiv) was charged with 10 volumes of methanol/THF (1:1 v/v), Pd/C (10%, 0.2 equiv) under hydrogen atmosphere to generate compound I-21. $^1H$ NMR (DMSO-$d_6$, 400 MHz): 8.45 (s, 1H), 8.26 (s, 1H), 8.20

(s, 1H), 7.47 (dd, J=12.0, 8.0 Hz, 1H), 7.35-7.30 (m, 3H), 7.07 (s, 1H), 6.30 (t, J=53.6 Hz, 1H), 5.60-5.50 (m, 1H), 4.12-4.02 (m, 1H), 3.19-3.17 (m, 2H), 2.82 (br s, 2H), 2.88 (br s, 2H), 1.95-1.65 (m, 4H). MS (ESI+): [M+H]+=613.05.

Example 4—Evalution of NSD2 Inhibitory Activity for Exemplary Compounds

Exemplary compounds were tested for NSD2 inhibitory activity using a modified RBC HotSpot HMT Assay. Experimental procedures and results are provided below.

Part I—Experimental Procedures

A reaction mixture was prepared by adding oligonucleosomes from Chicken (0.05 mg/ml) to freshly prepared reaction buffer containing 50 mM Tris-HCl (pH 8.5), 50 mM NaCl, 5 mM $MgCl_2$, 0.01% Brij35, 1 mM DTT, and 1% DMSO followed by the addition of recombinant human NSD2, (amino acids 2-end) with N-terminal His tag (2 nM; GenBank Accession No. NM_001042424; MW=155.5 kDa; expressed in Sf9 insect cells) and gentle mixing. The test compounds were diluted in DMSO, added to the reaction mixture in nanoliter amounts by using Acoustic Technology (Echo 550, LabCyte Inc. Sunnyvale, CA) and incubated for 20 minutes at room temperature. The reaction was initiated by the addition of S-Adenosyl-L-[methyl-$^3$H]methionine (3H-SAM; 1 μM), and the mixture was incubated for 1 hour at 30° C. The reaction mixture was delivered to filter paper and the methylated substrate was quantified by scintillation counting. Data analysis was performed using Excel and GraphPad Prism software for $IC_{50}$ curve fits. For additional information on the histone methyltransferase assay, see, for example, Horiuchi K Y, et al., "Assay Development for Histone Methyltransferases," Assay Drug Dev Technol. 2013 May; 11(4):227-36.

Part II—Results

The results of the NSD2 inhibitory assay are reported in Table 8 below. The symbol++++ indicates an $IC_{50}$ less than 0.002 μM. The symbol+++ indicates an $IC_{50}$ between 0.002 μM and 0.02 μM. The symbol++ indicates an $IC_{50}$ between 0.02 μM and 2 μM. The symbol+ indicates an $IC_{50}$ greater than 2 μM. Compound J has the following formula:

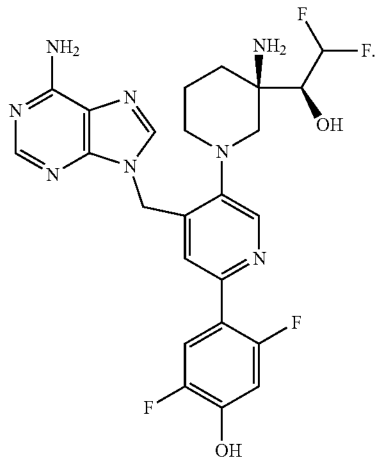 [SMILES: Nc1ncnc2c1ncn2Cc1cc(-c2cc(F)c(O)cc2F)ncc1N1CCC[C@](N)([C@H](O)C(F)F)C1]

TABLE 8

| Compound No. | NSD2 $IC_{50}$ |
|---|---|
| Compound J | +++ |
| III-35 | ++++ |

Example 5—Synthesis of N-(9-((5-((R)-3-amino-3-((S)-2,2-difluoro-1-hydroxyethyl)piperidin-1-yl)-2-(2,5-difluoro-4-methoxyphenyl)pyridin-4-yl)methyl)-9H-purin-6-yl)-2-(dimethylamino)acetamide (VI-4)

The title compound was prepared according to the following procedures.

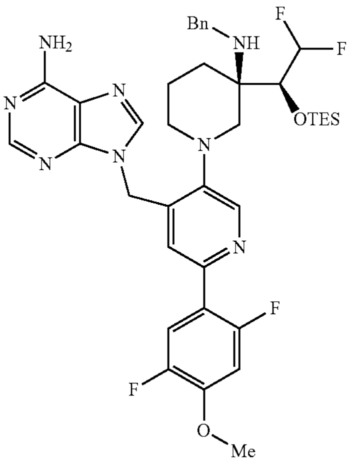

A

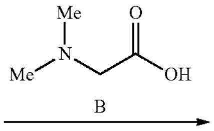

B

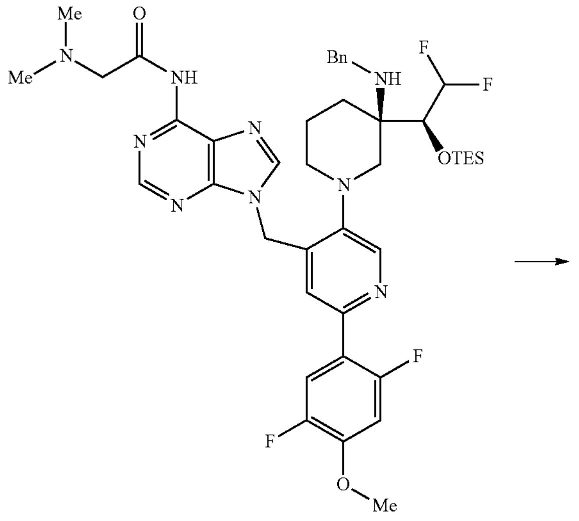

C

-continued

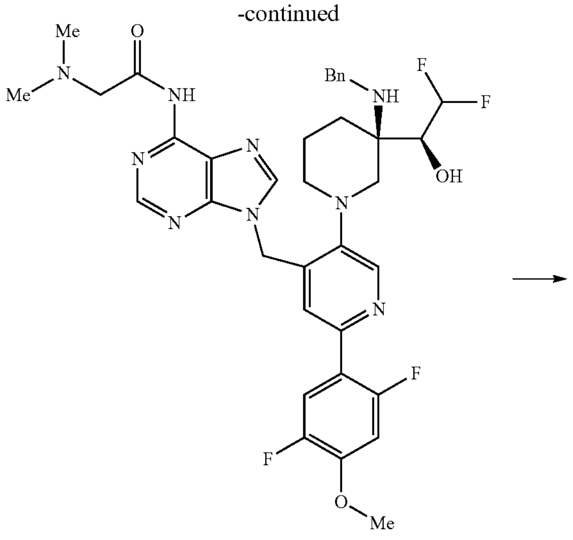

D

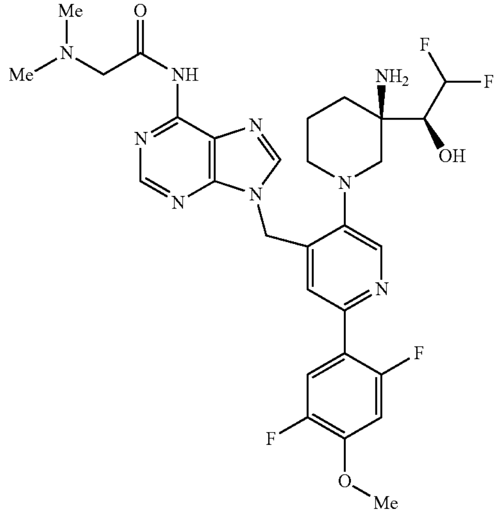

VI-4

Step 1: Synthesis of C

Compound A (1.0 g, 1.0 equiv.) was charged with 7 volumes of DCM, carboxylic acid B (1.0 equiv.), CDI (N,N'-carbonyldiimidazole) (1.0 equiv.) and DIPEA (2.0 equiv.) at 20° C. and allowed to stir for 12 hours to generate C.

Step 2: Synthesis of D

Compound C (0.6 g, 1.0 equiv.) was charged with 5 volumes of THF and TBAF (2.0 equiv.) was added at 20° C. and allowed to stir for 6 hours to generate D.

Step 3: Synthesis of VI-4

Compound D (0.4 g, 1.0 equiv.) was charged with 20 volumes of THE and then Pd/C:$Pd(OH)_2$ (1:1, 1.0 equiv.) and hydrogen gas at 30° C. and the mixture allowed to stir for 12 hours to generate VI-4. $^1H$ NMR: (400 MHz, MeOD) δ 8.69 (s, 1H), 8.54 (s, 1H), 8.53 (s, 1H), 7.61 (dd, J=12.0, 7.2 Hz, 1H), 7.19 (s, 1H), 6.92 (dd, J=12.4, 6.8 Hz, 1H), 6.09 (td, J=55.2, 4.4 Hz, 1H), 5.80 (s, 2H), 3.26-3.01 (m, 4H), 2.49 (s, 6H), 1.95-1.72 (m, 4H). MS (ESI+) 632.3 (M+H+).

Example 6—Synthesis of ((9-((5-((R)-3-amino-3-((S)-2,2-difluoro-1-hydroxyethyl)piperidin-1-yl)-2-(2,5-difluoro-4-methoxyphenyl)pyridin-4-yl)methyl)-9H-purin-6-yl)carbamoyl)glycine (VI-15)

The title compound was prepared according to the following procedures.

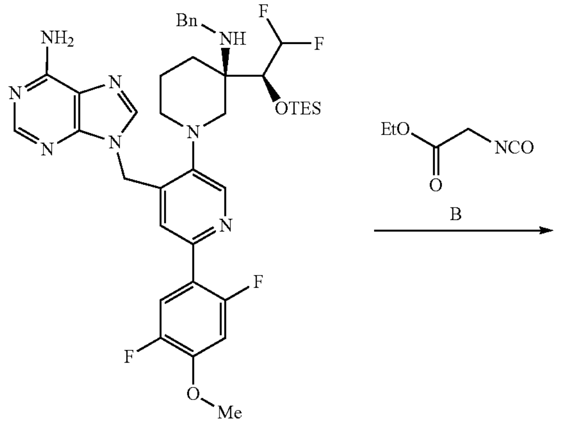

A

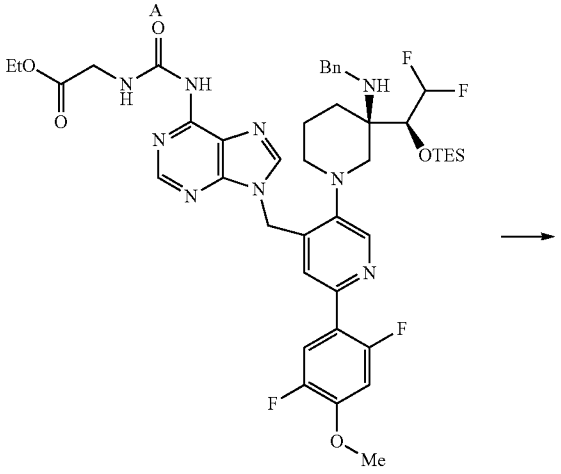

C

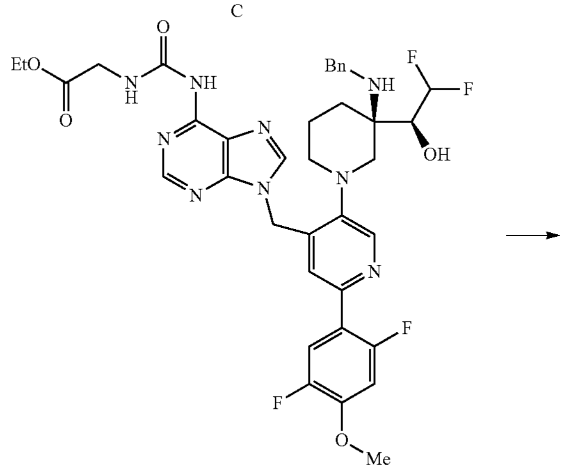

D

-continued

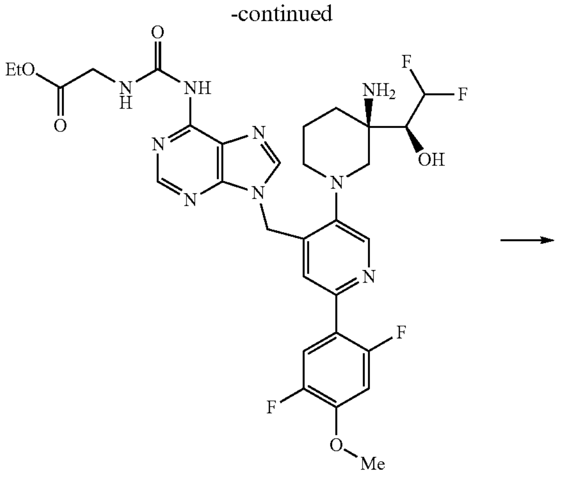

E

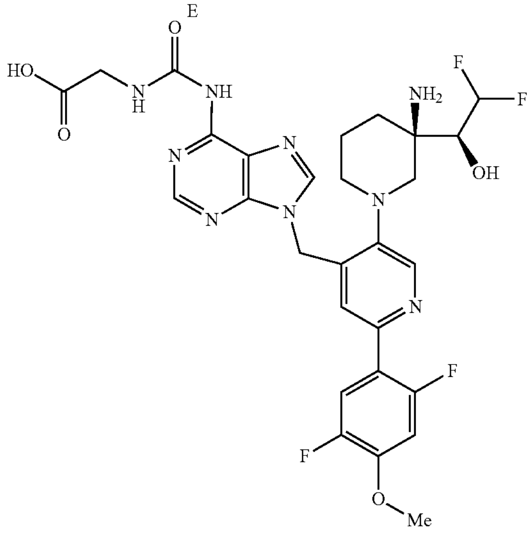

VI-15

Step 1: Synthesis of C

Compound A (0.8 g, 1.0 equiv.) was charged with 7 volumes of DCM, isocyanate B (1.0 equiv.) and triethylamine (2.0 equiv.) at 20° C. and allowed to stir for 12 hours to generate C.

Step 2: Synthesis of D

Compound C (0.7 g, 1.0 equiv.) was charged with 5 volumes of THF and TBAF (2.0 equiv.) at 20° C. and allowed to stir for 6 hours to generate D.

Step 3: Synthesis of E

Compound D (0.4 g, 1.0 equiv.) was charged with 20 volumes of THE and then Pd/C:Pd$(OH)_2$ (1:1, 1.0 equiv.) and hydrogen gas at 30° C. and allowed to stir for 12 hours to generate E.

Step 4: Synthesis of VI-15

Compound E (170 mg, 1.0 equiv.) was charged with THF/water (10 volumes, 1/1, v/v) and NaOH (2.0 equiv.) at 20° C. and allowed to stir for 6 hours to generate VI-15. $^1$H NMR: (400 MHz, MeOD) δ 8.53 (s, 1H), 8.51 (s, 1H), 8.44 (s, 1H), 7.57 (dd, J=12.0, 7.2 Hz, 1H), 7.15 (s, 1H), 6.86 (dd, J=12.8, 7.2 Hz, 1H), 6.17 (td, J=54.0, 2.8 Hz, 1H), 5.80 (d, J=16.8 Hz, 1H), 5.72 (d, J=16.8 Hz, 1H), 4.14 (br s, 1H), 3.99-3.94 (m, 2H), 3.90 (s, 3H), 3.35 (s, 2H), 3.17-3.03 (m, 2H), 2.06-1.92 (m, 4H). MS (ESI+) 648.3 (M+H+).

Example 7—Synthesis of methyl ((9-((5-((R)-3-amino-3-((S)-2,2-difluoro-1-hydroxyethyl)piperidin-1-yl)-2-(2,5-difluoro-4-methoxyphenyl)pyridin-4-yl)methyl)-9H-purin-6-yl)carbamoyl)glycinate (VI-19)

The title compound was prepared according to the following procedures.

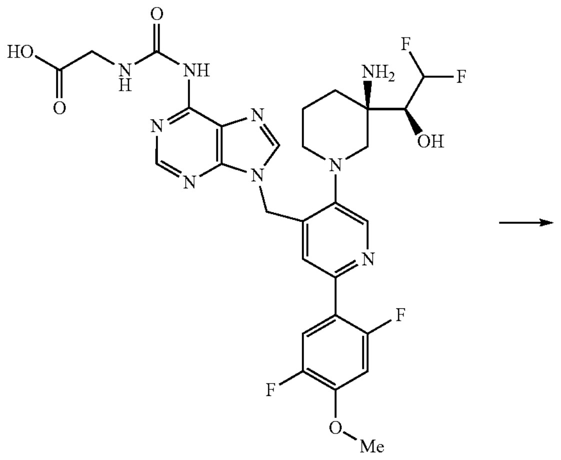

A

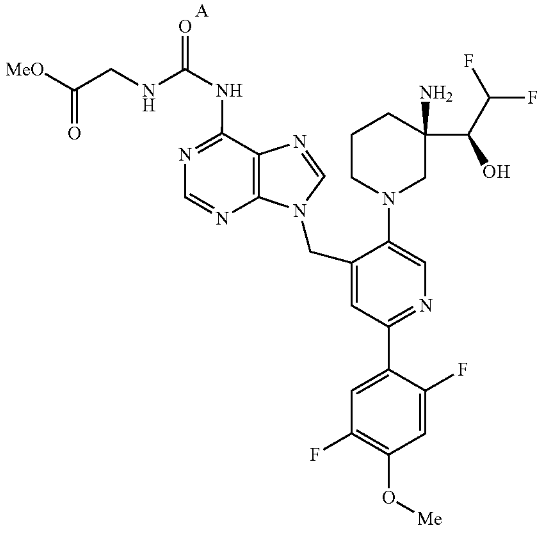

VI-19

Step 1: Synthesis of VI-19

Compound A (30 mg, 1.0 equiv.) was charged with 5 volumes of DCM and diazomethane (2.0 equiv.) at 20° C. and allowed to stir for 12 hours to generate compound VI-19. $^1$H NMR: (400 MHz, MeOD) δ 8.59 (s, 1H), 8.53 (s, 1H), 8.43 (s, 1H), 7.59 (dd, J=12.0, 7.2 Hz, 1H), 7.16 (s, 1H), 6.91 (dd, J=12.8, 7.2 Hz, 1H), 6.11 (td, J=55.2, 4.0 Hz, 1H), 5.80-5.75 (m, 2H), 4.18 (s, 2H), 3.87 (s, 3H), 3.77 (s, 3H), 3.13-3.03 (m, 4H), 1.98-1.79 (m, 3H). MS (ESI+) 662.3 (M+H$^+$).

Example 8—Evalution of NSD1 Inhibitory Activity for An Exemplary Compound

An exemplary compound was tested for NSD1 inhibitory activity. Experimental procedures and results are provided below.

Part I—Experimental Procedures

A reaction mixture was prepared by adding oligonucleosomes from Chicken (0.05 mg/ml) to freshly prepared reaction buffer containing 50 mM Tris-HCl (pH 8.5), 50 mM NaCl, 5 mM $MgCl_2$, 0.01% Brij35, 1 mM DTT, and 1% DMSO followed by the addition of recombinant human NSD1 (amino acids 2-end) with N-terminal His tag (2 nM) and gentle mixing. The test compounds were diluted in DMSO, added to the reaction mixture in nanoliter amounts by using Acoustic Technology (Echo 550, LabCyte Inc. Sunnyvale, CA) and incubated for 20 minutes at room temperature. The reaction was initiated by the addition of S-Adenosyl-L-[methyl-$^3$H] methionine (3H-SAM; 1 μM), and the mixture was incubated for 1 hour at 30° C. The reaction mixture was delivered to filter paper and the methylated substrate was quantified by scintillation counting. Data analysis was performed using Excel and GraphPad Prism software for $IC_{50}$ curve fits. For additional information on the histone methyltransferase assay, see, for example, Horiuchi K Y, et al., "Assay Development for Histone Methyltransferases," Assay Drug Dev Technol. 2013 May; 11(4):227-36.

Part II—Results

The results of the NSD1 inhibitory assay are reported in Table 9 below. The symbol++++ indicates an $IC_{50}$ less than 0.001 μM. The symbol+++ indicates an $IC_{50}$ between 0.001 μM and 0.01 μM. The symbol++ indicates an $IC_{50}$ between 0.01 μM and 1 μM. The symbol+ indicates an $IC_{50}$ greater than 1 μM.

TABLE 9

| Compound No. | NSD1 $IC_{50}$ |
|---|---|
| III-35 | ++++ |

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

The invention claimed is:

1. A compound represented by Formula I:

(I)

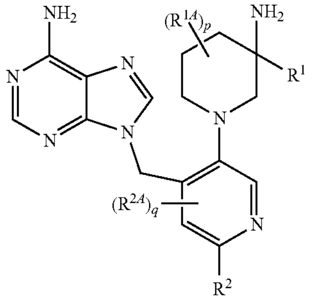

or a pharmaceutically acceptable salt thereof; wherein:

$R^1$ is selected from the group consisting of:

a. $C_{1-6}$ alkyl substituted with (i) 0, 1, 2, or 3 halo, and (ii) 0 or 1 occurrence of hydroxyl, $C_{1-6}$ alkoxyl, $C_{1-6}$ haloalkoxyl, —O—($C_{3-5}$ cycloalkyl), oxo, —C(O)$OR_3$, or —C(O)N$(R^4)_2$;

b. —C(O)$OR_3$, —C(O)N$(R^4)_2$, or —C(O)—($C_{0-4}$ alkylene)-($C_{3-7}$ cycloalkyl);

c. —($C_{0-2}$ alkylene)-(5-6 membered monocyclic heteroaryl having 1, 2, or 3 heteroatoms independently selected from nitrogen, oxygen, and sulfur), wherein said heteroaryl is substituted with m occurrences of $R^5$; and d. hydrogen;

$R^{1A}$ and $R^{2A}$ each represent independently for each occurrence halo, $C_{1-6}$ alkyl, $C_{1-6}$ haloalkyl, $C_{1-6}$ alkoxyl, or hydroxyl;

$R^2$ is phenyl; a 5-6 membered monocyclic heteroaryl having 1, 2, or 3 heteroatoms independently selected from nitrogen, oxygen, and sulfur; an 8-10 membered bicyclic heteroaryl having 1, 2, or 3 heteroatoms independently selected from nitrogen, oxygen, and sulfur; or $C_{3-7}$ cycloalkyl; each of which is substituted with (i) one —$OR_7$, and (ii) n occurrences of $R^6$;

$R^3$ represents independently for each occurrence $C_{1-6}$ alkyl or hydrogen;

$R^4$ represents independently for each occurrence $C_{1-6}$ alkyl or hydrogen, or two occurrences of $R^4$ attached to the same nitrogen atom are taken together with said nitrogen atom to form a 4-7 membered saturated ring having one nitrogen atom;

$R^5$ and $R^6$ each represents independently for each occurrence halo, $C_{1-4}$ alkyl, $C_{1-4}$ haloalkyl, $C_{1-4}$ hydroxyalkyl, $C_{3-7}$ cycloalkyl, $C_{1-4}$ alkoxyl, $C_{1-4}$ haloalkoxyl, hydroxyl, or cyano;

$R^7$ is —P(O)$(OR_8)_2$, —$CH_2$—P(O)$(OR_8)_2$, —$CH_2$—C(O)$OCH_3$, —C(O)$R^8$, —C(O)$OR_8$, —C$(R^3)_2$—$OR_8$, —C$(R^3)_2$—OC(O)$R^8$, —C$(R^3)_2$—OC(O)$OR_8$, —C$(R^3)_2$—OC(O)N$(R^4)(R^{11})$, —C(O)—C(H)$(R^9)$—N$(R^4)_2$, —C(O)—C(H)$(R^9)$—N(H)C(O)$R^3$, —C(O)N$(R^4)$—C(H)$(R^9)$—C(O)OH, or —C(O)N$(R^4)$—C(H)$(R^9)$—C(O)O($C_{1-20}$ aliphatic chain);

$R^8$ represents independently for each occurrence hydrogen, a $C_{1-20}$ aliphatic chain, $C_{3-7}$ cycloalkyl, phenyl, —$CH_2$-phenyl, or a 5-6 membered monocyclic heteroaryl having 1, 2, or 3 heteroatoms independently selected from nitrogen, oxygen, and sulfur; wherein said phenyl and heteroaryl is each substituted with r occurrences of $R^{10}$;

$R^9$ is hydrogen, $C_{1-6}$ alkyl, or —$CH_2$-phenyl;

$R^{10}$ represents independently for each occurrence halo, $C_{1-4}$ alkyl, $C_{1-4}$ haloalkyl, or $C_{1-4}$ alkoxyl;

$R^{11}$ is $C_{1-6}$ alkyl, phenyl, —$CH_2$-phenyl, or hydrogen; or $R^{11}$ and $R^4$ are taken together with the nitrogen atom to which they are attached to form a 4-7 membered saturated ring having one nitrogen atom and optionally one additional heteroatom selected from nitrogen, oxygen, and sulfur;

m and n are each independently 0, 1, 2, or 3; and p, q, and r are each independently 0, 1, or 2.

2. The compound of claim 1, wherein the compound is represented by Formula I-A:

(I-A)

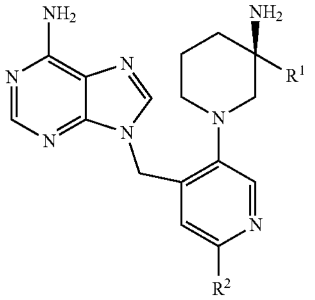

or a pharmaceutically acceptable salt thereof; wherein:

$R^1$ is selected from the group consisting of:

a. $C_{1-6}$ alkyl substituted with (i) 0, 1, 2, or 3 halo, and (ii) 0 or 1 occurrence of hydroxyl, $C_{1-6}$ alkoxyl, $C_{1-6}$ haloalkoxyl, —O—($C_{3-5}$ cycloalkyl), oxo, —C(O)$OR_3$, or —C(O)N$(R^4)_2$;

b. —C(O)$OR_3$, —C(O)N$(R^4)_2$, or —C(O)—($C_{0-4}$ alkylene)-($C_{3-7}$ cycloalkyl);

c. —($C_{0-2}$ alkylene)-(5-6 membered monocyclic heteroaryl having 1, 2, or 3 heteroatoms independently selected from nitrogen, oxygen, and sulfur), wherein said heteroaryl is substituted with m occurrences of $R^5$; and d. hydrogen;

$R^2$ is phenyl; a 5-6 membered monocyclic heteroaryl having 1, 2, or 3 heteroatoms independently selected from nitrogen, oxygen, and sulfur; an 8-10 membered bicyclic heteroaryl having 1, 2, or 3 heteroatoms independently selected from nitrogen, oxygen, and sulfur; or $C_{3-7}$ cycloalkyl; each of which is substituted with (i) one —$OR_7$, and (ii) n occurrences of $R^6$;

$R^3$ represents independently for each occurrence $C_{1-6}$ alkyl or hydrogen;

$R^4$ represents independently for each occurrence $C_{1-6}$ alkyl or hydrogen, or two occurrences of $R^4$ attached to the same nitrogen atom are taken together with said nitrogen atom to form a 4-7 membered saturated ring having one nitrogen atom;

$R^5$ and $R^6$ each represents independently for each occurrence halo, $C_{1-4}$ alkyl, $C_{1-4}$ haloalkyl, $C_{1-4}$ hydroxyalkyl, $C_{3-7}$ cycloalkyl, $C_{1-4}$ alkoxyl, $C_{1-4}$ haloalkoxyl, hydroxyl, or cyano;

$R^7$ is —P(O)$(OR_8)_2$, —$CH_2$—P(O)$(OR_8)_2$, —C(O)$R^8$, —C(O)$OR_8$, —C$(R^3)_2$—$OR_8$, —C$(R^3)_2$—OC(O)$R^8$, —C$(R^3)_2$—OC(O)$OR_8$, —C$(R^3)_2$—OC(O)N$(R^4)(R^{11})$, —C(O)—C(H)$(R^9)$—N$(R^4)_2$, —C(O)—C(H)$(R^9)$—N(H)C(O)$R^3$, —C(O)N$(R^4)$—C(H)$(R^9)$—C(O)OH, or —C(O)N$(R^4)$—C(H)$(R^9)$—C(O)O($C_{1-20}$ aliphatic chain);

$R^8$ represents independently for each occurrence hydrogen, a $C_{1-20}$ aliphatic chain, $C_{3-7}$ cycloalkyl, phenyl, —$CH_2$-phenyl, or a 5-6 membered monocyclic heteroaryl having 1, 2, or 3 heteroatoms independently selected from nitrogen, oxygen, and sulfur; wherein said phenyl and heteroaryl is each substituted with r occurrences of $R^{10}$;

$R^9$ is hydrogen, $C_{1-6}$ alkyl, or —$CH_2$-phenyl;

$R^{10}$ represents independently for each occurrence halo, $C_{1-4}$ alkyl, $C_{1-4}$ haloalkyl, or $C_{1-4}$ alkoxyl;

$R^{11}$ is $C_{1-6}$ alkyl, phenyl, —$CH_2$-phenyl, or hydrogen; or $R^{11}$ and $R^4$ are taken together with the nitrogen atom to which they are attached to form a 4-7 membered saturated ring having one nitrogen atom and optionally one additional heteroatom selected from nitrogen, oxygen, and sulfur;

m and n are each independently 0, 1, 2, or 3; and r is 0, 1, or 2.

3. The compound of claim 2, wherein $R^1$ is $C_{1-6}$ alkyl substituted with (i) 0, 1, 2, or 3 halo, and (ii) 0 or 1 occurrence of hydroxyl, $C_{1-6}$ alkoxyl, $C_{1-6}$ haloalkoxyl, —O—($C_{3-5}$ cycloalkyl), oxo, —C(O)$OR_3$, or —C(O)N$(R^4)_2$.

4. The compound of claim 2, wherein $R^1$ is $C_{1-6}$ alkyl substituted with (i) 1, 2, or 3 halo, and (ii) 0 or 1 occurrence of hydroxyl.

5. The compound of claim 2, wherein $R^1$ is

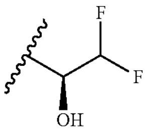

or

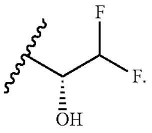

6. The compound of claim 2, wherein $R^1$ is a 6-membered monocyclic heteroaryl having 1 or 2 nitrogen atoms, wherein said heteroaryl is substituted with m occurrences of $R^5$.

7. The compound of claim 2, wherein $R^2$ is phenyl substituted with (i) one —$OR_7$, and (ii) n occurrences of $R^6$.

8. The compound of claim 2, wherein $R^2$ is

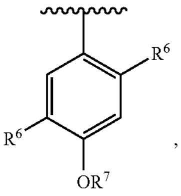

,

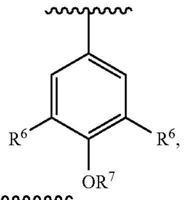

or

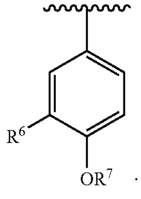

9. The compound of claim 2, wherein $R^2$ is a 5-6 membered monocyclic heteroaryl having 1, 2, or 3 heteroatoms independently selected from nitrogen, oxygen, and sulfur; wherein said heteroaryl is substituted with (i) one —$OR_7$, and (ii) n occurrences of $R^6$.

10. The compound of claim 2, wherein $R^2$ is

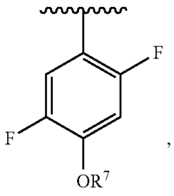

,

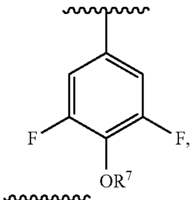

or

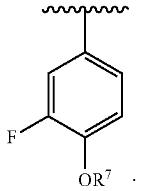

11. The compound of claim 2, wherein $R^7$ is —P(O)$(OR_8)_2$ or —$CH_2$—P(O)$(OR_8)_2$.

12. The compound of claim 2, wherein $R^7$ is —C(O)$R^8$ or —C(O)$OR_8$.

13. The compound of claim 2, wherein $R^7$ is —$C(R^3)_2$—$OR_8$, —$C(R^3)_2$—OC(O)$R^8$, —$C(R^3)_2$—OC(O)$OR_8$, or —$C(R^3)_2$—OC(O)N$(R^4)(R^{11})$.

14. The compound of claim 2, wherein $R^7$ is —C(O)—C(H)$(R^9)$—N$(R^4)_2$ or —C(O)—C(H)$(R^9)$—N(H)C(O)$R^3$.

15. The compound of claim 2, wherein $R^7$ is —C(O)N$(R^4)$—C(H)$(R^9)$—C(O)OH or —C(O)N$(R^4)$—C(H)$(R^9)$—C(O)O($C_{1-20}$ aliphatic chain).

16. The compound of claim 13, wherein $R^8$ represents independently for each occurrence a $C_{1-20}$ aliphatic chain, $C_{3-7}$ cycloalkyl, phenyl, or —$CH_2$-phenyl.

17. The compound of claim 13, wherein $R^8$ represents independently for each occurrence $C_{1-6}$ alkyl.

18. A compound represented by Formula II:

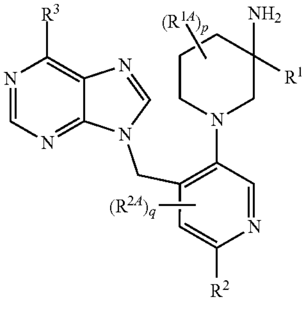

(II)

or a pharmaceutically acceptable salt thereof; wherein:

$R^1$ is selected from the group consisting of:

a. $C_{1-6}$ alkyl substituted with (i) 0, 1, 2, or 3 halo, and (ii) 0 or 1 occurrence of hydroxyl, $C_{1-6}$ alkoxyl, $C_{1-6}$ haloalkoxyl, —O—($C_{3-5}$ cycloalkyl), oxo, —C(O)$OR_4$, or —C(O)N$(R^4)_2$;

b. —C(O)$OR_4$, —C(O)N$(R^4)_2$, or —C(O)—($C_{0-4}$ alkylene)-($C_{3-7}$ cycloalkyl);

c. —($C_{0-2}$ alkylene)-(5-6 membered monocyclic heteroaryl having 1, 2, or 3 heteroatoms independently selected from nitrogen, oxygen, and sulfur), wherein said heteroaryl is substituted with m occurrences of $R^5$; and d. hydrogen;

$R^{1A}$ and $R^{2A}$ each represents independently for each occurrence halo, $C_{1-6}$ alkyl, $C_{1-6}$ haloalkyl, $C_{1-6}$ alkoxyl, or hydroxyl;

$R^2$ is phenyl; a 5-6 membered monocyclic heteroaryl having 1, 2, or 3 heteroatoms independently selected from nitrogen, oxygen, and sulfur; an 8-10 membered bicyclic heteroaryl having 1, 2, or 3 heteroatoms independently selected from nitrogen, oxygen, and sulfur; or $C_{3-7}$ cycloalkyl; each of which is substituted with n occurrences of $R^6$;

$R^3$ is —N(H) $R^7$ or —N═N—$R^{12}$;

$R^4$ represents independently for each occurrence $C_{1-6}$ alkyl or hydrogen, or two occurrences of $R^4$ attached to the same nitrogen atom are taken together with said nitrogen atom to form a 4-7 membered saturated ring having one nitrogen atom;

$R^5$ and $R^6$ each represents independently for each occurrence halo, $C_{1-4}$ alkyl, $C_{1-4}$ haloalkyl, $C_{1-4}$ hydroxyalkyl, $C_{3-7}$ cycloalkyl, $C_{1-4}$ alkoxyl, $C_{1-4}$ haloalkoxyl, hydroxyl, or cyano;

$R^7$ is —P(O)($OR_8$)$_2$, —$CH_2$—P(O)($OR_8$)$_2$, —C(O)$R^8$, —C(O)$OR_8$, —C($R^4$)$_2$—$OR_8$, —C($R^4$)$_2$—OC(O)$R^8$, —C($R^4$)$_2$—OC(O)$OR_8$, —C($R^4$)$_2$—OC(O)N($R^4$)($R^{11}$), —C(O)—C(H)($R^9$)—N($R^4$)$_2$, —C(O)—C(H)($R^9$)—N(H)C(O)$R^4$, —C(O)N($R^4$)—C(H)($R^9$)—C(O)OH, or —C(O)N($R^4$)—C(H)($R^9$)—C(O)O($C_{1-20}$ aliphatic chain);

$R^8$ represents independently for each occurrence hydrogen, a $C_{1-20}$ aliphatic chain, $C_{3-7}$ cycloalkyl, phenyl, —$CH_2$-phenyl, or a 5-6 membered monocyclic heteroaryl having 1, 2, or 3 heteroatoms independently selected from nitrogen, oxygen, and sulfur; wherein said phenyl and heteroaryl is each substituted with r occurrences of $R^{10}$;

$R^9$ is hydrogen, $C_{1-6}$ alkyl, or —$CH_2$-phenyl;

$R^{10}$ represents independently for each occurrence halo, $C_{1-4}$ alkyl, $C_{1-4}$ haloalkyl, or $C_{1-4}$ alkoxyl;

$R^{11}$ is $C_{1-6}$ alkyl, phenyl, —$CH_2$-phenyl, or hydrogen; or $R^{11}$ and $R^4$ are taken together with the nitrogen atom to which they are attached to form a 4-7 membered saturated ring having one nitrogen atom and optionally one additional heteroatom selected from nitrogen, oxygen, and sulfur;

$R^{12}$ is (i) —C(H)($R^9$)—C(O)$OR_4$, or (ii) phenyl substituted with 0, 1, or 2 substituents independently selected from hydroxyl and —($C_{0-2}$ alkylene)-C(O)$OR_4$;

m and n are each independently 0, 1, 2, or 3; and p, q, and r are each independently 0, 1, or 2.

19. A compound of Table 1, 2, 3, 4, 5, 6, or 7 below, or a pharmaceutically acceptable salt thereof

TABLE 1

| Compound No. | Chemical Structure |
|---|---|
| I-1 | 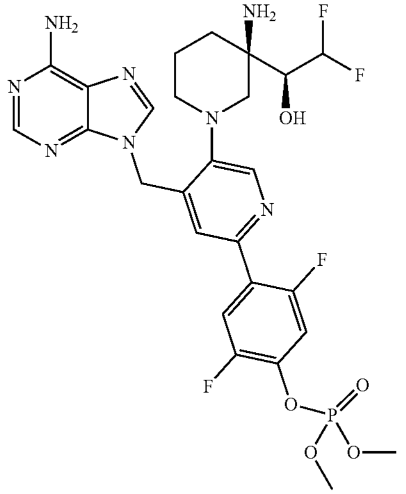 [SMILES: COP(=O)(OC)Oc1cc(F)c(-c2cc(Cn3cnc4c(N)ncnc43)c(N3CCC[C@](N)([C@H](O)C(F)F)C3)cn2)cc1F] |
| I-2 | 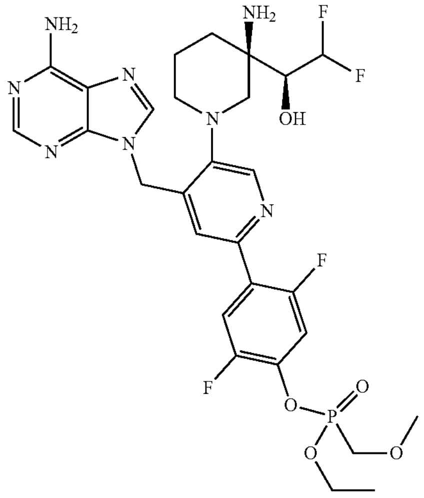 [SMILES: CCOP(=O)(COC)Oc1cc(F)c(-c2cc(Cn3cnc4c(N)ncnc43)c(N3CCC[C@](N)([C@H](O)C(F)F)C3)cn2)cc1F] |

TABLE 1-continued
| Compound No. | Chemical Structure |
|---|---|
| I-3 | 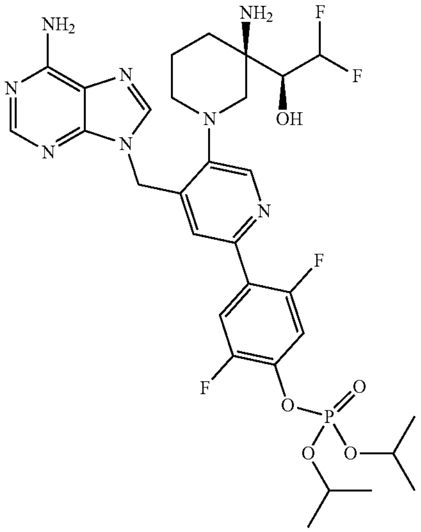 [SMILES: CC(C)OP(=O)(Oc1cc(F)c(-c2cc(Cn3cnc4c(N)ncnc43)c(N3CCC[C@](N)([C@H](O)C(F)F)C3)cn2)cc1F)OC(C)C] |
| I-4 | 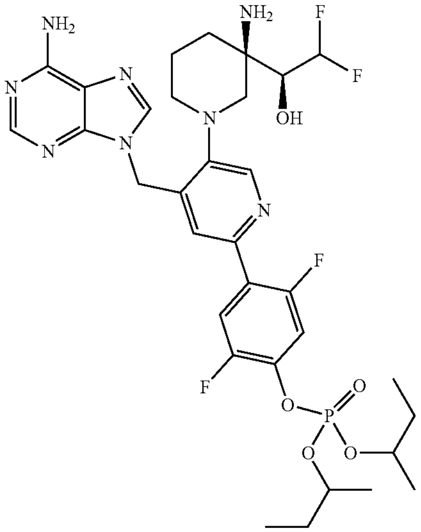 [SMILES: CCC(C)OP(=O)(Oc1cc(F)c(-c2cc(Cn3cnc4c(N)ncnc43)c(N3CCC[C@](N)([C@H](O)C(F)F)C3)cn2)cc1F)OC(C)CC] |

TABLE 1-continued
| Compound No. | Chemical Structure |
|---|---|
| I-5 | 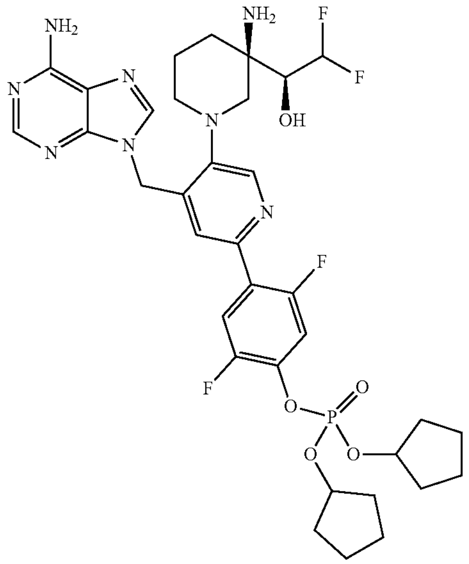 [SMILES: Nc1ncnc2c1ncn2Cc1cc(-c2cc(F)c(OP(=O)(OC3CCCC3)OC3CCCC3)cc2F)ncc1N1CCC[C@](N)([C@H](O)C(F)F)C1] |
| I-6 | 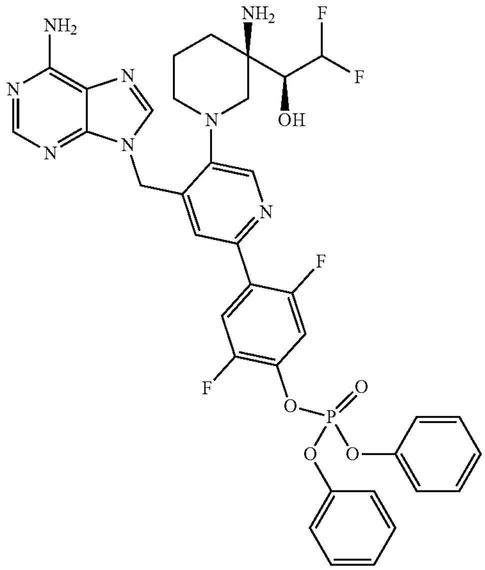 [SMILES: Nc1ncnc2c1ncn2Cc1cc(-c2cc(F)c(OP(=O)(Oc3ccccc3)Oc3ccccc3)cc2F)ncc1N1CCC[C@](N)([C@H](O)C(F)F)C1] |

TABLE 1-continued
| Compound No. | Chemical Structure |
|---|---|
| I-7 | 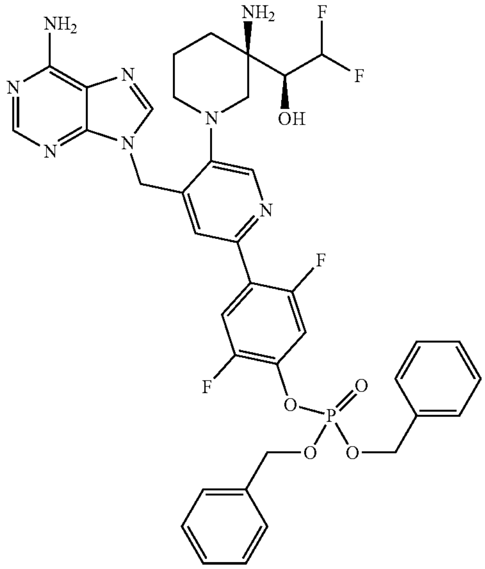 [SMILES: Nc1ncnc2c1ncn2Cc1cc(-c2cc(F)c(OP(=O)(OCc3ccccc3)OCc3ccccc3)cc2F)ncc1N1CCC[C@](N)([C@H](O)C(F)F)C1] |
| I-8 | 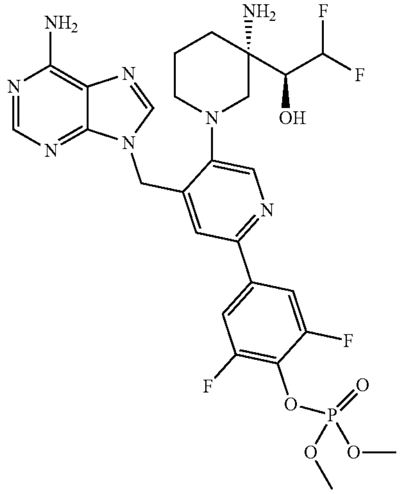 [SMILES: COP(=O)(OC)Oc1c(F)cc(-c2cc(Cn3cnc4c(N)ncnc43)c(N3CCC[C@@](N)([C@H](O)C(F)F)C3)cn2)cc1F] |

TABLE 1-continued
| Compound No. | Chemical Structure |
|---|---|
| I-9 | 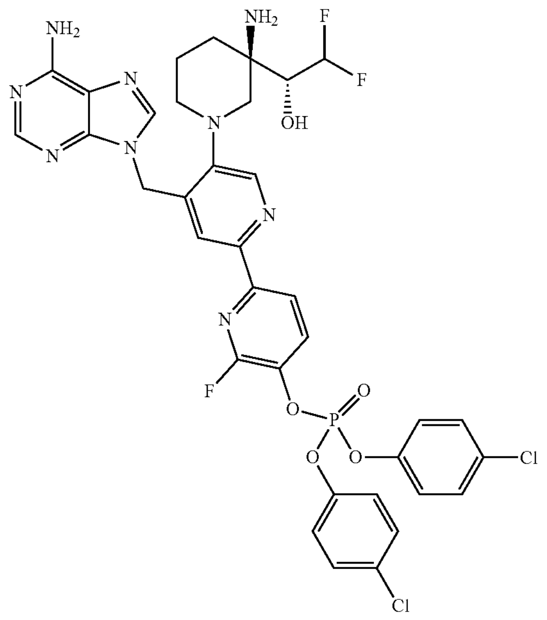 [SMILES: Nc1ncnc2c1ncn2Cc1cc(-c2ccc(OP(=O)(Oc3ccc(Cl)cc3)Oc3ccc(Cl)cc3)c(F)n2)ncc1N1CCC[C@](N)([C@@H](O)C(F)F)C1] |
| I-10 | 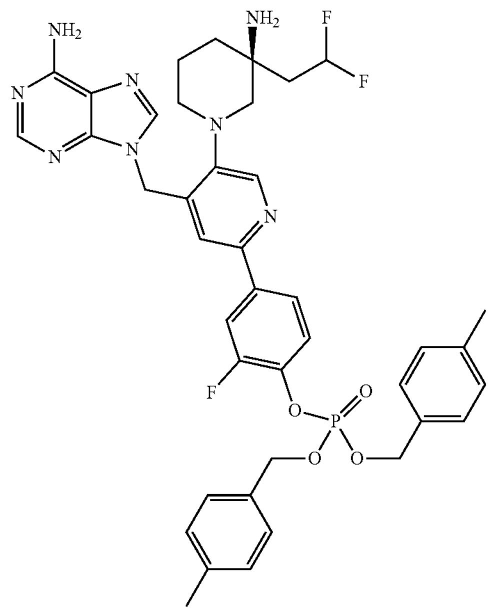 [SMILES: Cc1ccc(COP(=O)(OCc2ccc(C)cc2)Oc2ccc(-c3cc(Cn4cnc5c(N)ncnc54)c(N4CCC[C@](N)(CC(F)F)C4)cn3)cc2F)cc1] |

TABLE 1-continued
| Compound No. | Chemical Structure |
|---|---|
| I-11 | 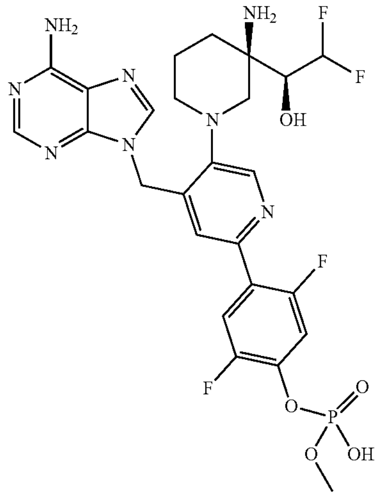 [SMILES: COP(=O)(O)Oc1cc(F)c(-c2cc(Cn3cnc4c(N)ncnc43)c(N3CCC[C@](N)([C@H](O)C(F)F)C3)cn2)cc1F] |
| I-12 | 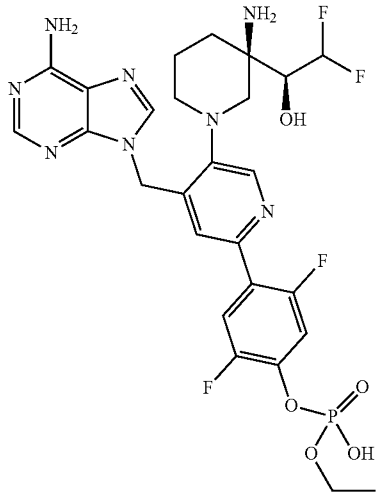 [SMILES: CCOP(=O)(O)Oc1cc(F)c(-c2cc(Cn3cnc4c(N)ncnc43)c(N3CCC[C@](N)([C@H](O)C(F)F)C3)cn2)cc1F] |
| I-13 | 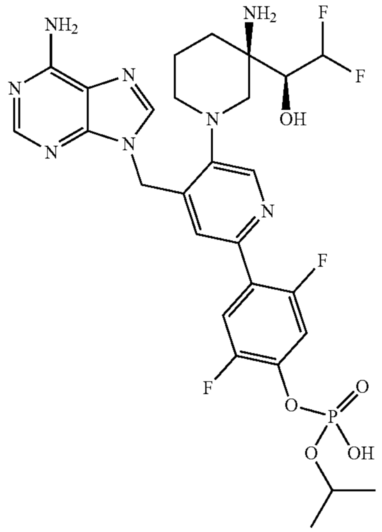 [SMILES: CC(C)OP(=O)(O)Oc1cc(F)c(-c2cc(Cn3cnc4c(N)ncnc43)c(N3CCC[C@](N)([C@H](O)C(F)F)C3)cn2)cc1F] |

TABLE 1-continued
| Compound No. | Chemical Structure |
| --- | --- |
| I-14 | 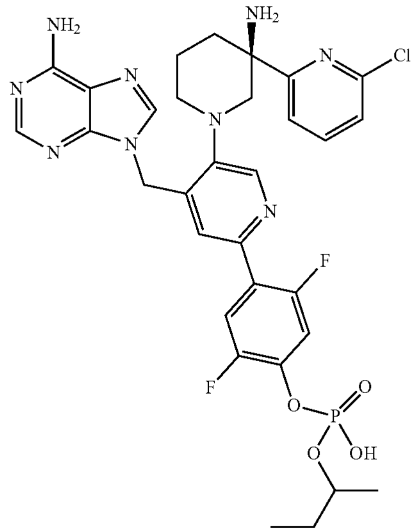 [SMILES: CCC(C)OP(=O)(O)Oc1cc(F)c(-c2cc(Cn3cnc4c(N)ncnc43)c(N3CCC[C@](N)(c4cccc(Cl)n4)C3)cn2)cc1F] |
| I-15 | 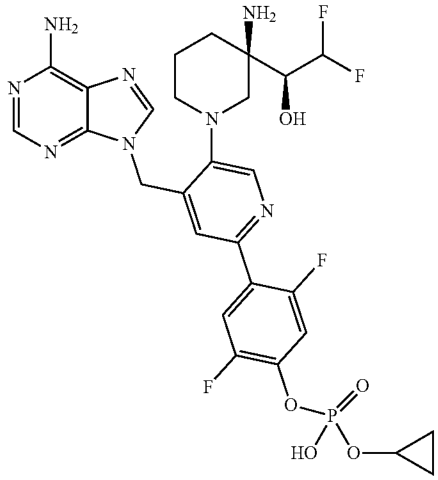 [SMILES: Nc1ncnc2c1ncn2Cc1cc(-c2cc(F)c(OP(=O)(O)OC3CC3)cc2F)ncc1N1CCC[C@](N)([C@H](O)C(F)F)C1] |
| I-16 | 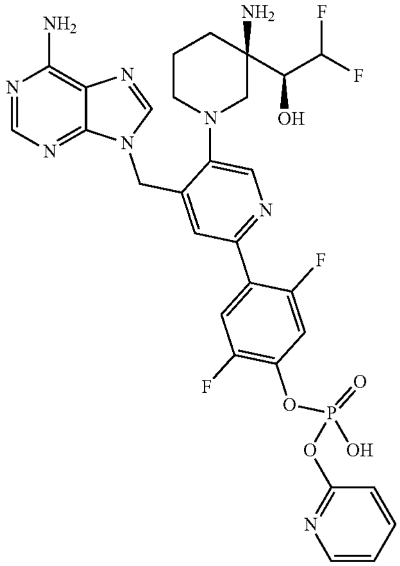 [SMILES: Nc1ncnc2c1ncn2Cc1cc(-c2cc(F)c(OP(=O)(O)Oc3ccccn3)cc2F)ncc1N1CCC[C@](N)([C@H](O)C(F)F)C1] |

TABLE 1-continued
| Compound No. | Chemical Structure |
|---|---|
| I-17 | 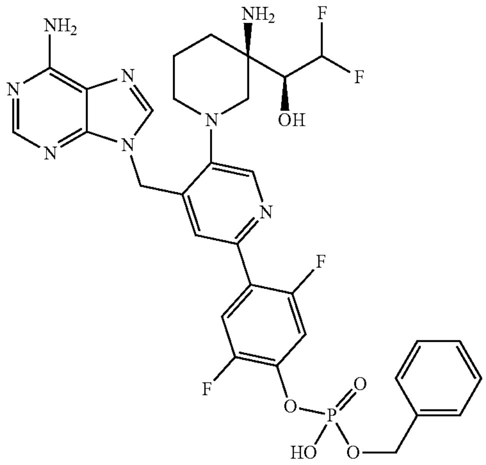 [SMILES: Nc1ncnc2c1ncn2Cc1cc(-c2cc(F)c(OP(=O)(O)OCc3ccccc3)cc2F)ncc1N1CCC[C@](N)([C@H](O)C(F)F)C1] |
| I-18 | 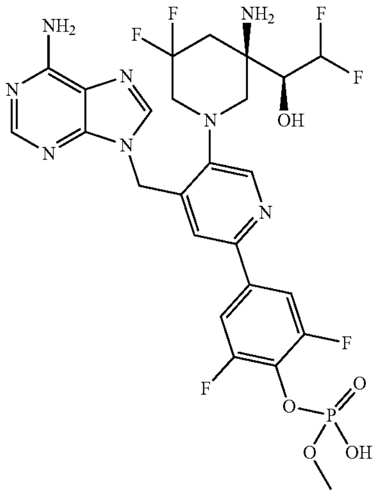 [SMILES: COP(=O)(O)Oc1c(F)cc(-c2cc(Cn3cnc4c(N)ncnc43)c(N3CC(F)(F)C[C@](N)([C@H](O)C(F)F)C3)cn2)cc1F] |
| I-19 | 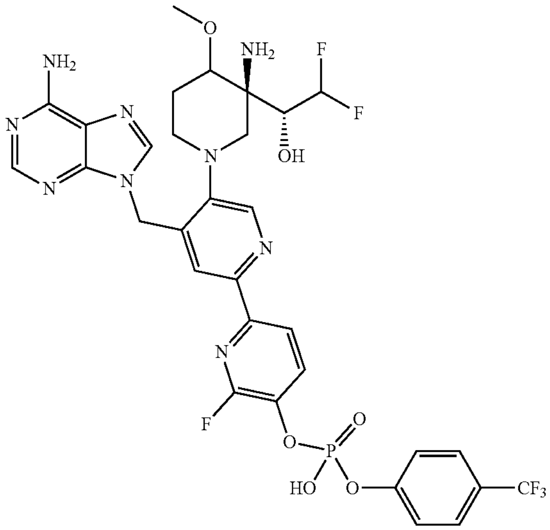 [SMILES: COC1CCN(c2cnc(-c3ccc(OP(=O)(O)Oc4ccc(C(F)(F)F)cc4)c(F)n3)cc2Cn2cnc3c(N)ncnc32)C[C@@]1(N)[C@@H](O)C(F)F] |

TABLE 1-continued
| Compound No. | Chemical Structure |
|---|---|
| I-20 | 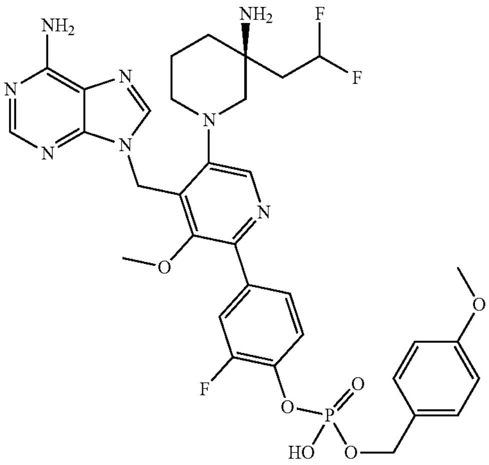 [SMILES: COc1ccc(COP(=O)(O)Oc2ccc(-c3ncc(N4CCC[C@](N)(CC(F)F)C4)c(Cn4cnc5c(N)ncnc54)c3OC)cc2F)cc1] |
| I-21 | 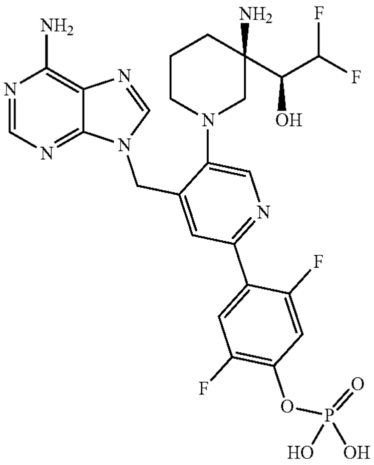 [SMILES: Nc1ncnc2c1ncn2Cc1cc(-c2cc(F)c(OP(=O)(O)O)cc2F)ncc1N1CCC[C@](N)([C@H](O)C(F)F)C1] |
| I-22 | 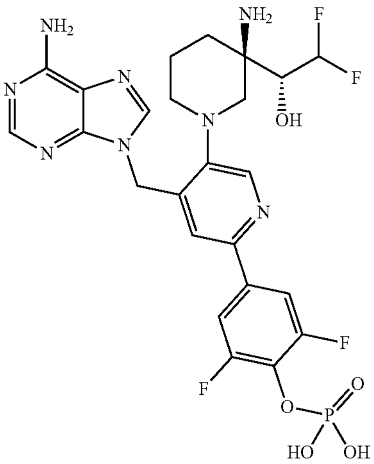 [SMILES: Nc1ncnc2c1ncn2Cc1cc(-c2cc(F)c(OP(=O)(O)O)c(F)c2)ncc1N1CCC[C@](N)([C@@H](O)C(F)F)C1] |

TABLE 1-continued
| Compound No. | Chemical Structure |
|---|---|
| I-23 | 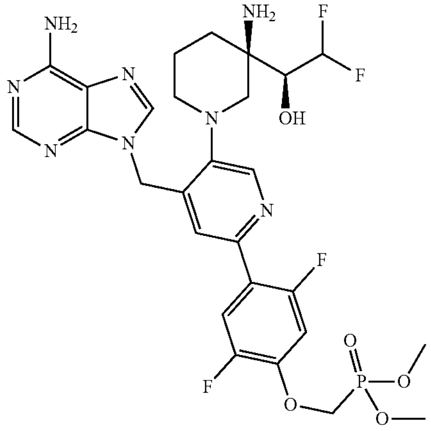 [SMILES: COP(=O)(COc1cc(F)c(-c2cc(Cn3cnc4c(N)ncnc43)c(N3CCC[C@](N)([C@H](O)C(F)F)C3)cn2)cc1F)OC] |
| I-24 | 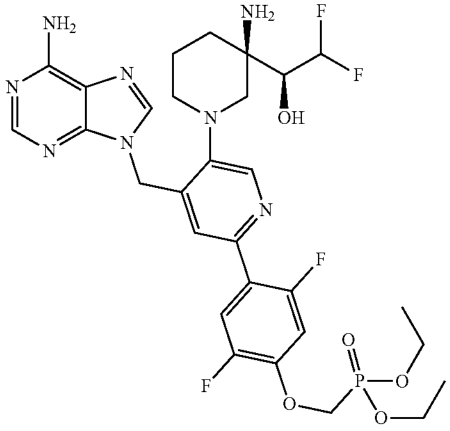 [SMILES: CCOP(=O)(COc1cc(F)c(-c2cc(Cn3cnc4c(N)ncnc43)c(N3CCC[C@](N)([C@H](O)C(F)F)C3)cn2)cc1F)OCC] |
| I-25 | 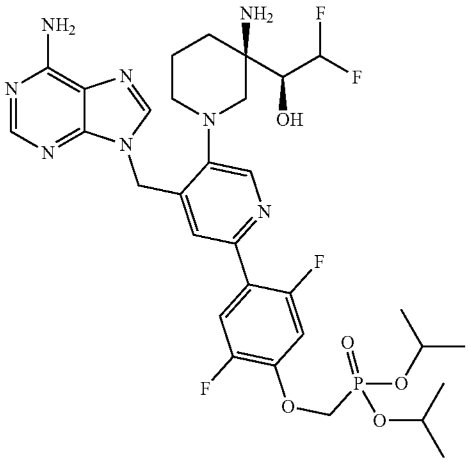 [SMILES: CC(C)OP(=O)(COc1cc(F)c(-c2cc(Cn3cnc4c(N)ncnc43)c(N3CCC[C@](N)([C@H](O)C(F)F)C3)cn2)cc1F)OC(C)C] |

TABLE 1-continued
| Compound No. | Chemical Structure |
|---|---|
| I-26 | 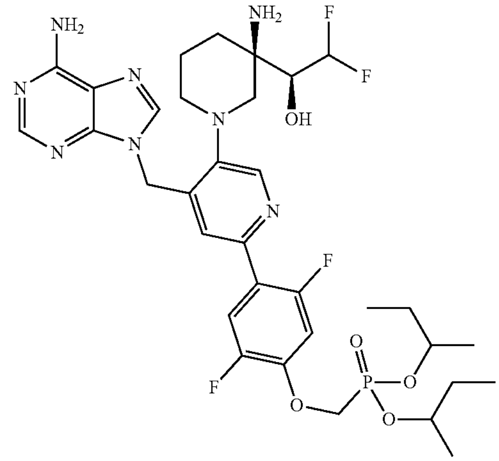 [SMILES: CCC(C)OP(=O)(COc1cc(F)c(-c2cc(Cn3cnc4c(N)ncnc43)c(N3CCC[C@](N)([C@H](O)C(F)F)C3)cn2)cc1F)OC(C)CC] |
| I-27 | 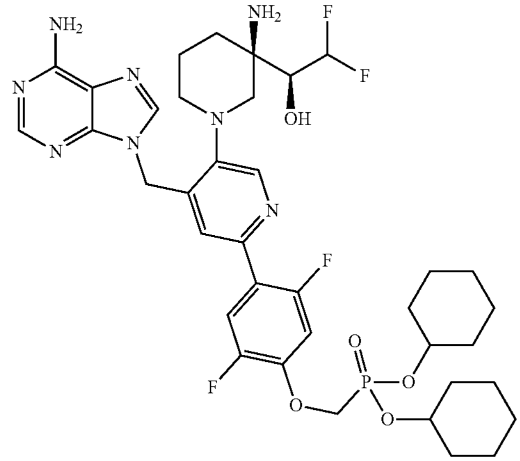 [SMILES: Nc1ncnc2c1ncn2Cc1cc(-c2cc(F)c(OCP(=O)(OC3CCCCC3)OC3CCCCC3)cc2F)ncc1N1CCC[C@](N)([C@H](O)C(F)F)C1] |
| I-28 | 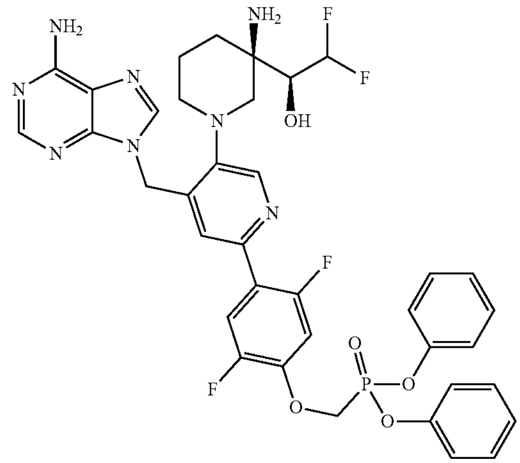 [SMILES: Nc1ncnc2c1ncn2Cc1cc(-c2cc(F)c(OCP(=O)(Oc3ccccc3)Oc3ccccc3)cc2F)ncc1N1CCC[C@](N)([C@H](O)C(F)F)C1] |

TABLE 1-continued
| Compound No. | Chemical Structure |
|---|---|
| I-29 | 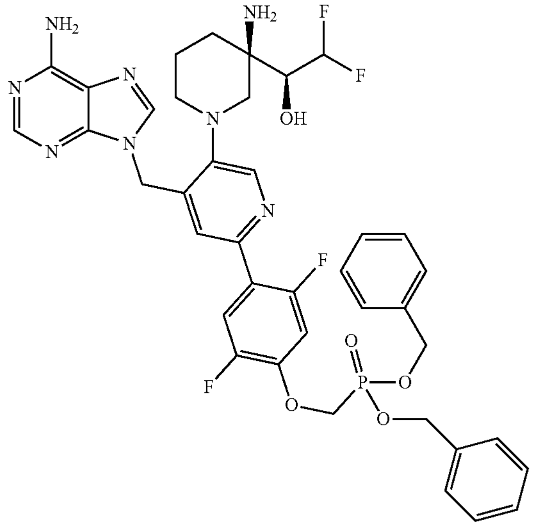 [SMILES: Nc1ncnc2c1ncn2Cc1cc(-c2cc(F)c(OCP(=O)(OCc3ccccc3)OCc3ccccc3)cc2F)ncc1N1CCC[C@](N)([C@H](O)C(F)F)C1] |
| I-30 | 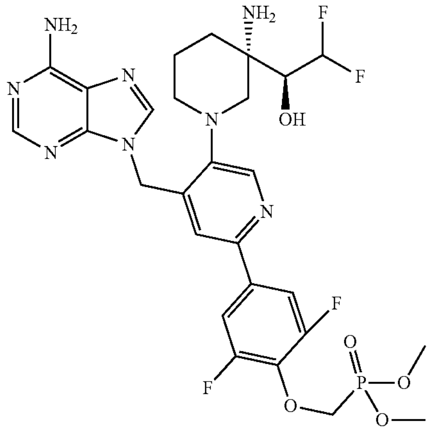 [SMILES: COP(=O)(COc1c(F)cc(-c2cc(Cn3cnc4c(N)ncnc43)c(N3CCC[C@@](N)([C@H](O)C(F)F)C3)cn2)cc1F)OC] |
| I-31 | 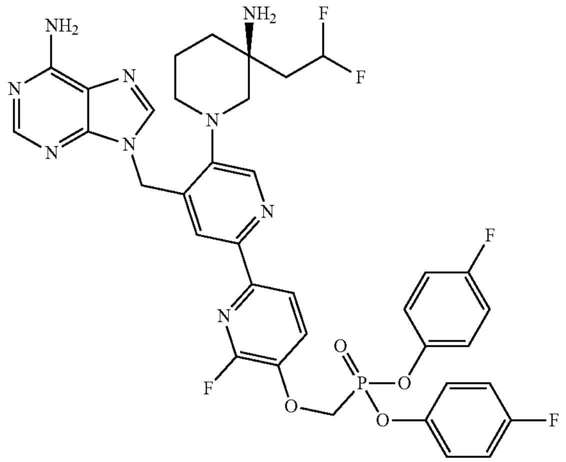 [SMILES: Nc1ncnc2c1ncn2Cc1cc(-c2ccc(OCP(=O)(Oc3ccc(F)cc3)Oc3ccc(F)cc3)c(F)n2)ncc1N1CCC[C@](N)(CC(F)F)C1] |

TABLE 1-continued
| Compound No. | Chemical Structure |
| --- | --- |
| I-32 | 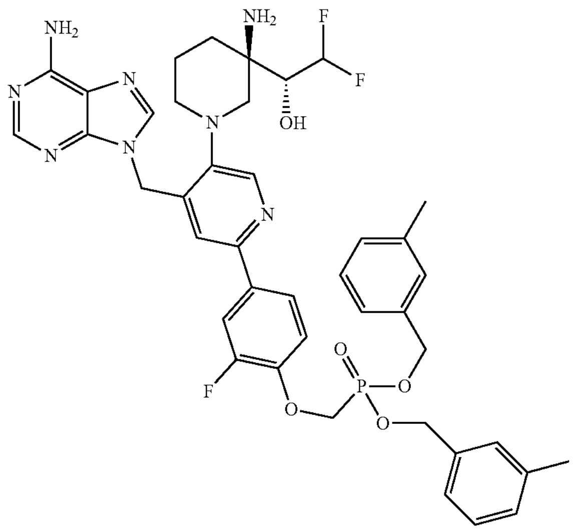 [SMILES: Cc1cccc(COP(=O)(COc2ccc(-c3cc(Cn4cnc5c(N)ncnc54)c(N4CCC[C@](N)([C@@H](O)C(F)F)C4)cn3)cc2F)OCc2cccc(C)c2)c1] |
| I-33 | 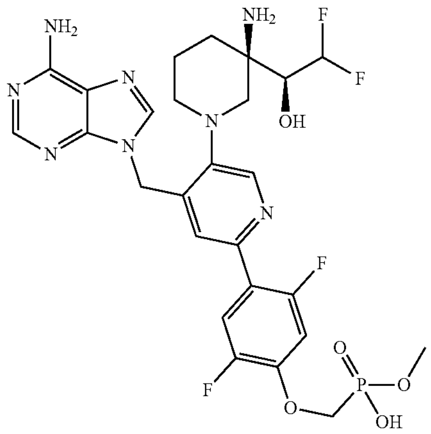 [SMILES: COP(=O)(O)COc1cc(F)c(-c2cc(Cn3cnc4c(N)ncnc43)c(N3CCC[C@](N)([C@H](O)C(F)F)C3)cn2)cc1F] |
| I-34 | 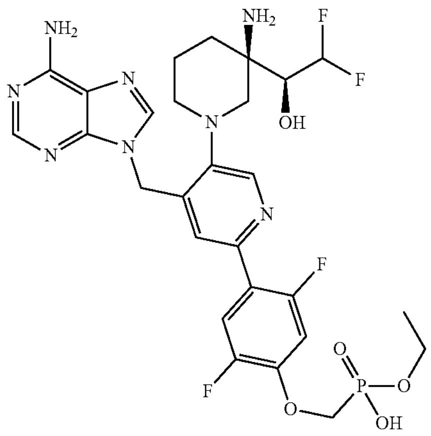 [SMILES: CCOP(=O)(O)COc1cc(F)c(-c2cc(Cn3cnc4c(N)ncnc43)c(N3CCC[C@](N)([C@H](O)C(F)F)C3)cn2)cc1F] |

TABLE 1-continued
| Compound No. | Chemical Structure |
| --- | --- |
| I-35 | 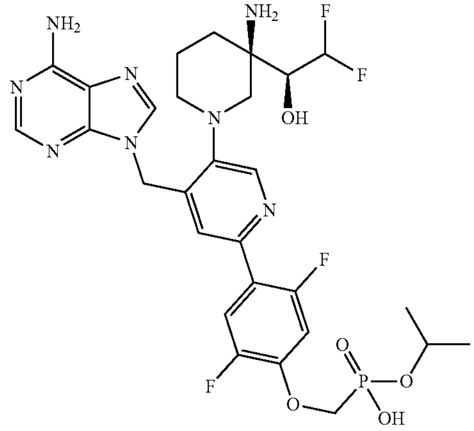 [SMILES: CC(C)OP(=O)(O)COc1cc(F)c(-c2cc(Cn3cnc4c(N)ncnc43)c(N3CCC[C@](N)([C@H](O)C(F)F)C3)cn2)cc1F] |
| I-36 | 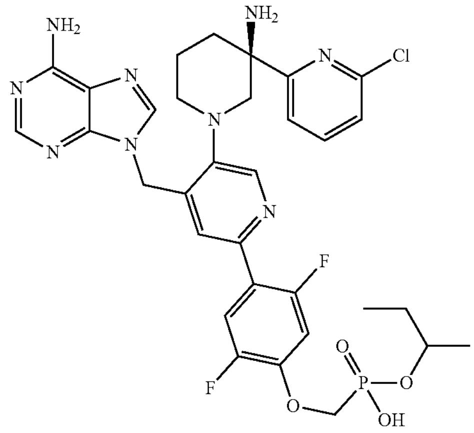 [SMILES: CCC(C)OP(=O)(O)COc1cc(F)c(-c2cc(Cn3cnc4c(N)ncnc43)c(N3CCC[C@](N)(c4cccc(Cl)n4)C3)cn2)cc1F] |
| I-37 | 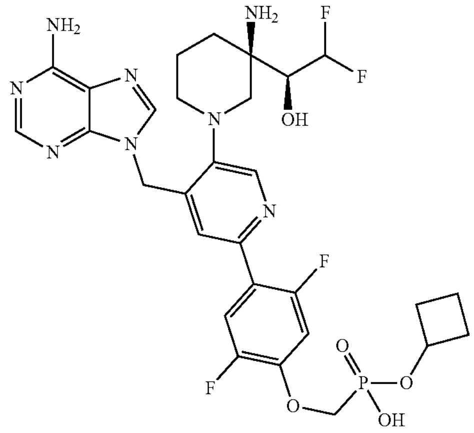 [SMILES: Nc1ncnc2c1ncn2Cc1cc(-c2cc(F)c(OCP(=O)(O)OC3CCC3)cc2F)ncc1N1CCC[C@](N)([C@H](O)C(F)F)C1] |

TABLE 1-continued
| Compound No. | Chemical Structure |
|---|---|
| I-38 | 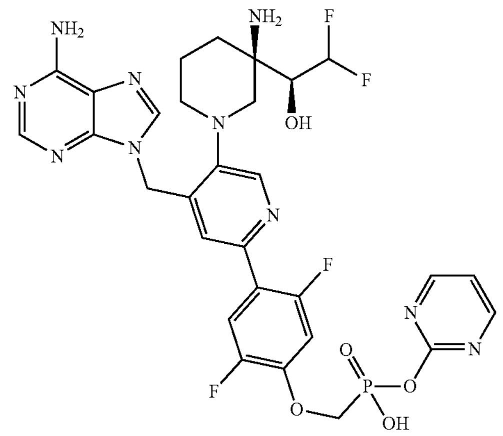 [SMILES: Nc1ncnc2c1ncn2Cc1cc(-c2cc(F)c(OCP(=O)(O)Oc3ncccn3)cc2F)ncc1N1CCC[C@](N)([C@H](O)C(F)F)C1] |
| I-39 | 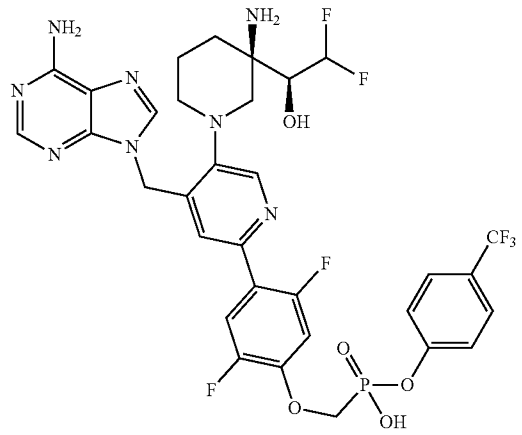 [SMILES: Nc1ncnc2c1ncn2Cc1cc(-c2cc(F)c(OCP(=O)(O)Oc3ccc(C(F)(F)F)cc3)cc2F)ncc1N1CCC[C@](N)([C@H](O)C(F)F)C1] |
| I-40 | 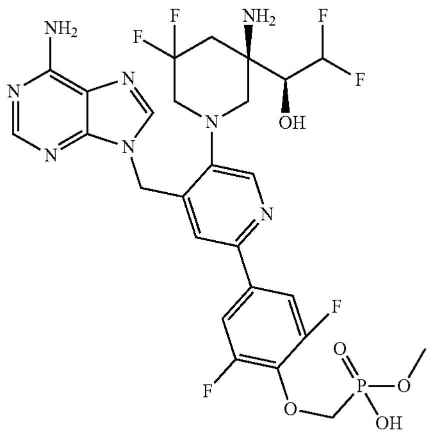 [SMILES: COP(=O)(O)COc1c(F)cc(-c2cc(Cn3cnc4c(N)ncnc43)c(N3CC(F)(F)C[C@](N)([C@H](O)C(F)F)C3)cn2)cc1F] |

TABLE 1-continued
| Compound No. | Chemical Structure |
|---|---|
| I-41 | 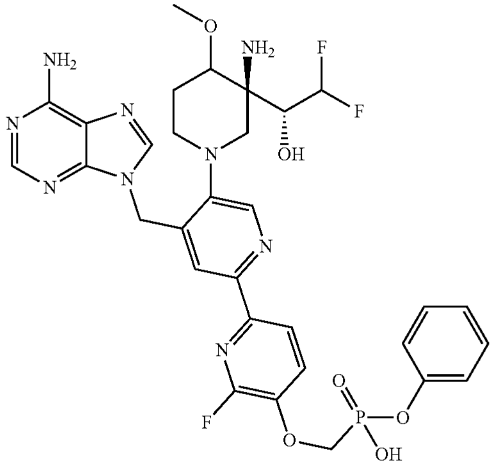 [SMILES: COC1CCN(c2cnc(-c3ccc(OCP(=O)(O)Oc4ccccc4)c(F)n3)cc2Cn2cnc3c(N)ncnc32)C[C@@]1(N)[C@@H](O)C(F)F] |
| I-42 | 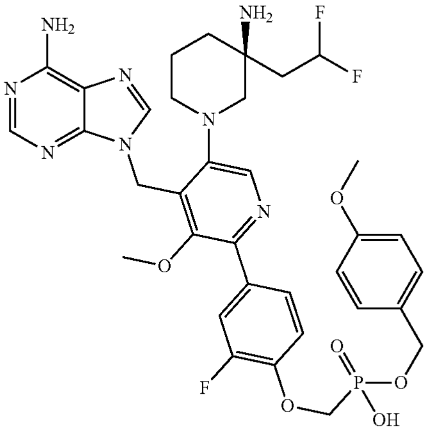 [SMILES: COc1ccc(COP(=O)(O)COc2ccc(-c3ncc(N4CCC[C@](N)(CC(F)F)C4)c(Cn4cnc5c(N)ncnc54)c3OC)cc2F)cc1] |
| I-43 | 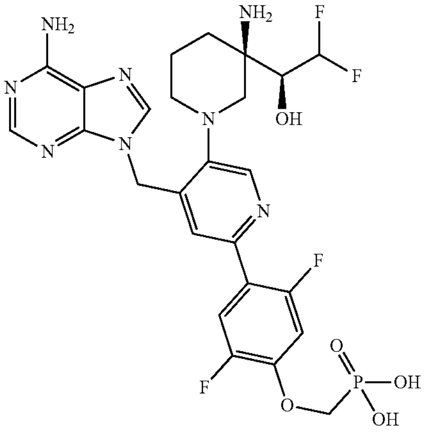 [SMILES: Nc1ncnc2c1ncn2Cc1cc(-c2cc(F)c(OCP(=O)(O)O)cc2F)ncc1N1CCC[C@](N)([C@H](O)C(F)F)C1] |

TABLE 1-continued
| Compound No. | Chemical Structure |
|---|---|
| I-44 | 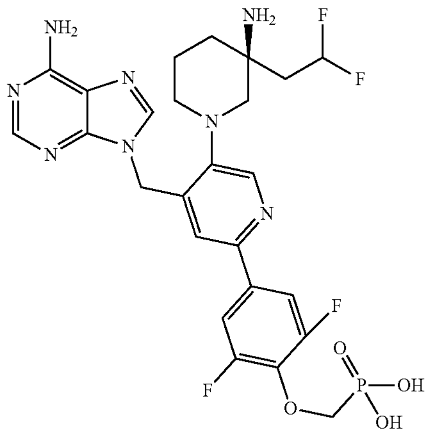 [SMILES: Nc1ncnc2c1ncn2Cc1cc(-c2cc(F)c(OCP(=O)(O)O)c(F)c2)ncc1N1CCC[C@](N)(CC(F)F)C1] |
| I-45 | 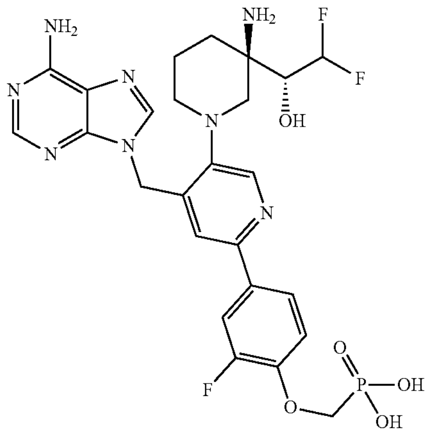 [SMILES: Nc1ncnc2c1ncn2Cc1cc(-c2ccc(OCP(=O)(O)O)c(F)c2)ncc1N1CCC[C@](N)([C@@H](O)C(F)F)C1] |
TABLE 2
| Compound | Chemical Structure |
|---|---|
| II-1 | 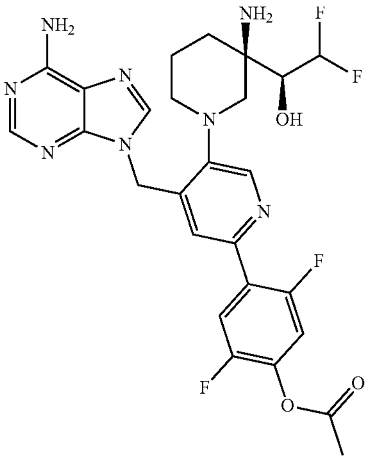 [SMILES: CC(=O)Oc1cc(F)c(-c2cc(Cn3cnc4c(N)ncnc43)c(N3CCC[C@](N)([C@H](O)C(F)F)C3)cn2)cc1F] |

TABLE 2-continued
| Compound | Chemical Structure |
| --- | --- |
| II-2 | 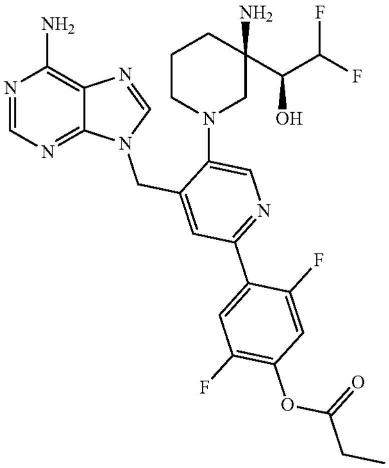 [SMILES: CCC(=O)Oc1cc(F)c(-c2cc(Cn3cnc4c(N)ncnc43)c(N3CCC[C@](N)([C@H](O)C(F)F)C3)cn2)cc1F] |
| II-3 | 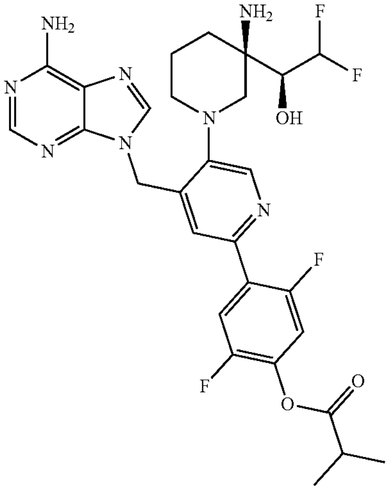 [SMILES: CC(C)C(=O)Oc1cc(F)c(-c2cc(Cn3cnc4c(N)ncnc43)c(N3CCC[C@](N)([C@H](O)C(F)F)C3)cn2)cc1F] |
| II-4 | 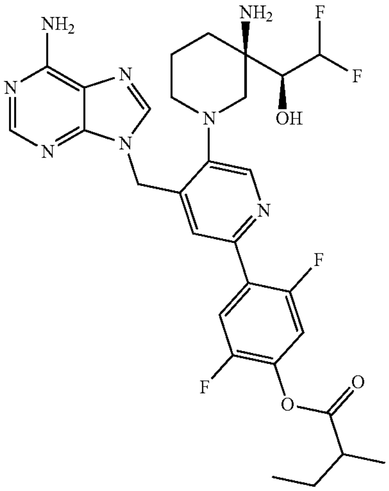 [SMILES: CCC(C)C(=O)Oc1cc(F)c(-c2cc(Cn3cnc4c(N)ncnc43)c(N3CCC[C@](N)([C@H](O)C(F)F)C3)cn2)cc1F] |

TABLE 2-continued
| Compound | Chemical Structure |
|---|---|
| II-5 | 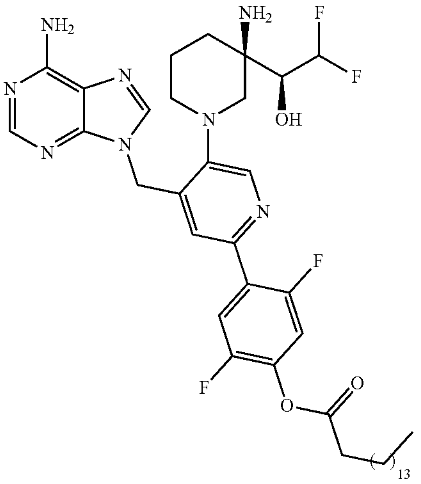 |
| II-6 | 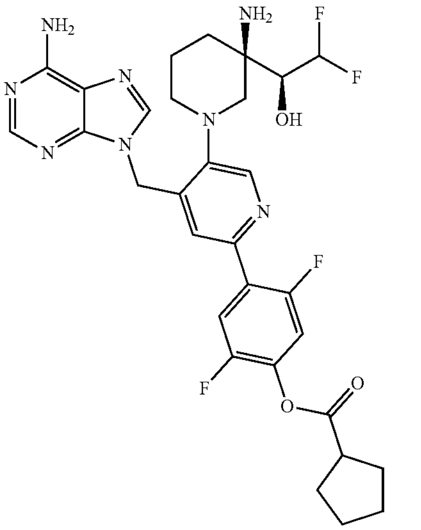 [SMILES: Nc1ncnc2c1ncn2Cc1cc(-c2cc(F)c(OC(=O)C3CCCC3)cc2F)ncc1N1CCC[C@](N)([C@H](O)C(F)F)C1] |
| II-7 | 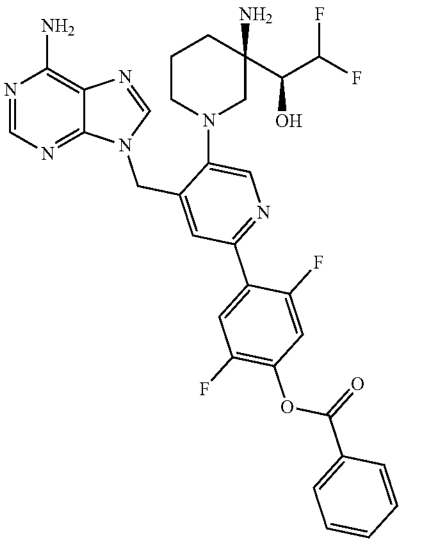 [SMILES: Nc1ncnc2c1ncn2Cc1cc(-c2cc(F)c(OC(=O)c3ccccc3)cc2F)ncc1N1CCC[C@](N)([C@H](O)C(F)F)C1] |

TABLE 2-continued
| Compound | Chemical Structure |
|---|---|
| II-8 | 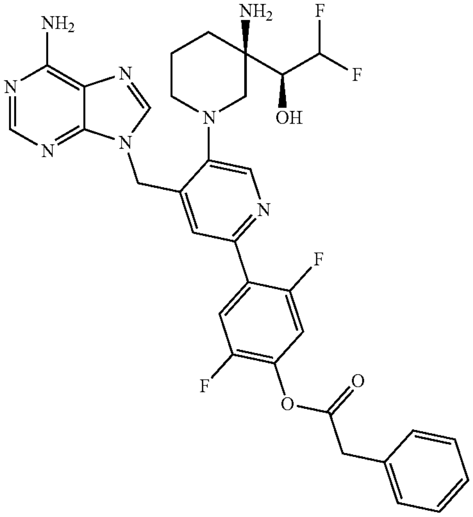 [SMILES: Nc1ncnc2c1ncn2Cc1cc(-c2cc(F)c(OC(=O)Cc3ccccc3)cc2F)ncc1N1CCC[C@](N)([C@H](O)C(F)F)C1] |
| II-9 | 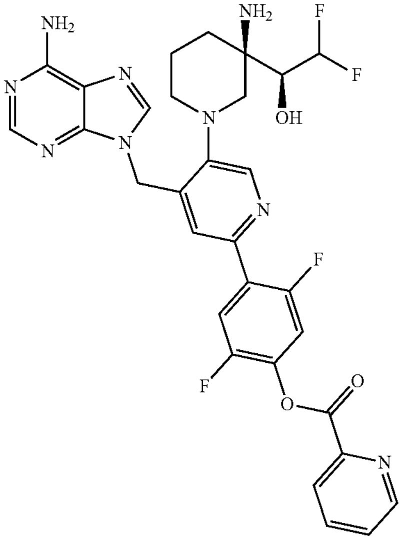 [SMILES: Nc1ncnc2c1ncn2Cc1cc(-c2cc(F)c(OC(=O)c3ccccn3)cc2F)ncc1N1CCC[C@](N)([C@H](O)C(F)F)C1] |
| II-10 | 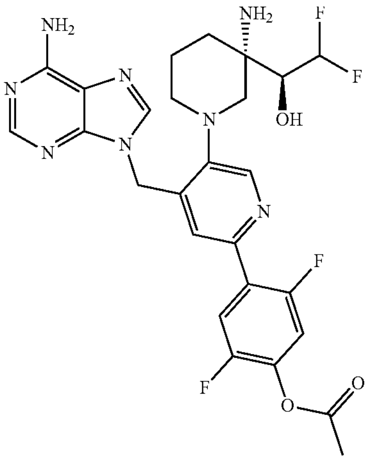 [SMILES: CC(=O)Oc1cc(F)c(-c2cc(Cn3cnc4c(N)ncnc43)c(N3CCC[C@@](N)([C@H](O)C(F)F)C3)cn2)cc1F] |

TABLE 2-continued
| Compound | Chemical Structure |
| --- | --- |
| II-11 | 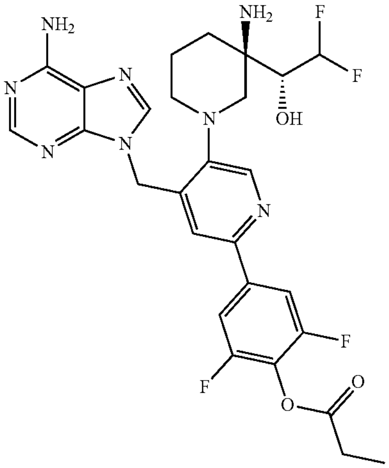 [SMILES: CCC(=O)Oc1c(F)cc(-c2cc(Cn3cnc4c(N)ncnc43)c(N3CCC[C@](N)([C@@H](O)C(F)F)C3)cn2)cc1F] |
| II-12 | 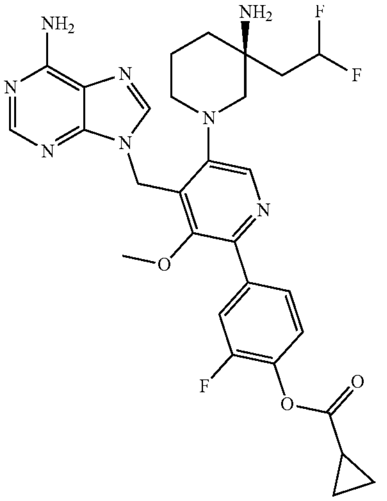 [SMILES: COc1c(-c2ccc(OC(=O)C3CC3)c(F)c2)ncc(N2CCC[C@](N)(CC(F)F)C2)c1Cn1cnc2c(N)ncnc21] |
| II-13 | 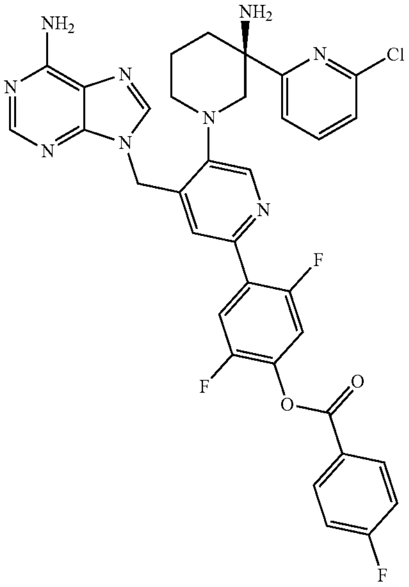 [SMILES: Nc1ncnc2c1ncn2Cc1cc(-c2cc(F)c(OC(=O)c3ccc(F)cc3)cc2F)ncc1N1CCC[C@](N)(c2cccc(Cl)n2)C1] |

TABLE 2-continued
| Compound | Chemical Structure |
| --- | --- |
| II-14 | 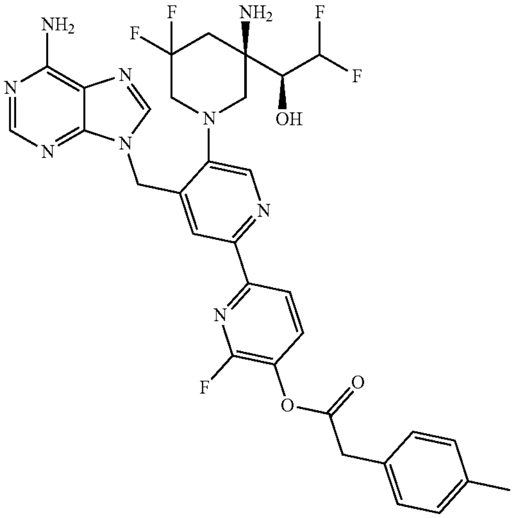 [SMILES: Cc1ccc(CC(=O)Oc2ccc(-c3cc(Cn4cnc5c(N)ncnc54)c(N4CC(F)(F)C[C@](N)([C@H](O)C(F)F)C4)cn3)nc2F)cc1] |
| II-15 | 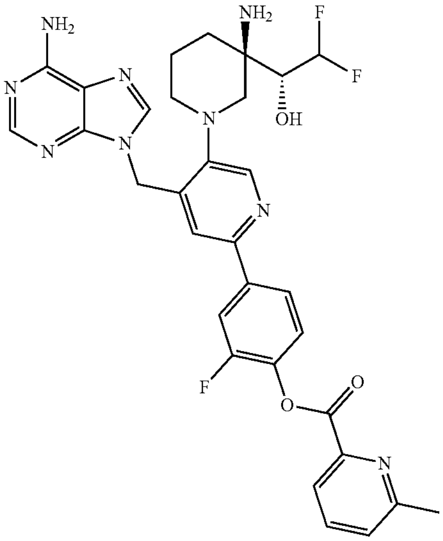 [SMILES: Cc1cccc(C(=O)Oc2ccc(-c3cc(Cn4cnc5c(N)ncnc54)c(N4CCC[C@](N)([C@@H](O)C(F)F)C4)cn3)cc2F)n1] |
| II-16 | 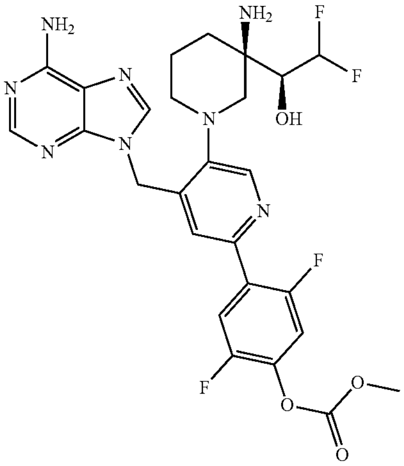 [SMILES: COC(=O)Oc1cc(F)c(-c2cc(Cn3cnc4c(N)ncnc43)c(N3CCC[C@](N)([C@H](O)C(F)F)C3)cn2)cc1F] |

TABLE 2-continued
| Compound | Chemical Structure |
|---|---|
| II-17 | 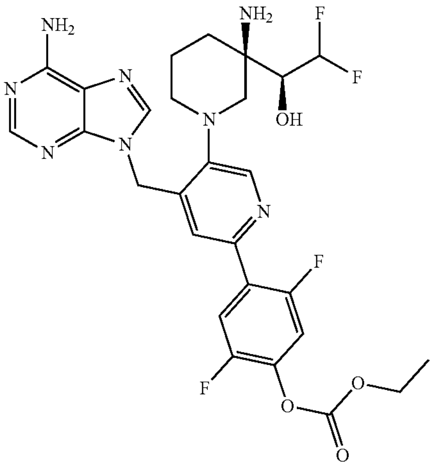 [SMILES: CCOC(=O)Oc1cc(F)c(-c2cc(Cn3cnc4c(N)ncnc43)c(N3CCC[C@](N)([C@H](O)C(F)F)C3)cn2)cc1F] |
| II-18 | 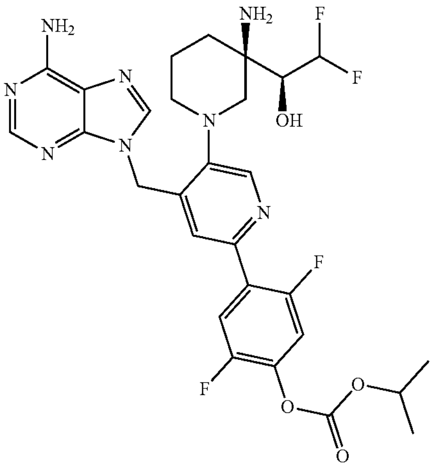 [SMILES: CC(C)OC(=O)Oc1cc(F)c(-c2cc(Cn3cnc4c(N)ncnc43)c(N3CCC[C@](N)([C@H](O)C(F)F)C3)cn2)cc1F] |
| II-19 | 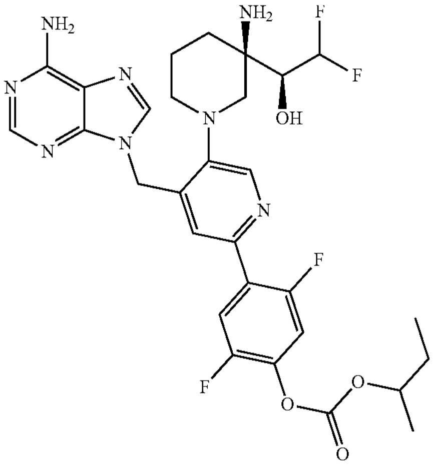 [SMILES: CCC(C)OC(=O)Oc1cc(F)c(-c2cc(Cn3cnc4c(N)ncnc43)c(N3CCC[C@](N)([C@H](O)C(F)F)C3)cn2)cc1F] |

TABLE 2-continued
| Compound | Chemical Structure |
| --- | --- |
| II-20 | 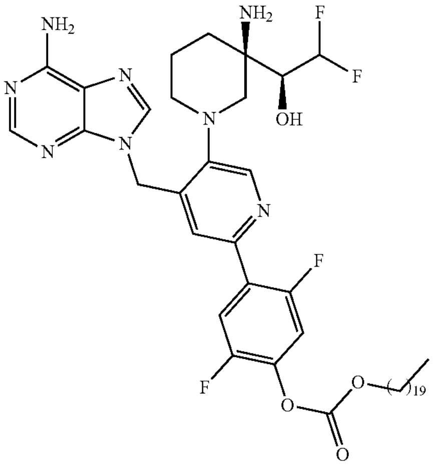 |
| II-21 | 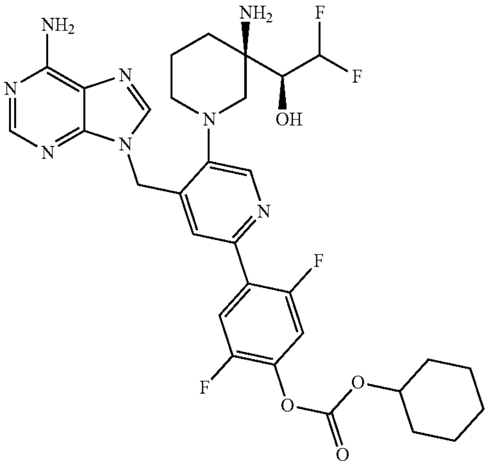 [SMILES: Nc1ncnc2c1ncn2Cc1cc(-c2cc(F)c(OC(=O)OC3CCCCC3)cc2F)ncc1N1CCC[C@](N)([C@H](O)C(F)F)C1] |
| II-22 | 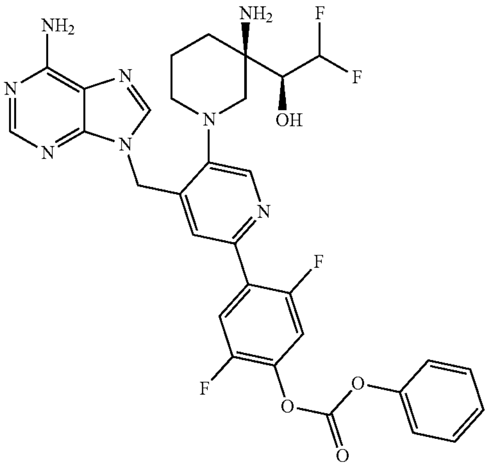 [SMILES: Nc1ncnc2c1ncn2Cc1cc(-c2cc(F)c(OC(=O)Oc3ccccc3)cc2F)ncc1N1CCC[C@](N)([C@H](O)C(F)F)C1] |

TABLE 2-continued
| Compound | Chemical Structure |
| --- | --- |
| II-23 | 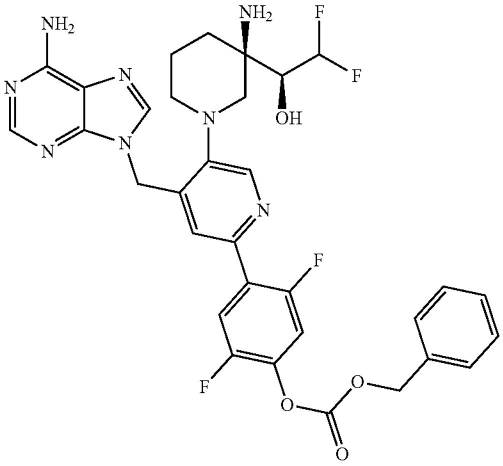 [SMILES: Nc1ncnc2c1ncn2Cc1cc(-c2cc(F)c(OC(=O)OCc3ccccc3)cc2F)ncc1N1CCC[C@](N)([C@H](O)C(F)F)C1] |
| II-24 | 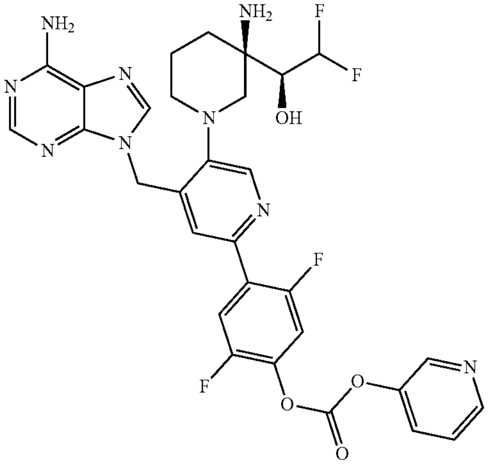 [SMILES: Nc1ncnc2c1ncn2Cc1cc(-c2cc(F)c(OC(=O)Oc3cccnc3)cc2F)ncc1N1CCC[C@](N)([C@H](O)C(F)F)C1] |
| II-25 | 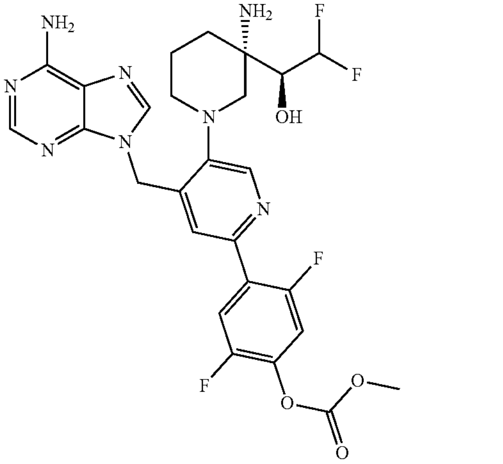 [SMILES: COC(=O)Oc1cc(F)c(-c2cc(Cn3cnc4c(N)ncnc43)c(N3CCC[C@@](N)([C@H](O)C(F)F)C3)cn2)cc1F] |

TABLE 2-continued
| Compound | Chemical Structure |
| --- | --- |
| II-26 | 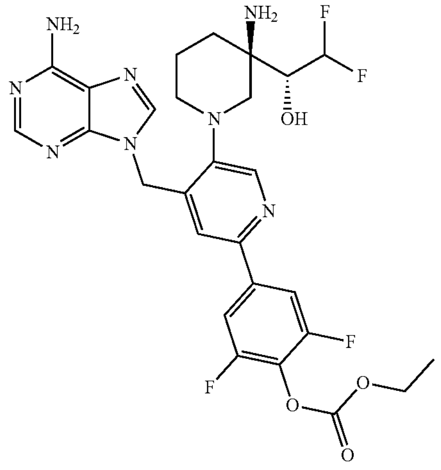 [SMILES: CCOC(=O)Oc1c(F)cc(-c2cc(Cn3cnc4c(N)ncnc43)c(N3CCC[C@](N)([C@@H](O)C(F)F)C3)cn2)cc1F] |
| II-27 | 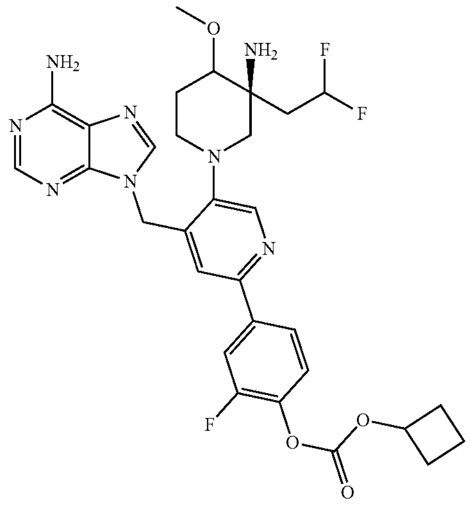 [SMILES: COC1CCN(c2cnc(-c3ccc(OC(=O)OC4CCC4)c(F)c3)cc2Cn2cnc3c(N)ncnc32)C[C@@]1(N)CC(F)F] |
| II-28 | 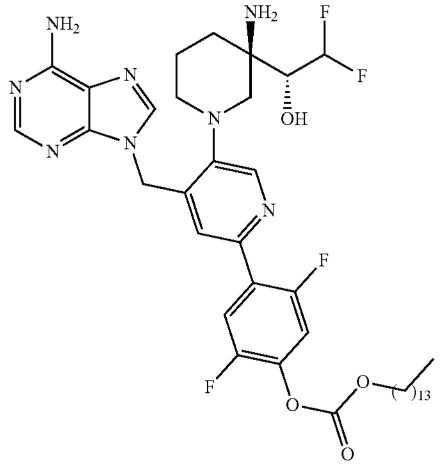 |

TABLE 2-continued
| Compound | Chemical Structure |
| --- | --- |
| II-29 | 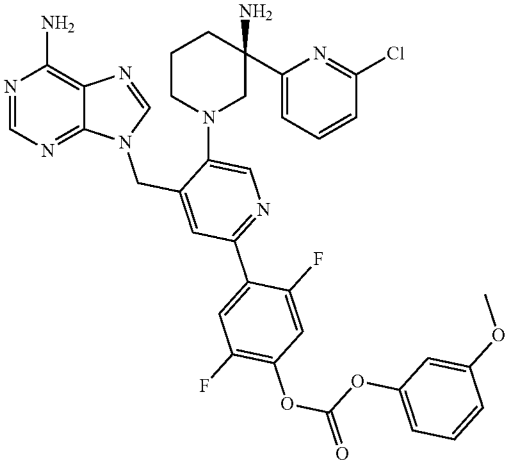 [SMILES: COc1cccc(OC(=O)Oc2cc(F)c(-c3cc(Cn4cnc5c(N)ncnc54)c(N4CCC[C@](N)(c5cccc(Cl)n5)C4)cn3)cc2F)c1] |
| II-30 | 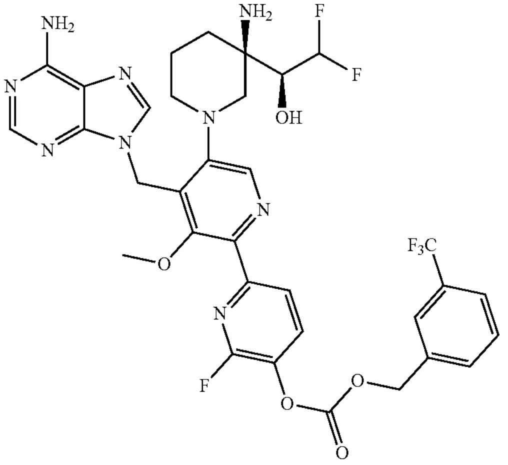 [SMILES: COc1c(-c2ccc(OC(=O)OCc3cccc(C(F)(F)F)c3)c(F)n2)ncc(N2CCC[C@](N)([C@H](O)C(F)F)C2)c1Cn1cnc2c(N)ncnc21] |
| II-31 | 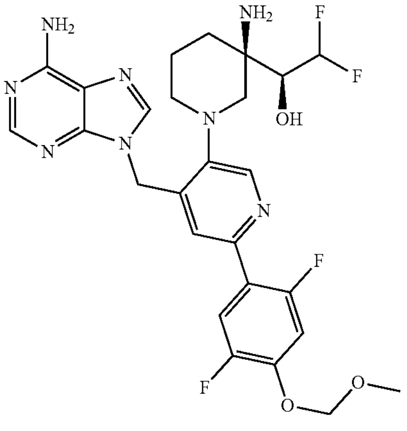 [SMILES: COCOc1cc(F)c(-c2cc(Cn3cnc4c(N)ncnc43)c(N3CCC[C@](N)([C@H](O)C(F)F)C3)cn2)cc1F] |

TABLE 2-continued
| Compound | Chemical Structure |
|---|---|
| II-32 | 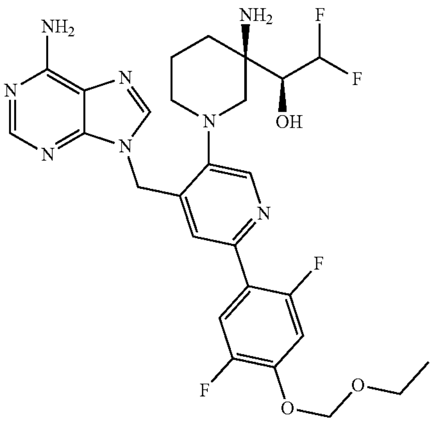 [SMILES: CCOCOc1cc(F)c(-c2cc(Cn3cnc4c(N)ncnc43)c(N3CCC[C@](N)([C@H](O)C(F)F)C3)cn2)cc1F] |
| II-33 | 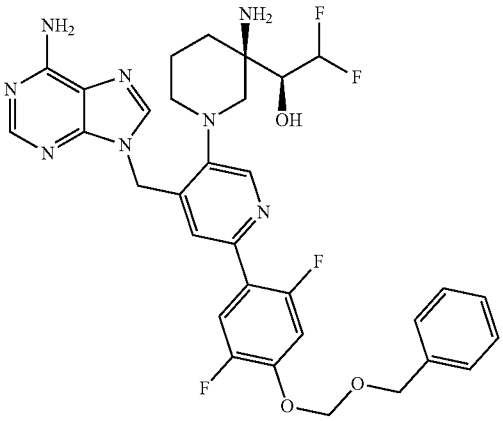 [SMILES: Nc1ncnc2c1ncn2Cc1cc(-c2cc(F)c(OCOCc3ccccc3)cc2F)ncc1N1CCC[C@](N)([C@H](O)C(F)F)C1] |
| II-34 | 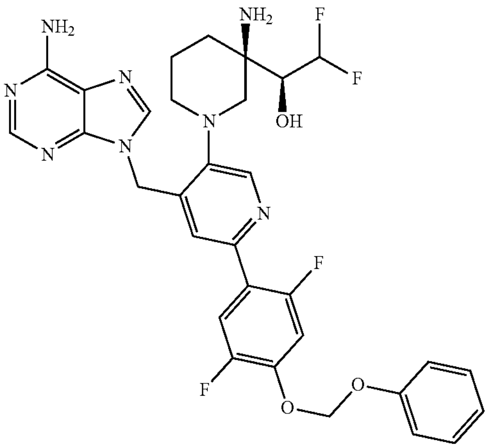 [SMILES: Nc1ncnc2c1ncn2Cc1cc(-c2cc(F)c(OCOc3ccccc3)cc2F)ncc1N1CCC[C@](N)([C@H](O)C(F)F)C1] |

TABLE 2-continued
| Compound | Chemical Structure |
|---|---|
| II-35 | 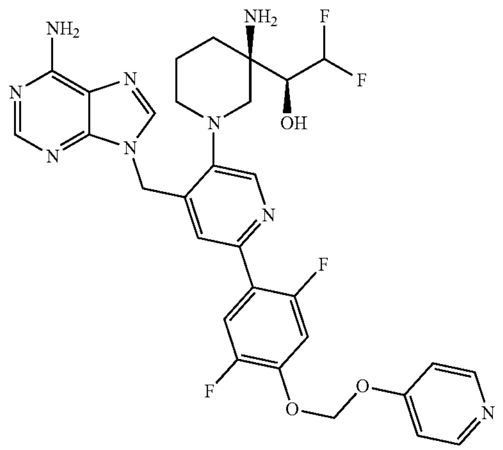 [SMILES: Nc1ncnc2c1ncn2Cc1cc(-c2cc(F)c(OCOc3ccncc3)cc2F)ncc1N1CCC[C@](N)([C@H](O)C(F)F)C1] |
| II-36 | 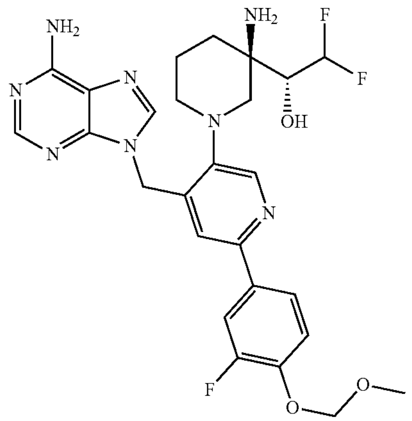 [SMILES: COCOc1ccc(-c2cc(Cn3cnc4c(N)ncnc43)c(N3CCC[C@](N)([C@@H](O)C(F)F)C3)cn2)cc1F] |
| II-37 | 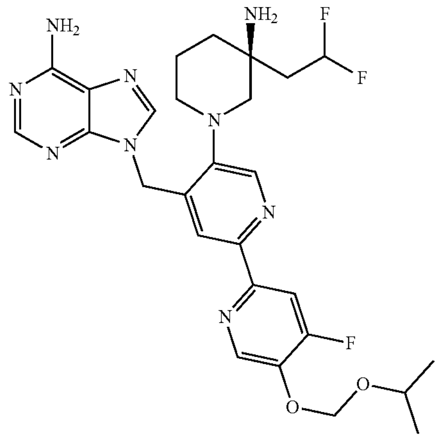 [SMILES: CC(C)OCOc1cnc(-c2cc(Cn3cnc4c(N)ncnc43)c(N3CCC[C@](N)(CC(F)F)C3)cn2)cc1F] |

TABLE 2-continued
| Compound | Chemical Structure |
|---|---|
| II-38 | 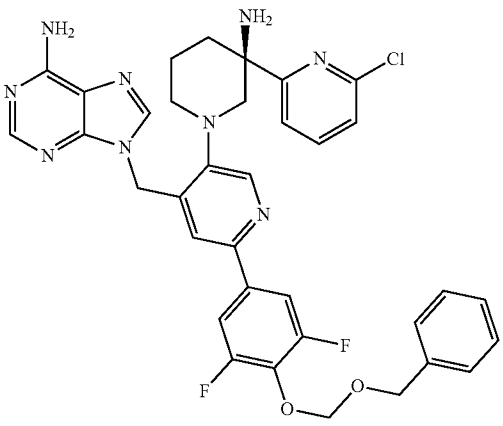 [SMILES: Nc1ncnc2c1ncn2Cc1cc(-c2cc(F)c(OCOCc3ccccc3)c(F)c2)ncc1N1CCC[C@](N)(c2cccc(Cl)n2)C1] |
| II-39 | 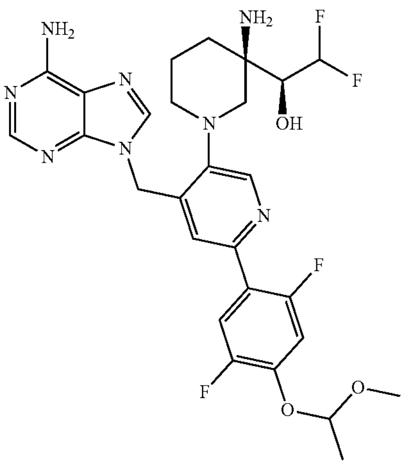 [SMILES: COC(C)Oc1cc(F)c(-c2cc(Cn3cnc4c(N)ncnc43)c(N3CCC[C@](N)([C@H](O)C(F)F)C3)cn2)cc1F] |
| II-40 | 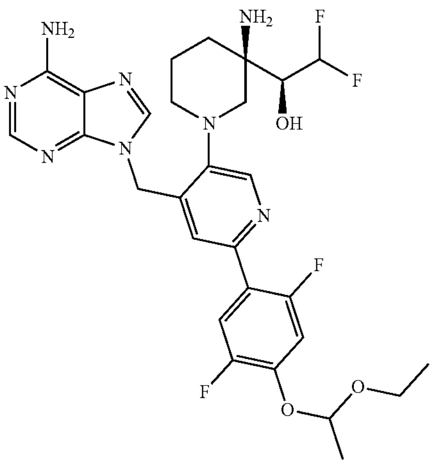 [SMILES: CCOC(C)Oc1cc(F)c(-c2cc(Cn3cnc4c(N)ncnc43)c(N3CCC[C@](N)([C@H](O)C(F)F)C3)cn2)cc1F] |

TABLE 2-continued
| Compound | Chemical Structure |
| --- | --- |
| II-41 | 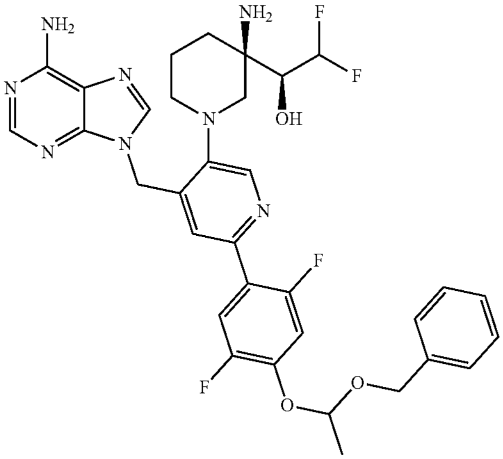 [SMILES: CC(OCc1ccccc1)Oc1cc(F)c(-c2cc(Cn3cnc4c(N)ncnc43)c(N3CCC[C@](N)([C@H](O)C(F)F)C3)cn2)cc1F] |
| II-42 | 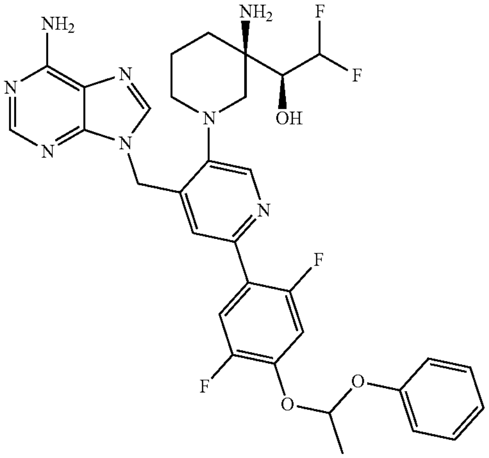 [SMILES: CC(Oc1ccccc1)Oc1cc(F)c(-c2cc(Cn3cnc4c(N)ncnc43)c(N3CCC[C@](N)([C@H](O)C(F)F)C3)cn2)cc1F] |
| II-43 | 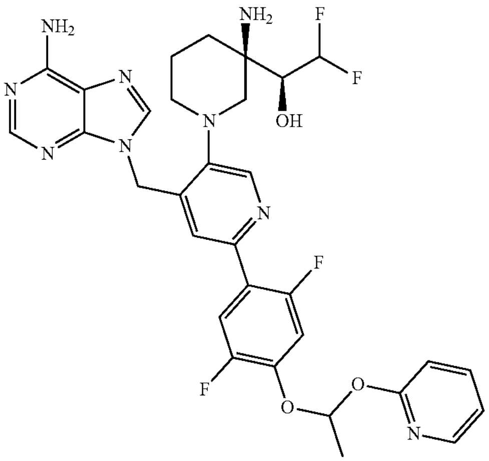 [SMILES: CC(Oc1ccccn1)Oc1cc(F)c(-c2cc(Cn3cnc4c(N)ncnc43)c(N3CCC[C@](N)([C@H](O)C(F)F)C3)cn2)cc1F] |

TABLE 2-continued
| Compound | Chemical Structure |
| --- | --- |
| II-44 | 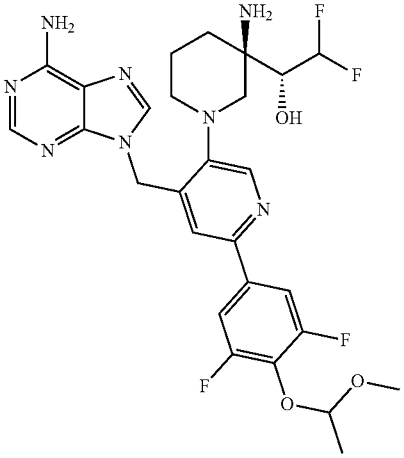 [SMILES: COC(C)Oc1c(F)cc(-c2cc(Cn3cnc4c(N)ncnc43)c(N3CCC[C@](N)([C@@H](O)C(F)F)C3)cn2)cc1F] |
| II-45 | 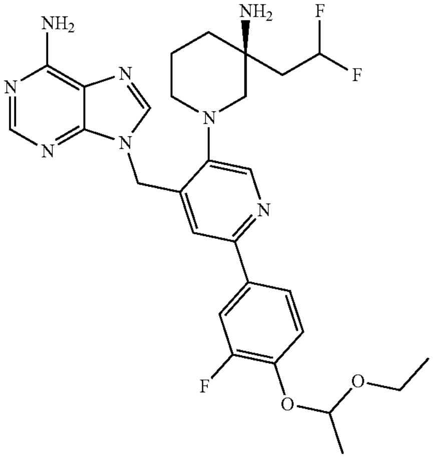 [SMILES: CCOC(C)Oc1ccc(-c2cc(Cn3cnc4c(N)ncnc43)c(N3CCC[C@](N)(CC(F)F)C3)cn2)cc1F] |
| II-46 | 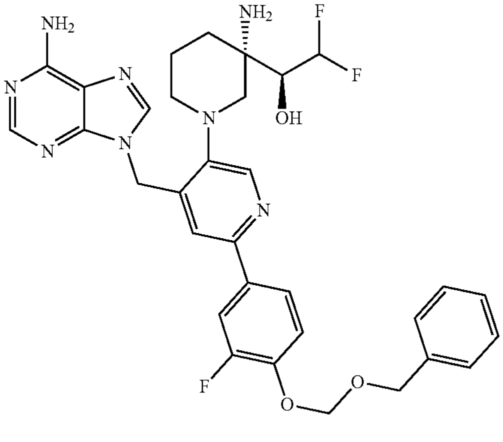 [SMILES: Nc1ncnc2c1ncn2Cc1cc(-c2ccc(OCOCc3ccccc3)c(F)c2)ncc1N1CCC[C@@](N)([C@H](O)C(F)F)C1] |

TABLE 2-continued
| Compound | Chemical Structure |
| --- | --- |
| II-47 | 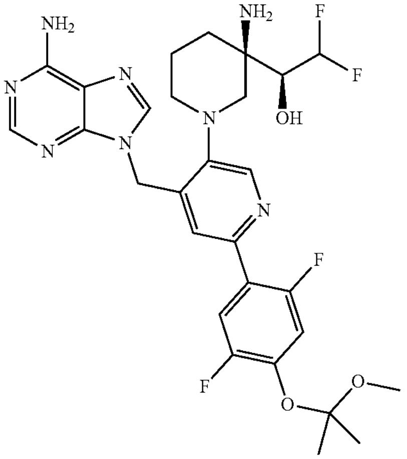 [SMILES: COC(C)(C)Oc1cc(F)c(-c2cc(Cn3cnc4c(N)ncnc43)c(N3CCC[C@](N)([C@H](O)C(F)F)C3)cn2)cc1F] |
| II-48 | 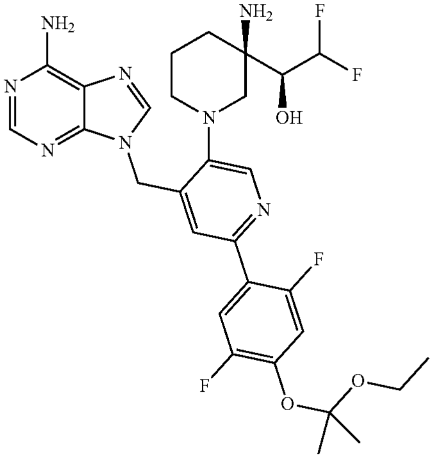 [SMILES: CCOC(C)(C)Oc1cc(F)c(-c2cc(Cn3cnc4c(N)ncnc43)c(N3CCC[C@](N)([C@H](O)C(F)F)C3)cn2)cc1F] |
| II-49 | 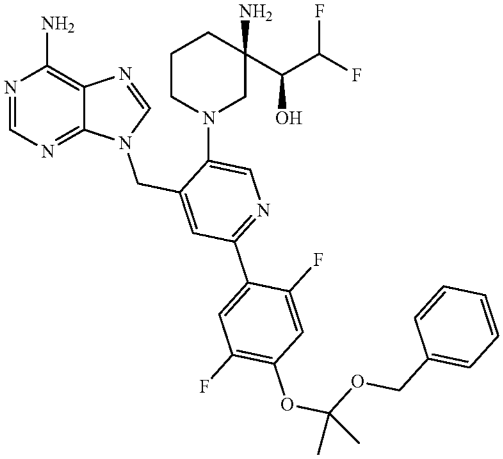 [SMILES: CC(C)(OCc1ccccc1)Oc1cc(F)c(-c2cc(Cn3cnc4c(N)ncnc43)c(N3CCC[C@](N)([C@H](O)C(F)F)C3)cn2)cc1F] |

TABLE 2-continued
| Compound | Chemical Structure |
|---|---|
| II-50 | 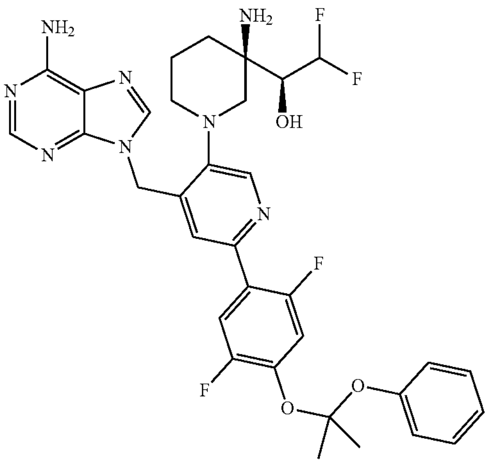 [SMILES: CC(C)(Oc1ccccc1)Oc1cc(F)c(-c2cc(Cn3cnc4c(N)ncnc43)c(N3CCC[C@](N)([C@H](O)C(F)F)C3)cn2)cc1F] |
| II-51 | 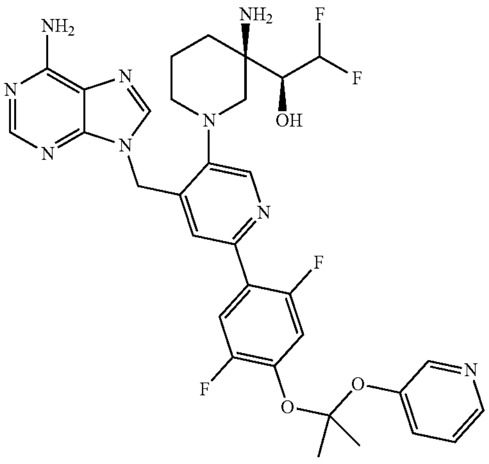 [SMILES: CC(C)(Oc1cccnc1)Oc1cc(F)c(-c2cc(Cn3cnc4c(N)ncnc43)c(N3CCC[C@](N)([C@H](O)C(F)F)C3)cn2)cc1F] |
| II-52 | 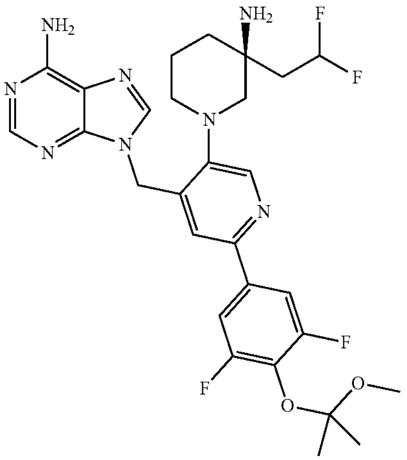 [SMILES: COC(C)(C)Oc1c(F)cc(-c2cc(Cn3cnc4c(N)ncnc43)c(N3CCC[C@](N)(CC(F)F)C3)cn2)cc1F] |

TABLE 2-continued
| Compound | Chemical Structure |
| --- | --- |
| II-53 | 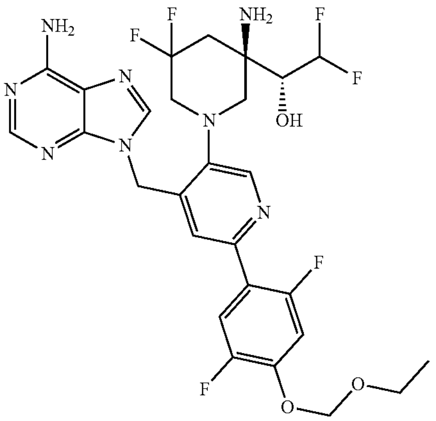 [SMILES: CCOCOc1cc(F)c(-c2cc(Cn3cnc4c(N)ncnc43)c(N3CC(F)(F)C[C@](N)([C@@H](O)C(F)F)C3)cn2)cc1F] |
| II-54 | 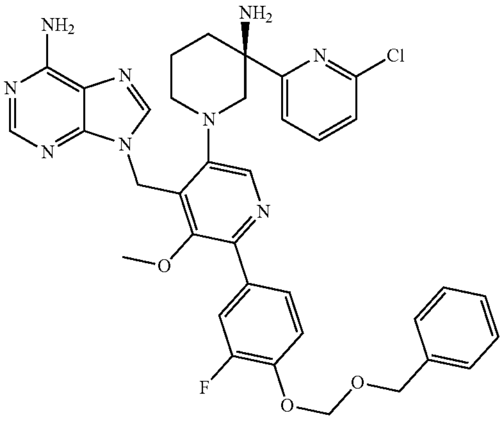 [SMILES: COc1c(-c2ccc(OCOCc3ccccc3)c(F)c2)ncc(N2CCC[C@](N)(c3cccc(Cl)n3)C2)c1Cn1cnc2c(N)ncnc21] |
| II-55 | 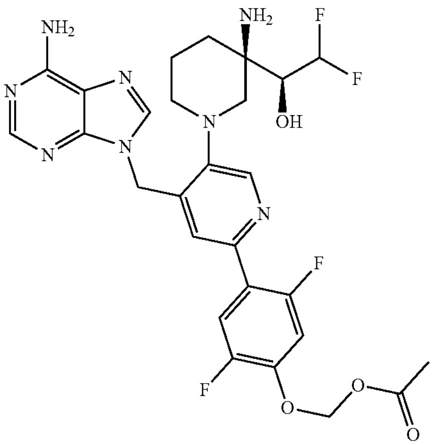 [SMILES: CC(=O)OCOc1cc(F)c(-c2cc(Cn3cnc4c(N)ncnc43)c(N3CCC[C@](N)([C@H](O)C(F)F)C3)cn2)cc1F] |

TABLE 2-continued
| Compound | Chemical Structure |
| --- | --- |
| II-56 | 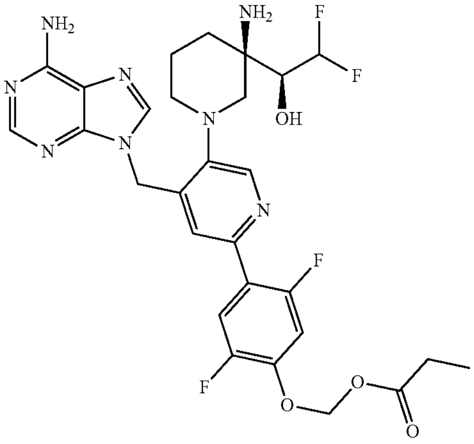 [SMILES: CCC(=O)OCOc1cc(F)c(-c2cc(Cn3cnc4c(N)ncnc43)c(N3CCC[C@](N)([C@H](O)C(F)F)C3)cn2)cc1F] |
| II-57 | 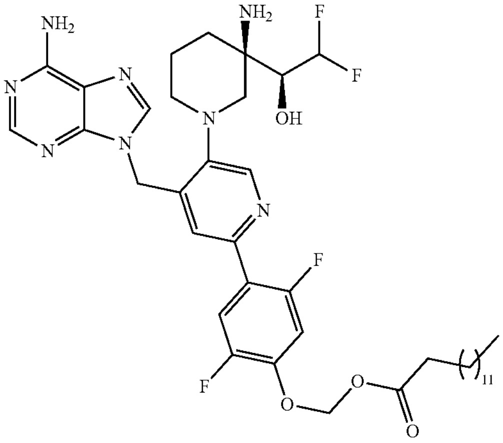 |
| II-58 | 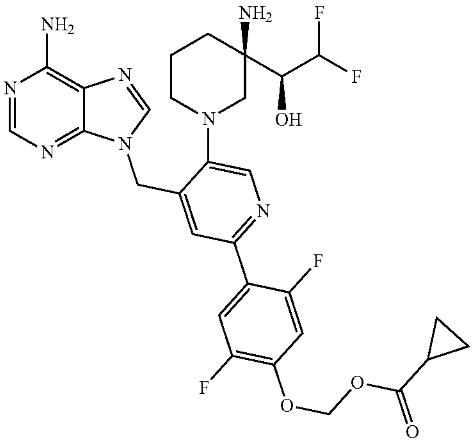 [SMILES: Nc1ncnc2c1ncn2Cc1cc(-c2cc(F)c(OCOC(=O)C3CC3)cc2F)ncc1N1CCC[C@](N)([C@H](O)C(F)F)C1] |

TABLE 2-continued
| Compound | Chemical Structure |
| --- | --- |
| II-59 | 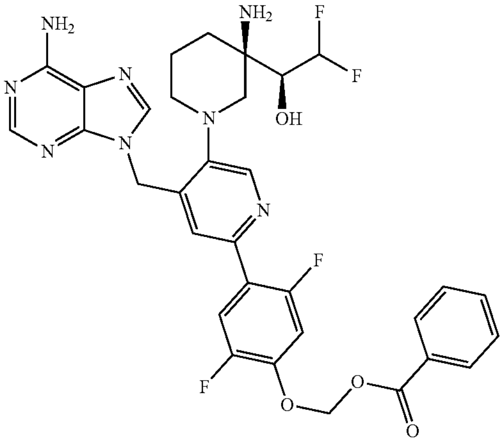 [SMILES: Nc1ncnc2c1ncn2Cc1cc(-c2cc(F)c(OCOC(=O)c3ccccc3)cc2F)ncc1N1CCC[C@](N)([C@H](O)C(F)F)C1] |
| II-60 | 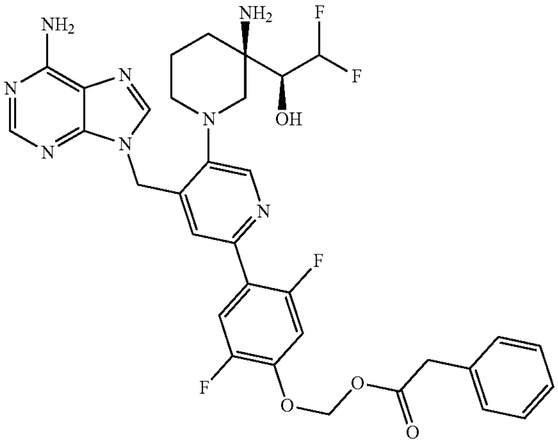 [SMILES: Nc1ncnc2c1ncn2Cc1cc(-c2cc(F)c(OCOC(=O)Cc3ccccc3)cc2F)ncc1N1CCC[C@](N)([C@H](O)C(F)F)C1] |
| II-61 | 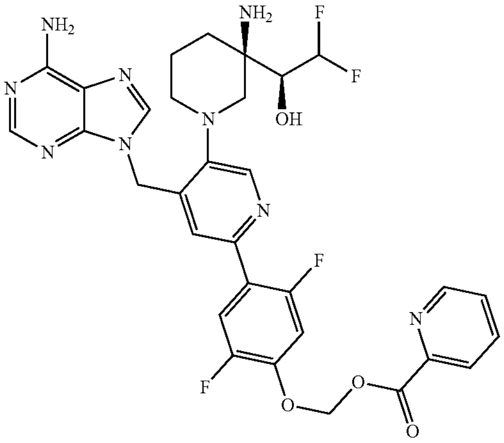 [SMILES: Nc1ncnc2c1ncn2Cc1cc(-c2cc(F)c(OCOC(=O)c3ccccn3)cc2F)ncc1N1CCC[C@](N)([C@H](O)C(F)F)C1] |

TABLE 2-continued
| Compound | Chemical Structure |
|---|---|
| II-62 | 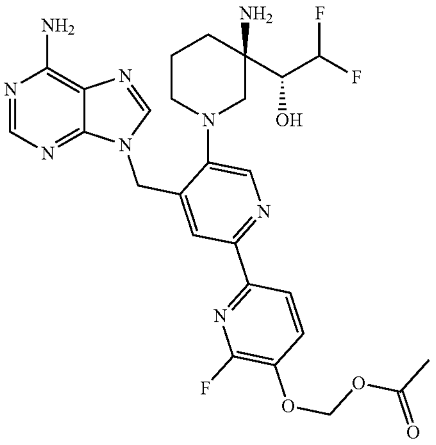 [SMILES: CC(=O)OCOc1ccc(-c2cc(Cn3cnc4c(N)ncnc43)c(N3CCC[C@](N)([C@@H](O)C(F)F)C3)cn2)nc1F] |
| II-63 | 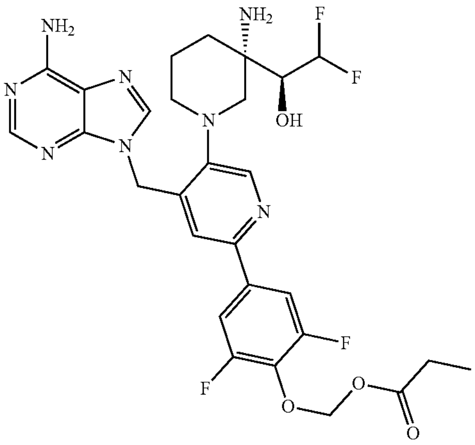 [SMILES: CCC(=O)OCOc1c(F)cc(-c2cc(Cn3cnc4c(N)ncnc43)c(N3CCC[C@@](N)([C@H](O)C(F)F)C3)cn2)cc1F] |
| II-64 | 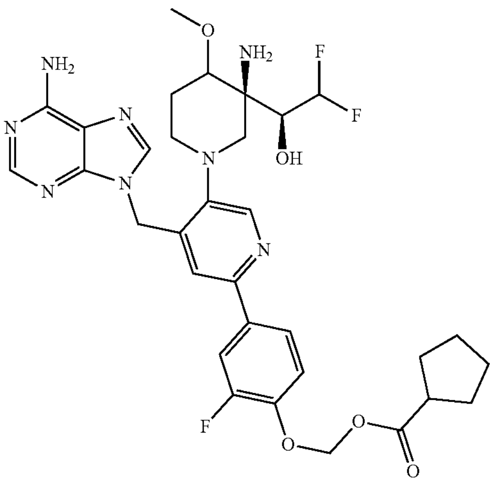 [SMILES: COC1CCN(c2cnc(-c3ccc(OCOC(=O)C4CCCC4)c(F)c3)cc2Cn2cnc3c(N)ncnc32)C[C@@]1(N)[C@H](O)C(F)F] |

TABLE 2-continued
| Compound | Chemical Structure |
| --- | --- |
| II-65 | 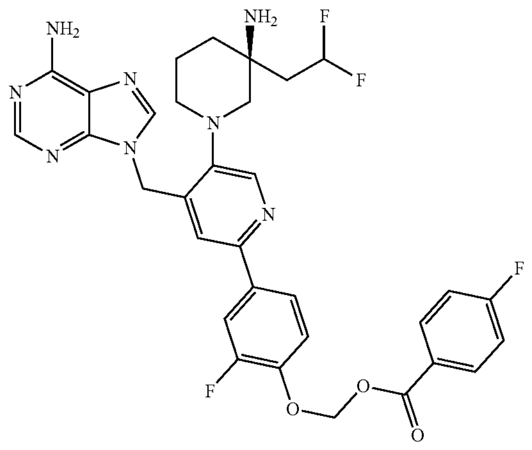 [SMILES: Nc1ncnc2c1ncn2Cc1cc(-c2ccc(OCOC(=O)c3ccc(F)cc3)c(F)c2)ncc1N1CCC[C@](N)(CC(F)F)C1] |
| II-66 | 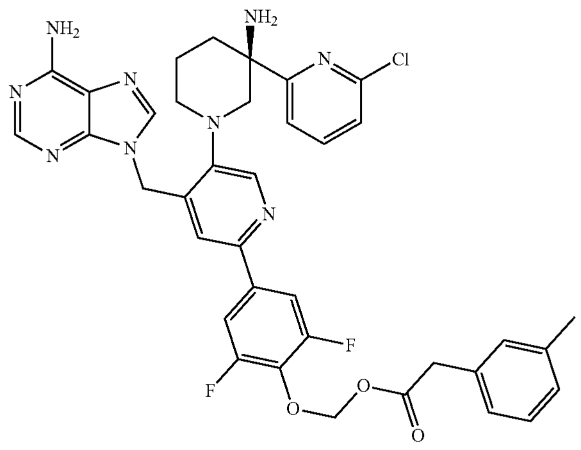 [SMILES: Cc1cccc(CC(=O)OCOc2c(F)cc(-c3cc(Cn4cnc5c(N)ncnc54)c(N4CCC[C@](N)(c5cccc(Cl)n5)C4)cn3)cc2F)c1] |
| II-67 | 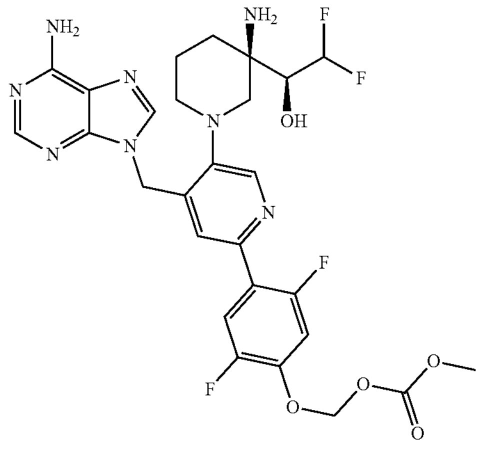 [SMILES: COC(=O)OCOc1cc(F)c(-c2cc(Cn3cnc4c(N)ncnc43)c(N3CCC[C@](N)([C@H](O)C(F)F)C3)cn2)cc1F] |

TABLE 2-continued
| Compound | Chemical Structure |
|---|---|
| II-68 | 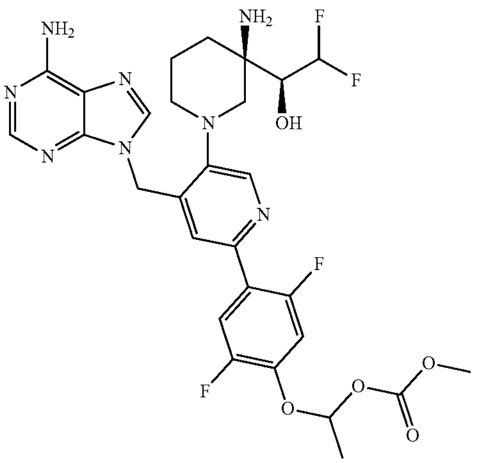 [SMILES: COC(=O)OC(C)Oc1cc(F)c(-c2cc(Cn3cnc4c(N)ncnc43)c(N3CCC[C@](N)([C@H](O)C(F)F)C3)cn2)cc1F] |
| II-69 | 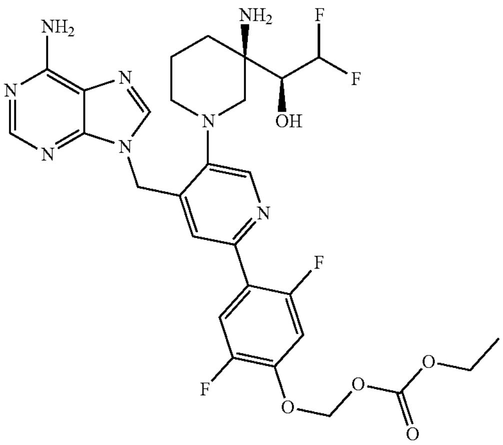 [SMILES: CCOC(=O)OCOc1cc(F)c(-c2cc(Cn3cnc4c(N)ncnc43)c(N3CCC[C@](N)([C@H](O)C(F)F)C3)cn2)cc1F] |
| II-70 | 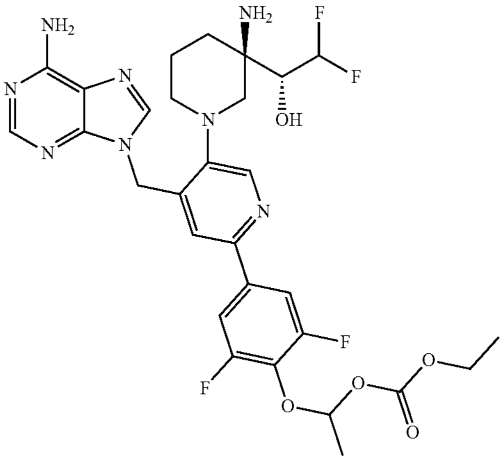 [SMILES: CCOC(=O)OC(C)Oc1c(F)cc(-c2cc(Cn3cnc4c(N)ncnc43)c(N3CCC[C@](N)([C@@H](O)C(F)F)C3)cn2)cc1F] |

TABLE 2-continued
| Compound | Chemical Structure |
|---|---|
| II-71 | 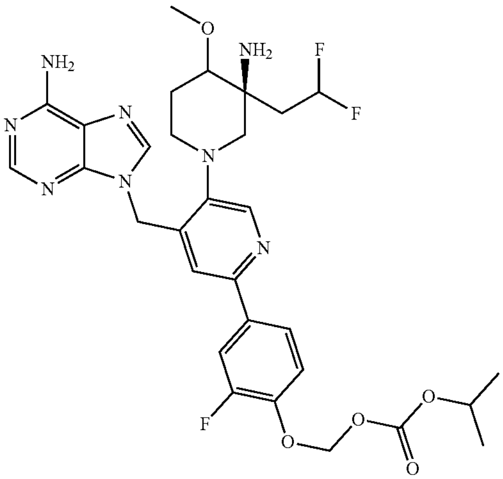 [SMILES: COC1CCN(c2cnc(-c3ccc(OCOC(=O)OC(C)C)c(F)c3)cc2Cn2cnc3c(N)ncnc32)C[C@@]1(N)CC(F)F] |
| II-72 | 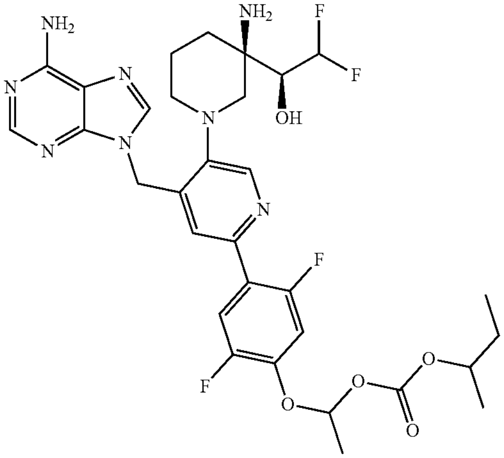 [SMILES: CCC(C)OC(=O)OC(C)Oc1cc(F)c(-c2cc(Cn3cnc4c(N)ncnc43)c(N3CCC[C@](N)([C@H](O)C(F)F)C3)cn2)cc1F] |
| II-73 | 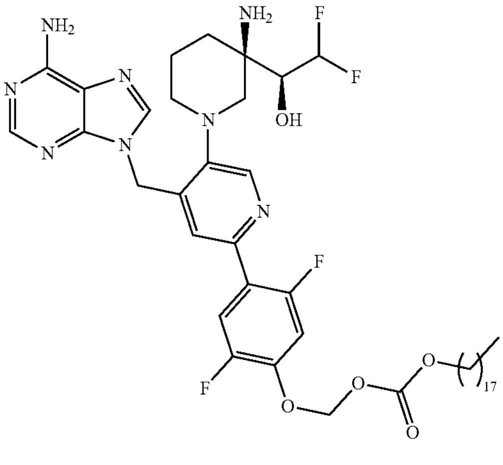 |

TABLE 2-continued
| Compound | Chemical Structure |
|---|---|
| II-74 | 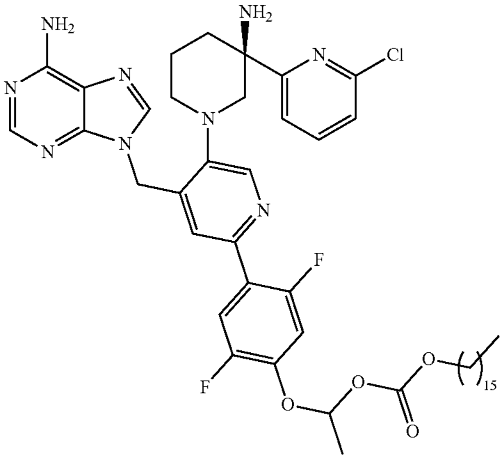 |
| II-75 | 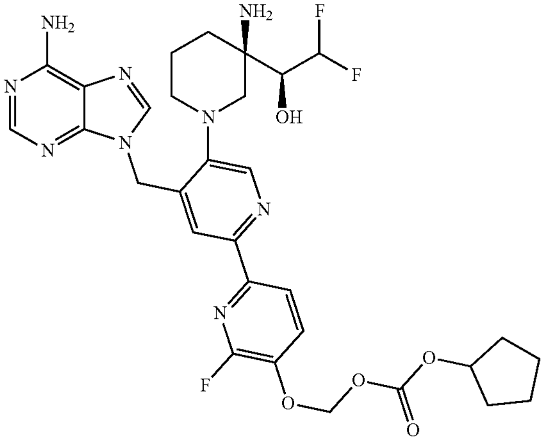 [SMILES: Nc1ncnc2c1ncn2Cc1cc(-c2ccc(OCOC(=O)OC3CCCC3)c(F)n2)ncc1N1CCC[C@](N)([C@H](O)C(F)F)C1] |
| II-76 | 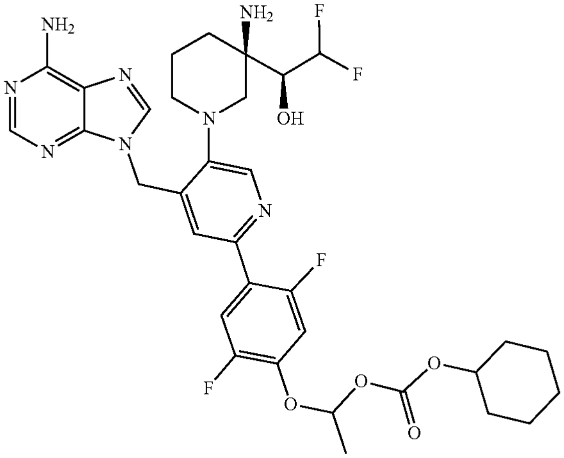 [SMILES: CC(OC(=O)OC1CCCCC1)Oc1cc(F)c(-c2cc(Cn3cnc4c(N)ncnc43)c(N3CCC[C@](N)([C@H](O)C(F)F)C3)cn2)cc1F] |

TABLE 2-continued
| Compound | Chemical Structure |
|---|---|
| II-77 | 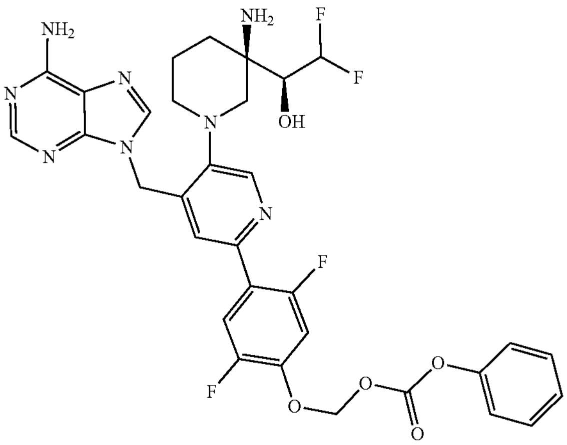 [SMILES: Nc1ncnc2c1ncn2Cc1cc(-c2cc(F)c(OCOC(=O)Oc3ccccc3)cc2F)ncc1N1CCC[C@](N)([C@H](O)C(F)F)C1] |
| II-78 | 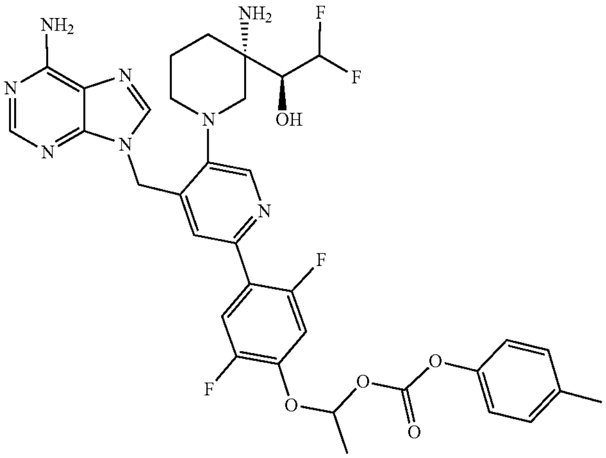 [SMILES: Cc1ccc(OC(=O)OC(C)Oc2cc(F)c(-c3cc(Cn4cnc5c(N)ncnc54)c(N4CCC[C@@](N)([C@H](O)C(F)F)C4)cn3)cc2F)cc1] |
| II-79 | 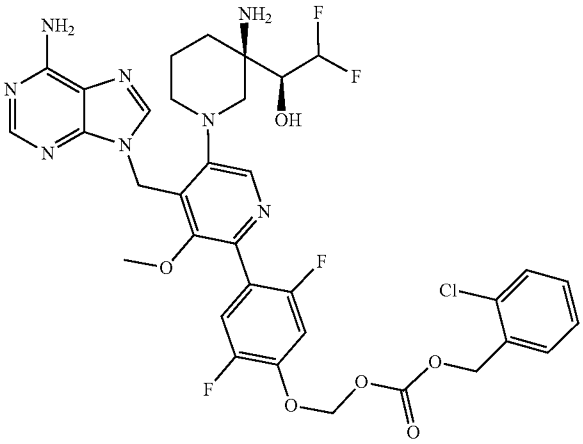 [SMILES: COc1c(-c2cc(F)c(OCOC(=O)OCc3ccccc3Cl)cc2F)ncc(N2CCC[C@](N)([C@H](O)C(F)F)C2)c1Cn1cnc2c(N)ncnc21] |

TABLE 2-continued
| Compound | Chemical Structure |
|---|---|
| II-80 | 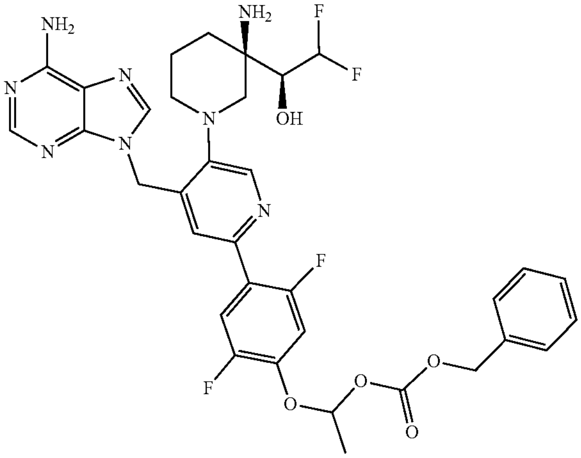 [SMILES: CC(OC(=O)OCc1ccccc1)Oc1cc(F)c(-c2cc(Cn3cnc4c(N)ncnc43)c(N3CCC[C@](N)([C@H](O)C(F)F)C3)cn2)cc1F] |
| II-81 | 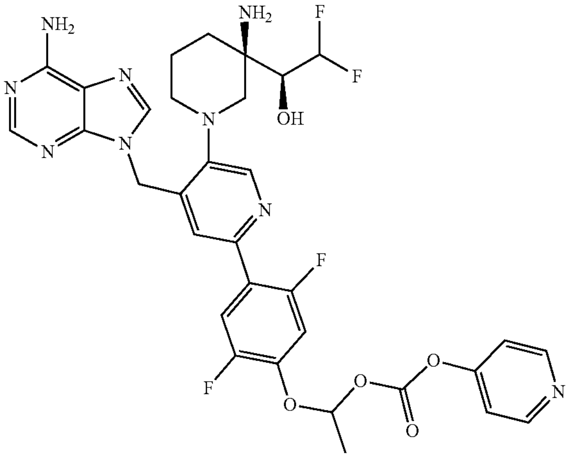 [SMILES: CC(OC(=O)Oc1ccncc1)Oc1cc(F)c(-c2cc(Cn3cnc4c(N)ncnc43)c(N3CCC[C@](N)([C@H](O)C(F)F)C3)cn2)cc1F] |
| II-82 | 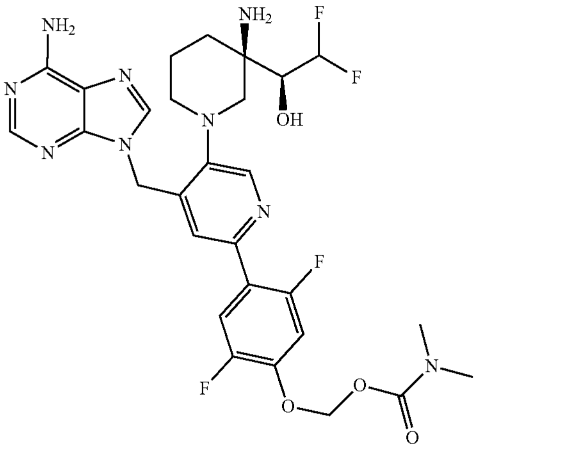 [SMILES: CN(C)C(=O)OCOc1cc(F)c(-c2cc(Cn3cnc4c(N)ncnc43)c(N3CCC[C@](N)([C@H](O)C(F)F)C3)cn2)cc1F] |

TABLE 2-continued
| Compound | Chemical Structure |
| --- | --- |
| II-83 | 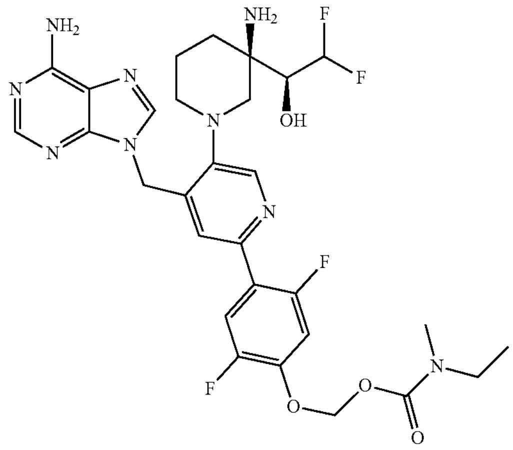 [SMILES: CCN(C)C(=O)OCOc1cc(F)c(-c2cc(Cn3cnc4c(N)ncnc43)c(N3CCC[C@](N)([C@H](O)C(F)F)C3)cn2)cc1F] |
| II-84 | 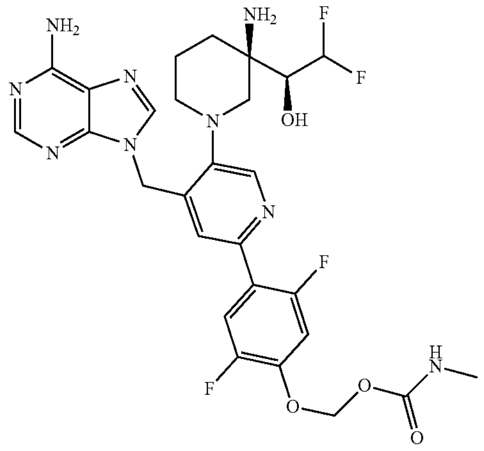 [SMILES: CNC(=O)OCOc1cc(F)c(-c2cc(Cn3cnc4c(N)ncnc43)c(N3CCC[C@](N)([C@H](O)C(F)F)C3)cn2)cc1F] |
| II-85 | 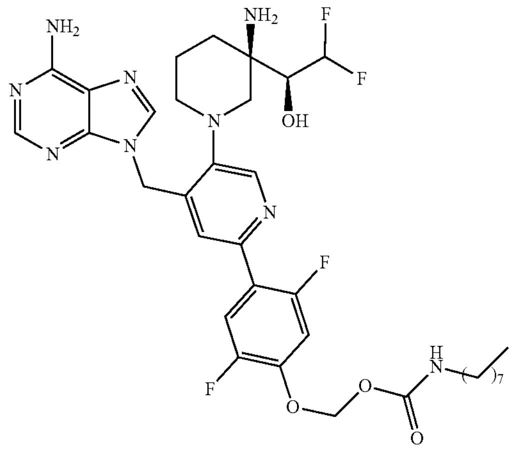 |

TABLE 2-continued
| Compound | Chemical Structure |
|---|---|
| II-86 | 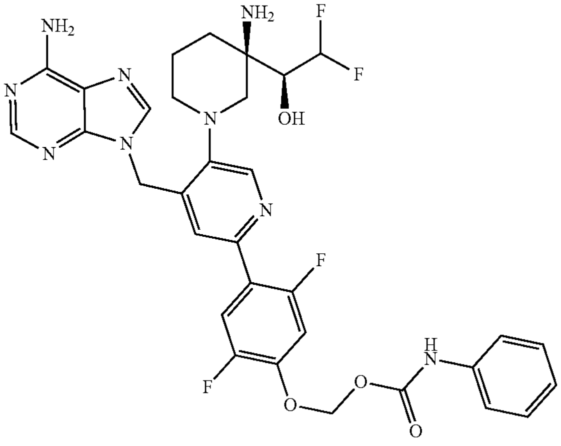 [SMILES: Nc1ncnc2c1ncn2Cc1cc(-c2cc(F)c(OCOC(=O)Nc3ccccc3)cc2F)ncc1N1CCC[C@](N)([C@H](O)C(F)F)C1] |
| II-87 | 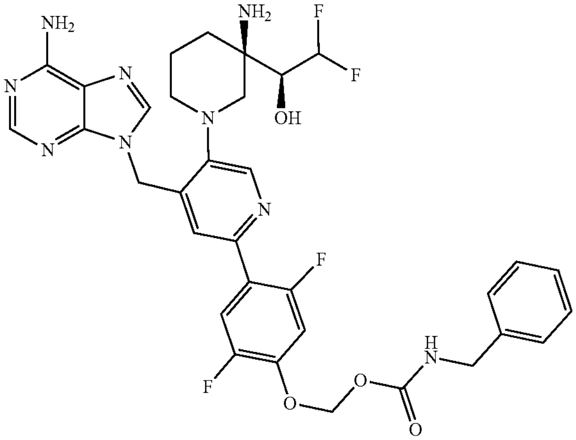 [SMILES: Nc1ncnc2c1ncn2Cc1cc(-c2cc(F)c(OCOC(=O)NCc3ccccc3)cc2F)ncc1N1CCC[C@](N)([C@H](O)C(F)F)C1] |
| II-88 | 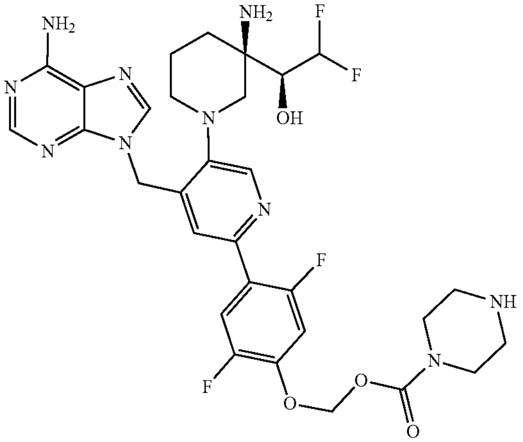 [SMILES: Nc1ncnc2c1ncn2Cc1cc(-c2cc(F)c(OCOC(=O)N3CCNCC3)cc2F)ncc1N1CCC[C@](N)([C@H](O)C(F)F)C1] |

TABLE 2-continued
| Compound | Chemical Structure |
|---|---|
| II-89 | 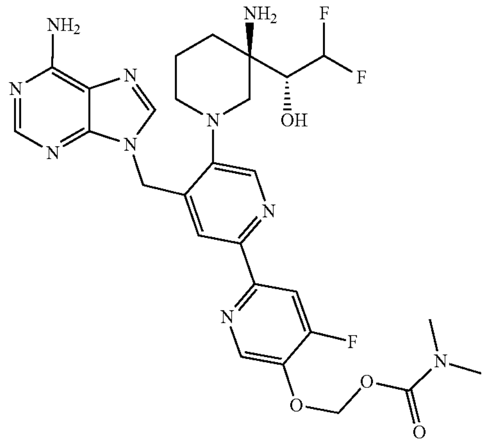 [SMILES: CN(C)C(=O)OCOc1cnc(-c2cc(Cn3cnc4c(N)ncnc43)c(N3CCC[C@](N)([C@@H](O)C(F)F)C3)cn2)cc1F] |
| II-90 | 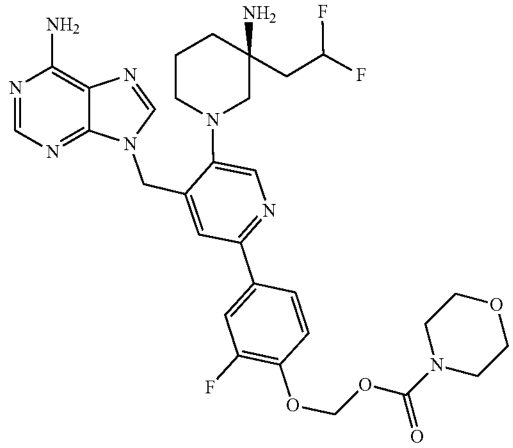 [SMILES: Nc1ncnc2c1ncn2Cc1cc(-c2ccc(OCOC(=O)N3CCOCC3)c(F)c2)ncc1N1CCC[C@](N)(CC(F)F)C1] |
TABLE 3
| Compound No. | Chemical Structure |
|---|---|
| III-1 | 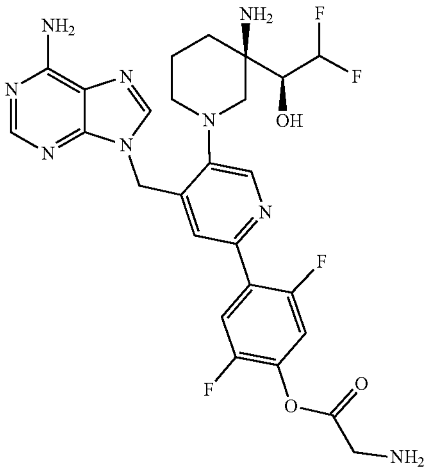 [SMILES: NCC(=O)Oc1cc(F)c(-c2cc(Cn3cnc4c(N)ncnc43)c(N3CCC[C@](N)([C@H](O)C(F)F)C3)cn2)cc1F] |

TABLE 3-continued
| Compound No. | Chemical Structure |
|---|---|
| III-2 | 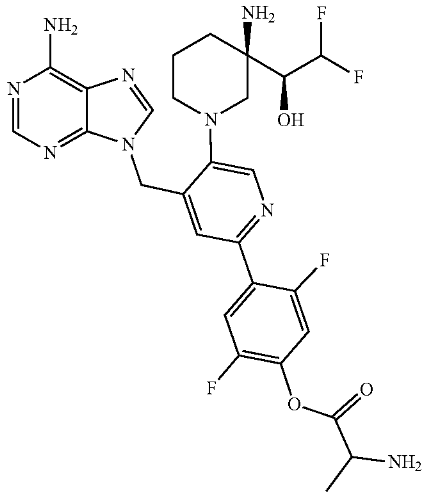 [SMILES: CC(N)C(=O)Oc1cc(F)c(-c2cc(Cn3cnc4c(N)ncnc43)c(N3CCC[C@](N)([C@H](O)C(F)F)C3)cn2)cc1F] |
| III-3 | 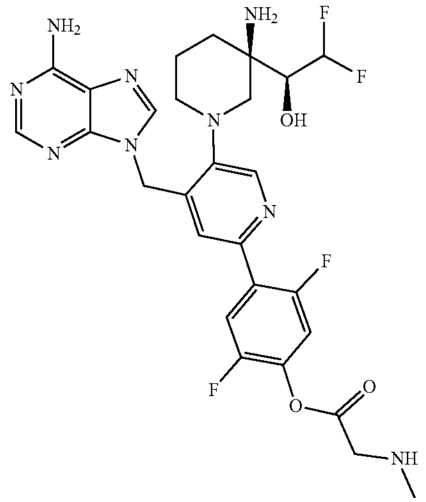 [SMILES: CNCC(=O)Oc1cc(F)c(-c2cc(Cn3cnc4c(N)ncnc43)c(N3CCC[C@](N)([C@H](O)C(F)F)C3)cn2)cc1F] |
| III-4 | 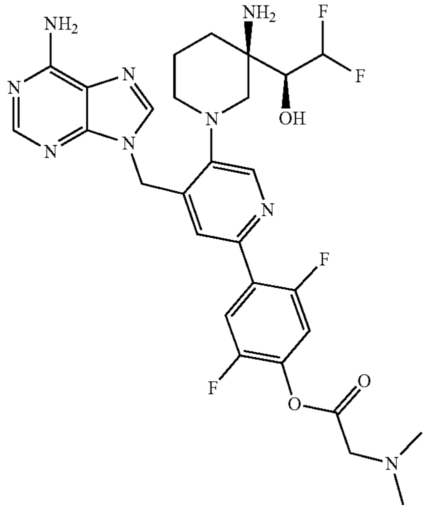 [SMILES: CN(C)CC(=O)Oc1cc(F)c(-c2cc(Cn3cnc4c(N)ncnc43)c(N3CCC[C@](N)([C@H](O)C(F)F)C3)cn2)cc1F] |

TABLE 3-continued
| Compound No. | Chemical Structure |
| --- | --- |
| III-5 | 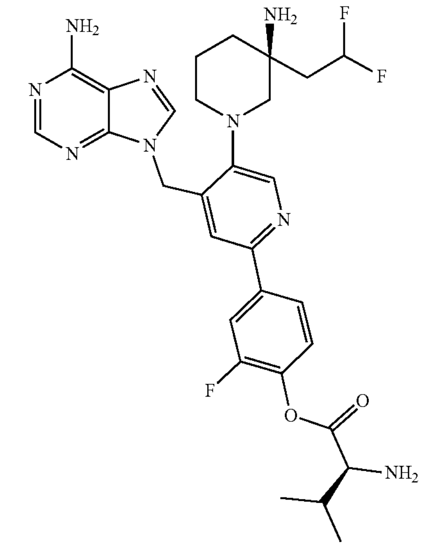 [SMILES: CC(C)[C@H](N)C(=O)Oc1ccc(-c2cc(Cn3cnc4c(N)ncnc43)c(N3CCC[C@](N)(CC(F)F)C3)cn2)cc1F] |
| III-6 | 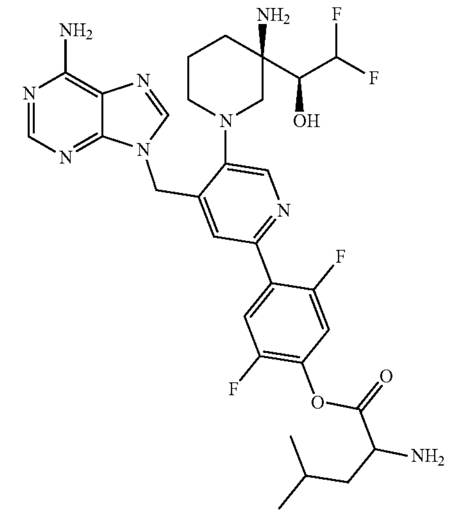 [SMILES: CC(C)CC(N)C(=O)Oc1cc(F)c(-c2cc(Cn3cnc4c(N)ncnc43)c(N3CCC[C@](N)([C@H](O)C(F)F)C3)cn2)cc1F] |
| III-7 | 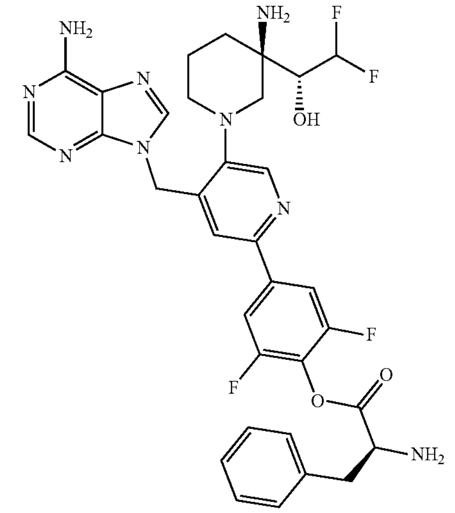 [SMILES: Nc1ncnc2c1ncn2Cc1cc(-c2cc(F)c(OC(=O)[C@@H](N)Cc3ccccc3)c(F)c2)ncc1N1CCC[C@](N)([C@@H](O)C(F)F)C1] |

TABLE 3-continued
| Compound No. | Chemical Structure |
| --- | --- |
| III-8 | 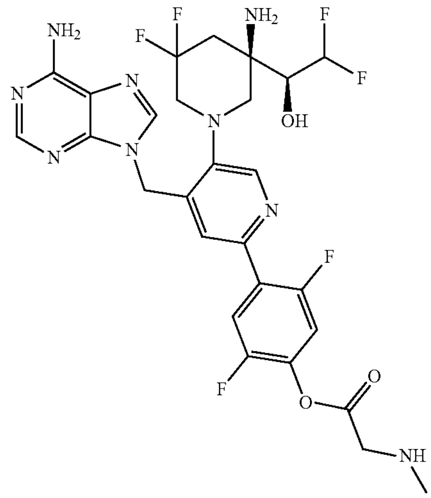 [SMILES: CNCC(=O)Oc1cc(F)c(-c2cc(Cn3cnc4c(N)ncnc43)c(N3CC(F)(F)C[C@](N)([C@H](O)C(F)F)C3)cn2)cc1F] |
| III-9 | 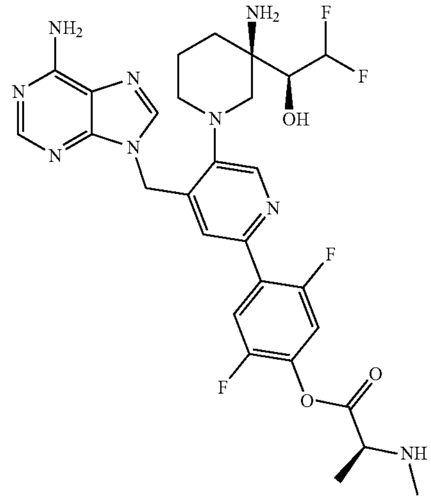 [SMILES: CN[C@@H](C)C(=O)Oc1cc(F)c(-c2cc(Cn3cnc4c(N)ncnc43)c(N3CCC[C@](N)([C@H](O)C(F)F)C3)cn2)cc1F] |
| III-10 | 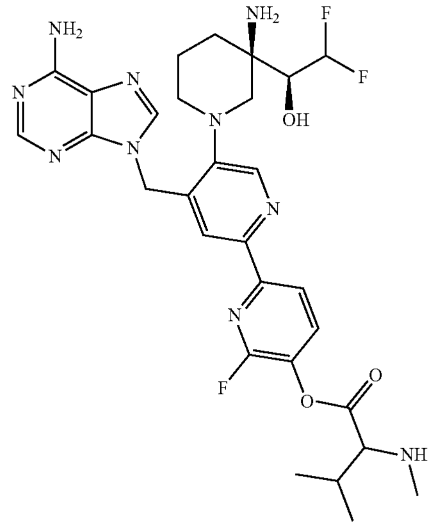 [SMILES: CNC(C(=O)Oc1ccc(-c2cc(Cn3cnc4c(N)ncnc43)c(N3CCC[C@](N)([C@H](O)C(F)F)C3)cn2)nc1F)C(C)C] |

TABLE 3-continued
| Compound No. | Chemical Structure |
|---|---|
| III-11 | 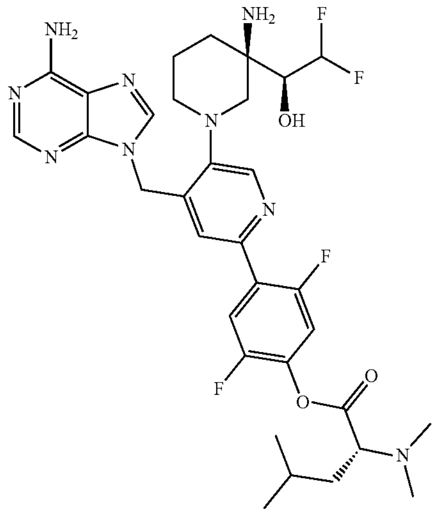 [SMILES: CC(C)C[C@H](C(=O)Oc1cc(F)c(-c2cc(Cn3cnc4c(N)ncnc43)c(N3CCC[C@](N)([C@H](O)C(F)F)C3)cn2)cc1F)N(C)C] |
| III-12 | 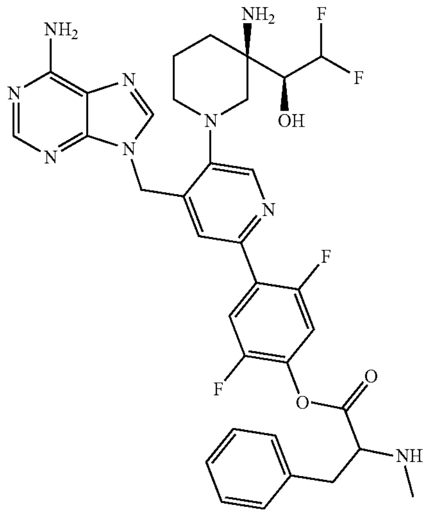 [SMILES: CNC(Cc1ccccc1)C(=O)Oc1cc(F)c(-c2cc(Cn3cnc4c(N)ncnc43)c(N3CCC[C@](N)([C@H](O)C(F)F)C3)cn2)cc1F] |
| III-13 | 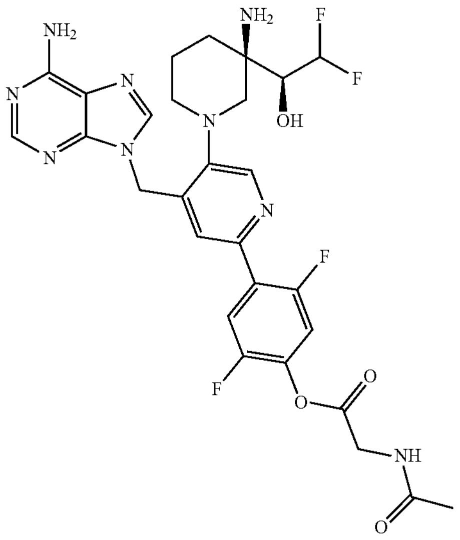 [SMILES: CC(=O)NCC(=O)Oc1cc(F)c(-c2cc(Cn3cnc4c(N)ncnc43)c(N3CCC[C@](N)([C@H](O)C(F)F)C3)cn2)cc1F] |

TABLE 3-continued
| Compound No. | Chemical Structure |
|---|---|
| III-14 | 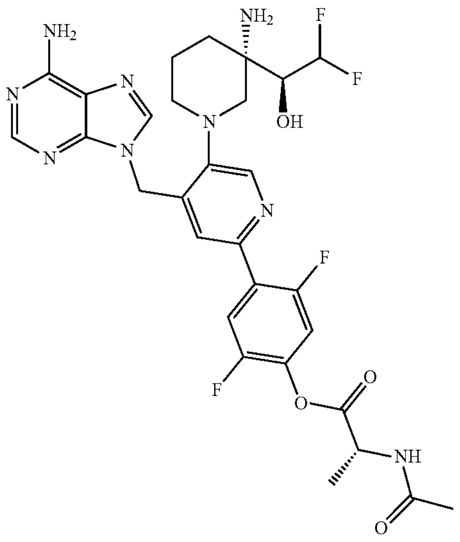 [SMILES: CC(=O)N[C@H](C)C(=O)Oc1cc(F)c(-c2cc(Cn3cnc4c(N)ncnc43)c(N3CCC[C@@](N)([C@H](O)C(F)F)C3)cn2)cc1F] |
| III-15 | 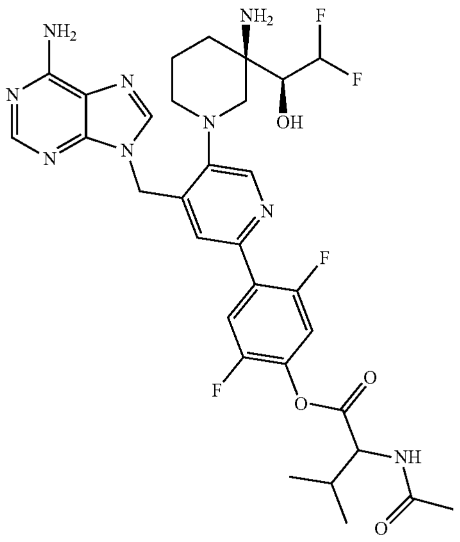 [SMILES: CC(=O)NC(C(=O)Oc1cc(F)c(-c2cc(Cn3cnc4c(N)ncnc43)c(N3CCC[C@](N)([C@H](O)C(F)F)C3)cn2)cc1F)C(C)C] |
| III-16 | 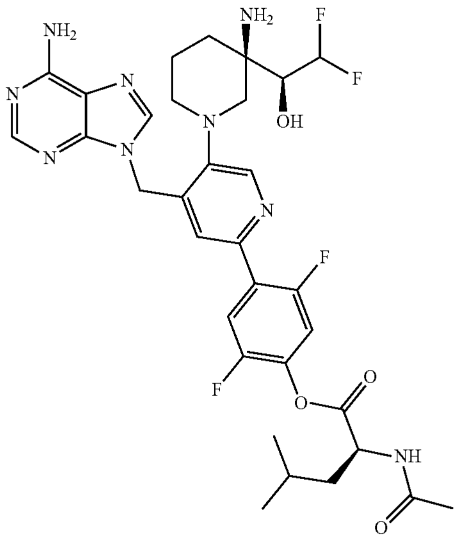 [SMILES: CC(=O)N[C@@H](CC(C)C)C(=O)Oc1cc(F)c(-c2cc(Cn3cnc4c(N)ncnc43)c(N3CCC[C@](N)([C@H](O)C(F)F)C3)cn2)cc1F] |

TABLE 3-continued
| Compound No. | Chemical Structure |
|---|---|
| III-17 | 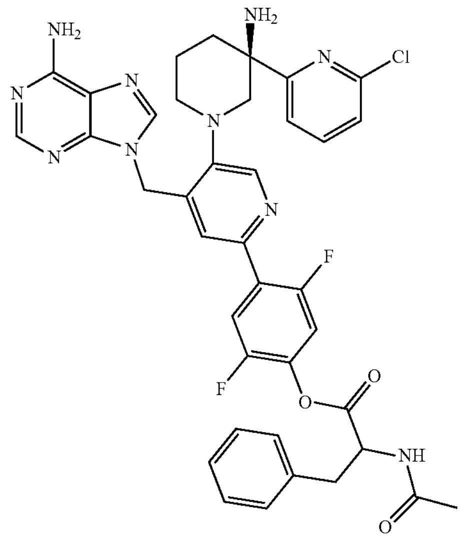 [SMILES: CC(=O)NC(Cc1ccccc1)C(=O)Oc1cc(F)c(-c2cc(Cn3cnc4c(N)ncnc43)c(N3CCC[C@](N)(c4cccc(Cl)n4)C3)cn2)cc1F] |
| III-18 | 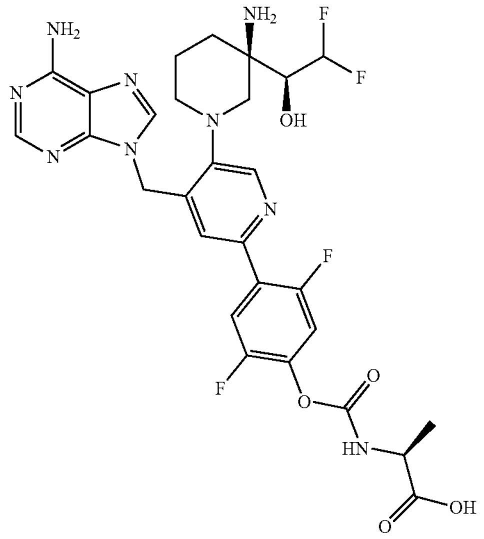 [SMILES: C[C@H](NC(=O)Oc1cc(F)c(-c2cc(Cn3cnc4c(N)ncnc43)c(N3CCC[C@](N)([C@H](O)C(F)F)C3)cn2)cc1F)C(=O)O] |

TABLE 3-continued
| Compound No. | Chemical Structure |
|---|---|
| III-19 | 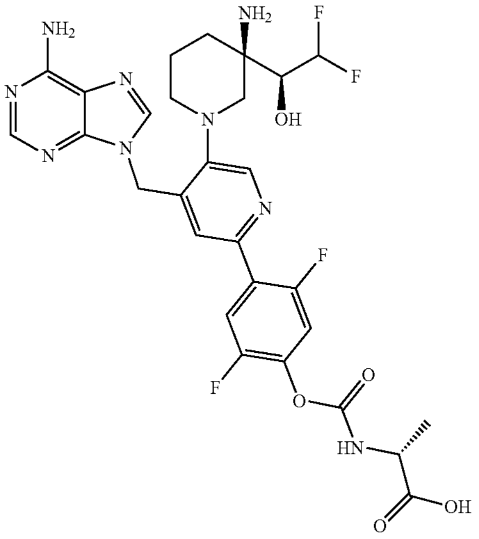 [SMILES: C[C@@H](NC(=O)Oc1cc(F)c(-c2cc(Cn3cnc4c(N)ncnc43)c(N3CCC[C@](N)([C@H](O)C(F)F)C3)cn2)cc1F)C(=O)O] |
| III-20 | 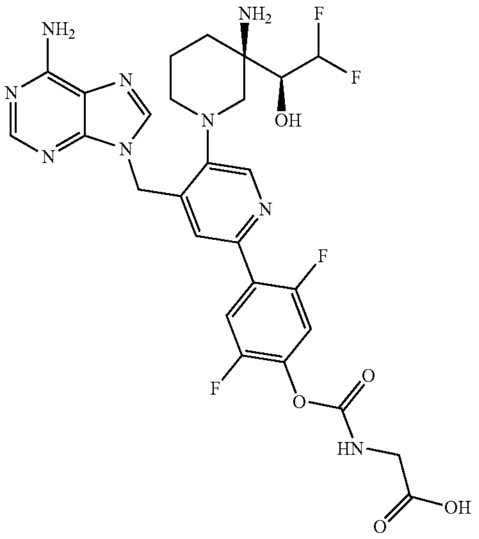 [SMILES: Nc1ncnc2c1ncn2Cc1cc(-c2cc(F)c(OC(=O)NCC(=O)O)cc2F)ncc1N1CCC[C@](N)([C@H](O)C(F)F)C1] |

TABLE 3-continued
| Compound No. | Chemical Structure |
| --- | --- |
| III-21 | 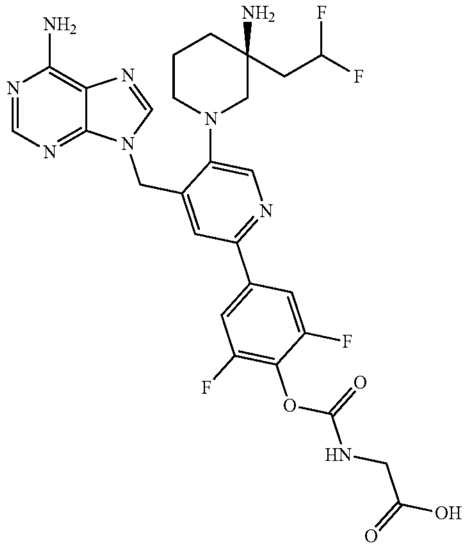 [SMILES: Nc1ncnc2c1ncn2Cc1cc(-c2cc(F)c(OC(=O)NCC(=O)O)c(F)c2)ncc1N1CCC[C@](N)(CC(F)F)C1] |
| III-22 | 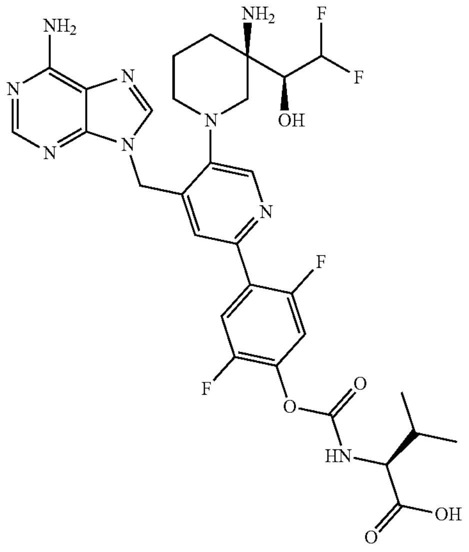 [SMILES: CC(C)[C@H](NC(=O)Oc1cc(F)c(-c2cc(Cn3cnc4c(N)ncnc43)c(N3CCC[C@](N)([C@H](O)C(F)F)C3)cn2)cc1F)C(=O)O] |

TABLE 3-continued
| Compound No. | Chemical Structure |
|---|---|
| III-23 | 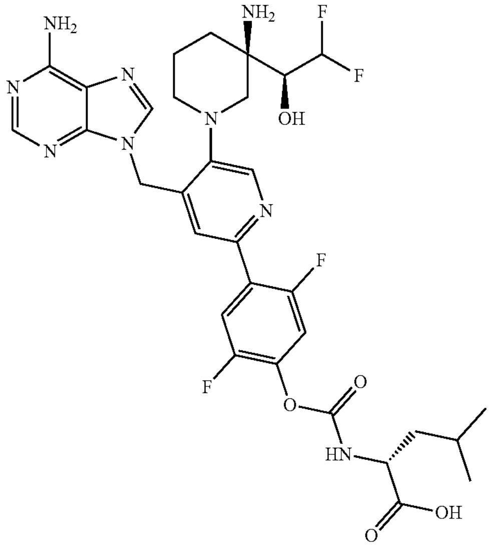 [SMILES: CC(C)C[C@@H](NC(=O)Oc1cc(F)c(-c2cc(Cn3cnc4c(N)ncnc43)c(N3CCC[C@](N)([C@H](O)C(F)F)C3)cn2)cc1F)C(=O)O] |
| III-24 | 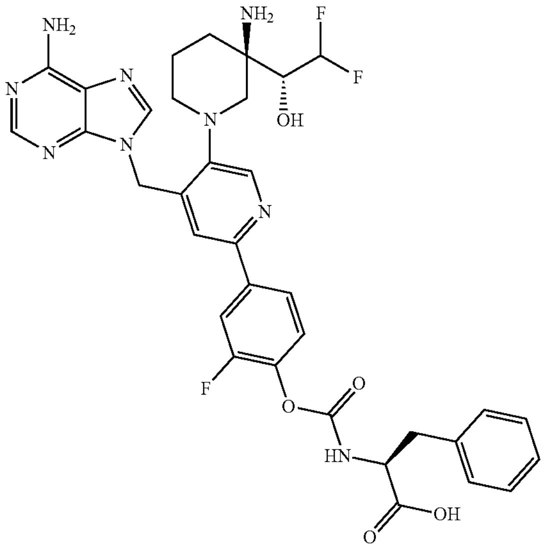 [SMILES: Nc1ncnc2c1ncn2Cc1cc(-c2ccc(OC(=O)N[C@@H](Cc3ccccc3)C(=O)O)c(F)c2)ncc1N1CCC[C@](N)([C@@H](O)C(F)F)C1] |

TABLE 3-continued
| Compound No. | Chemical Structure |
| --- | --- |
| III-25 | 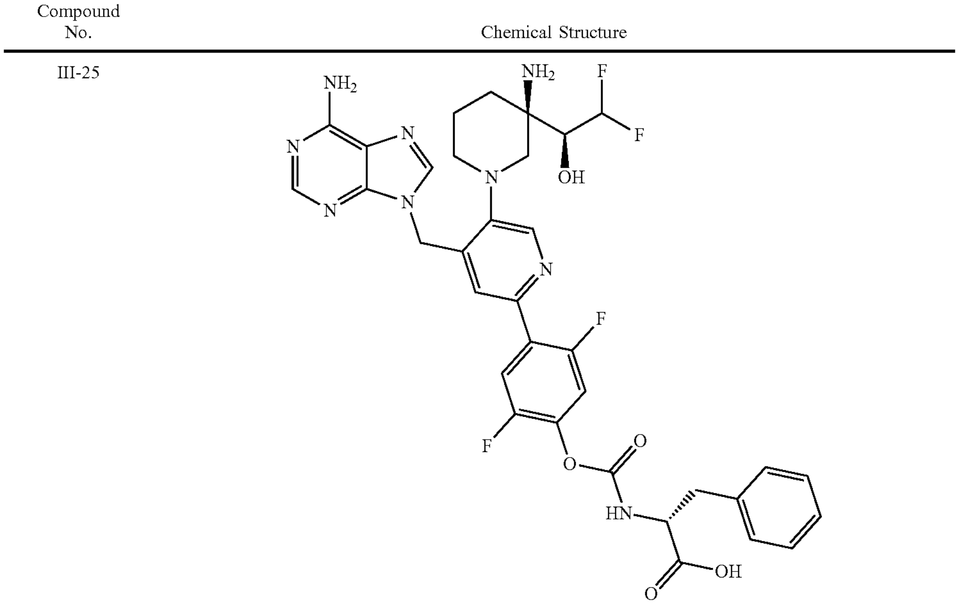 |
| III-26 | 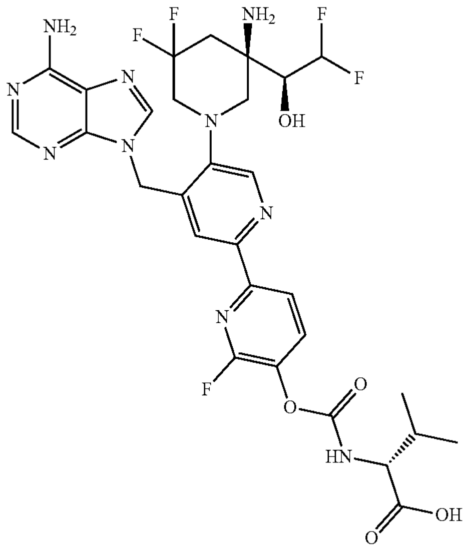 [SMILES: CC(C)[C@@H](NC(=O)Oc1ccc(-c2cc(Cn3cnc4c(N)ncnc43)c(N3CC(F)(F)C[C@](N)([C@H](O)C(F)F)C3)cn2)nc1F)C(=O)O] |

TABLE 3-continued
| Compound No. | Chemical Structure |
|---|---|
| III-27 | 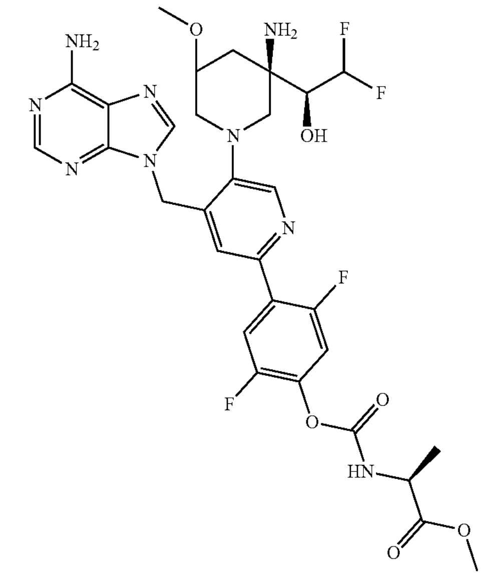 [SMILES: COC(=O)[C@H](C)NC(=O)Oc1cc(F)c(-c2cc(Cn3cnc4c(N)ncnc43)c(N3CC(OC)C[C@](N)([C@H](O)C(F)F)C3)cn2)cc1F] |
| III-28 | 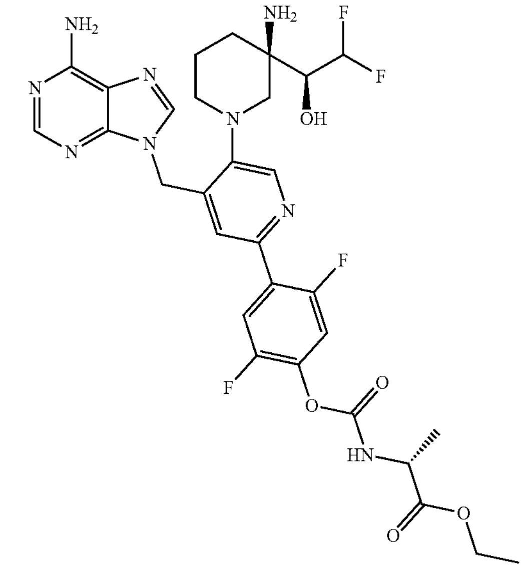 [SMILES: CCOC(=O)[C@@H](C)NC(=O)Oc1cc(F)c(-c2cc(Cn3cnc4c(N)ncnc43)c(N3CCC[C@](N)([C@H](O)C(F)F)C3)cn2)cc1F] |

TABLE 3-continued
| Compound No. | Chemical Structure |
| --- | --- |
| III-29 | 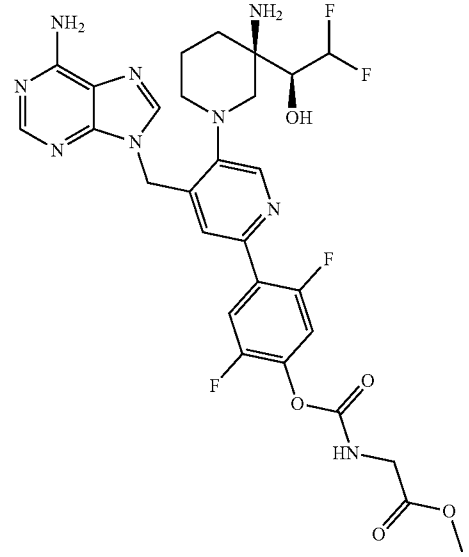 [SMILES: COC(=O)CNC(=O)Oc1cc(F)c(-c2cc(Cn3cnc4c(N)ncnc43)c(N3CCC[C@](N)([C@H](O)C(F)F)C3)cn2)cc1F] |
| III-30 | 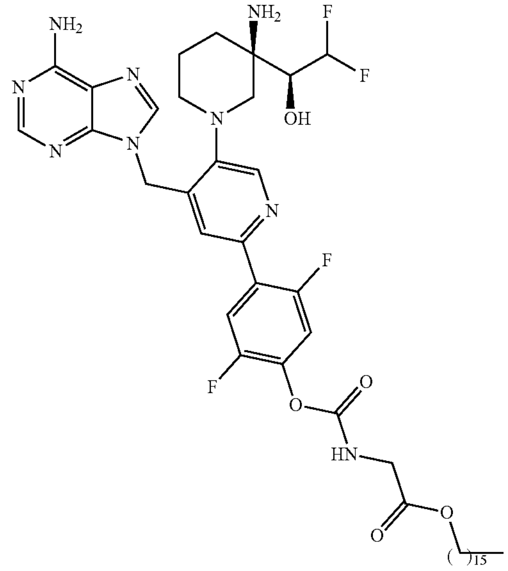 |

TABLE 3-continued
| Compound No. | Chemical Structure |
| --- | --- |
| III-31 | 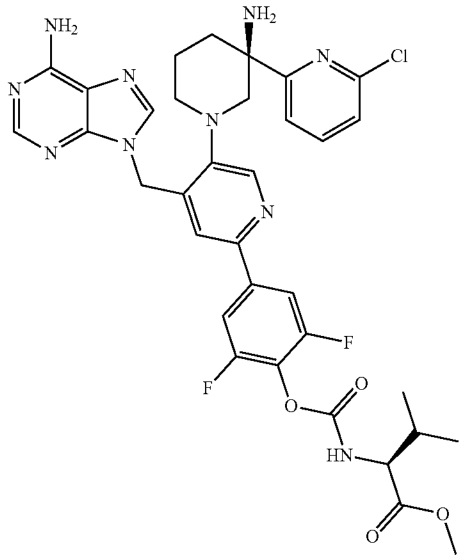 [SMILES: COC(=O)[C@@H](NC(=O)Oc1c(F)cc(-c2cc(Cn3cnc4c(N)ncnc43)c(N3CCC[C@](N)(c4cccc(Cl)n4)C3)cn2)cc1F)C(C)C] |
| III-32 | 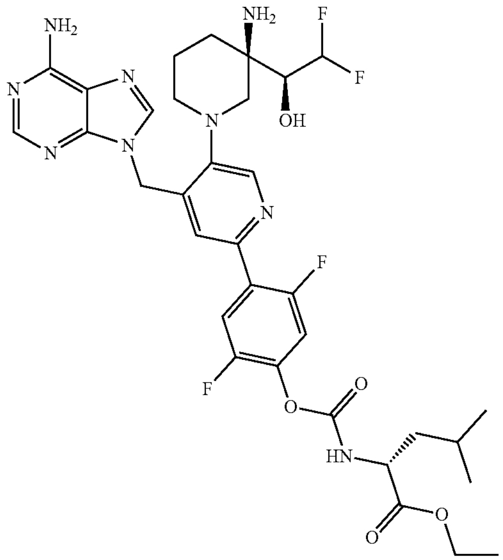 [SMILES: CCOC(=O)[C@@H](CC(C)C)NC(=O)Oc1cc(F)c(-c2cc(Cn3cnc4c(N)ncnc43)c(N3CCC[C@](N)([C@H](O)C(F)F)C3)cn2)cc1F] |

TABLE 3-continued
| Compound No. | Chemical Structure |
|---|---|
| III-33 | 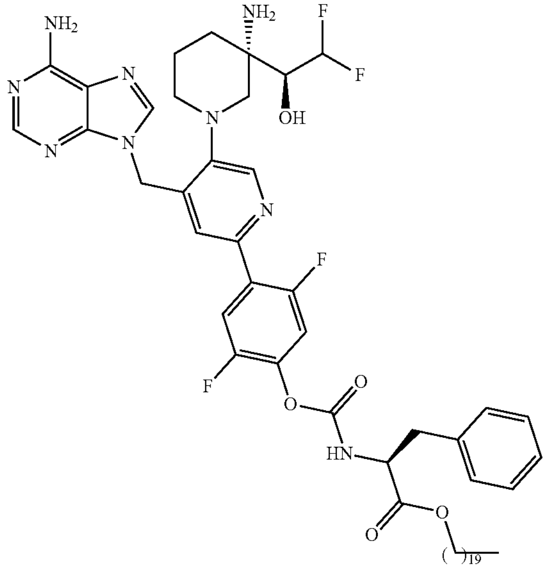 |
| III-34 | 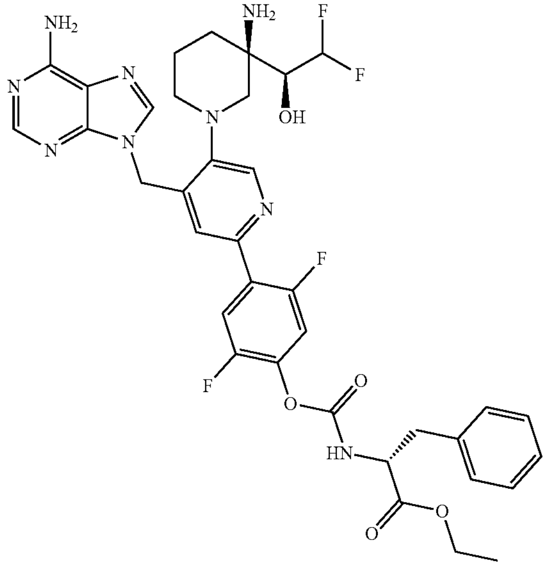 [SMILES: CCOC(=O)[C@@H](Cc1ccccc1)NC(=O)Oc1cc(F)c(-c2cc(Cn3cnc4c(N)ncnc43)c(N3CCC[C@](N)([C@H](O)C(F)F)C3)cn2)cc1F] |

TABLE 3-continued
| Compound No. | Chemical Structure |
|---|---|
| III-35 | 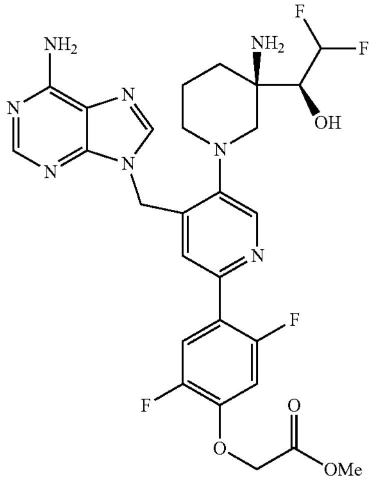 [SMILES: COC(=O)COc1cc(F)c(-c2cc(Cn3cnc4c(N)ncnc43)c(N3CCC[C@](N)([C@H](O)C(F)F)C3)cn2)cc1F] |
TABLE 4
| Compound No. | Chemical Structure |
|---|---|
| IV-1 | 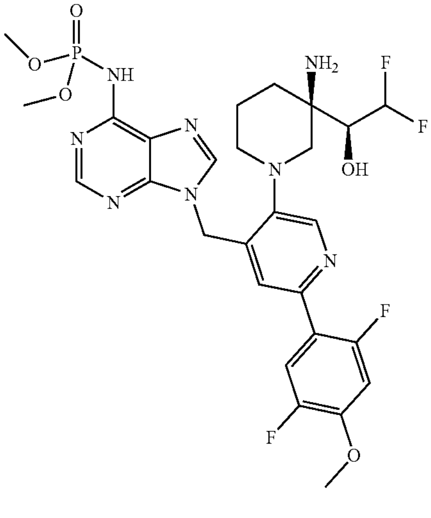 [SMILES: COc1cc(F)c(-c2cc(Cn3cnc4c(NP(=O)(OC)OC)ncnc43)c(N3CCC[C@](N)([C@H](O)C(F)F)C3)cn2)cc1F] |

TABLE 4-continued
| Compound No. | Chemical Structure |
|---|---|
| IV-2 | 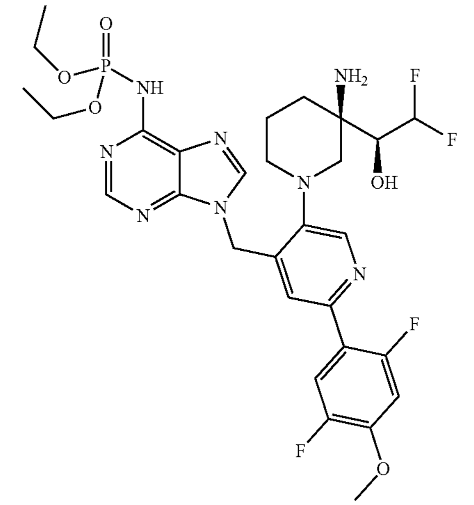 [SMILES: CCOP(=O)(Nc1ncnc2c1ncn2Cc1cc(-c2cc(F)c(OC)cc2F)ncc1N1CCC[C@](N)([C@H](O)C(F)F)C1)OCC] |
| IV-3 | 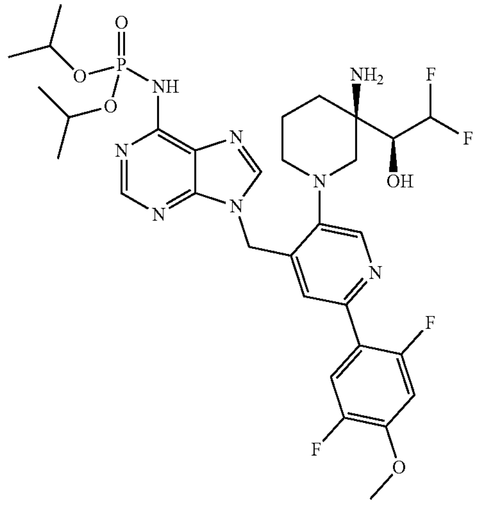 [SMILES: COc1cc(F)c(-c2cc(Cn3cnc4c(NP(=O)(OC(C)C)OC(C)C)ncnc43)c(N3CCC[C@](N)([C@H](O)C(F)F)C3)cn2)cc1F] |
| IV-4 | 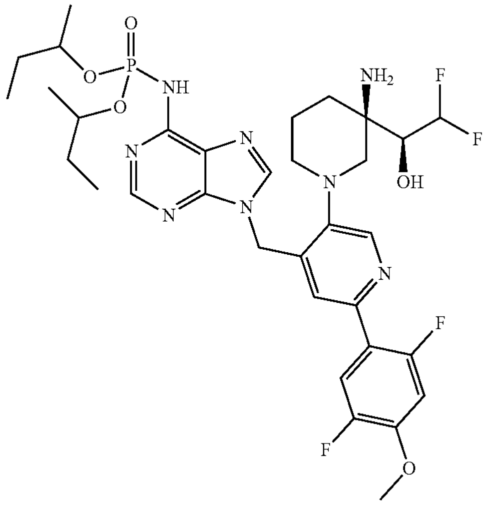 [SMILES: CCC(C)OP(=O)(Nc1ncnc2c1ncn2Cc1cc(-c2cc(F)c(OC)cc2F)ncc1N1CCC[C@](N)([C@H](O)C(F)F)C1)OC(C)CC] |

TABLE 4-continued
| Compound No. | Chemical Structure |
|---|---|
| IV-5 | 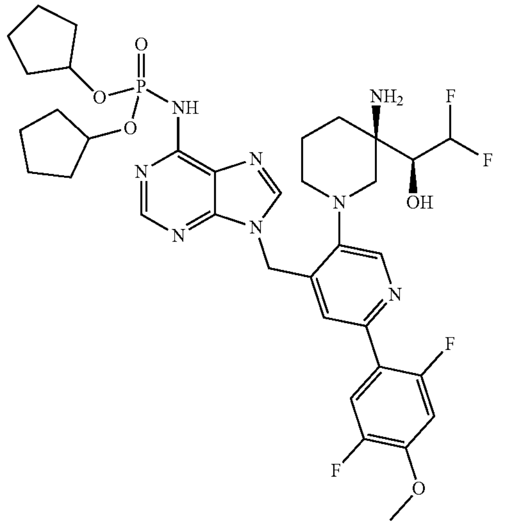 [SMILES: COc1cc(F)c(-c2cc(Cn3cnc4c(NP(=O)(OC5CCCC5)OC5CCCC5)ncnc43)c(N3CCC[C@](N)([C@H](O)C(F)F)C3)cn2)cc1F] |
| IV-6 | 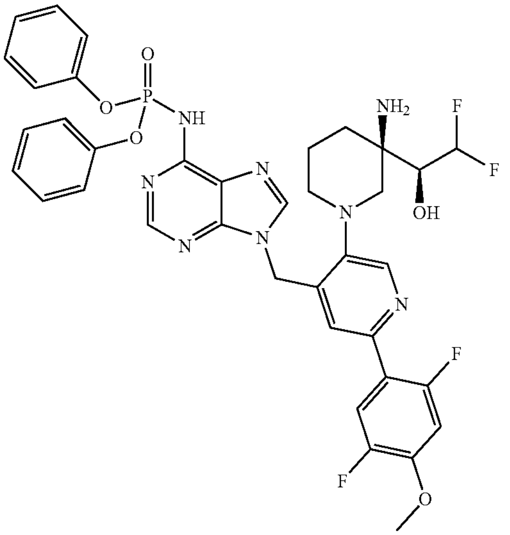 [SMILES: COc1cc(F)c(-c2cc(Cn3cnc4c(NP(=O)(Oc5ccccc5)Oc5ccccc5)ncnc43)c(N3CCC[C@](N)([C@H](O)C(F)F)C3)cn2)cc1F] |
| IV-7 | 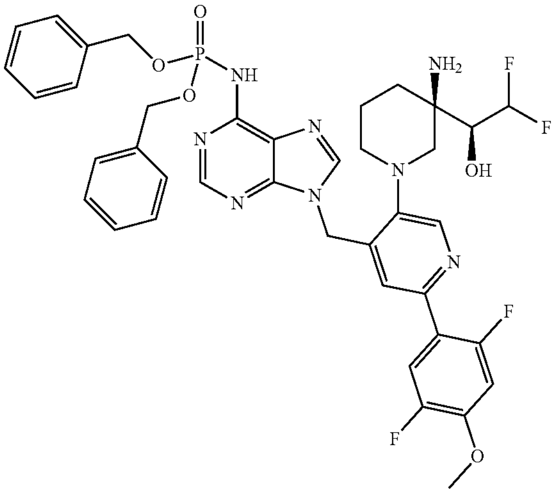 [SMILES: COc1cc(F)c(-c2cc(Cn3cnc4c(NP(=O)(OCc5ccccc5)OCc5ccccc5)ncnc43)c(N3CCC[C@](N)([C@H](O)C(F)F)C3)cn2)cc1F] |

TABLE 4-continued
| Compound No. | Chemical Structure |
|---|---|
| IV-8 | 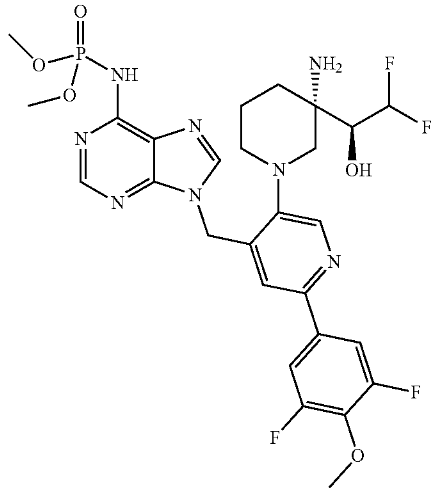 [SMILES: COc1c(F)cc(-c2cc(Cn3cnc4c(NP(=O)(OC)OC)ncnc43)c(N3CCC[C@@](N)([C@H](O)C(F)F)C3)cn2)cc1F] |
| IV-9 | 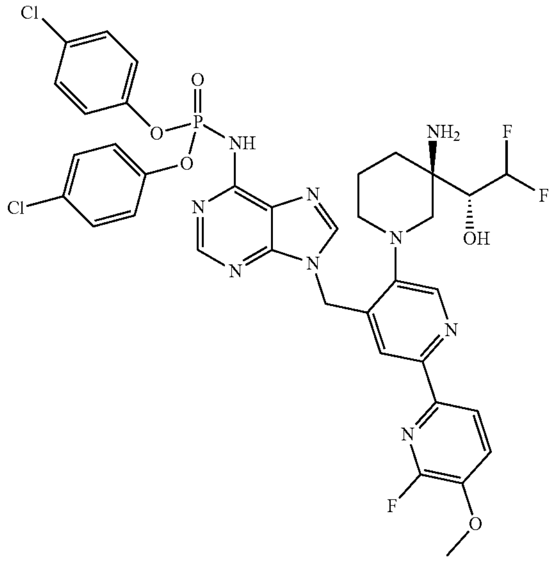 [SMILES: COc1ccc(-c2cc(Cn3cnc4c(NP(=O)(Oc5ccc(Cl)cc5)Oc5ccc(Cl)cc5)ncnc43)c(N3CCC[C@](N)([C@@H](O)C(F)F)C3)cn2)nc1F] |
| IV-10 | 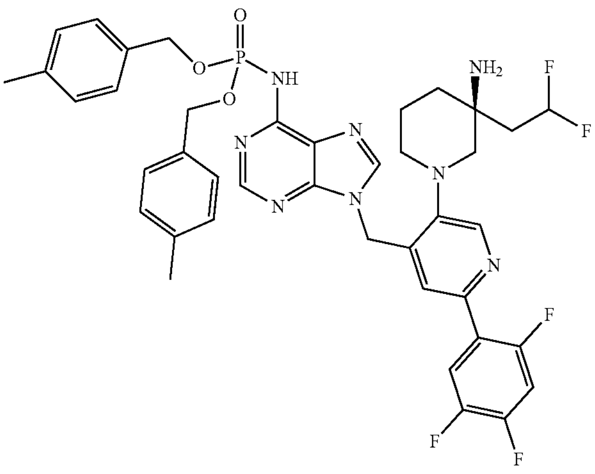 [SMILES: Cc1ccc(COP(=O)(Nc2ncnc3c2ncn3Cc2cc(-c3cc(F)c(F)cc3F)ncc2N2CCC[C@](N)(CC(F)F)C2)OCc2ccc(C)cc2)cc1] |

TABLE 4-continued
| Compound No. | Chemical Structure |
|---|---|
| IV-11 | 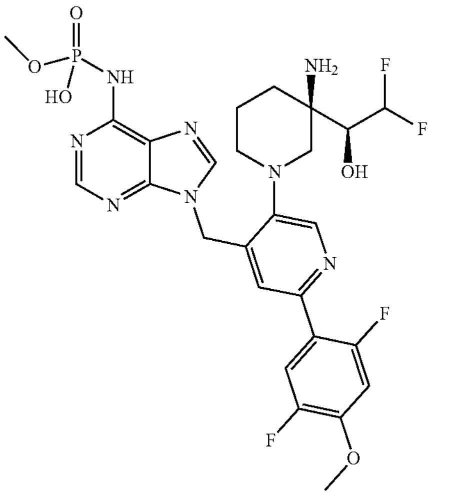 [SMILES: COc1cc(F)c(-c2cc(Cn3cnc4c(NP(=O)(O)OC)ncnc43)c(N3CCC[C@](N)([C@H](O)C(F)F)C3)cn2)cc1F] |
| IV-12 | 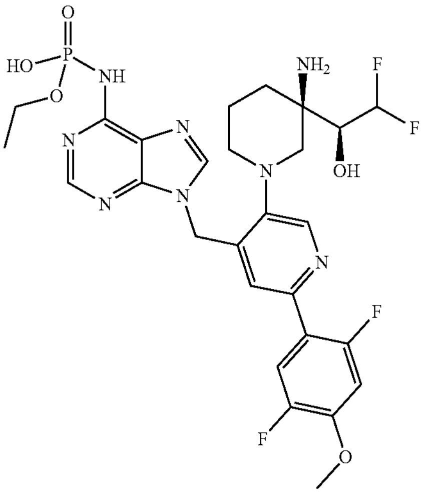 [SMILES: CCOP(=O)(O)Nc1ncnc2c1ncn2Cc1cc(-c2cc(F)c(OC)cc2F)ncc1N1CCC[C@](N)([C@H](O)C(F)F)C1] |
| IV-13 | 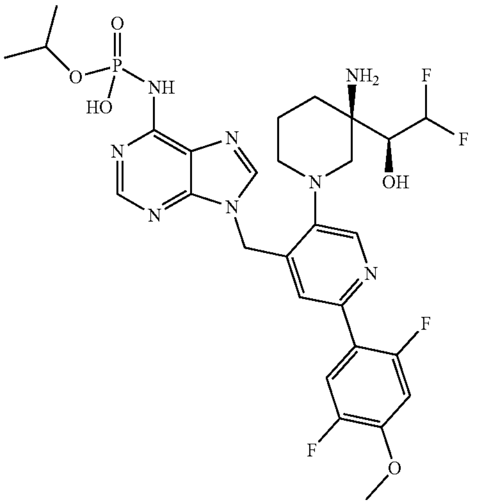 [SMILES: COc1cc(F)c(-c2cc(Cn3cnc4c(NP(=O)(O)OC(C)C)ncnc43)c(N3CCC[C@](N)([C@H](O)C(F)F)C3)cn2)cc1F] |

TABLE 4-continued
| Compound No. | Chemical Structure |
| --- | --- |
| IV-14 | 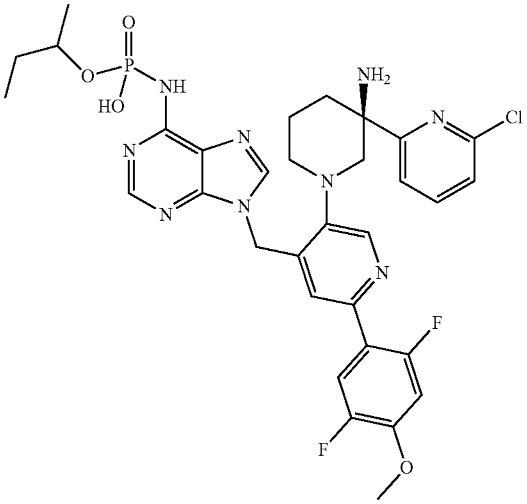 [SMILES: CCC(C)OP(=O)(O)Nc1ncnc2c1ncn2Cc1cc(-c2cc(F)c(OC)cc2F)ncc1N1CCC[C@](N)(c2cccc(Cl)n2)C1] |
| IV-15 | 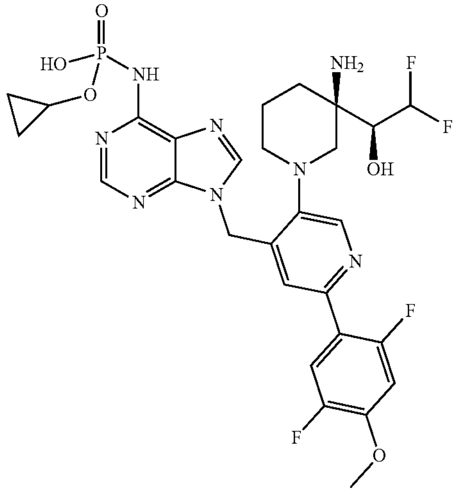 [SMILES: COc1cc(F)c(-c2cc(Cn3cnc4c(NP(=O)(O)OC5CC5)ncnc43)c(N3CCC[C@](N)([C@H](O)C(F)F)C3)cn2)cc1F] |
| IV-16 | 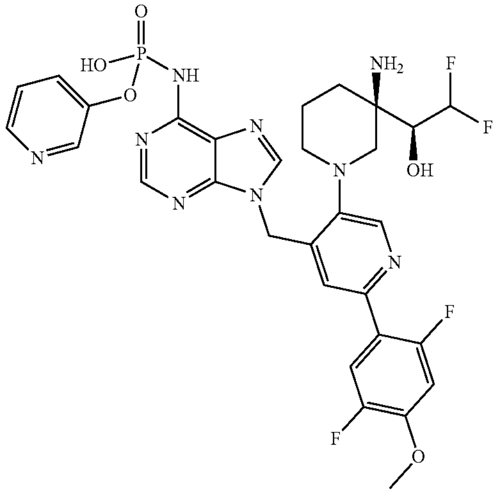 [SMILES: COc1cc(F)c(-c2cc(Cn3cnc4c(NP(=O)(O)Oc5cccnc5)ncnc43)c(N3CCC[C@](N)([C@H](O)C(F)F)C3)cn2)cc1F] |

TABLE 4-continued
| Compound No. | Chemical Structure |
|---|---|
| IV-17 | 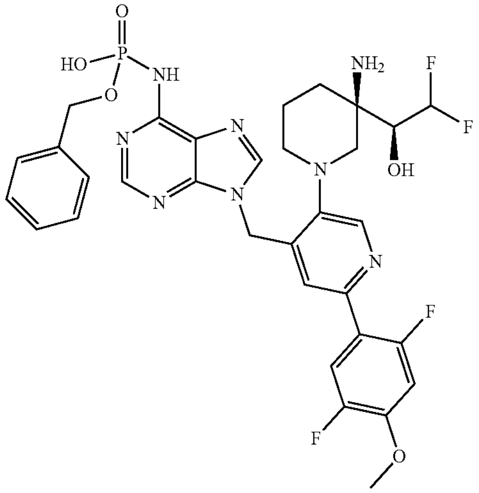 [SMILES: COc1cc(F)c(-c2cc(Cn3cnc4c(NP(=O)(O)OCc5ccccc5)ncnc43)c(N3CCC[C@](N)([C@H](O)C(F)F)C3)cn2)cc1F] |
| IV-18 | 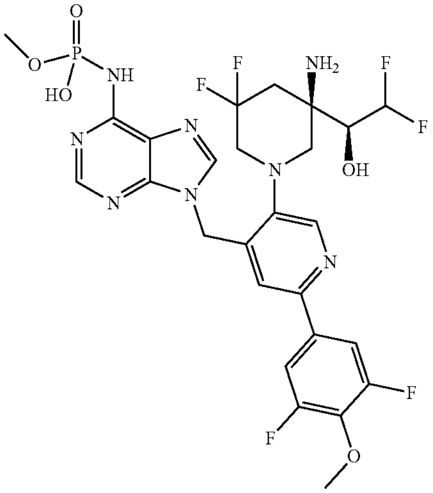 [SMILES: COc1c(F)cc(-c2cc(Cn3cnc4c(NP(=O)(O)OC)ncnc43)c(N3CC(F)(F)C[C@](N)([C@H](O)C(F)F)C3)cn2)cc1F] |
| IV-19 | 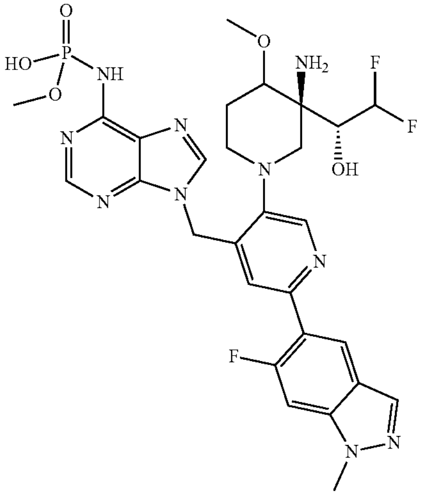 [SMILES: COC1CCN(c2cnc(-c3cc4cnn(C)c4cc3F)cc2Cn2cnc3c(NP(=O)(O)OC)ncnc32)C[C@@]1(N)[C@@H](O)C(F)F] |

TABLE 4-continued
| Compound No. | Chemical Structure |
| --- | --- |
| IV-20 | 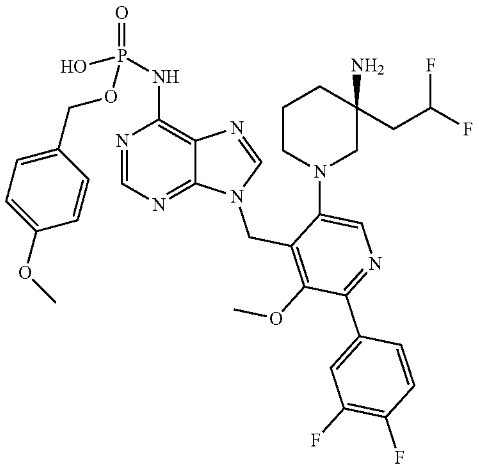 [SMILES: COc1ccc(COP(=O)(O)Nc2ncnc3c2ncn3Cc2c(N3CCC[C@](N)(CC(F)F)C3)cnc(-c3ccc(F)c(F)c3)c2OC)cc1] |
| IV-21 | 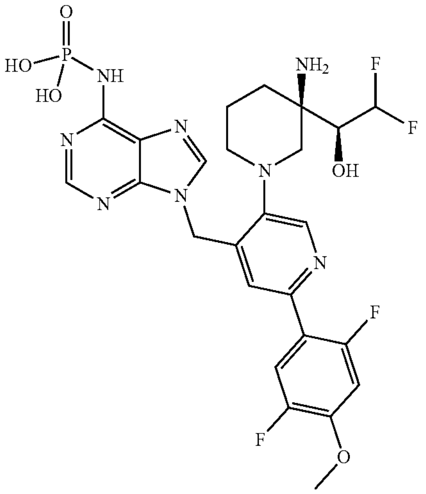 [SMILES: COc1cc(F)c(-c2cc(Cn3cnc4c(NP(=O)(O)O)ncnc43)c(N3CCC[C@](N)([C@H](O)C(F)F)C3)cn2)cc1F] |
| IV-22 | 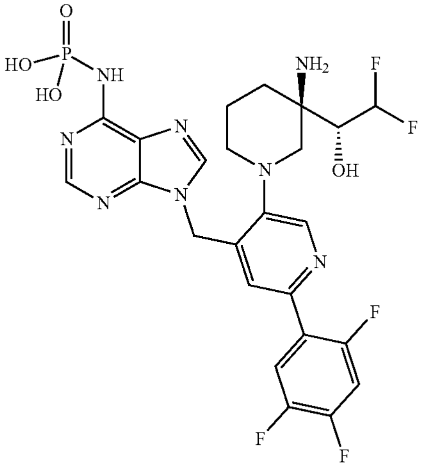 [SMILES: N[C@]1([C@@H](O)C(F)F)CCCN(c2cnc(-c3cc(F)c(F)cc3F)cc2Cn2cnc3c(NP(=O)(O)O)ncnc32)C1] |

TABLE 4-continued
| Compound No. | Chemical Structure |
|---|---|
| IV-23 | 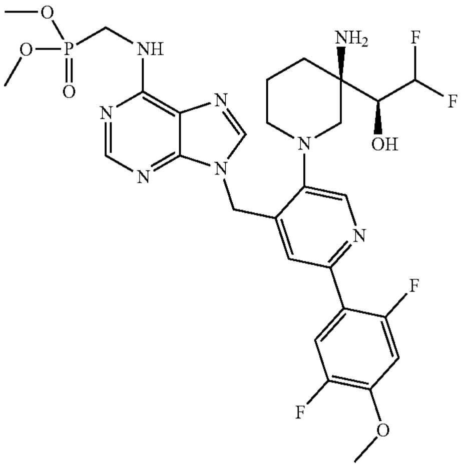 [SMILES: COc1cc(F)c(-c2cc(Cn3cnc4c(NCP(=O)(OC)OC)ncnc43)c(N3CCC[C@](N)([C@H](O)C(F)F)C3)cn2)cc1F] |
| IV-24 | 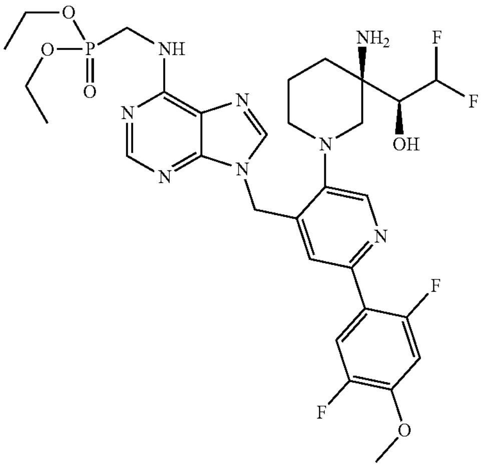 [SMILES: CCOP(=O)(CNc1ncnc2c1ncn2Cc1cc(-c2cc(F)c(OC)cc2F)ncc1N1CCC[C@](N)([C@H](O)C(F)F)C1)OCC] |
| IV-25 | 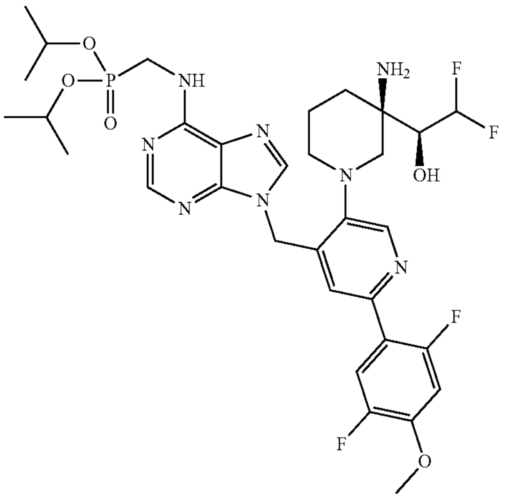 [SMILES: COc1cc(F)c(-c2cc(Cn3cnc4c(NCP(=O)(OC(C)C)OC(C)C)ncnc43)c(N3CCC[C@](N)([C@H](O)C(F)F)C3)cn2)cc1F] |

TABLE 4-continued
| Compound No. | Chemical Structure |
|---|---|
| IV-26 | 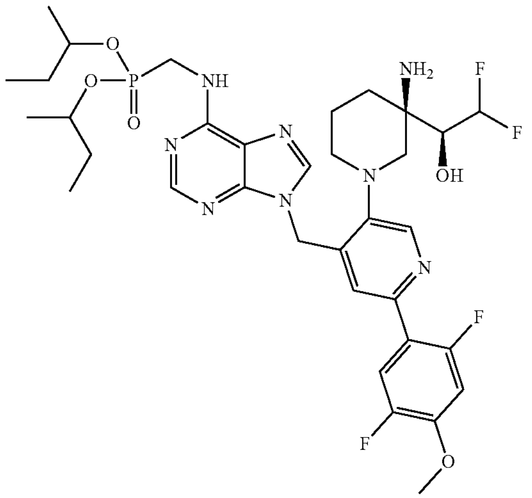 [SMILES: CCC(C)OP(=O)(CNc1ncnc2c1ncn2Cc1cc(-c2cc(F)c(OC)cc2F)ncc1N1CCC[C@](N)([C@H](O)C(F)F)C1)OC(C)CC] |
| IV-27 | 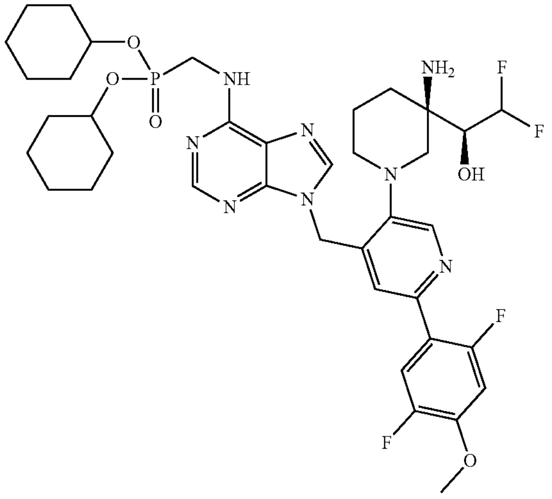 [SMILES: COc1cc(F)c(-c2cc(Cn3cnc4c(NCP(=O)(OC5CCCCC5)OC5CCCCC5)ncnc43)c(N3CCC[C@](N)([C@H](O)C(F)F)C3)cn2)cc1F] |
| IV-28 | 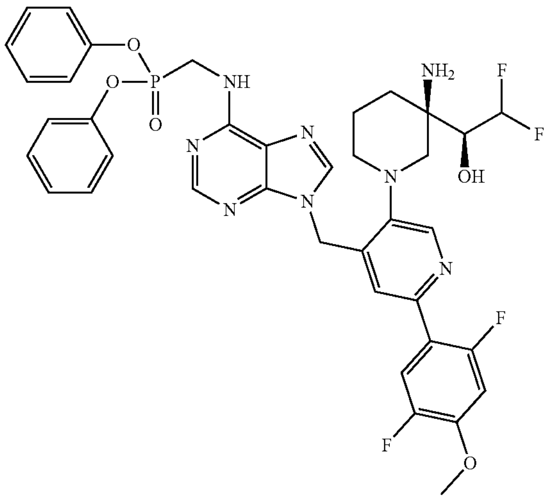 [SMILES: COc1cc(F)c(-c2cc(Cn3cnc4c(NCP(=O)(Oc5ccccc5)Oc5ccccc5)ncnc43)c(N3CCC[C@](N)([C@H](O)C(F)F)C3)cn2)cc1F] |

TABLE 4-continued
| Compound No. | Chemical Structure |
|---|---|
| IV-29 | 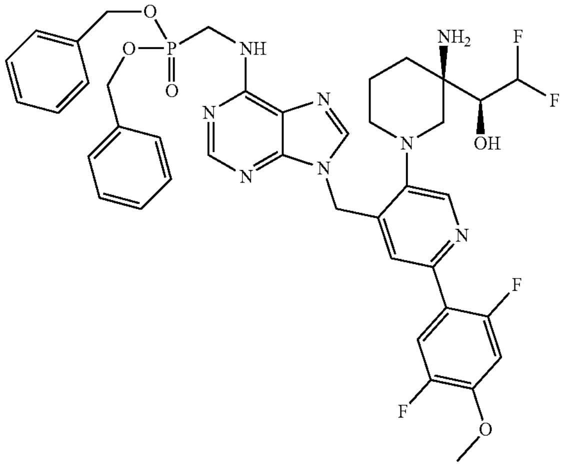 [SMILES: COc1cc(F)c(-c2cc(Cn3cnc4c(NCP(=O)(OCc5ccccc5)OCc5ccccc5)ncnc43)c(N3CCC[C@](N)([C@H](O)C(F)F)C3)cn2)cc1F] |
| IV-30 | 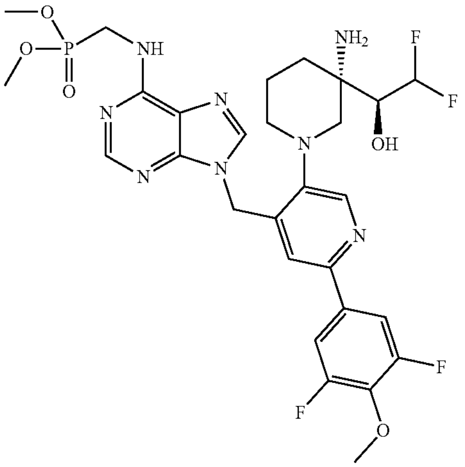 [SMILES: COc1c(F)cc(-c2cc(Cn3cnc4c(NCP(=O)(OC)OC)ncnc43)c(N3CCC[C@@](N)([C@H](O)C(F)F)C3)cn2)cc1F] |
| IV-31 | 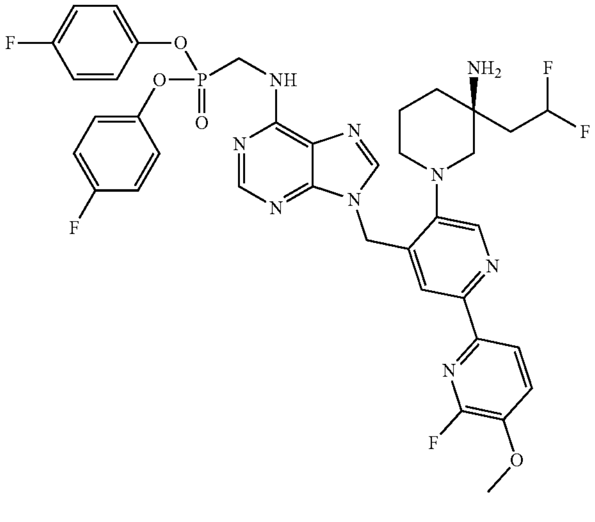 [SMILES: COc1ccc(-c2cc(Cn3cnc4c(NCP(=O)(Oc5ccc(F)cc5)Oc5ccc(F)cc5)ncnc43)c(N3CCC[C@](N)(CC(F)F)C3)cn2)nc1F] |

TABLE 4-continued
| Compound No. | Chemical Structure |
|---|---|
| IV-32 | 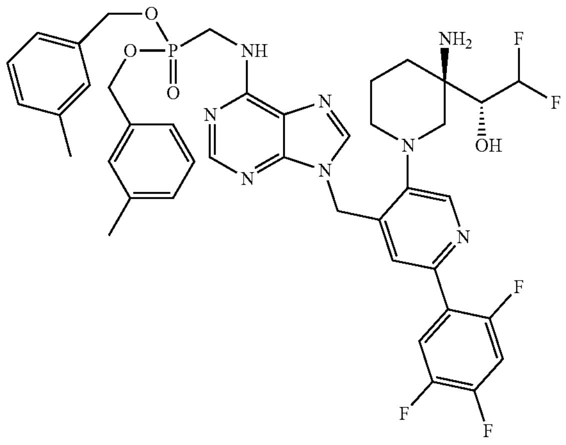 [SMILES: Cc1cccc(COP(=O)(CNc2ncnc3c2ncn3Cc2cc(-c3cc(F)c(F)cc3F)ncc2N2CCC[C@](N)([C@@H](O)C(F)F)C2)OCc2cccc(C)c2)c1] |
| IV-33 | 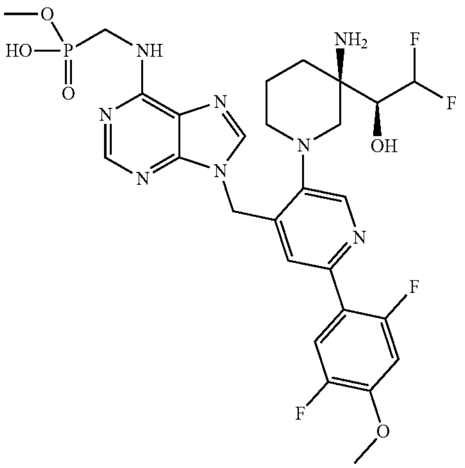 [SMILES: COc1cc(F)c(-c2cc(Cn3cnc4c(NCP(=O)(O)OC)ncnc43)c(N3CCC[C@](N)([C@H](O)C(F)F)C3)cn2)cc1F] |
| IV-34 | 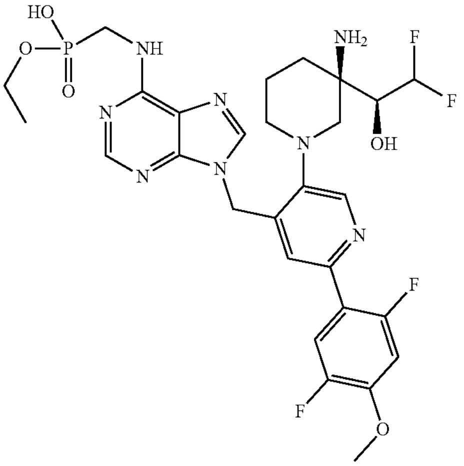 [SMILES: CCOP(=O)(O)CNc1ncnc2c1ncn2Cc1cc(-c2cc(F)c(OC)cc2F)ncc1N1CCC[C@](N)([C@H](O)C(F)F)C1] |

TABLE 4-continued
| Compound No. | Chemical Structure |
|---|---|
| IV-35 | 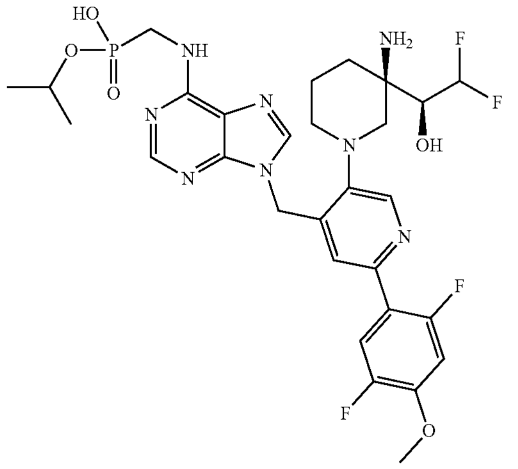 [SMILES: COc1cc(F)c(-c2cc(Cn3cnc4c(NCP(=O)(O)OC(C)C)ncnc43)c(N3CCC[C@](N)([C@H](O)C(F)F)C3)cn2)cc1F] |
| IV-36 | 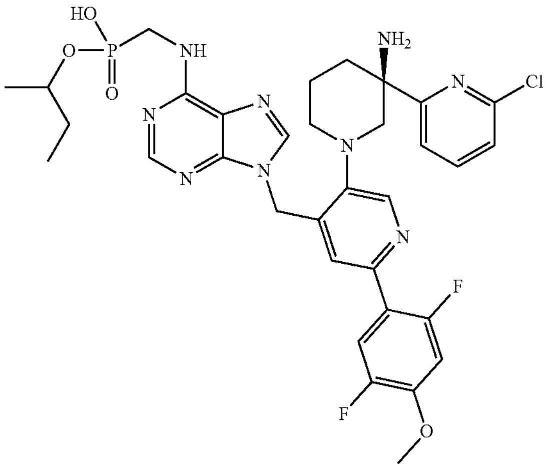 [SMILES: CCC(C)OP(=O)(O)CNc1ncnc2c1ncn2Cc1cc(-c2cc(F)c(OC)cc2F)ncc1N1CCC[C@](N)(c2cccc(Cl)n2)C1] |
| IV-37 | 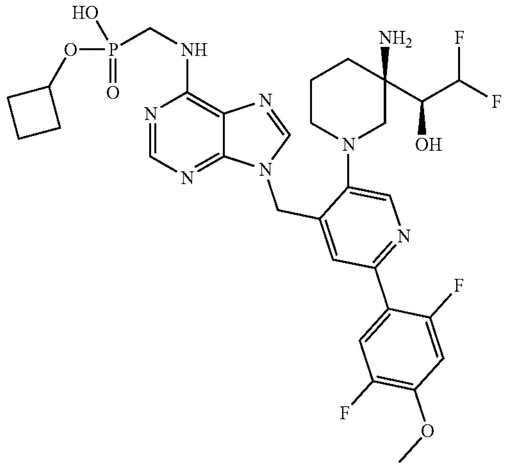 [SMILES: COc1cc(F)c(-c2cc(Cn3cnc4c(NCP(=O)(O)OC5CCC5)ncnc43)c(N3CCC[C@](N)([C@H](O)C(F)F)C3)cn2)cc1F] |

TABLE 4-continued
| Compound No. | Chemical Structure |
|---|---|
| IV-38 | 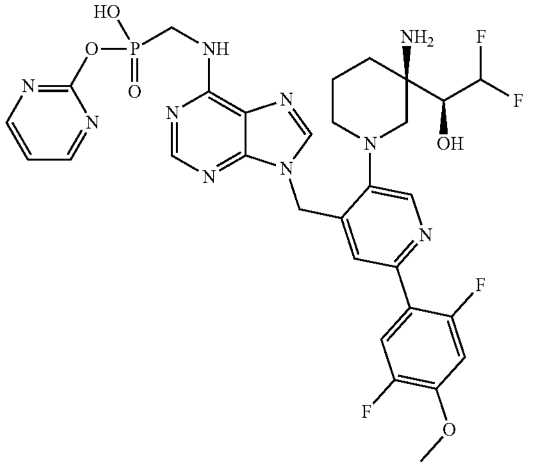 [SMILES: COc1cc(F)c(-c2cc(Cn3cnc4c(NCP(=O)(O)Oc5ncccn5)ncnc43)c(N3CCC[C@](N)([C@H](O)C(F)F)C3)cn2)cc1F] |
| IV-39 | 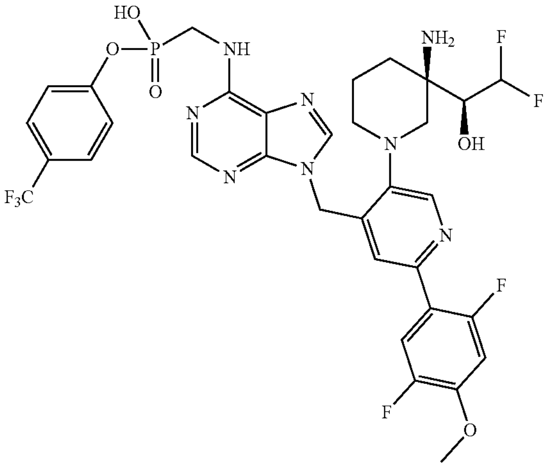 [SMILES: COc1cc(F)c(-c2cc(Cn3cnc4c(NCP(=O)(O)Oc5ccc(C(F)(F)F)cc5)ncnc43)c(N3CCC[C@](N)([C@H](O)C(F)F)C3)cn2)cc1F] |
| IV-40 | 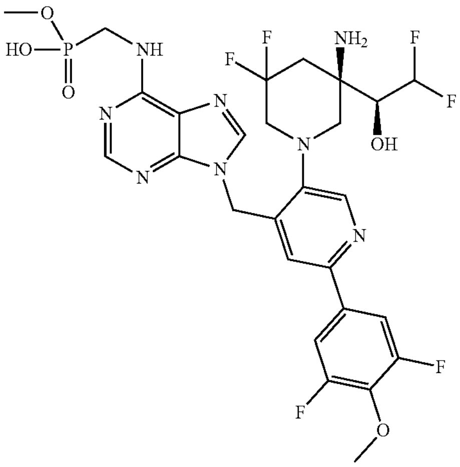 [SMILES: COc1c(F)cc(-c2cc(Cn3cnc4c(NCP(=O)(O)OC)ncnc43)c(N3CC(F)(F)C[C@](N)([C@H](O)C(F)F)C3)cn2)cc1F] |

TABLE 4-continued
| Compound No. | Chemical Structure |
| --- | --- |
| IV-41 | 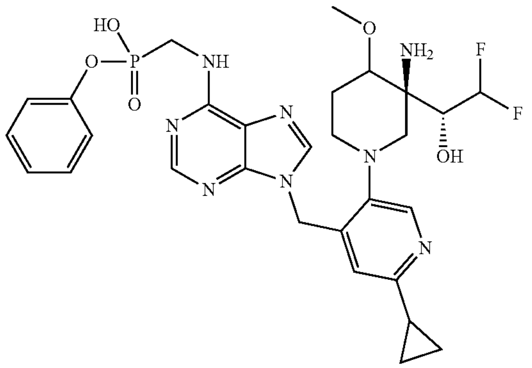 [SMILES: COC1CCN(c2cnc(C3CC3)cc2Cn2cnc3c(NCP(=O)(O)Oc4ccccc4)ncnc32)C[C@@]1(N)[C@@H](O)C(F)F] |
| IV-42 | 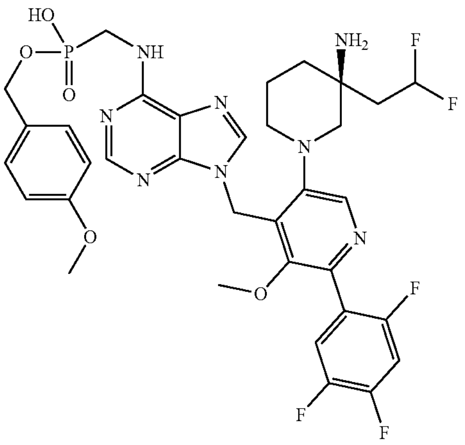 [SMILES: COc1ccc(COP(=O)(O)CNc2ncnc3c2ncn3Cc2c(N3CCC[C@](N)(CC(F)F)C3)cnc(-c3cc(F)c(F)cc3F)c2OC)cc1] |
| IV-43 | 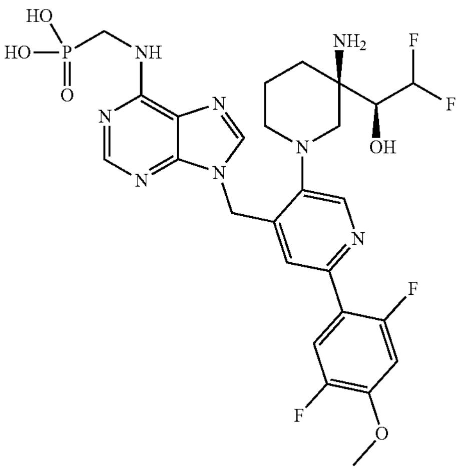 [SMILES: COc1cc(F)c(-c2cc(Cn3cnc4c(NCP(=O)(O)O)ncnc43)c(N3CCC[C@](N)([C@H](O)C(F)F)C3)cn2)cc1F] |

TABLE 4-continued
| Compound No. | Chemical Structure |
|---|---|
| IV-44 | 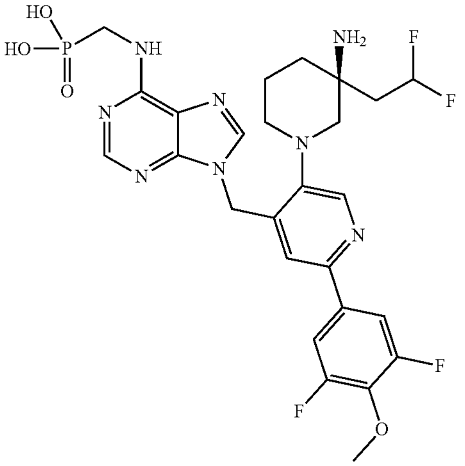 [SMILES: COc1c(F)cc(-c2cc(Cn3cnc4c(NCP(=O)(O)O)ncnc43)c(N3CCC[C@](N)(CC(F)F)C3)cn2)cc1F] |
| IV-45 | 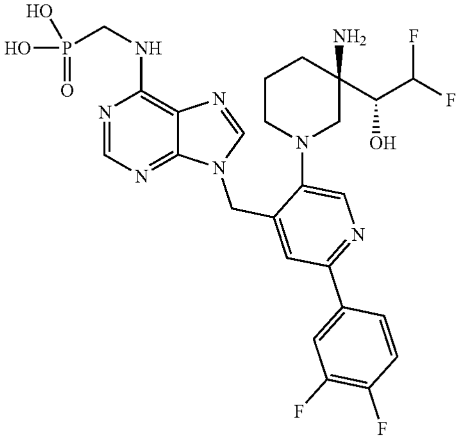 [SMILES: N[C@]1([C@@H](O)C(F)F)CCCN(c2cnc(-c3ccc(F)c(F)c3)cc2Cn2cnc3c(NCP(=O)(O)O)ncnc32)C1] |
TABLE 5
| Compound No. | Chemical Structure |
|---|---|
| V-1 | 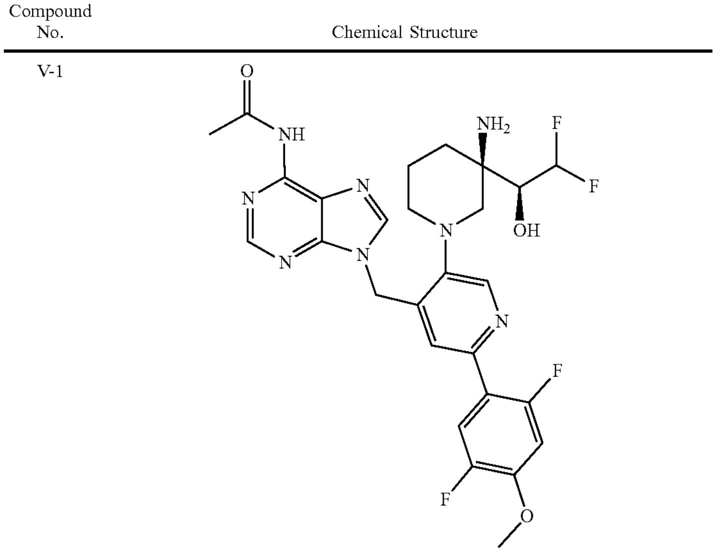 |

TABLE 5-continued
| Compound No. | Chemical Structure |
|---|---|
| V-2 | 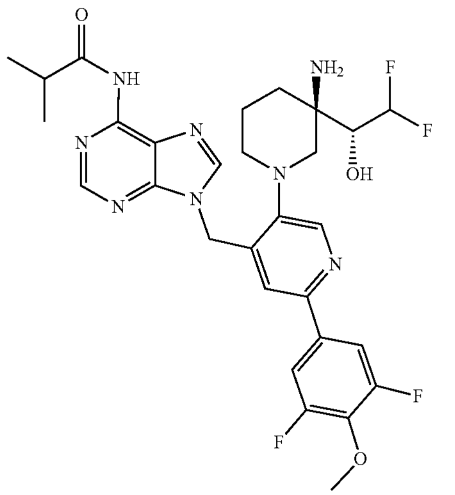 [SMILES: COc1c(F)cc(-c2cc(Cn3cnc4c(NC(=O)C(C)C)ncnc43)c(N3CCC[C@](N)([C@@H](O)C(F)F)C3)cn2)cc1F] |
| V-3 | 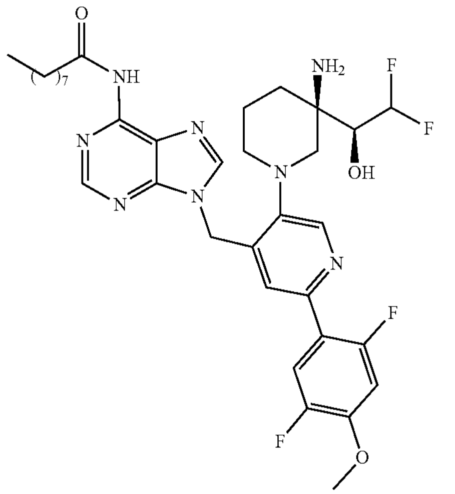 |
| V-4 | 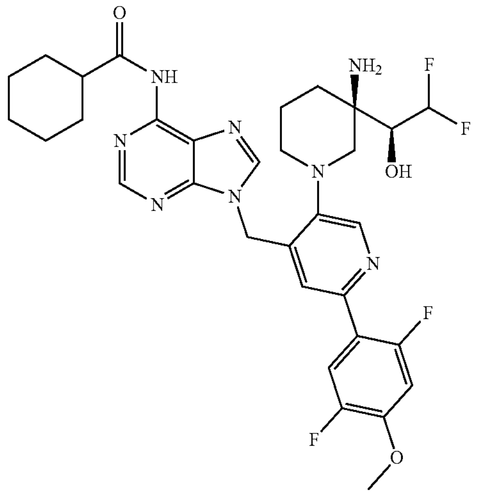 [SMILES: COc1cc(F)c(-c2cc(Cn3cnc4c(NC(=O)C5CCCCC5)ncnc43)c(N3CCC[C@](N)([C@H](O)C(F)F)C3)cn2)cc1F] |

TABLE 5-continued
| Compound No. | Chemical Structure |
| --- | --- |
| V-5 | 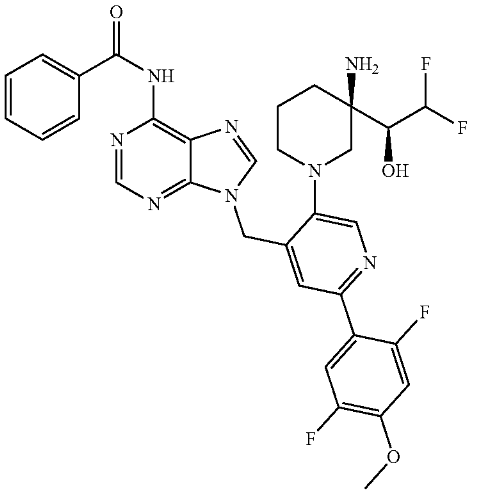 [SMILES: COc1cc(F)c(-c2cc(Cn3cnc4c(NC(=O)c5ccccc5)ncnc43)c(N3CCC[C@](N)([C@H](O)C(F)F)C3)cn2)cc1F] |
| V-6 | 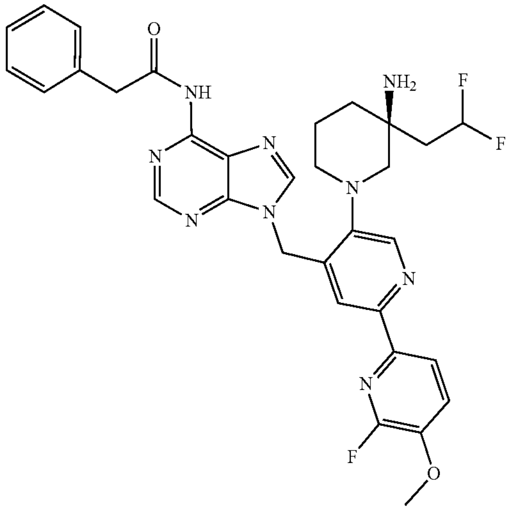 [SMILES: COc1ccc(-c2cc(Cn3cnc4c(NC(=O)Cc5ccccc5)ncnc43)c(N3CCC[C@](N)(CC(F)F)C3)cn2)nc1F] |
| V-7 | 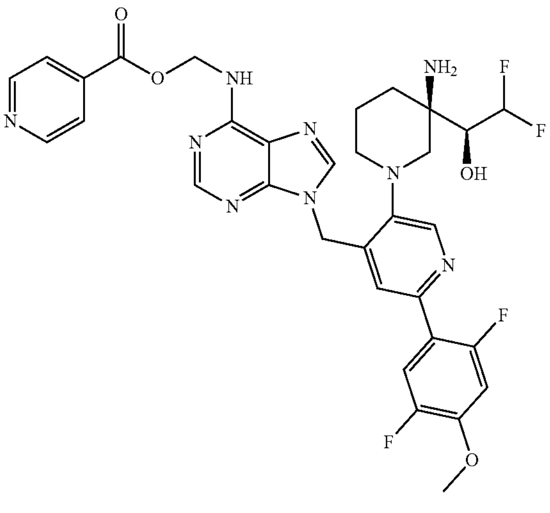 [SMILES: COc1cc(F)c(-c2cc(Cn3cnc4c(NCOC(=O)c5ccncc5)ncnc43)c(N3CCC[C@](N)([C@H](O)C(F)F)C3)cn2)cc1F] |

TABLE 5-continued
| Compound No. | Chemical Structure |
|---|---|
| V-8 | 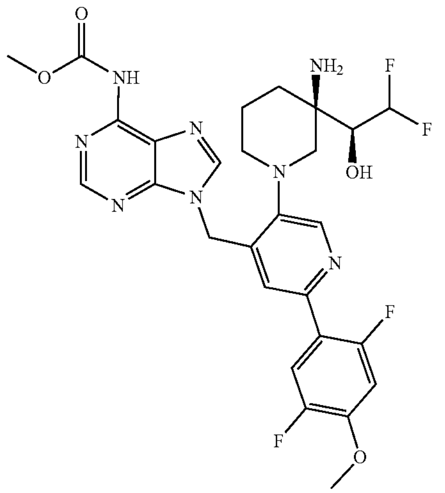 [SMILES: COC(=O)Nc1ncnc2c1ncn2Cc1cc(-c2cc(F)c(OC)cc2F)ncc1N1CCC[C@](N)([C@H](O)C(F)F)C1] |
| V-9 | 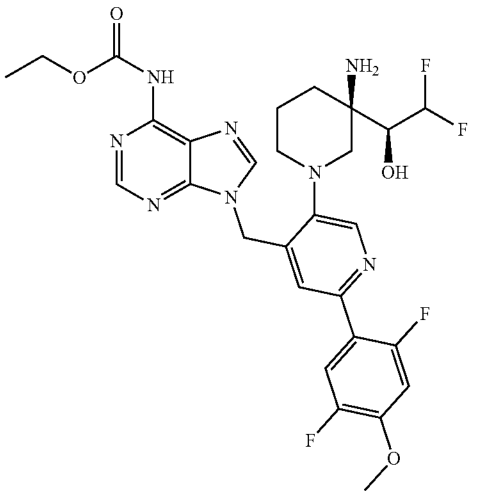 [SMILES: CCOC(=O)Nc1ncnc2c1ncn2Cc1cc(-c2cc(F)c(OC)cc2F)ncc1N1CCC[C@](N)([C@H](O)C(F)F)C1] |
| V-10 | 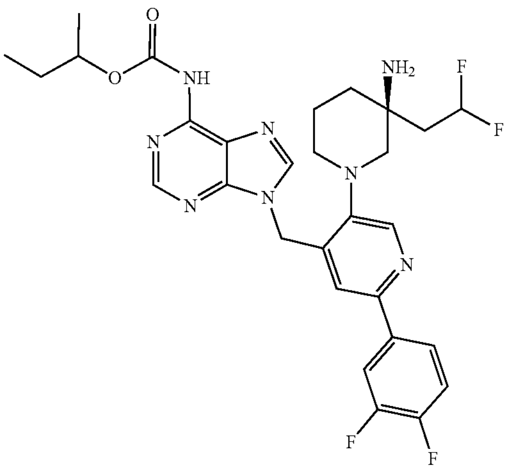 [SMILES: CCC(C)OC(=O)Nc1ncnc2c1ncn2Cc1cc(-c2ccc(F)c(F)c2)ncc1N1CCC[C@](N)(CC(F)F)C1] |

TABLE 5-continued
| Compound No. | Chemical Structure |
|---|---|
| V-11 | 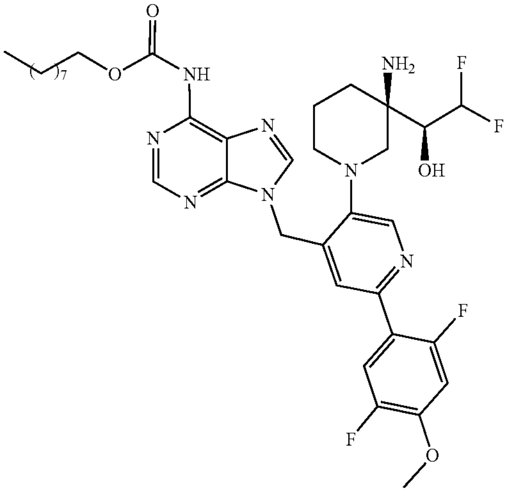 |
| V-12 | 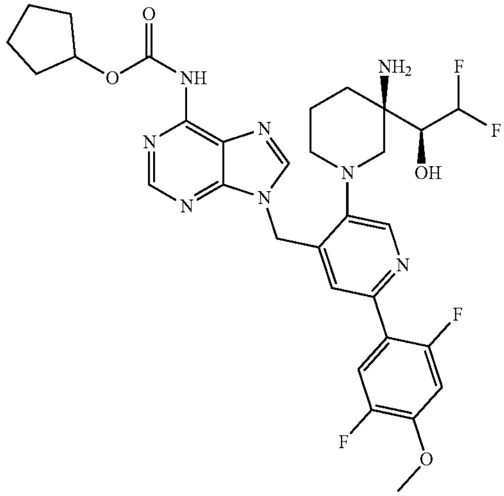 [SMILES: COc1cc(F)c(-c2cc(Cn3cnc4c(NC(=O)OC5CCCC5)ncnc43)c(N3CCC[C@](N)([C@H](O)C(F)F)C3)cn2)cc1F] |
| V-13 | 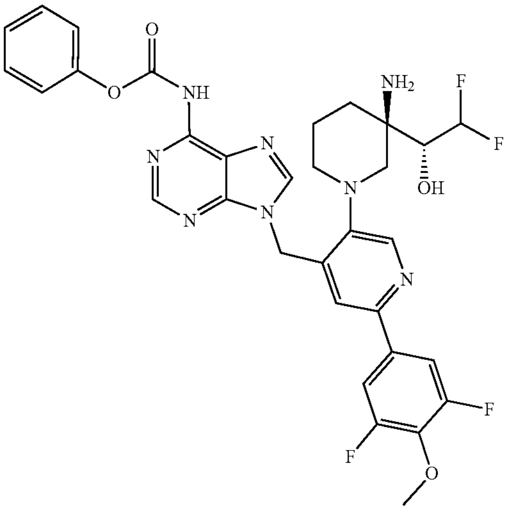 [SMILES: COc1c(F)cc(-c2cc(Cn3cnc4c(NC(=O)Oc5ccccc5)ncnc43)c(N3CCC[C@](N)([C@@H](O)C(F)F)C3)cn2)cc1F] |

TABLE 5-continued
| Compound No. | Chemical Structure |
|---|---|
| V-14 | 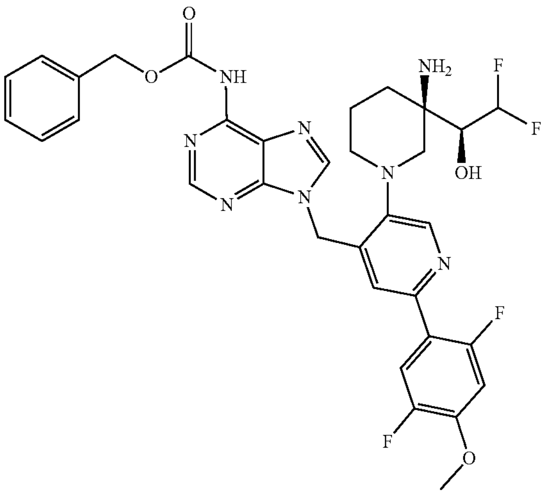 [SMILES: COc1cc(F)c(-c2cc(Cn3cnc4c(NC(=O)OCc5ccccc5)ncnc43)c(N3CCC[C@](N)([C@H](O)C(F)F)C3)cn2)cc1F] |
| V-15 | 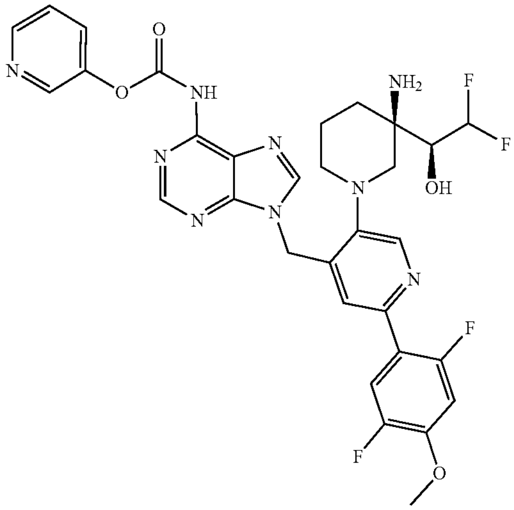 [SMILES: COc1cc(F)c(-c2cc(Cn3cnc4c(NC(=O)Oc5cccnc5)ncnc43)c(N3CCC[C@](N)([C@H](O)C(F)F)C3)cn2)cc1F] |
| V-16 | 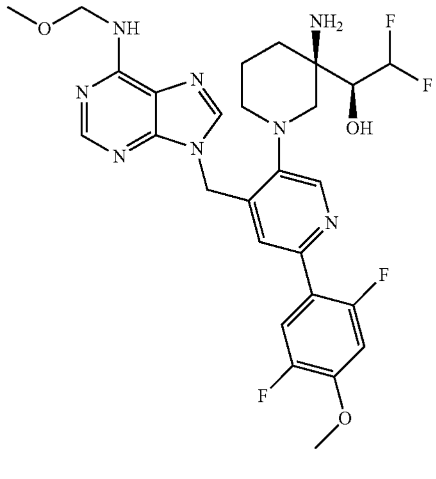 [SMILES: COCNc1ncnc2c1ncn2Cc1cc(-c2cc(F)c(OC)cc2F)ncc1N1CCC[C@](N)([C@H](O)C(F)F)C1] |

TABLE 5-continued
| Compound No. | Chemical Structure |
| --- | --- |
| V-17 | 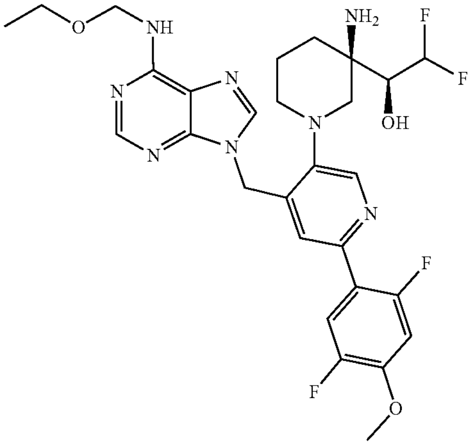 [SMILES: CCOCNc1ncnc2c1ncn2Cc1cc(-c2cc(F)c(OC)cc2F)ncc1N1CCC[C@](N)([C@H](O)C(F)F)C1] |
| V-18 | 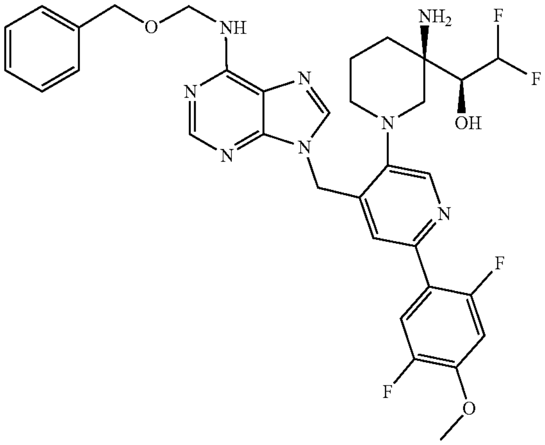 [SMILES: COc1cc(F)c(-c2cc(Cn3cnc4c(NCOCc5ccccc5)ncnc43)c(N3CCC[C@](N)([C@H](O)C(F)F)C3)cn2)cc1F] |
| V-19 | 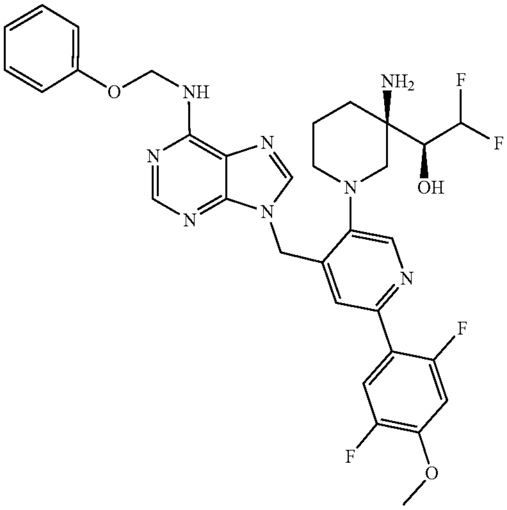 [SMILES: COc1cc(F)c(-c2cc(Cn3cnc4c(NCOc5ccccc5)ncnc43)c(N3CCC[C@](N)([C@H](O)C(F)F)C3)cn2)cc1F] |

TABLE 5-continued
| Compound No. | Chemical Structure |
|---|---|
| V-20 | 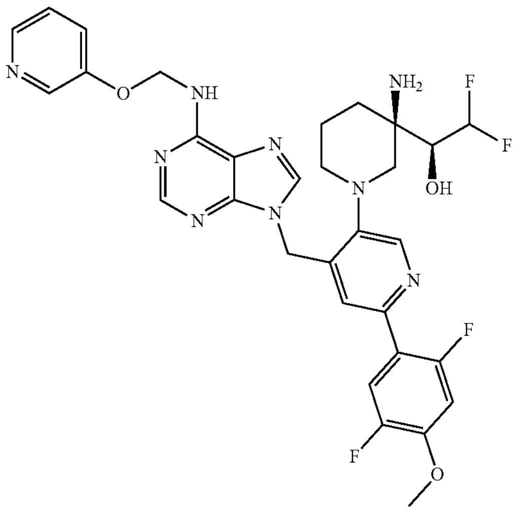 [SMILES: COc1cc(F)c(-c2cc(Cn3cnc4c(NCOc5cccnc5)ncnc43)c(N3CCC[C@](N)([C@H](O)C(F)F)C3)cn2)cc1F] |
| V-21 | 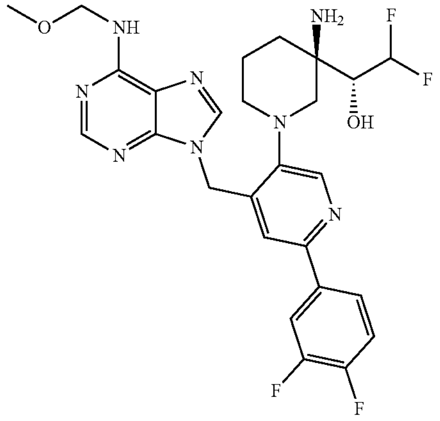 [SMILES: COCNc1ncnc2c1ncn2Cc1cc(-c2ccc(F)c(F)c2)ncc1N1CCC[C@](N)([C@@H](O)C(F)F)C1] |
| V-22 | 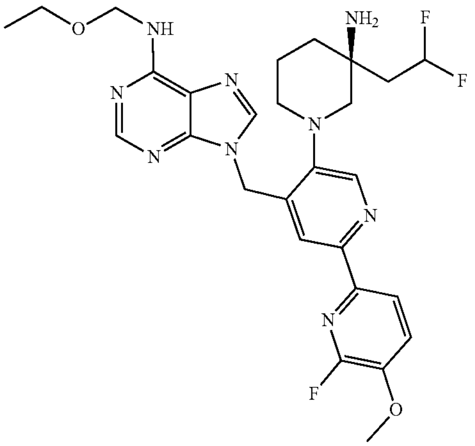 [SMILES: CCOCNc1ncnc2c1ncn2Cc1cc(-c2ccc(OC)c(F)n2)ncc1N1CCC[C@](N)(CC(F)F)C1] |

TABLE 5-continued
| Compound No. | Chemical Structure |
| --- | --- |
| V-23 | 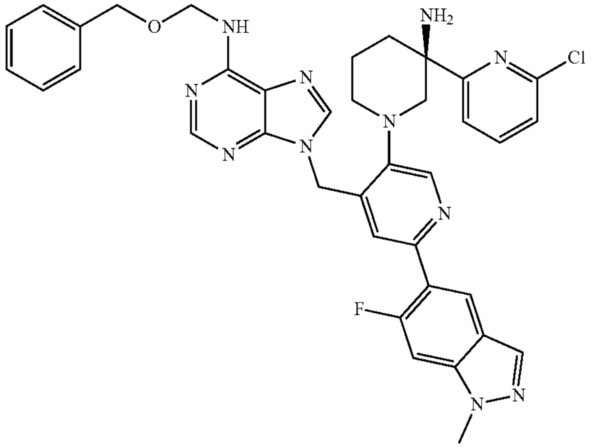 [SMILES: Cn1ncc2cc(-c3cc(Cn4cnc5c(NCOCc6ccccc6)ncnc54)c(N4CCC[C@](N)(c5cccc(Cl)n5)C4)cn3)c(F)cc21] |
| V-24 | 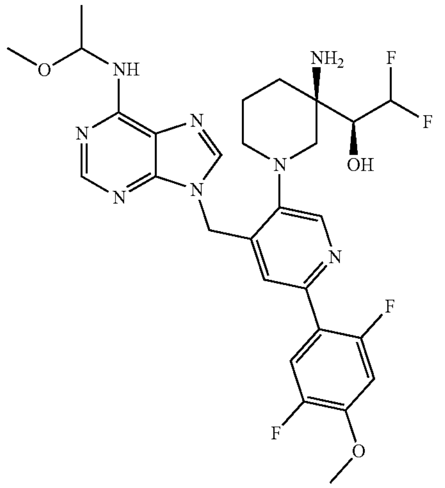 [SMILES: COc1cc(F)c(-c2cc(Cn3cnc4c(NC(C)OC)ncnc43)c(N3CCC[C@](N)([C@H](O)C(F)F)C3)cn2)cc1F] |
| V-25 | 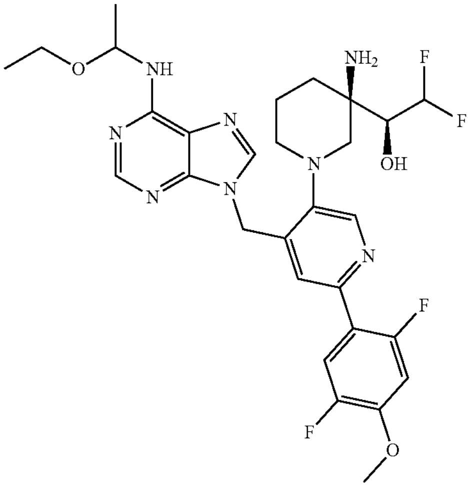 [SMILES: CCOC(C)Nc1ncnc2c1ncn2Cc1cc(-c2cc(F)c(OC)cc2F)ncc1N1CCC[C@](N)([C@H](O)C(F)F)C1] |

TABLE 5-continued
| Compound No. | Chemical Structure |
|---|---|
| V-26 | 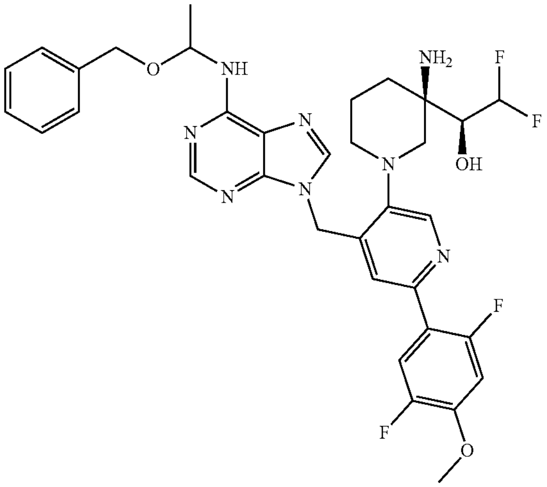 [SMILES: COc1cc(F)c(-c2cc(Cn3cnc4c(NC(C)OCc5ccccc5)ncnc43)c(N3CCC[C@](N)([C@H](O)C(F)F)C3)cn2)cc1F] |
| V-27 | 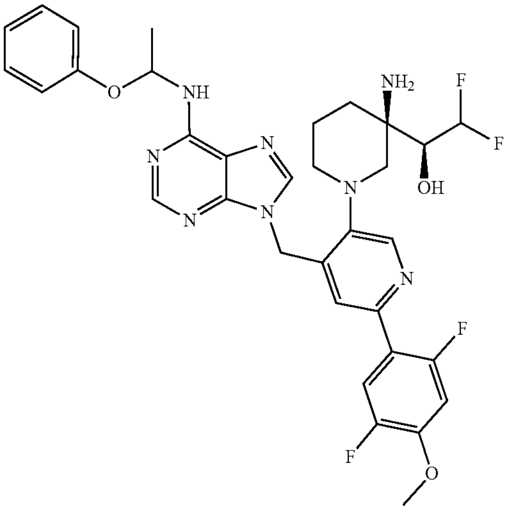 [SMILES: COc1cc(F)c(-c2cc(Cn3cnc4c(NC(C)Oc5ccccc5)ncnc43)c(N3CCC[C@](N)([C@H](O)C(F)F)C3)cn2)cc1F] |
| V-28 | 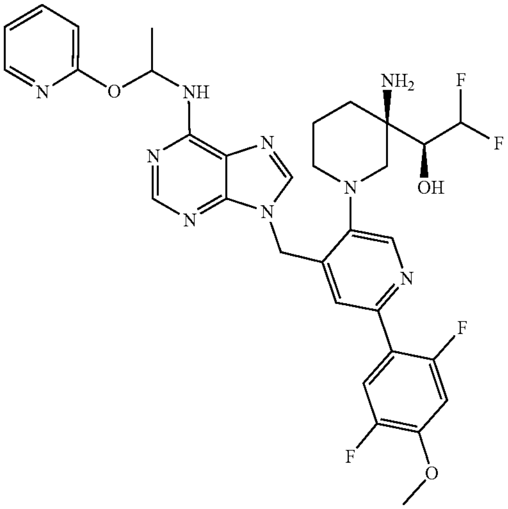 [SMILES: COc1cc(F)c(-c2cc(Cn3cnc4c(NC(C)Oc5ccccn5)ncnc43)c(N3CCC[C@](N)([C@H](O)C(F)F)C3)cn2)cc1F] |

TABLE 5-continued
| Compound No. | Chemical Structure |
|---|---|
| V-29 | 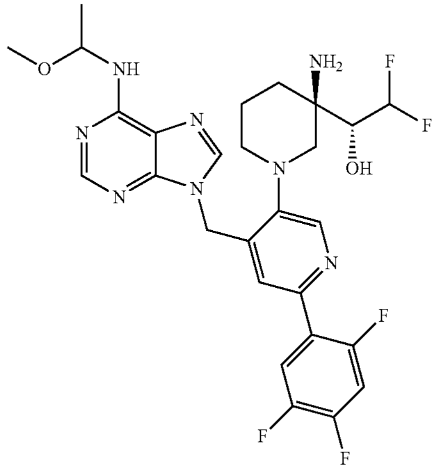 [SMILES: COC(C)Nc1ncnc2c1ncn2Cc1cc(-c2cc(F)c(F)cc2F)ncc1N1CCC[C@](N)([C@@H](O)C(F)F)C1] |
| V-30 | 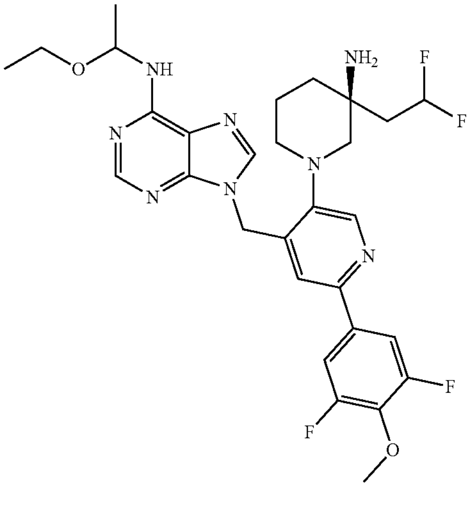 [SMILES: CCOC(C)Nc1ncnc2c1ncn2Cc1cc(-c2cc(F)c(OC)c(F)c2)ncc1N1CCC[C@](N)(CC(F)F)C1] |
| V-31 | 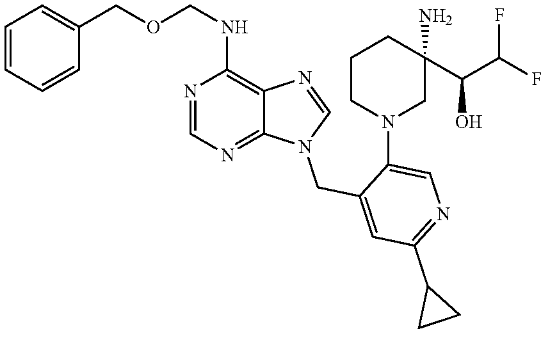 [SMILES: N[C@@]1([C@H](O)C(F)F)CCCN(c2cnc(C3CC3)cc2Cn2cnc3c(NCOCc4ccccc4)ncnc32)C1] |

TABLE 5-continued
| Compound No. | Chemical Structure |
|---|---|
| V-32 | 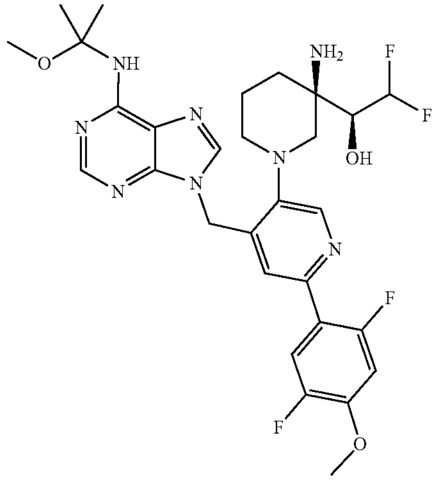 [SMILES: COc1cc(F)c(-c2cc(Cn3cnc4c(NC(C)(C)OC)ncnc43)c(N3CCC[C@](N)([C@H](O)C(F)F)C3)cn2)cc1F] |
| V-33 | 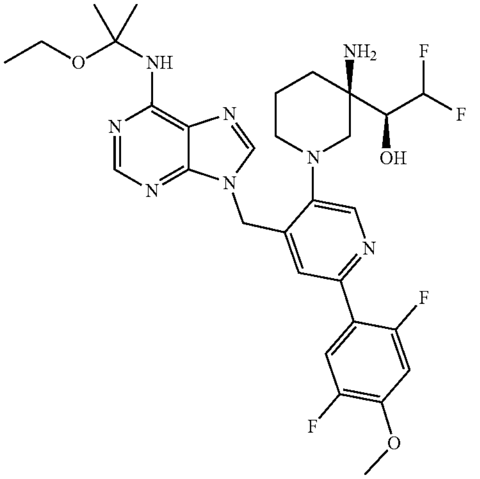 [SMILES: CCOC(C)(C)Nc1ncnc2c1ncn2Cc1cc(-c2cc(F)c(OC)cc2F)ncc1N1CCC[C@](N)([C@H](O)C(F)F)C1] |
| V-34 | 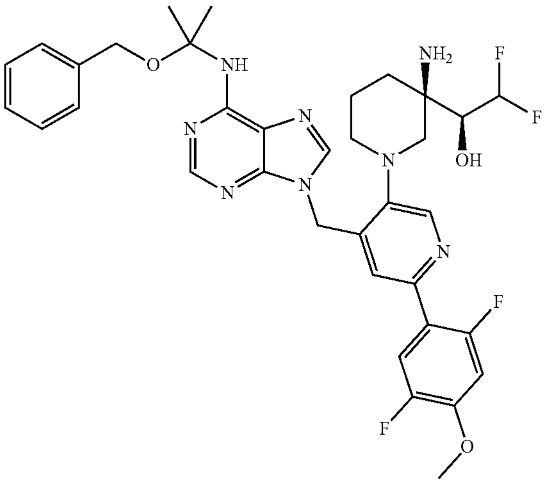 [SMILES: COc1cc(F)c(-c2cc(Cn3cnc4c(NC(C)(C)OCc5ccccc5)ncnc43)c(N3CCC[C@](N)([C@H](O)C(F)F)C3)cn2)cc1F] |

TABLE 5-continued
| Compound No. | Chemical Structure |
|---|---|
| V-35 | 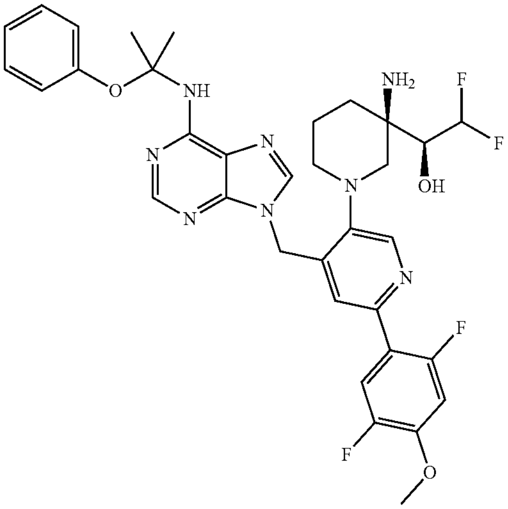 [SMILES: COc1cc(F)c(-c2cc(Cn3cnc4c(NC(C)(C)Oc5ccccc5)ncnc43)c(N3CCC[C@](N)([C@H](O)C(F)F)C3)cn2)cc1F] |
| V-36 | 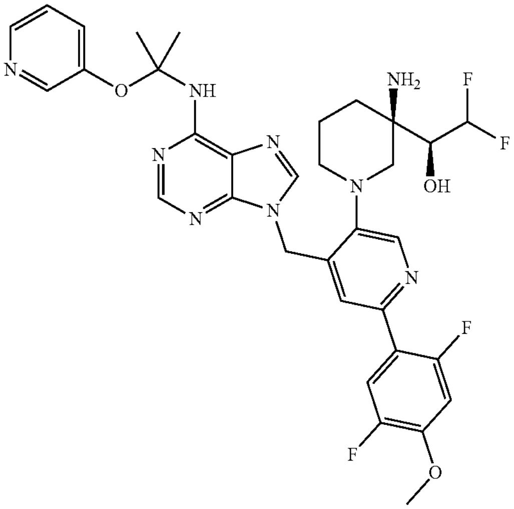 [SMILES: COc1cc(F)c(-c2cc(Cn3cnc4c(NC(C)(C)Oc5cccnc5)ncnc43)c(N3CCC[C@](N)([C@H](O)C(F)F)C3)cn2)cc1F] |
| V-37 | 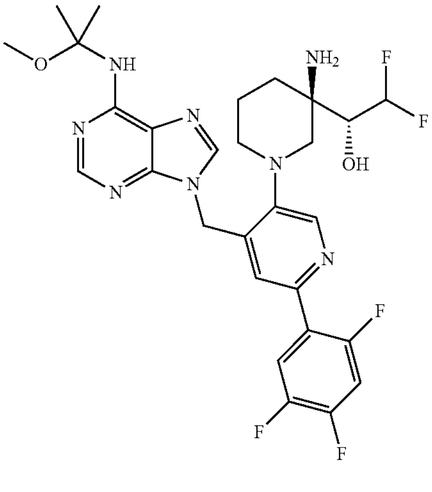 [SMILES: COC(C)(C)Nc1ncnc2c1ncn2Cc1cc(-c2cc(F)c(F)cc2F)ncc1N1CCC[C@](N)([C@@H](O)C(F)F)C1] |

TABLE 5-continued
| Compound No. | Chemical Structure |
| --- | --- |
| V-38 | 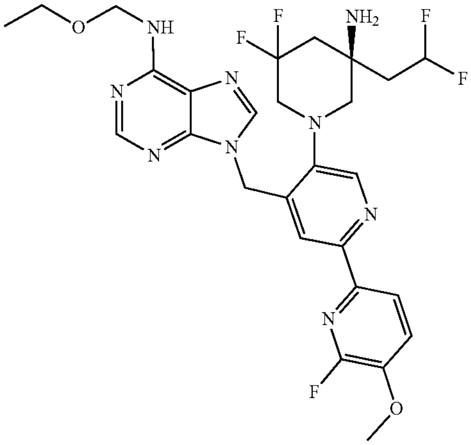 [SMILES: CCOCNc1ncnc2c1ncn2Cc1cc(-c2ccc(OC)c(F)n2)ncc1N1CC(F)(F)C[C@](N)(CC(F)F)C1] |
| V-39 | 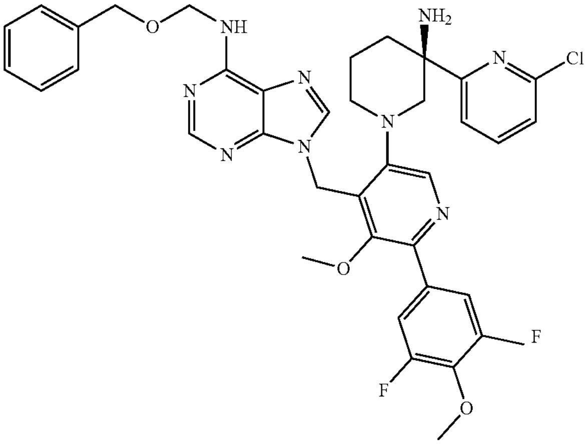 |
| V-40 | 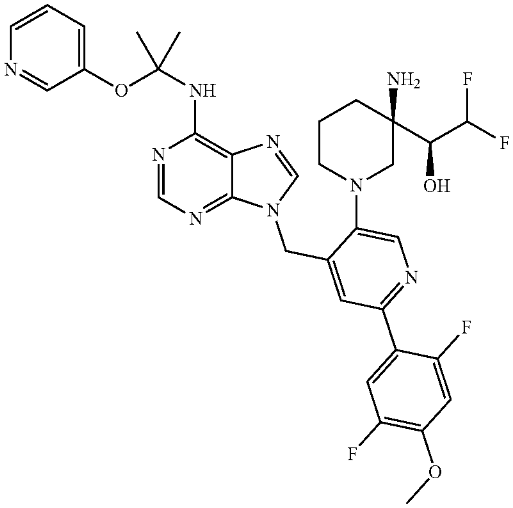 [SMILES: COc1cc(F)c(-c2cc(Cn3cnc4c(NC(C)(C)Oc5cccnc5)ncnc43)c(N3CCC[C@](N)([C@H](O)C(F)F)C3)cn2)cc1F] |

TABLE 5-continued
| Compound No. | Chemical Structure |
|---|---|
| V-41 | 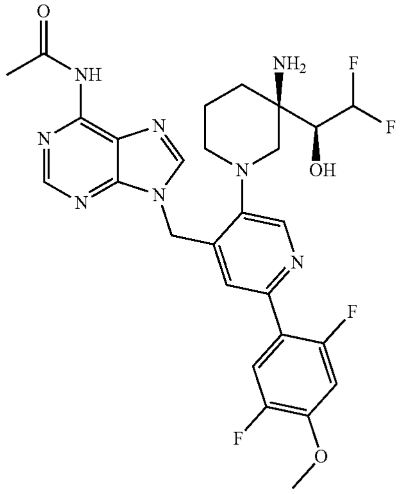 [SMILES: COc1cc(F)c(-c2cc(Cn3cnc4c(NC(C)=O)ncnc43)c(N3CCC[C@](N)([C@H](O)C(F)F)C3)cn2)cc1F] |
| V-42 | 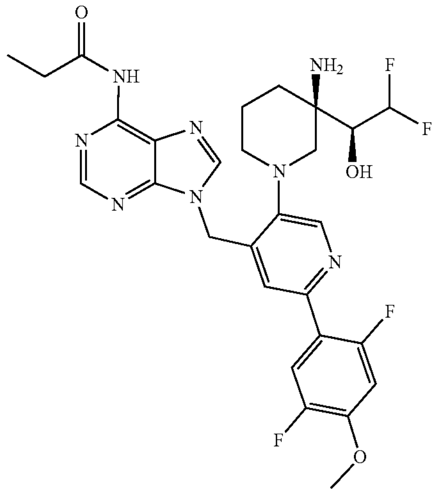 |
| V-43 | 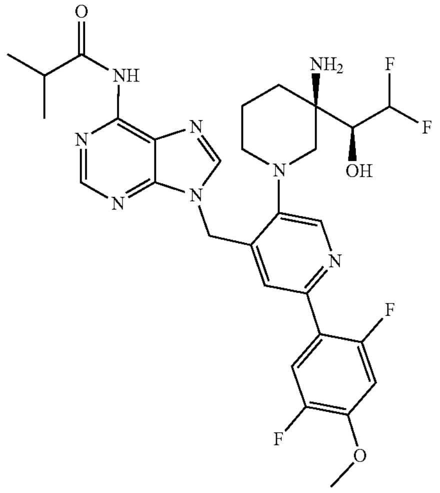 [SMILES: COc1cc(F)c(-c2cc(Cn3cnc4c(NC(=O)C(C)C)ncnc43)c(N3CCC[C@](N)([C@H](O)C(F)F)C3)cn2)cc1F] |

TABLE 5-continued
| Compound No. | Chemical Structure |
|---|---|
| V-44 | 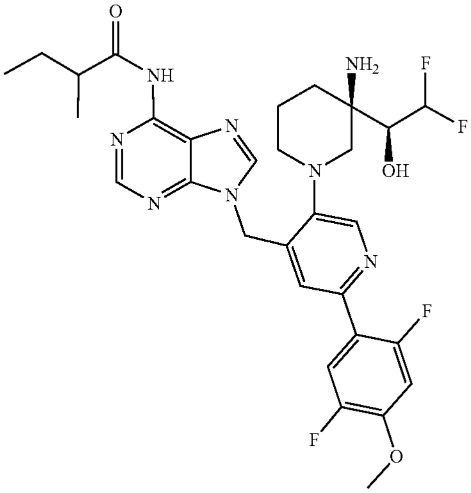 [SMILES: CCC(C)C(=O)Nc1ncnc2c1ncn2Cc1cc(-c2cc(F)c(OC)cc2F)ncc1N1CCC[C@](N)([C@H](O)C(F)F)C1] |
| V-45 | 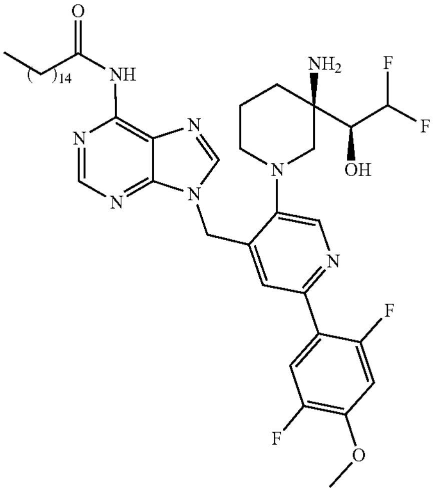 |
| V-46 | 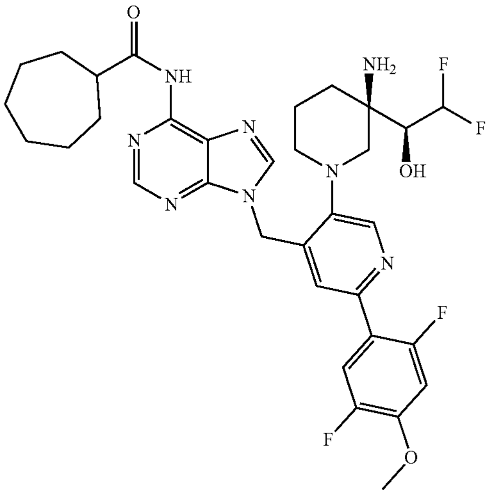 [SMILES: COc1cc(F)c(-c2cc(Cn3cnc4c(NC(=O)C5CCCCCC5)ncnc43)c(N3CCC[C@](N)([C@H](O)C(F)F)C3)cn2)cc1F] |

TABLE 5-continued
| Compound No. | Chemical Structure |
|---|---|
| V-47 | 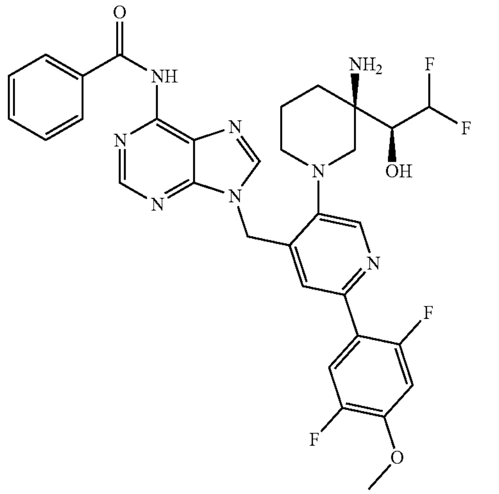 [SMILES: COc1cc(F)c(-c2cc(Cn3cnc4c(NC(=O)c5ccccc5)ncnc43)c(N3CCC[C@](N)([C@H](O)C(F)F)C3)cn2)cc1F] |
| V-48 | 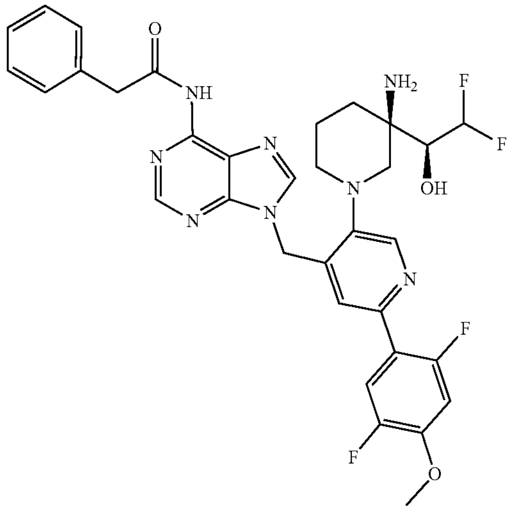 [SMILES: COc1cc(F)c(-c2cc(Cn3cnc4c(NC(=O)Cc5ccccc5)ncnc43)c(N3CCC[C@](N)([C@H](O)C(F)F)C3)cn2)cc1F] |
| V-49 | 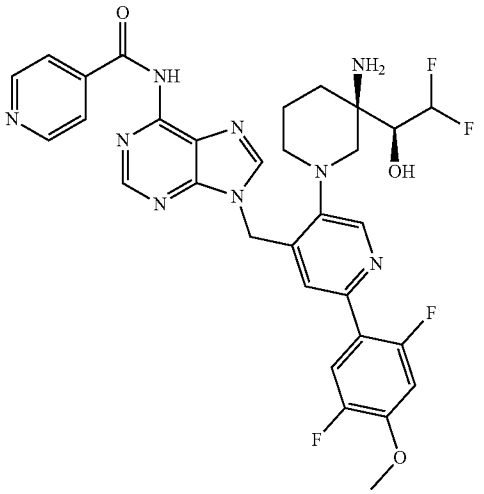 [SMILES: COc1cc(F)c(-c2cc(Cn3cnc4c(NC(=O)c5ccncc5)ncnc43)c(N3CCC[C@](N)([C@H](O)C(F)F)C3)cn2)cc1F] |

TABLE 5-continued
| Compound No. | Chemical Structure |
|---|---|
| V-50 | 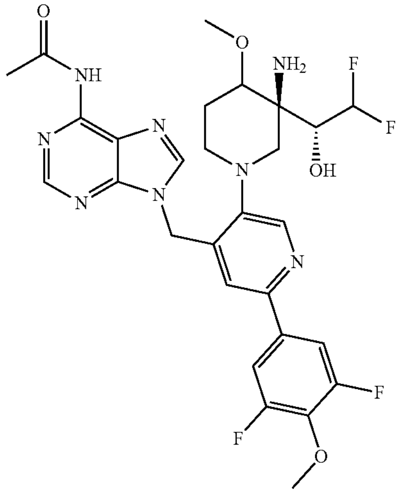 [SMILES: COc1c(F)cc(-c2cc(Cn3cnc4c(NC(C)=O)ncnc43)c(N3CCC(OC)[C@](N)([C@@H](O)C(F)F)C3)cn2)cc1F] |
| V-51 | 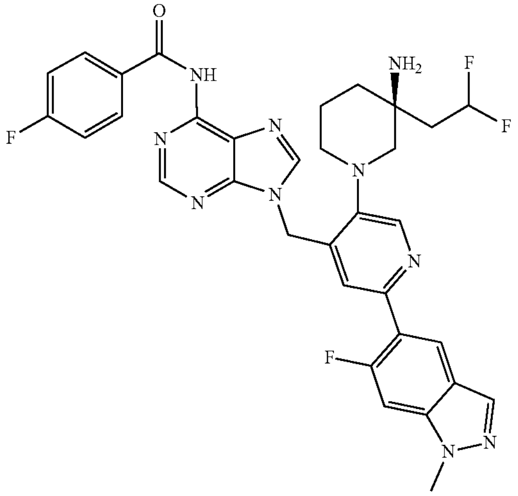 [SMILES: Cn1ncc2cc(-c3cc(Cn4cnc5c(NC(=O)c6ccc(F)cc6)ncnc54)c(N4CCC[C@](N)(CC(F)F)C4)cn3)c(F)cc21] |
| V-52 | 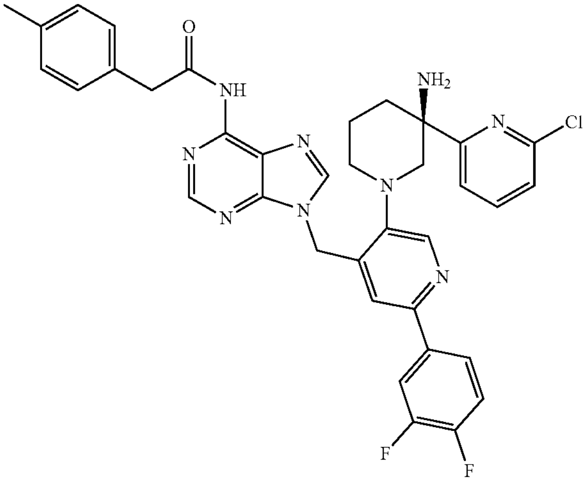 [SMILES: Cc1ccc(CC(=O)Nc2ncnc3c2ncn3Cc2cc(-c3ccc(F)c(F)c3)ncc2N2CCC[C@](N)(c3cccc(Cl)n3)C2)cc1] |

TABLE 5-continued
| Compound No. | Chemical Structure |
|---|---|
| V-53 | 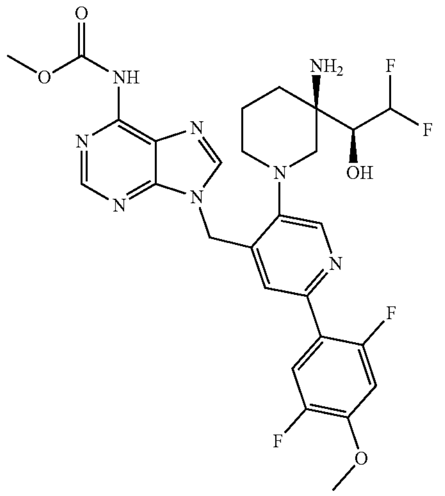 [SMILES: COC(=O)Nc1ncnc2c1ncn2Cc1cc(-c2cc(F)c(OC)cc2F)ncc1N1CCC[C@](N)([C@H](O)C(F)F)C1] |
| V-54 | 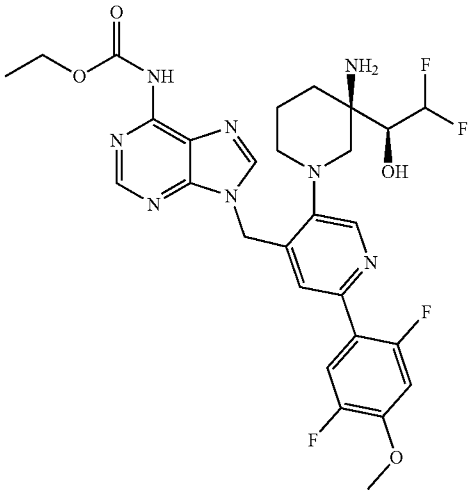 [SMILES: CCOC(=O)Nc1ncnc2c1ncn2Cc1cc(-c2cc(F)c(OC)cc2F)ncc1N1CCC[C@](N)([C@H](O)C(F)F)C1] |
| V-55 | 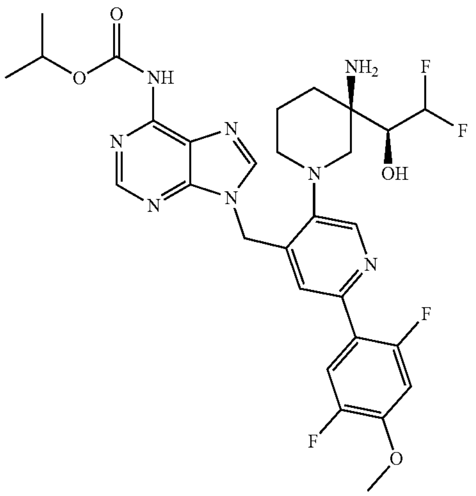 [SMILES: COc1cc(F)c(-c2cc(Cn3cnc4c(NC(=O)OC(C)C)ncnc43)c(N3CCC[C@](N)([C@H](O)C(F)F)C3)cn2)cc1F] |

TABLE 5-continued
| Compound No. | Chemical Structure |
|---|---|
| V-56 | 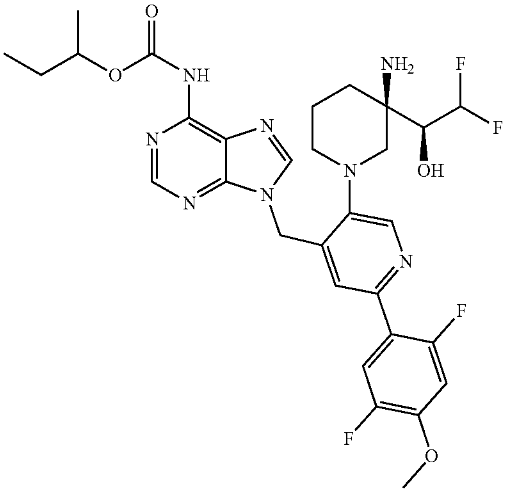 [SMILES: CCC(C)OC(=O)Nc1ncnc2c1ncn2Cc1cc(-c2cc(F)c(OC)cc2F)ncc1N1CCC[C@](N)([C@H](O)C(F)F)C1] |
| V-57 | 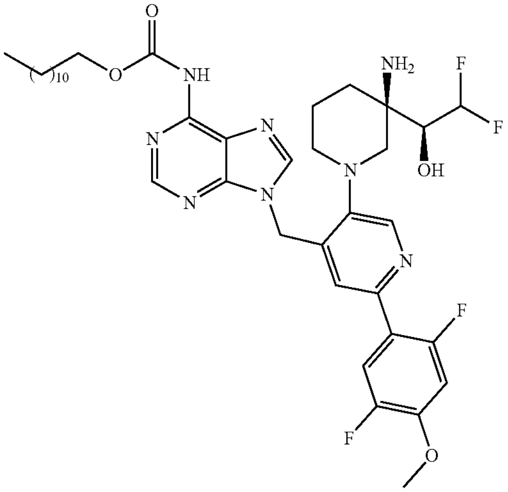 |
| V-58 | 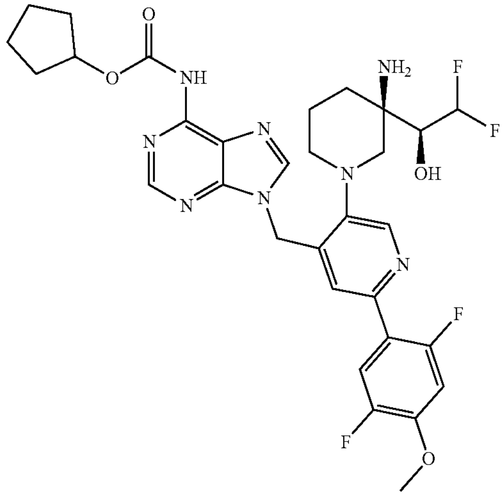 [SMILES: COc1cc(F)c(-c2cc(Cn3cnc4c(NC(=O)OC5CCCC5)ncnc43)c(N3CCC[C@](N)([C@H](O)C(F)F)C3)cn2)cc1F] |

TABLE 5-continued
| Compound No. | Chemical Structure |
|---|---|
| V-59 | 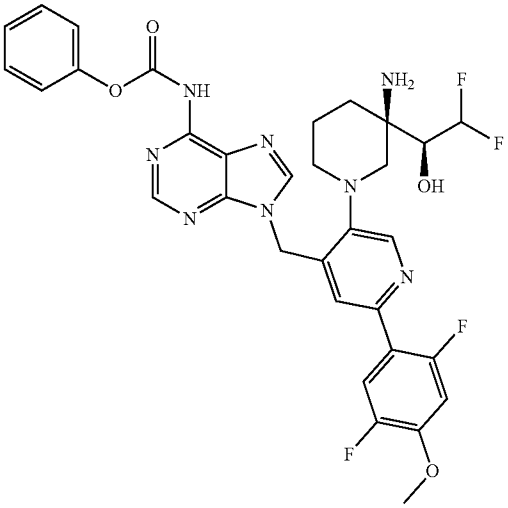 [SMILES: COc1cc(F)c(-c2cc(Cn3cnc4c(NC(=O)Oc5ccccc5)ncnc43)c(N3CCC[C@](N)([C@H](O)C(F)F)C3)cn2)cc1F] |
| V-60 | 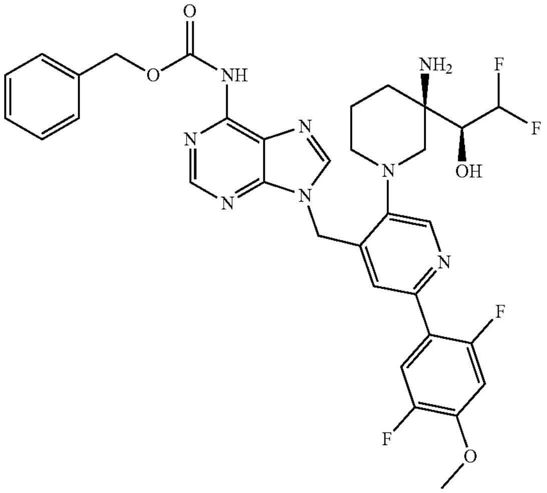 [SMILES: COc1cc(F)c(-c2cc(Cn3cnc4c(NC(=O)OCc5ccccc5)ncnc43)c(N3CCC[C@](N)([C@H](O)C(F)F)C3)cn2)cc1F] |
| V-61 | 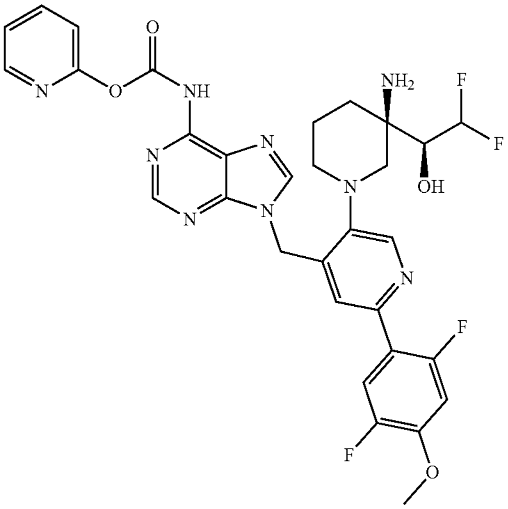 [SMILES: COc1cc(F)c(-c2cc(Cn3cnc4c(NC(=O)Oc5ccccn5)ncnc43)c(N3CCC[C@](N)([C@H](O)C(F)F)C3)cn2)cc1F] |

TABLE 5-continued
| Compound No. | Chemical Structure |
|---|---|
| V-62 | 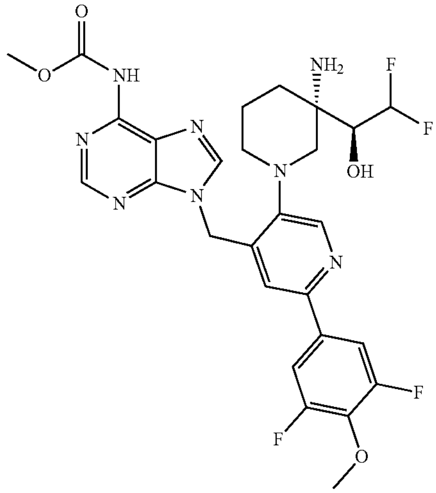 [SMILES: COC(=O)Nc1ncnc2c1ncn2Cc1cc(-c2cc(F)c(OC)c(F)c2)ncc1N1CCC[C@@](N)([C@H](O)C(F)F)C1] |
| V-63 | 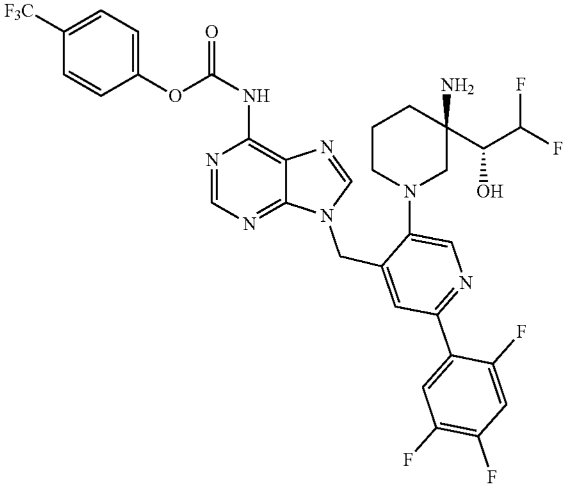 [SMILES: N[C@]1([C@@H](O)C(F)F)CCCN(c2cnc(-c3cc(F)c(F)cc3F)cc2Cn2cnc3c(NC(=O)Oc4ccc(C(F)(F)F)cc4)ncnc32)C1] |
| V-64 | 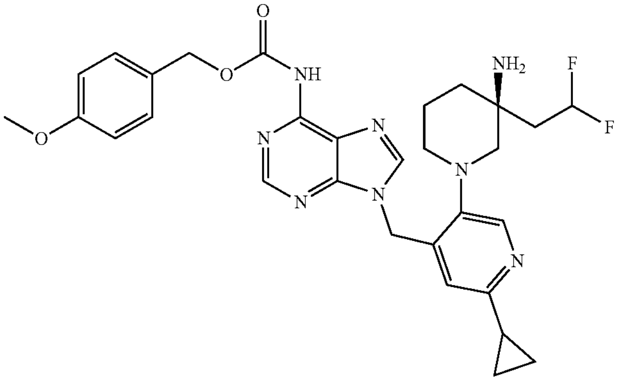 [SMILES: COc1ccc(COC(=O)Nc2ncnc3c2ncn3Cc2cc(C3CC3)ncc2N2CCC[C@](N)(CC(F)F)C2)cc1] |

TABLE 5-continued
| Compound No. | Chemical Structure |
|---|---|
| V-65 | 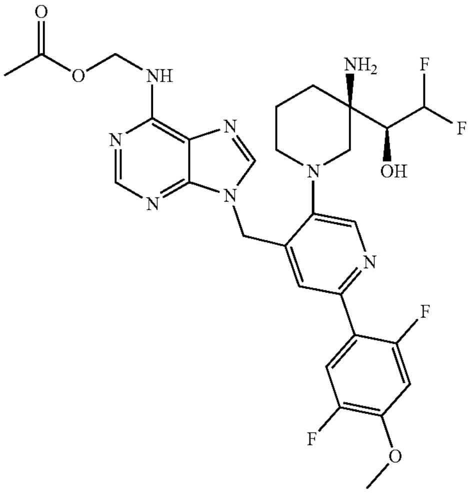 [SMILES: COc1cc(F)c(-c2cc(Cn3cnc4c(NCOC(C)=O)ncnc43)c(N3CCC[C@](N)([C@H](O)C(F)F)C3)cn2)cc1F] |
| V-66 | 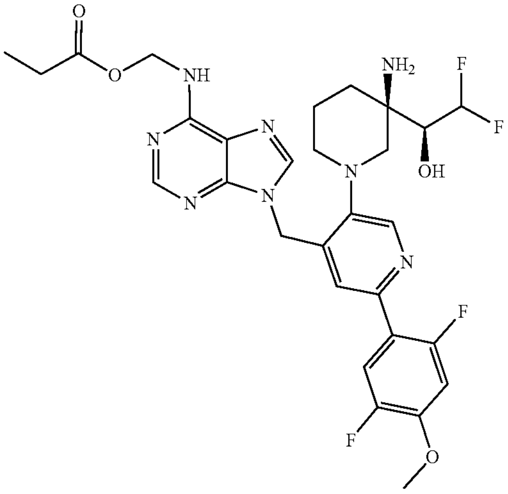 |
| V-67 | 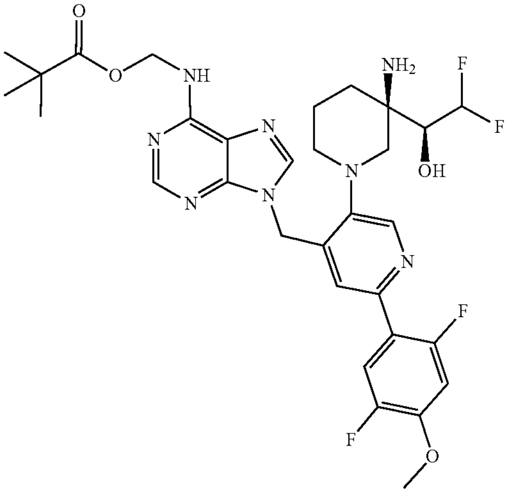 [SMILES: COc1cc(F)c(-c2cc(Cn3cnc4c(NCOC(=O)C(C)(C)C)ncnc43)c(N3CCC[C@](N)([C@H](O)C(F)F)C3)cn2)cc1F] |

TABLE 5-continued
| Compound No. | Chemical Structure |
| --- | --- |
| V-68 | 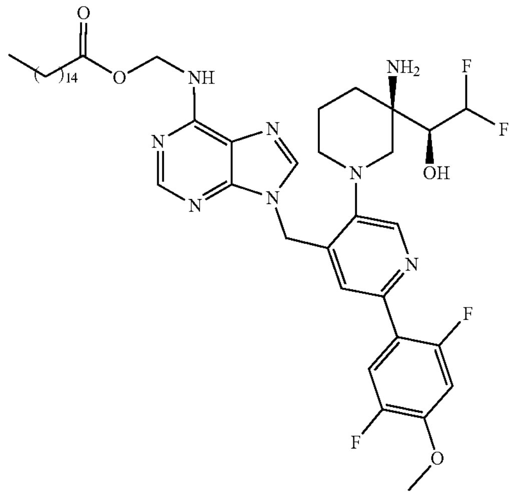 |
| V-69 | 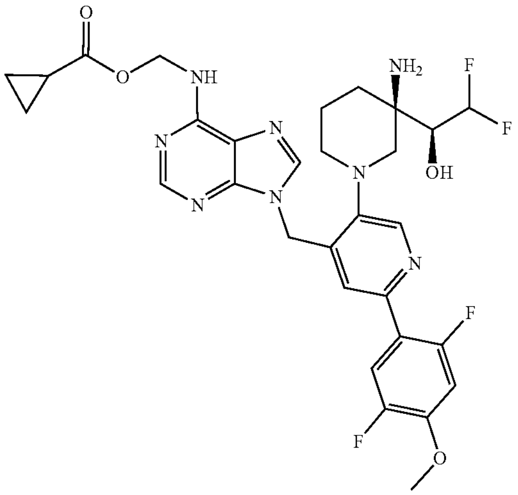 [SMILES: COc1cc(F)c(-c2cc(Cn3cnc4c(NCOC(=O)C5CC5)ncnc43)c(N3CCC[C@](N)([C@H](O)C(F)F)C3)cn2)cc1F] |
| V-70 | 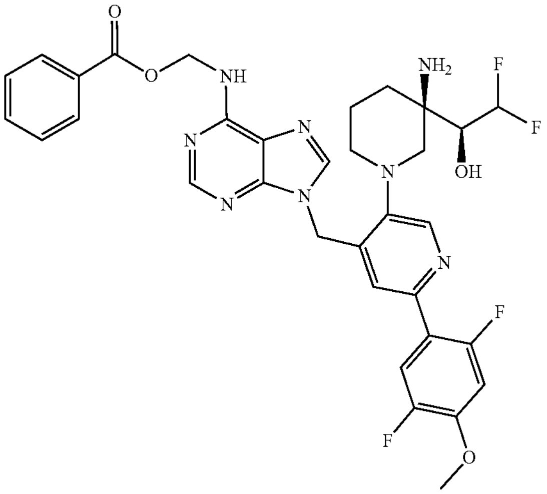 [SMILES: COc1cc(F)c(-c2cc(Cn3cnc4c(NCOC(=O)c5ccccc5)ncnc43)c(N3CCC[C@](N)([C@H](O)C(F)F)C3)cn2)cc1F] |

TABLE 5-continued
| Compound No. | Chemical Structure |
|---|---|
| V-71 | 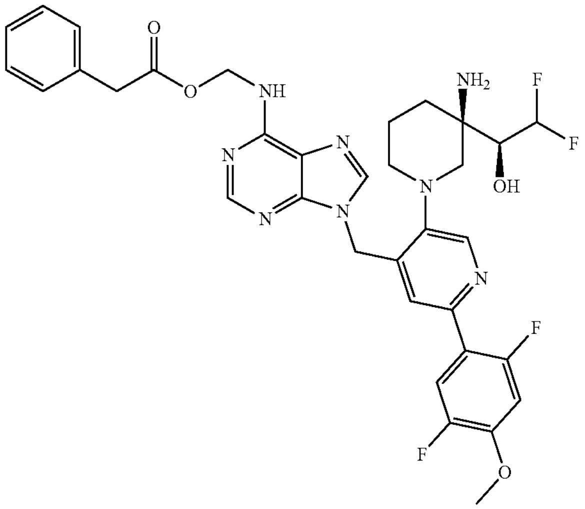 [SMILES: COc1cc(F)c(-c2cc(Cn3cnc4c(NCOC(=O)Cc5ccccc5)ncnc43)c(N3CCC[C@](N)([C@H](O)C(F)F)C3)cn2)cc1F] |
| V-72 | 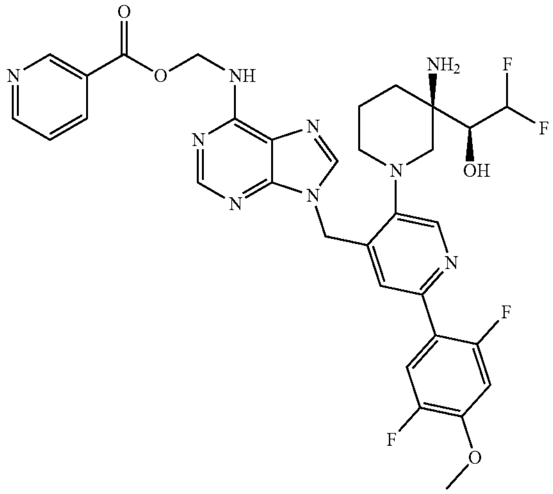 [SMILES: COc1cc(F)c(-c2cc(Cn3cnc4c(NCOC(=O)c5cccnc5)ncnc43)c(N3CCC[C@](N)([C@H](O)C(F)F)C3)cn2)cc1F] |
| V-73 | 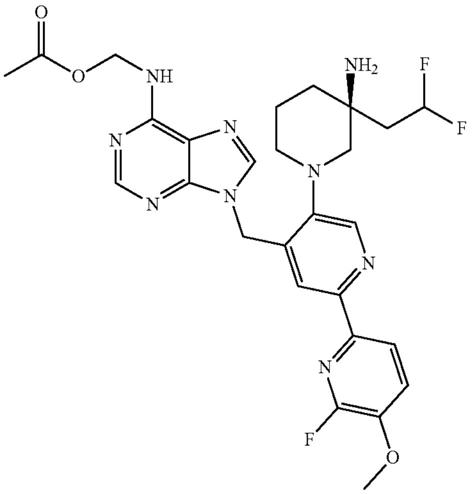 [SMILES: COc1ccc(-c2cc(Cn3cnc4c(NCOC(C)=O)ncnc43)c(N3CCC[C@](N)(CC(F)F)C3)cn2)nc1F] |

TABLE 5-continued
| Compound No. | Chemical Structure |
|---|---|
| V-74 | 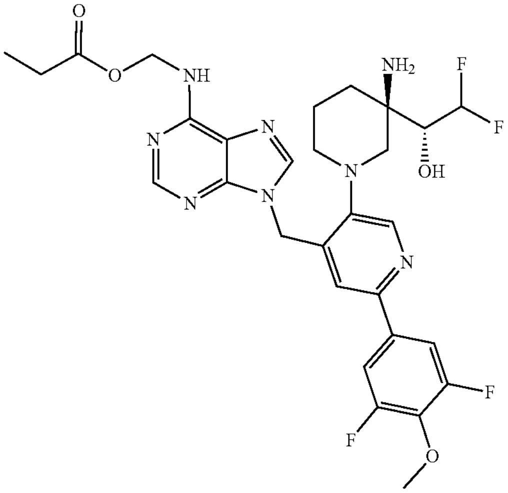 [SMILES: CCC(=O)OCNc1ncnc2c1ncn2Cc1cc(-c2cc(F)c(OC)c(F)c2)ncc1N1CCC[C@](N)([C@@H](O)C(F)F)C1] |
| V-75 | 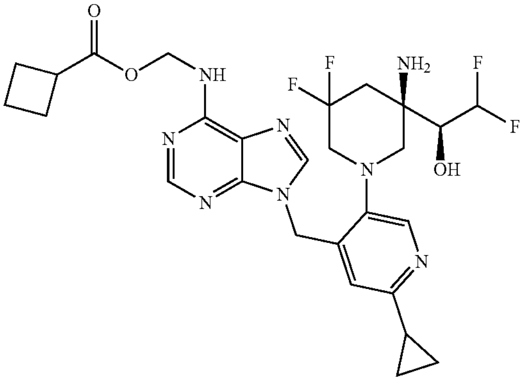 [SMILES: N[C@@]1([C@H](O)C(F)F)CN(c2cnc(C3CC3)cc2Cn2cnc3c(NCOC(=O)C4CCC4)ncnc32)CC(F)(F)C1] |
| V-76 | 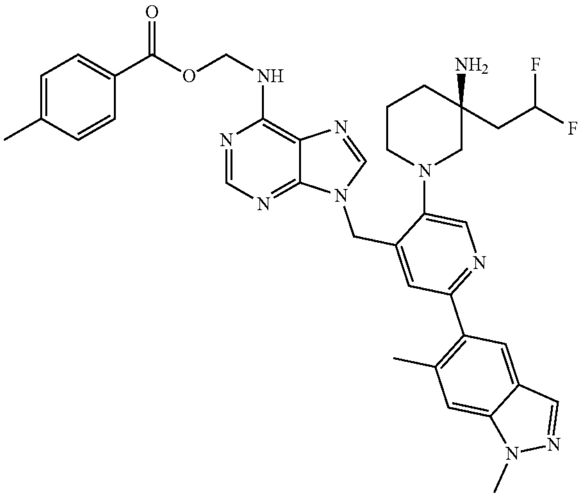 [SMILES: Cc1ccc(C(=O)OCNc2ncnc3c2ncn3Cc2cc(-c3cc4cnn(C)c4cc3C)ncc2N2CCC[C@](N)(CC(F)F)C2)cc1] |

TABLE 5-continued
| Compound No. | Chemical Structure |
| --- | --- |
| V-77 | 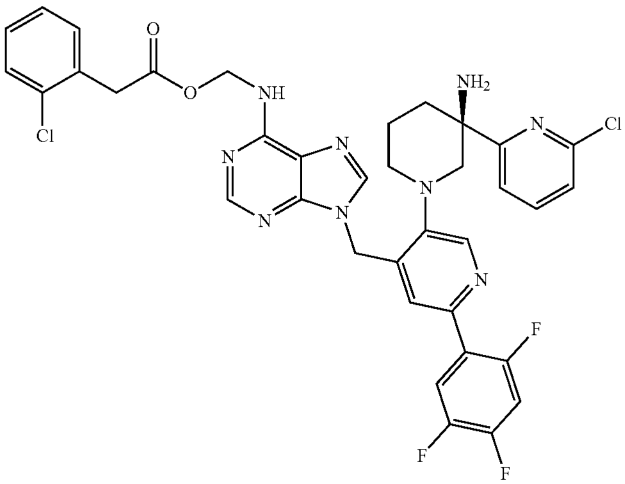 [SMILES: N[C@]1(c2cccc(Cl)n2)CCCN(c2cnc(-c3cc(F)c(F)cc3F)cc2Cn2cnc3c(NCOC(=O)Cc4ccccc4Cl)ncnc32)C1] |
| V-78 | 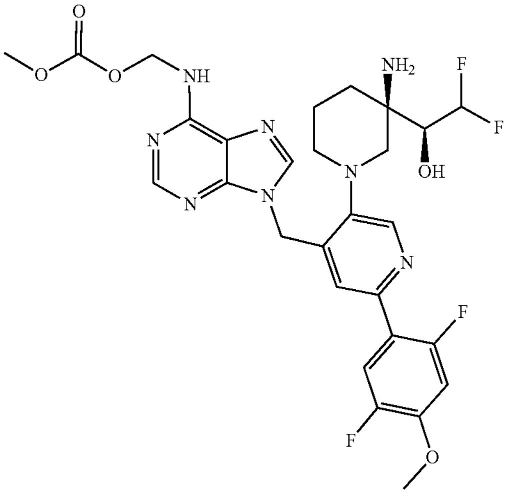 [SMILES: COC(=O)OCNc1ncnc2c1ncn2Cc1cc(-c2cc(F)c(OC)cc2F)ncc1N1CCC[C@](N)([C@H](O)C(F)F)C1] |
| V-79 | 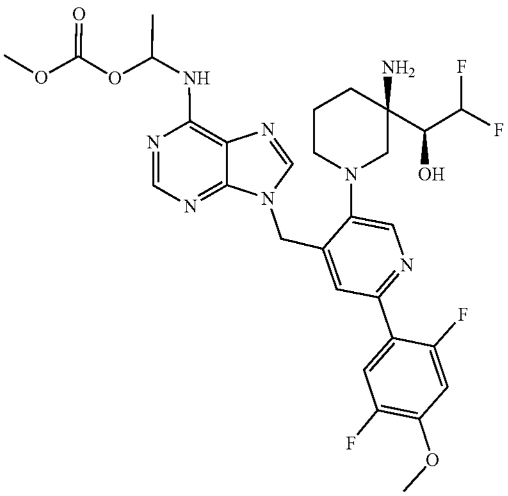 [SMILES: COC(=O)OC(C)Nc1ncnc2c1ncn2Cc1cc(-c2cc(F)c(OC)cc2F)ncc1N1CCC[C@](N)([C@H](O)C(F)F)C1] |

TABLE 5-continued
| Compound No. | Chemical Structure |
|---|---|
| V-80 | 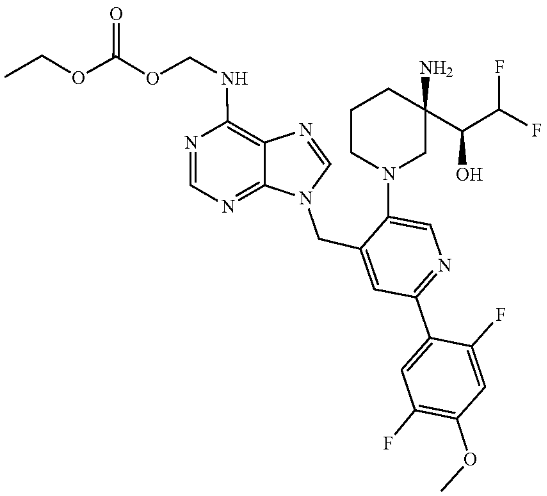 [SMILES: CCOC(=O)OCNc1ncnc2c1ncn2Cc1cc(-c2cc(F)c(OC)cc2F)ncc1N1CCC[C@](N)([C@H](O)C(F)F)C1] |
| V-81 | 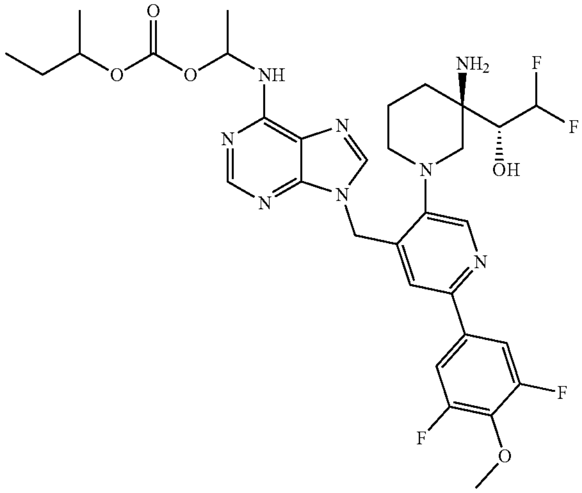 [SMILES: CCC(C)OC(=O)OC(C)Nc1ncnc2c1ncn2Cc1cc(-c2cc(F)c(OC)c(F)c2)ncc1N1CCC[C@](N)([C@@H](O)C(F)F)C1] |
| V-82 | 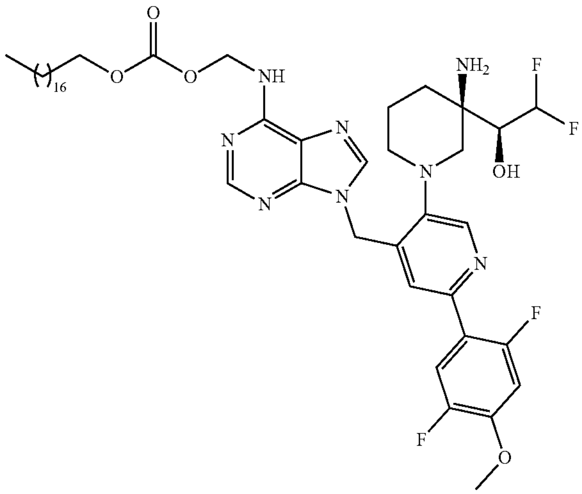 |

TABLE 5-continued
| Compound No. | Chemical Structure |
|---|---|
| V-83 | 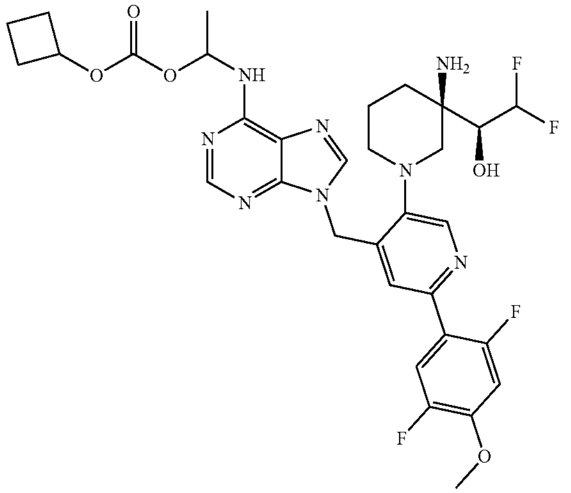 [SMILES: COc1cc(F)c(-c2cc(Cn3cnc4c(NC(C)OC(=O)OC5CCC5)ncnc43)c(N3CCC[C@](N)([C@H](O)C(F)F)C3)cn2)cc1F] |
| V-84 | 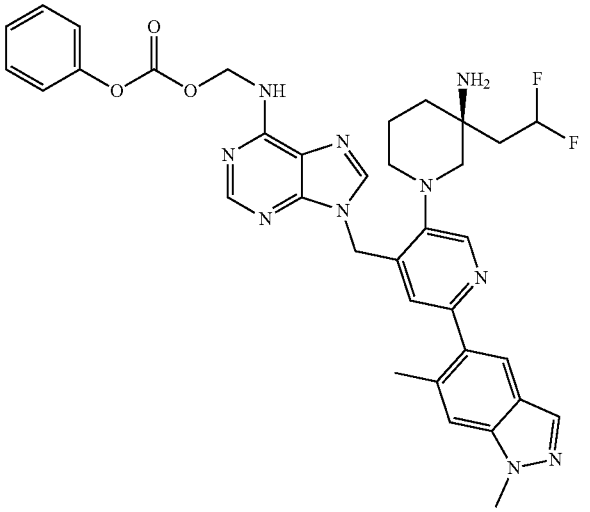 [SMILES: Cc1cc2c(cnn2C)cc1-c1cc(Cn2cnc3c(NCOC(=O)Oc4ccccc4)ncnc32)c(N2CCC[C@](N)(CC(F)F)C2)cn1] |
| V-85 | 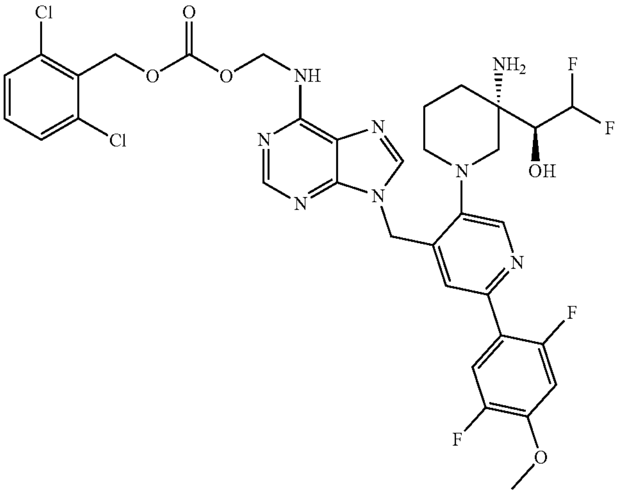 [SMILES: COc1cc(F)c(-c2cc(Cn3cnc4c(NCOC(=O)OCc5c(Cl)cccc5Cl)ncnc43)c(N3CCC[C@@](N)([C@H](O)C(F)F)C3)cn2)cc1F] |

TABLE 5-continued
| Compound No. | Chemical Structure |
| --- | --- |
| V-86 | 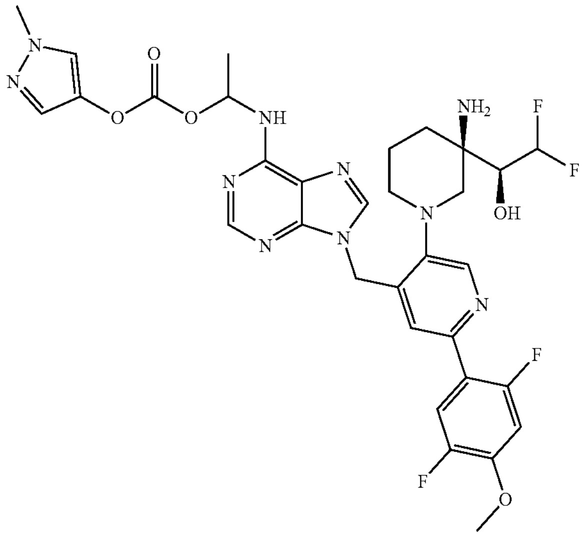 [SMILES: COc1cc(F)c(-c2cc(Cn3cnc4c(NC(C)OC(=O)Oc5cnn(C)c5)ncnc43)c(N3CCC[C@](N)([C@H](O)C(F)F)C3)cn2)cc1F] |
| V-87 | 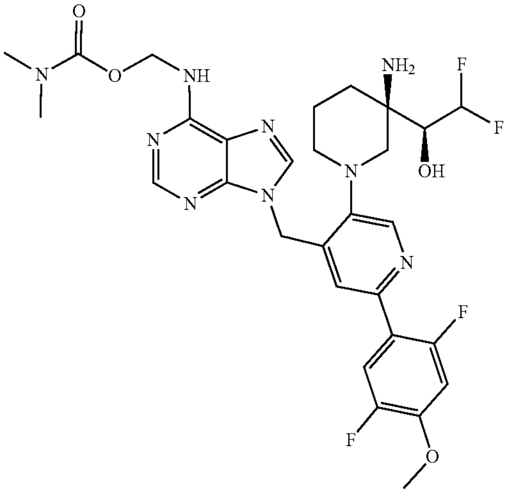 [SMILES: COc1cc(F)c(-c2cc(Cn3cnc4c(NCOC(=O)N(C)C)ncnc43)c(N3CCC[C@](N)([C@H](O)C(F)F)C3)cn2)cc1F] |
| V-88 | 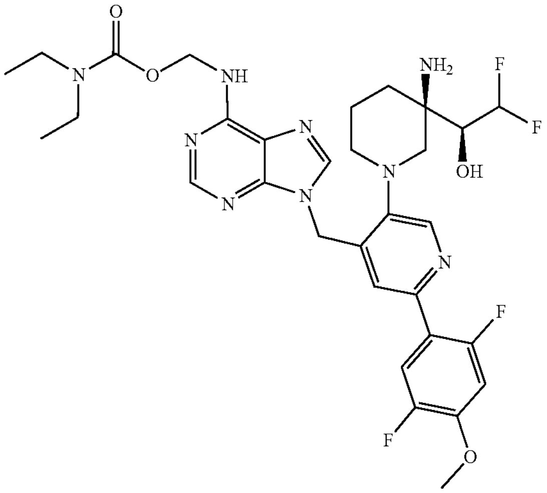 [SMILES: CCN(CC)C(=O)OCNc1ncnc2c1ncn2Cc1cc(-c2cc(F)c(OC)cc2F)ncc1N1CCC[C@](N)([C@H](O)C(F)F)C1] |

TABLE 5-continued
| Compound No. | Chemical Structure |
| --- | --- |
| V-89 | 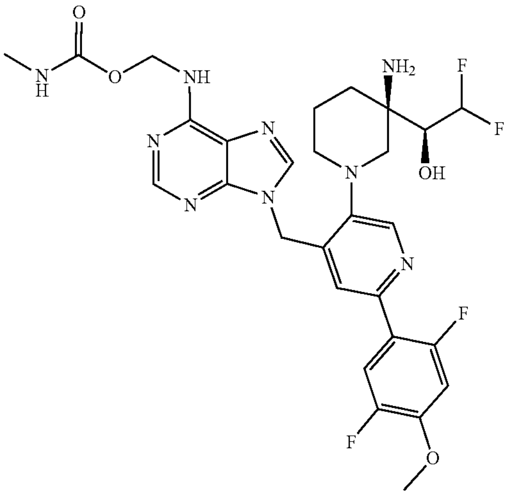 [SMILES: CNC(=O)OCNc1ncnc2c1ncn2Cc1cc(-c2cc(F)c(OC)cc2F)ncc1N1CCC[C@](N)([C@H](O)C(F)F)C1] |
| V-90 | 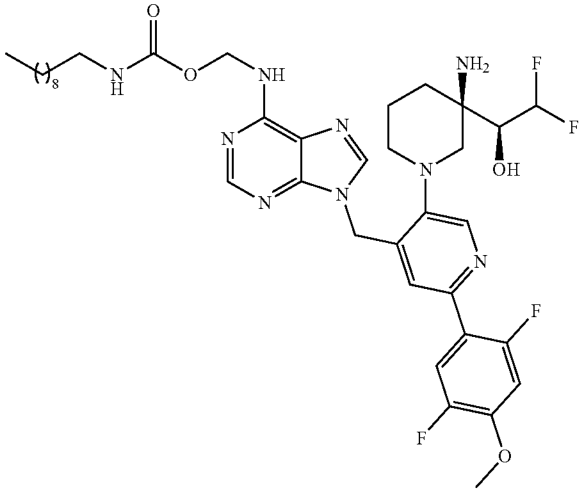 |
| V-91 | 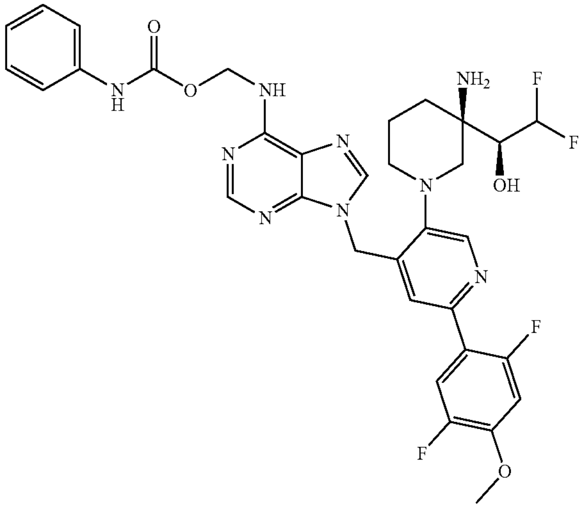 [SMILES: COc1cc(F)c(-c2cc(Cn3cnc4c(NCOC(=O)Nc5ccccc5)ncnc43)c(N3CCC[C@](N)([C@H](O)C(F)F)C3)cn2)cc1F] |

TABLE 5-continued
| Compound No. | Chemical Structure |
|---|---|
| V-92 | 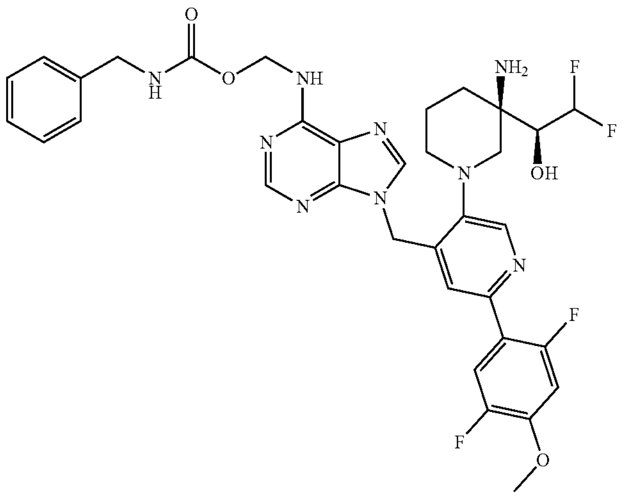 [SMILES: COc1cc(F)c(-c2cc(Cn3cnc4c(NCOC(=O)NCc5ccccc5)ncnc43)c(N3CCC[C@](N)([C@H](O)C(F)F)C3)cn2)cc1F] |
| V-93 | 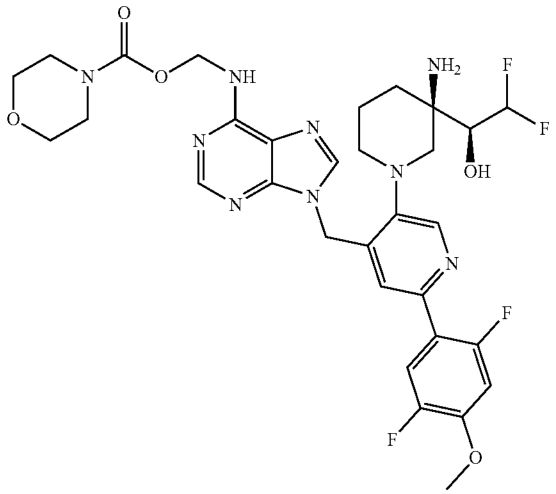 [SMILES: COc1cc(F)c(-c2cc(Cn3cnc4c(NCOC(=O)N5CCOCC5)ncnc43)c(N3CCC[C@](N)([C@H](O)C(F)F)C3)cn2)cc1F] |
| V-94 | 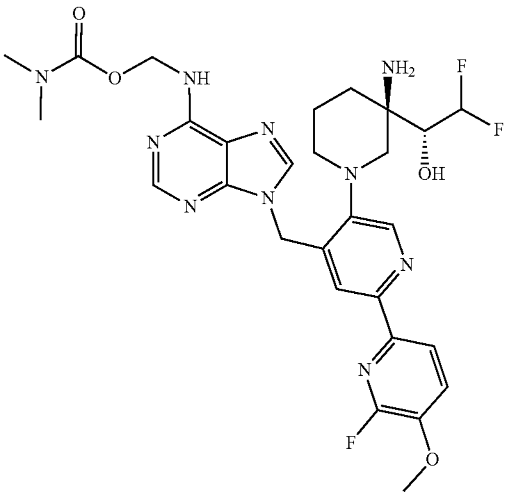 [SMILES: COc1ccc(-c2cc(Cn3cnc4c(NCOC(=O)N(C)C)ncnc43)c(N3CCC[C@](N)([C@@H](O)C(F)F)C3)cn2)nc1F] |

TABLE 5-continued
| Compound No. | Chemical Structure |
|---|---|
| V-95 | 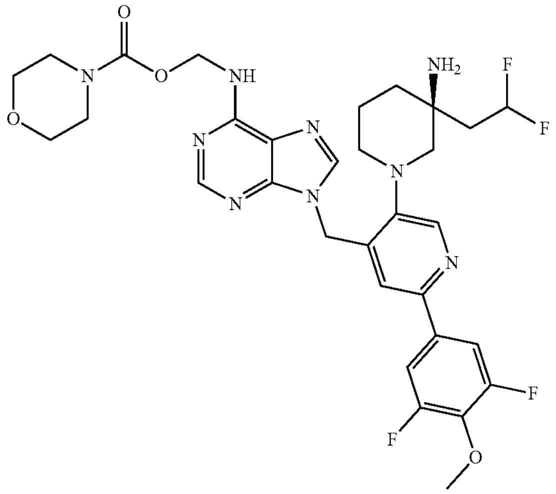 [SMILES: COc1c(F)cc(-c2cc(Cn3cnc4c(NCOC(=O)N5CCOCC5)ncnc43)c(N3CCC[C@](N)(CC(F)F)C3)cn2)cc1F] |
TABLE 6
| Compound No. | Chemical Structure |
|---|---|
| VI-1 | 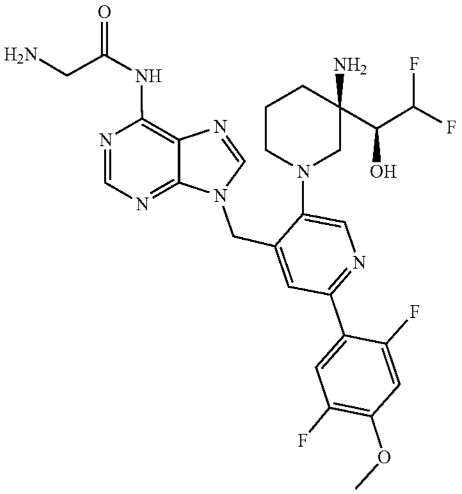 [SMILES: COc1cc(F)c(-c2cc(Cn3cnc4c(NC(=O)CN)ncnc43)c(N3CCC[C@](N)([C@H](O)C(F)F)C3)cn2)cc1F] |

TABLE 6-continued
| Compound No. | Chemical Structure |
| --- | --- |
| VI-2 | 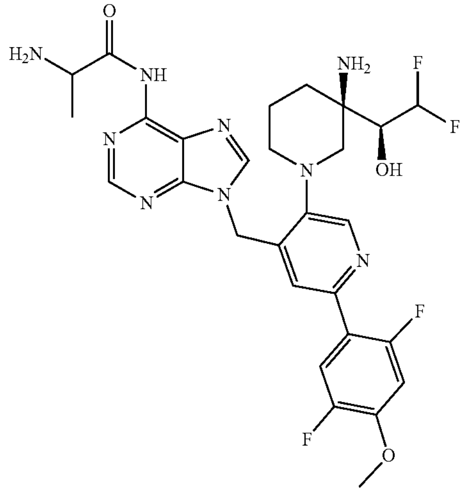 [SMILES: COc1cc(F)c(-c2cc(Cn3cnc4c(NC(=O)C(C)N)ncnc43)c(N3CCC[C@](N)([C@H](O)C(F)F)C3)cn2)cc1F] |
| VI-3 | 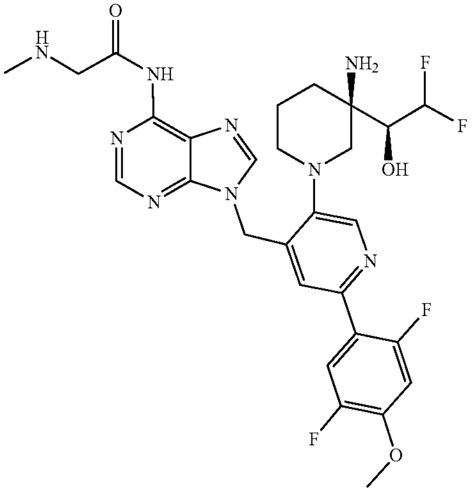 [SMILES: CNCC(=O)Nc1ncnc2c1ncn2Cc1cc(-c2cc(F)c(OC)cc2F)ncc1N1CCC[C@](N)([C@H](O)C(F)F)C1] |
| VI-4 | 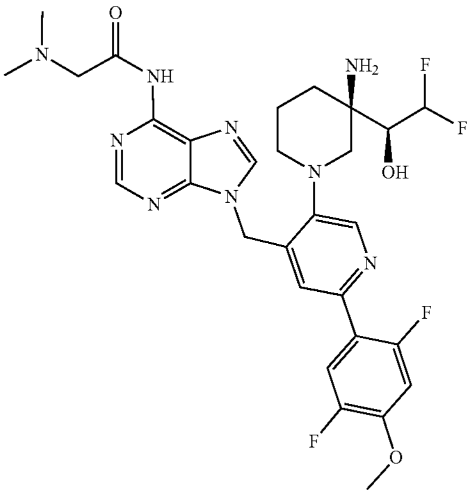 |

TABLE 6-continued
| Compound No. | Chemical Structure |
| --- | --- |
| VI-5 | 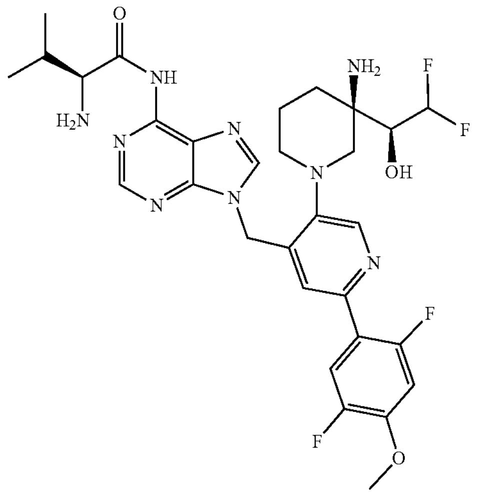 [SMILES: COc1cc(F)c(-c2cc(Cn3cnc4c(NC(=O)[C@@H](N)C(C)C)ncnc43)c(N3CCC[C@](N)([C@H](O)C(F)F)C3)cn2)cc1F] |
| VI-6 | 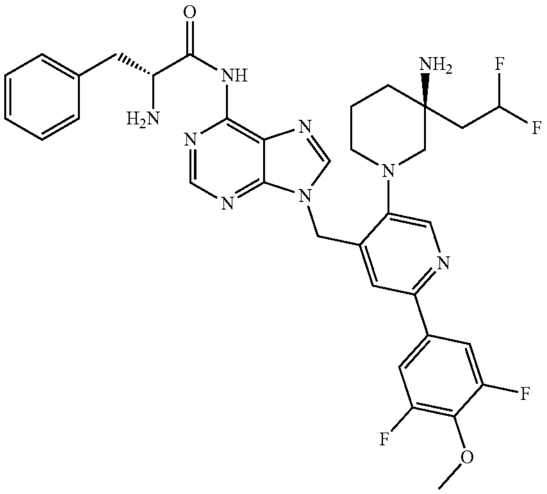 [SMILES: COc1c(F)cc(-c2cc(Cn3cnc4c(NC(=O)[C@H](N)Cc5ccccc5)ncnc43)c(N3CCC[C@](N)(CC(F)F)C3)cn2)cc1F] |
| VI-7 | 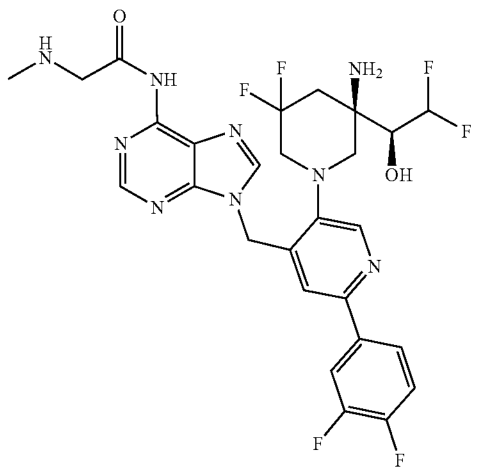 [SMILES: CNCC(=O)Nc1ncnc2c1ncn2Cc1cc(-c2ccc(F)c(F)c2)ncc1N1CC(F)(F)C[C@](N)([C@H](O)C(F)F)C1] |

TABLE 6-continued
| Compound No. | Chemical Structure |
|---|---|
| VI-8 | 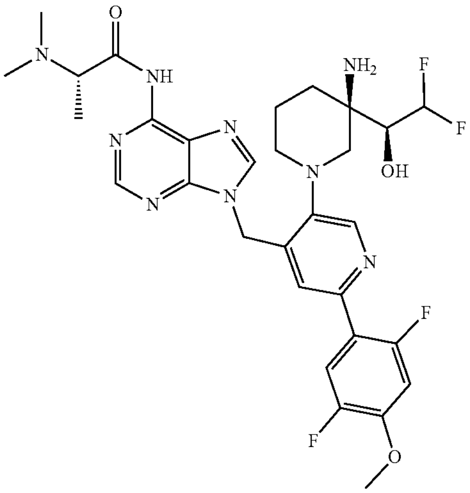 [SMILES: COc1cc(F)c(-c2cc(Cn3cnc4c(NC(=O)[C@H](C)N(C)C)ncnc43)c(N3CCC[C@](N)([C@H](O)C(F)F)C3)cn2)cc1F] |
| VI-9 | 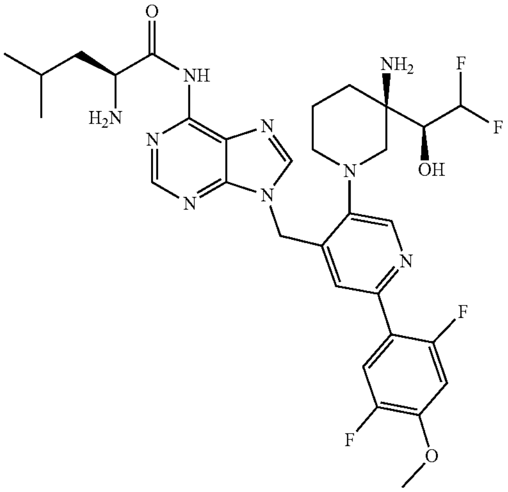 [SMILES: COc1cc(F)c(-c2cc(Cn3cnc4c(NC(=O)[C@@H](N)CC(C)C)ncnc43)c(N3CCC[C@](N)([C@H](O)C(F)F)C3)cn2)cc1F] |
| VI-10 | 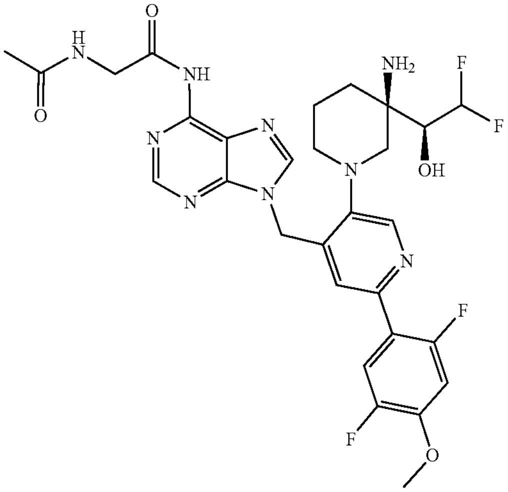 [SMILES: COc1cc(F)c(-c2cc(Cn3cnc4c(NC(=O)CNC(C)=O)ncnc43)c(N3CCC[C@](N)([C@H](O)C(F)F)C3)cn2)cc1F] |

TABLE 6-continued
| Compound No. | Chemical Structure |
| --- | --- |
| VI-11 | 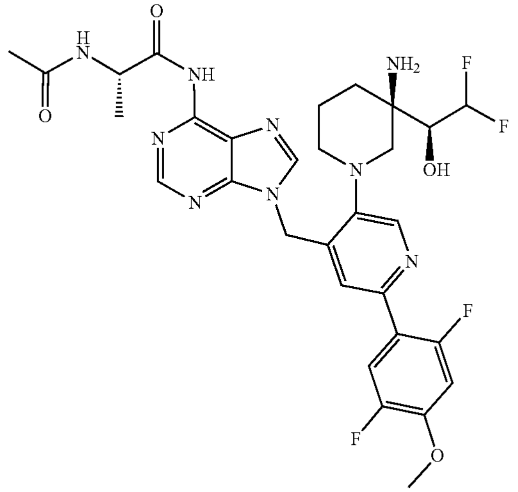 [SMILES: COc1cc(F)c(-c2cc(Cn3cnc4c(NC(=O)[C@H](C)NC(C)=O)ncnc43)c(N3CCC[C@](N)([C@H](O)C(F)F)C3)cn2)cc1F] |
| VI-12 | 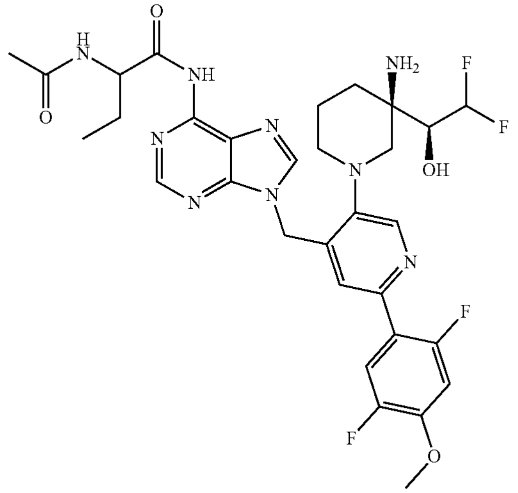 [SMILES: CCC(NC(C)=O)C(=O)Nc1ncnc2c1ncn2Cc1cc(-c2cc(F)c(OC)cc2F)ncc1N1CCC[C@](N)([C@H](O)C(F)F)C1] |
| VI-13 | 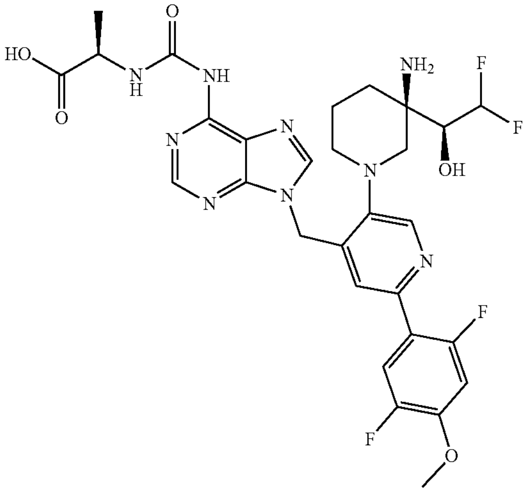 [SMILES: COc1cc(F)c(-c2cc(Cn3cnc4c(NC(=O)N[C@H](C)C(=O)O)ncnc43)c(N3CCC[C@](N)([C@H](O)C(F)F)C3)cn2)cc1F] |

TABLE 6-continued
| Compound No. | Chemical Structure |
|---|---|
| VI-14 | 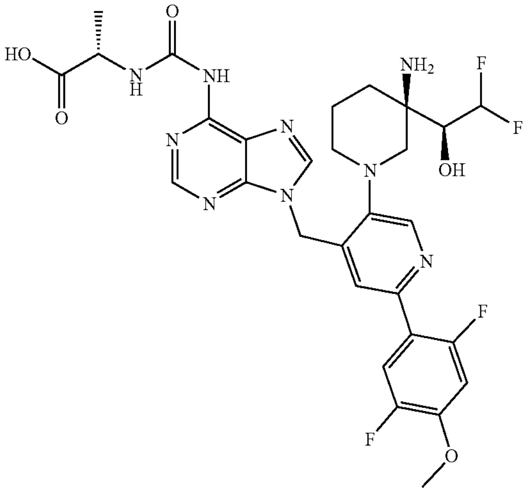 [SMILES: COc1cc(F)c(-c2cc(Cn3cnc4c(NC(=O)N[C@@H](C)C(=O)O)ncnc43)c(N3CCC[C@](N)([C@H](O)C(F)F)C3)cn2)cc1F] |
| VI-15 | 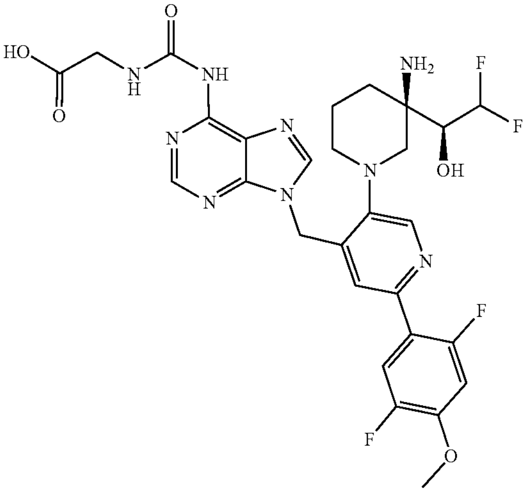 [SMILES: COc1cc(F)c(-c2cc(Cn3cnc4c(NC(=O)NCC(=O)O)ncnc43)c(N3CCC[C@](N)([C@H](O)C(F)F)C3)cn2)cc1F] |
| VI-16 | 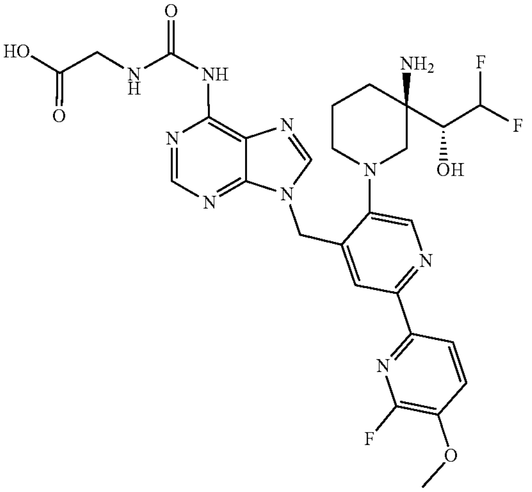 [SMILES: COc1ccc(-c2cc(Cn3cnc4c(NC(=O)NCC(=O)O)ncnc43)c(N3CCC[C@](N)([C@@H](O)C(F)F)C3)cn2)nc1F] |

TABLE 6-continued
| Compound No. | Chemical Structure |
|---|---|
| VI-17 | 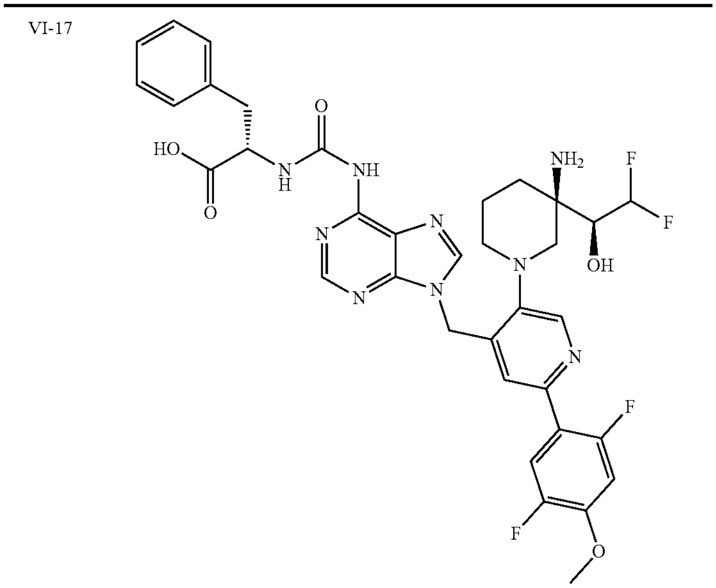 |
| VI-18 | 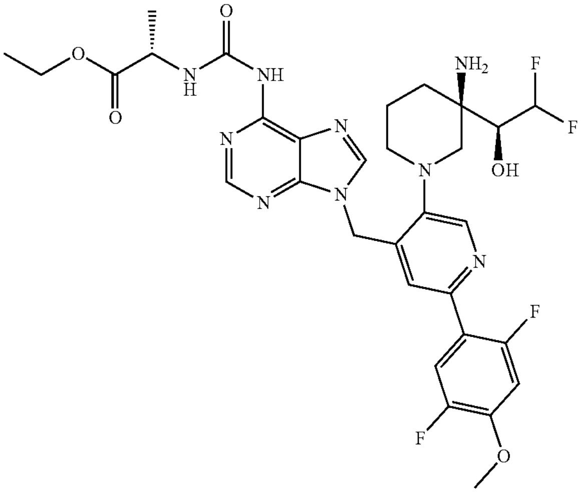 [SMILES: CCOC(=O)[C@H](C)NC(=O)Nc1ncnc2c1ncn2Cc1cc(-c2cc(F)c(OC)cc2F)ncc1N1CCC[C@](N)([C@H](O)C(F)F)C1] |
| VI-19 | 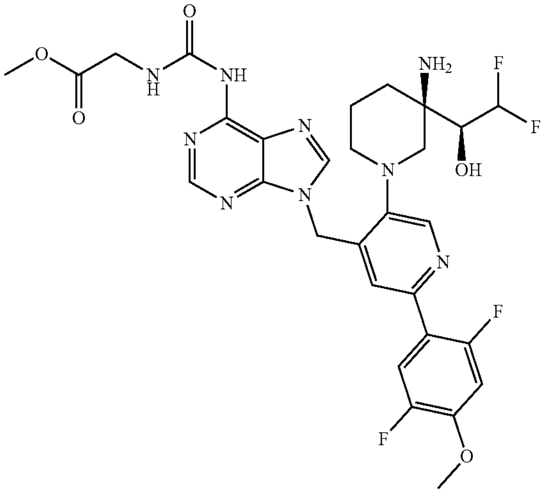 [SMILES: COC(=O)CNC(=O)Nc1ncnc2c1ncn2Cc1cc(-c2cc(F)c(OC)cc2F)ncc1N1CCC[C@](N)([C@H](O)C(F)F)C1] |

TABLE 6-continued
| Compound No. | Chemical Structure |
|---|---|
| VI-20 | 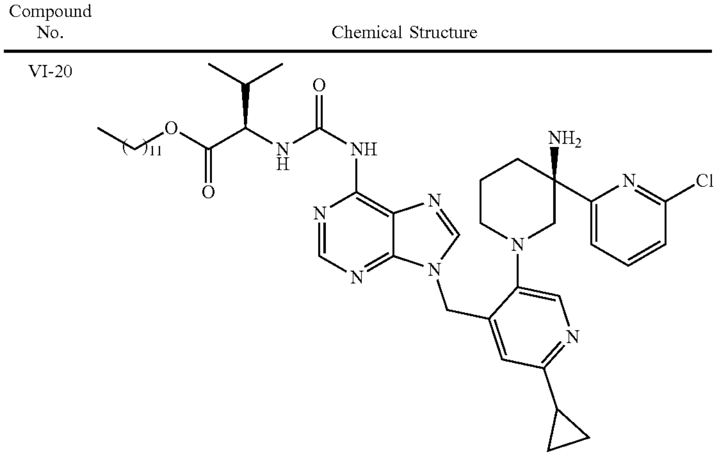 |
TABLE 7
| Compound No. | Chemical Structure |
|---|---|
| VII-1 | 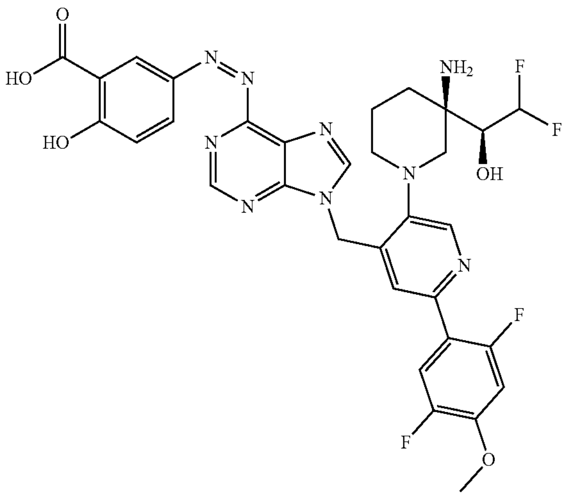 [SMILES: COc1cc(F)c(-c2cc(Cn3cnc4c(/N=N\c5ccc(O)c(C(=O)O)c5)ncnc43)c(N3CCC[C@](N)([C@H](O)C(F)F)C3)cn2)cc1F] |
| VII-2 | 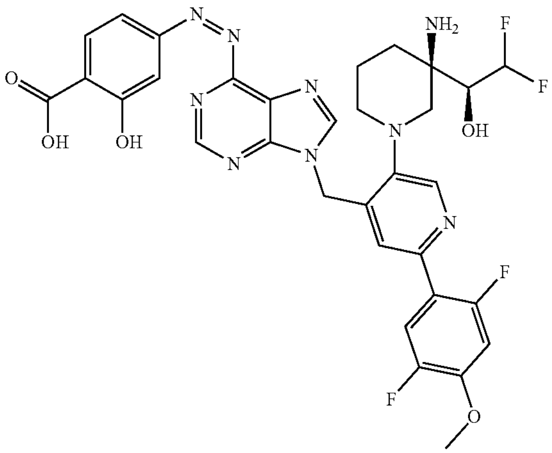 [SMILES: COc1cc(F)c(-c2cc(Cn3cnc4c(/N=N\c5ccc(C(=O)O)c(O)c5)ncnc43)c(N3CCC[C@](N)([C@H](O)C(F)F)C3)cn2)cc1F] |

TABLE 7-continued
| Compound No. | Chemical Structure |
|---|---|
| VII-3 | 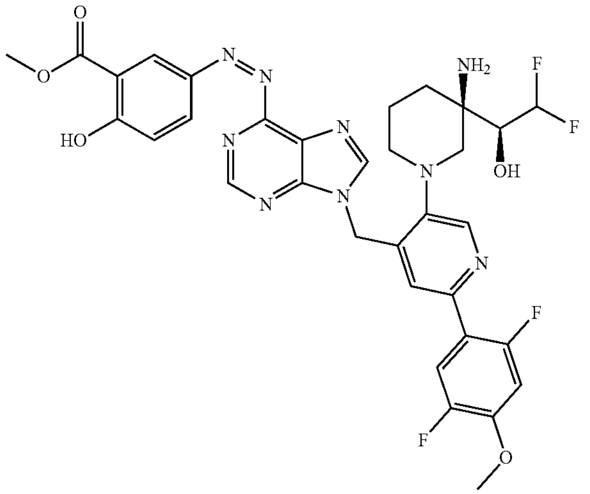 [SMILES: COC(=O)c1cc(/N=N\c2ncnc3c2ncn3Cc2cc(-c3cc(F)c(OC)cc3F)ncc2N2CCC[C@](N)([C@H](O)C(F)F)C2)ccc1O] |
| VII-4 | 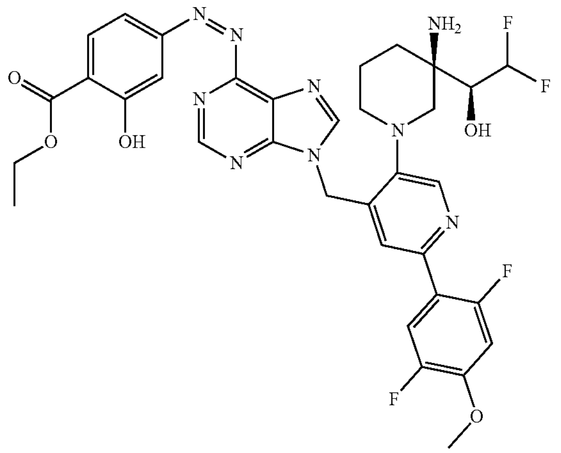 [SMILES: CCOC(=O)c1ccc(/N=N\c2ncnc3c2ncn3Cc2cc(-c3cc(F)c(OC)cc3F)ncc2N2CCC[C@](N)([C@H](O)C(F)F)C2)cc1O] |
| VII-5 | 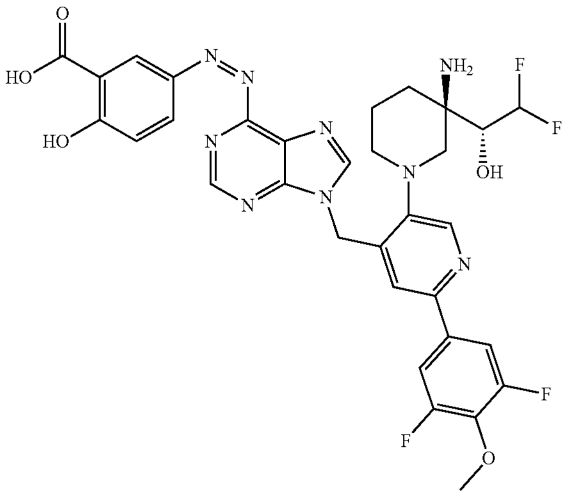 [SMILES: COc1c(F)cc(-c2cc(Cn3cnc4c(/N=N\c5ccc(O)c(C(=O)O)c5)ncnc43)c(N3CCC[C@](N)([C@@H](O)C(F)F)C3)cn2)cc1F] |

TABLE 7-continued
| Compound No. | Chemical Structure |
| --- | --- |
| VII-6 | 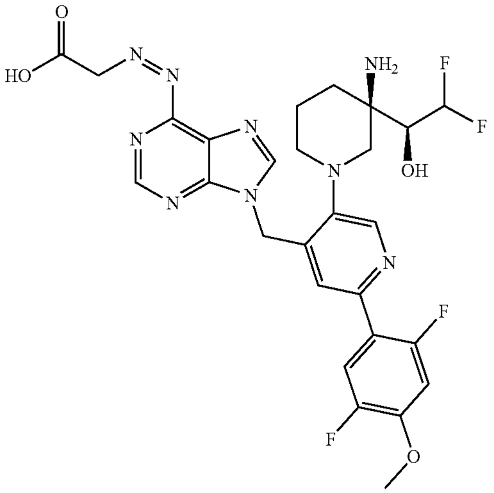 [SMILES: COc1cc(F)c(-c2cc(Cn3cnc4c(/N=N\CC(=O)O)ncnc43)c(N3CCC[C@](N)([C@H](O)C(F)F)C3)cn2)cc1F] |
| VII-7 | 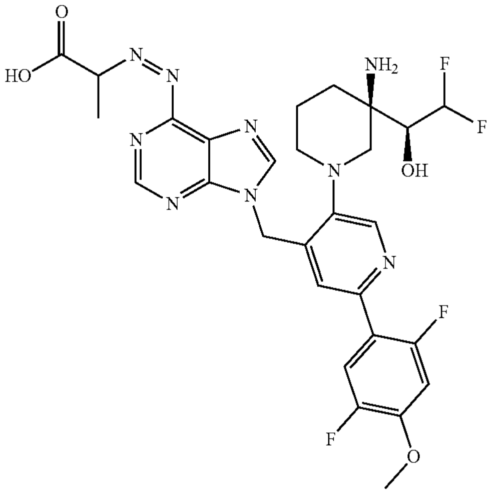 [SMILES: COc1cc(F)c(-c2cc(Cn3cnc4c(/N=N\C(C)C(=O)O)ncnc43)c(N3CCC[C@](N)([C@H](O)C(F)F)C3)cn2)cc1F] |
| VII-8 | 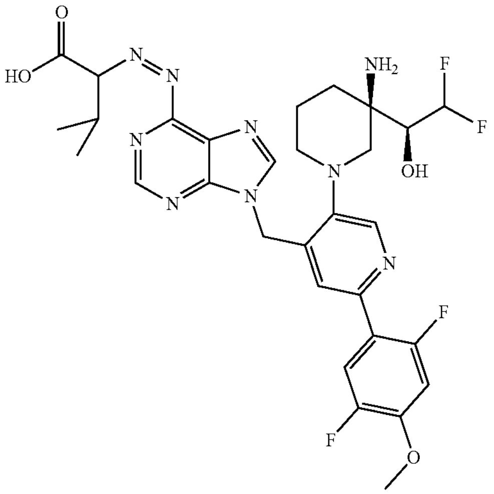 [SMILES: COc1cc(F)c(-c2cc(Cn3cnc4c(/N=N\C(C(=O)O)C(C)C)ncnc43)c(N3CCC[C@](N)([C@H](O)C(F)F)C3)cn2)cc1F] |

TABLE 7-continued
| Compound No. | Chemical Structure |
|---|---|
| VII-9 | 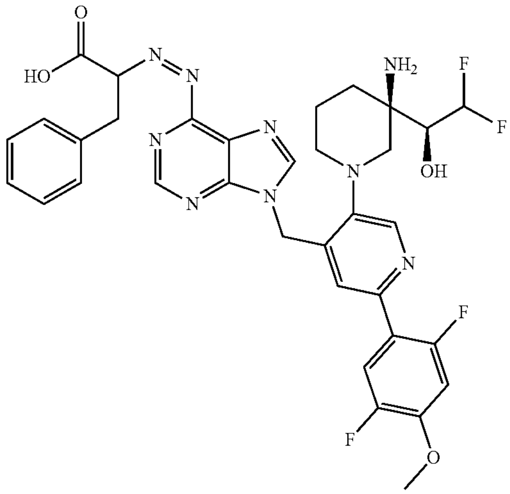 [SMILES: COc1cc(F)c(-c2cc(Cn3cnc4c(/N=N\C(Cc5ccccc5)C(=O)O)ncnc43)c(N3CCC[C@](N)([C@H](O)C(F)F)C3)cn2)cc1F] |
| VII-10 | 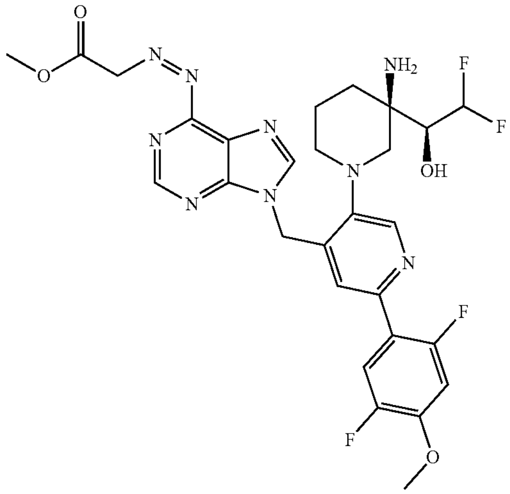 [SMILES: COC(=O)C/N=N\c1ncnc2c1ncn2Cc1cc(-c2cc(F)c(OC)cc2F)ncc1N1CCC[C@](N)([C@H](O)C(F)F)C1] |
| VII-11 | 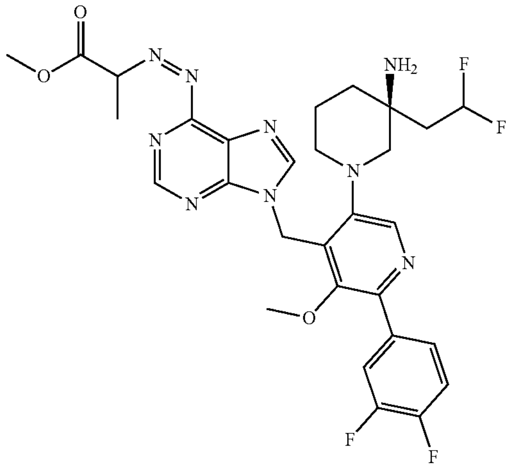 [SMILES: COC(=O)C(C)/N=N\c1ncnc2c1ncn2Cc1c(N2CCC[C@](N)(CC(F)F)C2)cnc(-c2ccc(F)c(F)c2)c1OC] |

TABLE 7-continued

| Compound No. | Chemical Structure |
| --- | --- |
| VII-12 | 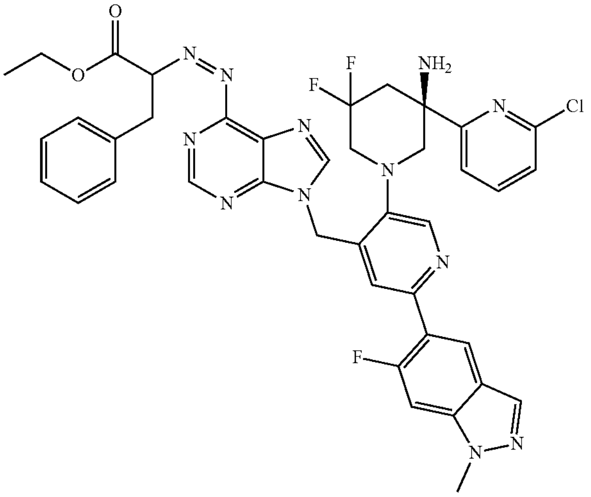 [SMILES: CCOC(=O)C(Cc1ccccc1)/N=N\c1ncnc2c1ncn2Cc1cc(-c2cc3cnn(C)c3cc2F)ncc1N1CC(F)(F)C[C@](N)(c2cccc(Cl)n2)C1] |

20. A pharmaceutical composition comprising a compound of claim 1 and a pharmaceutically acceptable carrier.

21. A method for treating a disease or condition mediated by nuclear SET domain-containing protein 2 (NSD2), comprising administering to a subject in need thereof a therapeutically effective amount of a compound of claim 1 to treat the disease or condition.

22. The method of claim 21, wherein said disease or condition mediated by NSD2 is selected from a solid tumor, leukemia, myeloma, lymphoma, and hypertension.

23. The method of claim 21, wherein said disease or condition mediated by NSD2 is breast cancer, cervical cancer, skin cancer, ovarian cancer, gastric cancer, prostate cancer, pancreatic cancer, lung cancer, hepatocellular carcinoma, head and neck cancer, peripheral nerve sheath tumor, osteosarcoma, multiple myeloma, neuroblastoma, leukemia, non-Hodgkin's lymphoma, or pulmonary arterial hypertension.

24. The method of claim 21, wherein said disease or condition mediated by NSD2 is acute lymphoblastic leukaemia, skin squamous cell carcinoma, or mantle cell lymphoma.

25. A method of inhibiting the activity of nuclear SET domain-containing protein 2 (NSD2), comprising contacting a NSD2 with an effective amount of a compound of claim 1 to inhibit the activity of said NSD2.

* * * * *